US006498165B1

(12) United States Patent
Armstrong et al.

(10) Patent No.: US 6,498,165 B1
(45) Date of Patent: Dec. 24, 2002

(54) SRC KINASE INHIBITOR COMPOUNDS

(75) Inventors: Helen M. Armstrong, Westfield, NJ (US); Richard Beresis, New York, NY (US); Joung L. Goulet, Westfield, NJ (US); Mark A. Holmes, Middlesex, NJ (US); Xingfang Hong, Westfield, NJ (US); Sander G. Mills, Scotch Plains, NJ (US); William H. Parsons, Belle Mead, NJ (US); Peter J. Sinclair, Scotch Plains, NJ (US); Mark G. Steiner, East Brunswick, NJ (US); Frederick Wong, Glen Ridge, NJ (US); Dennis M. Zaller, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 19 days.

(21) Appl. No.: 09/604,305

(22) Filed: Jun. 26, 2000

Related U.S. Application Data

(60) Provisional application No. 60/141,639, filed on Jun. 30, 1999.

(51) Int. Cl.[7] .................... A61K 31/505; A61K 31/517; C07D 239/02; C07D 401/00
(52) U.S. Cl. .................... 514/275; 514/256; 514/258.1; 544/330; 544/331
(58) Field of Search .............................. 514/258.1, 275, 514/256; 544/330, 331

(56) References Cited

U.S. PATENT DOCUMENTS

| | | | |
|---|---|---|---|
| 3,646,049 A | 2/1972 | Hoff et al. | 260/302 |
| 3,743,738 A | 7/1973 | Hoff et al. | 424/270 |
| 4,806,649 A | 2/1989 | Strupczewski | 546/193 |
| 5,521,184 A | 5/1996 | Zimmermann | 514/252 |
| 5,593,997 A | 1/1997 | Dow et al. | 514/258 |
| 5,902,813 A | 5/1999 | Teuber et al. | 514/275 |
| 5,958,934 A | 9/1999 | Berger et al. | 514/272 |

FOREIGN PATENT DOCUMENTS

| | | |
|---|---|---|
| EP | 0 233 461 A2 | 8/1987 |
| EP | 0 564 409 B1 | 10/1993 |
| EP | 0 588 762 A1 | 3/1994 |
| WO | WO 91/16313 | 10/1991 |
| WO | WO 93/07124 | 4/1993 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 96/35678 | 11/1996 |
| WO | WO 97/19065 | 5/1997 |
| WO | WO 97/33883 | 9/1997 |
| WO | WO 97/40019 | 10/1997 |
| WO | WO 98/02434 | 1/1998 |
| WO | WO 98/11095 | 3/1998 |
| WO | WO 98/18782 | 5/1998 |
| WO | WO 99/09845 | 3/1999 |
| WO | WO 99/41253 | 8/1999 |
| WO | WO 99/50251 | 10/1999 |
| WO | 00/53595 * | 9/2000 |

* cited by examiner

*Primary Examiner*—Richard L. Raymond
*Assistant Examiner*—Tamthom N. Truong
(74) *Attorney, Agent, or Firm*—Valerie J. Camara; Mark R. Daniel

(57) ABSTRACT

Pyrimidine compounds (Formula I), or their pharmaceutically acceptable salts, hydrates, solvates, crystal forms and individual diastereomers, and pharmaceutical compositions including the same, which are inhibitors of tyrosine kinase enzymes, and as such are useful in the prophylaxis and treatment of protein tyrosine kinase-associated disorders, such as immune diseases, hyperproliferative disorders and other diseases in which inappropriate protein kinase action is believed to play a role, such as cancer, angiogensis, atheroscelerosis, graft rejection, rheumatoid arthritis and psoriasis.

39 Claims, No Drawings

SRC KINASE INHIBITOR COMPOUNDS

This application claims the benefit of provisional application No. 60/141,639, filed Jun. 6, 1999.

BACKGROUND OF THE INVENTION

Tyrosine-specific Protein Kinases (PTKs) are a family of enzymes which catalyze the transfer of the terminal phosphate of adenosine triphosphate (ATP) to tyrosine residues in protein substrates [for review see: Hunter, T; Protein modification: phosphorylation on tyrosine residue; *Curr Opin Cell Biol* 1989; 1: 1168–1181]. The first members of this class of enzymes to be identified were PTKs encoded by viral oncogenes, which were capable of cell transformation (ie. pp60v-src and pp98v-fps). Later it was shown that there were normal cellular counterparts of these viral gene products (ie. pp60C-src and pp98c-fps). Since that discovery, a large number of genes encoding PTKs have been identified [for review see Hunter, T; Protein kinase classification; *Methods Enzymol* 1991; 200:3–37]. These include growth factor receptor PTKs such as the insulin and epidermal growth factor receptors, as well as non-receptor PTKs such as ZAP-70 and Lck. Although the molecular details have yet to be fully elucidated, PTK-mediated phosphorylation of tyrosine residues on protein substrates leads to the transduction of intracellular signals that regulate a variety of intracellular processes such as growth, transport, motility, and senescence. Many disease states are dependent on these cellular functions. Therefore, inhibitors of tyrosine kinases are useful for the prevention and chemotherapy of disease states that are dependent on these enzymes.

For example, tyrosine kinase inhibitors are useful for inhibiting T-cell activation and thus they are useful as immunosuppressive agents for the prevention or treatment of graft rejection following transplant surgery and for the prevention or treatment of autoimmune diseases such as rheumatoid arthritis and psoriasis. Graft rejection following transplant surgery is a common occurrence which arises when foreign antigens are recognized by the host immune system. In an effort to protect itself from the foreign tissue, the host immune system is then activated to release an arsenal of antibodies, soluble lymphokines, and cytotoxic lymphocytes which attack the foreign tissue, resulting in complications which often end in graft rejection. Similarly, a breakdown in self-tolerance can result in immune system attacks against the body's own tissues. These attacks can lead to autoimmune and chronic inflammatory diseases. Since T cells are the key regulators of these immune system attacks, inhibitors of T cell activation are useful therapeutic agents.

Currently the leading medicinal agent for the prevention or treatment of graft rejection is Cyclosporin A, approved by the United States Food and Drug Administration in 1983. Cyclosporin A is extremely effective at preventing transplant rejection and is efficacious in the treatment of autoimmune disorders such psoriasis, rheumatoid arthritis, inflammatory bowel disease, and type I diabetes. It work by forming complexes with a specific protein which can then inhibit the catalytic activity of calcineurin, a phosphatase that plays a key role in transducing signals from the T cell receptor (TcR) to the nucleus. However, calcineurin is ubiquitously expressed and is involved in many other signal transduction pathways. As a result, Cyclosporin A suffers drawbacks in that it can cause kidney failure, liver damage and ulcers; which in many cases can be very severe. Consequently, Cyclosporin A has a very narrow therapeutic index and is rarely used to treat chronic autoimmune diseases. Safer drugs which are more selective in their ability to affect the immune response system and which have fewer side effects are constantly being pursued. Thus, there is a continuing need and a continuing search in this field of art for alternative therapies. The Src-family protein tyrosine kinase, Lck, is upstream of calcineurin in the TcR-mediated signaling cascade. Lck is expressed almost exclusively in T cells and its catalytic activity is required for T cell signal transduction [for review see: Anderson S J, Levin S D, Perlmutter, R M; Involvement of the protein tyrosine kinase p56lck in T cell signaling and thymocyte development; *Adv Immunol* 1994; 56:151–178]. Thus, a potent Lck-selective kinase inhibitor would make a promising drug candidate.

Lck is one of 8 known members of the human Src-family of protein tyrosine kinases. The other members are Src, Fyn, Lyn, Fgr, Hck, Blk, and Yes. As a consequence of alternative mRNA splicing, Fyn exists as two distinct gene products, Fyn(T) and Fyn(B), that differ at their ATP binding sites. All Src-family kinases contain an N-terminal myristoylation site followed by a unique domain characteristic of each individual kinase, an SH3 domain that binds proline-rich sequences, an SH2 domain that binds phosphotyrosine-containing sequences, a linker region, a catalytic domain, and a C-terminal tail containing an inhibitory tyrosine. The activity of Src-family kinases is tightly regulated by phosphorylation. Two kinases, Csk and Ctk, can down-modulate the activity of Src-family kinases by phosphorylation of the inhibitory tyrosine. This C-terminal phosphotyrosine can then bind to the SH2 domain via an intramolecular interaction. In this closed state, the SH3 domain binds to the linker region, which then adopts a conformation that impinges upon the kinase domain and blocks catalytic activity. Dephosphorylation of the C-terminal phosphotyrosine by intracellular phosphatases such as CD45 and SHP-1 can partially activate Src-family kinases. In this open state, Src-family kinases can be fully activated by intermolecular autophosphorylation at a conserved tyrosine within the activation loop.

Src-family kinases display a variety of tissue-specific expression patterns. Src, Fyn(B), Yes, and Lyn are found in a broad range of tissues with especially high levels of expression in neuronal and hematopoietic cells. The expression of these particular Src-family kinases overlap to a great extent, however no cell types have been found that express all four of them. Expression of Lck, Fyn(T), Fgr, Hck, and Blk is restricted to cells of the hematopoietic lineage. In general, myeloid cells co-express Hck, Fgr, and Lyn; immature B cells co-express Hck, Lyn, and Blk; and mature B cells co-express Hck, Lyn, Blk, Fgr, and Fyn(T). T cells predominantly express Lck and Fyn(T). Lck is also expressed in NK cells.

A complex cascade of biochemical events mediates signal transduction in T cells [for review see: Chan A C, Desai D M, Weiss A; The role of protein tyrosine kinases and protein tyrosine phosphatases in T cell antigen receptor signal transduction; *Annu Rev Immunol* 1994;12:555–592]. While many proteins involved in this signaling cascade have been identified, the molecular details of this process are just beginning to be unraveled. The antigen-specific α/β TcR heterodimer is noncovalently associated with CD3-ε, -δ and ζ polypeptide chains. In the current paradigm of T cell activation, stimulation of the TcR by MHC/peptide complexes on the surface of antigen presenting cells (APCs) leads to the rapid activation of Lck. Activated Lck then phosphorylates CD3 and ζ proteins on tyrosine residues within conserved motifs known as ITAMs (Immunoreceptor-associated Tyrosine-based Activation Motifs). Another protein tyrosine kinase, ZAP-70, is recruited to the TcR complex via association of its tandem pair of SH2 domains to doubly phosphorylated ITAMs. Lck, in turn, activates TcR-associated ZAP-70 by phosphorylation of tyrosine 493 in the ZAP-70 activation loop. Activated ZAP-70 goes on to phosphorylate a variety of downstream adapter molecules such as LAT, SLP-76, and HS1. Lck can also phosphorylate additional protein substrates in activated T cells. One important substrate is Vav, a guanine nucleotide exchange protein that is regulated by Lck phosphorylation. Activated Vav mediates GDP release by Rac/Rho family members which, in turn, leads to the reorganization of the actin cytoskeleton, an event that is necessary for T cell activation. In addition to TcR recognition of MHC/peptide complexes on the surface of APCs, there are many co-receptor pairs that are important in T cell-APC interactions. Of note are CD4 and CD8, which are associated with Lck and bind to nonpolymorphic regions of MHC Class II and Class I molecules, respectively. Other co-receptor pairs include CD28/B7, CTLA-4/B7, LFA-2/LFA-3, LFA-1/ICAM, CD40/CD40L, SLAM/SLAM, and etc./etc. This vast array of cell-cell molecular interactions stabilizes T cell/APC conjugates and initiates additional intracellular signaling cascades. Signals derived from co-receptor engagement are integrated with signals derived from stimulation of the TcR to determine the magnitude and the quality of the T cell response.

Genetic data clearly validate Lck as an excellent therapeutic target. Mice in whom Lck expression was perturbed by either genetic deletion or by overexpression of a catalytically inactive version of Lck exhibited an early block in T cell development. The small number of mature T cells in the periphery of Lck-deficient mice were inefficient at transducing signals from the TcR and could not mediate a vigorous response to antigenic challenge. NK cells from Lck deficient mice appeared to function normally. No functional defects outside of the immune system were noted in these animals. In addition there is a report in the literature of a human patient with low levels of Lck expression due to an inability to properly splice Lck mRNA [see: Goldman F D, Ballas Z K, Schutte B C, Kemp J, Hollenback C, Noraz N, Taylor N.; Defective expression of p56lck in an infant with severe combined Immunodeficiency; *J Clin Invest* 1998; 102:421–429]. This patient presented with Severe Combined Immunodeficiency Syndrome (SCID). Again, no other phenotypic disturbances outside of this immune system disorder were noted. These results strongly suggest that Lck inhibitors would be effective in suppressing T cell mediated immune responses without causing mechanism-based toxicity.

SUMMARY OF THE INVENTION

The present invention provides substituted pyrimidine compounds of formula I:

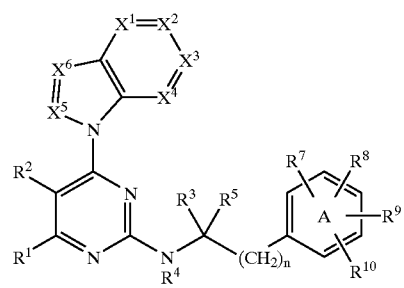

or a pharmaceutically acceptable salt, hydrate, solvate, crystal form or individual diastereomers thereof (as defined below), for use as a protein tyrosine kinase inhibitor. The invention also includes the use the compounds of formula I in the prophylaxis and treatment of immune diseases, hyperproliferative disorders and other diseases in which inappropriate protein kinase action is believed to have a role.

DETAILED DESCRIPTION OF THE INVENTION

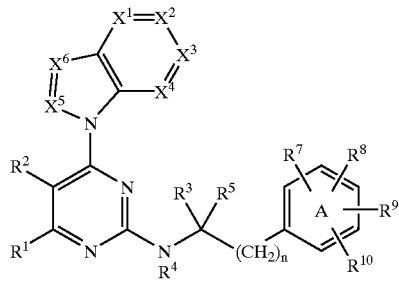

or pharmaceutically acceptable salts, hydrates, solvates, crystal forms or diastereomers thereof, wherein $R^1$ and $R^2$ are independently:
  a) H,
  b) halo (Br, Cl, I, or F)
  c) OH,
  d) SH,
  e) CN,
  f) $NO_2$,
  g) $R^{11}$,
  h) $OR^{11}$,
  i) $OC(=O)R^{11}$,
  j) $OC(=O)OR^{11}$,
  k) $OC(=O)NHR^{11}$,
  l) $OC(=O)NR^{11}R^{12}$,
  m) $SR^{11}$,
  n) $SOR^{11}$,
  o) $SO_2R^{11}$,
  p) $C(=O)R^{11}$,
  q) $C(=O)ORI^1$,
  r) $C(=O)NHR^{11}$,
  s) $C(=O)NR^{11}R^{12}$,
  t) $NH_2$,
  u) $NHR^{11}$,
  v) $NRR^{11}R^{12}$,
  w) $NHC(=O)R^{11}$,
  x) $NR^{11}C(=O)R^{12}$,
  y) $NR^{11}C(=O)NHR^{12}$,
  z) $NR^{11}C(=O)NR^{12}R^{13}$,
  aa) $SO_2NHR^{11}$,
  ab) $SO_2NR^{11}R^{12}$, ac) NHSO$_2$R$^{11}$,
ad) NR$^{11}$SO$_2$R$^{12}$,
ae) R$^1$ and R$^2$ can join together to form a fused methylenedioxy ring or a fused 6-membered aromatic ring;

R$^3$ and R$^5$ independently are:
  a) H,
  b) C$_1$–C$_6$-alkyl, unsubstituted or substituted with one, two, or three substituents selected from oxo, X', Y' and Z',
  c) aryl, wherein aryl is defined as phenyl or naphthyl unsubstituted or substituted with one, two or three substituents selected from: X', Y' and Z', or
  d) R$^3$ and R$^5$ taken together can represent =O;
  e) R$^3$ or R$^5$ can represent a 2 or 3 carbon methylene bridge forming a ring of 5 to 8 atoms fused to the A ring;

R$^4$ is:
  a) H, or
  b) C$_1$–C$_6$-alkyl, or
  c) C$_1$–C$_6$-alkoxyl;

X$^5$ and X$^6$ are independently CR$^a$ or N;
R$^a$ is: absent, H, or C$_1$–C$_6$-alkyl;
n is 0, 1 or 2;
—X$^1$—X$^2$—X$^3$—X$^4$— is:
  a) —CR$^6$=CR$^{6a}$—CR$^{6a}$=CR$^6$—,
  b) —CR$^{6a}$=CR$^6$—CR$^6$=CR$^6$—,
  c) —CR$^6$=CR$^{6a}$—CR$^6$=CR$^6$—,
  d) —CR$^6$=CR$^6$—CR$^6$=CR$^{6a}$—,
  e) —N=CR$^6$—CR$^6$=CR$^6$—,
  f) —CR$^6$=N—CR$^6$=CR$^6$—,
  g) —CR$^6$=CR$^6$—N=CR$^6$—,
  h) —CR$^6$=CR$^6$—CR$^6$=N—,
  i) —N=CR$^6$—N=CR$^6$—,
  j) —CR$^6$=N—CR$^6$=N—,
  k) —CR$^6$=N—N=CR$^6$—, or
  l) —N=CR$^6$—CR$^6$=N—;

R$^6$ and R$^{6a}$ are independently:
  a) H,
  b) halo( Br, Cl, I, or F),
  c) OH,
  d) SH,
  e) CN,
  f) NO$_2$,
  g) N$_3$,
  h) N$_2$+BF$_4$–,
  i) R$_{11}$,
  j) OR$^{11}$,
  k) OC(=O)R$^{11}$,
  l) OC(=O)OR$^{11}$,
  m) OC(=O)NHR$^{11}$,
  n) OC(=O)NR$^{11}$R$^{12}$,
  o) SR$^{11}$,
  p) SOR$^{11}$,
  q) SO$_2$R$^{11}$,
  r) C$_1$–C$_6$-alkyl, unsubstituted or substituted with one, two, or three substituents selected from R$^{11}$, R$^{12}$, and R$^{13}$,
  s) C(=O)R$^{11}$,
  t) C(=O)OR$^{11}$,
  u) C(=O)NHR$^{11}$,
  v) C(=O)NR$^{11}$R$^{12}$,
  w) C(=O)N(OR$^{11}$)R$^{12}$,
  x) NH$_2$,
  Y) NHR$^{11}$,
  z) NHC$_1$–C$_6$-alkyl, unsubstituted or substituted with one, two, or three substituents selected from R$^{11}$, R$^{12}$, and R$^{13}$,
  aa) NR$^{11}$R$^{12}$,
  ab) NHC(=O)R$^{11}$,
  ac) NR$^{11}$C(=O)R$^{12}$,
  ad) NHC(=O)NHR$^{11}$,
  ae) NR$^{11}$C(=O)NHR$^{12}$,
  af) NR$^{11}$C(=O)NR$^{12}$R$^{13}$,
  ag) SO$_2$NH$_2$,
  ah) SO$_2$NHR$^{11}$,
  ai) SO$_2$NR$^{11}$R$^{12}$,
  aj) NHSO$_2$R$^{11}$,
  ak) NR$^{11}$SO$_2$R$^{12}$,
  al) NHP(=O)(OC$_1$–C$_6$-alkyl)$_2$, or
  am) R$^6$ and R$^{6a}$ when on adjacent carbons can be joined to form a 5- or 6-membered ring having the following bridging atoms:
    i) —CH=CH—CH=CH—,
    ii) —OCH$_2$O—,
    iii) —C(O)N(R$^{11}$)C(O)—,
    iv) —CH$_2$N(R$^{11}$)CH$_2$—,
    v) —N=CHNHC(O)—,
    vi) —C(O)NHCH=N—,
    vii) —C(O)OC(O)—,
    viii) —NHC(O)NHC(O)—,
    ix) —C(O)NHC(O)NH—,
    x) —N=CHNH—,
    xi) —NHCH=N—,
    xii) —N=CHNR$^{11}$—,
    xiii) —NR$^{11}$CH=N—,
    xiv)

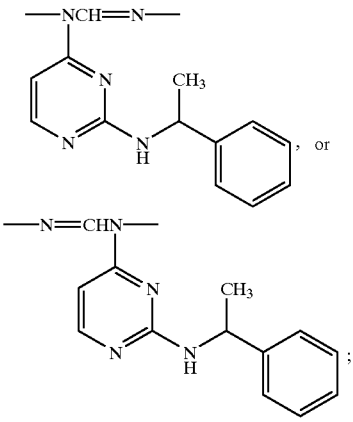

, or;

xv)

represents:
  a) phenyl,
  b) naphthyl,
  c) pyridyl,
  d) pyrazinyl,
  e) pyrimidinyl,
  f) pyrroly),
  g) thienyl,
  h) oxazolyl,
  i) isoxazolyl,
  j) thiazolyl,
  k) pyrazolyl, l) triazolyl,
m) tetrazolyl,
n) furanyl,
o) benzothienyl,
p) benzofuranyl,
q) indolyl,
r) imidazolyl,
s) benzimidazolyl, or
t) thiadiazolyl, $R^7$, $R^8$, $R^9$, and $R^{10}$ independently are selected from:
a) H,
b) halo( Br, Cl, I, or F)
c) OH,
d) SH,
e) CN,
f) $NO_2$,
g) $N_3$
h) $N_2+BF_4-$
i) $R^{11}$,
j) $OR^{11}$,
k) $SR^{11}$,
l) $SOR^{11}$,
m) $SO_2R^{11}$,
n) $C_1$–$C_6$-alkyl, unsubstituted or substituted with one, two, or three substituents selected from $R^{11}$, $R^{12}$, and $R^{13}$,
o) $C_1$–$C_6$-perfluoroalkyl,
p) C(=O)$R^{11}$,
q) C(=O)$OR^{11}$,
r) C(=O)$NHR^{11}$,
s) C(=O)$NR^{11}R^{12}$,
t) $NH_2$,
u) $NHR^{11}$,
v) $NHC_1$–$C_6$-alkyl, unsubstituted or substituted with one, two, or three substituents selected from $R^{11}$, $R^{12}$, and $R^{13}$,
w) $NR^{11}R^{12}$,
x) NHC(=O)$R^{11}$,
y) $NR^{11}$C(=O)$R^{12}$,
z) $NR^{11}$C(=O)$NHR^{12}$,
aa) $NR^{11}$C(=O)$NR^{12}R^{13}$,
ab) $SO_2NHR^{11}$,
ac) $SO_2NR^{11}R^{12}$,
ad) $NHSO_2R^{11}$,
ae) $NR^{11}SO_2R^{12}$, or
af) two of $R^7$, $R^8$, $R^9$, and $R^{10}$ when on adjacent carbons join together to form a methylenedioxy bridge;

$R^{11}$, $R^{12}$, and $R^{13}$ independently are selected from:
a) $C_1$–$C_6$-perfluoroalkyl,
b) $C_1$–$C_6$-alkyl, unsubstituted or substituted with one, two, or three substituents selected from oxo, X', Y' and Z',
c) $C_2$–$C_6$-alkenyl, unsubstituted or substituted with one, two, or three substituents selected from oxo, X', Y' and Z',
d) $C_2$–$C_6$-alkynyl, unsubstituted or substituted with one, two, or three substituents selected from oxo, X', Y' and Z',
e) aryl, wherein aryl is defined as phenyl or naphthyl, unsubstituted or substituted with one, two, or three substituents selected from X', Y' and Z',
f) heterocyclyl, wherein the heterocyclyl is unsubstituted or substituted with one, two, three or four substituents selected from oxo, X', Y', and Z', or
g) $C_3$–$C_6$-cycloalkyl, unsubstituted or substituted with one, two, or three substituents selected from oxo, X', Y' and Z';

X', Y' and Z' independently are selected from:
a) H,
b) halo,
c) CN,
d) $NO_2$,
e) hydroxy,
f) $C_1$–$C_6$-perfluoroalkyl,
g) $C_1$–$C_6$-alkoxyl, alkoxyl unsubstituted or substituted with aryl, wherein aryl is defined as phenyl or naphthyl,
h) (C=O)($C_1$–$C_6$-alkyl), alkyl unsubstituted or substituted with aryl, wherein aryl is defined as phenyl or naphthyl,
i) (C=O)O($C_1$–$C_6$-alkyl), alkyl unsubstituted or substituted with aryl, wherein aryl is defined as phenyl or naphthyl,
j) (C=O)NH($C_1$–$C_6$-alkyl),
k) (C=O)N($C_1$–$C_6$-alkyl)$_2$,
l) $NH_2$,
m) $NHC_1$–$C_6$-alkyl, wherein alkyl is unsubstituted or substituted with aryl or $NH_2$,
n) N($C_1$–$C_6$-alkyl)$_2$,
o) NHaryl, wherein aryl is defined as phenyl or naphthyl, unsubstituted or substituted with one, two, or three substituents selected from halo, phenyl, CN, $NO_2$, hydroxy, $C_1$–$C_6$-alkyl, $C_1$–$C_6$-alkoxyl, $NH_2$, $NHC_1$–$C_6$-alkyl, N($C_1$–$C_6$-alkyl)$_2$, (C=O)($C_1$–$C_6$-alkyl), (C=O)O($C_1$–$C_6$-alkyl), (C=O)NH($C_1$–$C_6$-alkyl), (C=O)N($C_1$–$C_6$-alkyl)$_2$, NH(C=O)($C_1$–$C_6$-alkyl),
p) NHheterocyclyl, wherein heterocyclyl is unsubstituted or substituted with one, two or three substituents selected from halo, phenyl, oxo, CN, $NO_2$, hydroxy, $C_1$–$C_6$-alkyl, $C_1$–$C_6$-alkyl substituted with $C_3$–$C_7$-cycloalkyl, $C_1$–$C_6$-alkoxyl, $NH_2$, $NHC_1$–$C_6$-alkyl, N($C_1$–$C_6$-alkyl)$_2$, (C=O)($C_1$–$C_6$-alkyl), (C=O)O($C_1$–$C_6$-alkyl), (C=O)OCH$_2$phenyl, (C=O)NH($C_1$–$C_6$-alkyl), (C=O)N($C_1$–$C_6$-alkyl)$_2$, NH(C=O)($C_1$–$C_6$-alkyl),
q) NHCHO,
r) NH(C=O)($C_1$–$C_6$-alkyl),
s) NH(C=O)(O$C_1$–$C_6$-alkyl),
t) aryl, wherein aryl is as defined above in o,
u) $C_1$–$C_6$-alkyl, wherein alkyl is unsubstituted or substituted with hydroxy, $C_3$–$C_7$-cycloalkyl, aryl or heterocyclyl, wherein aryl is defined as above in o and heterocyclyl is as defined above in p,
v) heterocyclyl, wherein heterocyclyl is as defined above in p,
w) when two of X', Y' and Z' are on adjacent carbons they can join to form a methylenedioxy bridge,
x) NH(C=O)aryl,
y) —$NR^{14}NHR^{15}$,
z) —S(O)x $C_1$–$C_6$-alkyl,
aa) $SO_2NH$ $C_1$–$C_6$-alkyl, or
ab) $CO_2H$;

$R^{14}$ and $R^{15}$ are independently: H, $C_1$–$C_6$-alkyl, aryl or $C_1$–$C_6$-alkylaryl; or x is 0, 1 or 2.

An embodiment of the invention is the compound of Formula I

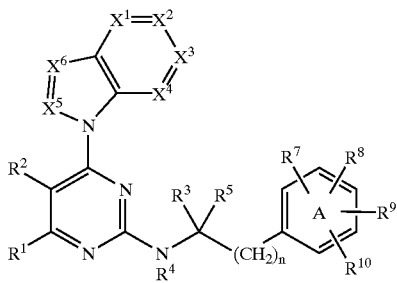

or pharmaceutically acceptable salts, hydrates, solvates, crystal forms or diastereomers thereof, wherein $R^1$ and $R^2$ are independently:
a) H,
b) halo (Br, Cl, I, or F)
c) OH,
d) SH,
e) CN,
f) $NO_2$,
g) $R^{11}$,
h) $OR^{11}$,
i) $OC(=O)R^{11}$,
j) $OC(=O)OR^{11}$,
k) $OC(=O)NHR^{11}$,
l) $OC(=O)NR^{11}R^{12}$,
m) $SR^{11}$,
n) $SOR^{11}$,
o) $SO_2R^{11}$,
p) $C(=O)R^{11}$,
q) $C(=O)OR^{11}$,
r) $C(=O)NHR^{11}$,
s) $C(=O)NR^{11}R^{12}$,
t) $NH_2$,
u) $NHR^{11}$,
v) $NR^{11}R^{12}$,
w) $NHC(=O)R^{11}$,
x) $NR^{11}C(=O)R^{12}$,
y) $NR^{11}C(=O)NHR^{12}$,
z) $NR^{11}C(=O)NR^{12}R^{13}$,
aa) $SO_2NHR^{11}$,
ab) $SO_2NR^{11}R^{12}$,
ac) $NHSO_2R^{11}$,
ad) $NR^{11}SO_2R^{12}$,
ae) $R^1$ and $R^2$ can join together to form a fused methylenedioxy ring or a fused 6-membered aromatic ring;

$R^3$ and $R^5$ independently are:
a) H,
b) $C_1$–$C_6$-alkyl, unsubstituted or substituted with one, two, or three substituents selected from oxo, X', Y' and Z',
c) aryl, wherein aryl is defined as phenyl or naphthyl unsubstituted or substituted with one, two or three substituents selected from: X', Y' and Z', or
d) $R^3$ and $R^5$ taken together can represent =O;
e) $R^3$ or $R^5$ can represent a 2 or 3 carbon methylene bridge forming a ring of 5 to 8 atoms fused to the A ring;

$R^4$ is:
a) H, or
b) $C_1$–$C_6$-alkyl, or
c) $C_1$–$C_6$-alkoxyl;

$X^5$ and $X^6$ are independently $CR^a$ or N;
$R^a$ is: absent, H, or $C_1$–$C_6$-alkyl;

n is 0, 1 or 2;
—$X^1$—$X^2$—$X^3$—$X^4$— is:
a) —$CR^6$=$CR^6$—$CR^{6a}$=$CR^6$—,
b) —$CR^{6a}$=$CR^6$—$CR^6$=$CR^6$—,
c) —N=$CR^6$—$CR^6$=$CR^6$—,
d) —$CR^6$=N—$CR^6$=$CR^6$—,
e) —$CR^6$=$CR^6$—N=$CR^6$—,
f) —$CR^6$=$CR^6$—$CR^6$=N—,
g) —N=$CR^6$—N=$CR^6$—,
h) —$CR^6$=N—$CR^6$=N—,
i) —$CR^6$=N—N=$CR^6$—, or
j) —N=$CR^6$—$CR^6$=N—;

$R^6$ and $R^{6a}$ are independently:
a) H,
b) halo( Br, Cl, I, or F)
c) OH,
d) SH,
e) CN,
f) $NO_2$,
g) $N_3$,
h) $N_2$+$BF_4$–,
i) $R^{11}$,
j) $OR^{11}$,
k) $OC(=O)R^{11}$,
l) $OC(=O)OR^{11}$
m) $OC(=O)NHR^{11}$,
n) $OC(=O)NR^{11}R^{12}$,
o) $SR^{11}$,
p) $SOR^{11}$,
q) $SO_2R^{11}$,
r) $C_1$–$C_6$-alkyl, unsubstituted or substituted with one, two, or three substituents selected from $R^{11}$, $R^{12}$, and $R^{13}$,
s) $C(=O)R^{11}$,
t) $C(=O)OR^{11}$,
u) $C(=O)NHR^{11}$,
v) $C(=O)NR^{11}R^{12}$,
w) $C(=O)N(OR^{11})R^{12}$,
x) $NH_2$,
Y) $NHR^{11}$,
z) $NHC_1$–$C_6$-alkyl, unsubstituted or substituted with one, two, or three substituents selected from $R^{11}$, $R^{12}$, and $R^{13}$,
aa) $NR^{11}R^{12}$,
ab) $NHC(=O)R^{11}$,
ac) $NR^{11}C(=O)R^{12}$,
ad) $NHC(=O)NHR^{11}$,
ae) $NR^{11}C(=O)NHR^{12}$,
af) $NR^{11}C(=O)NR^{12}R^{13}$,
ag) $SO_2NH_2$,
ah) $SO_2NHR^{11}$,
ai) $SO_2NR^{11}R^{12}$,
aj) $NHSO_2R^{11}$,
ak) $NR^{11}SO_2R^{12}$,
al) $NHP(=O)(OC_1$–$C_6$-alkyl)$_2$, or
am) $R^6$ and $R^{6a}$ when on adjacent carbons can be joined to form a 5- or 6-membered ring having the following bridging atoms:
i) —CH=CH—CH=CH—,
ii) —$OCH_2O$—,
iii) —C(O)N($R^{11}$)C(O)—,
iv) —$CH_2$N($R^{11}$)$CH_2$—,
v) —N=CHNHC(O)—,
vi) —C(O)NHCH=N—,
vii) —C(O)OC(O)—,
viii) —NHC(O)NHC(O)—,
ix) —C(O)NHC(O)NH—, x) —N═CHNH—, or
xi) —N═CHNR$^{11}$—, or
xii)

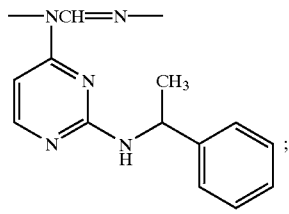

represents:
a) phenyl,
b) naphthyl,
c) pyridyl,
d) pyrazinyl,
e) pyrimidinyl,
f) pyrrolyl,
g) thienyl,
h) oxazolyl,
i) isoxazolyl,
j) thiazolyl,
k) pyrazolyl,
l) triazolyl,
m) tetrazolyl,
n) furanyl,
o) benzothienyl,
p) benzofuranyl,
q) indolyl,
r) imidazolyl,
s) benzimidazolyl, or
t) thiadiazolyl, $R^7$, $R^8$, $R^9$, and $R^{10}$ independently are selected from:
a) H,
b) halo( Br, Cl, I, or F)
c) OH,
d) SH,
e) CN,
f) $NO_2$,
g) $N_3$,
h) $N_2^+BF_4^-$
i) $R^{11}$,
j) $OR^{11}$,
k) $SR^{11}$,
l) $SOR^{11}$,
m) $SO_2R^{11}$,
n) $C_1$–$C_6$-alkyl, unsubstituted or substituted with one, two, or three substituents selected from $R^{11}$, $R^{12}$, and $R^{13}$,
o) $C_1$–$C_6$-perfluoroalkyl,
p) $C(═O)R^{11}$,
q) $C(═O)OR^{11}$,
r) $C(═O)NHR^{11}$,
s) $C(═O)NR^{11}R^{12}$,
t) $NH_2$,
u) $NHR^{11}$,
v) $NHC_1$–$C_6$-alkyl, unsubstituted or substituted with one, two, or three substituents selected from $R^{11}$, $R^{12}$, and $R^{13}$,
w) $NR^{11}R^{12}$,
x) $NHC(═O)R^{11}$,
y) $NR^{11}C(═O)R^{12}$,
z) $NR^{11}C(═O)NHR^{12}$,
aa) $NR^{11}C(═O)NR^{12}R^{13}$,
ab) $SO_2NHR^{11}$,
ac) $SO_2NR^{11}R^{12}$,
ad) $NHSO_2R^{11}$,
ae) $NR^{11}SO_2R^{12}$, or
af) two of $R^7$, $R^8$, $R^9$, and $R^{10}$ when on adjacent carbons join together to form a methylenedioxy bridge;

$R^{11}$, $R^{12}$, and $R^{13}$ independently are selected from:
a) $C_1$–$C_6$-perfluoroalkyl,
b) $C_1$–$C_6$-alkyl, unsubstituted or substituted with one, two, or three substituents selected from oxo, X', Y' and Z',
c) $C_2$–$C_6$-alkenyl, unsubstituted or substituted with one, two, or three substituents selected from oxo, X', Y' and Z',
d) $C_2$–$C_6$-alkynyl, unsubstituted or substituted with one, two, or three substituents selected from oxo, X', Y' and Z',
e) aryl, wherein aryl is defined as phenyl or naphthyl, unsubstituted or substituted with one, two, or three substituents selected from X', Y' and Z',
f) heterocyclyl, wherein the heterocyclyl is unsubstituted or substituted with one, two or three substituents selected from oxo, X', Y', and Z';
g) $C_3$–$C_6$-cycloalkyl, unsubstituted or substituted with one, two, or three substituents selected from oxo, X', Y' and Z', X', Y' and Z' independently are selected from:
a) H,
b) halo,
c) CN,
d) $NO_2$,
e) hydroxy,
f) $C_1$–$C_6$-perfluoroalkyl,
g) $C_1$–$C_6$-alkoxyl, alkoxyl unsubstituted or substituted with aryl, wherein aryl is defined as phenyl or naphthyl,
h) $(C═O)(C_1$–$C_6$-alkyl), alkyl unsubstituted or substituted with aryl, wherein aryl is defined as phenyl or naphthyl,
i) $(C═O)O(C_1$–$C_6$-alkyl), alkyl unsubstituted or substituted with aryl, wherein aryl is defined as phenyl or naphthyl,
j) $(C═O)NH(C_1$–$C_6$-alkyl),
k) $(C═O)N(C_1$–$C_6$-alkyl)_2$,
l) $NH_2$,
m) $NHC_1$–$C_6$-alkyl,
n) $N(C_1$–$C_6$-alkyl)_2$,
o) NHaryl, wherein aryl is defined as phenyl or naphthyl, unsubstituted or substituted with one, two, or three substituents selected from halo, phenyl, CN, $NO_2$, hydroxy, $C_1$–$C_6$-alkyl, $C_1$–$C_6$-alkoxyl, $NH_2$, $NHC_1$–$C_6$-alkyl, $N(C_1$–$C_6$-alkyl)$_2$, $(C═O)(C_1$–$C_6$-alkyl), $(C═O)O(C_1$–$C_6$-alkyl), $(C═O)NH(C_1$–$C_6$-alkyl), $(C═O)N(C_1$–$C_6$-alkyl)$_2$, $NH(C═O)(C_1$–$C_6$-alkyl),
p) NHheterocyclyl, wherein heterocyclyl is unsubstituted or substituted with one, two or three substituents selected from halo, phenyl, oxo, CN, $NO_2$, hydroxy, $C_1$–$C_6$-alkyl, $C_1$–$C_6$-alkoxyl, $NH_2$, $NHC_1$–$C_6$-alkyl, $N(C_1$–$C_6$-alkyl)$_2$, $(C═O)(C_1$–$C_6$-alkyl), $(C═O)O(C_1$–$C_6$-alkyl), (C═O)

OCH$_2$phenyl, (C=O)NH(C$_1$-C$_6$-alkyl), (C=O)N(C$_1$-C$_6$-alkyl)$_2$, NH(C=O)(C$_1$-C$_6$-alkyl),
q) NHCHO,
r) NH(C=O)(C$_1$-C$_6$-alkyl),
s) NH(C=O)(OC$_1$-C$_6$-alkyl),
t) aryl, wherein aryl is as defined above in o,
u) C$_1$-C$_6$-alkyl, wherein alkyl is unsubstituted or substituted with aryl or heterocyclyl, wherein aryl is defined as above in o and heterocyclyl is as defined above in p,
v) heterocyclyl, wherein heterocyclyl is as defined above in p, or
w) when two of X', Y' and Z' are on adjacent carbons they can join to form a methylenedioxy bridge.

Preferred compounds of the present invention include the compound of Formula Ia:

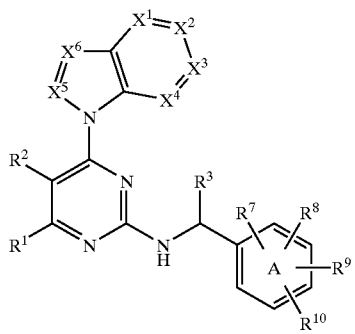

or pharmaceutically acceptable salts, hydrates, solvates, crystal forms, and individual diastereomers thereof, wherein R$^1$, R$^2$, and R$^3$ are as defined below and all other substituents are as defined above, R$^1$ and R$^2$ are independently:
a) H,
b) R$^{11}$,
c) NH$_2$,
d) NHR$^{11}$, or
e) NR$^{11}$R$^{12}$; and R$^3$ is:
a) H, or
b) C$_1$-C$_6$-alkyl, unsubstituted or substituted with one, two, or three substituents selected from oxo, X', Y' and Z'.

Preferred compounds of the present invention include the compound of Formula Ib:

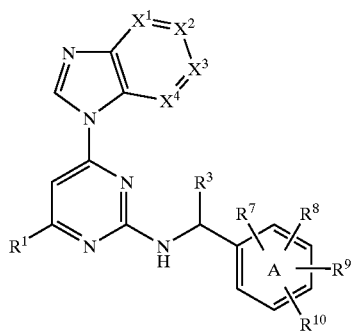

or a pharmaceutically acceptable salts, hydrates, solvates, crystal forms, and individual diastereomers thereof, wherein R$^1$ and —X$^1$—X$^2$—X$^3$—X$^4$— are as defined below and all other substituents are as defined above, R$^1$ is:
a) H,
b) R$^{11}$,
c) NH$_2$,
d) NHR$^{11}$, or
e) NR$^{11}$R$^{12}$; and —X$^1$—X$^2$—X$^3$—X$^4$— is:
a) —CR$^6$=CR$^6$—CR$^{6a}$=CR$^6$—,
b) —CR$^{6a}$=CR$^6$—CR$^6$=CR$^6$—,
c) —CR$^6$=N—CR$^6$=CR$^6$—, or
d) —CR$^6$=CR$^6$—N=CR$^6$—.

Preferred compounds of the present invention include the compounds of Formula Ic:

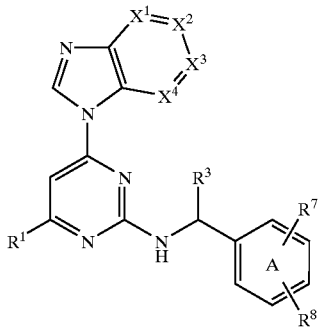

or pharmaceutically acceptable salts, hydrates, solvates, crystal forms, and individual diastereomers thereof, wherein R$^6$ and R$^{6a}$ are as defined below and all other substituents are as defined above, R$^6$ and R$^{6a}$ are independently:
a) H,
b) halo (Br, Cl, I, or F),
c) R$^{11}$,
d) OR$^{11}$,
e) C$_1$-C$_6$-alkyl, unsubstituted or substituted with one, two, or three substituents selected from R$^9$, R$^{10}$, and R$^{11}$,
f) NH$_2$,
g) NHR$^{11}$,
h) NHC$_1$-C$_6$-alkyl, unsubstituted or substituted with one, two, or three substituents selected from R$^9$, R$^{10}$, and R$^{11}$,
i) NR$^{11}$R$^{12}$,
j) NHC(=O)R$^{11}$,
k) NR$^{11}$C(=O)R$^{12}$,
l) NR$^{11}$C(=O)NHR$^{12}$,
m) NR$^{11}$C(=O)NR$^{12}$R$^{13}$,
n) NHSO$_2$R$^{11}$,
o) NR$^{11}$SO$_2$R$^{12}$, or
p) R$^6$ and R$^{6a}$ when on adjacent carbons can be joined to form a 5- or 6-membered ring having the following bridging atoms, when read from right to left, or left to right:

i) —N=CHNH—,
ii) —N=CHNR[11]—, or
iii)

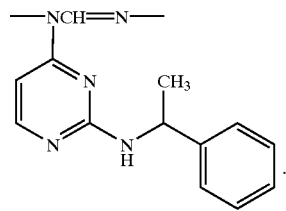

Preferred compounds of the present invention include those of Formula Ic:

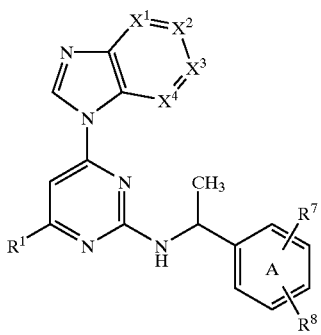

or pharmaceutically acceptable salts, hydrates, solvates, crystal forms, and individual diastereomers thereof, wherein $R^1$ is H, aryl, or heterocyclyl, and all other substituents are as defined above.

Preferred compounds of the present invention include those of Formula Ic:

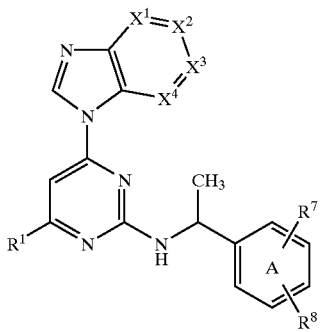

or pharmaceutically acceptable salts, hydrates, solvates, crystal forms, and individual diastereomers thereof, wherein A is defined as phenyl, naphthyl, pyridyl, pyrimidinyl, pyrazinyl, thienyl, oxazolyl, thiazolyl, pyrazolyl, tetrazolyl, imidazolyl, thiadiazolyl, and all other substituents are as defined above.

Preferred compounds of the present invention include those of Formula Id:

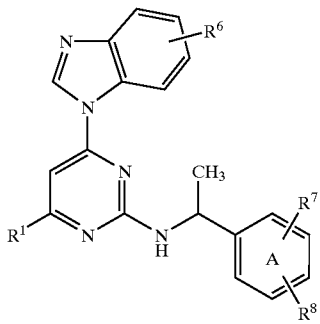

or pharmaceutically acceptable salts, hydrates, solvates, crystal forms, and individual diastereomers thereof, wherein all substituents are as defined above, except that $R^6$ is attached to the 5- or 6-position of the benzimidazole.

Preferred compounds of the present invention include those of Formula Ie:

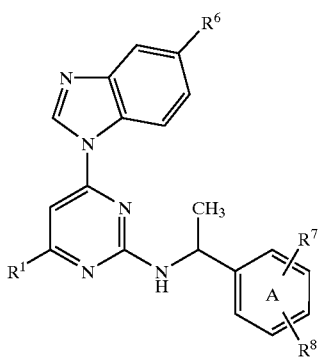

or pharmaceutically acceptable salts, hydrates, solvates, crystal forms, and individual diastereomers thereof, wherein $R^6$ is as defined below and all other substituents are as defined above, $R^6$ is:
 a) H,
 b) phenyl, unsubstituted or substituted with one, two, or three substituents selected from X', Y' and Z',
 c) pyridyl, unsubstituted or substituted with one, two or three substituents selected from X', Y', and Z',
 d) pyridazinyl, unsubstituted or substituted with one, two or three substituents selected from X', Y', and Z',
 e) pyriridinyl, unsubstituted or substituted with one, two or three substituents selected from X', Y', and Z',
 f) thiazolyl, unsubstituted or substituted with one, two, or three substituents selected from X', Y' and Z',
 g) thiadiazolyl, unsubstituted or substituted with one, two or three substituents selected from X', Y', and Z',
 h) thienyl, unsubstituted or substituted with one, two or three substituents selected from X', Y', and Z',
 i) pyrazinyl, unsubstituted or substituted with one, two or three substituents selected from X', Y', and Z',
 j) imidazolyl, unsubstituted or substituted with one, two or three substituents selected from X', Y', and Z',
 k) imidazolidinyl, unsubstituted or substituted with one, two or three substituents selected from oxo, X', Y', and Z',
 l) 1,3-diazobicyclo[3.3.0]octan-2-onyl,
 m) 1,3-diazobicyclo[4.3.0]nonan-2-onyl,
 n) $NH_2$,
 o) $NHR^8$, p) NHC$_1$–C$_6$-alkyl, unsubstituted or substituted with one, two, or three substituents selected from R$^8$, R$^9$, and R$^{10}$,
q) NR$^8$R$^9$,
r) NHC(=O)R$^8$,
s) NR$^8$C(=O)R$^9$,
t) NR$^8$C(=O)NHR$^9$,
u) NR$^8$C(=O)NR$^9$R$^{10}$,
v) NHSO$_2$R$^8$, or
w) NR$^8$SO$_2$R$^9$.

Preferred compounds of the present invention include those of Formula If:

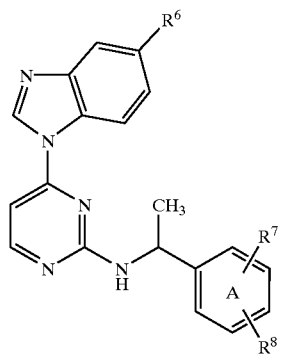

or pharmaceutically acceptable salts, hydrates, solvates, crystal forms, and individual diastereomers thereof, wherein R$^6$ is as defined below and all other substituents are as defined above, R$^6$ is:
a) H,
b) phenyl, unsubstituted or substituted with one, two, or three substituents selected from X', Y' and Z',
c) pynidyl, unsubstituted or substituted with one, two or three substituents selected from X', Y', and Z',
d) pyridazinyl, unsubstituted or substituted with one, two or three substituents selected from X', Y', and Z',
e) pyrimidinyl, unsubstituted or substituted with one, two or three substituents selected from X', Y', and Z',
f) imidazolidinyl, unsubstituted or substituted with one, two or three substituents selected from oxo, X', Y', and Z',
g) 1,3-diazobicyclo[3.3.0]octan-2-onyl,
h) 1,3-diazobicyclo[4.3.0]nonan-2-onyl,
i) NH$_2$,
j) NHR$^8$,
k) NHC$_1$–C$_6$-alkyl, unsubstituted or substituted with one, two, or three substituents selected from R$^8$, R$^9$, and R$^{10}$,
l) NR$^8$R$^9$,
m) NHC(=O)R$^8$,
n) NR$^8$C(=O)R$^9$,
o) NR$^8$C(=O)NHR$^9$,
p) NR$^8$C(=O)NR$^9$R$^{10}$,
q) NHSO$_2$R$^8$, or
r) NR$^8$SO$_2$R$^9$.

Preferred compounds of the present invention include those of Formula If:

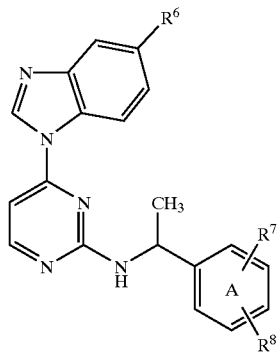

or pharmaceutically acceptable salts, hydrates, solvates, crystal forms, and individual diastereomers thereof, wherein A is phenyl, naphthyl, pyridyl, pyrimidinyl, thienyl, or thiazolyl, and all other substituents are as defined above.

The compound of Formula I, or a pharmaceutically acceptable salt, hydrate, solvate, crystal form or individual diastereomer thereof is selected from the group consisting of:

2-[(S)-1-Phenylethylamino]-4-[5-methylbenzimidazol-1-yl]pyrimidine;
2-[(S)-1-Phenylethylamino]-4-[6-methylbenzimidazol-1-yl]pyrimidine;
2-[(S)-1-Phenylethylamino]-4-[5-aminobenzimidazol-1-yl]pyrimidine;
2-[(S)-1-Phenylethylamino]-4-[6-aminobenzimidazol-1-yl]pyrimidine;
2-[(S)-1-Phenylethylamino]-4-[5-N,N-(dimethyl)-aminobenzimidazol-1-yl]-pyrimidine;
2-((S)-1-(3-nitro-phenyl)ethylamino)-4-[5-methyl-benzimidazol-1-yl]pyrimidine;
2-((S)-1-(3-nitro-phenyl)ethylamino)-4-[6-methyl-benzimidazol-1-yl]pyrimidine;
2-((R)-1-(3-nitro-phenyl)ethylamino)-4-[5-methyl-benzimidazol-1-yl]pyrimidine;
2-((R)-1-(3-nitro-phenyl)ethylamino)-4-[6-methyl-benzimidazol-1-yl]pyrimidine;
2-[(S)-1-Phenylethylamino]-4-[5-azabenzimidazol-1-yl]pyrimidine;
2-[(S)-1-Phenylethylamino]-4-[6-azabenzimidazol-1-yl]pyrimidine;
2-[(S)-1-Phenylethylamino]-4-[5-N-((morpholin-2-yl)methyl)-aminobenzimidazol-1-yl]pyrimidine;
2-[(S)-1-Phenylethylamino]-4-[5-N-((piperazin-2-yl)methyl)-aminobenzimidazol-1-yl]pyrimidine;
2-[(S)-1-Phenylethylamino]-4-[5-N-(2-aminoethyl)-aminobenzimidazol-1-yl]-pyrimidine;
2-[(S)-1-Phenylethylamino]-4-[5-N-((pyrrolidin-2-yl)methyl)-aminobenzimidazol-1-yl]pyrimidine;
2-[(S)-1-Phenylethylamino]-4-[5-N-(((R)-piperidin-2-yl)methyl)-aminobenzimidazol-1-yl]pyrimidine;
2-[(S)-1-Phenylethylamino]-4-[5-(1,3-diazobicyclo[3.3.0]octan-3-yl)benzimidazol-1-yl]pyrimidine;
2-[(S)-1-Phenylethylamino]-4-[5-(1,3-diazobicyclo[3.3.0]octan-2one-3-yl)-benzimidazol-1-yl]pyrimidine;
2-[(S)-1-Phenylethylamino]-4-[5-(1,3-diazobicyclo[4.3.0]nonan-2-one-3-yl)-benzimidazol-1-yl]pyrimidine;
2-[(S)-1-Phenylethylamino]4-[5-N-(N-methylcarbamoyl)-aminobenzimidazol-1-yl]pyrimidine;
2-[(S)-1-Phenylethylamino]-4-[5-N-(N-ethylcarbamoyl)-aminobenzimidazol-1-yl]pyrimidine;
2-[(S)-1-Phenylethylamino]-4-[5-N-(N-propylcarbamoyl)-aminobenzimidazol-1-yl]pyrimidine;

2-[(S)-1-Phenylethylamino]-4-[5-N-(N-((1-methyl)ethylcarbamoyl)aminobenzimidazol-1-yl]pyrimidine;

2-[(S)-1-Phenylethylamino]-4-[5-(tetrazol-1-yl)-benzimidazol-1-yl]pyrimidine;

2-[(S)-1-(3-Nitrophenyl)ethylamino]-4-[5-N-((pyrrolidin-2-yl)methyl)aminobenzimidazol-1-yl]pyrimidine;

2-[(S)-1-(3-Trifluoromethylphenyl)ethylamino]-4-[5-N-((pyrrolidin-2-yl)methyl)-aminobenzimidazol-1-yl]pyrimidine;

2-[(S)-1-(3-Nitrophenyl)ethylamino]-4-[5-(1,3-diazobicyclo[3.3.0]octan-2-one-3-yl)benzimidazol-1-yl]pyrimidine;

2-[(S)-1-(3-Trifluoromethylphenyl)ethylamino]-4-[5-(1,3-diazobicyclo[3.3.0]octan-2-one-3-yl)benzimidazol-1-yl]pyrimidine;

2-[(S)-1-(3-Nitrophenyl)ethylamino]-4-[5-(1,3-diazobicyclo[3.3.0]octan-3-yl)benzimidazol-1-yl]pyrimidine;

2-[(S)-1-(3-Trifluoromethylphenyl)ethylamino]4-[5-(1,3-diazobicyclo[3.3.0]octan-3-yl)benzimidazol-1-yl]pyrimidine;

2-[(S)-1-Phenylethylamino]-4-[5-phenylbenzimidazol-1-yl]pyrimidine;

2-[(S)-1-Phenylethylamino]-4-[5-(thiazol-2-yl)benzimidazol-1-yl]pyrimidine;

2-[(S)-1-Phenylethylamino]-4-[5-(furan-2-yl)benzimidazol-1-yl]pyrimidine;

2-[(S)-1-Phenylethylamino]-4-[benzimidazol-1-yl]-6-(2-methyl-phenyl)pyrimidine;

2-[(S)-1-Phenylethylamino]-4-[5-(pyridin-2-yl)benzimidazol-1-yl]pyrimidine;

2-[(S)-1-Phenylethylamino]-4-[5-(thiophen-3-yl)benzimidazol-1-yl]pyrimidine;

2-[(S)-1-Phenylethylamino]-4-[5-(pyrimidin-5-yl)benzimidazol-1-yl]pyrimidine;

2-[(S)-1-Phenylethylamino]-4-[5-(pyridin-3-yl)benzimidazol-1-yl]pyrimidine;

2-[(S)-1-Phenylethylamino]-4-[5-(4-methoxyphenyl)benzimidazol-1-yl]pyrimidine;

2-[(S)-1-Phenylethylamino]-4-[5-(3-chlorophenyl)-benzimidazol-1-yl]pyrimidine;

2-[(S)-1-Phenylethylamino]-4-[5-(3-methoxyphenyl)benzimidazol-1-yl]pyrimidine;

2-[(S)-1-Phenylethylamino]-4-[5-(4-(pyrrol-1-yl)phenyl)benzimidazol-1-yl]-pyrimidine;

2-[(S)-1-Phenylethylamino]-4-[5-(pyridin-4-yl)benzimidazol-1-yl]pyrimidine;

2-[(S)-1-Phenylethylamino]-4-[5-(4-methylphenyl)benzimidazol-1-yl]pyrimidine;

2-[(S)-1-Phenylethylamino]-4-[5-(pyrimidin-2-yl)benzimidazol-1-yl]-pyrimidine;

2-[(S)-1-Phenylethylamino]-4-[5-(3-methylphenyl)benzimidazol-1-yl]pyrimidine;

2-[(S)-1-Phenylethylamino]-4-[5-(thiophen-3-yl-carbonyl)benzimidazol-1-yl]-pyrimidine;

2-[(S)-1-Phenylethylamino]-4-[5-(2-aminopyrimidin-5-yl)benzimidazol-1-yl]-pyrimidine;

2-[(S)-1-Phenylethylamino]-4-[5-(2-aminopyrimidin-4-yl)benzimidazol-1-yl]-pyrimidine;

2-[(S)-1-Phenylethylamino]-4-[5-(2-aminopyrimidin-5-yl)benzimidazol-1-yl]pyrimidine;

2-[(S)-1-Phenylethylamino]-4-[5-(4-pyridyl)benzimidazol-1-yl]pyrimidine;

2-[(S)-1-Phenylethylamino]-4-[5-(3-methoxypyridazin-6-yl)benzimidazol-1-yl]pyrimidine;

2-[(S)-1-Phenylethylamino]-4-[5-(3-chloropyrimidine-6-yl)benzimidazol-1-yl]pyrimidine;

2-[(S)-1-Phenylethylamino]-4-[5-(6-methylpyridazin-3-yl)benzimidazol-1-yl]pyrimidine;

2-[(S)-1-Phenylethylamino]-4-[5-(pyridazin-3-yl)benzimidazol-1-yl]pyrimidine;

2-[(S)-1-Phenylethylamino]-4-[5-(3—N,N-dimethylaminopyridazin-6-yl)-benzimidazol-1-yl]pyrimidine;

2-[(S)-1-Phenylethylamino]-4-[benzimidazol-1-yl]-6-[2-hydroxymethylphenyl]-pyrimidine;

2-[(S)-1-Phenylethylamino]-4-[5-(2-aminopyrimidin-4-yl)benzimidazol-1-yl]pyrimidine;

2-[(S)-1-(3-Nitrophenyl)ethylamino]-4-[5-(2-aminopyrimidin-4-yl)benzimidazol-1-yl]pyrimidine;

2-[(S)-1-(3-Trifluoromethylphenyl)ethylamino]-4-[5-(2-aminopyrimidin-4-yl)benzimidazol-1-yl]pyrimidine;

2-[(S)-1-(3-Nitrophenyl)ethylamino]-4-[5-(pyridin-4-yl)benzimidazol-1-yl]pyrimidine;

2-[(S)-1-(3-Trifluoromethylphenyl)ethylamino]4-[5-(pyridin-4-yl)benzimidazol-1-yl]pyrimidine;

2-[(S)-1-(3-Nitrophenyl)ethylamino]-4-[5-(pyridazin-3-yl)benzimidazol-1-yl]pyrimidine;

2-[(S)-1-(3-Trifluoromethylphenyl)ethylamino]-4-[5-(pyridazin-3-yl)benzimidazol-1-y1]pyrimidine;

2-[(S)-1-(3-Nitrophenyl)ethylamino]-4-[5-(3—N,N-dimethylpyridazin-6-yl)benzimidazol-1-yl]pyrimidine;

2-[(S)-1-(3-Trifluoromethylphenyl)ethylamino]-4-[5-(3-N,N-dimethylpyridazin-6-yl)benzimidazol-1-yl]pyrimidine;

2-[(S)-1-Phenylethylamino]-4-[5-(2-aminopyrimidin-4-yl)benzimidazol-1-yl]-6-[2-methylphenyl]pyrimidine;

2-[(S)-1-Phenylethylamino]-4-[5-(pyridin4-yl)benzimidazol-1-yl]-6-[2-methylphenyl]pyrimidine;

2-[(S)-1-Phenylethylamino]-4-[5-(pyridazin-3-yl)benzimidazol-1-yl]-6-[2-methylphenyl]pyrimidine;

2-[(S)-1-Phenylethylamino]-4-[5-(3-N,N-dimethylpyridazin-6-yl)benzimidazol-1-yl]6-[2-methylphenyl]pyrimidine;

2-[(S)-1-Phenylethylamino]-4-[5-(2-aminopyrimidin-4-yl)benzimidazol-1-yl]-6-[2-hydroxymethylphenyl]pyrimidine;

2-[(S)-1-Phenylethylamino]-4-[5-(pyridin-4-yl)benzimidazol-1-yl]-6-[2-hydroxymethylphenyl]pyrimidine;

2-[(S)-1-Phenylethylamino]-4-[5-(pyridazin-3-yl)benzimidazol-1-yl]-6-[2-hydroxymethylphenyl]pyrimidine;

2-[(S)-1-Phenylethylamino]-4-[5-(3-N,N-dimethylpyridazin-6-yl)benzimidazol-1-yl]-6-[2-hydroxymethylphenyl]pyrimidine;

2-[(S)-1-(3-Nitrophenyl)ethylamino]-4-[5-(2-aminopyrimidin-4-yl)benzimidazol-1-yl]-6-[2-hydroxymethylphenyl]pyrimidine;

2-[(S)-1-(3-Nitromethylphenyl)ethylamino]-4-[5-(pyridin4-yl)benzimidazol-1-yl]-6-[2-hydroxymethylphenyl]pyrimidine;

2-[(S)-1-(3-Trifluorophenyl)ethylamino]-4-[5-(2-aminopyrimidin-4-yl)benzimidazol-1-yl]-6-[2-hydroxymethylphenyl]pyrimidine;

2-[(S)-1-(3-Trifluoromethylphenyl)ethylamino]-4-[5-(pyridin-4-yl)benzimidazol-1-yl]-6-[2-hydroxymethylphenyl]pyrimidine;

2-[(S)-1-(3-Nitrophenyl)ethylamino]-4-[5-(2-aminopyrimidin-4-yl)benzimidazol-1-yl]-6-[2-methylphenyl]pyrimidine;

2-[(S)-1-(3-Nitromethylphenyl)ethylamino]-4-[5-(pyridin-4-yl)benzimidazol-1-yl]-6-[2-methylphenyl]pyrimidine;

2-[(S)-1-(3-Trifluorophenyl)ethylamino]-4-[5-(2-aminopyrimidin-4-yl)benzimidazol-1-yl]-6-[2-methylphenyl]pyrimidine; and 2-[(S)-1-(3-Trifluoromethylphenyl)ethylamino]-4-[5-(pyridin-4-yl)benzimidazol-1-yl]-6-[2-methylphenyl]pyrimidine.

The preferred compounds of the present invention include the compounds of Formula I, or a pharmaceutically acceptable salt, hydrate, solvate, crystal form, and individual diastereomers thereof, wherein $X^5$ is $CR^a$ and $X^6$ is N, and $R^a$ is defined as H or $C_1$–$C_6$-alkyl, and preferably H.

The preferred compounds of the present invention include the compounds of Formula I, or a pharmaceutically acceptable salt, hydrate, solvate, crystal form, and individual diastereomers thereof, wherein $R^1$ and $R^2$ independently are: H, $R^{11}$, $NH_2$, $NHR^{11}$, or $NR^{11}R^{12}$.

The preferred compounds of the present invention include the compounds of Formula I, or a pharmaceutically acceptable salt, hydrate, solvate, crystal form, and individual diastereomers thereof, wherein —$X^1$—$X^2$—$X^3$—$X^4$— is: —$CR^6$=$CR^6$—$CR^{6a}$=$CR^6$—, —$CR^{6a}$=$CR^6$—$CR^6$=$CR^6$—, —$CR^6$=N—$CR^6$=$CR^6$—, or —$CR^6$=$CR^6$—N=$CR^6$—.

The preferred compounds of the present invention include the compounds of Formula I, or a pharmaceutically acceptable salt, hydrate, solvate, crystal form, and individual diastereomers thereof, wherein $R^6$ and $R^{6a}$ are independently: H; halo( Br, Cl, I, or F); $R^{11}$; $OR^{11}$; $C_1$–$C_6$-alkyl, unsubstituted or substituted with one, two, or three substituents selected from $R^{11}$, $R^{12}$, and $R^{13}$; $NH_2$; $NHR^{11}$; $NHC_1$–$C_6$-alkyl, unsubstituted or substituted with one, two, or three substituents selected from $R^{11}$, $R^{12}$, and $R^{13}$; $NR^{11}R^{12}$; $NHC(=O)R^{11}$; $NR^{11}C(=O)R^{12}$; $NR^{11}C(=O)NHR^{12}$; $NR^{11}C(=O)NR^{12}R^{13}$; $NHSO_2R^{11}$; $NR^{11}SO_2R^{12}$; or $R^6$ and $R^{6a}$ when on adjacent carbons can be joined to form a 5- or 6-membered ring having the following bridging atoms, when read from right to left, or left to right: —N=CHNH—, —NHCH=N—, —N=CHNR$^9$—, —NR$^9$CH=N—,

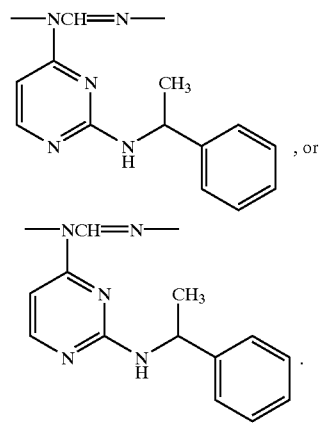

The preferred compounds of the present invention include the is compounds of Formula I, or a pharmaceutically acceptable salt, hydrate, solvate, crystal form, and individual diastereomers thereof, wherein A is: phenyl, naphthyl, and pyridyl.

The independent syntheses of the diastereomers or their chromatographic separations may be achieved as known in the art by appropriate modification of the methodology disclosed herein. Their absolute stereochemistry may be determined by the x-ray crystallography of crystalline products or crystalline intermediates, which are derivatized, if necessary, with a reagent containing an asymmetric center of known absolute configuration.

As appreciated by those of skill in the art, halo or halogen as used herein is intended to include chloro, fluoro, bromo and iodo. Similarly, $C_{1-6}$, as in $C_{1-6}$alkyl is defined to identify the group as having 1, 2, 3, 4, 5, or 6 carbons in a linear or branched arrangement, such that $C_{1-6}$ alkyl specifically includes methyl, ethyl, propyl, butyl, pentyl, and hexyl. Likewise, $C_0$, as in $C_0$alkyl is defined to identify the presence of a direct covalent bond. The term "heterocyclyl" as used herein is intended to include the following groups: benzimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, imidazolidinyl, imidazolidonyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidinyl, purinyl, pteridinyl, phthalazinyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, benzopiperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, methylenedioxybenzoyl, tetrahydrofuranyl, tetrahydrothienyl, 1,3-diazobicyclo[3.3.0]octan-2-onyl, 1,3-diazobicyclo[3.3.0]octanyl, 1,3-diazobicyclo[4.3.0]nonan-2-onyl and N-oxides thereof.

Utility

The compounds of Formula I of the present invention inhibit protein tyrosine kinases, especially Src-family kinases such as Lck, Fyn(B), Fyn(T), Lyn, Src, Yes, Hck, Fgr and Blk, and are thus useful in the treatment, including prevention and therapy, of protein tyrosine kinase-associated disorders such as immunologic disorders. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a preferred embodiment of the present invention. Compounds of the present invention which selectively block T cell activation and proliferation are preferred. Also, compounds of the present invention which may block the activation of endothelial cell protein tyrosine kinase by oxidative stress, thereby limiting surface expression of adhesion molecules that induce neutrophil binding, and which can inhibit protein tyrosine kinase necessary for neutrophil activation would be useful, for example, in the treatment of ischemia and reperfusion injury.

The present invention also provides methods for the treatment of protein tyrosine kinase-associated disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compound(s) of Formula I of the present invention in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides for a method for treating the aforementioned disorders such as atopic dermatitis by administration of a therapeutically effective amount of a compound of Formula I of the present invention, which is an inhibitor of protein tyrosine kinase, to a patient in need of such treatment.

Src-family kinases other than Lck, such as Hck and Fgr, are important in the Fc gamma receptor induced respiratory burst of neutrophils as well as the Fc gamma receptor responses of monocytes and macrophages. The compounds of the present invention may inhibit the Fc gamma induced respiratory burst response in neutrophils, and may also inhibit the Fc gamma dependent production of TNF alpha. The ability to inhibit Fc gamma receptor dependent neutrophil, monocyte and macrophage responses would result in additional anti-inflammatory activity for the present compounds in addition to their effects on T cells. This activity would be especially of value, for example, in the treatment of inflammatory diseases, such as arthritis or inflammatory bowel disease. The present compounds may also be of value for the treatment of autoimmune glomerulonephritis and other instances of glomerulonephritis induced by deposition of immune complexes in the kidney that trigger Fc gamma receptor responses and which can lead to kidney damage.

In addition, certain Src family kinases, such as Lyn and Fyn(B), may be important in the Fc epsilon receptor induced degranulation of mast cells and basophils that plays an important role in asthma, allergic rhinitis, and other allergic disease. Fc epsilon receptors are stimulated by IgE-antigen complexes. The compounds of the present invention may inhibit the Fc epsilon induced degranulation responses. The ability to inhibit Fc epsilon receptor dependent mast cell and basophil responses may result in additional anti-inflammatory activity for the present compounds beyond their effect on T cells.

The combined activity of the present compounds towards monocytes, macrophages, T cells, etc. may prove to be a valuable tool in the treatment of any of the aforementioned disorders.

In a particular embodiment, the compounds of formula I of the present invention are useful for the treatment of the aforementioned exemplary disorders irrespective of their etiology, for example, for the treatment of transplant rejection, rheumatoid arthritis, multiple sclerosis, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The present invention also provides pharmaceutical compositions comprising at least one of the compounds of the formula I capable of treating a protein tyrosine kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

The subjects treated in the above methods, in whom which protein tyrosine kinase inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy- propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-α inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require protein tyrosine kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The following assays can be employed in ascertaining the degree of activity of a compound as a protein tyrosine kinase inhibitor. Compounds described herein have been tested in one or more of the assays, and have shown activity. Representative compounds of the invention were tested and found to exhibit $IC_{50}$ values of at least <10 $\mu$M in any one of the described assays, thereby demonstrating and confirming the utility of the compounds of the invention as protein tyrosine kinase inhibitors and in the prophylaxis and treatment of immune diseases, hyperproliferative disorders, etc.

Jacks Assay

This assays measures the ability of compounds to block intracellular ZAP-70 kinase activation after stimulation of Jurkat T cells with anti-T cell receptor antibodies.

Step 1: Preparation of Jurkat Cells

Wash confluent Jurkat cells 2 times in serum-free RPMI (Gibco). Resuspend cells at $1.1 \times 10^6$ cells/ml in serum free-RPMI, keep on ice.

Step 2: Dilute Compounds

Titer test compounds in DMSO, prepare 110× concentrated solutions.

Step 3: Prepare Anti Vb8 Stock

Dilute anti-Vb8 (Pharmingen) to 917 ng/ml in Tris buffered saline.

Step 4: Run Cell Assay

For each test compound, place 12 V-bottom polypropylene PCR tubes in a thermal cycler (MJ Research) set at 0° C. Run no more than 4 compounds at a time. Also run 2 samples which receive just RPMI instead of anti-Vb8. These controls should be harvested at time=0 and time=2.5 minutes. To test for nonspecific interference with the assay, run cells plus anti-Vb8 for each drug tested and later, after these cells are lysed, add I ml of the test compound dilutions. Add 100 ml of Jurkat cells to each tube. Add 1 ml of test compounds diluted in DMSO. Add 9 ml of anti-Vb8 and mix. Incubate 5 min at 0° C. Add 2x Lysis Buffer to time=0 and no anti-Vb8 control. Set thermal cycler to 37° C. At time =2.5 minutes, add 110 ml of 2× Lysis Buffer to each well. Freeze samples in dry ice ethanol. They can be stored overnight at −80° C., or you can continue with the assay.

Step5: Run ZAP-70 Kinase Assay

Thaw cell lysates. Prepare 2× Kinase Reaction Buffer. Mix lysates well and put duplicate 25 ml aliquots into black U bottom plates (Falcon). Add 25 ml of 2× kinase mix. Seal plate and incubate 30 min at 30°. Add 50 ml 2× Quench solution. Leave plates in dark for 1 hour. Measure time-resolved fluorescent energy transfer in a Discovery plate reader (Packard).

| Solutions: | |
| --- | --- |
| 2X Lysis Buffer | 300 mM NaCl, 100 mM Tris, pH 7.5, 20% glycerol, 2 mg/ml BSA, 2% NP40, 1 mM vanadate, 1x protease inhibitors, 0.05% $NaN_3$, protease inhibitor mixture (Boehringer Mannheim) |
| 2X Kinase Buffer | 100 mM MOPS pH 7, 10% glycerol, 20 mM $MgCl_2$, 1 mg/ml BSA, 0.01% $NaN_3$, 200 mM ATP, 4 mM biotin-conjugated peptide substrate (long chain biotin-Glu-Gln-Glu-Asp-Glu-Pro-Glu-Gly-Asp-Tyr-Phe-Glu-Trp-Leu-Glu-NH2) |
| 2X Quench Buffer | 50 mM HEPES, pH 7.25, 30 mM EDTA, 0.2 M KF, 1 mg/ml BSA, 0.1% triton X100, 0.01% $NaN_3$, 420 nM XL665-avidin (Cis Biotech), Europium cryptate (Cis Biotech)-conjugated PY20 antibody (Transduction Laboratories)-add enough europium cryptate conjugate to each well to give around 8000 B counts. |

IL2_Mart Assay

Step 1: IL2 Secretion from Antigen-stimulated T Cells

Mix 30,000 Jurkat-mart#22 T cells with 30,000 T2 antigen presenting cells in 100 μl of RPMI medium containing 10% fetal calf serum in 96 well flat-bottom tissue culture plates (Falcon). Add 1 μl of compound titered in DMSO. Add 99 μl of 1 μM of M9-2 peptide [Ala-Ala-Gly-Ile-Gly-Ile-Leu-Thr-Val]. Incubate overnight at 37° C. in a 5% $CO_2$ incubator. Collect culture supernatants.

Step 2: Measurement of IL2 in Culture Supernatant

Coat Immulon2 plates (Dynatech) with 50 μl anti-human IL-2 (R &D) at 4 μg/ml in PBS/0.05% azide. Incubate overnight at 4° C. Block wells for at least 1 hour at room temperature with Block Buffer: Tris buffered saline (TBS)/1% BSA/0.05% azide. Wash wells 3 times with Wash Buffer: TBS/0.01% Tween 20. Add 50 μl of culture supernatants, or IL2 standards, to the microtiter wells. Incubate 1 hour at room temperature. Wash plate 3 times with Wash Buffer. Add 75 μl of anti-human IL-2-Biotin (R&D) at 450 ng/ml in Block Buffer. Incubate 1 hour at room temperature. Wash wells 3 times with Wash Buffer. Add 100 μl of 1 μg/ml europium-conjugated streptavidin (Wallac). Incubate 20 minutes at room temperature. Wash plate 3 times with Wash Buffer. Add 150 μl Enhancement solution (Wallac) Incubate 30 at least minutes at room temperature. Measure time resolved europium fluorescence on a Victor2 plate reader (Wallac).

A General HTRF Tyrosine Kinase Assay Protocol
(96-Well, 50 μL Kinase/100 μL Total Assay Volume)

Materials:

N-LCB-EQEDEPEGDYEEVLE-$NH_2$ (peptide substrate for Src family tyrosine kinases, Lck, Fyn(T), Fyn(B), Lyn, Src, Blk, Hck, Fgr, and Yes; LCB=aminohexanoylbiotin), N-LCB-EQEDEPEGIYGVLF-$NH_2$ (peptide substrate for ZAP-70, Syk, and Csk) were synthesized using an Applied Biosystem's 433A peptide synthesizer using FastMOC™ chemistry. All the Src family (Lck, Fyn(T), Fyn(B), Lyn, Src, Blk, Hck, Fgr, and Yes) as well as ZAP-70, Syk and Csk tyrosine kinases were expressed and purified using standard techniques known in the art. Streptavidin-XL665 (Streptavidin labeled with crosslinked allophycocyanin) was purchased from CISbio (France). Eu(K)-PY20 (Anti-phosphotyrosine antibody, PY20, labeled with Europium Cryptate) was using procedures described in: "Use Of A Phosphotyrosine-Antibody pair As A General Detection Method In Homogeneous Time Resolved Fluorescence: Application To Human Immunodeficency Viral Protease" Cummings, R. T., McGovern, H. M., Zheng, S., Park, Y. W., and Hermes, J. D. Analytical Biochemistry, Vol 269, 79–93 (1999); and "Homogeneous Proximity Tyrosine Kinase Assays: Scintialltion Proximity Assay Versus Homogeneous Time Resolved Fluorescence" Park, Y. W., Cummings, R. T., Wu, L., Zheng, S., Cameron, P. M., Woods, A., Zaller, D., Marcy, A. I., and Hermes, J. D. Analytical Biochemistry, Vol 269, 94–104 (1999). Anti-phosphotyrosine antibody PY20 and Europium Cryptate were purchased from Transduction Laboratories (Lexington, Ky.) and CISbio (France), respectively.

General Assay Protocol

Standard assay conditions were 50 μL kinase reaction consisting of 0.75 μM N-biotinyl peptide substrate and 10 μM ATP in assay buffer (50 mM Hepes, pH 7.0, 10 mM $MgCl_2$, 0.1% BSA, and 1 mM DTT). The kinase reaction was initiated by adding enzyme (2–20 pM) in a black MicroFluor 96-well plate (Dynatech, Chantilly, Va.). After a 40-minute incubation at room temperature, 50 μL of HTRF reagent mixture (420 nM streptavidin-XL665 and 2.0 nM Eu(K)-PY20) in quench buffer (50 mM Hepes, 30 mM EDTA, 0.1% BSA, 0.1% Triton X-100, 0.2 M KF, and pH 7.25) was added to the reaction mixture. The quenched reaction was incubated for 30 min. at room temperature and then read in Discovery (Packard, Meriden, Conn.).

Detailed Assay Procedure

General assay conditions: 0.75 μM substrate (biotinylated peptide), 10 μM ATP, 2–20 pM kinase, 210 nM SA-XL665 (Streptavidin labeled with crosslinked allophycocyanin), 1.0 nM Ab-K (anti-pTyr antibody, PY20, labeled with Europium Cryptate).

Assay Buffer: 50 mM HEPES, 10 mM $MgCl_2$, 1 mg/ml BSA, 1 mM DTT (fresh), 10 μM ATP (fresh), pH 7.0

Quench Buffer: 50 mM HEPES, 30 mM EDTA, 0.2 M KF, 1 mg/ml BSA, 0.1% Triton X-100, pH 7.25

Preparation:

1. 1.88 μM substrate[2] from 1 mM stock (in 100% DMSO).
2. 5.4 pM enzyme[2] from 500 nM stock (in 50% glycerol).
3. 420 nM (based on 4 biotin binding sites) SA-XL665 2.0 nM, Ab-K[3] in quench buffer.

[1]For 100 μL kinase/200 μL total assay, all the reagents should be doubled.
[2]diluted with assay buffer
[3]diluted with quench buffer Assay procedure:

1. Add 20 μl of 1.88 μM substrate in a round-bottom 96-well black plate (Dynatech or Costar).
2. Add 2 μl of inhibitor (or DMSO for controls).
3. Add 28 μl of 5.4 pM enzyme.
4. Incubate for 40 min. at RT.
5. Quench the kinase reaction by adding 50 μl of quench buffer with 420 nM XL and 2.0 nM Eu-PY20.
6. Incubate 30 min. at RT.
7. Read in Packard's Discovery.

Several methods for preparing the compounds of this invention are illustrated in the following Schemes and Examples. Starting materials are made from known procedures or as illustrated.

SCHEME 1

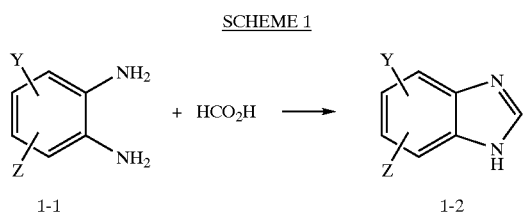

The preparation of substituted benzimidazoles such as 1-2 as intermediates that can be used for the synthesis of compounds within the scope of the instant invention is detailed in Scheme 1. Benzimidazoles of structure 1-2 can be obtained commercially or can be synthesized by reacting a suitably substituted ortho-diaminobenzene 1-1 with formic acid, formamidine, triazine, dimethylformamide, dimethylformamide dialkylacetal, chloromethylenedimethylammonium chloride, trialkylorthoformate, (dimethylaminomethylene)-aminomethylenedi methylammonium chloride (Gold's reagent) or the like. The ortho-diaminobenzene 1-1 can be obtained commercially or can be prepared in a variety of ways from commercial materials. The benzimidazole can be further substituted via aromatic substitution or modification of the substituents prior to or after incorporation onto the pyrimidine ring of the instant invention. The substituents Y and Z may include but are not limited to alkyl, aryl, heteroaryl, nitro, amino, substituted amino, disubstituted amino, hydroxy, alkoxy, aryloxy, chloro, bromo, iodo, fluoro, azido, cyano, thio, alkylthio, arylthio, carboxy, acyl, alkoxycarbonyl and alkylaminocarbonyl groups. Additionally, substituents Y and Z may form a third ring fused to the benzimidazole. Additionally, other heterocycles such as unsubstituted and substituted indoles, azaindoles, azabenzimidazoles, benzotriazoles, purines or the like can also be used.

SCHEME 2

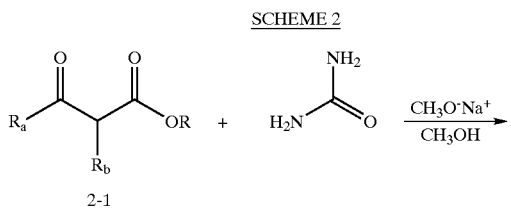

The preparation of 2,4-dichloropyrimidines such as 2-3 as intermediates that can be used for the synthesis of compounds within the scope of the instant invention is detailed in Scheme 2. Pyrimidines of structure 2-3 can be obtained commercially or can be synthesized by condensation of a β-keto-ester, β-keto-acid, β-keto-nitrile, β-aldehydo-ester, β-aldehydo-acid, β-aldehydo-nitrile, β-diester, β-ester-nitrile or the like with urea in a suitable solvent such as methanol, ethanol isopropanol or the like in the presence of a base such as a sodium or potassium alkoxide to give a substituted uracil. Other methods of pyrimidine ring formation can be used (see Katritzky, A. R. and Rees, C. W. "Comprehensive Heterocyclic Chemistry" Pergamon Press pp. 106–142 (1984)). The uracil can be chlorinated at the 2- and 4-positions by treatment with phosphoryl chloride, phosphorous pentachloride, phosphorous trichloride or mixtures thereof, or with chloromethylenedimethylammonium chloride added separately or prepared in situ by treatment of dimethylformamide with thionyl chloride, phosgene or the like in methylene chloride, chloroform, tetrahydrofuran, dioxane, ether or other suitable solvent. Alternately, other halides such as bromine or iodine can be incorporated in place of chlorine.

SCHEME 3

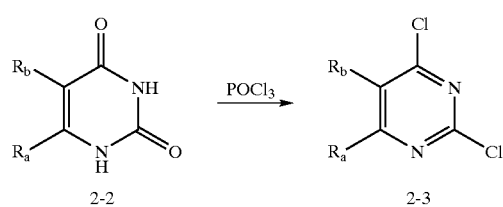

The preparation of some 2-amino-4-chloropyrimidines such as 3-3 as intermediates that can be used for the synthesis of compounds within the scope of the instant invention is detailed in Scheme 3. 2-Amino-4-chloropyrimidines 3-3 can be obtained commercially or can be synthesized by treatment of a 2,4-dichloropyrimidine 3-1 with a primary or secondary amine 3-2 in ethanol, methanol, isopropanol, tetrahydrofuran, ether, dioxane, dichloromethane, chloroform or other suitable solvent with or without the presence of a tertiary amine base. The regioisomeric 2-amino-4-chloropyrimidines are also obtained and can be used as intermediates in the instant invention.

SCHEME 4

$$\underset{4\text{-}1}{\overset{O\qquad\qquad O}{R_a\diagdown\!\!\!\diagup\!\!\!\diagdown\!\!\!\diagup OR}} + \underset{4\text{-}2}{\overset{NH}{H_2N\diagdown\!\!\!\diagup NR_cR_d}} \xrightarrow{\underset{CH_3OH}{CH_3O^-Na^+}}$$

$$\underset{4\text{-}3}{\overset{OH}{R_b\diagdown\!\!\!\diagup N\diagdown\!\!\!\diagup NR_cR_d}} \xrightarrow{\underset{CHCl_3}{\overset{H_3C}{\underset{H_3C}{\diagdown}}\overset{+}{N}\overset{H}{\diagdown\!\!\!\diagup Cl}\,Cl^-}}$$

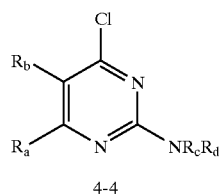

4-4

The preparation of some 2-amino-4-chloropyrimidines such as 4-4 as intermediates that can be used for the synthesis of compounds within the scope of the instant invention is detailed in Scheme 4. 2-Amino-4-chloropyrimidines 4-4 can be obtained commercially or can be synthesized by treatment of a β-keto-ester, β-keto-acid, β-keto-nitrile, β-aldehydo-ester, β-aldehydo-acid, β-aldehydo-nitrile, β-diester, β-ester-nitrile or the like with with an N-alkylguanidine 4-2 to give 2-amino-4-hydroxypyrimidine 4-3 generally in an alcoholic solvent such as methanol, ethanol, isopropanol in the presence of a strong base such as sodium methoxide, sodium ethoxide or the like. N-alkylguanidine 4-2 can be prepared according to the procedure of Kim et al (Tetrahedron Letters, 1988, 29, 3183 and references cited therein). The 2-amino-4-hydroxypyrimidine 4-3 can be chlorinated by treatment with phosphoryl chloride, phosphorous pentachloride, phosphorous trichloride or mixtures thereof, or with chloromethylenedimethylammonium chloride added separately or prepared in situ by treatment of dimethylformamide with thionyl chloride, phosgene or the like in methylene chloride, chloroform, tetrahydrofuran, ether or other suitable solvent. Alternately, other halides such as bromine or iodine can be incorporated in place of chlorine.

SCHEME 5

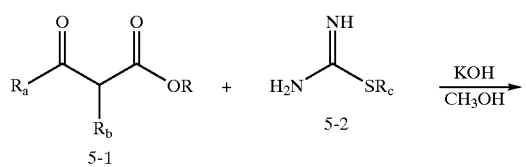

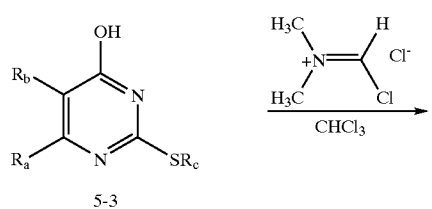

The preparation of some 2-alkylthio-4-chloropyrimidines such as 5-4 as intermediates that can be used for the synthesis of compounds within the scope of the instant invention is detailed in Scheme 5. 2-Alkylthio-4-chloropyrimidines 5-4 can be obtained commercially or can be synthesized by treatment of a β-keto-ester, β-keto-acid, β-keto-nitrile, β-aldehydo-ester, β-aldehydo-acid, β-aldehydo-nitrile, β-diester, β-ester-nitrile or the like in an alcoholic solvent such as methanol, ethanol or the like with an S-alkylthiopseudourea to give 2-alkylthio-4-hydroxy pyrimidine 5-3. The 2-alkylthio4-hydroxy pyrimidine 5-3 can be chlorinated by treatment with phosphoryl chloride, phosphorous pentachloride, phosphorous trichloride or mixtures thereof, or with chloromethylenedimethylammonium chloride added separately or prepared in situ by treatment of dimethylformamide with thionyl chloride, phosgene or the like in methylene chloride, chloroform, tetrahydrofuran, ether or other suitable solvent. Alternately, other halides such as bromine or iodine can be incorporated in place of chlorine.

SCHEME 6

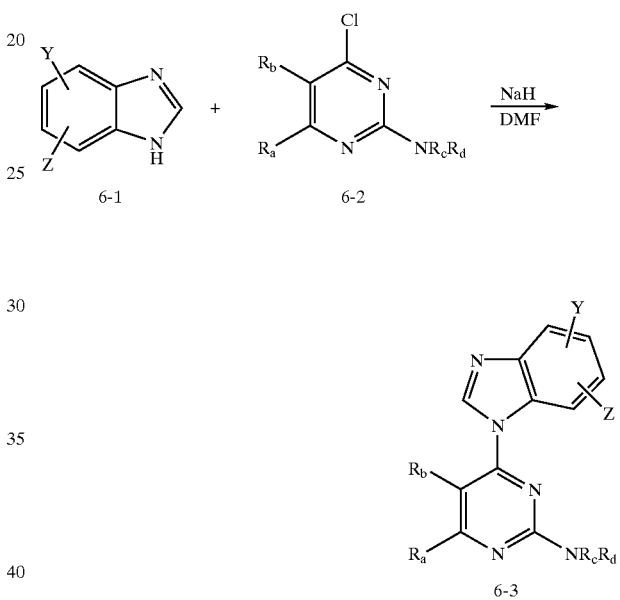

The preparation of some 2-alkylamino-4-[benzimidazol-1-yl]pyrimidines such as 6-3 within the scope of the instant invention is detailed in Scheme 6. A benzimidazole 6-1 is condensed with a 2-amino-4-chloropyrimidine 6-2 in a suitable solvent such as dimethylformamide, dimethylsulfoxide, toluene, tetrahydrofuran, xylene, 1-methyl-2-pyrrolidinone, isopropanol or the like at or above room temperature. The benzimidazole 6-1 can first be deprotonated by addition of a base such as sodium hydride, potassium hydride, sodium hydroxide, potassium hydroxide, lithium diisopropylamide, lithium bis(trimethylsilyl)amide or the like prior to condensation with 2-amino-4-chloropyrimidine 6-2.

SCHEME 7

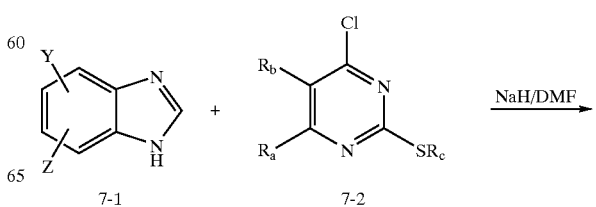

SCHEME 8

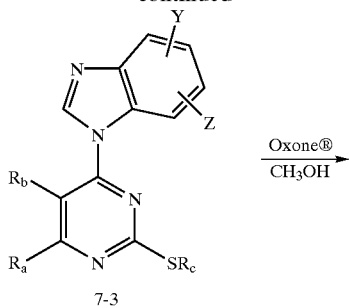

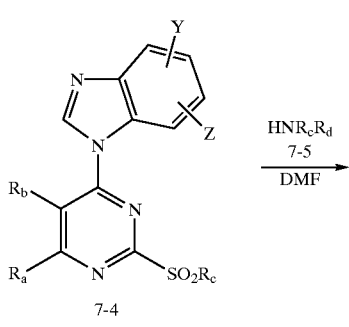

The preparation of some 2-alkylamino-4-[benzimidazol-1-yl]pyrimidines such as 7-6 within the scope of the instant invention is detailed in Scheme 7. A benzimidazole 7-1 is condensed with a 2-alkylthio-4-chloropyrimidine 7-2 in a suitable solvent such as dimethylformamide, dimethylsulfoxide, toluene, tetrahydrofuran, xylene, 1-methyl-2-pyrrolidinone, isopropanol or the like at or above room temperature to afford a 2-alkylthio-4-[benzimidazol-1-yl]pyrimidine 7-3. The benzimidazole 7-1 can first be deprotonated by addition of a base such as sodium hydride, potassium hydride, sodium hydroxide, potassium hydroxide, lithium diisopropylamide, lithium bis(trimethylsilyl)amide or the like prior to condensation with 2-alkylthio4-chloropyrimidine7-2. The 2-alkylthio-group of 7-3 can be displaced by an alkyl amine 7-5 or preferably, the alkylthio group of 7-3 can first be oxidized to the corresponding sulfoxide or sulfone using hydrogen peroxide, sodium periodate, sodium chlorite, sodium hypochlorite, peracids, Oxone® or the like and then displaced with an alkylamine 7-5 to give 2-alkylamino-4-[benzimidazol-1-yl]pyrimidines such as 7-6.

The preparation of some 2-alkylamino-4-[benzimidazol-1-yl]-6-arylpyrimidines such as 8-9 within the scope of the instant invention is detailed in Scheme 8. A 2,4,6-trichloropyrimidine 8-1 is condensed with an alkylamine 8-2 in ethanol, methanol, isopropanol, tetrahydrofuran, ether, methylene chloride, chloroform or other suitable solvent with or without the presence of a tertiary amine base to afford a 2-alkylamino-4,6-dichloropyrimidine 8-3. A benzimidazole 8-5 is condensed with 2-alkylamino-4,6-dichloropyrimidine 8-3 in a suitable solvent such as dimethylformamide, dimethylsulfoxide, toluene, tetrahydrofuran, xylene, 1-methyl-2-pyrrolidinone, isopropanol or the like at or above room temperature to afford the 2-alkylamino-4-[benzimidazol-1-yl]-6-chloropyrimidine 8-6. The benzimidazole 8-5 can first be deprotonated by addition of a base such as sodium hydride, potassium hydride, sodium hydroxide, potassium hydroxide, lithium diisopropylamide, lithium bis(trimethylsilyl)amide or the like prior to condensation with 2-alkylamino-4,6-dichloropyrimidine 8-3. The 2-alkylamino4-benzimidazol-1-yl-6-chloropyrimidine 8-6 is arylated via a palladium mediated coupling with an arylboronic acid or an aryltrialkyltin reagent to give 2-alkylamino-4-[benzimidazol-1-yl]-6-arylpyrimidine such as 8-9.

SCHEME 9

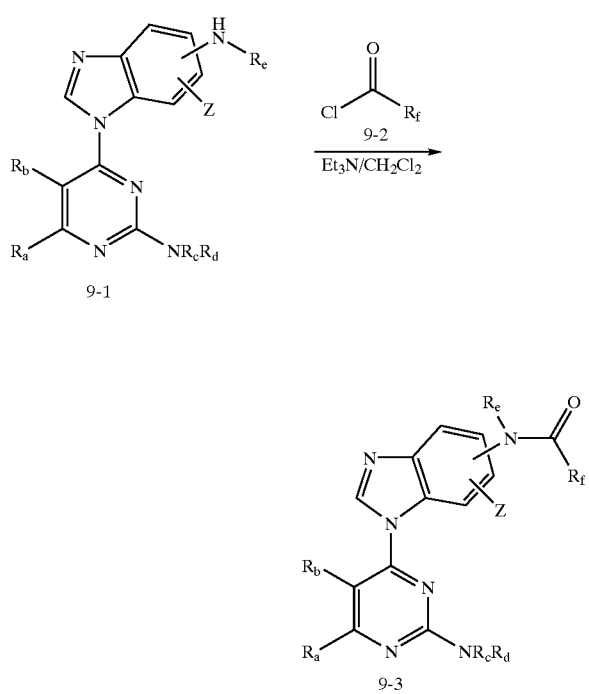

The preparation of 2-alkylamino-4-[acylamino-benzimidazol-1-yl]pyrimidines such as 9-3 within the scope of the instant invention is detailed in Scheme 9. A 2-aminoalkyl-4-[aminobenzimidazol-1-yl]pyrimidine 9-1 is treated with an acid chloride 9-2 in pyridine or in a nonprotic solvent such as methylene chloride, chloroform, tetrahydrofuran, toluene or the like in the presence of a tertiary amine base to give 2-alkylamino-4-[acylamino-benzimidazol-1-yl]pyrimidines such as 9-3. In place of the acid chloride one can use another acid halide, or other acylating agent such as acid anhydrides, esters, isocyanates, chloroformates, alkylsulfonylchlorides, arylsulfonylchlorides, or an acid with a coupling reagent such as 1-(3-dimethylaminopropyl)-3-ethylcarbodiimide hydrochloride, 1,3-dicyclohexylcarbodiimide or the like. Alternatively, the acylation can be carried out on a 1-N-protected-amino-benzimidazole. The protecting group for the benzimidazole can be, but is not limited to, a trimethylsilylethoxymethyl (SEM) group. After removal of the 1-N-protecting group the acylamino-benzimidazole can be incorporated onto the pyrimidine nucleus as outlined in Scheme 6, Scheme 7 or Scheme 8 to give compounds of the instant invention.

SCHEME 10

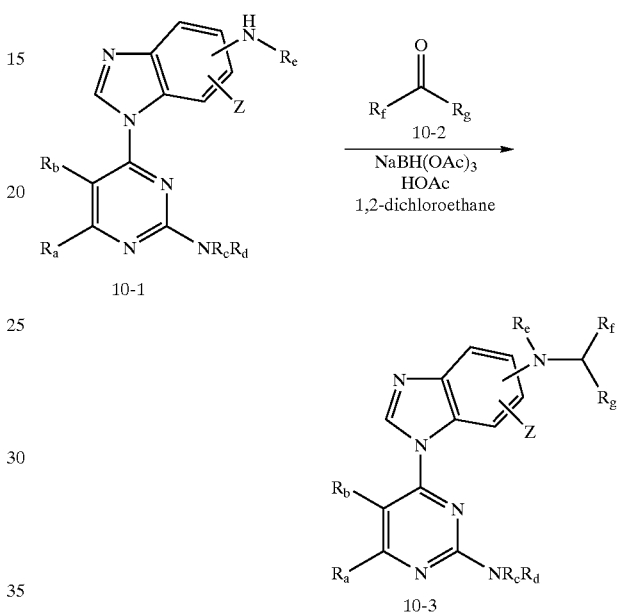

The preparation of 2-alkylamino-4-[alkylamino-benzimidazol-1-yl]pyrimidines such as 10-3 within the scope of the instant invention is detailed in Scheme 10. A 2-aminoalkyl-4-[aminobenzimidazol-1-yl]pyrimidine 10-1 is treated with an aldehyde or ketone 10-2 in a suitable solvent such as dichloromethane, dichloroethane, tetrahydrofuran methanol, ethanol, acetic acid or the like to which is added a hydride source such as sodium borohydride, sodium cyanoborohydride, borane, sodium triacetoxyborohydride or the like to give 2-alkylamino-4-[alkylamino-benzimidazol-1-yl]pyrimidines such as 10-3. An alternative method of preparation of 2-alkylamino-4-[alkylamino-benzimidazol-1-yl]pyrimidines such as 10-3 is by the reduction of the amide group of a 2-alkylamino-4-[acylamino-benzimidazol-1-yl]pyrimidine using borane, lithium aluminum hydride or the like. An alternative method of preparation of 2-alkylamino4-[alkylamino-benzimidazol-1-yl]pyrimidines such as 10-3 is by alkylation of a 2-aminoalkyl-4-[aminobenzimidazol-1-yl]pyrimidine 10-1 with an alkylhalide or alkylsulfonate. Alternatively, the alkylation can be carried out on a 1-N-protected-amino-benzimidazole. The protecting group for the benzimidazole can be, but is not limited to, a trimethylsilylethoxymethyl (SEM) group. After removal of the 1-N-protecting group the alkylamino-benzimidazole can be incorporated onto the pyrimidine nucleus as outlined in Scheme 6, Scheme 7 or Scheme 8 to give compounds of the instant invention.

SCHEME 11

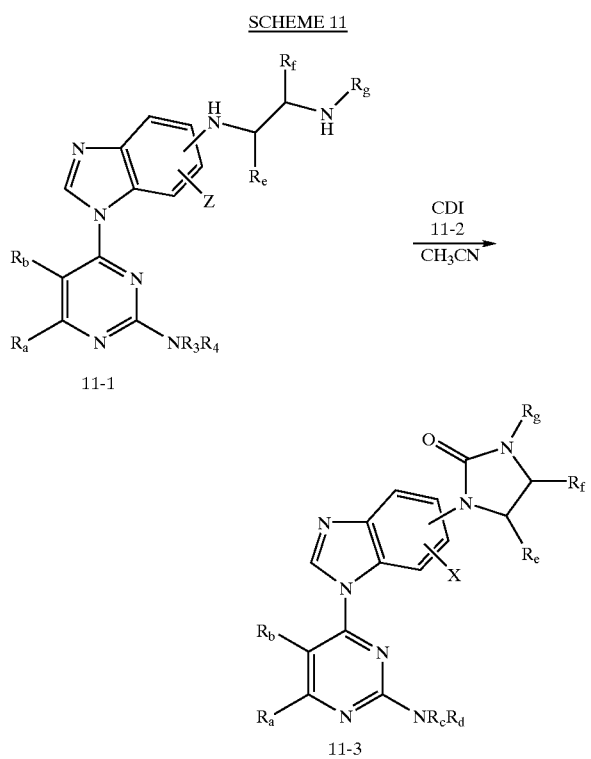

The preparation of 2-alkylamino-4-[imidazolidin-2-one-1-yl-benzimidazol-1-yl]pyrimidines such as 11-3 within the scope of the instant invention is detailed in Scheme 11. A 2-alkylamino-4-[(aminoalkyl)amino-benzimidazol-1-yl] pyrimidine 11-1 is treated with carbonyldiimidazole 11-2 or phosgene, triphosgene, 4-nitrophenylchloroformate or the like in a suitable solvent such as dichloromethane, dichloroethane, tetrahydrofuran, acetonitrile, dimethylformamide or the like with or without the presence of a tertiary amine base such as triethylamine, diisopropylethylamine, 4-dimthylaminopyridine or the like to afford the 2-alkylamino-4-[imidazolidin-2-one-1-yl-benzimidazol-1-yl]pyrimidine 11-3. Alternatively, the cyclization can be carried out on a 1-N-protected-(aminoalkyl)amino-benzimidazole. The protecting group for the benzimidazole can be, but is not limited to, a trimethylsilylethoxymethyl (SEM) group. After removal of the 1-N-protecting group the imidazolidin-2-one-1-yl -benzimidazole can be incorporated onto the pyrimidine nucleus as outlined in Scheme 6, Scheme 7 or Scheme 8 to give compounds of the instant invention.

SCHEME 12

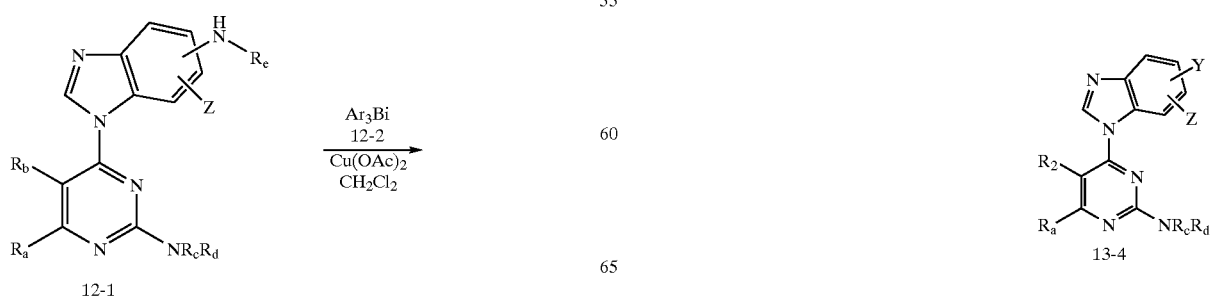

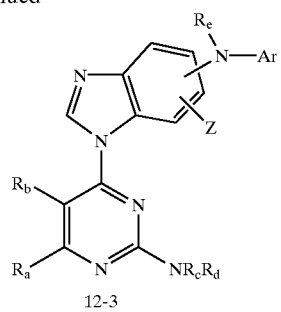

The preparation of 2-alkylamino-4-[arylaminobenzimidazol-1-yl]pyrimidines such as 12-3 within the scope of the instant invention is detailed in Scheme 12. A 2-aminoalkyl-4-[aminobenzimidazol-1-yl] pyrimidine 12-1 is treated with a triarylbismuth 12-2 in the presence of stoichiometric copper(II)acetate or with a triarylbismuth diacetate or other pentavalent organobismuth in the presence of catalytic copper(II)acetate. An alternate procedure involves reaction of a 2-aminoalkyl-4-[aminobenzimidazol-1-yl]pyrimidine 12-1 with an aryl halide in the presence of a palladium catalyst and strong base according to the procedure of Buchwald et al (J. Am. Chem. Soc. 1997, 119, 8451). Alternatively, the arylation can be carried out on a 1-N-protected-amino-benzimidazole. The protecting group for the benzimidazole can be, but is not limited to, a trimethylsilylethoxymethyl (SEM) group. After removal of the 1-N-protecting group the arylamino-benzimidazole can be incorporated onto the pyrimidine nucleus as outlined in Scheme 6, Scheme 7 or Scheme 8 to give compounds of the instant invention.

SCHEME 13

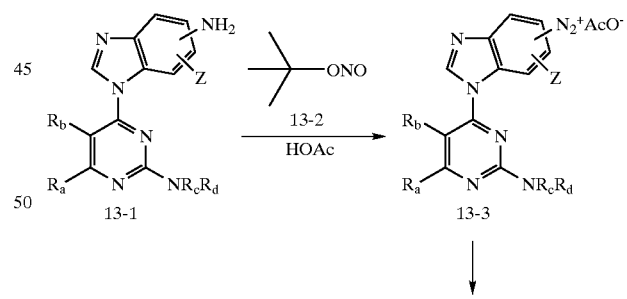

The preparation of 2-alkylamino-4-[substituted-benzimidazol-1-yl]pyrimidine such as 13-4 within the scope of the instant invention is detailed in Scheme 13. A 2-aminoalkyl-4-[aminobenzimidazol-1-yl]pyrimidine 13-1 is treated with an acid such as acetic acid, tetrafluoroboric acid, hydrochloric acid or the like followed by isoamylnitrite, sodium nitrite, nitrous acid or the like to afford the diazonium salt 13-3. The 2-alkylamino-4-[diazonium-benzimidazol-1-yl]pyrimidines 13-3 can then be treated with cuprous chloride or cuprous bromide or sodium iodide or potassium iodide or the like to afford the corresponding 2-alkylamino-4-[halo-benzimidazol-1-yl]pyrimidine. The 2-alkylamino-4-[diazonium-benzimidazol-1-yl]pyrimidines 13-3 can also be treated with cuprous cyanide to afford the corresponding 2-alkylamino-4-[cyano-benzimidazol-1-yl]pyrimidine. The 2-alkylamino-4-[diazonium-benzimidazol-1-yl]pyrimidines 13-3 can also be treated with sodium azide to afford the corresponding 2-alkylamino-4-[azido-benzimidazol-1-yl]pyrimidine. The 2-alkylamino-4-[diazonium-benzimidazol-1-yl]pyrimidines 12-3 can also be treated with an olefin, a vinylstannane, an arylboronic acid, an arylstannane or the like in the presence of a palladium catalyst to afford the corresponding 2-alkylamino-4-[(aryl or vinyl)-benzimidazol-1-yl]pyrimidine. The stannane couplings can also be done in the presence of carbon monoxide to afford the carbonyl insertion products.

Alternatively, the diazotization and subsequent substitution reaction can be carried out on a 1-N-protected-amino-benzimidazole. The protecting group for the benzimidazole can be, but is not limited to, a trimethylsilylethoxymethyl (SEM) group. After removal of the 1-N-protecting group the substituted-benzimidazole can be incorporated onto the pyrimidine nucleus as outlined in Scheme 6, Scheme 7 or Scheme 8 to give compounds of the instant invention.

SCHEME 14

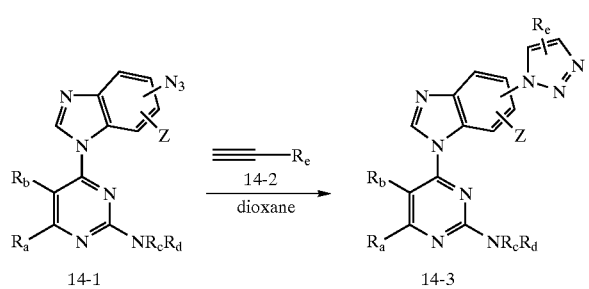

The preparation of 2-alkylamino-4-[triazol-1-yl-benzimidazol-1-yl]pyrimidine such as 14-3 within the scope of the instant invention is detailed in Scheme 14. A 2-alkylamino-4-[azido-benzimidazol-1-yl]pyrimidine can be treated with an alkyne or aminoacrylate with heating to afford the 2-alkylamino-4-[triazolyl-benzimidazol-1-yl]pyrimidine. When the alkyne used is tributylethynylstannane, the resulting tributylstannyltriazole ($R_5$=bu$_3$Sn) can be used for further palladium catalysed couplings with aryl or olefinic groups or can be protodestannylated. Alternatively, the triazole formation can be carried out on a 1-N-protected-azido-benzimidazole. The protecting group for the benzirnidazole can be, but is not limited to, a trimethylsilylethoxymethyl (SEM) group. After removal of the 1-N-protecting group the triazol-1-yl-benzimidazole can be incorporated onto the pyrimidine nucleus as outlined in Scheme 6, Scheme 7 or Scheme 8 to give compounds of the instant invention.

SCHEME 15

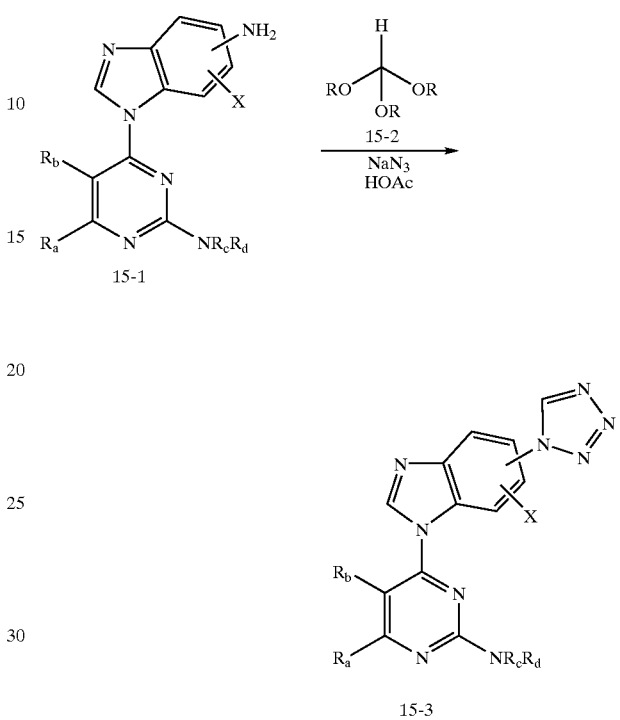

The preparation of 2-alkylamino-4-[tetrazol-1-yl-benzimidazol-1--yl]pyrimidines such as 15-3 within the scope of the instant invention is detailed in Scheme 15. A 2-alkylamino-4-[amino-benzimidazol-1-yl]pyrimidine 15-1 is treated with a trialkyl orthoformate 15-2 followed by treatment with sodium azide to give the 2-alkylamino-4-[tetrazolyl-benzimidazol-1-yl]pyrimidine 15-3. Alternatively, the tetrazole formation can be carried out on a 1-N-protected-amino-benzimidazole. The protecting group for the benzimidazole can be, but is not limited to, a trimethylsilylethoxymethyl (SEM) group. After removal of the 1-N-protecting group the tetrazol-1-yl-benzimidazole can be incorporated onto the pyrimidine nucleus as outlined in Scheme 6, Scheme 7 or Scheme 8 to give compounds of the instant invention.

SCHEME 16

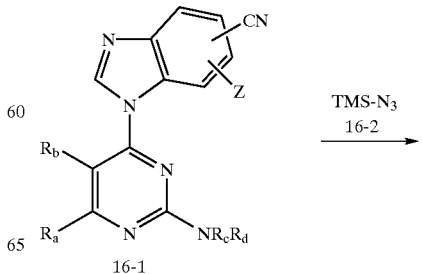

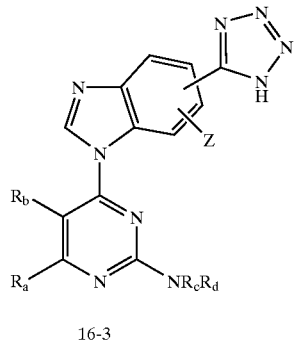

16-3

The preparation of 2-alkylamino-4-[tetrazol-5-yl-benzimidazol-1-yl]pyrimidines such as 16-3 within the scope of the instant invention is detailed in Scheme 16. A 2-alkylamino-4-[cyano-benzimidazol-1-yl]pyrimidine 16-1 is treated with trimethylsilyl azide 16-2 or trialkyltin azide or sodium azide or the like at or above room temperature to give the 2-alkylamino-4-[tetrazol-5-yl-benzimidazol-1-yl]pyrimidine 16-3. Alternatively, the tetrazole formation can be carried out on a 1-N-protected-cyano-benzimidazole. The protecting group for the benzimidazole can be, but is not limited to, a trimethylsilylethoxymethyl (SEM) group. After removal of the 1-N-protecting group the tetrazol-5-yl-benzimidazole can be incorporated onto the pyrimidine nucleus as outlined in Scheme 6, Scheme 7 or Scheme 8 to give compounds of the instant invention.

SCHEME 17

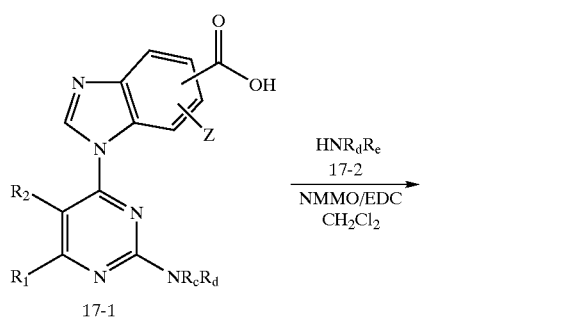

17-1

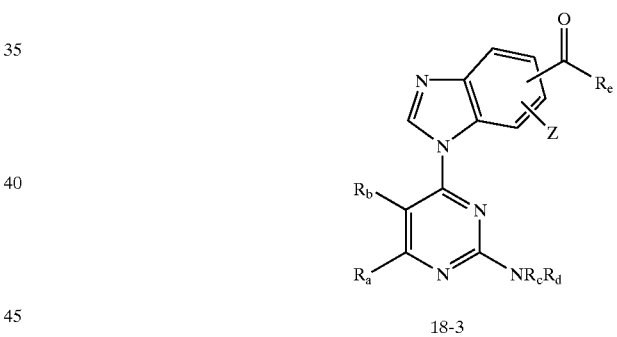

17-3

The preparation of 2-alkylamino-4-[(alkylaminocarbonyl)-benzimidazol-1-yl]pyrimidines such as 17-3 within the scope of the instant invention is detailed in Scheme 17. A 2-alkylamino-4-[carboxy-benzimidazol-1-yl]pyrimidine 17-1 is treated with an amine 17-2 in the presence of a tertiary amine such as N-methylmorpholine, triethylamine or the like and a coupling reagent such as 1,3-dicyclohexylcarbodiimide, 1-(3-dimethylaminopropyl)-3-ethylcarbodiimide hydrochloride or the like to give the 2-alkylamino-4-[(alkylaminocarbonyl)-benzimidazol-1-yl]pyrimidine 17-3. Alternatively, the amide formation can be carried out on a 1-N-protected-carboxy-benzimidazole. The protecting group for the benzimidazole can be, but is not limited to, a trimethylsilylethoxymethyl (SEM) group. After removal of the 1-N-protecting group the (alkylaminocarbonyl)-benzimidazole can be incorporated onto the pyrimidine nucleus as outlined in Scheme 6, Scheme 7 or Scheme 8 to give compounds of the instant invention.

SCHEME 18

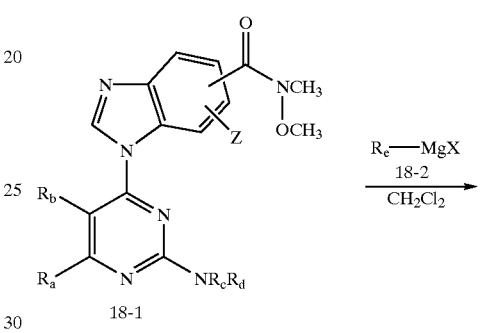

18-1

18-3

The preparation of 2-alkylarnino-4-[alkyl (or aryl) carbonyl-benzimidazol-1-yl]pyrimidines such as 18-3 within the scope of the instant invention is detailed in Scheme 18. A 2-alkylamino-4-[(N-methyl-N-methoxyamino)carbonyl-benzimidazol-1-yl]pyrimidine 18-1 is treated with an organomagnesium halide 18-2 or organolithium or the like in a suitable solvent such as dichloromethane, ethe,r tetrahydrofuran, dichloroethane, dioxane or the like to give the 2-alkylamino-4-[alkyl (or aryl)carbonyl -benzimidazol-1-yl]pyrimidine 18-3. Alternatively, the ketone formation can be carried out on a 1-N-protected-(N-methyl-N-methoxyamino)carbonyl-benzimidazole. The protecting group for the benzimidazole can be, but is not limited to, a trimethylsilylethoxymethyl (SEM) group. After removal of the 1-N-protecting group the alkyl (or aryl)carbonyl-benzimidazole can be incorporated onto the pyrimidine nucleus as outlined in Scheme 6, Scheme 7 or Scheme 8 to give compounds of the instant invention.

SCHEME 19

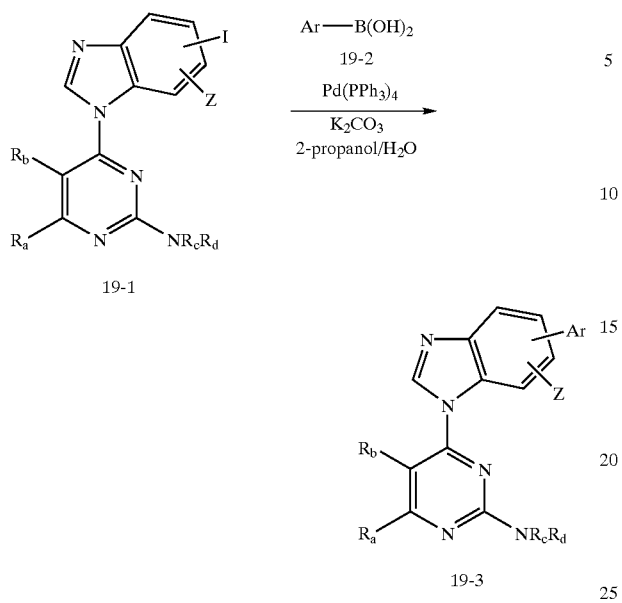

The preparation of 2-alkylamino-4-[substituted-benzimidazol-1-yl]pyrimidine such as 19-3 within the scope of the instant invention is detailed in Scheme 19. A 2-aminoalkyl-4-[iodobenzimidazol-1-yl]pyrimidine 19-1 or 2-aminoalkyl-4-[bromobenzimidazol-1-yl]pyrimidine or 2-aminoalkyl-4-[chlorobenzimidazol-1-yl]pyrimidine is treated with an olefin, arylstannane, vinylstannane, arylboronic acid, vinylboronic acid or the like in the presence of a palladium catalyst to afford the corresponding 2-alkylamino-4-[(aryl or vinyl)-benzimidazol-1-yl]pyrimidine 19-3. The stannane couplings can also be done in the presence of carbon monoxide to afford carbonyl insertion products. Alternatively, the 2-aminoalkyl-4-[iodobenzimidazol-1-yl]pyrimidine 19-1 or 2-aminoalkyl-4-[bromobenzimidazol-1-yl]pyrimidine or 2-aminoalkyl-4-[chlorobenzimidazol-1-yl]pyrimidine can be treated with hexabutylditin or hexamethylditin in the presence of a palladium catalyst to afford the corresponding 2-aminoalkyl-4-[trialkylstannylbenzimidazol-1-yl]pyrimidine which can also be employed in palladium mediated couplings with arylboronic acids, vinyl boronic acids, arylhalides, vinyl halides or the like. Alternatively, the arylation or vinylation can be carried out on a 1-N-protected-halo (or stannyl)-benzimidazole. The protecting group for the benzimidazole can be, but is not limited to, a trimethylsilylethoxymethyl (SEM) group. After removal of the 1-N-protecting group the substituted-benzimidazole can be incorporated onto the pyrimidine nucleus as outlined in Scheme 6, Scheme 7 or Scheme 8 to give compounds of the instant invention.

SCHEME 20

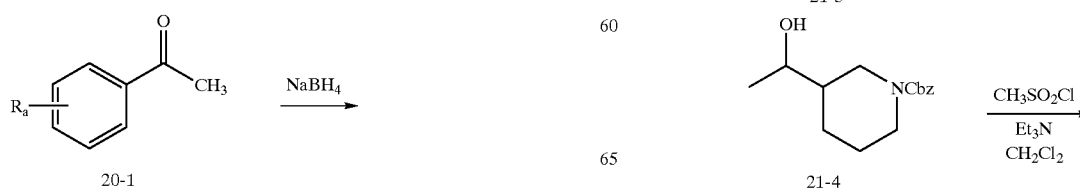

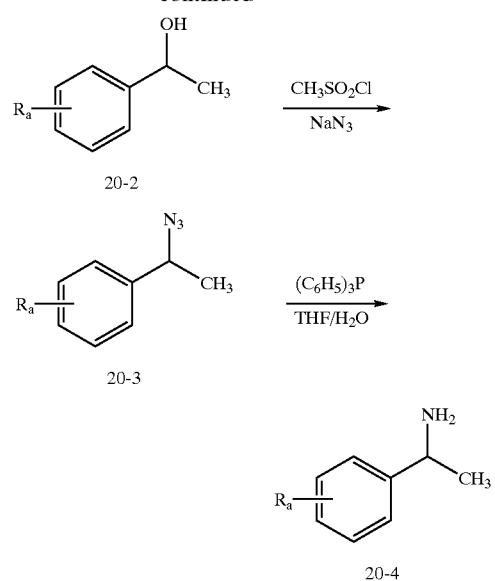

The preparation of some I-phenylethylamines such as 20-4 as intermediates that can be used for the synthesis of compounds within the scope of the instant invention is detailed in Scheme 20. 1-phenylethylamines of structure 20-4 can be obtained commercially or can be synthesized by the reduction of an acetophenone to the corresponding alcohol. Activation of the alcohol towards displacement by formation of the methanesulfonate, toluenesulfonate, halhalide or the like followed by substitution with the azide anion affords azido compound 20-3. Reduction of the azide by treatment with triphenylphosphine in aqueous THF or by hydrogenation over a palladium catalyst affords the amine 20-4. Other methods of amine formation can be used (see March J. "Advanced Organic Chemistry", 4th ed., John Wiley & Sons, New York, pp. 1276–1277(1992)).

SCHEME 21

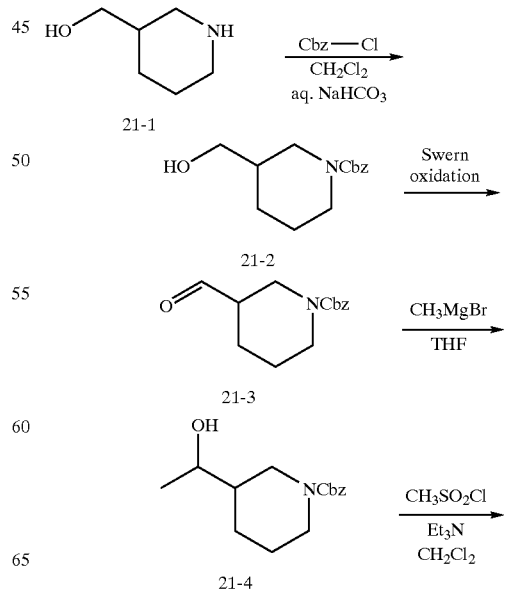

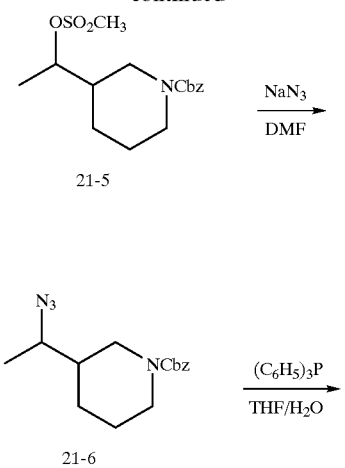

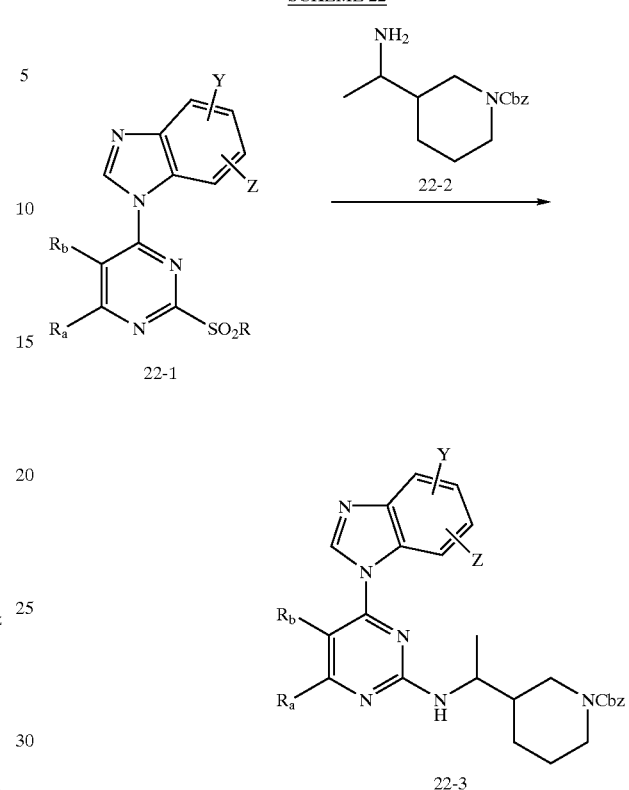

The preparation of piperidine substituted ethylamines such as 21-7 as intermediates that can be used for the synthesis of compounds within the scope of the instant invention is detailed in Scheme 21. The nitrogen of the commercially available 3-piperidinemethanol can be protected with a benzyloxycarbonyl group or other suitable protecting group such as tert-butyloxycarbonyl-, allyloxycarbonyl- or the like to afford 21-2. The hydroxyl group of 21-2 can be oxidized to the corresponding carbonyl group under Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Addition of methyl magnesium bromide or methyl lithium can afford the secondary alcohol 21-4. The hydroxyl group of 21-4 can be activated towards displacement by formation of methanesulfonate, toluenesulfonate, halide or the like. Treatment of 21-5 with sodium azide in dimethylformamide or other suitable solvent affords azido compound 21-6. Alternatively, 21-4 can be treated with azide ion under Mitsunobu coupling conditions to give azide 21-6 directly. Reduction of the azide to the corresponding amine by treatment of the azide with triphenylphosphine in aqueous THF gives the desired amine 21-7. Alternatively, the azide can be reduced by hydrogenation over a suitable catalyst. Alkylamines substituted with other heterocycles such as, but not limited to, 2-pyrrolidine, 3-pyrrolidine, 2-piperidine, 4-piperidine, piperazine, 2-morpholine, 3-morpholine, 2-thiomorpholine and the corresponding S-oxides, 3-thiomorpholine and the corresponding S-oxides, can also be prepared in like manner.

The preparation of 2-(piperidin-3-yl)ethylamino-4-[benzimidazol-1-yl]pyrimidines such as 22-3 within the scope of the instant invention is detailed in Scheme 22. Sulfone 22-1 described in Scheme 7 can be reacted with a piperidine-substituted alkylamines such as 22-2 in dimethyformamide, dimethylsulfoxide, toluene, 1-methyl-2-pyrrolidinone, isopropanol or other suitable solvent with or without heating to give the N-benzyloxycarbonyl-protected heterocycle 22-3. Alternatively, the (piperidin-3-yl)ethylamino can be affixed to the pyrimidine ring prior to the benzimidazole as described in Scheme 3, Scheme 6 and Scheme 8. Additionally, other (heterocyclic)alkylamines such as alkylamines substituted with, for example, 2-pyrrolidine, 3-pyrrolidine, 2-piperidine, 4-piperidine, piperazine, 2-morpholine, 3-morpholine, 2-thiomorpholine and the corresponding S-oxides, 3-thiomorpholine and the corresponding S-oxides, can also be used.

SCHEME 23

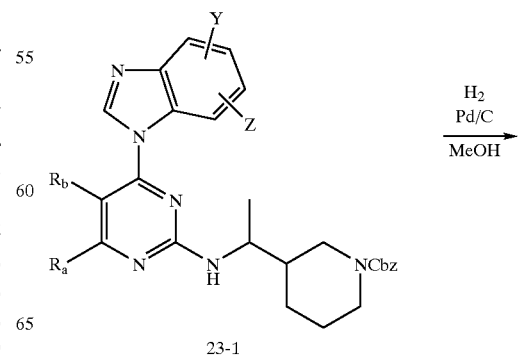

SCHEME 24

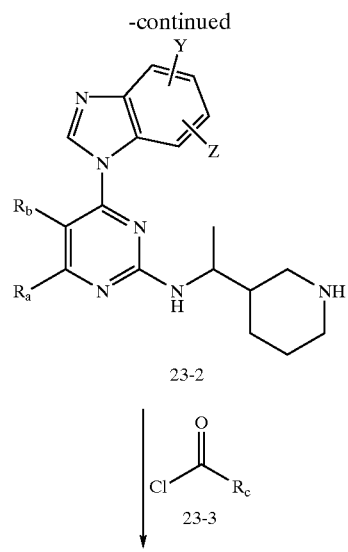

23-2

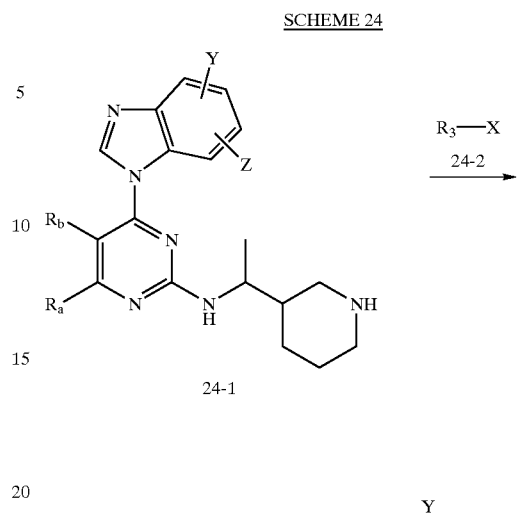

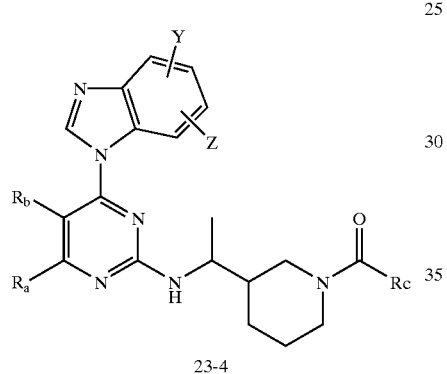

23-4

The preparation of 2-(piperidin-3-yl)ethylamino-4-[benzimidazol-1-yl]pyrimidines such as 23-4 within the scope of the instant invention is detailed in Scheme 23. Removal of the benzyloxycarbonyl protecting group of 23-1 via hydrogenolysis using a palladium catalyst or by solvolysis using HBr in acetic acid affords the deprotected compound 23-2 within the scope of the instant invention. Subsequent acylation with an acid chloride 22-3 in pyridine or in a solvent such as methylene chloride, chloroform, tetrahydrofuran, toluene or the like in the presence of a tertiary amine base gives 22-4. In place of the acid chloride one can use another acid halide, or other acylating agent such as acid anhydrides, esters, isocyanates, chloroformates, alkylsulfonyl halides, arylsulfonyl halides or an acid with a coupling reagent such as 1-(3-dimethylaminopropyl)-3-ethylcarbodiimide hydrochloride or 1,3-dicyclohexylcarbodiimide or the like. Alternatively, the acylation can be carried out on the (heterocyclic)alkylamine prior to incorporation onto the pyrimidine ring of the instant invention.

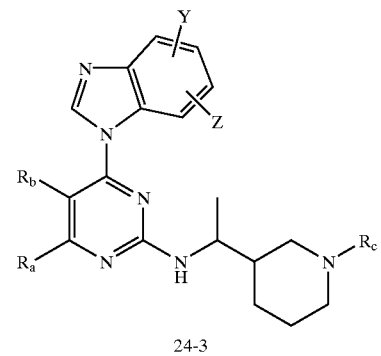

The preparation of 2-(piperidin-3-yl)ethylamino-4-[benzimidazol-1-yl]pyrimidines such as 24-3 within the scope of the instant invention is detailed in Scheme 24. Treatment of piperidine 24-1 with an alkyl halide, or alkylsulfonate or the like in dichloromethane, dichloroethane, tetrahydrofuran, dioxane, dimethylformamide, dimethylsulfoxide acetone or other suitable solvent in the presence of a tertiary amine base such as triethylamine, diisopropylethylamine or the like affords the alkylpiperidine derivative 24-3. Alternatively, 24-1 can be treated with an aldehyde or ketone under reductive alkylation conditions to give the alkylpiperidine derivative 24-3. Alternatively, the alkylation can be carried out on the (heterocyclic)alkylamine prior to incorporation onto the pyrimidine ring of the instant invention.

SCHEME 25

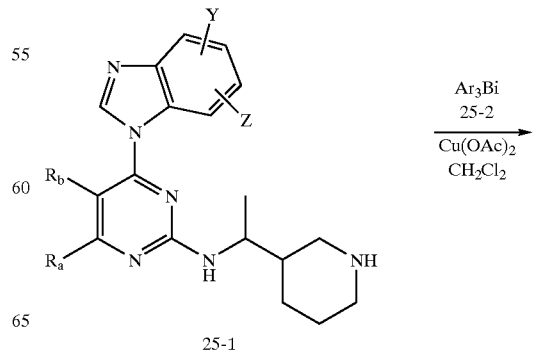

-continued

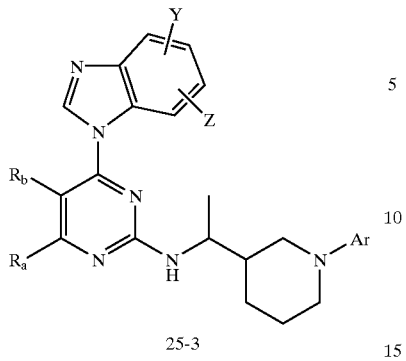

25-3

The preparation of 2-(N-arylpiperidine)ethylamino-4-[benzimidazol-1-yl]pyrimidines such as 25-3 within the scope of the instant invention is detailed in Scheme 12. A 2-(piperidin-3-yl)ethylamino-4-[benzimidazol-1-yl]pyrimidine 25-1 is treated with a triarylbismuth 25-2 in the presence of stoichiometric copper(II)acetate or with a tri-arylbismuth diacetate or other pentavalent organobismuth in the presence of catalytic copper(II)acetate to afford 25-3. An alternate procedure involves reaction of a 2-(piperidin-3-yl)ethylamino-4-[benzimidazol-1-yl]pyrimidine 25-1 with an aryl halide in the presence of a palladium catalyst and strong base according to the procedure of Buchwald et al (J. Am. Chem. Soc. 1997, 119, 8451). Alternatively, the arylation can be carried out on the (heterocyclic)alkylamine prior to incorporation onto the pyrimidine ring of the instant invention.

SCHEME 26

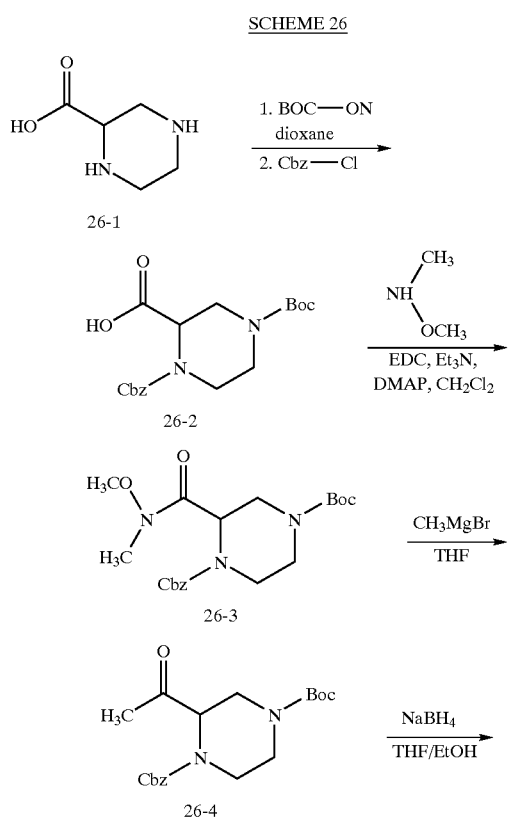

-continued

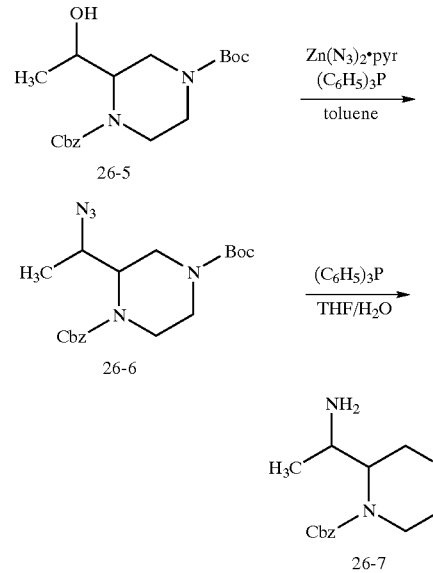

The preparation of piperazine substituted alkylamines such as 26-7 as intermediates that can be used for the synthesis of compounds within the scope of the instant invention is detailed in Scheme 26. The nitrogens of the commercially available piperazine-2-carboxylic acid can be sequentially protected with a tert-butyloxycarbonyl group using tert-(butoyxcarbonyloxyimino)-2-phenylacetonitrile (BOC—ON) and benzyloxycarbonyl group using benzyl-chloroformate to afford 26-2. Condensation of the carboxylic acid group of 26-2 with N-methoxy-N-methyl amine using a coupling agent such as 1,3-dicyclohexylcarbodiimide, 1-(3-dimethylaminopropyl)-3-ethylcarbodiimide hydrochloride or the like affords the corresponding amide 26-3. Addition of methylmagnesium bromide affords the acetylpiperazine 26-4. The carbonyl of 26-4 is reduced using sodium borohydride to give alcohol 26-5. Treatment of 26-5 with zinc azide pyridine complex in the presence of triphenylphosphine in toluene affords azido compound 26-6. Reduction of the azide to the corresponding amine by treatment with triphenylphosphine in aqueous THF gives the desired amine 26-7. Alternatively, the azide can be reduced by hydrogenation over a catalyst.

SCHEME 27

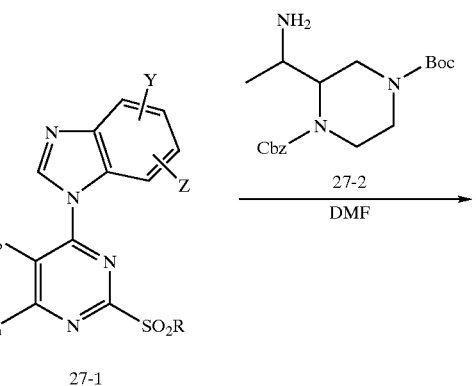

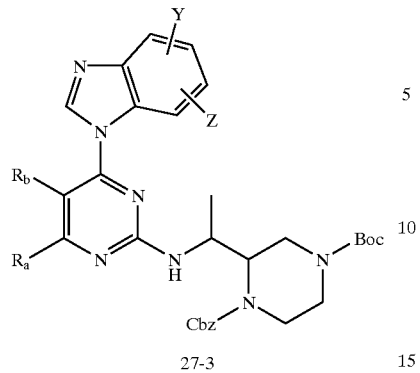

27-3

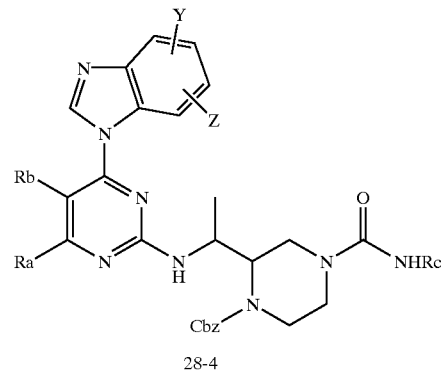

28-4

The preparation of 2-(piperazin-2-yl)ethylamino-4-[benzimidazol-1-yl]pyrimidines such as 27-3 within the scope of the instant invention is detailed in Scheme 27. Sulfone 27-1 described in Scheme 7 can be reacted with a piperazine-substituted alkylamines such as 27-2 in dimethyformamide, dimethylsulfoxide, toluene, 1-methyl-2-pyrrolidinone, isopropanol or other suitable solvent with or without heating to give the N-benzyloxycarbonylprotected heterocycle 27-3. Alternatively, the (piperidin-3-yl)ethylamino can be affixed to the pyrimidine ring prior to the benzimidazole as described in Scheme 3, Scheme 6 and Scheme 8.

SCHEME 28

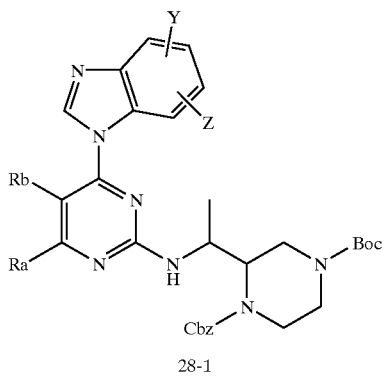

28-1

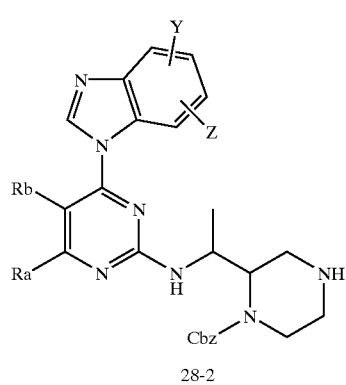

28-2

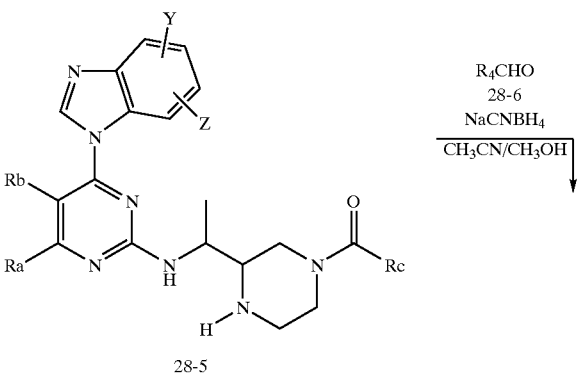

28-5

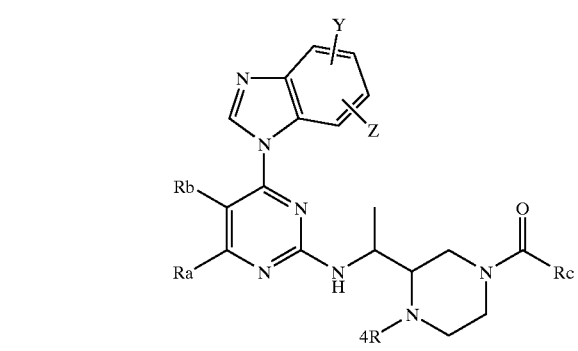

28-7

The preparation of 2-(piperazin-2-yl)ethylamino-4-[benzimidazol-1-yl]pyrimidines such as 28-7 within the scope of the instant invention is detailed in Scheme 23. Removal of the tert-butyloxycarbonyl protecting group of 28-1 via hydrolysis using trifluoroacetic acid affords the mono-deprotected compound 28-2 within the scope of the instant invention. Subsequent acylation with an isocyanate 28-3 in pyridine gives 28-4. Alternatively, acylation can be carried out using an acid chloride or another acid halide, or other acylating agents such as acid anhydrides, esters, chloroformates, alkylsulfonyl halides, arylsulfonyl halides in pyridine or in a non-protic solvent such as methylene chloride, chloroform, tetrahydrofuran, toluene or the like in the presence of a tertiary amine base. Additionally, acylation can be carried out with an acid employing a coupling reagent such as 1-(3-dimethylaminopropyl)-3-ethylcarbodiimide hydrochloride or 1,3-dicyclohexylcarbodiimide or the like. Alternatively, the secondary amine of the piperazine of compound 28-2 may be alkylated as described in Scheme 24 or arylated as described in Scheme 25. Deprotection of the benzyloxycarbonyl group can be effected by HBr in acetic acid to afford 28-5. Alkylation of 28-5 can be achieved by condensation with an aldehyde 28-6 followed by reduction using sodium borohydride, sodium cyanoborohydride, sodium triacetoxyborohydride or the like. Alternatively, the secondary amine of compound 28-5 can be acylated, alkylated or arlated as described above. Alternatively, modification of the piperazine-substituted-ethylamine can be carried out prior to incorporation onto the pyrimidine ring of the instant invention.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims, which follow, and that such claims be interpreted as broadly as is reasonable.

EXAMPLE 1

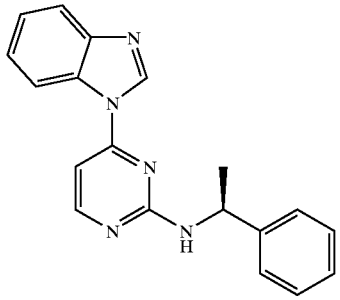

2-[(S)-1-Phenylethylamino]-4-[benzimidazol-1-yl]pyrimidine

Step A: 2-Methylthio-4-[benzimidazol-1-yl]pyrimidine

A mixture of NaH (0.548 mg, 22.8 mmol), benzimidazole (0.52 g, 21.3 mmol) and 4-chloro-2-methylthiopyrimidine (2.48 mL, 21.3 mmol) in 30 mL of DMF was heated to 100° C. for 30 min. The reaction was quenched with $H_2O$ and extracted with EtOAc. The combined organic fractions were washed with brine, dried over $MgSO_4$, filtered and concentrated. The residue was purified by chromatography (silica, 0–10% MeOH:$CH_2Cl_2$) to give 1.99 g of the title compound. $^1$H NMR (500 MHz, $CDCl_3$): δ 8.69 (s, 1H); 8.64 (d, J=5.5 Hz, 1H); 8.22 (dd, J=1.4, 7.3 Hz); 7.89 (dd, J=1.6, 7.3 Hz); 7.44 (m, 2H); 7.23 (d, J=5.7 Hz, 1H); 2.69 (s, 3H).

Step B: 2-Methanesulfonyl-4-[benzimidazol-1-yl]pyrimidine

To a solution of 2-methylthio-4-[benzimidazol-1-yl]pyrimidine (1.99 g, 8.21 mmol) in $CH_2Cl_2$ (50 mL) at 0° C. was added 3-chloroperoxybenzoic acid (2.8 g, 16 mmol). The reaction was permitted to warm to room temperature and stirred. After 24 h, 2.8 g more of 3-chloroperoxybenzoic acid was added. After 24 h, saturated $NaHCO_3$ solution was added and the mixture was extracted twice with $CH_2Cl_2$. The combined organic fractions were washed with brine, dried over $MgSO_4$, filtered and the filtrate was concentrated. The residue was purified by chromatography (silica, 1:1 hexanes: EtOAc) give 0.59 g of the title compound. $^1$H NMR (500 MHz, $CDCl_3$): δ 9.00 (d, J=5.7 Hz, 1H); 8.72 (s, 1H); 8.40 (d, J=8.2 Hz, 1H); 7.91 (d, J=7.7 Hz, 1H); 7.76 (d, J=5.7 Hz, 1H); 7.53 (m, 1H); 7.48 (m, 1H); 3.46 (s, 3H).

Step C: 2-[(S)-1-Phenylethylamino]-4-[benzimidazol-1-yl]pyrimidine

A solution of 2-methanesulfonyl-4-[benzimidazol-1-yl]pyrimidine (0.203 g, 0.74 mmol) and (S)-1-phenylethylamine (0.15 mL, 1.16 mmol) in 2 mL of xylenes was heated to 100° C. After 8 h, the reaction mixture was concentrated and purified by chromatography (silica, 1:1 hexanes: EtOAc, then 1:1 $CH_2Cl_2$: EtOAc) to give 0.133 g of the title compound. $^1$H NMR (500 MHz, $CDCl_3$): δ 8.49 (br s, 1H); 8.39 (d, J=5.5 Hz, 1H); 7.83 (d, J=8.0 Hz, 1H); 7.3–7.5 (m, 8H); 6.79 (d, J=5.5 Hz, 1H); 5.75 (br s, 1H); 5.21 (br s, 1H); 1.65 (d, J=6.9 Hz, 3H).

EXAMPLE 2

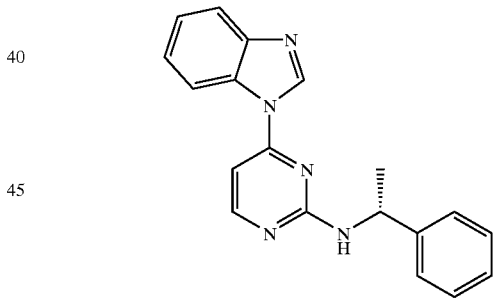

2-[(R)-1-Phenylethylamino]-4-[benzimidazol-1-yl]pyrimidine 2-methanesulfonyl-4-[benzimidazol-1-yl]pyrimidine was reacted with (R)-1-phenylethylamine according to the procedure described in EXAMPLE 1, Step C to afford the title compound. Mass Spectrum (CI): m/e 316.1 (M+1). $^1$H NMR (500 MHz, $CDCl_3$): δ 8.49 (br s, 1H); 8.37 (d, J=5.1 Hz, 1H); 7.83 (d, J=8.0 Hz, 1H); 7.3–7.5 (m, 8H); 6.77 (d, J=5.3 Hz, 1H); 6.03 (br s, 1H); 5.22 (br s, 1H); 1.65 (d, J=7.0 Hz, 3H).

EXAMPLE 3

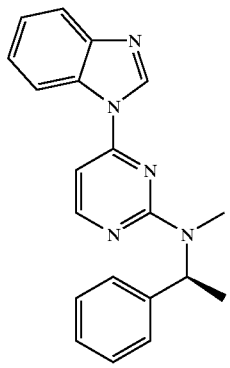

2-[(S)-1-Phenylethyl-N-methylamino]-4-[benzimidazol-1-yl]pyrimidine

2-Methanesulfonyl-4-[benzimidazol-1-yl]pyrimidine was reacted with (S)-N-α-dimethylbenzylamine according to the procedure described in EXAMPLE 1, Step C to afford the title compound. Mass Spectrum (ESI): m/e 330.2 (M+1). $^1$H NMR (500 MHz, CD$_3$OD): δ 8.89 (s, 1H); 8.48 (d, J=5.5 Hz, 1H); 8.28 (br s, 1H); 7.73 (m, 1H); 7.36 (m, 6H); 7.25 (m, 1H); 7.04 (d, J=5.5 Hz, 1H); 6.28 (m, 1H); 2.98 (s, 3H); 1.66 (d, J=7.1 Hz, 3H).

EXAMPLE 4

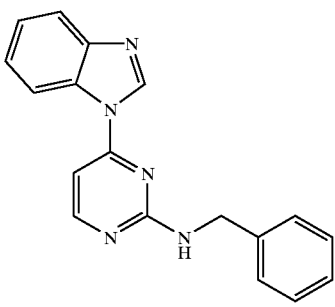

2-Benzylamino-4-[benzimidazol-1-yl]pyrimidine

2-Methanesulfonyl-4-[benzimidazol-1-yl]pyrimidine was reacted with benzylamine according to the procedure described in EXAMPLE 1, Step C to afford the title compound.

EXAMPLE 5

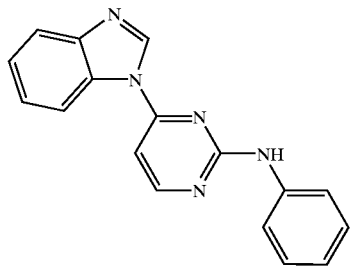

2-Phenylamino-4-[benzimidazol-1-yl]pyrimidine

2-Methanesulfonyl-4-[benzimidazol-1-yl]pyrimidine was reacted with analine according to the procedure described in EXAMPLE 1, Step C to afford the title compound.

EXAMPLE 6

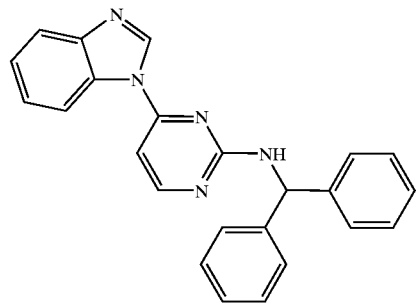

2-[1,1-Diphenylmethylamino]-4-[benzimidazol-1-yl]pyrimidine

2-Methanesulfonyl-4-[benzimidazol-1-yl]pyrimidine was reacted with aminodiphenylmethane according to the procedure described in EXAMPLE 1, Step C to afford the title compound. Mass Spectrum (ESI): m/e 378.3 (M+1). $^1$H NMR (500 MHz, CDCl$_3$): δ partial 8.41 (br s, 1H); 8.24 (br s, 1H); 7.33 (m, 2H); 6.79 (s, 1H); 6.45 (br s, 1H); 6.29 (br s, 1H).

EXAMPLE 7

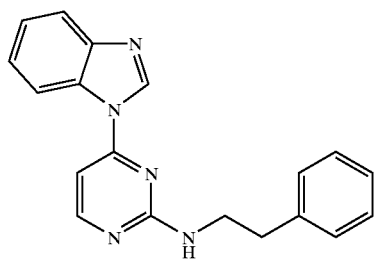

2-[2-Phenylethylamino]-4-[benzimidazol-1-yl]pyrimidine

2-Methanesulfonyl-4-[benzimidazol-1-yl]pyrimidine was reacted with 2-phenylethylamine according to the procedure described in EXAMPLE 1, Step C to afford the title compound.

EXAMPLE 8 omitted

EXAMPLE 9

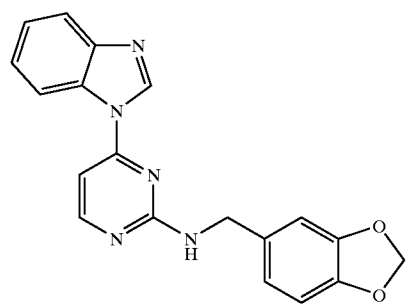

2-[3,4-Methylenedioxybenzylamino]-4-[benzimidazol-1-yl]pyrimidine

2-Methanesulfonyl-4-[benzimidazol-1-yl]pyrimidine was reacted with piperonylamine according to the procedure described in EXAMPLE 1, Step C to afford the title compound. Mass Spectrum (ESI): m/e 346.2 (M+1). $^1$H NMR (500 MHz, CDCl$_3$): δ 8.61 (s, 1H); 8.42 (br s, 1H); 8.11 (br s, 1H); 7.86 (m, 1H); 7.38 (m, 2H); 6.89 (m, 2H); 6.83 (m, 2H); 5.97 (s, 2H); 5.79 (br s, 1H); 4.65 (d, J=5.7 Hz, 2H).

EXAMPLE 10

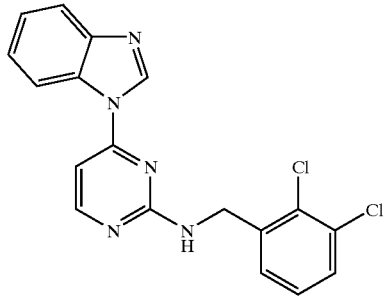

2-[2,3-Dichlorobenzylamino]-4-[benzimidazol-1-yl] pyrimidine

2-Methanesulfonyl-4-[benzimidazol-1-yl]pyrimidine was reacted with 2,3-dichlorobenzylamine according to the procedure described in EXAMPLE 1, Step C to afford the title compound. Mass Spectrum (ESI): m/e 370.1 (M+1). $^1$H NMR (500 MHz, CDCl$_3$): δ partial 8.58 (s, 1H); 8.44 (d, J=5.5 Hz, 1H); 7.93 (br s, 1H); 7.85 (d, J=8.3 Hz, 1H); 7.19 (t, J=5.8 Hz, 1H); 6.86 (d, J=5.5 Hz, 1H); 5.88 (br s, 1H); 4.86 (d, J=6.4 Hz, 2H).

EXAMPLE 11

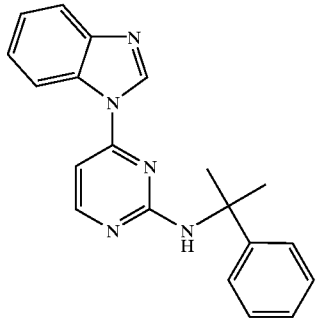

2-[1-Phenyl-1-methylethylamino]-4-[benzimidazol-1-yl]pyrimidine

2-Methanesulfonyl-4-[benzimidazol-1-yl]pyrimidine was reacted with cumylamine according to the procedure described in EXAMPLE 1, Step C to afford the title compound. Mass Spectrum (ESI): m/e 330.1 (M+1). $^1$H NMR (500 MHz, CDCl$_3$): δ partial 8.37 (d, J=4.8 Hz, 1H); 8.05 (br s, 1H); 7.77 (d, J=7.6 Hz; 1H); 7.54 (d, J=7.8 Hz, 2H); 7.41 (m, 2H); 6.75 (d, J=5.5 Hz; 1H); 5.91 (br s, 1H); 1.81 (s, 6H).

EXAMPLE 12

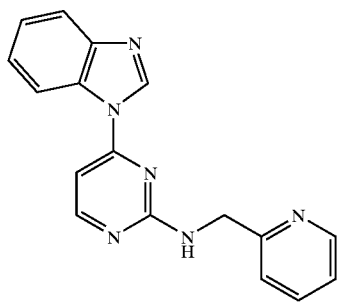

2-[2-Pyridylmethylamino]-4-[benzimidazol-1-yl] pyrimidine

2-Methanesulfonyl-4-[benzimidazol-1-yl]pyrimidine was reacted with 2-(aminomethyl)pyridine according to the procedure described in EXAMPLE 1, Step C to afford the title compound. Mass Spectrum (ESI): m/e 303.0 (M+1). $^1$H NMR (500 MHz, CDCl$_3$): δ 8.63 (m, 2H); 8.46 (d, J=5.3 Hz, 1H); 8.12 (br s, 1H); 7.86 (m, 1H); 7.70 (m, 1H); 7.38 (m, 3H); 7.24 (m, 1H); 6.85 (d, J=5.3 Hz, 1H); 6.50 (br s, 1H); 4.87 (d, J=5.4 Hz, 2H).

EXAMPLE 13

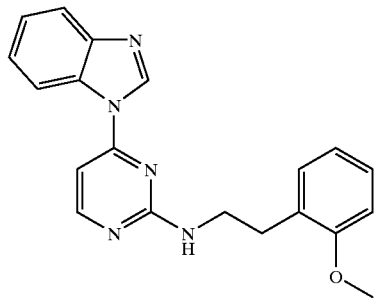

2-[2-[2-Methoxyphenyl)ethylamino]-4-[benzimidazol-1-yl]pyrimidine

2-Methanesulfonyl-4-[benzimidazol-1-yl]pyrimidine was reacted with 2-(2-methoxyphenyl)ethylamine according to the procedure described in EXAMPLE 1, Step C to afford the title compound. Mass Spectrum (ESI): m/e 346.1 (M+1). $^1$H NMR (500 MHz, CDCl$_3$): δ 8.66 (br s, 1H); 8.38 (br s, 1H); 8.22 (br s, 1H); 7.88 (d, J=6.7 Hz, 1H); 7.40 (m, 2H); 7.22 (m, 2H); 6.92 (m, 2H); 6.78 (d, J=5.4 Hz, 1H); 5.60 (br s, 1H); 3.88 (s, 3H); 3.78 (m, 2H); 3.03 (t, J=6.7 Hz, 2H).

EXAMPLE 14

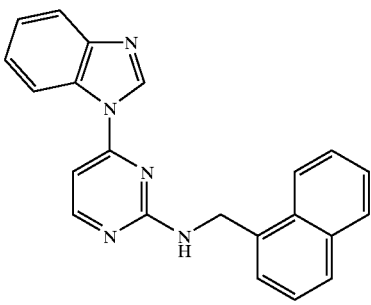

2-[1-Naphthylmethylamino]-4-[benzimidazol-1-yl]pyrimidine

2-Methanesulfonyl-4-[benzimidazol-1-yl]pyrimidine was reacted with 1-naphthalenemethylamine according to the procedure described in EXAMPLE 1, Step C to afford the title compound. Mass Spectrum (ESI): m/e 352.0 (M+1). $^1$H NMR (500 MHz, CDCl$_3$): δ partial 8.60 (s, 1H); 8.44 (br s, 1H); 8.12 (m, 1H); 7.94 (m, 1H); 7.85 (m, 2H); 7.59 (m, 2H); 7.48 (m, 1H); 7.32 (br s, 1H); 6.86 (br s, 1H); 5.20 (d, J=5.5 Hz, 2H).

EXAMPLE 15

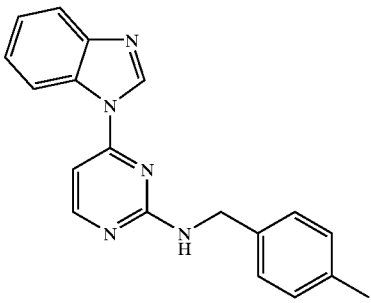

2-[4-Methylbenzylamino]-4-[benzimidazol-1-yl]pyrimidine

2-Methanesulfonyl-4-[benzimidazol-1-yl]pyrimidine was reacted with 4-methylbenzylamine according to the procedure described in EXAMPLE 1, Step C to afford the title compound. Mass Spectrum (ESI): m/e 316.1 (M+1). $^1$H NMR (500 MHz, CDCl$_3$): δ partial 8.60 (s, 1H); 8.41 (br s, 1H); 8.09 (br s, 1H); 7.86 (m, 1H); 7.20 (d, J=8.0 Hz, 1H); 6.83 (d, J=5.3 Hz, 1H); 5.80 (br s, 1H); 4.71 (d, J=5.8 Hz, 2H); 2.37 (s, 3H).

EXAMPLE 16

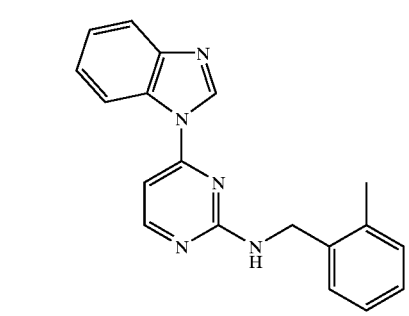

2-[2-Methylbenzylamino]-4-[benzimidazol-1-yl]pyrimidine

2-Methanesulfonyl-4-[benzimidazol-1-yl]pyrimidine was reacted with 2-methylbenzylamine according to the procedure described in EXAMPLE 1, Step C to afford the title compound. Mass Spectrum (CI): m/e 316.2 (M+1). $^1$H NMR (500 MHz, CDCl$_3$): δ partial 8.60 (s, 1H); 8.43 (br s, 1H); 8.05 (br s, 1H); 7.85 (d, J=8.7 Hz, 1H); 6.84 (d, J=5.4 Hz, 1H); 4.73 (d, J=5.7 Hz, 1H); 2.43 (s, 3H).

EXAMPLE 17

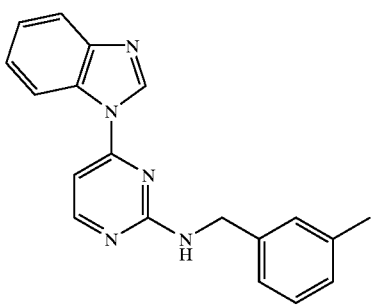

2-[3-Methylbenzylamino]-4-[benzimidazol-1-yl]pyrimidine

2-Methanesulfonyl-4-[benzimidazol-1-yl]pyrimidine was reacted with 3-methylbenzylamine according to the procedure described in EXAMPLE 1, Step C to afford the title compound. Mass Spectrum (CI): m/e 316.2 (M+1). $^1$H NMR (500 MHz, CDCl$_3$): δ partial 8.60 (s, 1H); 8.42 (br s, 1H); 8.09 (br s, 1H); 7.85 (m, 1H); 7.14 (d, J=7.3 Hz, 1H); 6.84 (d, J=5.5 Hz, 1H); 5.82 (br s, 1H); 4.72 (d, J=5.9 Hz, 2H); 2.38 (s, 3H).

EXAMPLE 18

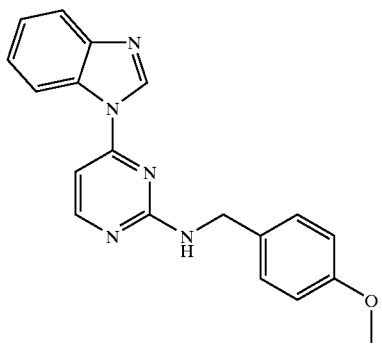

2-[4-Methoxybenzylamino]-4-[benzimidazol-1-yl]pyrimidine

2-Methanesulfonyl-4-[benzimidazol-1-yl]pyrimidine was reacted with 4-methoxybenzylamine according to the procedure described in EXAMPLE 1, Step C to afford the title compound. Mass Spectrum (ESI): m/e 332.2 (M+1). $^1$H NMR (500 MHz, CDCl$_3$): δ 8.61 (s, 1H); 8.42 (br s, 1H); 8.12 (br s, 1H); 7.86 (m, 1H); 7.36 (m, 4H); 6.92 (m, 2H); 6.83 (d, J=5.5 Hz, 1H); 5.76 (br s, 1H); 4.68 (d, J=5.7 Hz, 2H); 3.83 (s, 3H).

EXAMPLE 19

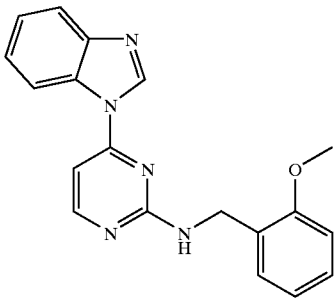

2-[2-Methoxybenzylamino]-4-[benzimidazol-1-yl]pyrimidine

2-Methanesulfonyl-4-[benzimidazol-1-yl]pyrimidine was reacted with 2-methoxybenzylamine according to the procedure described in EXAMPLE 1, Step C to afford the title compound. Mass Spectrum (ESI): m/e 332.1 (M+1). $^1$H NMR (500 MHz, CDCl$_3$): δ partial 8.63 (s, 1H); 8.41 (br s, 1H); 8.12 (br s, 1H); 7.86 (m, 1H); 6.94 (m, 2H); 6.79 (d, J=5.2 Hz, 1H); 5.95 (br s, 1H); 4.74 (d, J=5.9 Hz, 2H); 3.92 (s, 3H).

EXAMPLE 20

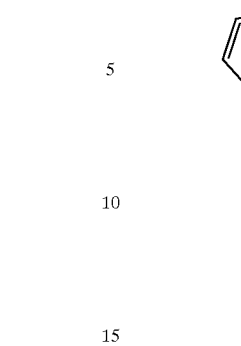

2-[3-Methoxybenzylamino]-4-[benzimidazol-1-yl]pyrimidine

2-Methanesulfonyl-4-[benzimidazol-1-yl]pyrimidine was reacted with 3-methoxybenzylamine according to the procedure described in EXAMPLE 1, Step C to afford the title compound. $^1$H NMR (500 MHz, CDCl$_3$): δ 0.60 (br s, 1H); 8.44 (br s, 1H); 8.08 (br s, 1H); 7.86 (d, J=8.5 Hz, 1H); 7.3–7.5 (m, 3H); 7.02 (d, J=7.6 Hz; 1H); 6.98 (s, 1H); 6.85 (m, 2H); 5.86 (br s, 1H); 4.73 (d, J=5.7 Hz, 2H); 3.82 (s, 3H).

EXAMPLE 21

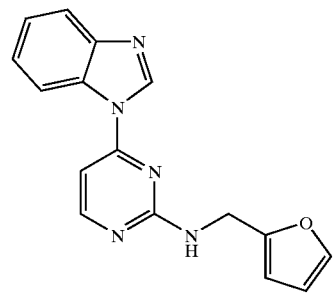

2-[2-Furanylmethylamino]-4-[benzimidazol-1-yl]pyrimidine

2-Methanesulfonyl-4-[benzimidazol-1-yl]pyrimidine was reacted with furfurylamine according to the procedure described in EXAMPLE 1, Step C to afford the title compound. Mass Spectrum (ESI): m/e 292.1 (M+1). $^1$H NMR (500 MHz, CDCl$_3$): δ 8.64 (s, 1H); 8.45 (s, 1H); 8.18 (m, 1H); 7.87 (m, 1H); 7.40 (m, 4H); 6.86 (d, J=5.5 Hz, 1H); 6.35 (m, 1H); 5.71 (br s, 1H); 4.75 (d, J=5.0 Hz, 2H).

EXAMPLE 22

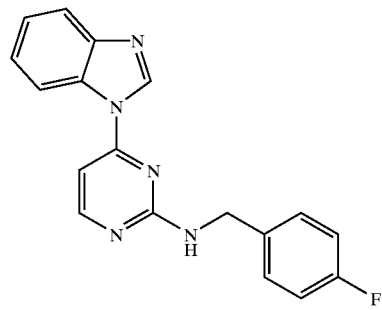

2-[(4-Fluorobenzyl)amino]-4-[benzimidazol-1-yl]pyrimidine

2-Methanesulfonyl-4-[benzimidazol-1-yl]pyrimidine was reacted with 4-fluorobenzylamine according to the procedure described in EXAMPLE 1, Step C to afford the title compound. Mass Spectrum (ESI): m/e 320.1 (M+1). $^1$H NMR (500 MHz, CDCl$_3$): δ 8.60 (s, 1H); 8.43 (br s, 1H); 8.07 (br s, 1H); 7.86 (m, 1H); 7.38 (m, 5H); 7.07 (t, J=8.7 Hz, 1H); 6.85 (d, J=5.5 Hz, 1H); 5.79 (br s, 1H); 4.72 (d, J=5.7 Hz, 2H).

EXAMPLE 23

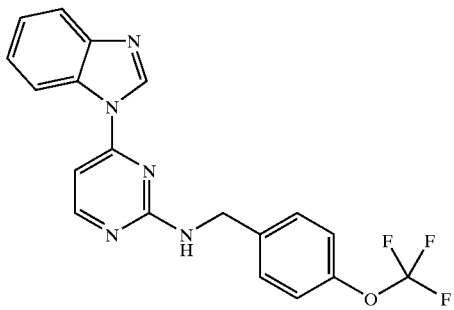

2-[4-Trifluoromethoxybenzylamino]-4-[benzimidazol-1-yl]pyrimidine

2-Methanesulfonyl-4-[benzimidazol-1-yl]pyrimidine was reacted with 4-trifluoromethoxybenzylamine according to the procedure described in EXAMPLE 1, Step C to afford the title compound. Mass Spectrum (ESI): m/e 386.2 (M+1). 1H NMR (500 MHz, CDCl$_3$): d partial 8.59 (s, 1H); 8.44 (br s, 1H); 8.02 (br s, 1H); 7.86 (d, J=8.3 Hz, 1H); 7.45 (d, J=8.4 Hz, 2H); 7.24 (d, J=8.3 Hz, 1H); 6.87 (d, J=5.2 Hz, 1H); 5.84 (br s, 1H); 4.76 (d, J=6.1 Hz, 2H).

EXAMPLE 24

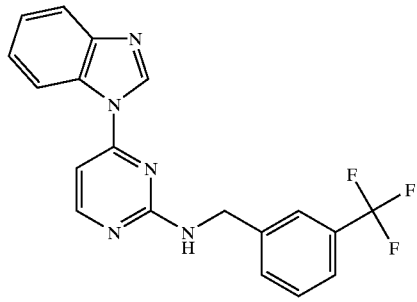

2-[3-Trifluoromethylbenzylamino]-4-[benzimidazol-1-yl]pyrimidine

2-Methanesulfonyl-4-[benzimidazol-1-yl]pyrimidine was reacted with 3-trifluoromethylbenzylamine according to the procedure described in EXAMPLE 1, Step C to afford the title compound. Mass Spectrum (ESI): m/e 370.2 (M+1). $^1$H NMR (500 MHz, CDCl$_3$): δ partial 8.58 (br s, 1H); 8.39 (br s, 1H); 7.85 (d, J=8.2 Hz, 1H); 7.69 (s, 1H); 7.61 (d, J=7.6 Hz, 1H); 7.57 (d, J=7.6 Hz, 1H); 7.49 (m, 1H); 6.85 (d, J=5.3 Hz, 1H); 6.38 (br s, 1H); 4.81 (d, J=6.2 Hz, 2H).

EXAMPLE 25

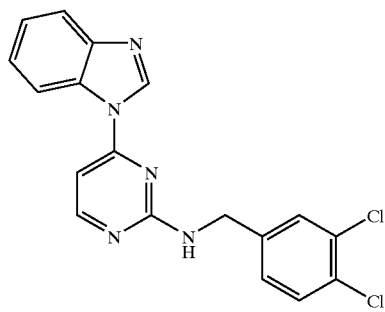

2-[3,4-Dichlorobenzylamino]-4-[benzimidazol-1-yl]pyrimidine

2-Methanesulfonyl-4-[benzimidazol-1-yl]pyrimidine was reacted with 3,4-dichlorobenzylamine according to the procedure described in EXAMPLE 1, Step C to afford the title compound. Mass Spectrum (ESI): m/e 370.1 (M+1). $^1$H NMR (500 MHz, CDCl$_3$): δ partial 8.58 (s, 1H); 8.43 (d, J=5.0 Hz, 1H); 8.01 (br s, 1H); 7.85 (d, J=8.7 Hz, 1H); 7.52 (d, J=1.6 Hz, 1H); 7.25 (m, 1H); 6.87 (d, J=5.5 Hz, 1H); 6.00 (br s, 1H); 4.71 (d, H=6.0 Hz, 2H).

EXAMPLE 26

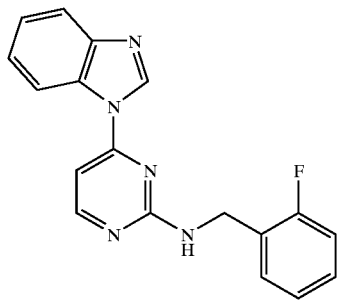

2-[2-Fluorobenzylamino]-4-[benzimidazol-1-yl]pyrimidine

2-Methanesulfonyl-4-[benzimidazol-1-yl]pyrimidine was reacted with 2-fluorobenzylamine according to the procedure described in EXAMPLE 1, Step C to afford the title compound. Mass Spectrum (ESI): m/e 320.1 (M+1). $^1$H NMR (500 MHz, CDCl$_3$): δ partial 8.62 (s, 1H); 8.43 (br s, 1H); 8.09 (br s, 1H); 7.86 (m, 1H); 7.13 (m, 2H); 6.85 (d, J=5.3 Hz, 1H; 5.87 (br s, 1H); 4.81 (d, J=6.1 Hz, 2H).

EXAMPLE 27

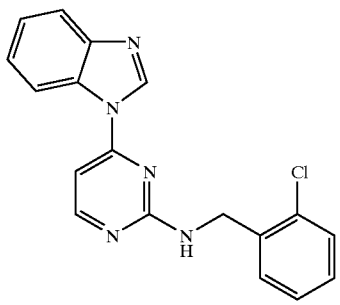

2-[2-Chlorobenzylamino]-4-[benzimidazol-1-yl]pyrimidine

2-Methanesulfonyl-4-[benzimidazol-1-yl]pyrimidine was reacted with 2-chlorobenzylamine according to the procedure described in EXAMPLE 1, Step C to afford the title compound. Mass Spectrum (EI): m/e 335.0 (M+). $^1$H NMR (500 MHz, CDCl$_3$): δ partial 8.60 (s, 1H); 8.43 (d, J=3.9 Hz, 1H); 8.02 (br s, 1H); 7.85 (m, 1H); 7.37 (m, 2H); 6.85 (d, J=5.5 Hz, 1H); 5.93 (br s, 1H); 4.85 (d, J=6.2 Hz, 2H).

EXAMPLE 28

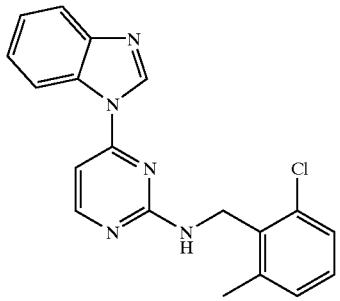

2-[2-Chloro-6-methylbenzylamino]-4-[benzimidazol-1-yl]pyrimidine

2-Methanesulfonyl-4-[benzimidazol-1-yl]pyrimidine was reacted with 2-chloro-6-methylbenzylamine according to the procedure described in EXAMPLE 1, Step C to afford the title compound. Mass Spectrum (EI): m/e 350.3 (M+1). $^1$H NMR (500 MHz, CDCl$_3$): δ 8.66 (s, 1H); 8.40 (br s, 1H); 8.21 (s, 1H); 7.87 (d, J=7.6 Hz, 1H); 7.40 (m, 2H); 7.30 (d, J=8.0 Hz, 1H); 7.17 (m, 2H); 6.85 (d, J=5.5 Hz, 1H); 5.56 (br s, 1H); 4.90 (d, J=5.0 Hz, 2H); 2.51 (s, 3H).

EXAMPLE 29

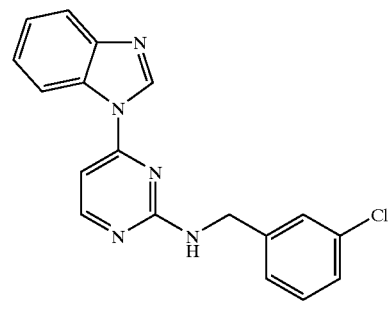

2-[3-Chlorobenzylamino]-4-[benzimidazol-1-yl]pyrimidine

2-Methanesulfonyl-4-[benzimidazol-1-yl]pyrimidine was reacted with 3-chlorobenzylamine according to the procedure described in EXAMPLE 1, Step C to afford the title compound. Mass Spectrum (ESI): m/e 336.1 (M+1). $^1$H NMR (500 MHz, CDCl$_3$): δ 8.58 (s, 1H); 8.45 (d, J=5.3 Hz, 1H); 8.01 (br s, 1H); 7.86 (m, 1H); 7.28 (m, 6H); 6.87 (d, J=5.3 Hz, 1H); 5.80 (br s, 1H); 4.74 (d, J=5.9 Hz, 2H).

EXAMPLE 30

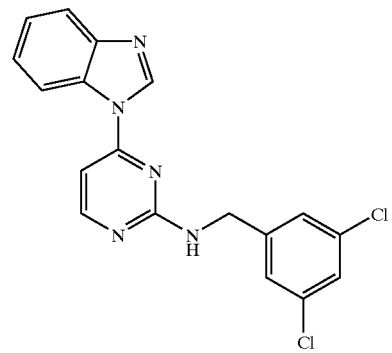

2-[3,5-Dichlorobenzylamino]-4-[benzimidazol-1-yl]pyrimidine

2-Methanesulfonyl-4-[benzimidazol-1-yl]pyrimidine was reacted with 3,5-dichlorobenzylamine according to the procedure described in EXAMPLE 1, Step C to afford the title compound. Mass Spectrum (EI): m/e 370.3 (M+1). $^1$H NMR (500 MHz, CDCl$_3$): δ 8.58 (s, 1H); 8.45 (d, J=5.5 Hz, 1H); 7.98 (br s, 1H); 7.86 (m, 1H); 7.38 (m, 2H); 7.31 (s, 2H); 6.89 (d, J=5.5 Hz, 1H); 5.88 (br s, 1H); 4.72 (d, J=6.4 Hz, 2H).

EXAMPLE 31

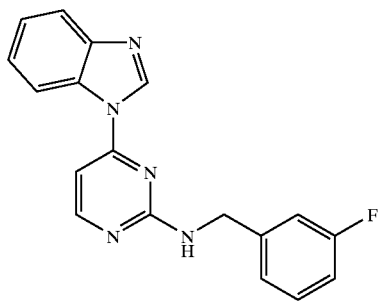

2-[3-Fluorobenzylamino]-4-[benzimidazol-1-yl]
pyrimidine

2-Methanesulfonyl-4-[benzimidazol-1-yl]pyrimidine was reacted with 3-fluorobenzylamine according to the procedure described in EXAMPLE 1, Step C to afford the title compound. Mass Spectrum (ESI): m/e 320.2 (M+1). $^1$H NMR (500 MHz, CD$_3$OD): δ partial 8.84 (br s, 1H); 8.39 (d, J=5.5 Hz, 1H); 7.97 (br s, 1H); 7.71 (d, J=8.2 Hz, 1H); 7.13 (d, J=10.1 Hz, 1H); 7.06 (d, J=5.5 Hz, 1H); 6.96 (m, 1H); 4.69 (s, 2H).

EXAMPLE 32

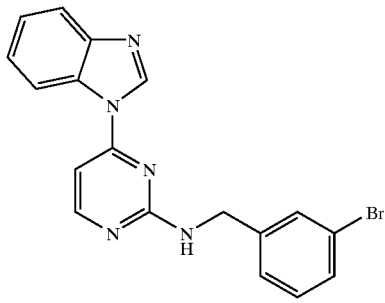

2-[3-Bromobenzylamino]-4-[benzimidazol-1-yl]
pyrimidine

2-Methanesulfonyl-4-[benzimidazol-1-yl]pyrimidine was reacted with 3-bromobenzylamine according to the procedure described in EXAMPLE 1, Step C to afford the title compound. Mass Spectrum (ESI): m/e 380.2, 382.2 (M+1). $^1$H NMR (500 MHz, CDCl$_3$): δ partial 8.58 (s, 1H); 8.44 (d, J=5.3 Hz, 1H); 8.01 (br s, 1H); 7.85 (m, 1H); 7.58 (s, 1H); 7.45 (d, J=7.5 Hz, 1H); 6.87 (d, J=5.5 Hz, 1H); 5.83 (br s, 1H); 4.74 (d, J=6.1 Hz, 2H).

EXAMPLE 33

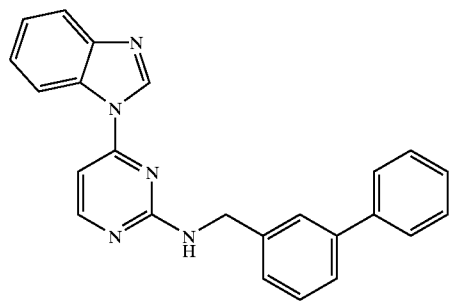

2-[3-Phenylbenzylamino]-4-[benzimidazol-1-yl]
pyrimidine

2-Methanesulfonyl-4-[benzimidazol-1-yl]pyrimidine was reacted with 3-phenylbenzylamine according to the procedure described in EXAMPLE 1, Step C to afford the title compound. Mass Spectrum (ESI): m/e 378.1 (M+1). $^1$H NMR (500 MHz, CDCl$_3$): δ 8.60 (s, 1H); 8.44 (br s, 1H); 8.09 (br s, 1H); 7.85 (m, 1H); 7.65 (s, 1H); 7.59 (d, J=7.3 Hz, 2H); 7.56 (m, 1H); 7.41–7.49 (m, 4H); 7.36 (m, 3H); 6.85 (d, J=5.2 Hz, 1H); 5.83 (br s, 1H); 4.83 (d, J=5.9 Hz, 2H).

EXAMPLE 34

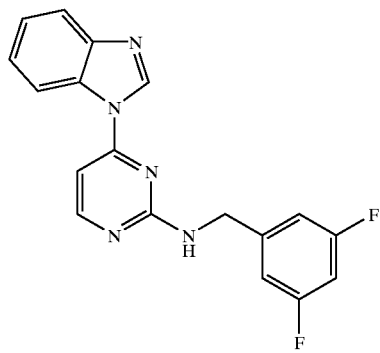

2-[3,5-Difluorobenzylamino]-4-[benzimidazol-1-yl]
pyrimidine

2-Methanesulfonyl-4-[benzimidazol-1-yl]pyrimidine was reacted with 3,5-difluorobenzylamine according to the procedure described in EXAMPLE 1, Step C to afford the title compound. Mass Spectrum (ESI): m/e 338.1 (M+1). $^1$H NMR (500 MHz, CDCl$_3$): δ 8.58 (s, 1H); 8.45 (d, J=5.5 Hz, 1H); 7.98 (br s, 1H); 7.85 (d, J=8.5 Hz, 1H); 7.36 (m, 2H); 6.95 (d, J=6.4 Hz, 2H); 6.89 (d, J=5.4 Hz, 1H); 6.74 (m, 1H); 5.87 (br s, 1H); 4.75 (d, J=6.4 Hz, 2H).

EXAMPLE 35

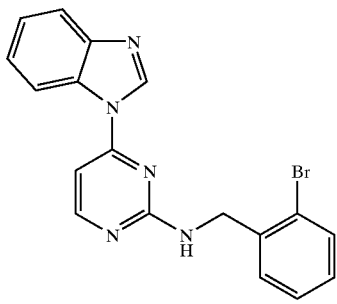

2-[2-Bromobenzylamino]-4-[benzimidazol-1-yl]
pyrimidine

2-Methanesulfonyl-4-[benzimidazol-1-yl]pyrimidine was reacted with 2-bromobenzylamine according to the procedure described in EXAMPLE 1, Step C to afford the title compound. Mass Spectrum (CI): m/e 380.2, 382.2 (M+1). $^1$H NMR (500 MHz, CDCl$_3$): δ partial 8.60 (s, 1H); 8.44 (br s, 1H); 8.02 (br s, 1H); 7.85 (m, 1H); 7.64 (d, J=5.6 Hz, 1H); 7.48 (d, J=7.3 Hz, 1H); 7.18 (m, 1H); 6.86 (d, J=5.5 Hz, 1H); 6.18 (br s, 1H); 4.83 (d, J=6.4 Hz, 2H).

EXAMPLE 36

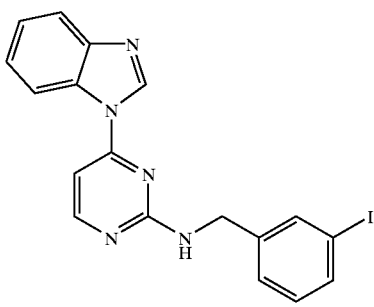

2-[3-Iodobenzylamino]-4-[benzimidazol-1-yl]
pyrimidine

2-Methanesulfonyl-4-[benzimidazol-1-yl]pyrimidine was reacted with 3-iodobenzylamine according to the procedure described in EXAMPLE 1, Step C to afford the title compound. Mass Spectrum (ESI): m/e 428.1 (M+1). $^1$H NMR (500 MHz, CDCl$_3$): δ 8.59 (s, 1H); 8.44 (d, J=4.7 Hz, 1H); 8.02 (br s, 1H); 7.86 (m, 1H); 7.79 (s, 1H); 7.65 (d, J=7.8 Hz, 1H); 7.38 (m, 3H); 7.12 (t, J=7.8 Hz, 1H); 6.87 (d, J=5.3 Hz, 1H); 5.78 (br s, 1H); 4.71 (d, J=5.9 Hz, 2H).

EXAMPLE 37

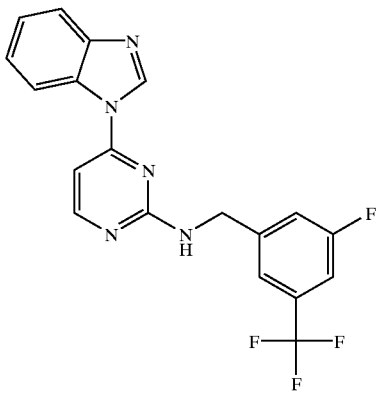

2-[3-Fluoro-5-trifluoromethylbenzylamino]-4-
[benzimidazol-1-yl]pyrimidine

2-Methanesulfonyl-4-[benzimidazol-1-yl]pyrimidine was reacted with 3-fluoro-5-trifluoromethylbenzylamine according to the procedure described in EXAMPLE 1, Step C to afford the title compound. Mass Spectrum (ESI): m/e 388.1 (M+1). $^1$H NMR (500 MHz, CDCl$_3$): δ partial 8.58 (s, 1H); 8.46 (d, J=5.4 Hz, 1H); 7.99 (br s, 1H); 7.86 (d, J=8.7 Hz, 1H); 7.49 (s, 1H); 6.90 (d, J=5.5 Hz, 1H); 5.88 (br s, 1H); 4.82 (d, J=6.2 Hz, 2H).

EXAMPLE 38

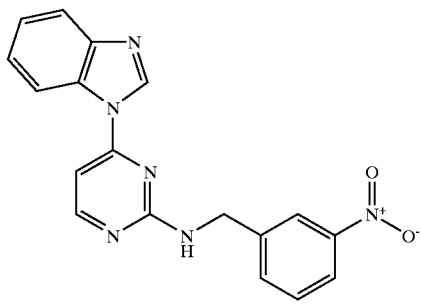

2-[3-Nitrobenzylamino]-4-[benzimidazol-1-yl]
pyrimidine

2-Methanesulfonyl-4-[benzimidazol-1-yl]pyrimidine was reacted with 3-nitrobenzylamine according to the procedure described in EXAMPLE 1, Step C to afford the title compound. Mass Spectrum (ESI): m/e 347.0 (M+1). $^1$H NMR (500 MHz, CDCl$_3$): δ 8.58 (br s, 1H); 8.46 (d, J=5.5 Hz, 1H); 8.31 (s, 1H); 8.17 (d, J=8.5 Hz, 1H); 8.00 (br s, 1H); 7.85 (d, J=8.0 Hz, 1H); 7.77 (d, J=7.6 Hz, 1H); 7.56 (t, J=7.9 Hz, 1H); 7.38 (m, 2H); 6.90 (d, J=5.5 Hz, 1H); 5.94 (br s, 1H); 4.87 (d, J=6.2 Hz, 2H).

EXAMPLE 39

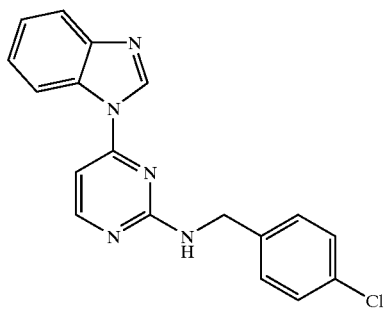

2-[4-Chlorobenzylamino]-4-[benzimidazol-1-yl]pyrimidine

2-Methanesulfonyl-4-[benzimidazol-1-yl]pyrimidine was reacted with 4-chlorobenzylamine according to the procedure described in EXAMPLE 1, Step C to afford the title compound. Mass Spectrum (ESI): m/e 336.0 (M+1). $^1$H NMR (500 MHz, CDCl$_3$): δ partial 8.59 (s, 1H); 8.43 (d, J=4.6 Hz, 1H); 8.02 (br s, 1H); 7.86 (m, 1H); 6.86 (d, J=5.5 Hz, 1H); 5.79 (br s, 1H ); 4.73 (d, J=5.9 Hz, 2H).

EXAMPLE 40

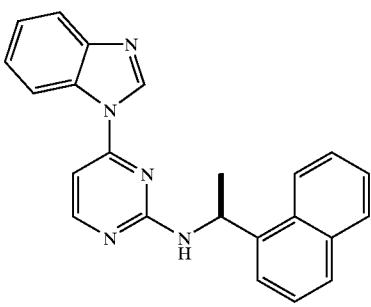

2-[(S)-1-(1-Naphthyl)ethylamino]-4-[benzimidazol-1-yl]pyrimidine

2-Methanesulfonyl-4-[benzimidazol-1-yl]pyrimidine was reacted with (S)-1-(1-naphthyl)ethylamine according to the procedure described in EXAMPLE 1, Step C to afford the title compound. Mass Spectrum (ESI): m/e 366.1 (M+1). $^1$H NMR (500 MHz, CDCl$_3$): δ partial 8.40 (d, J=4.6 Hz, 1H); 8.34 (br s, 1H); 8.23 (d, J=8.2 Hz, 1H); 7.97 (d, J=7.6 Hz, 1H); 7.82 (d, J=8.2 Hz, 1H); 7.67 (d, J=6.9 Hz, 1H); 7.47 (t, J=7.7 Hz, 1H); 6.77 (s, 1H); 6.03 (br s, 2H); 1.80 (d, J=6.7 Hz, 3H).

EXAMPLE 41

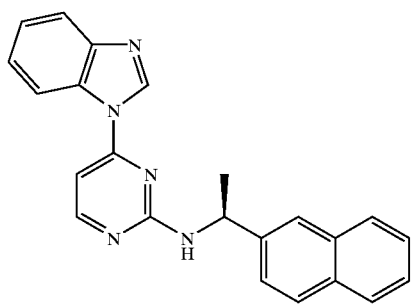

2-1(S)-1-(2-Naphthyl)ethylamino]-4-[benzimidazol-1-yl]pyrimidine

2-Methanesulfonyl-4-[benzimidazol-1-yl]pyrimidine was reacted with (S)-1-(2-naphthyl)ethylamine according to the procedure described in EXAMPLE 1, Step C to afford the title compound. Mass Spectrum (ESI): m/e 366.3 (M+1). $^1$H NMR (500 MHz, CDCl$_3$): δ partial 8.51 (br s, 1H); 8.40 (d, J=5.5 Hz, 1H); 7.58 (m, 1H); 7.48 (m, 2H); 7.32 (br s, 1H); 6.78 (d, J=5.2 Hz, 1H); 5.87 (br s, 1H); 5.39 (br s, 1H); 1.73 (d, J=6.8 Hz, 3H).

EXAMPLE 42

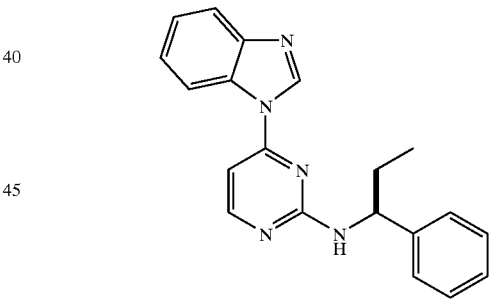

2-[(S)-1-Phenylpropylamino]-4-[benzimidazol-1-yl]pyrimidine

2-Methanesulfonyl-4-[benzimidazol-1-yl]pyrimidine was reacted with (S)-1-phenylpropylamine according to the procedure described in EXAMPLE 1, Step C to afford the title compound. Mass Spectrum (ESI): m/e 330.3 (M+1). $^1$H NMR (500 MHz, CDCl$_3$): δ partial 8.49 (br s, 1H); 8.38 (d, J=5.5 Hz, 1H); 7.83 (d, J=7.6 Hz, 1H); 7.27–7.44 (m, 6H); 6.77 (d, J=5.5 Hz, 1H); 5.88 (br s, 1H); 4.97 (br s, 1H); 1.97 (m, 2H); 1.03 (t, J=7.5 Hz, 3H).

EXAMPLE 43

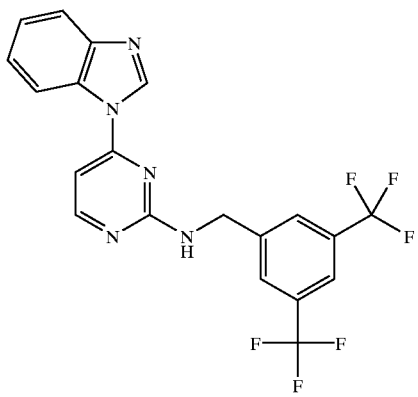

2-[3 5-Bis-trifluoromethylbenzylamino]-4-[benzimidazol-1-yl]pyrimidine

2-Methanesulfonyl-4-[benzimidazol-1-yl]pyrimidine was reacted with 3,5-bis-trifluoromethylbenzylamine according to the procedure described in EXAMPLE 1, Step C to afford the title compound. Mass Spectrum (CI): m/e 438.1 (M+1). $^1$H NMR (500 MHz, CDCl$_3$): δ partial 8.58 (br s, 1H); 8.47 (d, J=5.4 Hz, 1H); 7.89 (s, 1H); 7.38 (m, 2H); 6.92 (d, J=5.5 Hz, 1H); 5.90 (br s, 1H); 4.89 (d, J=6.2 Hz, 2H).

EXAMPLE 44

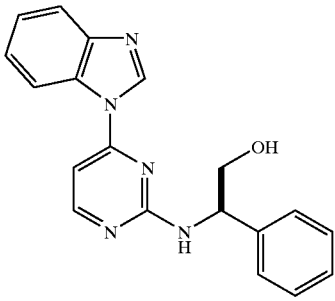

2-[(S)-1-Phenyl-2-hydroxyethylamino]-4-[benzimidazol-1-yl]pyrimidine

2-Methanesulfonyl-4-[benzimidazol-1-yl]pyrimidine was reacted with (S)-1-phenyl-2-hydroxyethylamine according to the procedure described in EXAMPLE 1, Step C to afford the title compound. Mass Spectrum (CI): m/e 332.2 (M+1). $^1$H NMR (500 Mz, CD$_3$OD): δ partial 8.58 (br s, 1H); 8.38 (s, 1H); 7.69 (d, J=7.3 Hz, 1H); 7.47 (d, J=7.3 Hz, 2H); 7.02 (d, J=5.5 Hz, 1H); 5.16 (s, 1H); 3.81–3.91 (m, 2H).

EXAMPLE 45

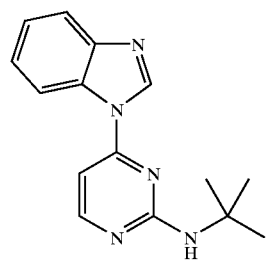

2-[1,1-Dimethylethylamino]-4-[benzimidazol-1-yl]pyrimidine

The title compound was prepared from 2-methanesulfonyl-4-[benzimidazol-1-yl]pyrimidine according to the procedure described in EXAMPLE 1, Step C except using 1,1-dimethylethylamine as the solvent and heating at 40° C. Mass Spectrum (CI): m/e 268.3 (M+1). ). $^1$H NMR (500 MHz, CDCl$_3$): δ 8.69 (s, 1H); 8.40 (d, J=5.5 Hz, 1H); 8.07 (d, J=7.3 Hz, 1H); 7.88 (m, 1H); 7.40 (m, 2H); 6.81 (d, J=5.2 Hz, 1H); 5.40 (br s, 1H); 1.54 (s, 9H).

EXAMPLE 46

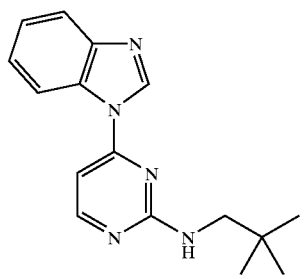

2-[2,2-Dimethylpropylamino]-4-[benzimidazol-1-yl]pyrimidine

2-Methanesulfonyl-4-[benzimidazol-1-yl]pyrimidine was reacted with 2,2-dimethylpropylamine according to the procedure described in EXAMPLE 1, Step C to afford the title compound. Mass Spectrum (CI): 282.2 (M+1). $^1$H NMR (500 MHz, CDCl$_3$): δ partial 8.66 (s, 1H); 8.39 (br s, 1H); 8.19 (d, J=6.6 Hz, 1H); 7.88 (m, 1H); 7.41 (m, 2H); 6.79 (m, 1H); 5.46 (br s, 1H); 3.40 (d, J=6.4 Hz, 2H); 1.04 (s, 9H).

EXAMPLE 47

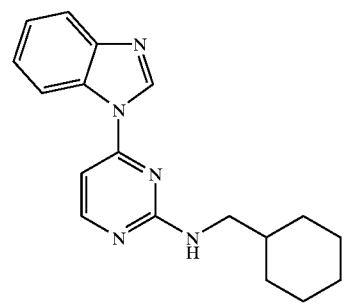

2-[Cyclohexylmethylamino]-4-[benzimidazol-1-yl]pyrimidine

2-Methanesulfonyl-4-[benzimidazol-1-yl]pyrimidine was reacted with aminomethylcyclohexane according to the procedure described in EXAMPLE 1, Step C to afford the title compound. Mass Spectrum (ESI): 308.3 (M+1). ¹H NMR (500 MHz, CDCl₃): δ 8.64 (s, 1H); 8.39 (br s, 1H); 8.23 (br s, 1H); 7.87 (m, 1H); 7.41 (m, 2H); 6.78 (d, J=5.5 Hz, 1H); 5.50 (br s, 1H); 3.39 (t, J=6.3 Hz, 2H) 1.70–1.93 (m, 6H); 1.18–1.38 (m, 3H); 1.02–1.12 (m, 2H).

EXAMPLE 48

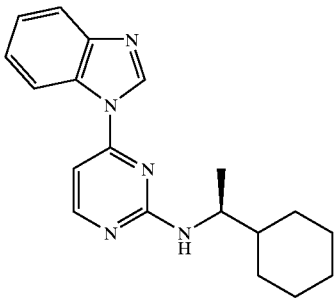

(S)-2-[1-Cyclohexylethylamino]-4-[benzimidazol-1-yl]pyrimidine

2-Methanesulfonyl-4-[benzimidazol-1-yl]pyrimidine was reacted with (S)-1-cyclohexylethylamine according to the procedure described in EXAMPLE 1, Step C to afford the title compound. Mass Spectrum (ESI): 322.3 (M+1). ¹H NMR (500 MHz, CDCl₃): δ partial 8.63 (s, 1H); 8.30 (br s, 1H); 8.23 (br s, 1H); 7.88 (d, J=7.3 Hz, 1H); 7.43 (m, 2H); 6.80 (d, J=5.2 Hz, 1H); 4.10 (m, 1H); 1.69–1.91 (m, 4H); 1.10–1.35 (m, 10H).

EXAMPLE 49

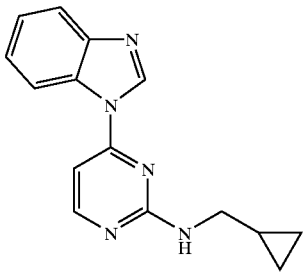

2-[Cyclopropylmethylamino]-4-[benzimidazol-1-yl]pyrimidine

2-Methanesulfonyl-4-[benzimidazol-1-yl]pyrimidine was reacted with aminomethylcyclopropane according to the procedure described in EXAMPLE 1, Step C to afford the title compound. Mass Spectrum (CI): 266.1 (M+1). ¹H NMR (500 MHz, CDCl₃): δ 8.65 (s, 1H); 8.38 (br s, 1H); 8.23 (d, J=7.8 Hz, 1H); 7.88 (d, J=7.8 Hz, 1H); 7.42 (m, 2H); 6.82 (d, J=5.5 Hz, 1H); 5.30–6.25 (br, 1H); 3.42 (br s, 2H); 1.19 (br s, 1H); 0.62 (m, 2H); 0.35 (m, 2H).

EXAMPLE 50

2-[4-Pyridylmethylamino]-4-[benzimidazol-1-yl]pyrimidine

2-Methanesulfonyl-4-[benzimidazol-1-yl]pyrimidine was reacted with 4-(aminomethyl)pyridine according to the procedure described in EXAMPLE 1, Step C to afford the title compound. Mass Spectrum (CI): 303.1 (M+1). ¹H NMR (500 MHz, CDCl₃): δ partial 8.61 (d, J=5.8 Hz, 2H); 8.57 (br s, 1H); 8.44 (d, J=5.5 Hz, 1H); 7.85 (d, J=8.0 Hz, 1H); 6.89 (d, J=5.5 Hz, 1H); 5.96 (br s, 1H); 4.78 (d, J=6.4 Hz, 2H).

EXAMPLE 51

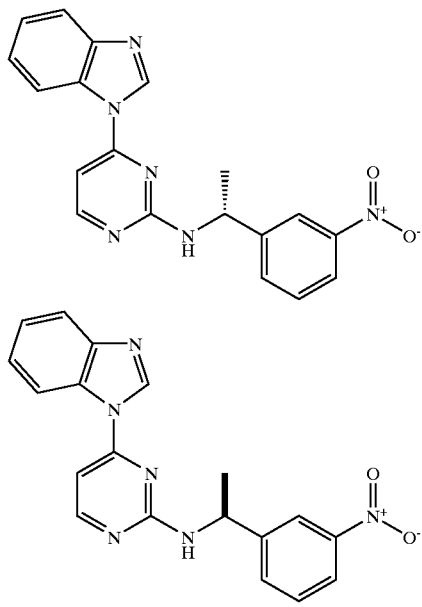

2-[1-(3-Nitrophenyl)ethylamino]-4-[benzimidazol-1-yl]pyrimidine

The title compounds were prepared according to the procedure outlined in EXAMPLE 1, Step C. The 1-(3-nitrophenyl)ethylamine was prepared in racemic fashion according to procedures described by Kelley et al. in J. Medicinal Chemistry 33, 1910–1914, 1990. The racemic product was purified by chromatography (silica, 2% MeOH:CH₂Cl₂. The enantiomers of the racemic product of the coupling with 2-methanesulfonyl-4-[benzimidazol-1-yl]pyrimidine were separated by HPLC (ChiralPak AS, 80:20 hexanes: EtOH) to give the title compounds.

2-[(R or S)-1-(3-Nitrophenyl)ethylamino]-4-[benzimidazol-1-yl]pyrimidine

Enantiomer #1 (faster enantiomer): Mass Spectrum (ESI): m/e 361.2 (M+1). ¹H NMR (500 MHz, CDCl₃): δ partial 8.42 (br s, 1H); 8.34 (s, 1H); 8.16 (m, 1H); 7.84 (br s, 1H); 7.80 (d, J=7.6 Hz, 1H); 7.57 (t, J=8.0 Hz, 1H); 5.82 (br s, 1H); 5.35 (br s, 1H); 1.69 (d, J=6.9 Hz, 3H).

Enantiomer #2 (slower enantiomer): Mass Spectrum (ESI): m/e 361.2 (M+1). ¹H NMR (500 MHz, CDCl₃): δ partial 8.44 (br s, 1H); 8.42 (d, J=5.7 Hz, 1H); 8.34 (s, 1H); 8.15 (m, 1H); 7.84 (m, 1H); 7.80 (d, J=7.1 Hz, 1H); 7.56 (t, J=7.9 Hz, 1H); 7.36 (m, 1H); 6.85 (d, J=5.5 Hz, 1H); 5.72 (br s, 1H); 5.30 (br s, 1H); 1.69 (d, J=6.9 Hz, 3H).

EXAMPLE 52

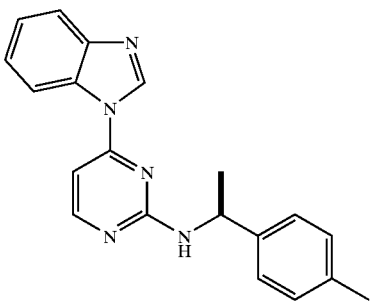

2-[(S)-1-(4-Methylphenyl)ethylamino]-4-
[benzimidazol-1-yl]pyrimidine

2-Methanesulfonyl-4-[benzimidazol-1-yl]pyrimidine was reacted with (S)-1-(4-methylphenyl)ethylamine according to the procedure described in EXAMPLE 1, Step C to afford the title compound. Mass Spectrum (ESI): m/e 330.3 (M+1). $^1$H NMR (500 MHz, CDCl$_3$): δ partial 8.53 (s, 1H); 8.39 (d, J=5.3 Hz, 1H), 7.84 (d, J=8.3 Hz, 1H); 6.78 (d, J=5.5 Hz, 1H); 5.75 (br s, 1H); 5.20 (br s, 1H); 2.36 (s, 3H); 1.63 (d, J=6.8 Hz, 3H).

EXAMPLE 53
omitted

EXAMPLE 54

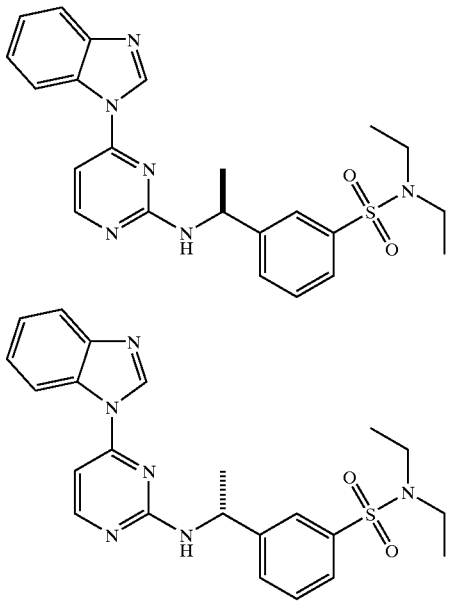

2-[1-(3-N,N-Diethylaminosulfonylphenyl))
ethylamino]-4-[benzimidazol-1-yl]-pyrimidine
(Faster Enantiomer) and 2-[1-(3-N,N-
diethylaminosulfonylphenyl))-ethylamino]-4-
[benzimidazol-1-yl]pyrimidine (Slower Enantiomer)

Step A: 3-(N,N-Diethylaminosulfonyl)benzoic Acid

To a solution of 3-(chlorosulfonyl)benzoic acid (1.02 g, 4.62 mmol) in CH$_2$Cl$_2$ (100 mL) at 0° C. was added diethylamine (2.4 mL, 23 mmol). The resulting mixture was stirred at 0° C. for 3 h then worked up by adding 2N aqueous HCl and extracting 3× with EtOAc. The combined organic was washed with brine then dried over MgSO$_4$ and concentrated under reduced pressure. The residue was used without further purification.

Step B: 3-(N,N-Diethylaminosulfonyl)-N-methoxy-
N-methylbenzamide 3-(N,N-diethylaminosulfonyl)benzoic acid (1.17 g, 4.55 mmol) and N,O-dimethylhydroxylamine hydrochloride (498 mg, 5.11 mmol) were dissolved in CH$_2$Cl$_2$ (30 mL). To this solution was added triethylamine (1.9 mL, 14 mmol), 1-(3-dimethylaminopropyl)-3-ethylcarbodiimide hydrochloride (970 mg, 5.06 mmol) and 4-(N,N-dimethylamino)pyridine (117 mg, 0.958 mmol). The resulting solution was stirred at room temperature for 17 h then poured into saturated aqueous NaHCO$_3$ and extracted 3× with ethyl acetate. The combined organics were washed with brine then dried over MgSO$_4$ and concentrated under reduced pressure. The residue was purified by column chromatography (silica, 70:30 hexanes:acetone) to yield 522 mg of the title compound.

Step C: 3-(N,N-Diethylaminosulfonyl)acetophenone 3-(N,N-diethylaminosulfonyl)-N-methoxy-N-methylbenzamide (522 mg, 1.74 mmol) was dissolved in freshly-distilled diethyl ether (10 mL), the resulting solution was cooled to −78° C. Methylmagnesium bromide (1.0 mL, 3.0 mmol) was added slowly, the −78° C. cold bath then switched for a 0° C. cold bath. Stirred at 0° C. for 2 h then quenched by adding aqueous NH$_4$Cl and H$_2$O then extracting 3× with ethyl acetate. The combined organic was washed with brine then dried over MgSO$_4$ and concentrated under reduced pressure. The residue was purified by column chromatography (silica, 80:20 hexanes:acetone) then another chromatography (silica, 95:5 dichloromethane:ethyl acetate) to yield 245 mg of the title compound.

Step D: 3-(N,N-Diethylaminosulfonyl)
acetophenone-O-benzyl Oxime

To a solution of 3-(N,N-diethylaminosulfonyl) acetophenone (245 mg, 0.960 mmol) in absolute ethanol (10 mL) was added pyridine (0.388 mL, 4.80 mmol) then O-benzylhydroxylamine hydrochloride (380 mg, 2.38 mmol). The resulting mixture was stirred at room temperature for 1.5 h then poured into H$_2$O and extracted 3× with EtOAc. The combined organic was washed with H$_2$O then with brine, dried over MgSO$_4$ and concentrated under reduced pressure. The residue was purified by column chromatography (silica, CH$_2$Cl$_2$) to yield 232 mg of the title compound.

Step E: 1-(3-N,N-Diethylaminosulfonylphenyl))
ethylamine

A solution of borane in THF (1.0M, 0.220 mL, 0.220 mmol) was diluted with THF (5 mL), the resulting solution cooled to 0° C. 3-(N,N-diethylaminosulfonyl)acetophenone-O-benzyl oxime (232 mg, 0.644 mmol) was taken up in 2 1-mL portions of THF, and each portion added slowly to the borane-THF solution. After 1 h the reaction mixture was allowed to warm to room temperature and stirred for 24 h. No reaction progress was seen so more borane in THF solution (1.0M, 1.0 mL, 1.0 mmol) was added and the resulting mixture left stirring for 72 h longer. Little progress was seen at this point and more borane in THF solution (1.0M, 1.0 mL, 1.0 mmol) was added and the mixture stirred 24 h longer. Quenched by acidifying with 2N HCl, the resulting aqueous mixture washed 2× with diethyl ether. The aqueous layer was then made basic by adding concentrated NH$_4$OH then was extracted 2× with diethyl ether, these extracts were combined and dried over MgSO$_4$ then concentrated under reduced pressure. The residue was used without further purification. $^1$H NMR (500 MHz, CDCl$_3$): δ 7.82 (s, 1H); 7.70 (d, 1H); 7.59 (d, 1H); 7.46 (dd, 1H); 4.22 (q, 1H); 3.37 (q, 4H); 1.59 (br s); 1.41 (d, 3H); 1.18 (t, 6H).

Step F: 2-[1-(3-N,N-Diethylaminosulfonylphenyl))ethylamino]-4-[benzimidazol-1-yl]pyrimidine (Faster Enantiomer) and 2-[1-(3-N,N-diethylaminosulfonylphenyl))ethylamino]-4-[benzimidazol-1-yl]pyrimidine (Slower Enantiomer)

The title compound was prepared as a racemate from 1-(3-N,N-diethylaminosulfonylphenyl))ethylamine and 2-methanesulfonyl-4-[benzimidazol-1-yl]pyrimidine according to the procedure described in EXAMPLE 1, Step C. The enantiomers were separated by chiral HPLC.

2-[1-(3-N,N-diethylaminosulfonylphenyl))ethylamino]-4-[benzimidazol-1-yl]-pyrimidine (Faster Enantiomer) Enantiomer #1

Mass Spectrum (ESI): m/e 451.3 (M+1). $^1$H NMR (500 MHz, CD$_3$OD): δ partial 8.78 (br s, 1H); 8.39 (br s, 1H); 7.86 (s, 1H); 7.68–7.77 (M, 2H); 7.66 (M, 1H); 7.57 (M, 1H); 7.35 (br s, 2H); 7.04 (d, J=5.5 Hz, 1H); 5.24 (q, J=6.9 Hz, 1H); 2.97 (br s, 4H); 1.63 (d, J=7.1 Hz, 1H); 1.29 (s, 6H).

2-[1-(3-N,N-diethylaminosulfonylphenyl))ethylamino]-4-[benzimidazol-1-yl]-pyrimidine Enantiomer #2

Mass Spectrum (ESI): m/e 451.3 (M+1). $^1$H NMR (500 MHz, CD$_3$OD): δ partial 8.78 (br s, 1H); 8.39 (br s, 1H); 7.86 (s, 1H); 7.68–7.77 (M, 2H); 7.66 (M, 1H); 7.57 (M, 1H); 7.35 (br s, 2H); 7.04 (d, J=5.5 Hz, 1H); 5.24 (q, J=6.9 Hz, 1H); 2.97 (br s, 4H); 1.63 (d, J=6.8 Hz, 1H); 1.29 (s, 6H).

EXAMPLE 55

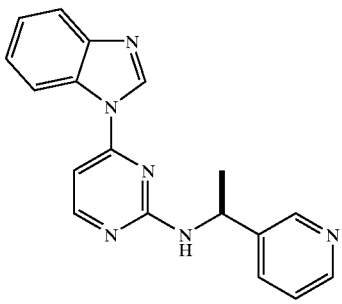

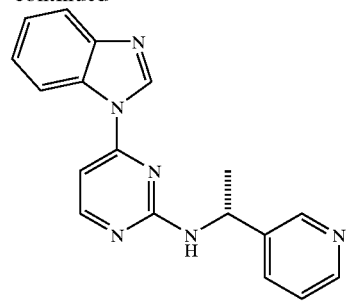

2-[1-(3-pyridyl)ethylamino]-4-[benzimidazol-1-yl]pyrimidine

Step A: 3-acetylpyridinehydroxime

To a solution of 3-acetylpyridine (23 mmol) in methanol (50 mL) was added hydroxylamine hydrochloride (27.5 mmol), and the resulting solution cooled to 0° C. Triethylamine (36 mmol) was added dropwise over 30 min, the resultant mixture then stirred at room temperature for approximately 19 h. The reaction was worked up by pouring into saturated aqueous NaHCO$_3$ solution and extracted 3× with ethyl acetate. The combined organic extracts were washed with brine, dried over MgSO$_4$ and concentrated to yield 2.66 g of crude which was used without further purification. By NMR this crude contains approximately 20% of a minor isomer of the oxime as well as approximately 5% starting 3-acetylpyridine. $^1$H NMR (500 MHz, CD$_3$OD, partial): δ 8.82 (m, 1H major); 8.49 (dd, J=4.8, 1.6 Hz, 1H minor); 8.09 (m, 1H major); 7.43 (m, 1H major); 2.24 (s, 3H major).

Step B: 1-(3-pyridyl)ethylamine

To a solution of 3-acetylpyridinehydroxime (7.23 mmol) in trifluoroacetic acid (14 mL) was added zinc dust (40.1 mmol). The resultant mixture was stirred at room temperature for 30 min then poured into 5N aqueous NaOH and extracted twice with CH$_2$Cl$_2$. The combined organic extracts were washed with brine, dried (MgSO$_4$) and concentrated. The resulting oil was purified by silica chromatography (5% (2M NH$_3$ in MeOH)/CH$_2$Cl$_2$) to yield 238 mg of the desired product. $^1$H NMR (500 MHz, CDCl$_3$): δ 8.61 (d, J=2.2 Hz, 1H); 8.51 (dd, J=1.6, 4.8 Hz); 7.73 (m, 1H); 7.28 (m, 1H); 4.20 (q, J=6.6 Hz, 1H); 1.43 (d, J=6.7 Hz, 3H).

Step C: 2-[1-(3-pyridyl)ethylamino]-4-[benzimidazol-1-yl]pyrimidine

The title compound was prepared from 1-(3-pyridyl)ethylamine according to the procedure outlined in EXAMPLE 1, Step C. The enantiomers were resolved by chiral HPLC (Chiralcel OD, 30–50%IPA in hexanes).
Enantiomer #1 (Faster Enantiomer)
$^1$H NMR (500 MHz, CDCl$_3$, partial): δ 8.75 (d, J=2.1 Hz, 1H); 8.55 (dd, J=1.6, 4.9 Hz, 1H); 8.51 (br s, 1H); 8.41 (d, J=5.5 Hz, 1H); 7.84 (m, 1H); 7.76 (m, 1H); 6.84 (d, J=5.4 Hz, 1H); 5.69 (br s, 1H); 5.26 (m, 1H); 1.69 (d, J=7.1 Hz, 3H).
Enantiomer #2 (Slower Enantiomer)
$^1$H NMR (500 MHz, CDCl$_3$, partial): δ 8.75 (d, J=2.3 Hz, 1H); 8.55 (dd, J=1.6, 4.8 Hz, 1H); 8.51 (br s, 1H); 8.41 (d, J=5.5 Hz, 1H); 7.84 (m, 1H); 7.76 (m, 1H); 6.84 (d, J=5.5 Hz, 1H); 5.67 (br s, 1H); 5.26 (m, 1H); 1.69 (d, J=6.9 Hz, 3H).

EXAMPLE 56

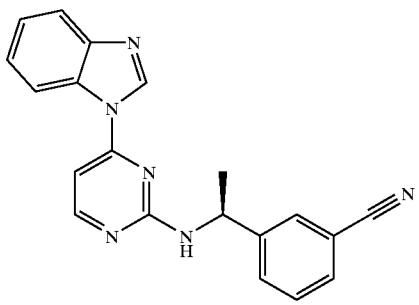

2-[(S)-1-(3-cyanophenyl)ethylamino]-4-[benzimidazol-1-yl]pyrimidine

Step A: (R)-1-(3-cyanophenyl)ethanol

To a solution of (S)-oxazaborolidine (3.44 mmol) in CH₂Cl₂ (3.5 mL) at −20° C. was added a solution of 3-acetylbenzonitrile (3.47 mmol) in CH₂Cl₂ (3.5 mL) over a period of approximately 30 minutes. The mixture was then allowed to warm to room temperature for 1 hour then quenched by transferring to a stirred flask of methanol at −20° C. The resultant mixture was concentrated under reduced pressure and the residue taken up in methanol and concentrated twice more and dried overnight under high vacuum. This residue was purified on silica gel chromatography (70:30 hexanes:ethyl acetate) to yield the title compound (373 mg). ¹H NMR (500 MHz, CDCl₃): δ 7.71 (m, 1H); 7.63 (d, J=7.8 Hz, 1H); 7.58 (m, 1H); 7.48 (t, J=7.7 Hz, 1H); 4.97 (m, 1H); 1.90 (d, J=3.9 Hz,, 1H); 1.53 (d, J=6.6 Hz, 3H).

Step B: (S)-1-(3-cyanophenyl)-1-azidoethane

Zn(N₃)₂.py₂ was suspended in a solution of (R)-1-(3-cyanophenyl)-ethanol (2.53 mmol) and triphenylphosphine (5.11 mmol) in toluene (12 mL). Diethylazodicarboxylate (5.06 mmol) was added dropwise, the resultant mixture stirred at room temperature for approximately 18 h. The mixture was then filtered through celite, the filtrate then washed 1×100 mL 1N HCl, 1×100 mL sat. NaHCO₃, 1×100 mL brine then dried (MgSO₄) and concentrated. The crude was purified on silica gel chromatography (10–40% acetone/hexanes) to yield the title compound (244 mg). ¹H NMR (500 MHz, CDCl₃): δ 7.64 (m, 2H); 7.59 (m, 1H); 7.52 (t, J=7.7 Hz, 1H); 4.69 (q, J=6.8 Hz, 1H); 1.57 (d, J=6.9 Hz, 3H).

Step C: (S)-1-(3-cyanophenyl)ethylamine (S)-1-(3-cyanophenyl)-1-azidoethane (1.42 mmol) was dissolved in benzene (4 mL), H₂O (500 μL) was added followed by triphenylphosphine (2.90 mmol). The resultant mixture was heated to 80° C. for 3.5 h. 25 mL of 2N HCl was added and the mixture washed 3×20 mL diethyl ether. These washes were discarded and the aqueous phase made strongly basic by the addition of 5N NaOH. This basic aqueous phase was then extracted 3×25 mL diethyl ether, these extracts combined, washed with brine, dried (MgSO₄) and concentrated under reduced pressure. The residue was used without further purification (150 mg). ¹H NMR (500 MHz, CDCl₃): δ 7.70 (m, 1H); 7.62 (d, J=7.8 Hz, 1H); 7.54 (m, 1H); 7.44 (t, J=7.8 Hz, 1H); 4.20 (q, J=6.6 Hz, 1H); 1.40 (d, J=6.6 Hz, 3H).

Step D: 2-[(S)-1-(3-cyanophenyl)ethylamino]-4-[benzimidazol-1-yl]pyrimidine

The title compound was prepared from (S)-1-(3-cyanophenyl)ethyl-amine according to the procedure outlined in EXAMPLE 1, Step C. ¹H NMR (500 MHz, CDCl₃, partial): δ 8.42 (d, J=5.5 Hz, 1H); 7.84 (d, J=8.2 Hz, 1H); 7.75 (m, 1H); 7.70 (d, J=7.8 Hz, 1H); 7.58 (m, 1H); 7.50 (m, 1H); 6.85 (d, J=5.5 Hz, 1H); 5.73 (br s, 1H); 5.23 (m, 1H); 1.65 (d, J=7.1 Hz, 3H). Mass Spectrum (ESI): m/e 341.1 (M+1).

EXAMPLE 57

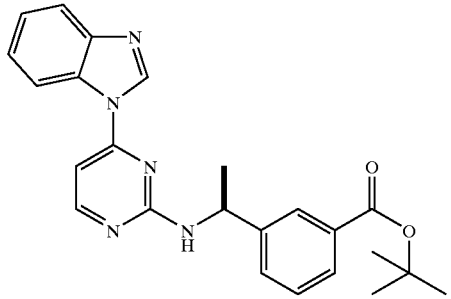

2-[(S)-1-(3-Tert-butyloxycarbonyl)phenylethylamino]-4-[benzimidazol-1-yl]-pyrimidine

Step A: Tert-butyl (3-acetyl)benzoate

In a dry flask under nitrogen, MgSO₄ (23.3 mmol) was suspended in CH₂Cl₂ (23 mL), the mixture was stirred vigorously as concentrated H₂SO₄ (5.85 mmol) was added dropwise. The resultant mixture was stirred for 20 min and 3-acetylbenzoic acid (5.84 mmol) was added in one portion followed by the dropwise addition of tert-butanol (29.3 mmol). This mixture was stoppered tightly and stirred at room temperature for 114 hours. Worked up by adding 100 mL saturated aqueous NaHCO₃ and extracting 3× with 50 mL diethyl ether. The combined extracts were washed with brine, dried over MgSO₄ and concentrated. Purified the residue by silica gel chromatography (90:10 hexanes:ethyl acetate) to yield 924 mg of the title compound. ¹H NMR (500 MHz, CDCl₃): δ 8.56 (m, 1H); 8.20 (m, 1H); 8.14 (m, 1H); 7.55 (t, J=7.6 Hz, 1H); 2.67 (s, 3H); 1.64 (s, 9H).

Step B: (R)-1-(3-Tert-butyloxycarbonylphenyl)ethanol

In a dry flask under nitrogen, (S)-oxazaborolidine (4.81 mmol) was dissolved in dry CH₂Cl₂ (12 mL). This solution was maintained between −20° C. and −25° C. as a solution of tert-butyl (3-acetyl)benzoate (4.20 mmol) in dry CH₂Cl₂ (12 mL) was added dropwise over 20 minutes. The reaction mixture was then allowed to warm to room temperature for 45 minutes. This mixture was then cooled to −78° C. and methanol (20 mL) added dropwise. The mixture was allowed to warm to room temperature. Solvent was removed under reduced pressure then the residue dissolved in methanol and concentrated under reduced pressure twice more. The dried residue was purified by silica gel chromatography in 10–30% ethyl acetate/hexanes to yield 865 mg of the title compound. ¹H NMR (500 MHz, CDCl₃): δ 8.00 (m, 1H); 7.92 (m, 1H); 7.58 (d, J=7.5 Hz, 1H); 7.42 (t, J=7.7 Hz, 1H); 4.98 (m, 1H); 1.62 (s, 9H); 1.54 (d, J=6.4 Hz, 3H).

Step C: (R)-1-(3-Tert-butyloxycarbonylphenyl) ethylmethanesulfonyl Ether (R)-1-(3-Tert-butyloxycarbonylphenyl)ethanol (3.28 mmol) was dissolved in CH$_2$Cl$_2$ (10 mL), diisopropylethylamine (4.92 mmol) added and the resultant solution cooled to 0° C. This mixture was stirred as methanesulfonyl chloride (3.94 mmol) was added dropwise. After 45 min the mixture was poured into water and extracted 3× with diethyl ether. The organic extracts were combined, washed with brine, dried (MgSO$_4$) and concentrated under reduced pressure to yield 1.01 g of an oil which was used with out further purification. $^1$H NMR (500 MHz, CDCl$_3$): δ 8.03 (m, 1H); 8.01 (m, 1H); 7.60 (m, 1H); 7.48 (t, J=7.6 Hz, 1H); 5.80 (q, J=6.6 Hz, 1H); 2.81 (s, 3H); 1.76 (d, J=6.6 Hz, 3H); 1.63 (s, 9H).

Step D: (S)-1-(3-Tert-butyloxycarbonylphenyl)-1-azidoethane (R)-1-(3-tert-butyloxycarbonylphenyl)-ethyl methanesulfonyl ether (3.28 mmol) was dissolved in N,N-dimethylformamide (20 mL) and sodium azide (8.57 mmol) was added. The resultant mixture was heated to 60° C. for 45 min then stirred at room temperature overnight. Worked up by pouring into water and extracting 3× with diethyl ether. The combined organic extracts were washed with brine, dried (MgSO$_4$) and concentrated under reduced pressure to yield 769 mg of an oil which was used without further purification. $^1$H NMR (500 MHz, CDCl$_3$): δ 7.96 (m, 2H); 7.52 (m, 1H); 7.45 (m, 1H); 4.69 (q, J=6.9 Hz, 1H): 1.63 (s, 9H); 1.57 (d, J=6.8 Hz, 3H).

Step E: (S)-1-(3-Tert-butyloxycarbonylphenyl) ethylamine (S)-1-(3-Tert-butyloxycarbonylphenyl)-1-azidoethane (3.10 mmol) was dissolved in benzene (8 mL). Water (1 mL) was added followed by triphenylphosphine (6.18 mmol), and the resultant mixture heated to 80° C. for 2 h. The reaction was poured into 1N HCl solution, this solution then washed twice with diethyl ether. These ether washes were discarded and the aqueous phase made strongly basic (pH~14) by the addition of 5N NaOH solution. This aqueous phase was then extracted 3× with diethyl ether. These ether extracts were combined, washed with brine, dried (MgSO$_4$) and concentrated under reduced pressure to yield 568 mg of an oil which was used without further purification. $^1$H NMR (500 MHz, CDCl$_3$): δ7.97 (m, 1H); 7.88 (m, 1H); 7.55 (d, J=7.5 Hz, 1H); 7.39 (t, J=7.8 Hz, 1H); 4.19 (q, J=6.6 Hz, 1H); 1.62 (s, 9H); 1.42 (d, J=6.7 Hz, 3H).

Step F: 2-[(S)-1-(3-Tert-butyloxycarbonyl) phenylethylamino]-4-[benzimidazol-1-yl]pyrimidine 2-Methanesulfonyl-4-[benzimidazol-1-yl]pyrimidine (EXAMPLE 1, Step B) (1.27 mmol) and (S)-1-(3-tert-butyloxy-carbonylphenyl)-ethylamine (1.34 mmol) were mixed in xylenes (10 mL), the mixture stirred at 120° C. for 23 h. The reaction mixture was then cooled and eluted on silica gel chromatography (ethyl acetate) to yield 179 mg of the title compound. $^1$H NMR (500 MHz, CDCl$_3$): δ 8.50 (br s, 1H); 8.40 (d, J=5.5 Hz, 1H); 8.09 (s, 1H); 7.91 (m, 1H); 7.83 (d, J=8.0 Hz, 1H); 7.62 (d, J=7.8 Hz, 1H); 7.43 (t, J=7.7 Hz, 1H); 7.35 (m, 3H); 6.80 (d, J=5.5 Hz, 1H); 5.73 (br s, 1H); 5.26 (br s, 1H); 1.66 (d, J=7.1 Hz, 3H); 1.61 (s, 9H).

EXAMPLE 58

2-[(S)-1-(3-carboxyphenyl)ethylamino]-4-[benzimidazol-1-yl]pyrimidine

2-[(S)-1-(3-tert-butyloxycarbonyl)phenylethylamino]-4-[benzimidazol-1-yl]pyrimidine (0.426 mmol) was dissolved in CH$_2$Cl$_2$ (5 mL) and trifluoroacetic acid (0.5 mL) was added. This solution was stirred at room temperature for 20 h then the solvent and TFA removed under reduced pressure. The residue was purified by silica gel chromatography (95:5 CH$_2$Cl$_2$:MeOH) to yield 169 mg of the title compound. $^1$H NMR (500 MHz, CDCl$_3$, partial): δ 8.72 (s, 1H); 8.32 (m, 2H); 8.05 (d, J=7.8 Hz, 1H); 7.92 (m, 2H); 7.72 (d, J=7.8 Hz, 1H); 7.52 (t, J=7.8 Hz, 1H); 7.47 (m, 2H); 6.98 (d, J=6.4 Hz, 1H); 5.31 (m, 1H); 1.78 (d, J=6.8 Hz, 3H). Mass Spectrum (ESI): m/e 360.2 (M+1).

EXAMPLE 59

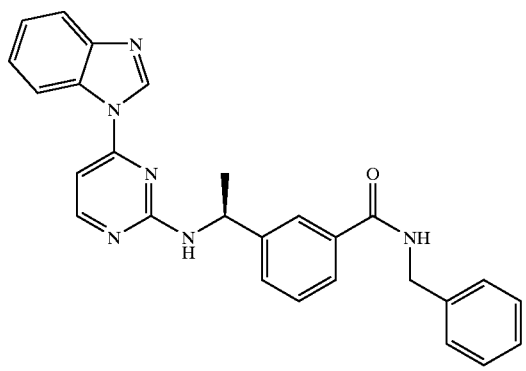

2-[(S)-1-(3-(benzylaminocarbonyl)phenyl) ethylamino]-4-[benzimidazol-1-yl]pyrimidine 2-[(S)-1-(3-carboxyphenyl)ethylamino]-4-[benzimidazol-1-yl]pyrimidine (22.6 mg) and benzylamine (7.5 μL) were mixed in CH$_2$Cl$_2$ under nitrogen. Triethylamine (26 μL), 1-(3-dimethylaminopropyl)-3-ethylcarbodiimide hydrochloride (approx. 18 mg) and 4-dimethylaminopyridine (approx. 1 mg) were added and the mixture stirred at room temperature. After approximately 1.5 h another portion of 1-(3-dimethylaminopropyl)-3-ethylcarbodiimide hydrochloride (13.5 mg) was added. One hour later the mixture was eluted directly on silica gel (95:5 CH$_2$Cl$_2$:MeOH) to yield 17.8 mg of the title compound. $^1$H NMR (500 MHz, CDCl$_3$, partial): δ 8.46 (br s, 1H); 8.38 (d, J=5.2 Hz, 1H); 7.94 (s, 1H); 7.81 (d, J=7.7 Hz); 7.67 (m, 1H); 7.59 (d, J=7.8 Hz, 1H); 7.44 (t, J=7.7 Hz, 1H); 6.78 (d, J=5.5 Hz, 1H); 6.44 (s, 1H); 5.77 (br s, 1H); 5.24 (br s, 1H); 4.65 (m, 2H); 1.65 (d, J=6.8 Hz, 3H). Mass Spectrum (ESI): m/e 449.2 (M+1).

EXAMPLE 60

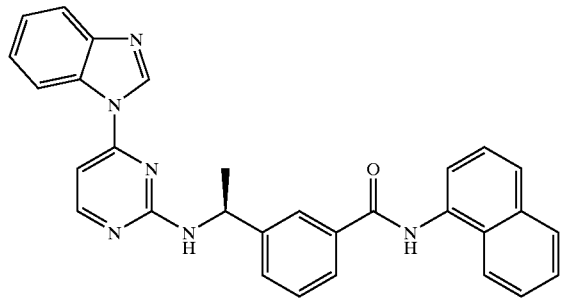

2-[(S)-1-(3-(1-naphthylaminocarbonyl)phenyl) ethylamino]-4-[benzimidazol-1-yl]-pyrimidine 2-[(S)-1-(3-carboxyphenyl)ethylamino]-4-[benzimidazol-1-yl]-pyrimidine (0.0376 mmol) and 1-naphthylamine (0.169 mmol) were mixed in CH$_2$Cl$_2$ (2 mL) and then triethylamine (0.187 mmol), 1-(3-dimethylaminopropyl)-3-ethyl-carbodiimide hydrochloride (0.172 mmol), and 4-dimethylaminopyridine (~1 mg) were added in that order. Poor overall solubility was observed so THF (1 mL) was then added to the mixture, which became more homogeneous. The mixture was stirred at room temperature for 22 h then concentrated under reduced pressure. Purified by silica gel chromatography (1–2% MeOH in CH$_2$Cl$_2$) to yield 3.4 mg of the title compound. $^1$H NMR (500 MHz, CDCl$_3$): δ 8.49 (br s, 1H); 8.41 (d, J=5.5 Hz, 1H); 8.17 (br s, 1H); 8.12 (br s, 1H); 8.02 (br s, 1H); 7.85–7.92 (m, 3H); 7.81 (m, 1H); 7.77 (d, J=8.2 Hz, 1H); 7.69 (d, J=7.5 Hz, 1H); 7.51–7.58 (m, 4H); 7.33 (br s, 2H); 6.82 (d, J=5.5 Hz, 1H); 5.78 (br s, 1H); 5.32 (br s, 1H); 1.71 (d, J=6.9 Hz, 3H). Mass Spectrum (ESI): m/e 485.2 (M+1).

EXAMPLE 61

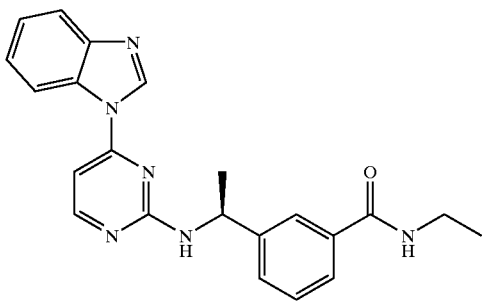

2-[(S)-1-(3-(1-ethylaminocarbonyl)phenyl)ethylamino]-4-[benzimidazol-1-yl]-pyrimidine 2-[(S)-1-(3-carboxyphenyl)ethylamino]-4-[benzimidazol-1-yl]-pyrimidine (27.4 mg) was dissolved in THF (1 mL), and triethylamine (53 μL) was added. A solution of 2.0M ethylamine in THF (76 μL) was added followed by 1-(3-dimethylaminopropyl)-3-ethylcarbodiimide hydrochloride (26.9 mg) and 4-dimethylaminopyridine (~1 mg). Stirred at room temperature for 2 h then another portion of 2.0M ethylamine in THF (76 μL) was added along with more 1-(3-dimethylaminopropyl)-3-ethylcarbodiimide hydrochloride (27.4 mg). 1.5 h later the mixture was concentrated under reduced pressure then purified by silica gel chromatography (98:2 CH$_2$Cl$_2$:MeOH) to yield 18.2 mg of the title compound. $^1$H NMR (500 MHz, CDCl$_3$): δ 8.48 (br s, 1H); 8.39 (d, J=5.5 Hz, 1H); 7.90 (m, 1H); 7.82 (d, J=7.5 Hz, 1H); 7.64 (m, 1H); 7.58 (d, J=5.8 Hz, 1H); 7.44 (t, J=7.7 Hz, 1H); 7.34 (m, 3H); 6.79 (d, J=5.5 Hz, 1H); 6.11 (br s, 1H); 5.81 (br s, 1H); 5.25 (br s, 1H); 3.49 (m, 2H); 1.65 (d, J=6.9 Hz, 3H); 1.25 (t, J=7.3 Hz, 3H). Mass Spectrum (ESI): m/e 387.1 (M+1).

EXAMPLE 62

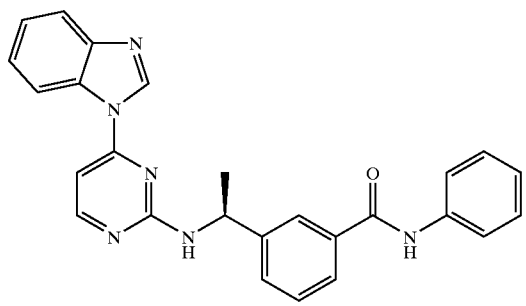

2-[(S)-1-(3-(phenylaminocarbonyl)phenyl)ethylamino]-4-[benzimidazol-1-yl]-pyrimidine 2-[(S)-1-(3-carboxyphenyl)ethylamino]-4-[benzimidazol-1-yl]pyrimidine (32.2 mg) was dissolved in CH$_2$Cl$_2$ (2 mL), then triethylamine (62 μL), aniline (25 μL), 1-(3-dimethylaminopropyl)-3-ethylcarbodiimide hydrochloride (62.7 mg) and 4-dimethylaminopyridine (~1 mg) were added in that order. Mixture stirred 16 h at room temperature then 2 mL more CH$_2$Cl$_2$ added (reaction had gone dry overnight) and thin layer chromatography showed complete conversion of starting material. Concentrated under reduced pressure then purified by silica gel chromatography (98:2 CH$_2$Cl$_2$:MeOH) to yield 16.9 mg of the title compound. $^1$H NMR (500 MHz, CDCl$_3$): δ 8.48 (br s, 1H); 8.48 (br s, 1H); 8.41 (d, J=5.5 Hz, 1H); 8.00 (s, 1H); 7.75–7.84 (m, 3H); 7.61–7.66 (m, 3H); 7.51 (t, J=7.8 Hz, 1H); 7.33–7.41 (m, 4H); 7.17 (t, J=7.5 Hz, 1H); 6.81 (d, J=5.5 Hz, 1H); 5.73 (br s, 1H); 5.28 (br s, 1H); 1.68 (d, J=6.8 Hz, 3H). Mass Spectrum (ESI): m/e 435.1 (M+1).

EXAMPLE 63

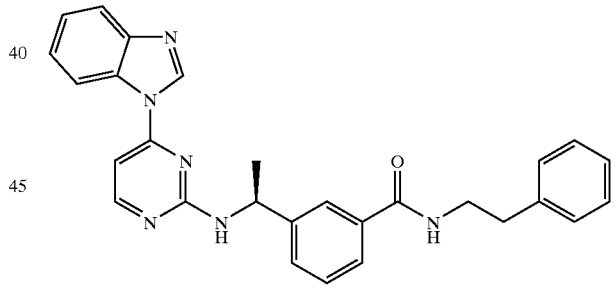

2-[(S)-1-(3-(2-phenylethylaminocarbonyl)phenyl)ethylamino]-4-[benzimidazol-1-yl]pyrimidine Made in the same manner as EXAMPLE 62 using 2-[(S)-1-(3-carboxyphenyl)ethylamino]-4-[benzimidazol-1-yl]pyrimidine (37.2 mg), CH$_2$Cl$_2$ (2 mL), triethylamine (72 μL), phenethylamine (39 μL), 1-(3-dimethylaminopropyl)-3-ethylcarbodiimide hydrochloride (58 mg) and 4-dimethylaminopyridine (~1 mg). Run for 18 h then concentrated under reduced pressure and purified by silica gel chromatography (98:2 CH$_2$Cl$_2$:MeOH) to yield 21.6 mg of the title compound. $^1$H NMR (500 MHz, CDCl$_3$ partial): δ 8.48 (br s, 1H); 8.40 (d, J=5.5 Hz, 1H); 7.84 (m, 2H); 7.56 (m, 2H); 7.42 (t, J=7.7 Hz, 1H); 6.80 (d, J=5.5 Hz,1H); 6.10 )br s, 1H); 5.69 (br s, 1H); 5.23 (br s, 1H); 3.72 (m, 2H); 2.94 (t, J=7.0 Hz, 2H); 1.65 (d, J=6.9 Hz, 3H). Mass Spectrum (ESI): m/e 463.2 (M+1).

EXAMPLE 64

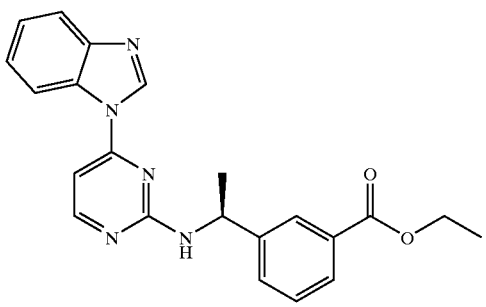

2-[(S)-1-(3-(ethoxycarbonyl)phenyl)ethylamino]-4-[benzimidazol-1-yl]pyrimidine

2-[(S)-1-(3-carboxyphenyl)ethylamino]-4-[benzimidazol-1-yl]pyrimidine (35.6 mg) was dissolved in ethanol (3 mL) and p-toluenesulfonic acid hydrate (~1 mg) was added. The reaction was heated to 80° C. for 20 h after which no reaction progress was observed by thin layer chromatography. To this mixture was then added triethylamine (69 µL), 1-(3-dimethylaminopropyl)-3-ethylcarbodiimide hydrochloride (62 mg) and 4-dimethylaminopyridine (~1 mg). Stirred at room temperature for 18 h. The mixture was concentrated under reduced pressure. This residue was purified first by silica gel column chromatography (98.5:1.5 $CH_2Cl_2$:MeOH) then on a 250 µM silica gel prep plate (1:1 hexanes:acetone) to yield 6.8 mg of the title compound. $^1$H NMR (500 MHz, $CDCl_3$ partial): δ 8.49 (br s, 1H); 8.45 (d, J=5.4 Hz, 1H); 8.15 (s, 1H); 7.97 (m, 1H); 7.83 (d, J=8.0 Hz, 1H); 7.65 (d, J=7.8 Hz, 1H); 7.46 (t, J=7.7 Hz, 1H); 6.81 (d, J=5.5 Hz, 1H); 5.72 (br s, 1H); 5.27 (br s, 01H); 4.40 (q, J=7.2 Hz, 2H); 1.66 (d, J=7.1 Hz, 3H); 1.41 (t, J=7.2 Hz, 3H). Mass Spectrum (ESI): m/e 388.1 (M+1).

EXAMPLE 65

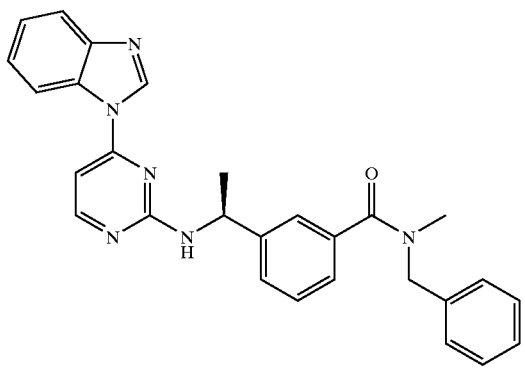

2-[(S)-1-(3-(N-benzyl-N-methylaminocarbonyl)phenyl)ethylamino]-4-[benzimidazol-1-yl]pyrimidine 2-[(S)-1-(3-carboxyphenyl)ethylamino]-4-[benzimidazol-1-yl]pyrimidine (32.7 mg) was dissolved in $CH_2Cl_2$ (2 mL), triethylamine (63 µL) added followed by N-benzylmethylamine (35 µL), 1-(3-dimethylaminopropyl)-3-ethylcarbodiimide hydrochloride (53 mg) and 4-dimethylaminopyridine (~1 mg). Mixture was stirred at room temperature for 17 h then the solvent removed under reduced pressure. The residue was eluted on silica gel chromatography (1–2% MeOH in $CH_2Cl_2$) to yield 28.3 mg of the title compound. Mass Spectrum (ESI): m/e 463.2 (M+1).

EXAMPLE 66

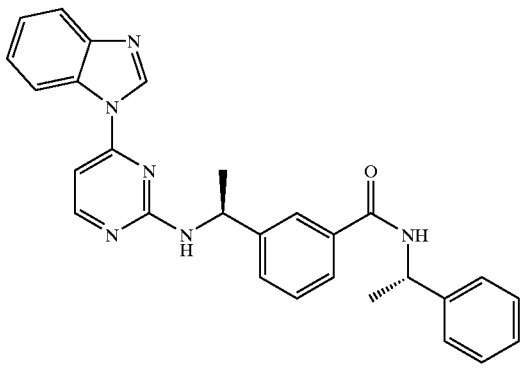

2-[(S)-1-(3-((S)-1-phenylethylaminocarbonyl)phenyl)ethylamino]-4-[benzimidazol-1-yl]pyrimidine 2-[(S)-1-(3-carboxyphenyl)ethylamino]-4-[benzimidazol-1-yl]pyrimidine (15.5 mg) was dissolved in $CH_2Cl_2$ (2 mL), then triethylamine (30 µL) was added followed by (S)-1-phenylethylamine (17 µL), 1-(3-dimethylaminopropyl)-3-ethylcarbodimide hydrochloride (32.7 mg) and 4-dimethylaminopyridine (~1 mg). The mixture was stirred at room temperature for 17 h then purified directly by silica gel column (60:40 hexanes:acetone) then on one 250 µm silica gel plate (90:10 $CH_2Cl_2$:MeOH) to yield 6.9 mg of the title compound. $^1$H NMR (500 MHz, $CDCl_3$, partial): δ 8.48 (br s, 1H); 8.37 (d, J=5.5 Hz, 1H); 7.95 (s, 1H); 7.82 (d, J=7.5 Hz, 1H); 7.64 (d, J=7.8 Hz, 1H); 7.59 (d, J=7.5 Hz, 1H); 6.79 (d, J=5.5 Hz, 1H); 6.33 (d, J=7.8 Hz, 1H); 5.80 (br s, 1H); 5.36 (m, 1H); 5.24 (br s, 1H); 1.65 (d, J=6.9 Hz, 3H); 1.61 (d, J=6.9 Hz, 3H). Mass Spectrum (ESI): m/e 463.2 (M+1).

EXAMPLE 67

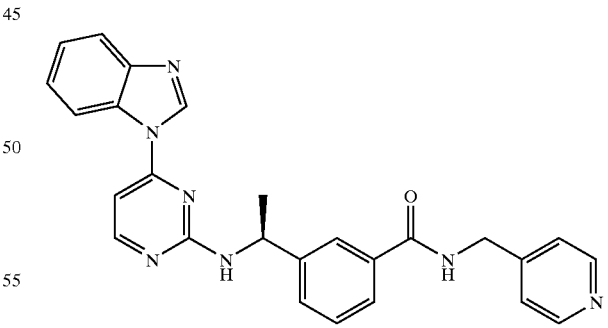

2-[(S)-1-(3-(4-pyridylmethylaminocarbonyl)phenyl)ethylamino]-4-[benzimidazol-1-yl]pyrimidine 2-[(S)-1-(3-carboxyphenyl)ethylamino]-4-[benzimidazol-1-yl]pyrimidine (15.4 mg) was dissolved in $CH_2Cl_2$ (2 mL), then triethylamine (30 µL) was added followed by 4-aminomethylpyridine (14 µL), 1-(3-dimethylaminopropyl)-3-ethylcarbodimide hydrochloride (26.8 mg) and 4-dimethylaminopyridine (~1 mg). The mixture was stirred at room temperature for 19 h then eluted directly on silica gel column (2–10%MeOH in CH$_2$Cl$_2$) to yield 8.9 mg of the title compound. $^1$H NMR (500 MHz, CDCl$_3$,partial): δ 8.56 (m, 2H); 8.46 (br s, 1H); 8.39 (d, J=5.5 Hz, 1H); 7.96 (s, 1H); 7.81 (d, J=7.9 Hz, 1H); 7.71 (d, J=7.8 Hz, 1H); 7.63 (d, J=7.8 Hz, 1H); 7.47 (t, J=7.7 Hz, 1H); 7.24 (d, J=5.9 Hz, 1H); 6.79 (d, J=5.5 Hz, 1H); 6.64 (br s, 1H); 5.77 (br s, 1H); 5.5.24 (br s, 1H); 4.65 (m, 2H); 1.66 (d, J=7.1 Hz, 3H). Mass Spectrum (ESI): m/e 450.2 (M+1).

EXAMPLE 68

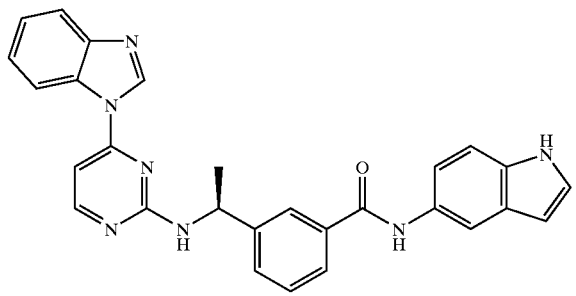

2-[(S)-1-(3-(indol-5-ylaminocarbonyl)phenyl) ethylamino]-4-[benzimidazol-1-yl]pyrimidine 2-[(S)-1-(3-carboxyphenyl)ethylamino]-4-[benzimidazol-1-yl]pyrimidine (19.2 mg) was dissolved in CH$_2$Cl$_2$ (2 mL), then triethylamine (37 μL) was added followed by 5-aminoindole (19.0 mg), 1-(3-dimethylaminopropyl)-3-ethylcarbodiimide hydrochloride (27.3 mg) and 4-dimethylaminopyridine (~1 mg). The mixture was stirred at room temperature for 30 min then eluted on silica gel column (2–4%MeOH in CH$_2$Cl$_2$) then on one 250 μm silica gel plate (1:1 hexanes:acetone) to yield 3.7 mg of the title compound. $^1$H NMR (500 MHz, CDCl$_3$,partial): δ 8.50 (br s, 1H); 8.40 (d, J=5.5 Hz, 1H); 8.22 (br s, 1H); 8.03 (s, 1H); 7.96 (br s, 1H); 7.87 (s, 1H); 7.64 (d, J=7.8 Hz, 1H); 7.51 (t, J=7.8 Hz, 1H); 7.25 (m, 1H); 6.81 (d, J=5.5 Hz, 1H); 6.56 (br s, 1H); 5.89 (br s, 1H); 5.29 (br s, 1H); 1.69 (d, J=6.9 Hz, 3H). Mass Spectrum (ESI): m/e 474.3 (M+1).

EXAMPLE 69

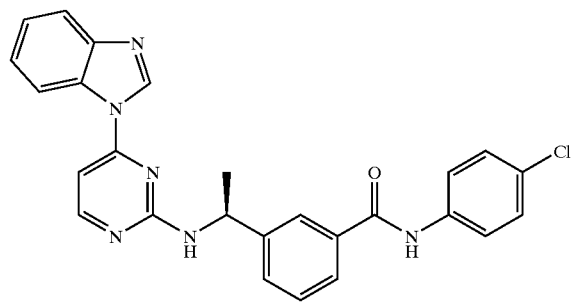

2-[(S)-1-(3-((4-chlorophenyl)aminocarbonyl)phenyl) ethylamino]-4-[benzimidazol-1-yl]pyrimidine 2-[(S)-1-(3-carboxyphenyl)ethylamino]-4-[benzimidazol-1-yl]pyrimidine (38.1 mg) was dissolved in CH$_2$Cl$_2$ (2 mL), then triethylamine (73 μL) was added followed by 4-chloroaniline (58.9 mg), 1-(3-dimethylaminopropyl)-3-ethylcarbodiimide hydrochloride (58.0 mg) and 4-dimethylaminopyridine (~1 mg). The mixture was stirred at room temperature for 45 min then eluted directly on silica gel column (98:2 CH$_2$Cl$_2$:MeOH) then on one 250 μm silica gel plate (1:1 hexanes:acetone) to yield 9.5 mg of the title compound. $^1$H NMR (500 MHz, CDCl$_3$): δ 8.46 (br s, 1H); 8.39 (d, J=5.5 Hz, 1H); 7.98 (s, 1H); 7.90 (s, 1H); 7.82 (d, J=6.4 Hz, 1H); 7.75 (d, J=7.6 Hz, 1H); 7.65 (d, J=7.6 Hz, 1H); 7.58 (d, J=8.7 Hz, 2H); 7.51 (t, J=7.7 Hz, 1H); 7.33 (m, 3H); 6.80 (d, J=5.5 Hz, 1H); 5.94 (br s, 1H); 5.26 (br s, 1H); 1.67 (d, J=6.9 Hz, 3H). Mass Spectrum (ESI): m/e 469.2 (M+1).

EXAMPLE 70

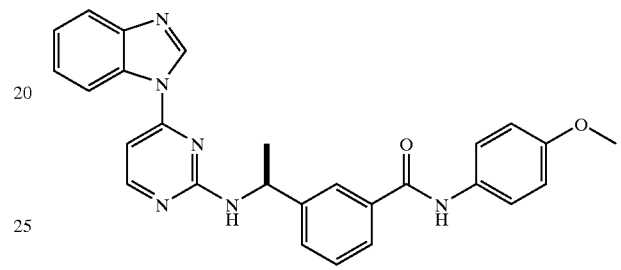

2-[(S)-1-(3-((4-methoxyphenyl)aminocarbonyl) phenyl)ethylamino]-4-[benzimidazol-1-yl] pyrimidine 2-[(S)-1-(3-carboxyphenyl)ethylamino]-4-[benzimidazol-1-yl]pyrimidine (28.9 mg) was dissolved in CH$_2$Cl$_2$ (2 mL), then triethylamine (55 μL) was added followed by 4-methoxyaniline (62 mg), 1-(3-dimethylaminopropyl)-3-ethylcarbodiimide hydrochloride (53.4 mg) and 4-dimethylaminopyridine (~1 mg). The mixture was stirred at room temperature for 18 h then directly eluted on silica gel column (1–4% MeOH:CH$_2$Cl$_2$) to yield 19.7 mg of the title compound. $^1$H NMR (500 MHz, CDCl$_3$): δ 8.45 (br s, 1H); 8.37 (d, J=5.5 Hz, 1H); 7.99 (s, 1H); 7.88 (s, 1H); 7.80 (d, J=6.2 Hz, 1H); 7.75 (d, J=7.5 Hz, 1H); 7.62 (d, J=7.8 Hz, 1H); 7.49 (m, 3H); 7.33 (m, 2H); 6.90 (d, J=8.9 Hz, 2H); 6.77 (d, J=5.5 Hz, 1H); 5.87 (br s, 1H); 5.26 (br s, 1H); 3.81 (s, 3H); 1.65 (d, J=6.8 Hz, 3H). Mass Spectrum (ESI): m/e 465.2 (M+1).

EXAMPLE 71

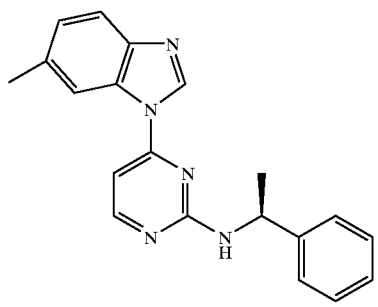

-continued

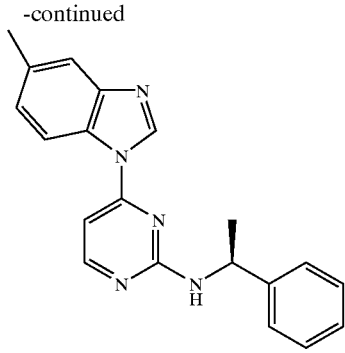

2-[(S)-1-Phenylethylamino]-4-[5-methylbenzimidazol-1-yl]pyrimidine and 2-[(S)-1-Phenylethylamino]-4-[6-methylbenzimidazol-1-yl]pyrimidine The title compounds were prepared from 4-chloro-2-methylthiopyrimidine and 5-methylbenzimidazole according to the three step procedure described in EXAMPLE 1. The products were separated by chromatography (3:1 Hexane:acetone) to afford pure products.

2-[(S)-1-phenylethylamino]-4-[5-methyl-benzimidazol-1-yl]pyrimidine

Partial $^1$H NMR (500 MHz CDCl$_3$): δ 8.45 (bs, 1H); 8.38 (d J=5.5 Hz, 1H); 7.72 (br, 1H); 7.61 (bs, 1H); 7.13 (bd J=8 Hz, 1H); 6.76 (d J=5.5 Hz, 1H); 5.21 (br, 1H); 2.49 (s, 3H); 1.61 (d J=6.8 Hz, 3H).

2-[(S)-1-phenylethylamino]-4-[6-methyl-benzimidazol-1-yl]pyrimidine

Partial $^1$H NMR (500 MHz CDCl$_3$): δ 8.45 (bs, 1H); 8.36 (d J=5.0 Hz, 1H); 7.82 (bs, 1H); 7.70 (d J=8.0 Hz, 1H); 7.18 (d J=8.0 Hz, 1H); 6.77 (d, J=5.0 Hz, 1H); 5.26 (m, 1H); 2.53 (s, 3H); 1.62 (s, 3H).

EXAMPLE 72

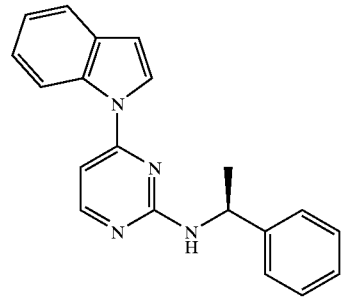

2-[(S)-1-Phenylethylamino]-4-[2-methylbenzimidazol-1-yl]pyrimidine

The title compound was prepared from 4-chloro-2-methylthio-pyrimidine and 2-methylbenzimidazole according to the three step procedure described in EXAMPLE 1. Partial $^1$H NMR (500 MHz CDCl$_3$): δ 8.42 (d J=5.0 Hz, 1H); 7.72 (d J=8.0, 1H); 6.68 (d J=5.0, 1H); 5.16 (brm, 1H); 2.55 (br, 3H); 1.59 (d J=6.5, 3H).

EXAMPLE 73

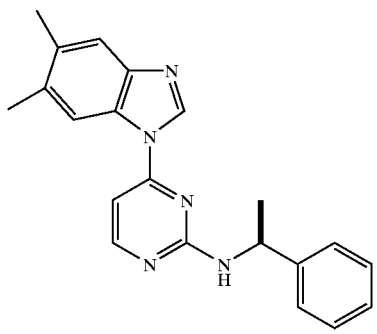

2-[(S)-1-Phenylethylamino]-4-[5,6-dimethylbenzimidazol-1-yl]pyrimidine

The title compound was prepared from 4-chloro-2-methylthio-pyrimidine and 5,6-dimethylbenzimidazole according to the three step procedure described in EXAMPLE 1. Partial $^1$H NMR (500 MHz CDCl$_3$): δ 8.30 (s, 1H); 8.18 (d J=5.0 Hz,1H); 7.59 (s, 1H); 5.23 (br, 1H); 2.40 (s, 3H); 2.38 (s, 3H); 1.63 (d J=6.0 Hz, 3H).

EXAMPLE 74

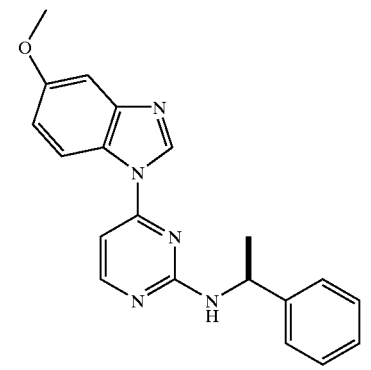

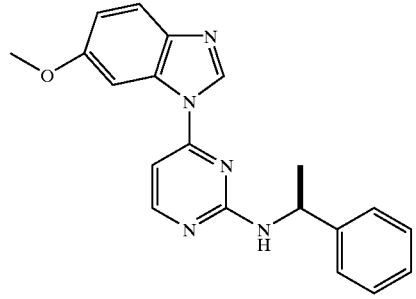

2-[(S)-1-Phenylethylamino]-4-[5-methoxybenzimidazol-1-yl]pyrimidine and 2-[(S)-1-Phenylethylamino]-4-[6-methoxybenzimidazol-1-yl]pyrimidine The title compounds were prepared from 4-chloro-2-methylthiopyrimidine and 5-methoxybenzimidazole according to the three-step procedure described in EXAMPLE 1. 2-[(S)-1-phenylethylamino]-4-[5-methoxy-benzimidazol-1-yl]pyrimidine Partial $^1$H NMR (500 MHz CDCl$_3$): δ 8.92 (s, 1H); 8.30 (br, 1H); 8.15 (d J=5.0 Hz, 1H); 6.96 (d J=5.0 Hz, 1H); 5.40 )br, 1H); 3.90 (s, 3H); 1.63 (d J=6.5 Hz, 3H).

Partial ¹H NMR (500 MHz CDCl₃): δ 9.03 (s, 1H); 8.13–8.18 (m, 2H); 7.76 (d J=10 Hz, 1H); 7.03 (dd J=8.0, 1.5 Hz, 1H); 5.72 (br, 1H); 3.92 (s, 3H); 1.63 (d J=7.0, 3H).

EXAMPLE 75

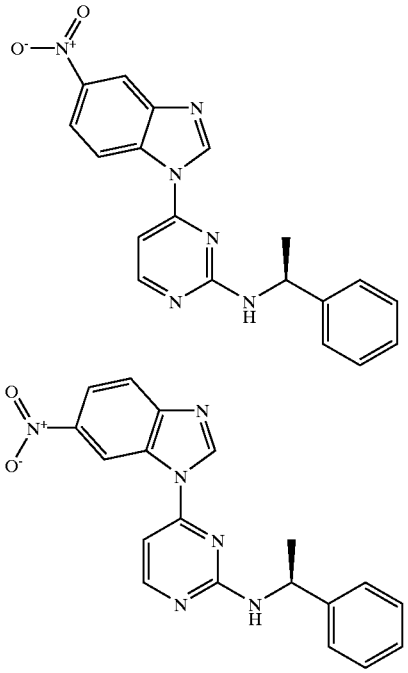

2-[(S)-1-Phenylethylamino]-4-[5-nitrobenzimidazol-1-yl]pyrimidine and 2-[(S)-1-Phenylethylamino]-4-[6-nitrobenzimidazol-1-yl]pyrimidine The title compounds were prepared from 4-chloro-2-methylthio-pyrimidine and 5-nitrobenzimidazole according to the three step procedure described in EXAMPLE 1. The products were separated by preparative HPLC on silica gel to afford:

2-[(S)-1-phenylethylamino]-4-[5-nitro-benzimidazol-1-yl]pyrimidine

Partial ¹H NMR (500 MHz CDCl₃): δ 8.70 (s, 1H); 8.57 (brs, 1H); 8.43 (d J=5.5 Hz, 1H); 8.15 (br, 1H); 7.68 (br, 1H); 6.76 (d J=5.5 Hz, 1H); 5.16 (br, 1H); 1.63 (d J=6.9, 3H).

2-[(S)-1-phenylethylamino]-4-[6-nitro-benzimidazol-1-yl]pyrimidine

Partial ¹H NMR (500 MHz CDCl₃): δ 9.23 (bs, 1H); 8.68 (br,1H); 8.43 (br, 1H); 8.30 (dd J=9.0, 2.0 Hz, 1H); 7.92 (d J=9, 1H); 6.80 (d J=5.5 Hz, 1H); 5.32 (m J=7.0, 1H); 1.67 (d J=7.0, 3H).

EXAMPLE 76

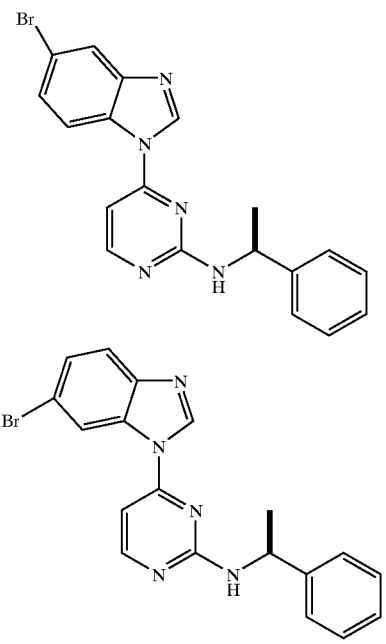

2-[(S)-1-Phenylethylamino]-4-[5-bromobenzimidazol-1-yl]pyrimidine and 2-[(S)-1-Phenylethylamino]-4-[6-bromobenzimidazol-1-yl]pyrimidine The title compounds were prepared from 4-chloro-2-methylthiopyrimidine and 5-bromobenzimidazole according to the three-step procedure described in EXAMPLE 1.

2-[(S)-1-phenylethylamino]-4-[5-bromo-benzimidazol-1-yl]pyrimidine

Partial ¹H NMR (500 MHz CDCl₃): δ 8.42 (br, 1H); 8.37 (d J=5.5 Hz, 1H); 7.94 (s, 1H); 7.57 (br, 1H); 6.70 (d J=5.5 Hz, 1H); 5.18 (br, 1H); 1.63 (d J=6.5 Hz, 3H).

2-[(S)-1-phenylethylamino]-4-[6-bromo-benzimidazol-1-yl]pyrimidine

Partial ¹H NMR (500 MHz CDCl₃) δ 8.42 (br, 1H); 8.36 (br, 1H); 7.68 (d J=10 Hz, 1H); 6.73 (d J=5.5 Hz, 1H); 5.24 (br, 1H); 1.63 (d J=6.5 Hz, 3H).

EXAMPLE 77

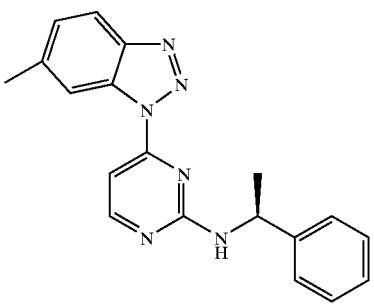

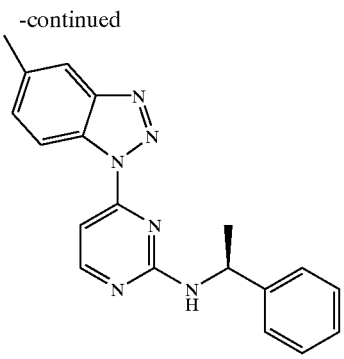

2-[(S)-1-Phenylethylamino]-4-[5-methylbenzotriazol-1-yl]pyrimidine

The title compound was prepared from 4-chloro-2-methylthiopyrimidine and 5-methyl benzotriazole according to the three step procedure described in EXAMPLE 1. Partial $^1$H NMR (500 MHz CDCl$_3$): δ 8.42 (d J=5.0, 1H); 7.83 (s, 1H); 5.12 (br, 1H); 2.55 (s, 3H); 1.65 (d J=6.5 Hz).

EXAMPLE 78 omitted

EXAMPLE 79

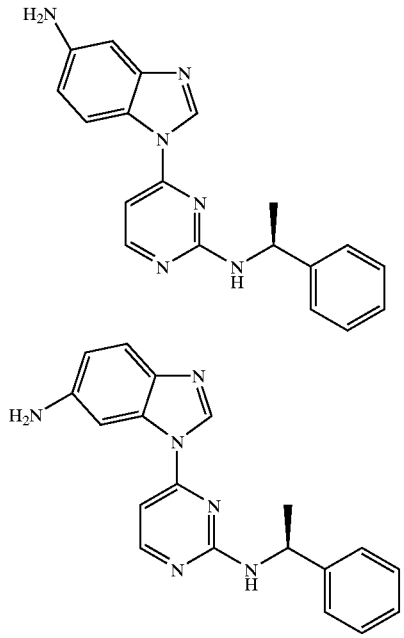

2-[(S)-1-Phenylethylamino]-4-[5-aminobenzimidazol-1-yl]pyrimidine and 2-[(S)-1-Phenylethylamino]-4-[6-aminobenzimidazol-1-yl]pyrimidine A 1:1 mixture of 2-[(S)-1-phenylethylamino]-4-[5-nitrobenzimidazol-1-yl]pyrimidine and 2-[(S)-1-phenylethylamino]-4-[6-nitrobenzimidazol-1-yl]pyrimidine (100 mg, 0.28 mmol) from EXAMPLE 75, ethanol (5 mL), and Raney nickel (ca. 40 mg, wet) was vigorously stirred under an H$_2$ atmosphere for 2 hours. The catalyst was removed by filtration and the filter cake washed with ethanol. The filtrate and washings were combined and concentrated under reduced pressure to afford a 1:1 mixture of the title compounds as a colorless solid (80 mg). The products were separated and purified by preparative thin layer chromatography (Silica, 4% CH$_3$OH in CH$_2$Cl$_2$) to give the title compounds.

2-[(S)-1-phenylethylamino]-4-[5-aminobenzimidazol-1-yl]pyrimidine

Partial $^1$H NMR (500 MHz CDCl$_3$): δ 8.40 (brs, 1H); 8.28 (d J=5.5 Hz, 1H); 7.60 (br,1H); 7.05 (s, 1H); 6.65 (d J=5.5 Hz, 1H); 5.19 (br, 1H); 1.61 (d J=6.9 Hz, 3H).

2-[(S)-1-phenylethylamino]-4-[6-aminobenzimidazol-1-yl]pyrimidine

Partial $^1$H NMR (500 MHz CDCl$_3$): δ 8.36 (d J=5.5 Hz, 1H); 8.25 (brs, 1H); 7.56 (d J=9.0 Hz, 1H); 7,05 (br, 1H); 6.68 (d J=5.5 Hz, 1H); 5.21 (br, 1H); 1.61 (d J=6.9 Hz, 3H).

EXAMPLE 80

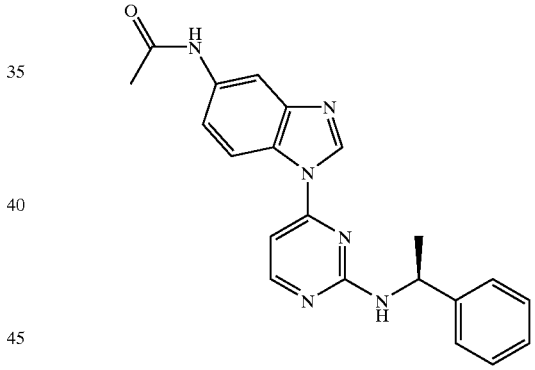

2-[(S)-1-Phenylethylamino]-4-[5-N-(acetyl)-aminobenzimidazol-1-yl]pyrimidine

To a solution of 2-[(S)-1-phenylethylamino]-4-[5-aminobenzimidazol-1-yl]pyrimidine (20 mg, 0.06 mmol), pyridine (0.20 mL), and CH$_2$Cl$_2$ (1 mL) was added acetyl chloride (8 μL, 0.11 mmol). The mixture was stirred for 18 hours at ambient temperature then partitioned between water and CH$_2$Cl$_2$. The organic layer was separated, dried with Na$_2$SO$_4$, filtered and concentrated under reduced pressure. The product was purified by chromatography (Silica, 10% CH$_3$OH: CH$_2$Cl$_2$) to give the title compound. Partial $^1$H NMR (500 MHz CD$_3$OD): δ 8.68 (br, 1H); 8.30 (d J=5.0 Hz, 1H); 8.0 (s, 1H); 7.65 (br, 1H); 6.90 (d J=5.0 Hz, 1H); 5.12 (br, 1H); 2.18 (s, 3H); 1.58 (d J=6.9 Hz, 3H).

EXAMPLE 81

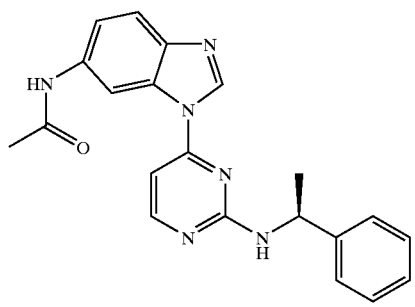

2-[(S)-1-Phenylethylamino]-4-[6-N-(acetyl)aminobenzimidazol-1-yl]pyrimidine

The title compound was prepared from 2-[(S)-1-phenylethylamino]-4-[6-aminobenzimidazol-1-yl]pyrimidine and acetyl chloride according to the procedure described in EXAMPLE 80. Partial ¹H NMR (500 MHz CD$_3$OD): δ 8.75 (s, 1H); 8.58 (br, 1H); 8.22 (d J=5.5 Hz, 1H); 7.54 (d J=8.5 Hz, 1H); 6.80 (d J=5.5 Hz, 1H); 5.22 (br, 1H); 2.18 (s, 3H); 1.57 (d J=6.9 Hz, 3H).

EXAMPLE 82

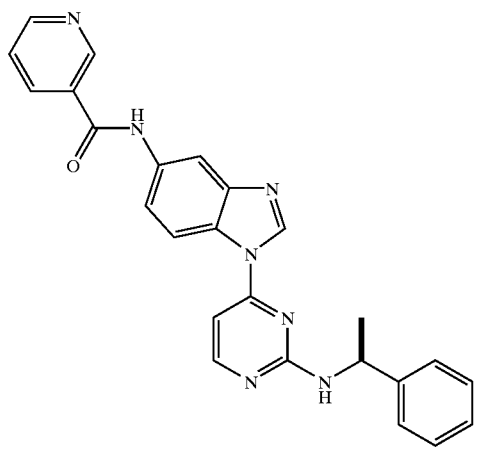

2-[(S)-1-Phenylethylamino]-4-[5-N-(pyridin-3-oyl)-aminobenzimidazol-1-yl]-pyrimidine The title compound was prepared from 2-[(S)-1-phenylethylamino]-4-[5-aminobenzimidazol-1-yl]pyrimidine and nicotinoyl chloride hydrochloride according to the procedure described in EXAMPLE 80. Partial ¹H NMR (500 MHz CD$_3$OD): δ 9.10 (s, 1H); 8.68(dd J=4.5,1.0 Hz,1H); 8.62 (br, 1H); 8.34 (dt J=7.5,1.0 Hz, 1H); 8.30 (d J=5.5 Hz); 8.10 (s, 1H); 7.73 (br, 1H); 7.57 (br, 1H); 7.53 (dd J=7.5, 4.5 Hz, 1H); 6.86 (d J=5.5 Hz, 1H); 5.16 (br, 1H); 1.58 (d J=6.9 Hz, 3H).

EXAMPLE 83

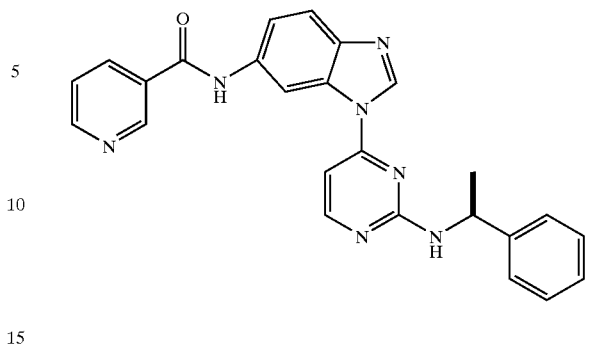

2-[(S)-1-Phenylethylamino]-4-[6-N-(pyridin-3-oyl)-aminobenzimidazol-1-yl]-pyrimidine The title compound was prepared from 2-[(S)-1-phenylethylamino]-4-[6-aminobenzimidazol-1-yl]pyrimidine and nicotinoyl chloride hydrochloride according to the procedure described in EXAMPLE 80. Partial ¹H NMR (500 MHz CD$_3$OD): δ 9.16 (s, 1H); 8.73 (br, 1H); 8.68 (br, 1H); 8.45 (br, 1H); 8.30 (d J=5.5 Hz, 1H); 8.21 (d J=7.5 Hz); 7.68 (d J=8.0 Hz, 1H); 6.72 (d J=5.5 Hz, 1H); 5.26 (m J=6.5 Hz, 1H); 1.58 (d J=6.5 Hz, 3H).

EXAMPLE 84

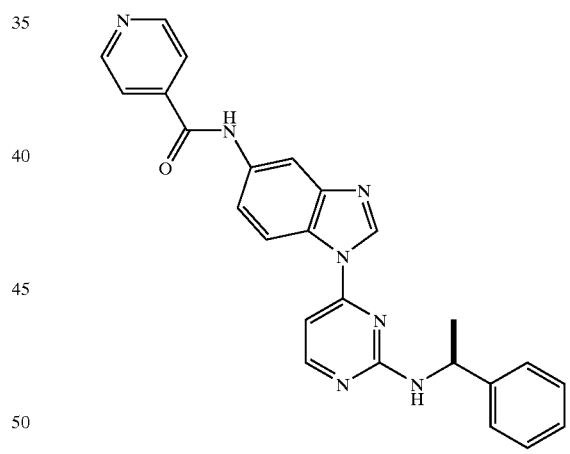

2-[(S)-1-Phenylethylamino]-4-[5-N-(pyridin-4-oyl)-aminobenzimidazol-1-yl]-pyrimidine The title compound was prepared from 2-[(S)-1-phenylethylamino]-4-[5-aminobenzimidazol-1-yl]pyrimidine and isonicotinoyl chloride hydrochloride according to the procedure described in EXAMPLE 80. Partial ¹H NMR (500 MHz CD$_3$OD): δ 8.67 (d J=5.5, 2H); 8.41 (br, 1H); 8.30 (d, J=5.5 Hz, 1H); 7.92 (s, 1H); 7.80 (d J=5.5, 2H); 7.77 (br, 1H); 6.68 (d, J=5.5 Hz, 1H); 5.15 (br, 1H); 1.59 (d J=6.9 Hz, 3H).

EXAMPLE 85

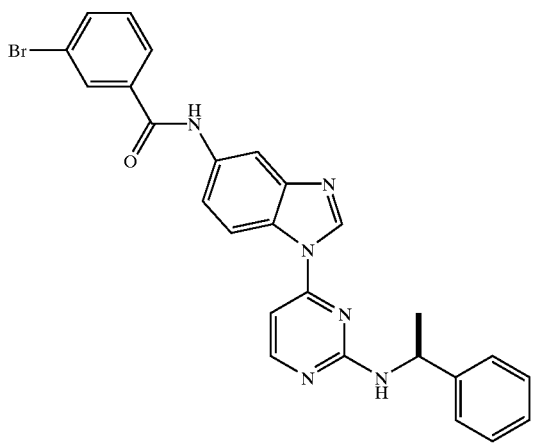

2-[(S)-1-Phenylethylamino]-4-[5-N-(3-bromobenzoyl)-aminobenzimidazol-1-yl]-pyimidine The title compound was prepared from 2-[(S)-1-phenylethylamino]-4-[5-aminobenzimidazol-1-yl]pyrimidine and 3-bromobenzoyl chloride according to the procedure described in EXAMPLE 80. Partial $^1$H NMR (500 MHz CD$_3$OD) δ 8.62 (br, 1H); 8.30 (d J=5.5 Hz, 1H); 8.05–8.15 (m, 2H); 7.93 (d J=8.0 Hz, 1H); 7.88 (d J=7.5 Hz, 1H); 7.66 (d J=8.0 Hz, 1H); 7.58 (br, 1H); 6.86 (d J=5.5 Hz, 1H) 5.13 (br, 1H); 1.58 (d J=6.9 Hz, 3H).

EXAMPLE 86

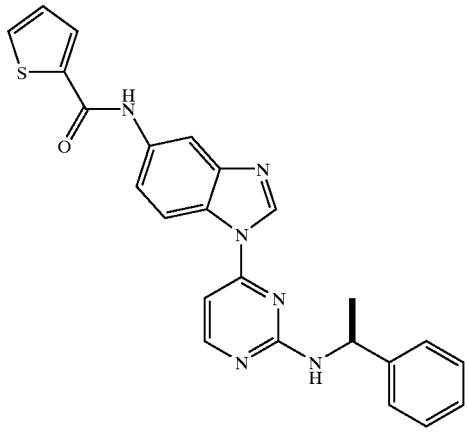

2-[(S)-1-Phenylethylamino]-4-[5-N-(thiophen-2-oyl)-aminobenzimidazol-1-yl]-pyrimidine The title compound was prepared from 2-[(S)-1-phenylethylamino]-4-[5-aminobenzimidazol-1-yl]pyrimidine and 2-thiophenecarbonyl chloride according to the procedure described in EXAMPLE 80. Partial $^1$H NMR (500 MHz CD$_3$OD) δ : 7.95 (s, 1H); 7.88 (s, 1H); 7.75 (d, J=5.5 Hz, 1H); 7.60 (m, 2H); 7.55 (d, J=5.0 Hz, 1 H); 7.38 (bs, 1 H); 5.95 (d, J=5.5 Hz, 1 H).

EXAMPLE 87

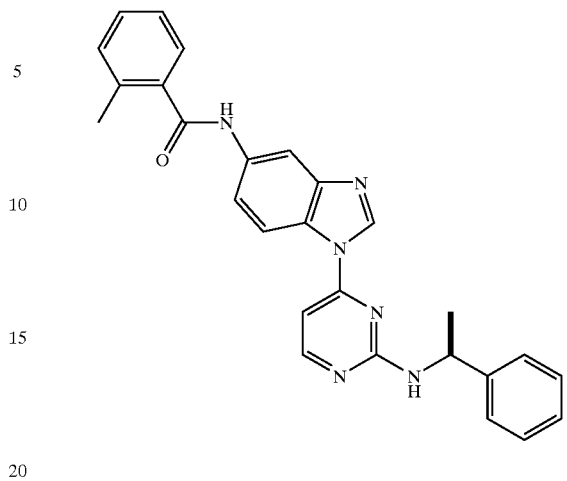

2-[(S)-1-Phenylethylamino]-4-[5-N-(2-methylbenzoyl)aminobenzimidazol-1-yl]-pyrimidine The title compound was prepared from 2-[(S)-1-phenylethylamino]-4-[5-aminobenzimidazol-1-yl]pyrimidine and 2-toluoyl chloride according to the procedure described in EXAMPLE 80. Partial $^1$H NMR (500 MHz CDCl$_3$): δ 8.39 (br, 1H); 8.32 (d J=5.0 Hz, 1H); 8.03 (s,1H); 7.80 (br,1H); 7.62 (bd, 1H); 6.69 (δ J=5.0 Hz, 1H); 5.19 (br, 1H); 2.52 (s, 3H); 1.61 (d J=6.5 HZ,3H).

EXAMPLE 88

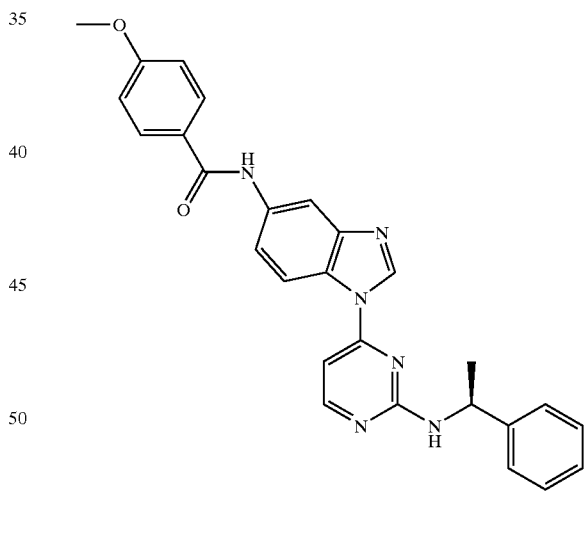

2-[(S)-1-Phenylethylamino]-4-[5-N-(4-methoxybenzoyl)aminobenzimidazol-1-yl]-pyrimidine The title compound was prepared from 2-[(S)-1-phenylethylamino]-4-[5-aminobenzimidazol-1-yl]pyrimidine and 4-anisoyl chloride according to the procedure described in EXAMPLE 80. Partial $^1$H NMR (500 MHz CDCl$_3$): δ 8.42 (br, 1H); 8.33 (d J=5.5 Hz, 1H); 8.01 (s, 1H); 7.88 (d, J=8.5, 2H); 7.70 (br, 1H); 7.62 (d J=7.0 Hz, 1H); 6.93 (d J=8.5 Hz, 2H); 6.67(δ J=5.5 Hz); 5.18 (br, 1H); 3.82 (s, 3H); 1.60 (d J=6.9 Hz), 3H).

EXAMPLE 89

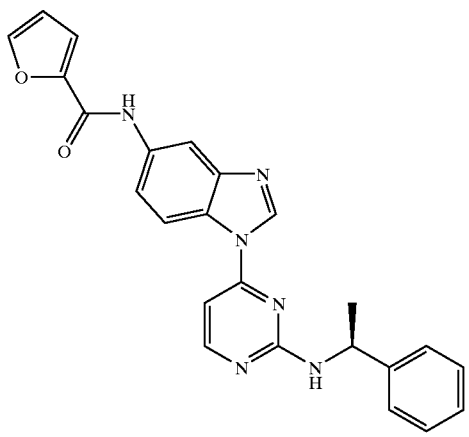

2-[(S)-1-Phenylethylamino]-4-[5-N-(furan-2-oyl)
aminobenzimidazol-1-yl]pyrimidine The title compound was prepared from 2-[(S)-1-phenylethylamino]-4-[5-aminobenzimidazol-1-yl]pyrimidine and 2-furoyl chloride according to the procedure described in EXAMPLE 80. Partial $^1$H NMR (500 MHz CDCl$_3$): δ 8.43 (br, 1H); 8.34 (d J=5.5 Hz, 1H); 8.09 (s,1H); 7.75 (br, 1H); 7.63 (br,1H); 7.55 (s, 1H); 6.76 (d J=5.5 Hz, 1H); 6.60 (m, 1H); 5.19 (br, 1H); 1.62 (d, J=6.9 Hz, 3H).

EXAMPLE 90

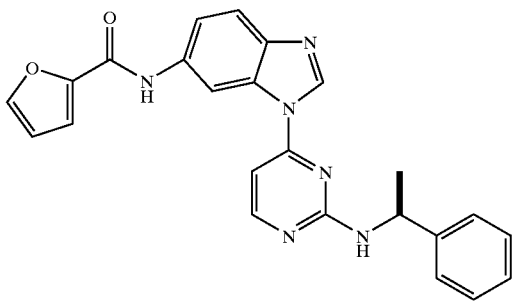

2-[(S)-1-Phenylethylamino]-4-[6-N-(furan-2-oyl)
aminobenzimidazol-1-yl]pyrimidine The title compound was prepared from 2-[(S)-1-phenylethylamino]-4-[6-aminobenzimidazol-1-yl]pyrimidine and 2-furoyl chloride according to the procedure described in EXAMPLE 80. Partial 1H NMR (500 MHz CDCl3): d 8.48 (br, 1H); 8.32–8.36 (m, 2H); 7.73 (d, J=8.5 Hz, 1H); 7.52 (s, 1H); 6.80 (d J=5.5 Hz, 1H); 6.57 (bs, 1H); 5.28 (m, 1H); 1.61 (d J=6.5 Hz, 3H).

EXAMPLE 91

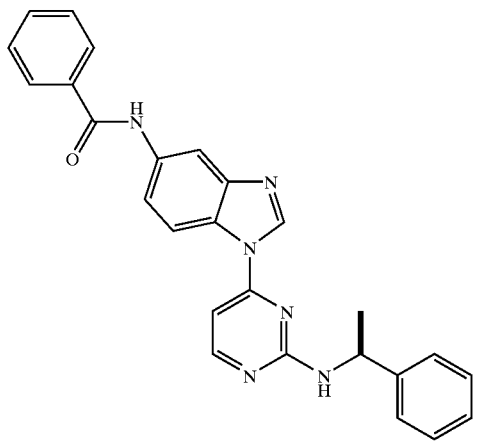

2-[(S)-1-Phenylethylamino]-4-[5-N-(benzoyl)-
aminobenzimidazol-1-yl]pyrimidine

The title compound was prepared from 2-[(S)-1-phenylethylamino]-4-[5-aminobenzimidazol-1-yl]pyrimidine and benzoyl chloride according to the procedure described in EXAMPLE 80. Partial $^1$H NMR (500 MHz CDCl$_3$): δ 8.42 (br, 1H); 8.35 (br, 1H); 8.05 (s, 1H); 7.90 (δ J=10 Hz, 1H); 7.60 (br, 1H); 6.68 (d J=5.5 Hz, 1H); 5.19 (br, 1H); 1.62 (d J=6.5 Hz, 3H).

EXAMPLE 92

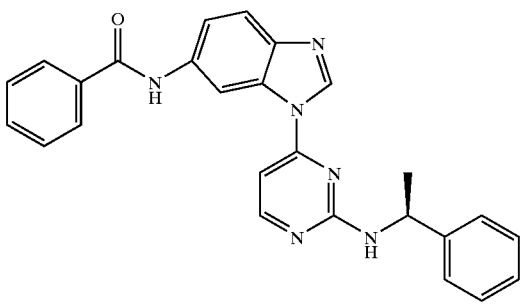

2-[(S)-1-Phenylethylamino]-4-[6-N-(benzoyl)-
aminobenzimidazol-1-yl]pyrimidine

The title compound was prepared from 2-[(S)-1-phenylethylamino]-4-[6-aminobenzimidazol-1-yl]pyrimidine and benzoyl chloride according to the procedure described in EXAMPLE 80. Partial $^1$H NMR (500 MHz CDCl$_3$): δ 8.92 (s,1H); 8.68 (br, 1H); 8.30 (d J=5.5 Hz, 1H); 7.98 (d J=10 Hz, 1H); 7.40 (d J=10 Hz, 1H); 6.93 (d J=5.5 Hz, 1H); 5.30 (br, 1H); 1.58 (d J=6.5 Hz, 3H).

EXAMPLE 93

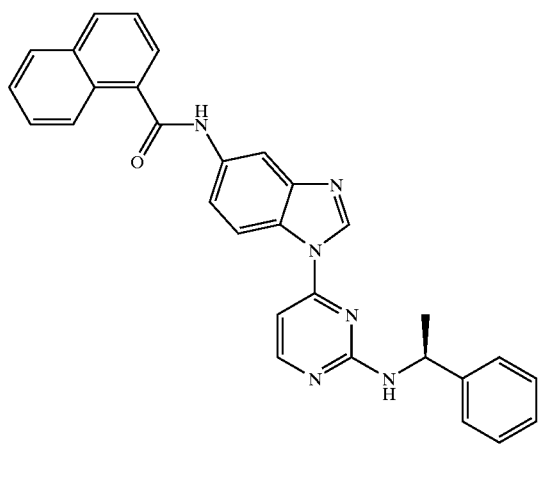

2-[(S)-1-Phenylethylamino]-4-[5-N-(naphth-1-oyl)-aminobenzimidazol-1-yl]-pyrimidine The title compound was prepared from 2-[(S)-1-phenylethylamino]-4-[5-aminobenzimidazol-1-yl]pyrimidine and 1-naphthoyl chloride according to the procedure described in EXAMPLE 80. Partial $^1$H NMR (500 MHz CDCl$_3$): δ 8.73 (s, 1H); 8.34 (d J=10 Hz, 1H); 8.26 (br, 1H); 8.24 (br, 1H);8.06 (br, 1H); 7.82 (d J=10 Hz, 1H); 7.77 (d J=10 Hz, 1H); 6.56 (d J=5.0 Hz, 1H); 5.16 (br, 1H); 1.61 (d J=6.5 Hz, 3H).

EXAMPLE 94

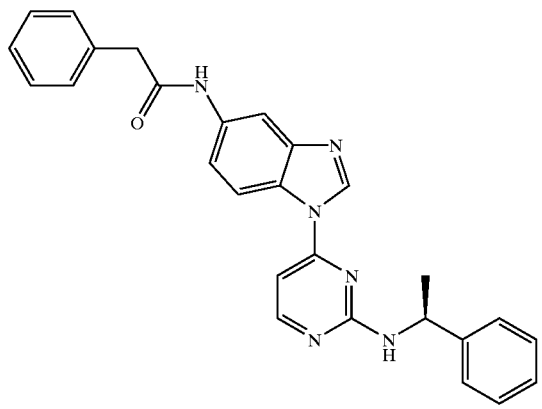

2-[(S)-1-Phenylethylamino]-4-[5-N-(phenylacetyl)-aminobenzimidazol-1-yl]-primidine The title compound was prepared from 2-[(S)-1-phenylethylamino]-4-[5-aminobenzimidazol-1-yl]pyrimidine and phenylacetyl chloride according to the procedure described in EXAMPLE 80. Partial $^1$H NMR (500 MHz CDCl$_3$): δ 8.42 (br, 1H); 8.30 (d J=5.5, 1H); 7.85 (s, 1H); 7.65 (s, 1H); 6.68 (d J=5.5 Hz, 1H); 5.16 (br, 1H); 3.88 (s, 2H); 1.60 (d J=6.5 Hz, 3H).

EXAMPLE 95

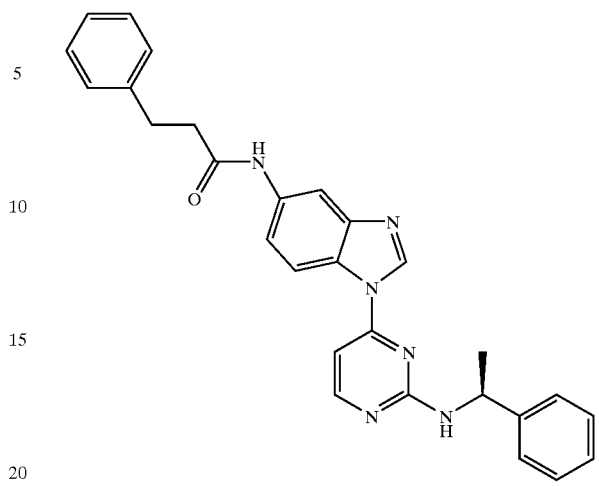

2-[(S)-1-Phenylethylamino]-4-[5-N-(1-phenylpropionoyl)aminobenzimidazol-1-yl]-pyrimidine The title compound was prepared from 2-[(S)-1-phenylethylamino]-4-[5-aminobenzimidazol-1-yl]pyrimidine and hydrocinnamoyl chloride according to the procedure described in EXAMPLE 80. Partial $^1$H NMR (500 MHz CDCl$_3$): δ 8.38 (br, 1H); 8.30 (d J=5.0 Hz, 1H0; 7.82 (br, 2H); 7.18 (br, 1H); 6.65 (d J=5.0 Hz, 1H); 5.16 (br, 1H); 3.05 (t J=6.0 Hz, 2H); 2.67 (t J=6.0 Hz, 2H); 1.61 (d J=6.5 Hz, 3H).

EXAMPLE 96

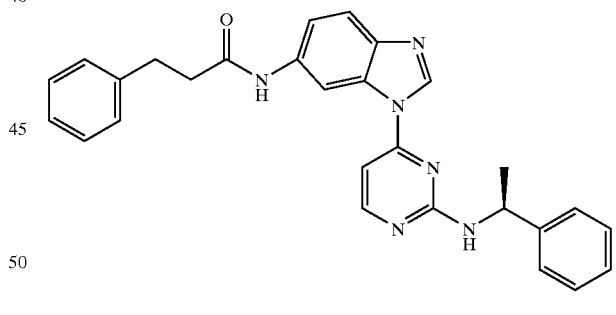

2-[(S)-1-Phenylethylamino]-4-[6-N-(1-phenylpropionoyl)aminobenzimidazol-1-yl]-pyrimidine The title compound was prepared from 2-[(S)-1-phenylethylamino]-4-[6-aminobenzimidazol-1-yl]pyrimidine and hydrocinnamoyl chloride according to the procedure described in EXAMPLE 80. Partial $^1$H NMR (500 MHz CDCl$_3$): δ 8.63 (br, 1H); 8.40 (br, 1H); 8.30 (d J=5.0 Hz, 1H); 7.62 (d J=11 Hz, 1H); 6.76 (d J=5.0 Hz, 1H); 5.23 (m, 1H); 3.05 (t J=6.0 Hz, 2 H); 2.68 (t J=6.0 Hz, 2H); 1.60 (d J=6.5 Hz, 3H).

EXAMPLE 97

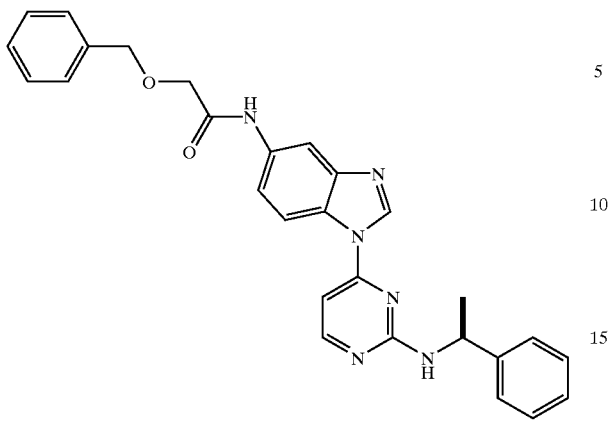

2-[(S)-1-Phenylethylamino]-4-[5-N-(benzyloxyacetyl)aminobenzimidazol-1-yl]-pyrimidine The title compound was prepared from 2-[(S)-1-phenylethylamino]-4-[5-aminobenzimidazol-1-yl]pyrimidine and benzyloxyacetyl chloride according to the procedure described in EXAMPLE 80. Partial $^1$H NMR (500 MHz CDCl$_3$): δ 8.48 (br, 1H); 8.42 (s, 1H); 8.36 (d J=5.0 Hz, 1H); 8.00 (s, 1H); 7.53 (br, 1H); 6.76 (d J=5.0 Hz, 1H); 5.20 (br, 1H); 4.70 (s, 2H); 4.18 (s, 2H); 1.63 (d J=6.5 Hz, 3H).

EXAMPLE 98

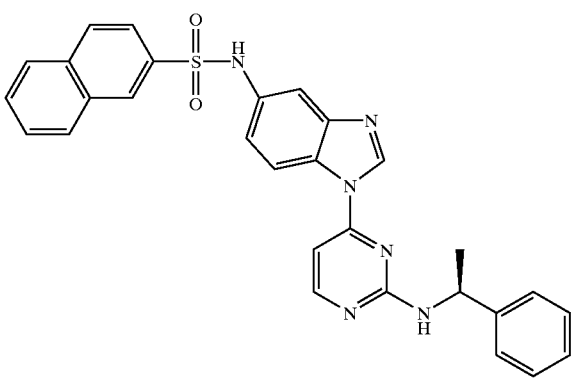

2-[(S)-1-Phenylethylamino]-4-[5-N-(naphthylene-2-sulfonyl)aminobenzimidazol-1-yl]pyrimidine The title compound was prepared from 2-[(S)-1-phenylethylamino]-4-[5-aminobenzimidazol-1-yl]pyrimidine and 2-naphthalenesulfonyl chloride according to the procedure described in EXAMPLE 80. Partial $^1$H NMR (500 MHz CDCl$_3$): δ 8.38 (br, 1H); 8.35 (s, 1H); 8.31 (d J=5.5 Hz, 1H); 7.73–7.87 (m, 5H); 6.63 (d J=5.5 Hz, 1H); 5.10 (br, 1H); 1.61 (d J=6.5 Hz, 3H).

EXAMPLE 99

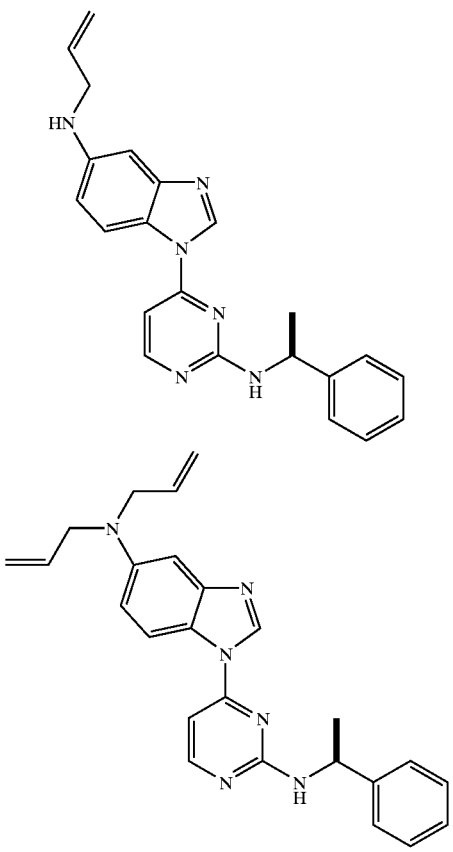

2-[(S)-1-Phenylethylamino]-4-[5-N-(allyl)aminobenzimidazol-1-yl]pyrimidine and 2-[(S)-1-Phenylethylamino]-4-[5-N,N-(diallyl)aminobenzimidazol-1-yl]pyrimidine To a solution of 2-[(S)-1-phenylethylamino]-4-[5-aminobenzimidazol-1-yl]pyrimidine (30 mg, 0.09 mmol) (EXAMPLE 79) and EtOH (2 mL) was added allyl iodide (14 μL, 0.15 mmol). The mixture was heated to reflux for 4 hours. The products were separated and purified by chromatography ( Silica, 5% CH$_3$OH: CH$_2$Cl$_2$) to give the title compounds.

2-[(S)-1-phenylethylamino]-4-[5-allylaminobenzimidazol-1-yl]pyrimidine

Partial $^1$H NMR (500 MHz CD$_3$OD): δ 8.40 (br, 1H); 8.31 (d J=5.5 Hz, 1H); 7.62 (br, 1H); 7.00 (s, 1H); 6.70 (d J=5.5, 1H); 6.66 (br, 1H); 6.00 (m, 2H); 5.33 (d J=17.5 Hz, 1H); 5.20 (d J=12 Hz, 1H); 3.82 (d J=4.5 Hz, 2H); 1.62 (d J=6.5 Hz, 3H).

2-[(S)-1-phenylethylamino]-4-[5-diallylaminobenzimidazol-1-yl]pyrimidine

Partial $^1$H NMR (500 MHz CD$_3$OD): δ 8.40 (br, 1H); 8.32 (d J=5.5 Hz, 1H); 7.68 (br, 1H); 7.12 (s, 1H); 6.80 (br, 1H); 6.72 (d J=5.5 Hz, 1H); 5.90 (m, 3H); 5.20 (m, 5H); 3.99 (d J=4.5 Hz, 4H); 1.62 (d J=6.5 Hz, 3H).

EXAMPLE 100

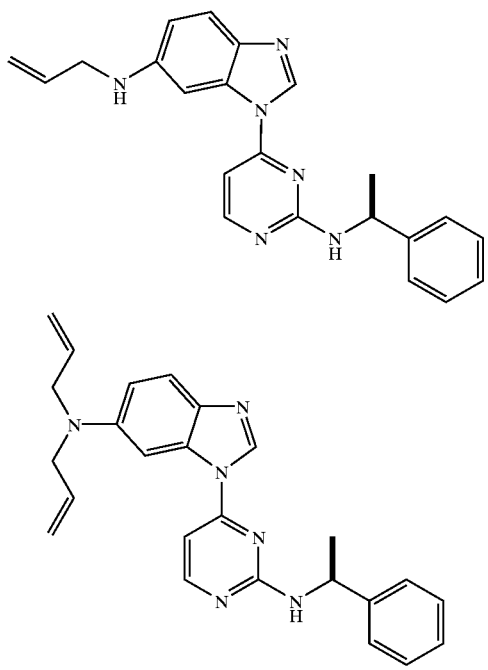

2-[(S)-1-Phenylethylamino]-4-[6-N-(allyl) aminobenzimidazol-1-yl]pyrimidine and 2-[(S)-1-Phenylethylamino]-4-[6-N,N-(diallyl) aminobenzimidazol-1-yl]pyrimidine The title compounds were prepared from 2-[(S)-1-phenylethylamino]-4-[6-aminobenzimidazol-1-yl] pyrimidine and allyl iodide according to the procedure described in EXAMPLE 99.

2-[(S)-1-phenylethylamino]-4-[6-allylaminobenzimidazol-1-yl]pyrimidine

Partial $^1$H NMR (500 MHz CD$_3$OD): δ 8.33 (d J=5.5 Hz, 1H); 8.27 (br, 1H); 7.59 (d J=8.0 Hz, 1H); 7.18 (br, 1H); 6.72 (d J=5.5 Hz, 1H); 6.69 (dd J=8.0, 1.5 Hz, 1H); 5.98 (m, 1H); 5.32 (d J=17.5 Hz, 1H); 5.26 (m, 1H); 5.21 (δ J=10.0 Hz, 1H); 3.82 (d J=4.0 Hz, 2H); 1.62 (d J=6.9 Hz, 3H).

2-[(S)-1-phenylethylamino]-4-[6-diallylaminobenzimidazol-1-yl]pyrimidine

Partial 1H NMR (500 MHz CD$_3$OD): δ 8.34 (d J=5.5 Hz, 1H); 8.31 (br, 1H); 7.62 (d J=8.0 Hz, 1H); 6.83 (dd J=8.0, 1.5 Hz, 1H); 6.72 (d J=5.5 Hz, 1H); 5.89 (m, 2H); 5.27 (m, 1H); 5.22 (d J=17.5 Hz, 2H); 5.18 (d J=10.0 Hz, 2H); 3.99 (d J=4.0 Hz, 4H); 1.62 (d J=6.9 Hz, 3H).

EXAMPLE 101

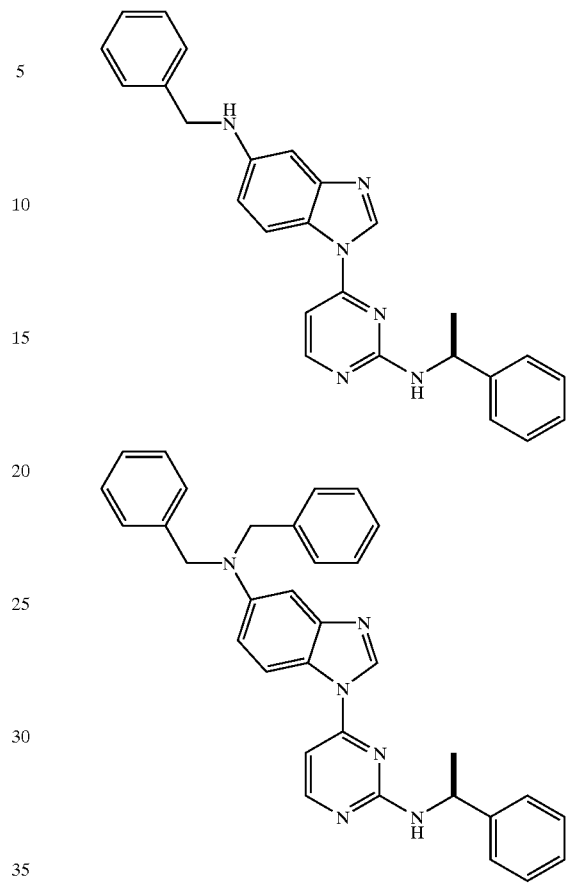

2-[(S)-1-Phenylethylamino]-4-[5-N-(benzyl) aminobenzimidazol-1-yl]pyrimidine and 2-[(S)-1-Phenylethylamino]-4-[5-N,N-(dibenzyl) aminobenzimidazol-1-yl]pyrimidine The title compounds were prepared from 2-[(S)-1-phenylethylamino]-4-[5-aminobenzimidazol-1-yl] pyrimidine and benzyl bromide according to the procedure described in EXAMPLE 99.

2-[(S)-1-phenylethylamino]-4-[5-benzylaminobenzimidazol-1-yl]pyrimidine

Partial $^1$H NMR (500 MHz CD$_3$OD): δ 8.38 (br, 1H); 8.31 (d J=5.5 Hz, 1H); 7.60 (br, 1H); 7.02 (s, 1H); 6.69 (d J=5.5 Hz, 1H); 6.57 (br, 1H); 5.19 (br, 1H); 4.40 (s, 2H); 1.61 (d J=6.5 Hz, 3H).

2-[(S)-1-phenylethylamino]-4-[5-dibenzylaminobenzimidazol-1-yl]pyrimidine

Partial $^1$H NMR (500 MHz CD$_3$OD): δ 8.38 (br, 1H); 8.31 (d J=5.5 Hz, 1H); 7.60 (br, 1H); 7.15 (s, 1H); 6.79 (br, 1H); 6.65 (d J=5.5 Hz, 1H); 5.19 (br, 1H); 4.70 (s, 4H); 1.61 (d J=6.5 Hz, 3H).

EXAMPLE 102

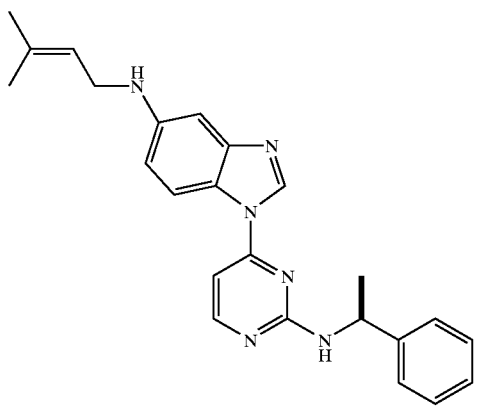

2-[(S)-1-Phenylethylamino]-4-[5-N-(3,3-dimethylallyl)aminobenzimidazol-1-yl]primidine The title compounds were prepared from 2-[(S)-1-phenylethylamino]-4-[5-aminobenzimidazol-1-yl]pyrimidine and 3,3-dimethylallyl bromide according to the procedure described in EXAMPLE 99. Partial 1H NMR (500 MHz CD$_3$OD): δ 8.39 (br, 1H); 8.34 (d J=5.5 Hz, 1H); 7.62 (br, 1H); 6.99 (s, 1H); 6.62 (br, 1H); 5.38 (t J=6.0 Hz, 1H); 5.20 (br, 1H); 3.86 (d J=6.0 Hz, 2H); 1.76 (s, 3H); 1.74 (s, 3H); 1.62 (d J=6.5 Hz, 3H).

EXAMPLE 103

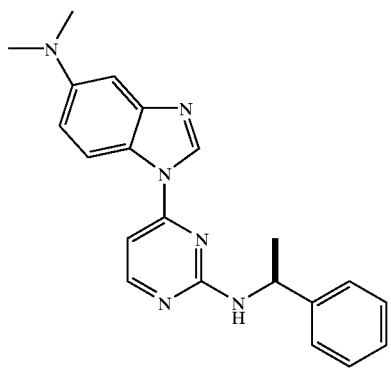

2-[(S)-1-Phenylethylamino]-4-[5-N,N-(dimethyl)aminobenzimidazol-1-yl]pyrimidine

To a solution of 2-[(S)-1-phenylethylamino]-4-[5-aminobenzimidazol-1-yl]pyrimidine (100 mg, 0.30 mmol) (EXAMPLE 79) and CH$_3$CN (3 mL) was added 37% aqueous formaldehyde (1 mL, 12.3 mmol) followed by NaBH$_3$CN (100 mg, 1.6 mmol) and glacial acetic acid (0.075 mL). The reaction mixture was stirred for two hours at room temperature then partitioned between ether and aqueous Na$_2$CO$_3$. The organic layer was dried with Na$_2$SO$_4$ and concentrated. The product was purified by preparative thin layer chromatography (silica, 5% CH$_3$OH in CH$_2$Cl$_2$) to afford 15 mg of the title compound. Partial $^1$H NMR (500 MHz CD$_3$OD): δ 8.42 (br, 1H); 8.35 (d J=5.5 Hz, 1H); 7.65 (br, 1H); 7.15 (s, 1H); 6.83 (d J=7 Hz, 1H); 6.73 (d J=5.5 Hz, 1H); 5.21 (br, 1H); 3.02 (s, 6H); 1.62 (d J=6.5 Hz, 3H).

EXAMPLE 104

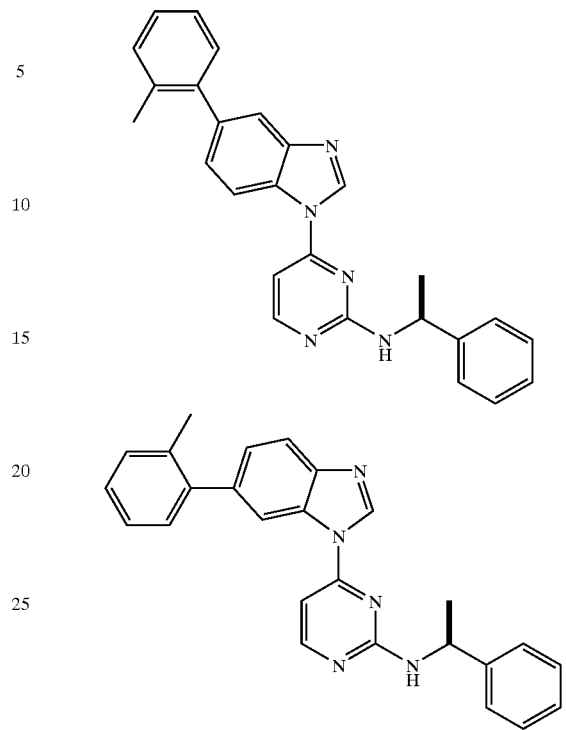

2-[(S)-1-Phenylethylamino]-4-[5-(2-methylphenyl)benzimidazol-1-yl]pyrimidine and 2-[(S)-1-Phenylethylamino]-4-[6-(2-methylphenyl)benzimidazol-1-yl]pyrimidine To a solution of a mixture of 2-[(S)-1-phenylethylamino]-4-[5-bromobenzimidazol-1-yl]pyrimidine and 2-[(S)-1-phenylethylamino]-4-[6-bromobenzimidazol-1-yl]pyrimidine (50 mg, 0.13 mmol), 2-methylphenylboronic acid (25 mg, 0.18 mmol), EtOH (0.20 mL), and toluene (1.0 mL) was added 1M aqueous Na$_2$CO$_3$ (0.40 mL) and [1,1'-Bis(diphenylphosphino)ferrocene]dichloro-pallidium (II) (10 mg, 0.01 mmol). The mixture was heated to 100° C. for 10 h, cooled and partitioned between water and CH$_2$Cl$_2$. The extracts were dried with NaSO$_4$, and concentrated under reduced pressure. The products were separated and purified by preparative HPLC (Silica.2:1 Hexane/acetone) to afford the title compounds.

2-[(S)-1-phenylethylamino]-4-[5-(2-methylphenyl)-benzimidazol-1-yl]pyrimidine

Partial 1H NMR (500 MHz CDCl$_3$): δ 8.52 (br,1H); 8.38 (d J=5.5 Hz, 1H); 7.77 (s, 1H); 6.81 (δ J=5.5 Hz, 1H); 5.23 (br, 1H); 2.31 (s, 3H); 1.63 (d J=6.5 Hz, 3H).

2-[(S)-1-phenylethylamino]-4-[6-(2-methylphenyl)-benzimidazol-1-yl]pyrimidine

Partial $^1$H NMR (500 MHz CDCl$_3$): δ 8.57 (br, 1H); 8.38 (d J=5.5 Hz, 1H); 8.03 (br, 1H); 7.85 (d J=10 Hz, 1H); 6.79 (d J=5.5 Hz, 1H); 5.20 (br, 1H0; 2.28 (s, 3H); 1.59 (d J=6.5 Hz, 3H).

EXAMPLE 105

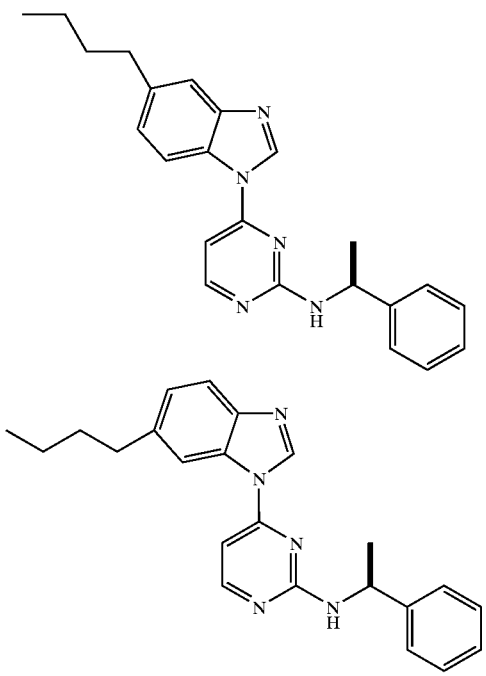

2-[(S)-1-Phenylethylamino]-4-[5-(n-butyl)-
benzimidazol-1-yl]pyrimidine and 2-[(S)-1-
Phenylethylamino]-4-[6-(n-butyl)-benzimidazol-1-
yl]pyrimidine The title compounds were prepared from 2-[(S)-1-phenylethylamino]-4-[5-bromobenzimidazol-1-yl]pyrimidine and 2-[(S)-1-phenylethylamino]-4-[6-bromobenzimidazol-1-yl]pyrimidine and butylboronic acid according to the procedure described in EXAMPLE 104. Partial $^1$H NMR (500 MHz CD$_3$OD): δ 8.47 (br,1H); 8.35 (d J=5.0 Hz, 1H); 7.74 (br, 1H); 7.62 (s, 1H); 7.16 (d J=6.0 Hz, 1H); 6.78 (δ J=5.0 Hz, 1H); 5.22 (br, 1H); 2.75 (t J=6.5, 2H); 1.60–1.70 (m, 5H); 1.39 (m J=6.5 Hz, 2H); 0.95 (t, J=6.5, 3H). Partial $^1$H NMR (500 MHz CD$_3$OD): δ 8.47 (br,1H); 8.35 (d J=5.0 Hz, 1H); 7.86 (s, 1 H); 7.74 (d J=8.0 HZ, 1H); 7.22 (d J=8.0 Hz, 1H); 6.82 (d, J=5.0 Hz, 1H) 5.28 ( m, 1H); 2.78 (t J=6.0, 2 H); 1.6–1.7 (m, 5H); 1.39 (m J=6.5, 2H); 0.95 (t J=6.5 Hz, 3 H).

EXAMPLE 106

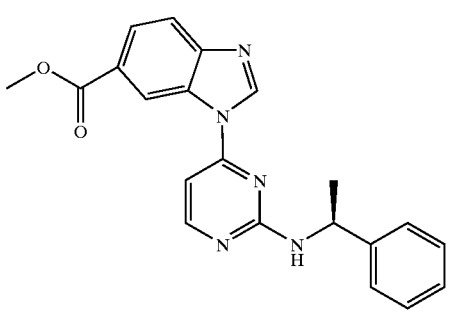

2-[(S)-1-Phenylethylamino]-4-[6-methoxycarbonyl-
benzimidazol-1-yl]pyrimidine

Step A: 2-methylthio-4-[5-carboxy-benzimidazol-1-
yl]pyrimidine and 2-methylthio-4-[6-carboxy-
benzimidazol-1-yl]pyrimidine A mixture of 60% NaH (0.168 mg, 4.2 mmol), benzimidazole carboxylic acid (0.52 gm,1.97 mmol) and 4-chloro-2-methylthiopyrimidine (320 mg, 2.0 mmol) in 7 mL of DMF was heated to 80° C. for 75 min The reaction mixture was poured onto ice water, acidified with 2N HCl and the waxy product filtered. The solid was air dried to afford 298 mg of a mixture of the title compounds as a tan solid.

Step B: 2-methanesulfonyl-4-[5-carboxy-
benzimidazol-1-yl]pyrimidine and 2-
methanesulfonyl-4-[6-carboxybenzimidazol-1-yl]
pyrimidine To a solution of 2-methylthio-4-[6-carboxybenzimidazol-1-yl]-pyrimidine (250 mg, 0.87 mmol) in CH$_2$Cl$_2$ (5.0 mL) at 0° C. was added 3-chloro-peroxybenzoic acid (500 mg, 2.9 mmol). The reaction was stirred for 18 h at room temperature. The reaction mixture was washed with water, dried with Na$_2$SO$_4$, concentrated to 1/2 volume and diluted with ether. The products were collected by filtration to afford 170 mg of a mixture of the title compounds.

Step C: 2-[(S)-1-Phenylethylamino]-4-[5-carboxy-
benzimidazol-1-yl]-pyrimidine and 2-[(S)-1-
Phenylethylamino]-4-[6-carboxy-benzimidazol-1-yl]
pyrimidine A solution of 2-methanesulfonyl-4-[6-carboxy-benzimidazol-1-yl]pyrimidine (140 mg, 0.44 mmol) and (S)-1-phenylethylamine (0.20 mL, 1.54 mmol) in 5 mL of toluene was heated to 100° C. After 20 h, the reaction mixture was concentrated and the residue washed with dilute aqueous HCl. The solid was filtered and air dried. The products were separated by chromatography (silica, 15% CH$_3$OH in CH$_2$Cl$_2$).

Step D: 2-[(S)-1-Phenylethylamino]-4-[6-
methoxycarbonyl-benzimidazol-1-yl]pyrimidine To a solution of 2-[(S)-1-phenylethylamino]-4-[6-carboxy-benzimidazol-1-yl]pyrimidine in 0.2 mL of benzene and 0.1 mL of methanol was added 0.015 mL of (trimethylsilyl)diazomethane (2 M in hexanes). The solution was stirred for 30 min at room temperature then concentrated. The product was purified by chromatography to afford the title compound. Partial $^1$H NMR (500 MHz CD$_3$OD): δ 8.9 (s, 1H); 8.63 (br, 1H); 8.42 (d J=5.0 Hz, 1H); 8.09 (d J=11 Hz, 1H); 7.87 (d J=11 Hz, 1H); 6.83 (d J=5.0 Hz, 1H); 5.29 m, 1H); 3.98 (s, 3H); 1.64 (d J=7.0 Hz, 3H).

EXAMPLE 107

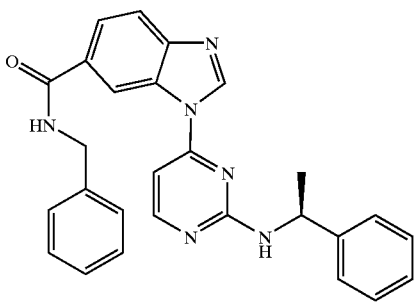

2-[(S)-1-Phenylethylamino]-4-[6-benzylaminocarbonyl-benzimidazol-1-yl]pyrimidine To a solution of a mixture 10 mg (0.028 mmol) of 2-[(S)-1-phenylethylamino]-4-[5-carboxy-benzimidazol-1-yl]pyrimidine and 2-[(S)-1-phenylethylamino]-4-[6-carboxy-benzimidazol-1-yl]pyrimidine (EXAMPLE 106 Step C) and benzylamine (0.003 mL, 0.028 mmol) in 0.6 mL $CH_2Cl_2$ was added N-methylmopholine (0.004 mL) followed by 1-[3-(dimethylamino)propyl]-3-ethylcarbodiimide hydrochloride (10 mg). The solution was stirred for 4 hours then quenched with water. The organic fraction was concentrated and the product purified by chromatography to afford the title compounds. Partial $^1$H NMR (500 MHz $CD_3OD$): δ 8.73 (brs, 1H); 8.57 (brs, 1H); 8.33 (brs, 1H); 7.82 (d J=10 Hz, 1H); 7.70 (d J=10 Hz, 1H); 6.82 (brs, 1H); 6.63 (brs, 1H); 5.23 (br, 1H); 4.70 (d J=5.5 Hz, 2H); 1.63 (d J=6.5 Hz, 3H). Partial $^1$H NMR (500 MHz $CD_3OD$): δ 8.47 (br, 1H); 8.36 (br, 1H); 8.20 (s, 1H); 6.79 (d J=5.5 Hz, 1H); 6.60 (br, 1H); 5.18 (br, 1H); 4.72 (d J=5.5 Hz, 2H); 1.62 (d, J=6.5 Hz, 3H).

EXAMPLE 108

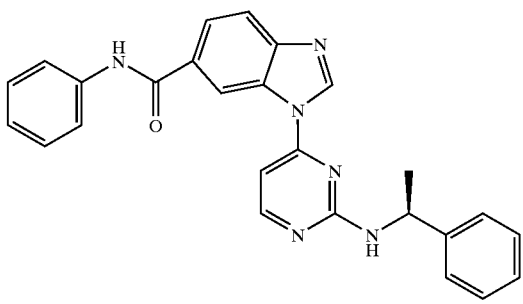

2-[1-Phenylethylamino]-4-[6-phenylaminocarbonyl-benzimidazol-1-yl]pyrimidine

The title compound was prepared from aniline and 2-[(S)-1-phenylethylamino]-4-[6-carboxy-benzimidazol-1-yl]pyrimidine according to the procedure described in EXAMPLE 107. Partial $^1$H NMR (500 MHz $CD_3OD$): δ 8.72 (br, 1H); 8.55 (br, 1H); 8.32 (br, 1H); 8.18 (s, 1H); 7.83 (d J=7.5 Hz, 1H); 7.76 (d J=7.5 Hz, 1H); 7.70 (d J=7.0 Hz, 2H); 6.78 (δ J=5.0 Hz, 1H); 5.23 (br, 1H); 1.63 (d J=6.0 Hz, 3H).

EXAMPLE 109

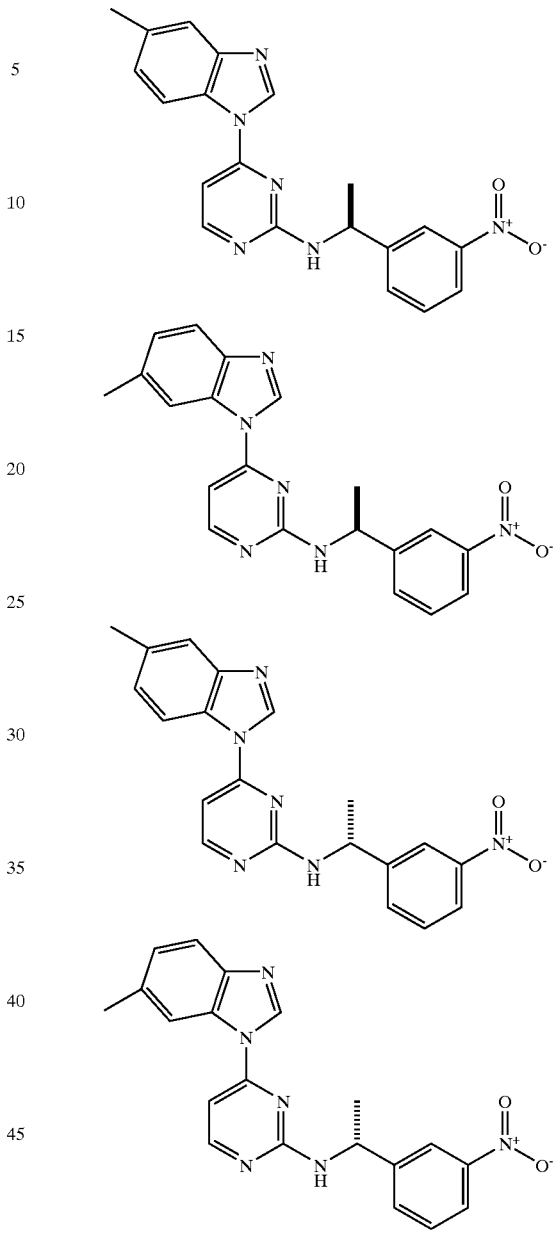

2-((S)-1-(3-nitro-phenyl)ethylamino)-4-[5-methyl-benzimidazol-1-yl]pyrimidine, 2-((S)-1-(3-nitro-phenyl)ethylamino)-4-[6-methyl-benzimidazol-1-yl]pyrimidine, 2-((R)-1-(3-nitro-phenyl)ethylamino)-4-[5-methyl-benzimidazol-1-yl]pyrimidine and 2-((R)-1-(3-nitro-phenyl)ethylamino)-4-[6-methyl-benzimidazol-1-yl]pyrimidine A solution of a mixture of 2-methanesulfonyl-4-[5-methyl-benzimidazol-1-yl]pyrimidine and 2-methanesulfonyl-4-[6-methyl-benzimidazol-1-yl]pyrimidine (150 mg, 0.52 mmol) and 1-(3-nitrophenyl)ethylamine (0.10 mL, 1.16 mmol) in 5 mL of xylenes was heated to 130° C. After 20 h, the reaction mixture was concentrated and purified by chromatography (silica, 3% $CH_3OH$ in $CH_2Cl_2$) to give 0.69 gm of a mixture of four compounds.

EXAMPLE 110

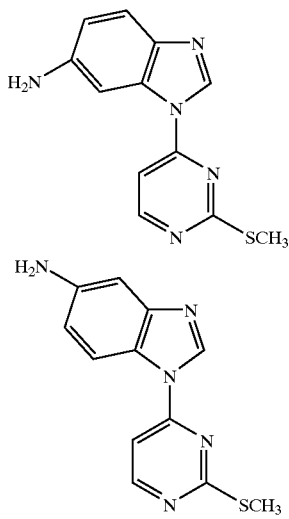

2-Methylthio-4-[5-aminobenzimidazol-1-yl]
pyrimidine and 2-methylthio-4-[6-
aminobenzimidazol-1-yl]pyrimidine

Step A: 5-Aminobenzimidazole

To a stirred solution of 5-nitrobenzimidazole (1 g, 6.13 mmol, 1 eq) in THF (100 mL) was added 10% palladium on carbon (385 mg). The flask was purged with $H_2$ and the mixture was stirred under a balloon of $H_2$ for several hours. The flask was purged with $N_2$. The catalyst was filtered and washed with MeOH. The solution was concentrated under reduced pressure giving 800 mg of the desired product.

Step B: 2-Methylthio-4-[5-aminobenzimidazol-1-yl] pyrimidine and 2-methylthio-4-[6-aminobenzimidazol-1-yl]pyrimidine To a stirred solution of 5-aminobenzimidazole (700 mg, 5.26 mmol, 1 eq) in DMF (21 mL) was added NaH (231 mg, 5.78 mmol, 1.1 eq, (60% suspension in oil)). The mixture was allowed to stir until gas evolution ceased. To the DMF solution was added 2-methylthio-4-chloropyrimidine (0.612 mL, 5.26 mmol, 1 eq) dropwise via syringe. The mixture was allowed to stir overnight. The DMF was removed under reduced pressure and the residue was diluted with water and extracted 3× with $CH_2Cl_2$. The organic extracts were combined, dried over anhydrous $Na_2SO_4$, filtered and concentrated under reduced pressure. The mixture was purified by preparative thin layer chromatography (eluted 2× with 3.5% MeOH/$CH_2Cl_2$) to give 149 mg 2-methylthio-4-[6-aminobenzimidazol-1-yl]pyrimidine (faster regioisomer) and 89 mg 2-methylthio-4-[5-aminobenzimidazol-1-yl]pyrimidine (slower regioisomer).

2-methylthio-4-[6-aminobenzimidazol-1-yl] pyrimidine (faster regioisomer)

$^1$H NMR (500 MHz, $CD_3OD$): δ 8.68 (1H, s); 8.58 (1H, d, J=5.5 Hz); 7.68 (1H, d, J=2 Hz); 7.45 (2H, m); 6.81 (1H, dd, J=2 Hz, J=8.5 Hz); 2.67 (3H, s).

2-methylthio-4-[5-aminobenzimidazol-1-yl] pyrimidine (slower regioisomer)

$^1$H NMR (500 MHz, $CD_3OD$): δ 8.81 (1H, s); 8.56 (1H, d, J=5.5 Hz); 8.11 (1H, d, J=8.5 Hz); 7.46 (1H, d, J=5.5 Hz); 7.04 (1H, d, J=2 Hz); 6.87 (1H, dd, J=2 Hz, J=8.5 Hz); 2.65 (3H, s).

EXAMPLE 111

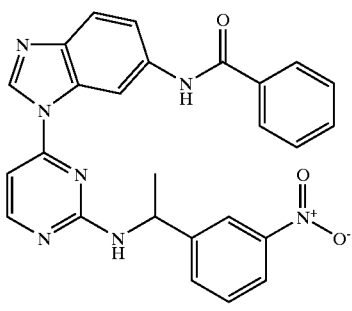

2-[(3-Nitrophenyl)ethylamino]-4-[6-N-(benzoyl)-
aminobenzimidazol-1-yl]pyrimidine

Step A: 2-methylthio-4-[6-N-(benzoyl)-aminobenzimidazol-1-yl]pyrimidine

To a stirred solution of 2-methylthio-4-[6-amino-benzimidazol-1-yl]pyrimidine (43 mg, 0.167 mmol, 1 eq) in THF (1.5 mL) was added diisopropylethylamine (0.058 mL, 0.33 mmol, 2 eq) followed by addition of benzoyl chloride (0.023 mL, 0.196 mmol, 1.2 eq). After 2 h the reaction was quenched with water and extracted 3× with $CH_2Cl_2$. The organic extracts were combined, dried over anhydrous $Na_2SO_4$, filtered and concentrated. The material was purified by preparative thin layer chromatography (eluted with 3.5% MeOH in $CH_2Cl_2$) giving 21 mg of the desired product.

Step B: 2-Methanesulfonyl-4-[6-N-(benzoyl)-aminobenzimidazol-1-yl]-pyrimidine To a suspension of 2-methylthio-4-[6-N-(benzoyl)amino-benzimidazol-1-yl]pyrimidine (12 mg, 0.033 mmol, 1 eq) in $CH_2Cl_2$ (0.5 mL) was added 3-chloroperoxybenzoic acid (19 mg, 0.066 mmol, 2 eq (60% pure). The mixture was allowed to stir overnight. The mixture was still a suspension. Diluted with $CH_2Cl_2$ and added small amount MeOH. All the solids dissolved. Thin layer chromatography analysis indicated some starting material still present. Added 10 mg 3-chloroperoxybenzoic acid and let stir 30 minutes. Thin layer chromatographic analysis indicated complete consumption of starting material. Quenched the reaction with saturated aqueous $NaHCO_3$ and extracted 3× with $CH_2Cl_2$. The organic extracts were combined, dried over anhydrous $Na_2SO_4$, filtered and concentrated. The material was carried on crude.

Step C: 2-[(3-Nitrophenyl)ethylamino]-4-[6-N-(benzoyl)-aminobenzimidazol-1-yl]pyrimidine To a stirred solution of 2-methanesulfonyl-4-[6-N-(benzoyl)-aminobenzimidazol-1-yl]pyrimidine 0.033 mmol, crude product mixture from preceding reaction) in DMF (0.3 mL) was added 1-(3-nitro-phenyl)ethylamine. The mixture was warmed to 100° C. for 4 h. The DMF was removed under reduced pressure. The residue was purified by preparative thin layer chromatography (eluted with 7% MeOH in MeOH) to give 7.2 mg of the desired product. $^1$H NMR (500 MHz, $CDCl_3$): δ 1.68 (3H, d, J=7 Hz), 5.59 (1H, br), 5.91 (1H, br m), 6.85 (1H, d, J=5.5 Hz), 7.15 (1H, br s), 7.46 (1H, m), 7.50–7.63 (3H, m), 7.74 (1H, d, J=8.5 Hz), 7.84 (1H, d, J=8 Hz), 7.95 (1H, d, J=7 Hz), 8.03 (1H, br d), 8.13 (1H, s), 8.3–8.5 (3H, m),9.1 (1H, br s). Mass spectrum (ESI) 480.2 (M+1).

EXAMPLE 112

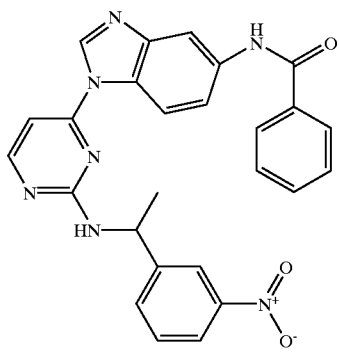

2-[(3-Nitrophenyl)ethylamino]-4-[5-N-(benzoyl)-aminobenzimidazol-1-yl]pyrimidine The titled compound was prepared according to the three-step sequence described in EXAMPLE 111 using 2-methylthio-4-[5-aminobenzimidazol-1-yl]pyrimidine instead of 2-methylthio4-[6-aminobenzimidazol-1-yl]pyrimidine giving 7.5 mg of the desired product. $^1$H NMR (500 MHz, CDCl$_3$): δ 1.69 (3H, d, J=7 Hz), 5.29 (1H, m), 5.85 (1H, br), 6.83 (1H, d, J=5.5 Hz), 7.40–7.70 (6H, m), 7.80 (1H, d, J=8 Hz), 7.93 (1H, d, J=7.5 Hz), 7.98 (1H, s), 8.09(1H, s), 8.15 (1H, dd, J=1 Hz, J=7 Hz), 8.33 (1H, s), 8.41 (1H, d, J=5.5 Hz), 8.45 (1H, br s). Mass spectrum (ESI) 480.0 (M+1).

EXAMPLE 113
omitted

EXAMPLE 114
omitted

EXAMPLE 115

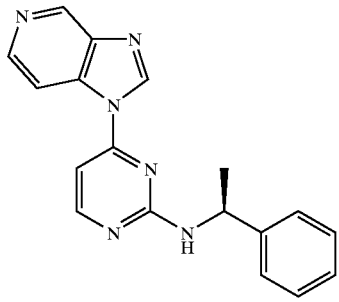

2-[(S)-1-Phenylethylamino]-4-[5-azabenzimidazol-1-yl]pyrimidine

Step 1: 2-Methylthio-4-[5-azabenzimidazol-1-yl]pyrimidine and 2-methylthio-4-[6-azabenzimidazol-1-yl]pyrimidine To a stirred solution of 5-azabenzimidazole (200 mg, 1.68 mmol, 1 eq) in DMF (10 mL) was added sodium hydride (67 mg of a 60% suspension in oil, 1.68 mmol, 1 eq). After gas evolution ceased $^4$-chloro-2-methylthiopyrimidine (0.195 mL, 1.68 mmol, 1 eq) was added dropwise via syringe. The mixture was allowed to stir 3 days. The reaction mixture was diluted with 100 mL water and stirred. The precipitated solids were collected giving 167 mg of the product mixture. The products were purified by preparative thin layer chromatography (eluted 2× with 3.5% MeOH in CH$_2$Cl$_2$) to give 52.7 mg 2-methylthio-4-[6-azabenzimidazol-1-yl]pyrimidine and 80.3 mg 2-methylthio-4-[5-azabenzimidazol-1-yl]pyrimidine.

Step B: 2-Methanesulfonyl-4-[5-azabenzimidazol-1-yl]pyrimidine

To a stirred solution of 2-methylthio-4-[5-azabenzimidazol-1-yl]-pyrimidine (78 mg, 0.32 mmol, 1 eq) in CH$_2$Cl$_2$ (12 mL) containing a few drops MeOH was added 3-chloroperbenzoic acid (111 mg, 0.64 mmol, 2 eq). The mixture was stirred 2 h. The reaction was diluted with CH$_2$Cl$_2$ and washed with saturated aqueous NaHCO$_3$. The aqueous layer was back extracted with CH$_2$Cl$_2$. The organic extracts were combined, dried over anhydrous Na$_2$SO$_4$, filtered and concentrated giving 33.8 mg of the title compound that was used crude in the next step.

Step C: 2-[(S)-1-Phenylethylamino]-4-[5-azabenzimidazol-1-yl]pyrimidine

To a flask containing 2-methanesulfonyl-4-[5-azabenzimidazol-1-yl]pyrimidine (33.8 mg) was added toluene (0.25 mL) and (S)-1-phenylethylamine (0.25 mL). The mixture was warmed to 100° C. The 2-methanesulfonyl-4-[5-azabenzimidazol-1-yl]pyrimidine did not dissolve so DMF (0.25 mL) was added and the mixture was maintained at 100° C. overnight. The reaction mixture was cooled and the solvents were removed under reduced pressure. The product was purified by preparative thin layer chromatography (eluted with 7% MeOH in CH$_2$Cl$_2$) to give 28 mg of the title compound. $^1$H NMR (500 MHz, CD$_2$Cl$_2$): δ 1.63 (3H, d, J=7 Hz), 5.18, (1H, br s), 5.96 (1H, br s), 6.78 (1H, d, J=5.5 Hz), 7.28 (1H, t, J=7 Hz), 7.38 (2H, t, J=7 Hz), 7.46 (2H, m), 7.62 (1H, br), 8.43 (1H, d, J=5 Hz), 8.4–8.6 (2H, m), 9.07 (1H, s).

EXAMPLE 116

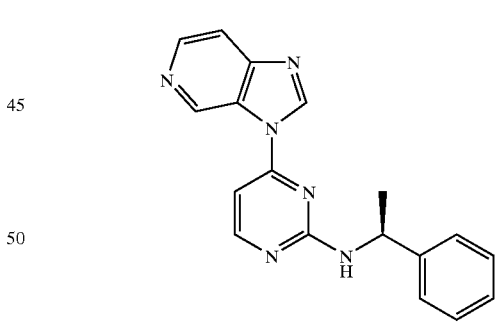

2-[(S)-1-Phenylethylamino]-4-[6-azabenzimidazol-1-yl]pyrimidine

The title compound was prepared from 2-methylthio-4-[6-azabenzimidazol-1-yl]pyrimidine (EXAMPLE 115, Step A) according to the two step procedure described in EXAMPLE 115, Steps B and C. $^1$H NMR (500 MHz, CD$_2$Cl$_2$): δ 1.64 (3H, d, J=7 Hz), 5.26 (1H, q, J=7 Hz), 6.0 (1H br s), 6.81 (1H, d, J=5.5 Hz), 7.26 (1H, t, J=7 Hz), 7.37 (1H, t, J=7 Hz), 7.46 (1H, d, J=7.5 Hz), 7.76 (1H, d, J=5.5 Hz), 8.41 (1H, d, J=5.5 Hz), 8.52 (1H, d, J=5.5 Hz), 8.61 (1H, br s).

EXAMPLE 117

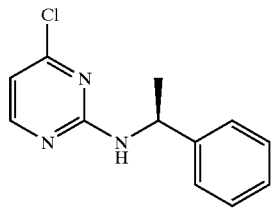

2-[(S)-1-Phenylethylamino]-4-chloropyrimidine

To a stirred solution of 2,4-dichloropyrimidine (500 mg, 3.38 mmol, 1 eq) in THF (15 mL) was added (S)-1-phenylethylamine. After 48 h the precipitate was filtered off and washed with THF. The THF was removed under reduced pressure and the material was purified by silica gel chromatography (eluted with 4:1 hexanes/acetone) to give 167 mg of the desired product. [Note: 2-[(S)-1-phenylethylamino]-4-chloropyrimidine is the faster but minor regioisomer. The major, slower product is 2-chloro-4-[(S)-1-phenylethylamino]pyrimidine.]

EXAMPLE 118

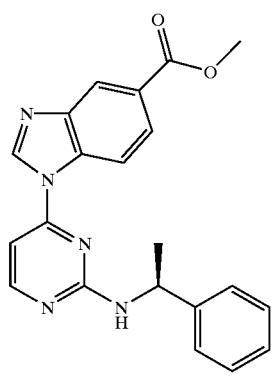

2-[(S)-1-Phenylethylamino]-4-[5-(methoxycarbonyl)
benzimidazol-1-yl]pyrimidine and 2-[(S)-1-
Phenylethylamino]-4-[6-(methoxycarbonyl)
benzimidazol-1-yl]-pyrimidine

Step A: 5-Methoxycarbonylbenzimidazole

To a suspension of benzimidazole-5-carboxylic acid (100 mg, 0.616 mmol, 1 eq) in MeOH (4 mL) was added a 2N solution of trimethylsilyldiazomethane in hexanes (3×0.3 mL, 1.8 mmol, 3 eq). Nitrogen evolution was evident. Eventually a yellow color persisted. The reaction was quenched by the addition of a small amount of acetic acid. The MeOH was removed under reduced pressure and the mixture was purified by preparative thin layer chromatography (eluted with 7% MeOH in CH$_2$Cl$_2$) giving 66 mg of the desired product.

Step B: 2-[(S)-1-Phenylethylamino]-4-[5-(methoxycarbonyl)-benzimidazol-1-yl]pyrimidine and 2-[(S)-1-Phenylethylamino]-4-[6-(methoxycarbonyl)benzimidazol-1-yl]pyrimidine To a solution of 5-methoxycarbonylbenzimidazole (66 mg, 0.375 mmol, 1 eq) in DMF (2 mL) was added NaH (15 mg, 0.375 mmol, 1 eq). The mixture was stirred until gas evolution ceased. To the DMF solution was added 2-[(S)-1-phenylethylamino]-4-chloro-pyrimidine (87.5 mg, 0.375 mmol, 1 eq). The mixture was heated to 80° C. and stirred for several hours. The DMF was removed under reduced pressure and the residue was diluted with ethyl acetate and washed with water. The aqueous layer was back extracted with ethyl acetate. The organic extracts were combined, dried over anhydrous Na$_2$SO$_4$, filtered and concentrated under reduced pressure. The product was purified by preparative thin layer chromatography (eluted with 7% MeOH in CH$_2$Cl$_2$) to give 30 mg 2-[(S)-1-phenylethylamino]-4-[6-(methoxycarbonyl)benzimidazol-1-yl]pyrimidine (faster regioisomer) and 26 mg 2-[(S)-1-phenylethylamino]-4-[5-(methoxycarbonyl)benzimidazol-1-yl]pyrimidine (slower regioisomer). 1H NMR (500 MHz, CD$_3$OD): δ 1.58 (3H, d, J=7.5 Hz), 3.94 (3H, s), 4.59 (1H, br s), 5.1 (1H, br s) 6.97 (1H, d, J=5.5 Hz), 7.23 (1H, br t, J=7 Hz), 7.35 (2H, br m), 7.44 (2H, d, J=7.5 Hz), 7.6–8.1 (2H, m), 8.3–8.4 (2H, m), 8.91 (1H, br s). Mass spectrum (ESI) 374.2 (M+1).

EXAMPLE 119

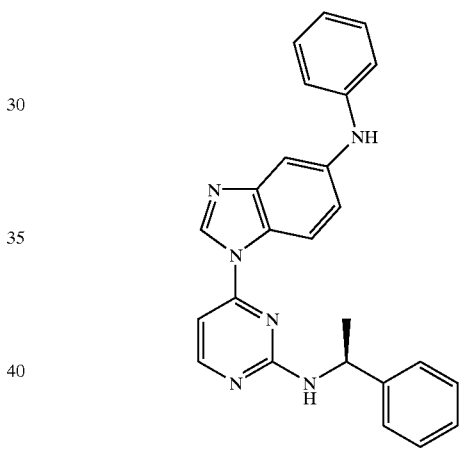

2-[(S)-1-Phenylethylamino]-4-[5-(phenylamino)
benzimidazol-1-yl]pyrimidine

To a stirred solution of 2-[(S)-1-phenylethylamino]-4-[5-aminobenzimidazol-1-yl]pyrimidine (54 mg, 0.163 mmol, 1 eq) in CH$_2$Cl$_2$ (3 mL) was added triphenylbismuth (86 mg, 0.196 mmol, 1.2 eq) followed by addition of Cu(OAc)$_2$ (30 mg, 0.163 mmol, 1 eq). The reaction was stirred at room temperature for 24 h, then diluted with CH$_2$Cl$_2$ and washed with water. The organic extracts were combined, dried over anhydrous Na$_2$SO$_4$, filtered and concentrated under reduced pressure. The material was purified by preparative thin layer chromatography giving 43 mg of the desired product. $^1$H NMR (500 MHz, CDCl$_3$): δ 1.64 (3H, d, J=7 Hz), 5.21 (1H, br), 5.74 (1H, br), 5.80 (1H, s), 6.75 (1H, d, J=5.5 Hz), 6.93 (1H, t, J=7 Hz), 7.08 (2H, d, J=8 Hz), 7.55 (1H, s), 7.7 (1H, br, 8.38 (1H, d, J=5 Hz), 8.45 (1H, br s). Mass spectrum (ESI) 407.3 (M+1).

EXAMPLE 120

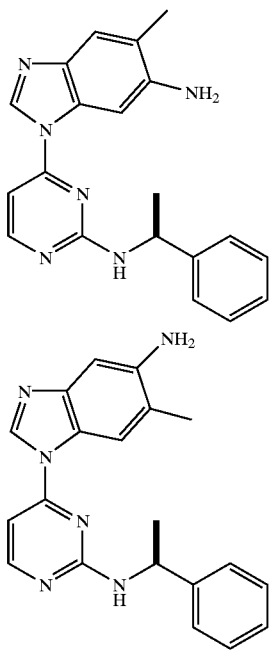

2-[(S)-1-Phenylethylamino]-4-[5-methyl-6-amino-benzimidazol-1-yl]pyrimidine and 2-[(S)-1-Phenylethylamino]-4-[5-amino-6-methyl-benzimidazol-1-yl]pyrimidine Step A: 6-Methyl-5-nitrobenzimidazole and 5-methyl-4-nitrobenzimidazole To a flask containing concentrated $HNO_3$ (20 mL) at 0° C. was added 5-methylbenzimidazole portionwise. To this mixture at 0° C. was added concentrated $H2SO_4$ carefully. The cooling bath was removed. The mixture was warmed to 100° C. and maintained at that temperature for 1.5 h. The heating bath was removed and the reaction was allowed to stir for 72 h. The reaction mixture was carefully poured into ice water. The solids were filtered, washed with ice water and collected. The solides were dissolved in hot EtOH and the solution filterred. The solvent was removed under reduced pressure giving 2.5 g of a mixture of 6-Methyl-5-nitrobenzimidazole and 5-methyl-4-nitrobenzimidazole. The regioisomers were separated by silica gel chromatography (eluted with EtOAC/hexanes). 5-Methyl4-nitrobenzimidazole (faster regioisomer) and 6-methyl-5-nitrobenzimidazole (slower regioisomer).

Step B: 5-Amino-6-methylbenzimidazole

To a solution of 6-Methyl-5-nitrobenzimidazole (300 mg) in THF (35 mL) was added 10% Pd/C (100 mg). The flask was evacuated and charged with $H_2$ several times. The mixture was stirred under a balloon of $H_2$. After 24 h the flask was purged with $N_2$. The catalyst was filtered off and washed with THF. The solvent was removed under reduced pressure giving 230 mg of the title compound.

Step C: 2-[(S)-1-Phenylethylamino]-4-[5-methyl-6-amino-benzimidazol-1-yl]pyrimidine and 2-[(S)-1-Phenylethylamino]-4-[5-amino-6-methyl-benzimidazol-1-yl]pyrimidine To a stirred solution of 5-amino-6-methybenzimidazole (28 mg, 0.19 mmol, 1 eq) in DMF was added NaH (60% dispersion in oil, 7.6 mg, 0.19 mmol, 1 eq). After gas evolution ceased, 2-[(S)-1-phenylethylamino]-4-chloro-pyrimidine (45 mg, 0.19 mmol, 1 eq) was added and the mixture was warmed to 90° C. and stirred 7 h. The heating bath was turned off and the mixture was allowed to stir overnight at room temperature. The DMF was removed under reduced pressure. The residue was diluted with water and extracted wth $CH_2Cl_2$. The organic extracts were combined, dried over anhydrous $Na_2SO_4$, filtered and concentrated under reduced pressure. The products were purified by preparative thin layer chromatography to afford 10.5 mg of 2-[(S)-1-phenylethylamino]-4-[5-methyl-6-amino-benzimidazol-1-yl]pyrimidine $^1$H NMR (500 MHz, $CDCl_3$): δ 1.64 (3H, d, J=7 Hz), 2.27 (3H, s), 3.59 (2H, br s), 5.23 (1H, br m), 5.75 (1H, br s), 6.71 (1H, d, J=5.5 Hz), 7.04 (1H, br), 7.31 (1H, t, J=7.5 Hz), 7.40 (2H, t, J=7.5 Hz), 7.47 (2H, d, J=7.5 Hz), 8.25 (1H, br s), 8.35 (1H, d, J=5.5 Hz). Mass spectrum (ESI) 345.2 (M+1). and 10.3 mg of 2-[(S)-1-phenylethylamino]-4-[5-amino-6-methyl-benzimidazol-1-yl]pyrimidine $^1$H NMR (500 MHz, $CDCl_3$): δ 1.65 (3H, d, J=7 Hz), 2.31 (3H, s), 3.68 (2H, br s), 5.26 (1H, m), 5.74 (1H, br s), 6.75 (1H, d, J=5.5 Hz), 7.11 (1H, s), 7.28 (1H, m), 7.37 (2H, t, J=7 Hz), 7.75 (2H, d, J=7 Hz), 7.75 (1H, br s), 8.34 (1H, d, J=5.5 Hz), 8.38 (1H, br s). Mass spectrum (ESI) 345.2 (M+1).

EXAMPLE 121

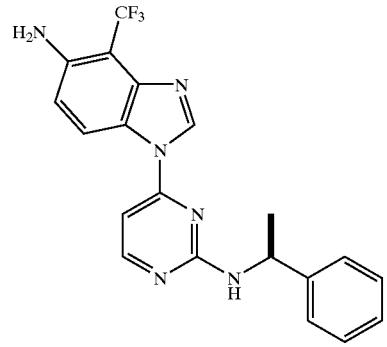

2-[(S)-1-Phenylethylamino]-4-[4-trifluoromethyl-5-aminobenzimidazol-1-yl]pyrimidine To a stirred solution of 2-[(S)-1-phenylethylamino]-4-[5-amino-benzimidazol-1-yl]pyrimidine (330 mg, 1 mmol, 1 eq) in DMF (2 mL) was added S-(trifluoromethyl)-dibenzothiophenium-3-sulfonate (166 mg, 0.5 mmol, 0.5 eq) and the mixture was heated to 80° C. for 7 hours. The reaction was cooled and the DMF was removed under reduced pressure. The residue was diluted with water and extracted wth $CH_2Cl_2$. The organic extracts were combined, dried over anhydrous $Na_2SO_4$, filtered and concentrated under reduced pressure. The product was purified by column chromatography (eluted with 3.5% $MeOH/CH_2Cl_2$) followed by preparative thin layer chromatography (eluted 2× with 3.5% $MeOH/CH_2Cl_2$) to give 46 mg of the title compound. $^1$H NMR (500 MHz, $CDCl_3$): δ 1.63 (3H, d, J=7 Hz), 4.32 (3H, s), 5.13 (1H, br s), 5.80 (1H, br s), 6.62 (1H, br), 6.70 (1H, d, J=5.5 Hz), 7.29 (1H, m), 7.39 (2H, t, J=7.5 Hz), 7.43 (2H, d, J=7 Hz), 7.62 (1H, br), 8.38 (1H, d, J=5.5 Hz), 8.40 (1H, br). Mass spectrum (ESI) 398.14 (M+1).

EXAMPLE 122

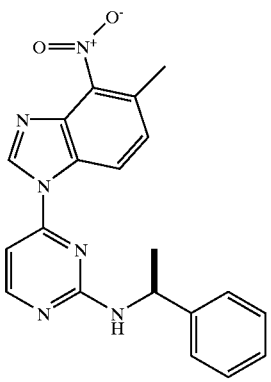

2-[(S)-1-Phenylethylamino]-4-[4-nitro-5-methyl-benzimidazol-1-yl]pyrimidine

To a stirred solution of 4-nitro-5-methyl-benzimidazole (50 mg, 0.28 mmol, 1.1 eq) in DMF was added NaH (60% dispersion in oil, 11.4 mg, 0.28 mmol, 1.1 eq). After gas evolution ceased, 2-[(S)-1-phenylethylamino]-4-chloropyrimidine (60 mg, 0.26 mmol, 1 eq) was added and the mixture was warmed to 80° C. and stirred overnight. The reaction was cooled and the DMF was removed under reduced pressure. The products were purified by preparative thin layer chromatography to afford 35.8 mg of the title compound. Mass spectrum (ESI) 375 (M+).

EXAMPLE 123

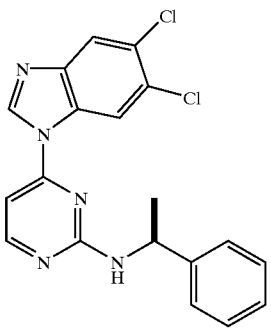

2-[(S)-1-Phenylethylamino]-4-[5,6-dichlorobenzimidazol-1-yl]pyrimidine

Step A: 5,6-Dichlorobenzimidazole

A solution of 200 mg of 1,2-diamino-4,5-dichlorobenzene dissolved in 5 mL of 97% formic acid was heated to 100° C. in a sealed tube for 15 hours. After cooling to room temperature, the reaction was quenched by the addition of 3.3 mL of concentrated aqueous $NH_4OH$ and stirred for 30 minutes. Following dilution with 20 mL of $H_2O$, and extraction with 2×20 mL EtOAc, the organic phases were dried over $MgSO_4$ and concentrated under reduced pressure to yield 210 mg of the title compound as a brown oil. No further purification was performed. $R_F$: 0.38 (5% MeOH in $CH_2Cl_2$). $^1$H NMR (500 MHz, $CD_3OD$): δ 8.22 (s, 1H), 7.74 (s, 2H). Mass Spectrum (ESI) 188 (M+1).

Step B: 2-[(S)-1-Phenylethylamino]-4-[5,6-dichlorobenzimidazol-1-yl]pyrimidine To a solution of 100 mg of 5,6-dichlorobenzimidazole in 3 mL of DMF was added 26 mg of NaH (60% dispersion in oil) and the resulting suspension was stirred at room temperature for 15 minutes. Then, 138 mg of 2-[(S)-1-phenethylamino]-4-chloropyrimidine (EXAMPLE 117) was added and the reaction was heated to 100° C. for 3 hours. After cooling to room temperature, the solution was then diluted with 10 mL of $H_2O$ and extracted with 2×10 mL EtOAc. The organic phases were then dried over $MgSO_4$ and concentrated under reduced pressure. The residue was purified with preparatory thin-layer chromatography ($SiO_2$, 5% MeOH in $CH_2Cl_2$) to yield 205 mg of the title compound as a yellow oil. $R_F$: 0.63 (5% MeOH in $CH_2Cl_2$). $^1$H NMR (500 MHz, $CD_3OD$): δ 8.89 (br S, 1H), 8.36 (s, 1H), 7.86 (s, 1H), 7.74–7.45 (m, 2H), 7.32–7.28 (m, 3H), 7.19 (t, 1H, J=7.0 Hz), 6.99 (d, 1H, J=5.5 Hz), 5.19 (q, 1H, J=7.0 Hz), 1.59 (d, 3H, J=7.0 Hz). Mass Spectrum (ESI) 384 (M+).

EXAMPLE 124

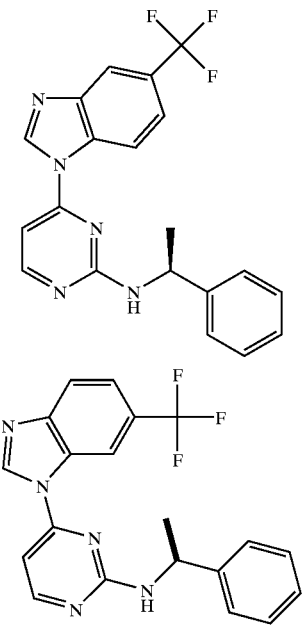

2-[(S)-1-Phenylethylamino]-4-[5-trifluoromethylbenzimidazol-1-yl]pyrimidine and 2-[(S)-1-Phenylethylamino]-4-[6-trifluoromethylbenzimidazol-1-yl]pyrimidine

Step A: 5-Trifluoromethylbenzimidazole

Following the procedure described in EXAMPLE 123 Step A, 500 mg of 1,2-diamino-4-trifluoromethylbenzene gave 409 mg of the title compound. Mass Spectrum (ESI) 187 (M+1).

Step B: 2-[(S)-1-Phenylethylamino]-4-[5-trifluoromethyl-benzimidazol-1-yl]pyrimidine and 2-[(S)-1-Phenyl-ethylamino]-4-[6-trifluoromethyl-benzimidazol-1-yl]pyrimidine Following the procedure described in EXAMPLE 123 Step B, 200 mg of 5-trifluoromethylbenzimidazole yielded 192 mg of a 1:1 separable mixture of the title compounds.

2-[(S)-1-phenethylamino]-4-[5-trifluoromethylbenzimidazol-1-yl]pyrimidine.

$^1$H NMR (500 MHz, $CD_3OD$): δ 8.85 (br s, 1H), 8.74 (br s, 1H), 8.33 (d, 1H, J=4.4 Hz), 7.81 (d, 1H, J=8.0 Hz), 7.60

(d, 1H, J=8.0 Hz), 7.42–7.37 (m, 2H), 7.28–7.24 (m, 2H), 7.15 (t, 1H, J=7.1 Hz), 6.94 (d, 1H, J=5.5 Hz), 5.20 (q, 1H, J=7.0 Hz), 1.58 (d, 3H, J=7.0 Hz). Mass Spectrum (ESI) 383 (M+).

2-[(S)-1-phenethylamino]-4-[6-trifluoromethylbenzimidazol-1-yl]pyrimidine.

$^1$H NMR (500 MHz, CD$_3$OD): δ 8.79 (br s, 1H), 8.35 (s, 1H), 8.11 (br s, 1H), 7.95 (s, 1H), 7.43–7.38 (m, 2H), 7.34–7.28 (m, 2H), 7.20 (t, 1H, 7.1 Hz), 6.91 (d, 1H, J=5.5 Hz), 5.13 (br s, 1H), 1.56 (d, 3H, J=7.0 Hz). Mass Spectrum (ESI) 383 (M+).

EXAMPLE 125

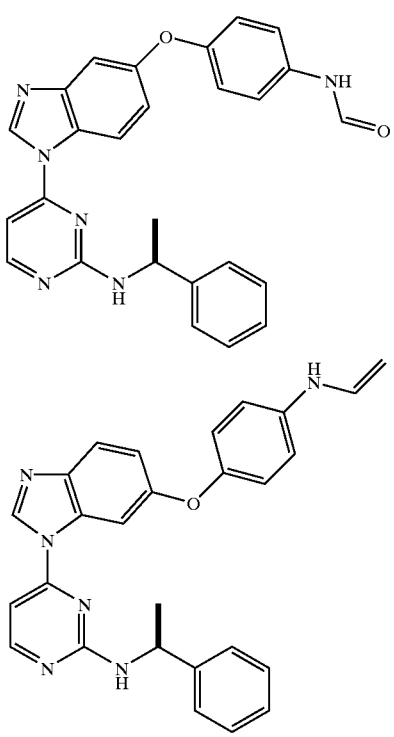

2-[(S)-1-Phenylethylamino]-4-[5-(4-formylamino-phenoxy)benzimidazol-1-yl]pyrimidine and 2-[(S)-1-Phenylethylamino]-4-[6-(4-formylaminophenoxy)-benzimidazol-1-yl]pyrimidine Step A: 5-(4-Formylamino-phenoxy)benzimidazole Following the procedure described in EXAMPLE 123 Step A, 500 mg of 3,4,4-triamino-diphenylether gave 575 mg of the title compound. $^1$H NMR (500 MHz, CD$_3$OD): δ 8.23 (s, 1H), 8.15 (s, 1H), 7.59 (d, 1H, J=8.5 Hz), 7.54 (d, 1H, J=8.5 Hz) 7.19–7.16 (m, 1H), 7.05–6.94 (m, 3H). Mass Spectrum (ESI) 254 (M+1).

Step B: 2-[(S)-1-Phenylethylamino]-4-[5-(4-formylaminophenoxy)-benzimidazol-1-yl]pyrimidine and 2-[(S)-1-Phenylethylamino]-4-[6-(4-formylaminophenoxy)benzimidazol-1-yl]pyrimidine Following the procedure described in EXAMPLE 123 Step B, 200 mg of 5-(4-formylamino-phenoxy) benzimidazole yielded 236 mg of a 1:1 separable mixture of the title compounds.

2-[(S)-1-phenethylamino]-4-[5-(4-formylamino-phenoxy)benzimidazol-1-yl]pyrimidine $^1$H NMR (500 MHz, CD$_3$OD): δ 8.77 (br s, 1H), 8.31 (d, 1H, J=5.5 Hz), 8.03 (br s, 1H), 7.68 (d, 1H, J=8.5 Hz), 7.59 (d, 1H, J=8.5 Hz), 7.26–7.02 (m, 9H), 6.95 (d, 1H, J=5.5 Hz), 4.87 (br s, 1H), 1.45 (d, 3H, J=6.0 Hz). Mass Spectrum (ESI) 450 (M+).

2-[(S)-1-phenethylamino]-4-[6-(4-formylamino-phenoxy)benzimidazol-1-yl]pyrimidine $^1$H NMR (500 MHz, CD$_3$OD): δ 8.76 (br s, 1H), 8.35 (br s, 1H), 7.80 (br s, 1H), 7.58 (d, 2H, J=9.0 Hz), 7.42 (d, 2H, J=7.5 Hz)7.31 (t, 2H, J=7.5 Hz), 7.21–7.18 (m, 2H), 7.04–6.97 (m, 4H), 5.14 (br s, 1H), 1.57 (d, 3H, J=7.0 Hz). Mass Spectrum (ESI) 450 (M+).

EXAMPLE 126

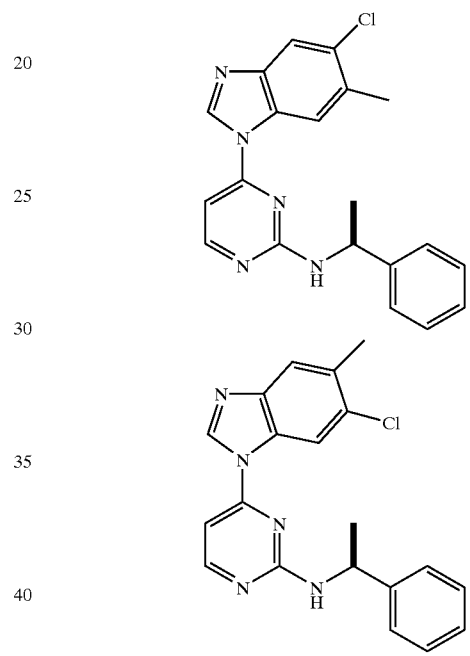

2-[(S)-1-Phenylethylamino]-4-[5-chloro-6-methylbenzimidazol-1-yl]pyrimidine and 2-[(S)-1-Phenylethylamino]-4-[6-chloro-5-methylbenzimidazol-1-yl]pyrimidine Step A: 5-Chloro-6-methylbenzimidazole Following the procedure described in EXAMPLE 123 Step A, 500 mg of 1,2-diamino-4-chloro-5-methylbenzene gave 489 mg of the title compound. $^1$H NMR (500 MHz, CD$_3$OD): δ 8.24 (s, 1H), 7.75 (2, 2H). Mass Spectrum (ESI) 167 (M+1).

Step B: 2-[(S)-1-Phenylethylamino]-4-[5-chloro-6-methyl-benzimidazol-1-yl]pyrimidine and 2-[(S)-1-Phenyl-ethylamino]-4-[6-chloro-5-methylbenzimidazol-1-yl]pyrimidine Following the procedure described in EXAMPLE 123 Step B, 200 mg 5-chloro-6-methylbenzimidazole yielded 220 mg of a 1:1 separable mixture of the title compounds.

2-[(S)-1-phenethylamino]-4-[5-chloro-6-methylbenzimidazol-1-yl]pyrimidine $^1$H NMR (500 MHz, CD$_3$OD): δ 8.64 (br s, 1H), 8.29 (br s, 1H), 7.91 (br s, 1H), 7.58 (s, 1H), 7.42 (d, 2H, J=7.0 Hz), 7.29 (t, 2H, J=7.0 Hz), 7.20 (m, 1H), 6.85 (d, 1H, J=6.0 Hz), 5.16 (m, 1H), 1.58 (d, 3H, J=7.0 Hz). Mass Spectrum (ESI) 364 (M+).

2-[(S)-1-phenethylamino]-4-[6-chloro-5-methylbenzimidazol-1-yl]pyrimidine $^1$H NMR (500 MHz, CD$_3$OD): δ 8.64 (br s, 1H), 8.29 (br s, 2H), 7.46–7.41 (m, 2H), 7.31–7.28 (m, 3H), 7.20–7.18 (m, 1H), 6.85 (d, 1H, J=6.0 Hz), 5.16 (q, 1H, J=7.0 Hz), 1.58 (d, 3H, J=7.0 Hz). Mass Spectrum (ESI) 364 (M+).

EXAMPLE 127

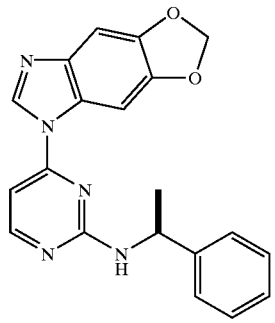

2-[(S)-1-Phenylethylamino]-4-[5,6-methylenedioxy-benzimidazol-1-yl]pyrimidine

Step A: 5,6-Methylenedioxy-benzimidazole

Following the procedure described in EXAMPLE 123 Step A, 100 mg of 1,2-diamino-4,5-methylenedioxybenzene gave 50 mg of the title compound. $^1$H NMR (500 MHz, CD$_3$OD): δ 7.82 (s, 1H), 7.20 (s, 2H), 6.13 (s, 2H). Mass Spectrum (ESI) 161 (M+1).

Step B: 2-[(S)-1-Phenylethylamino]-4-[5,6-methylenedioxybenzimidazol 1-yl]pyrimidine Following the procedure described in EXAMPLE 123 Step B, 50 mg of 5,6-methylenedioxy-benzimidazole yielded 42 mg of the title compounds. 1H NMR (500 MHz, CD$_3$OD): δ 8.49 (br s, 1H), 8.28 (d, 1H, J=5.5 Hz), 7.65 (br s, 1H), 7.41 (d, 2H, J=7.5 Hz), 7.29 (t, 2H, J=7.5 Hz), 7.18 (t, 1H, J=7.5 Hz), 6.83 (d, 1H, J=5.5 Hz), 5.99 (s, 2H), 5.98 (s, 2H), 5.13 (q, 1H, J=6.5 Hz), 1.56 (d, 3H, J=6.5 Hz). Mass Spectrum (ESI) 359 (M+).

EXAMPLE 128

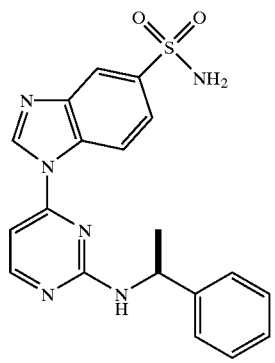

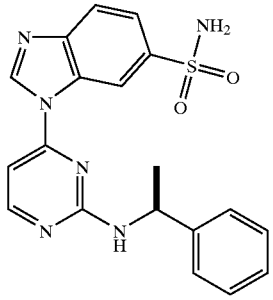

2-[(S)-1-Phenylethylamino]-4-[5-sulfonamido-benzimidazol-1-yl]pyrimidine and 2-[(S)-1-Phenylethylamino]-4-[6-sulfonamido-benzimidazol-1-yl]pyrimidine

Step A: 5-Sulfonamido-benzimidazole

Following the procedure described in EXAMPLE 123 Step A, 500 mg of 1,2-diamino-4-trifluoromethylbenzene gave 100 mg of the title compound. Mass Spectrum (ESI) 187 (M+1).

Step B: 2-[(S)-1-Phenylethylamino]-4-[5-sulfonamido-benzimidazol-1-yl]pyrimidine and 2-[(S)-1-Phenylethylamino]-4-[6-sulfonamido-benzimidazol-1-yl]pyrimidine Following the procedure described in EXAMPLE 123 Step B, 100 mg of 5-sulfonamido-benzimidazole yielded 64 mg of a 1:1 separable mixture of the title compounds.

2-[(S)-1-phenethylamino]-4-[5-sulfonamido-benzimidazol-1-yl]pyrimidine $^1$H NMR (500 MHz, CD$_3$OD): δ 8.99 (m, 2H), 8.37 (d, 1H, J=5.0 Hz), 7.94 (d, 1H, J=7.5 Hz), 7.85 (d, 1H, J=7.5 Hz), 7.50–7.14 (m, 5H), 6.98 (d, 1H, J=5.5 Hz), 5.21 (br s, 1H), 1.60 (d, 3H, J=7.5 Hz). Mass Spectrum (ESI) 394 (M+).

2-[(S)-1-phenethylamino]-4-[6-sulfonamido-benzimidazol-1-yl]pyrimidine

¹H NMR (500 MHz, CD₃OD): δ 8.89 (br, s, 1H), 8.39 (s, 1H), 8.24 (s, 1H), 7.81 (m, 2H), 7.44 (d, 2H, J=8.0 Hz), 7.34–7.21 (m, 3H), 7.00 (d, 1H, J=5.5 Hz), 5.14 (br s, 1H), 1.58 (d, 1H, J=7.5 Hz). Mass Spectrum (ESI) 394 (M+).

EXAMPLE 129

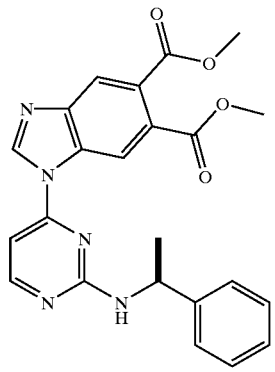

2-[(S)-1-Phenylethylamino]-4-[5,6-di-(methoxycarbonyl)-benzimidazol-1-yl]-pyrimidine Step A: 5,6-di-(methoxycarbonyl)-benzimidazole To a solution of 200 mg of 5,6-benzimidazoledicarboxylic acid dissolved in 2.0 mL of MeOH and 2.0 mL of diethyll ether was added 4 mL of trimethylsilyldiazomethane [2.0 M in hexanes]. The resulting solution was stirred for 1 hour before dilution with 20 mL of H₂O and extraction with 2×10 mL of EtOAc. the organic phases were dried over MgSO₄ and concentrated under reduced pressure. Column chromatography (SiO₂, 5% MeOH in CH₂Cl₂) yielded 210 mg of the title compound as a yellow oil. Mass Spectrum (ESI) 231 (M+1).

Step B: 2-[(S)-1-Phenylethylamino]-4-[5,6-di-(methoxycarbonyl)-benzimidazol-1-yl]-pyrimidine Following the procedure described in EXAMPLE 123 Step B, 70 mg of 5,6-di-(methoxycarbonyl)-benzimidazole yielded 25 mg of the title compound. ¹H NMR (500 MHz, CD₃OD): δ 8.99 (br s, 1H), 8.79 (br s, 1H), 8.37 (d, 1H, J=5.5 Hz), 8.08 (s, 1H), 7.43 (d, 2H, J=7.5 Hz), 7.32–7.15 (m, 3H), 7.01 (d, 1H, J=5.5 Hz), 5.23 (q, 1H, J=6.5 Hz), 3.95 (s, 3H), 3.92 (s, 3H), 1.60 (d, 3H, J=6.5 Hz). Mass Spectrum (ESI) 431 (M+).

EXAMPLE 130

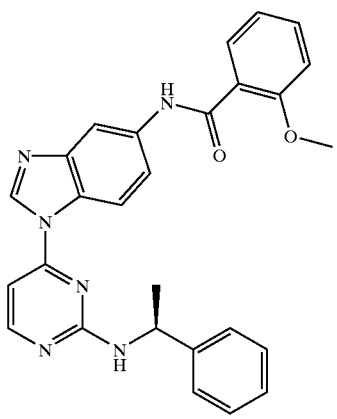

2-[(S)-1-Phenylethylamino]-4-[5-N-(2-methoxybenzoyl)aminobenzimidazol-1-yl]-pyrimidine To a mixture of 30 mg of 2-[(S)-1-phenylethylamino]-4-[5-amino-benzimidazol-1-yl]pyrimidine (EXAMPLE 79) in 2 mL of methylene chloride was added 38 μL of triethylamine and 15 μL of o-anisoyl chloride at 0° C. After stirring at 0° C. for 0.5–1 h, the reaction was quenched with saturated NaHCO₃ and diluted with ethyl acetate. The organic layer was washed with saturated ammonium chloride, water and brine and then dried over anhydrous Na₂SO₄. Removal of the solvent and subsequent purification by preparative thin layer chromatography (silica gel eluted with 50% acetone/hexane) provided 26 mg of the title product. Mass spectrum (ESI): 465 (M+1). ¹H NMR (500 MHz, CDCl₃): δ 8.50 (br s, 1H); 8.40 (d, J=5.2 Hz, 1H); 8.35 (d, 1H); 8.05 (s, 1H); 7.78 (br d, 1H); 7.60–7.10 (m, 8H); 7.08 (d, 1H); 6.78 (d, J=5.3 Hz, 1H); 5.79 (br s, 1H); 5.22 (br s, 1H); 4.12 (s, 3H); 1.65 (d, J=6.8 Hz, 3H).

EXAMPLE 131

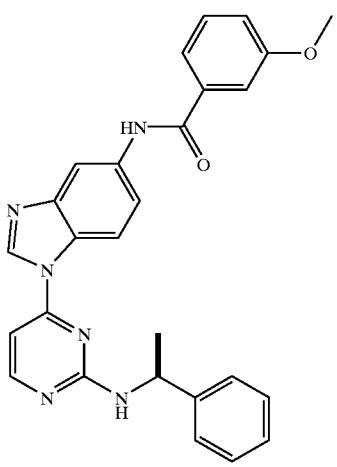

2-[(S)-1-Phenylethylamino]-4-[5-N-(3-methoxybenzoyl)aminobenzimidazol-1-yl] pyrimidine The title compound (25 mg) was prepared from 30 mg of 2-[(S)-1-phenylethylamino]-4-[5-aminobenzimidazol-1-yl]

pyrimidine (EXAMPLE 79), 14 μL of m-anisoyl chloride and 38 μL of triethylamine in 2 mL of CH$_2$Cl$_2$ using the procedure described in EXAMPLE 130. Mass spectrum (ESI): 465 (M+1). $^1$H NMR (500 MHz, CDCl$_3$): δ 8.48 (br s, 1H); 8.40 (d, J=5.2 Hz, 1H); 8.07 (s, 1H); 7.93 (s, 1H); 7.62 (br s, 1H); 7.55–7.22 (m, 8H); 7.12 (d, 1H); 6.78 (d, J=5.3 Hz, 1H); 5.82 (br d, 1H); 5.21 (br d, 1H); 3.92 (s, 3H); 1.65 (d, J=6.6 Hz, 3H).

EXAMPLE 132

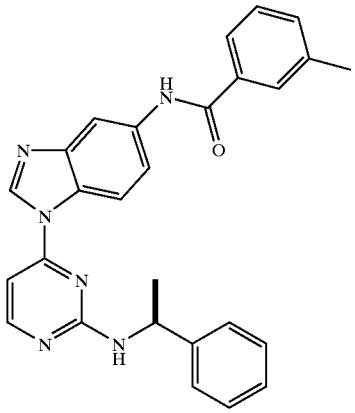

2-[(S)-1-Phenylethylamino]-4-[5-N-(3-methylbenzoyl)aminobenzimidazol-1-yl]-pyrimidine The title compound was prepared from 30 mg of 2-[(S)-1-phenylethylamino]-4-[5-aminobenzimidazol-1-yl] pyrimidine (EXAMPLE 79), 13 μL of m-toluoyl chloride and 38 μL of triethylamine in 2 mL of CH$_2$Cl$_2$ using the procedure described in EXAMPLE 130, except that the reaction was stirred for 12 min and the residue was purified by preparative thin layer chromatography (60% acetone in hexane) to provide 26 mg of the title compound. Mass spectrum (ESI): 449 (M+1). $^1$H NMR (500 MHz, CDCl$_3$): δ 8.48 (br s, 1H); 8.40 (d, J=5.2 Hz, 1H); 8.06 (s, 1H); 7.92 (s, 1H); 7.76 (s, 1H); 7.70 (br d, 1H); 7.66 (br s, 1H); 7.50–7.22 (m, 7H); 6.78 (d, J=5.3 Hz, 1H); 5.76 (br s, 1H); 5.21 (br s, 1H); 2.47 (s, 3H); 1.65 (d, J=6.9 Hz, 3H).

EXAMPLE 133

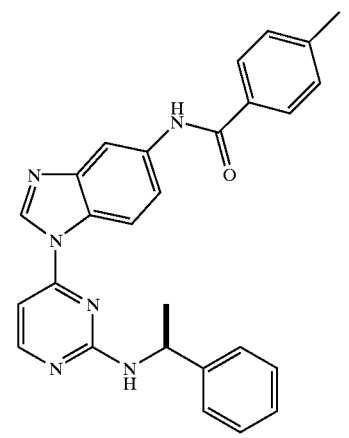

2-[(S)-1-Phenylethylamino]-4-[5-N-(4-methylbenzoyl)aminobenzimidazol-1-yl]pyrimidine The title compound (23 mg) was prepared from 30 mg of 2-[(S)-1-phenylethylamino]-4-[5-aminobenzimidazol-1-yl] pyrimidine (EXAMPLE 79), 13 μL of p-anisoyl chloride and 38 μL of triethylamine in 2 mL of CH$_2$Cl$_2$ using the procedure described in EXAMPLE 130. Mass spectrum (ESI): 449 (M+1). $^1$H NMR (500 MHz, CDCl$_3$): δ 8.48 (br s, 1H); 8.40 (d, J=5.2 Hz, 1H); 8.05 (s, 1H); 7.92 (s, 1H); 7.83 (d, J=8.0 Hz, 1H), 7.65 (br s, 1H); 7.50–7.22 (m, 8H); 6.77 (d, J=5.0 Hz, 1H); 5.71 (br s, 1H); 5.21 (br s, 1H); 2.46 (s, 3H); 1.65 (d, J=6.8 Hz, 3H).

EXAMPLE 134

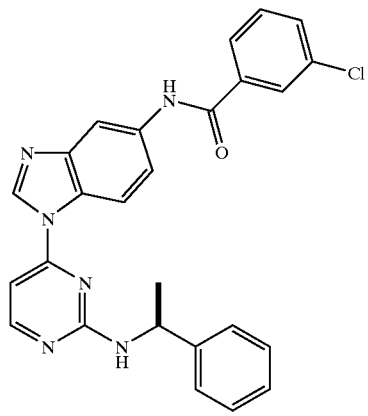

2-[(S)-1-Phenylethylamino]-4-[5-N-(3-chlorobenzoyl)aminobenzimidazol-1-yl]-pyrimidine The title compound (17 mg) was prepared from 30 mg of 2-[(S)-1-phenylethylamino]-4-[5-aminobenzimidazol-1-yl] pyrimidine (EXAMPLE 79), 12 μL of 3-chlorobenzoyl chloride and 38 μL of triethylamine in 2 mL of CH$_2$Cl$_2$ using the procedure described in EXAMPLE 130. Mass spectrum (ESI): 469 (M+1). $^1$H NMR (500 MHz, CDCl$_3$): δ 8.46 (br s, 1H); 8.38 (d, J=5.5 Hz, 1H); 8.13 (s, 1H); 8.04 (s, 1H); 7.91 (s, 1H); 7.79 (d, J=7.6 Hz, 1H), 7.60 (br s, 1H); 7.55–7.25 (m, 7H); 6.73 (d, J=5.5 Hz, 1H); 5.81 (br s, 1H); 5.20 (br s, 1H); 1.64 (d, J=6.9 Hz, 3H).

EXAMPLE 135

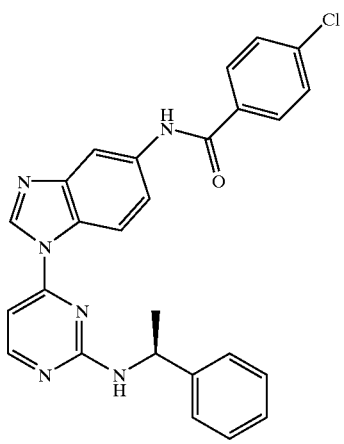

2-[(S)-1-Phenylethylamino]-4-[5-N-(4-chlorobenzoyl)aminobenzimidazol-1-yl]pyrimidine The title compound was prepared from 30 mg of 2-[(S)-1-phenylethylamino]-4-[5-aminobenzimidazol-1-yl]pyrimidine (EXAMPLE 79), 12 μL of 4-chlorobenzoyl chloride and 38 μL of triethylamine in 2 mL CH$_2$Cl$_2$ using the procedure described in EXAMPLE 130, except that the residue was purified by preparative thin layer chromatography (66% acetone in hexane) to provide 22 mg of the title compound. Mass spectrum (ESI): 469 (M+1). $^1$H NMR (500 MHz, CDCl$_3$): δ 8.48 (br s, 1H); 8.40 (d, J=5.2 Hz, 1H); 8.04 (s, 1H); 7.93 (s, 1H); 7.87 (d, J=8.3 Hz, 1H); 7.60 (br s, 1H); 7.52–7.22 (m, 8H); 6.76 (d, J=5.0 Hz, 1H); 5.72 (br s, 1H); 5.20 (br s, 1H); 1.65 (d, J=6.9 Hz, 3H).

EXAMPLE 136

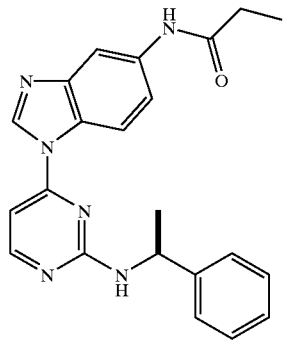

2-[(S)-1-Phenylethylamino]-4-[5-N-(propanoyl)aminobenzimidazol-1-yl]pyrimidine The title compound was prepared from 30 mg of 2-[(S)-1-phenylethylamino]-4-[5-aminobenzimidazol-1-yl]pyrimidine (EXAMPLE 79), 8 μL of propionyl chloride and 38 μL of triethylamine in 2 mL CH$_2$Cl$_2$ using the procedure described in EXAMPLE 130, except that the residue was purified by preparative thin layer chromatography (66% acetone in hexane) to provide 17 mg of the title compound. Mass spectrum (ESI): 487 (M+1). $^1$H NMR (500 MHz, CDCl$_3$): δ 8.45 (br s, 1H); 8.36 (d, J=5.2 Hz, 1H); 7.92 (s, 1H); 7.72 (br s, 1H); 7.60–7.22 (m, 6H); 6.73 (d, J=5.0 Hz, 1H); 5.82 (br d, 1H); 5.20 (br d, 1H); 2.46 (q, J=7.3 Hz, 2H); 1.64 (d, J=6.8 Hz, 3H); 1.30 (t, J=7.5 Hz, 3H).

EXAMPLE 137

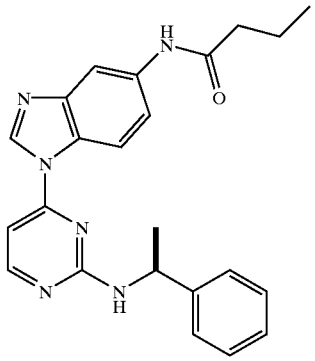

2-[(S)-1-Phenylethylamino]-4-[5-N-(butanoyl)-aminobenzimidazol-1-yl]pyrimidine The title compound (20 mg) was prepared from 30 mg of 2-[(S)-1-phenylethylamino]-4-[5-aminobenzimidazol-1-yl]pyrimidine (EXAMPLE 79), 10 μL of butyryl chloride and 38 μL of triethylamine in 2 mL CH$_2$Cl$_2$ using the procedure described in EXAMPLE 130. Mass spectrum (ESI): 401 (M+1). $^1$H NMR (500 MHz, CDCl$_3$): δ 8.44 (br s, 1H); 8.35 (d, J=5.3 Hz, 1H); 7.92 (s, 1H); 7.72 (br s, 1H); 7.63–7.22 (m, 6H); 6.71 (d, J=5.3 Hz, 1H); 5.90 (br s, 1H); 5.19 (br s, 1H); 2.39 (t, J=7.5 Hz, 2H); 1.82 (m, J=7.5 Hz, 2H); 1.63 (d, J=6.9 Hz, 3H); 1.05 (t, J=7.3 Hz, 3H).

EXAMPLE 138

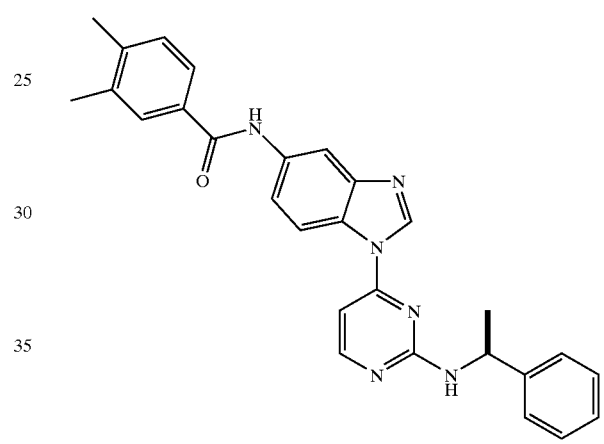

2-[(S)-1-Phenylethylamino]-4-[5-N-(3,4-dimethylbenzoyl)aminobenzimidazol-1-yl]pyrimidine To a solution of 40 mg of 2-[(S)-1-phenylethylamino]-4-[5-amino-benzimidazol-1-yl]pyrimidine (EXAMPLE 79) in 2 mL of methylene chloride was added 27 mg of 3,4-dimethylbenzoic acid followed by addition of 40 mg of 1-(3-dimethylaminopropyl)-3-ethylcarbodiimide hydrochloride and 30 mg of 4-N,N-dimethylaminopyridine. The reaction mixture was stirred at room temperature overnight. Removal of the solvent and subsequent purification by preparative thin layer chromatography (5% of MeOH in CH$_2$Cl$_2$) provided 48 mg of the title product. Mass spectrum (ESI): 463 (M+1). $^1$H NMR (500 MHz, CDCl$_3$): δ 8.47 (br s, 1H); 8.38 (d, J=5.3 Hz, 1H); 8.05 (s, 1H); 7.98 (s, 1H); 7.72 (br s, 1H); 7.68–7.22 (m, 8H); 6.75 (d, J=5.3 Hz, 1H); 5.90 (br s, 1H); 5.20 (br s, 1H); 2.38 (s, 3H); 2.36 (s, 3H); 1.65 (d, J=6.9 Hz, 3H).

EXAMPLE 139

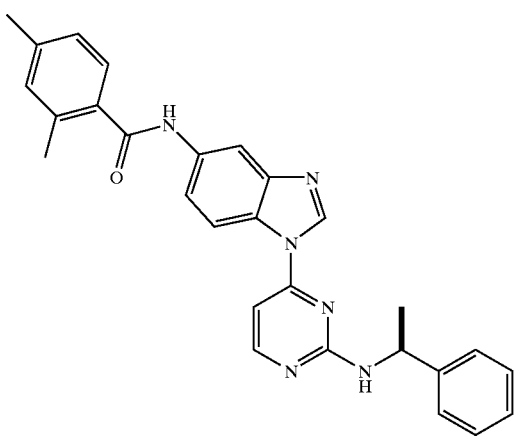

2-[(S)-1-Phenylethylamino]-4-[5-N-(2,4-dimethylbenzoyl)aminobenzimidazol-1-yl]primidine The title compound (46 mg) was prepared from 40 mg of 2-[(S)-1-phenylethylamino]-4-[5-aminobenzimidazol-1-yl] pyrimidine (EXAMPLE 79), 27 mg of 2,4-dimethylbenzoic acid, 40 mg of 1-(3-dimethylaminopropyl)-3-ethylcarbodiimide hydrochloride and 30 mg of 4-N,N-dimethylaminopyridine in 2 mL of $CH_2Cl_2$ using the procedure described in EXAMPLE 138. Mass spectrum (ESI): 463 (M+1). $^1$H NMR (500 MHz, $CDCl_3$): δ 8.47 (br s, 1H); 8.39 (d, J=5.3 Hz, 1H); 8.02 (s, 1H); 7.68 (s, 1H); 7.63 (br s, 1H); 7.50–7.00 (m, 8H); 6.75 (d, J=5.3 Hz, 1H); 5.80 (br s, 1H); 5.20 (br s, 1H); 2.53 (s, 3H); 2.39 (s, 3H); 1.65 (d, J=6.9 Hz, 3H).

EXAMPLE 140

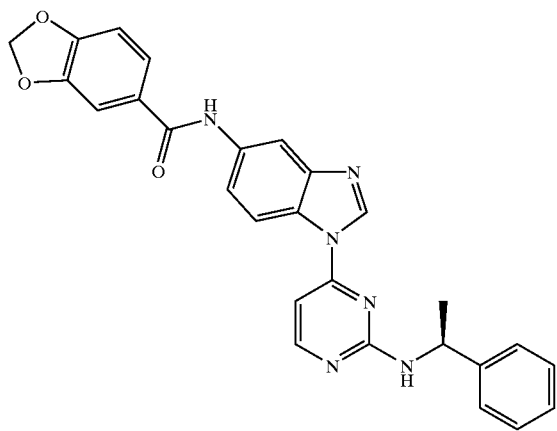

2-[(S)-1-Phenylethylamino]-4-[5-N-(3,4-methylenedioxybenzoyl)amino-benzimidazol-1-yl]pyrimidine The title compound was prepared from 30 mg of 2-[(S)-1-phenylethylamino]-4-[5-aminobenzimidazol-1-yl] pyrimidine (EXAMPLE 79), 17 mg of piperonylic acid, 21 mg of 1-(3-dimethylaminopropyl)-3-ethylcarbodiimide hydrochloride and 11 mg of 4-N,N-dimethylaminopyridine in 2 mL of $CH_2Cl_2$ using the procedure described in EXAMPLE 138, except that the residue was purified by preparative thin layer chromatography (50% acetone in hexane) to provide 33 mg of the title compound. Mass spectrum (ESI)-479 (M+1). $^1$H NMR (500 MHz, $CDCl_3$): δ8.48 (br s, 1H); 8.39 (d, J=5.3 Hz, 1H); 8.02 (s, 1H); 7.83 (s, 1H); 7.62 (br s, 1H); 7.50–7.22 (m, 7H); 6.91 (d, 1H); 6.77 (d, J=5.3 Hz, 1H); 6.08 (s, 2H); 5.82 (br s, 1H); 5.20 (br s, 1H); 1.65 (d, J=6.9 Hz, 3H).

EXAMPLE 141

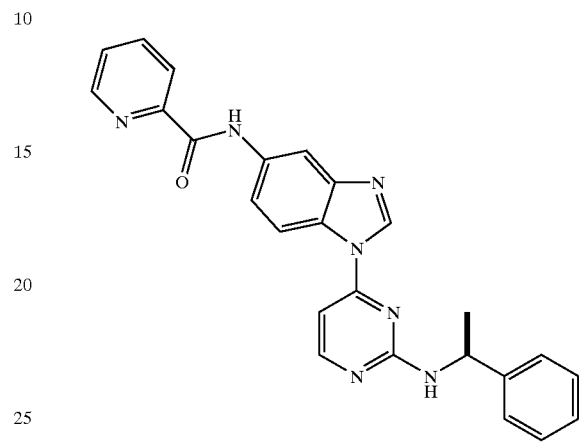

2-[(S)-1-Phenylethylamino]-4-[5-N-(picolinoyl)-aminobenzimidazol-1-yl]pyrimidine The title compound was prepared from 30 mg of 2-[(S)-1-phenylethylamino]-4-[5-aminobenzimidazol-1-yl] pyrimidine (EXAMPLE 79), 13 mg of picolinic acid, 21 mg of 1-(3-dimethylaminopropyl)-3-ethylcarbodiimide hydrochloride and 11 mg of 4-N,N-dimethylaminopyridine in 2 mL of $CH_2Cl_2$ using the procedure described in EXAMPLE 138, except that the residue was purified by preparative thin layer chromatography (50% acetone in hexane) to provide 33 mg of the title compound. Mass spectrum (ESI): 436 (M+1). $^1$H NMR (500 MHz, $CDCl_3$): δ 10.18 (s, 1H); 8.67 (d, J=5.0 Hz, 1H); 8.50 (br s, 1H); 8.40 (d, J=5.5 Hz, 1H); 8.36 (d, J=7.8 Hz, 1H); 8.27 (s, 1H); 7.95 (dt, 1H); 7.76 (br s, 1H); 7.55–7.25 (m, 6H); 6.78 (d, J=5.2 Hz, 1H); 5.79 (br s, 1H); 5.21 (br s, 1H); 1.65 (d, J=6.9 Hz, 3H).

EXAMPLE 142

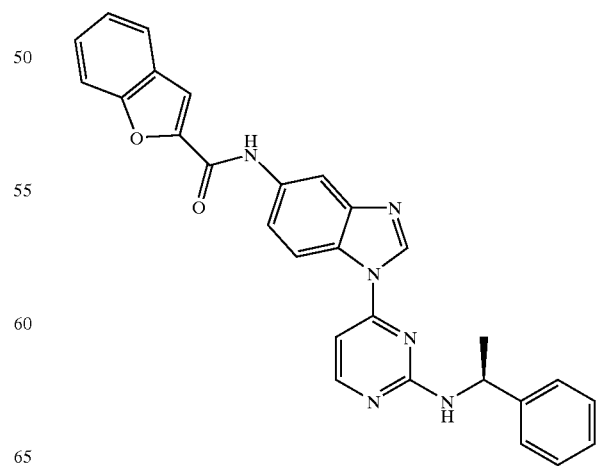

2-[(S)-1-Phenylethylamino]-4-[5-N-(benzofuran-2-oyl)aminobenzimidazol-1-yl]pyrimidine The title compound was prepared from 30 mg of 2-[(S)-1-phenylethylamino]-4-[5-aminobenzimidazol-1-yl]pyrimidine (EXAMPLE 79), 16 mg of 2-benzofurancarboxylic acid, 21 mg of 1-(3-dimethylaminopropyl)-3-ethylcarbodiimide hydrochloride and 11 mg of 4-N,N-dimethylaminopyridine in 2 mL of CH2Cl2 using the procedure described in EXAMPLE 138, except that the residue was purified by preparative thin layer chromatography (50% acetone in hexane) to provide 30 mg of the title compound. Mass spectrum (ESI): 475 (M+1). 1H NMR (500 MHz, CDCl3): d 8.48 (s, 1H); 8.40 (d, J=5.0 Hz, 1H); 8.17 (s, 1H); 7.75 (d, 1H); 7.71 (br s, 1H); 7.65 (s, 1H); 7.61 (d, 1H); 7.52–7.25 (m, 8H); 6.78 (d, J=5.2 Hz, 1H); 5.86 (br s, 1H); 5.21 (br s, 1H); 1.65 (d, J=6.9 Hz, 3H).

EXAMPLE 143

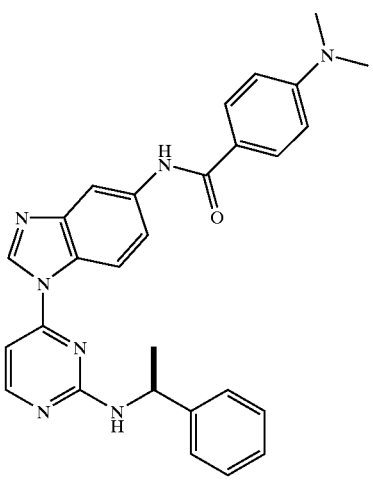

2-[(S)-1-Phenylethylamino]-4-[5-N-(4-N,N-dimethylaminobenzoyl)amino-benzimidazol-1-yl]pyrimidine The title compound was prepared from 30 mg of 2-[(S)-1-phenylethylamino]-4-[5-aminobenzimidazol-1-yl]pyrimidine (EXAMPLE 79), 18 mg of 4-(N,N-dimethylamino)benzoic acid, 23 mg of 1-(3-dimethylaminopropyl)-3-ethylcarbodiimide hydrochloride and 11 mg of 4-N,N-dimethylaminopyridine in 2 mL of CH$_2$Cl$_2$ using the procedure described in EXAMPLE 138, except that the residue was purified by preparative thin layer chromatography (80% acetone in hexane) to provide 25 mg of the title compound. Mass spectrum (ESI): 478 (M+1). $^1$H NMR (500 MHz, CDCl$_3$): δ 8.43 (br s, 1H); 8.32 (d, J=5.0 Hz, 1H); 8.14 (s, 1H); 8.02 (s, 1H); 7.82 (d, 2H); 7.65 (br d, 1H); 7.45–7.20 (m, 5H); 6.71 (d, J=5.2 Hz, 1H); 6.68 (d, 2H); 5.96 (br s, 1H); 5.16 (br s, 1H); 3.02 (s, 6H); 1.61 (d, J=6.9 Hz, 3H).

EXAMPLE 144

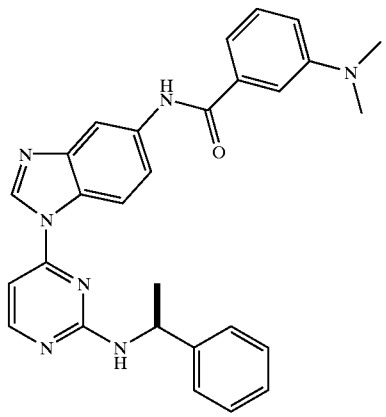

2-[(S)-1-Phenylethylamino]-4-[5-N-(3-N,N-dimethylaminobenzoyl)amino-benzimidazol-1-yl]pyrimidine The title compound was prepared from 50 mg of 2-[(S)-1-phenylethylamino]-4-[5-aminobenzimidazol-1-yl]pyrimidine (EXAMPLE 79), 30 mg of 3-(N,N-dimethylamino)benzoic acid, 37 mg of 1-(3-dimethylaminopropyl)-3-ethylcarbodiimide hydrochloride and 18 mg of 4-N,N-dimethylaminopyridine in 4 mL of CH$_2$Cl$_2$ using the procedure described in EXAMPLE 138, except that the residue was purified by preparative thin layer chromatography (66% acetone in hexane) to provide 56 mg of the title compound. Mass spectrum (ESI): 478 (M+1). $^1$H NMR (500 MHz, CDCl$_3$): δ 8.46 (br s, 1H); 8.37 (d, J=5.5 Hz, 1H); 8.08 (s, 1H); 8.05 (s, 1H); 7.80 (br s, 1H); 7.65 (br s, 1H); 7.50–7.25 (m, 6H); 7.14 (d, J=7.6 Hz, 1H); 6.89 (dd, J$_1$=2.7 Hz, J$_2$=8.7 Hz,1H); 6.74 (d, J=5.5 Hz, 2H); 5.87 (br s, 1H); 5.20 (br s, 1H); 3.03 (s, 6H); 1.64 (d, J=7.1 Hz, 3H).

EXAMPLE 145

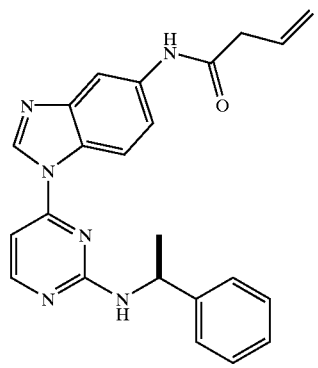

141

2-[(S)-1-Phenylethylamino]-4-[5-N-(3-butenoyl)-aminobenzimidazol-1]pyrimidine The title compound was prepared from 50 mg of 2-[(S)-1-phenylethylamino]-4-[5-aminobenzimidazol-1-yl]pyrimidine (EXAMPLE 79), 15 μL of vinyl acetic acid, 37 mg of 1-(3-dimethylaminopropyl)-3-ethylcarbodiimide hydrochloride and 18 mg of 4-N,N-dimethylaminopyridine in 4 nL of $CH_2Cl_2$ using the procedure described in EXAMPLE 138, except that the residue was purified by preparative thin layer chromatography (66% acetone in hexane) to provide 50 mg of the title compound. Mass spectrum (ESI): 399 (M+1). $^1$H NMR (500 MHz, $CDCl_3$): δ 8.46 (br s, 1H); 8.37 (d, J=5.5 Hz, 1H); 7.93 (s, 1H); 7.74 (br s, 1H); 7.52–7.22 (m, 6H); 6.73 (d, J=5.5 Hz, 1H); 6.2 (m, 1H); 5.83 (br s, 1H); 5.39 (s, 1H); 5.36 (d, J=9.4 Hz, 1H); 5.18 (br s, 1H); 3.24 (d, J=7.1 Hz, 2H); 1.63 (d, J=6.9 Hz, 3H).

EXAMPLE 146

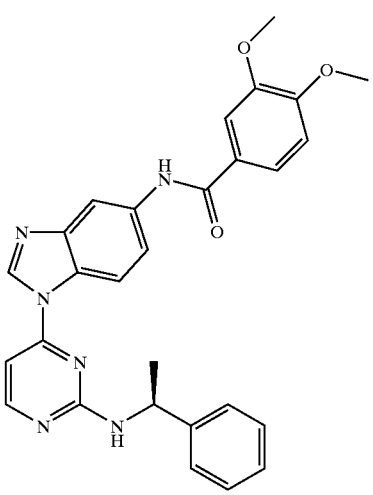

2-[(S)-1-Phenylethylamino]-4-[5-N-(3,4-dimethoxybenzoyl)aminobenzimidazol-1-yl]pyrimidine The title compound was prepared from 50 mg of 2-[(S)-1-phenylethylamino]-4-[5-aminobenzimidazol-1-yl]pyrimidine (EXAMPLE 79), 33 mg of 3,4-dimethoxybenzoic acid, 37 mg of 1-(3-dimethylaminopropyl)-3-ethylcarbodiimide hydrochloride and 18 mg of 4-N,N-dimethylaminopyridine in 2 mL of $CH_2Cl_2$ using the procedure described in EXAMPLE 138, except that the residue was purified by preparative thin layer chromatography (66% acetone in hexane) to provide 60 mg of the title compound. Mass spectrum (ESI): 495 (M+1). $^1$H NMR (500 MHz, $CDCl_3$): δ 8.44 (br s, 1H); 8.36 (d, J=5.5 Hz, 1H); 8.24 (s, 1H); 8.04 (s, 1H); 7.74 (br s, 1H); 7.64 (br d, 1H); 7.57–7.22 (m, 6H); 6.89 (d, J=8.5 Hz, 1H); 6.72 (d, J=5.5 Hz, 1H); 5.92 (br s, 1H); 5.18 (br s, 1H); 3.93 (s, 6H); 1.63 (d, J=6.9 Hz, 3H).

142

EXAMPLE 147

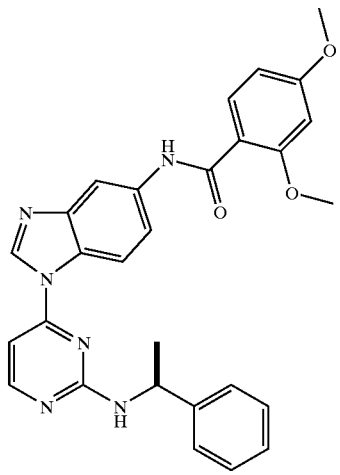

2-[(S)-1-Phenylethylamino]-4-[5-N-(2,4-dimethoxybenzoyl)aminobenzimidazol-1-yl]pyrimidine The title compound was prepared from 50 mg of 2-[(S)-1-phenylethylamino]-4-[5-aminobenzimidazol-1-yl]pyrimidine (EXAMPLE 79), 33 mg of 2,4-dimethoxybenzoic acid, 37 mg of 1-(3-dimethylaminopropyl)-3-ethylcarbodiimide hydrochloride and 18 mg of 4-N,N-dimethylaminopyridine in 2 mL of $CH_2Cl_2$ using the procedure described in EXAMPLE 138, except that the residue was purified by preparative thin layer chromatography (66% acetone in hexane) to provide 62 mg of the title compound. Mass spectrum (ESI): 495 (M+1). $^1$H NMR (500 MHz, $CDCl_3$): δ 9.84 (s, 1H); 8.49 (br s, 1H); 8.39 (br t, 1H); 8.31 (d, J=5.5 Hz, 1H); 8.03 (s, 1H); 7.86 (br s, 1H); 7.75 (br d, 1H); 7.50–7.22 (m, 5H); 6.77 (br t, 1H); 6.69 (d, J=5.5 Hz, 1H); 6.57 (s, 1H); 5.72 (br s, 1H); 5.22 (br s, 1H); 4.08 (s, 3H); 3.90 (s, 3H); 1.65 (d, J=6.9 Hz, 3H).

EXAMPLE 148

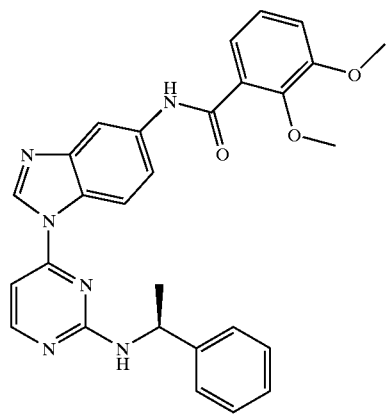

2-[(S)-1-Phenylethylamino]-4-[5-N-(2,3-dimethoxybenzoyl)aminobenzimidazol-1-yl]pyrimidine The title compound was prepared from 50 mg of 2-[(S)-1-phenylethylamino]-4-[5-aminobenzimidazol-1-yl]pyrimidine (EXAMPLE 79), 33 mg of 2,3-dimethoxybenzoic acid, 37 mg of 1-(3-dimethylaminopropyl)-3-ethylcarbodiimide hydrochloride and 18 mg of 4-N,N-dimethylaminopyridine in 2 mL of $CH_2Cl_2$ using the procedure described in EXAMPLE 138, except that the residue was purified by preparative thin layer chromatography (66% acetone in hexane) to provide 61 mg of the title compound. Mass spectrum (ESI): 495 (M+1). $^1$H NMR (500 MHz, $CDCl_3$): δ 10.15 (s, 1H); 8.49 (br s, 1H); 8.40 (d, J=5.2 Hz, 1H); 8.12 (s, 1H); 7.84 (d, J=8.0); 7.71 (br s, 1H); 7.50–7.20 (m, 7H); 7.13 (d, J=8.2 Hz, 1H); 6.78 (d, J=5.3 Hz, 1H); 5.75 (br s, 1H); 5.22 (br s, 1H); 4.05 (s, 3H); 3.97 (s, 3H); 1.65 (d, J=6.9 Hz, 3H).

EXAMPLE 149

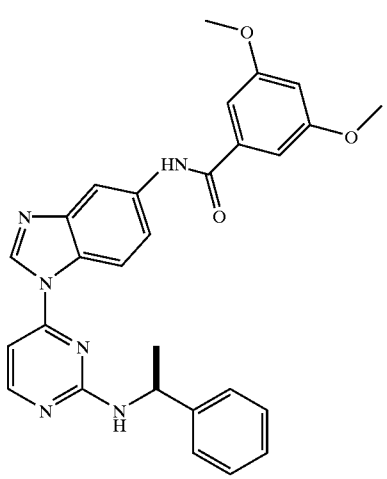

2-[(S)-1-Phenylethylamino]-4-[5-N-(3,5-dimethoxybenzoyl)-aminobenzimidazol-1-yl]pyrimidine The title compound was prepared from 50 mg of 2-[(S)-1-phenylethylamino]-4-[5-aminobenzimidazol-1-yl]pyrimidine (EXAMPLE 79), 33 mg of 3,5-dimethoxybenzoic acid, 37 mg of 1-(3-dimethylaminopropyl)-3-ethylcarbodiimide hydrochloride and 18 mg of 4-N,N-dimethylaminopyridine in 2 mL of $CH_2Cl_2$ using the procedure described in EXAMPLE 138, except that the residue was purified by preparative thin layer chromatography (66% acetone in hexane) to provide 60 mg of the title compound. Mass spectrum (ESI): 495 (M+1). $^1$H NMR (500 MHz, $CDCl_3$): δ 8.48 (br s, 1H); 8.40 (d, J=5.5 Hz, 1H); 8.07 (s, 1H); 7.92 (s, 1H); 7.60 (br s, 1H); 7.50–7.22 (m, 5H); 7.04 (d, J=2.0 Hz, 2H); 6.77 (d, J=5.5 Hz, 1H); 6.65 (t, J=2.2 Hz, 1H); 5.72 (br s, 1H); 5.20 (br s, 1H); 3.89 (s, 6H); 1.65 (d, J=6.9 Hz, 3H).

EXAMPLE 150

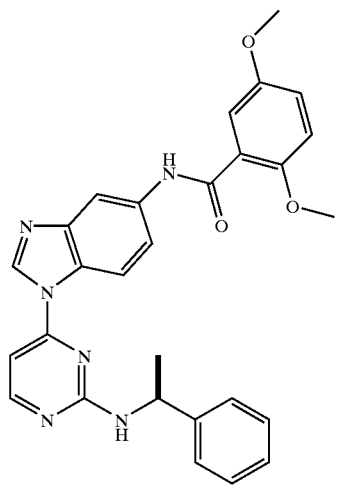

2-[(S)-1-Phenylethylamino]-4-[5-N-(2,5-dimethoxybenzoyl)aminobenzimidazol-1-yl]pyrimidine The title compound was prepared from 50 mg of 2-[(S)-1-phenylethylamino]-4-[5-aminobenzimidazol-1-yl]pyrimidine (EXAMPLE 79), 33 mg of 2,5-dimethoxybenzoic acid, 37 mg of 1-(3-dimethylaminopropyl)-3-ethylcarbodiimide hydrochloride and 18 mg of 4-N,N-dimethylaminopyridine in 2 mL of $CH_2Cl_2$ using the procedure described in EXAMPLE 138, except that the residue was purified by preparative thin layer chromatography (66% acetone in hexane) to provide 60 mg of the title compound. Mass spectrum (ESI): 495 (M+1). $^1$H NMR (500 MHz, $CDCl_3$): δ 10.10 (s, 1H); 8.50 (br s, 1H); 8.38 (d, J=5.5 Hz, 1H); 8.08 (s, 1H); 7.89 (d, J=3.2 Hz, 1H); 7.74 (br d, 1H); 7.50–7.22 (m, 5H); 7.07 (dd, $J_1$=3.2 Hz, $J_2$=8.9 Hz, 1H); 7.01 (d, J=8.9 Hz, 1H); 6.77 (d, J=5.5 Hz, 1H); 5.83 (br s, 1H); 5.22 (br s, 1H); 4.06 (s, 3H); 3.87 (s, 3H); 1.65 (d, J=6.9 Hz, 3H).

EXAMPLE 151

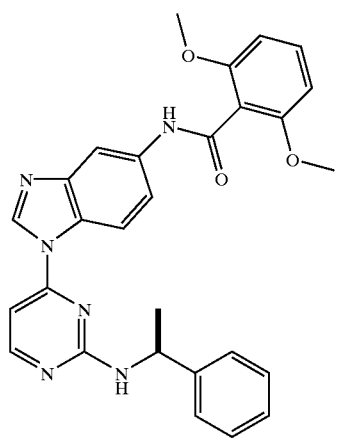

2-[(S)-1-Phenylethylamino]-4-[5-N-(2,6-dimethoxybenzoyl)aminobenzimidazol-1-yl]pyrimidine The title compound was prepared from 50 mg of 2-[(S)-1-phenylethylamino]-4-[5-aminobenzimidazol-1-yl]pyrimidine (EXAMPLE 79), 33 mg of 2,6-dimethoxybenzoic acid, 37 mg of 1-(3-dimethylaminopropyl)-3-ethylcarbodiimide hydrochloride and 18 mg of 4-N,N-dimethylaminopyridine in 2 mL of $CH_2Cl_2$ using the procedure described in EXAMPLE 138, except that the residue was purified by preparative thin layer chromatography (66% acetone in hexane) to provide 60 mg of the title compound. Mass spectrum (ESI): 495 (M+1). $^1$H NMR (500 MHz, $CDCl_3$): δ 8.46 (br s, 1H); 8.38 (d, J=5.5 Hz, 1H); 8.02 (s, 1H); 7.76 (br d, 1H); 7.68 (s, 1H); 7.50–7.25 (m, 6H); 6.76 (d, J=5.5 Hz, 1H); 6.62 (d, J=8.5 Hz, 1H); 5.79 (br s, 1H); 5.20 (br s, 1H); 3.87 (s, 6H); 1.65 (d, J=6.9 Hz, 3H).

EXAMPLE 152

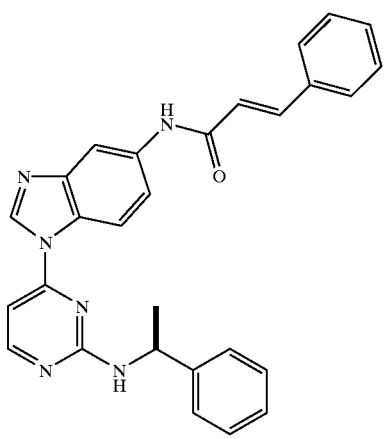

2-[(S)-1-Phenylethylamino]-4-[5-N-(3-phenyl-2-propenoyl)aminobenzimidazol-1-yl]pyrimidine The title compound was prepared from 60 mg of 2-[(S)-1-phenylethylamino]-4-[5-aminobenzimidazol-1-yl]pyrimidine (EXAMPLE 79), 33 mg of cinnamic acid, 45 mg of 1-(3-dimethylaminopropyl)-3-ethylcarbodiimide hydrochloride and 22 mg of 4-N,N-dimethylaminopyridine in 2 mL of $CH_2Cl_2$ using the procedure described in EXAMPLE 138, except that the reaction was stirred at room temperature for 4 h and the residue was purified by preparative thin layer chromatography (66% acetone in hexane) to provide 75 mg of the title compound. Mass spectrum (ESI): 461 (M+1). $^1$H NMR (500 MHz, $CDCl_3$): δ 8.45 (br s, 1H); 8.37 (d, J=5.5 Hz, 1H); 8.04 (s, 1H); 7.82 (s, 1H); 7.80 (d, J=15.5 Hz, 1H); 7.68 (br s, 1H); 7.58–7.22 (m, 10H); 6.71 (d, J=5.2 Hz, 1H); 6.61 (d, J=15.3 Hz, 1H); 5.79 (br s, 1H); 5.20 (br s, 1H); 1.64 (d, J=6.9 Hz, 3H).

EXAMPLE 153

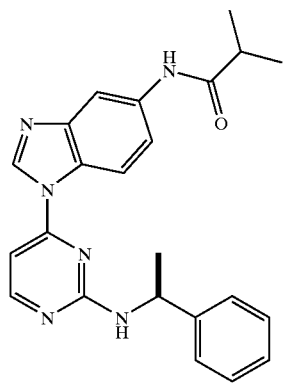

2-[(S)-1-Phenylethylamino]-4-[5-N-(3-methyl-2-propanoyl)aminobenzimidazol-1-yl]pyrimidine The title compound was prepared from 60 mg of 2-[(S)-1-phenylethylamino]-4-[5-aminobenzimidazol-1-yl]pyrimidine (EXAMPLE 79), 20 µL of isobutyric acid, 45 mg of 1-(3-dimethylaminopropyl)-3-ethylcarbodiimide hydrochloride and 22 mg of 4-N,N-dimethylaminopyridine in 2.5 mL of $CH_2Cl_2$ using the procedure described in EXAMPLE 138, except that the residue was purified by preparative thin layer chromatography (66% acetone in hexane) to provide 65 mg of the title compound. Mass spectrum (ESI): 401 (M+1). $^1$H NMR (500 MHz, $CDCl_3$): δ 8.45 (br s, 1H); 8.36 (d, J=5.3 Hz, 1H); 7.92 (s, 1H); 7.72 (br s, 1H); 7.56 (br d, 1H); 7.50–7.22 (m, 5H); 6.73 (d, J=5.5 Hz, 1H); 5.96 (br s, 1H); 5.18 (br s, 1H); 2.57 (m, 1H); 1.63 (d, J=6.9 Hz, 3H); 1.31 (t, J=6.9 Hz, 6H).

EXAMPLE 154

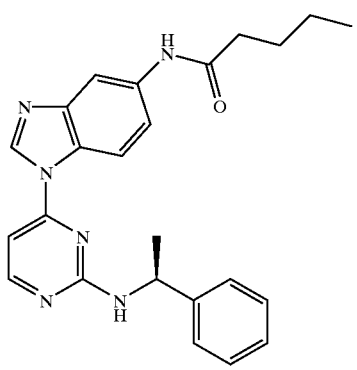

2-[(S)-1-Phenylethylamino]4-[5-N-(pentanoyl)-aminobenzimidazol-1-yl]pyrimidine

The title compound was prepared from 60 mg of 2-[(S)-1-phenylethylamino]-4-[5-aminobenzimidazol-1-yl]pyrimidine (EXAMPLE 79), 24 μL of valeric acid, 45 mg of 1-(3-dimethylaminopropyl)-3-ethylcarbodiimide hydrochloride and 22 mg of 4-N,N-dimethylaminopyridine in 2.5 mL of $CH_2Cl_2$ using the procedure described in EXAMPLE 138, except that the residue was purified by preparative thin layer chromatography (60% acetone in hexane) to provide 68 mg of the title compound. Mass spectrum (ESI): 415 (M+1). $^1$H NMR (500 MHz, $CDCl_3$): δ 8.44 (br s, 1H); 8.35 (d, J=5.2 Hz, 1H); 7.91 (s, 1H); 7.72 (br s, 1H); 7.59 (s, 1H); 7.54 (br d, 1H); 7.50–7.22 (m, 5H); 6.71 (d, J=5.5 Hz, 1H); 6.0 (br s, 1H); 5.18 (br s, 1H); 2.41 (t, J=7.5 Hz, 2H); 1.76 (m, J=7.5 Hz, 2H); 1.63 (d, J=6.9 Hz, 3H); 1.44 (m, J=7.3 Hz, 2H); 0.97 (t, J=7.3 Hz, 3H).

EXAMPLE 155

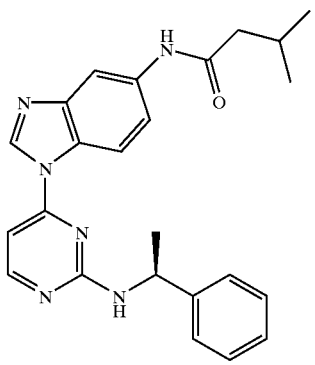

2-[(S)-1-Phenylethylamino]-4-[5-N-(3-methylbutanoyl)aminobenzimidazol-1-yl]pyrimidine The title compound was prepared from 60 mg of 2-[(S)-1-phenylethylamino]-4-[5-aminobenzimidazol-1-yl]pyrimidine (EXAMPLE 79), 24 μL of isovaleric acid, 45 mg of 1-(3-dimethylaminopropyl)-3-ethylcarbodiimide hydrochloride and 22 mg of 4-N,N-dimethylaminopyridine in 2.5 mL of $CH_2Cl_2$ using the procedure described in EXAMPLE 138, except that the residue was purified by preparative thin layer chromatography (60% acetone in hexane) to provide 70 mg of the title compound. Mass spectrum (ESI): 415 (M+1). $^1$H NMR (500 MHz, $CDCl_3$): δ 8.44 (br s, 1H); 8.35 (d, J=5.3 Hz, 1H); 7.92 (s, 1H); 7.72 (br s, 1H); (br d, 1H); 7.53 (s, 1H); 7.46–7.24 (m, 5H); 6.72 (d, J=5.3 Hz, 1H); 6.02 (br s, 1H); 5.19 (br s, 1H); 2.27 (s, 3H); 1.63 (d, J=6.7 Hz, 3H); 1.05 (d, 6H).

EXAMPLE 156

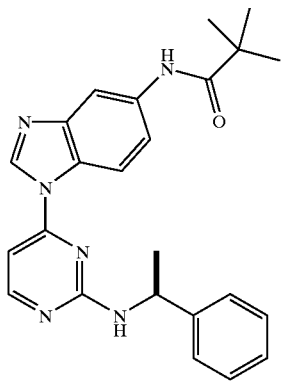

2-[(S)-1-Phenylethylamino]-4-[5-N-(pivaloyl)-aminobenzimidazol-1-yl]pyrimidine

The title compound was prepared from 60 mg of 2-[(S)-1-phenylethylamino]-4-[5-aminobenzimidazol-1-yl]pyrimidine (EXAMPLE 79), 22 mg of trimethylacetic acid, 45 mg of 1-(3-dimethylaminopropyl)-3-ethylcarbodiimide hydrochloride and 22 mg of 4-N,N-dimethylaminopyridine in 2.5 mL of $CH_2Cl_2$ using the procedure described in EXAMPLE 138, except that the residue was purified by preparative thin layer chromatography (60% acetone in hexane) to provide 68 mg of the title compound. Mass spectrum (ESI): 415 (M+1). $^1$H NMR (500 MHz, $CDCl_3$): δ 8.45 (br s, 1H); 8.34 (d, J=5.3 Hz, 1H); 7.92 (s, 1H); 7.76 (br s, 1H); 7.53 (br d, 1H); 7.51 (s, 1H); 7.46–7.24 (m, 5H); 6.73 (d, J=5.5 Hz, 1H); 6.16 (br s, 1H); 5.19 (br s, 1H); 1.63 (d, J=6.9 Hz, 3H); 1.37 (s, 9H).

EXAMPLE 157

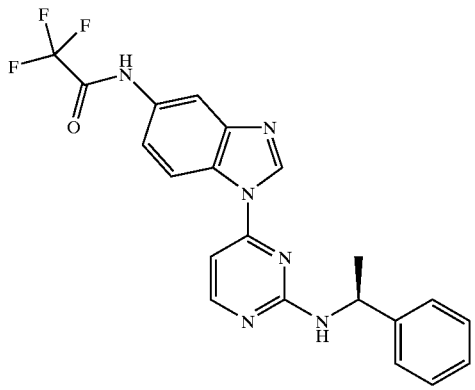

2-[(S)-1-Phenylethylamino]-4-[5-N-(trifluoroacetyl)aminobenzimidazol-1-yl]pyrimidine The title compound was prepared from 500 mg of 2-[(S)-1-phenylethyl-amino]-4-[5-aminobenzimidazol-1-yl]pyrimidine (EXAMPLE 79), 0.17 mL of trifluoroacetic acid, 435 mg of 1-(3-dimethylaminopropyl)-3-ethylcarbodiimide hydrochloride and 184 mg of 4-N,N-dimethylaminopyridine in 6 mL of $CH_2Cl_2$ using the procedure described in EXAMPLE 138, except that the residue was purified by preparative thin layer chromatography (33% acetone in hexane) to provide 622 mg of the title compound. Mass spectrum (ESI): 427 (M+1). $^1$H NMR (500 MHz, $CDCl_3$): δ 8.48 (br s, 1H); 8.35 (br d, 1H); 8.31 (s, 1H); 7.76 (br s, 1H); 7.52 (br d, 1H); 7.48–7.24 (m, 5H); 6.94 (br s, 1H); 6.79 (d, J=5.5 Hz, 1H); 5.19 (br s, 1H); 1.67 (d, J=6.9 Hz, 3H).

EXAMPLE 158

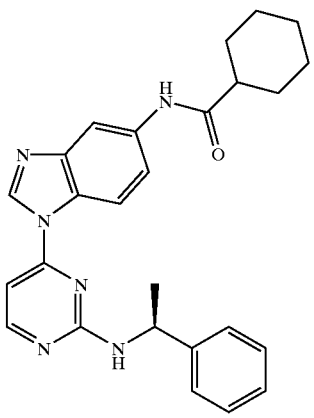

2-[(S)-1-Phenylethylamino]-4-[5-N-(cyclohexanoyl)aminobenzimidazol-1-yl]-pyrimidine The title compound was prepared from 60 mg of 2-[(S)-1-phenylethylamino]-4-[5-aminobenzimidazol-1-yl]pyrimidine (EXAMPLE 79), 27 µL of cyclohexane carboxylic acid, 45 mg of 1-(3-dimethylaminopropyl)-3-ethylcarbodiimide hydrochloride and 22 mg of 4-N,N-dimethylaminopyridine in 2.5 mL of $CH_2Cl_2$ using the procedure described in EXAMPLE 138, except that the residue was purified by preparative thin layer chromatography (60% acetone in hexane) to provide 72 mg of the title compound. Mass spectrum (ESI): 441 (M+1). $^1$H NMR (500 MHz, $CDCl_3$): δ 8.43 (br s, 1H); 8.33 (d, J=5.3 Hz, 1H); 7.92 (s, 1H); 7.70 (br s, 1H); (br d, 1H); 7.46–7.22 (m, 5H); 6.70 (d, J=5.5 Hz, 1H); 6.12 (br s, 1H); 5.19 (br s, 1H); 2.28 (m, 1H); 2.00 (br d, 2H); 1.85 (m, 2H); 1.72 (m, 1H); 1.62 (d, J=6.9 Hz, 3H); 1.59 (m, 1H); 1.3 (m, 4H).

EXAMPLE 159

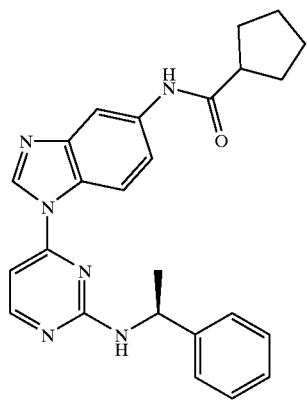

2-[(S)-1-Phenylethylamino]-4-[5-N-(cyclopentanoyl)aminobenzimidazol-1-yl]pyrimidine The title compound was prepared from 60 mg of 2-[(S)-1-phenylethylamino]-4-[5-aminobenzimidazol-1-yl]pyrimidine (EXAMPLE 79), 24 µL of cyclopentane carboxylic acid, 45 mg of 1-(3-dimethylaminopropyl)-3-ethylcarbodiimide hydrochloride and 22 mg of 4-N,N-dimethylaminopyridine in 2.5 mL of $CH_2Cl_2$ using the procedure described in EXAMPLE 138, except that the residue was purified by preparative thin layer chromatography (60% acetone in hexane) to provide 70 mg of the title compound. Mass spectrum (ESI): 427 (M+1). $^1$H NMR (500 MHz, $CDCl_3$): δ 8.43 (br s, 1H); 8.33 (d, J=4.8 Hz, 1H); 7.68 (br s, 1H); 7.67 (s, 1H); 7.56 (br d, J=8.3 Hz, 1H); 7.46–7.22 (m, 5H); 6.70 (d, J=5.5 Hz, 1H); 6.18 (br s, 1H); 5.19 (br s, 1H); 2.73 (m, J=8.1 Hz, 1H); 1.96 (m, 4H); 1.81 (m, 2H); 1.65 (m, 2H); 1.62 (d, J=6.9 Hz, 3H).

EXAMPLE 160

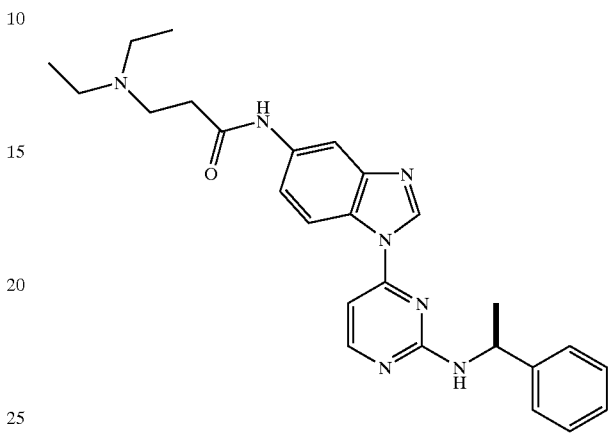

2-[(S)-1-Phenylethylamino]-4-[5-N-(3-N,N-diethylaminopropanoyl)amino-benzimidazol-1-yl]pyrimidine The title compound was prepared from 60 mg of 2-[(S)-1-phenylethylamino]-4-[5-aminobenzimidazol-1-yl]pyrimidine (EXAMPLE 79), 43 mg of 3-(diethylamino)propionic acid hydrochloride, 45 mg of 1-(3-dimethylaminopropyl)-3-ethylcarbodiimide hydrochloride, 22 mg of 4-N,N-dimethylaminopyridine and 102 µL of triethylamine in 2.5 mL of $CH_2Cl_2$ using the procedure described in EXAMPLE 138, except that the residue was purified by preparative thin layer chromatography (66% acetone in hexane) to provide 55 mg of the title compound. Mass spectrum (ESI): 458 (M+1). $^1$H NMR (500 MHz, $CDCl_3$): δ 11.46(s, 1H); 8.46 (br s, 1H); 8.35 (d, J=5.3 Hz, 1H); 7.90 (s, 1H); 7.74 (br s, 1H); 7.63 (br d, 1H); 7.47–7.24 (m, 5H); 6.74 (d, J=5.5 Hz, 1H); 6.00 (br s, 1H); 5.20 (br s, 1H); 2.81 (t, J=5.9 Hz, 2H); 2.70 (q, J=7.2 Hz, 4H); 2.55 (t, J=5.7 Hz, 2H); 1.63 (d, J=6.9 Hz, 3H); 1.17 (t, J=7.1 Hz, 6H).

EXAMPLE 161

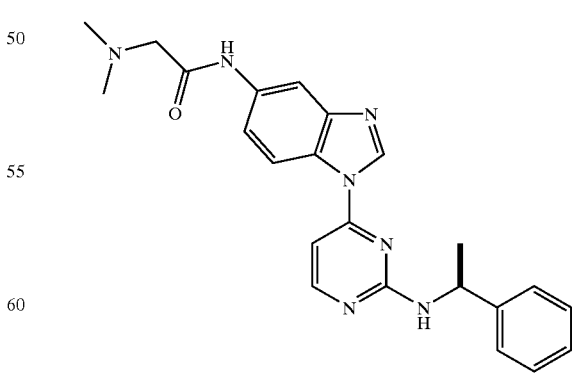

2-[(S)-1-Phenylethylamino]-4-[5-N-(N,N-dimethylaminoacetyl)aminobenzimidazol-1-yl]pyrimidine

151

The title compound was prepared from 80 mg of 2-[(S)-1-phenylethylamino]-4-[5-aminobenzimidazol-1-yl]pyrimidine (EXAMPLE 79), 33 mg of N,N-dimethyl glycine, 70 mg of 1-(3-dimethylaminopropyl)-3-ethylcarbodiimide hydrochloride and 15 mg of 4-N,N-dimethylaminopyridine in 4 mL of $CH_2Cl_2$ using the procedure described in EXAMPLE 138, except that the reaction was stirred at room temperature for 4 h and the residue was purified by preparative thin layer chromatography (66% acetone in hexane) to provide 100 mg of the title compound. Mass spectrum (ESI): 416 (M+1). $^1$H NMR (500 MHz, $CDCl_3$): δ 9.35 (br s, 1H); 8.48 (br s, 1H); 8.39 (d, J=5.3 Hz, 1H); ); 8.05 (s, 1H); 7.80 (br s, 1H); 7.60 (br s, 1H); 7.48–7.26 (m, 5H); 6.76 (d, J=5.2 Hz, 1H); 5.75 (br s, 1H); 5.20 (br s, 1H); 3.22 (s, 2H); 2.49 (s, 6H); 1.64 (d, J=6.9 Hz, 3H).

EXAMPLE 162

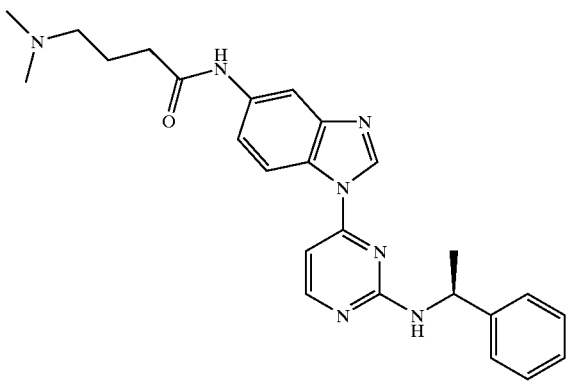

2-[(S)-1-Phenylethylamino]-4-[5-N-(4-N,N-dimethylaminobutanoyl)amino-benzimidazol-1-yl]pyrimidine The title compound was prepared from 80 mg of 2-[(S)-1-phenylethylamino]-4-[5-aminobenzimidazol-1-yl]pyrimidine (EXAMPLE 79), 54 mg of 4-(dimethylamino)butyric acid hydrochloride, 70 mg of 1-(3-dimethylaminopropyl)-3-ethylcarbodiimide hydrochloride and 44 mg of 4-N,N-dimethylaminopyridine in 3 mL of $CH_2Cl_2$ using the procedure described in EXAMPLE 138, except that the residue was purified by preparative thin layer chromatography (10% 2N NH3 in MeOH/$CH_2Cl_2$) to provide 97 mg of the title compound. Mass spectrum (ESI): 444 (M+1). $^1$H NMR (500 MHz, $CDCl_3$): δ 10.04 (s, 1H); 8.45 (br s, 1H); 8.36 (d, J=5.0 Hz, 1H); ); 7.92 (s, 1H); 7.74 (br s, 1H); 7.61 (br s, 1H); 7.48–7.22 (m, 5H); 6.74 (d, J=5.5 Hz, 1H); 5.86 (br s, 1H); 5.20 (br s, 1H); 2.55 (t, J=6.3 Hz, 2H); 2.50 (t, J=6.0 Hz, 2H); 2.36 (s, 6H); 1.93 (m, J=6.2 Hz, 2H); 1.63 (d, J=6.9 Hz, 3H).

152

EXAMPLE 163

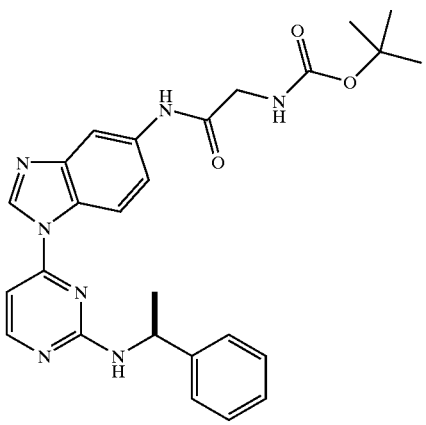

2-[(S)-1-Phenylethylamino]-4-[5-N-(N-(tert-butyloxycarbonyl)aminoacetyl)amino-benzimidazol-1-yl]pyrimidine The title compound was prepared from 400 mg of 2-[(S)-1-phenylethyl-amino]-4-[5-aminobenzimidazol-1-yl]pyrimidine (EXAMPLE 79), 233 mg of N-(tert-butyloxycarbonyl)glycine, 348 mg of 1-(3-dimethylaminopropyl)-3-ethylcarbodiimide hydrochloride and 74 mg of 4-N,N-dimethylaminopyridine in 8 mL of $CH_2Cl_2$ using the procedure described in EXAMPLE 138, except that the residue was purified by preparative thin layer chromatography (50% acetone in hexane) to provide 586 mg of the title compound. Mass spectrum (ESI): 488 (M+1). $^1$H NMR (500 MHz, $CDCl_3$): δ 8.46 (br s, 1H); 8.36 (d, J=5.0 Hz, 1H); ); 8.32 (br s, 1H); 7.98 (s, 1H); 7.72 (br s, 1H); 7.55–7.25 (m, 6H); 6.75 (d, J=5.5 Hz, 1H); 6.10 (br s, 1H); 5.34 (br s, 1H); 5.19 (br s, 1H); 4.0 (d, J=6.0 Hz, 2H); 1.65 (d, J=6.9 Hz, 3H); 1.52 (s, 9H).

EXAMPLE 164

2-[(S)-1-Phenylethylamino]-4-[5-N-(aminoacetyl)-aminobenzimidazol-1-yl]pyrimidine To a solution of 2-[(S)-1-phenylethylamino]-4-[5-N-(N-(tert-butyloxy-carbonyl)aminoacetyl)-aminobenzimidazol-1-yl]pyrimidine (328 mg) in THF (3 mL) was added 3N aqueous HCl (4 mL). The reaction mixture was stirred at room temperature for 5 h followed by addition of 5N NaOH to pH=10–11. The mixture was extracted with $CH_2Cl_2$ (3×40 mL). The combined $CH_2Cl_2$ layer was washed with water and brine and dried over anhydrous $Na_2SO_4$. Removal of the solvent and subsequent silica gel preparative thin layer chromatography purification (10% of 2N $NH_3$ in MeOH/$CH_2Cl_2$) provided the title compound (180 mg). Mass spectrum (ESI): 388 (M+1). $^1$H NMR (500 MHz, $CDCl_3$): δ 8.50 (br s, 1H); 8.41 (d, J=5.5 Hz, 1H); 8.38 (d, 1H); 8.40 (s, 1H);

7.84 (br s, 1H); 7.64 (br s, 1H); 7.55–7.20 (m, 5H); 7.10 (br s, 1H); 6.75 (d, J=5.5 Hz, 1H); 6.10 (br s, 1H); 5.14 (br s, 1H); 3.55 (s, 2H); 1.64 (d, J=6.7 Hz, 3H).

EXAMPLE 165

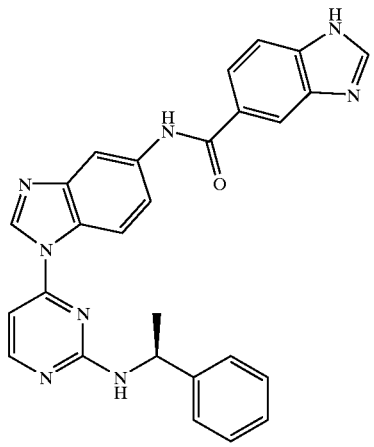

2-[(S)-1-Phenylethylamino]-4-[5-N-(benzimidazol-5-oyl)aminobenzimidazol-1-yl]pyrimidine To a solution of 2-[(S)-1-phenylethylamino]-4-[5-aminobenzimidazol-1-yl]pyrimidine (EXAMPLE 79) (40 mg) in DMF (1.5 mL) was added 5-benzimidazolecarboxylic acid (24 mg) followed by addition of 1-(3-dimethylaminopropyl)-3-ethylcarbodiimide hydrochloride (30 mg) and N-methylmorphorine (20 μL). The reaction mixture was stirred at 80° C. for 6 h. Removal of the solvent and subsequent purification by preparative thin layer chromatography (10% of 2N NH₃ in MeOH/CH₂Cl₂) provided 20 mg of the title product. Mass spectrum (ESI): 475 (M+1). ¹H NMR (CD₃OD): δ 8.72 (br s, 1H); 8.31 (m, 2H); ); 8.15 (s, 1H); 7.91 (d, J=8.0 Hz, 1H); 7.71 (br s, 1H); 7.59 (br s, 1H); 7.50–7.18 (m, 5H); 6.93 (d, J=5.5 Hz, 1H); 5.15 (br d, 1H); 1.59 (d, J=6.9 Hz, 3H).

EXAMPLE 166

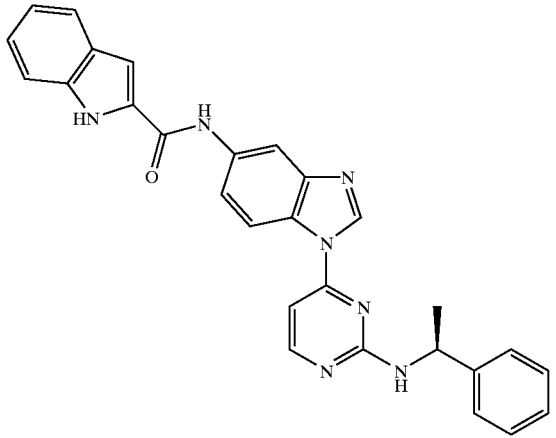

2-[(S)-1-Phenylethylamino]-4-[5-N-(indol-2-oyl)aminobenzimidazol-1-yl]pyrimidine The title compound was prepared from 100 mg of 2-[(S)-1-phenylethylamino]-4-[5-aminobenzimidazol-1-yl] pyrimidine (EXAMPLE 79), 75 mg of indole-2-carboxylic acid, 87 mg of 1-(3-dimethylaminopropyl)-3-ethylcarbodiimide hydrochloride and 37 mg of 4-N,N-dimethylaminopyridine in 4 mL of CH₂Cl₂ using the procedure described in EXAMPLE 165. 50 mg of the title compound was obtained. Mass spectrum (ESI): 474 (M+1). ¹H NMR (500 MHz, CDCl₃ & a few drops of CD₃OD): δ 8.40 (br s, 1H); 8.20 (d,J=5.2 Hz, 1H); ); 7.88 (br s, 1H); 7.60 (br s, 1H); 7.52 (d, J=8.0 Hz, 1H); 7.35–6.94 (m, 8H); 6.70 (d, J=5.5 Hz, 1H); 5.00 (br s, 1H); 1.47 (d, J=6.6 Hz, 3H).

EXAMPLE 167

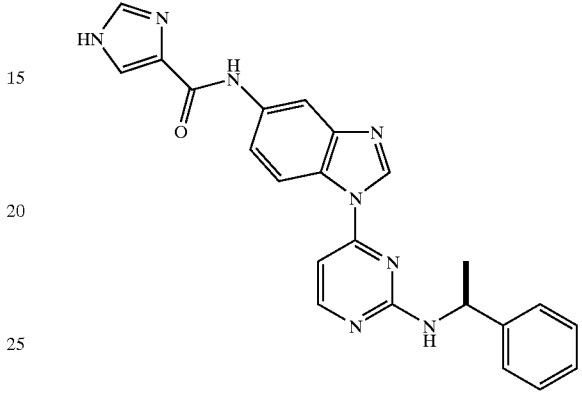

2-[(S)-1-Phenylethylamino]-4-[5-N-(imidazol-4-oyl)aminobenzimidazol-1-yl]-pyrimidine The title compound was prepared from 80 mg of 2-[(S)-1-phenylethylamino]-4-[5-aminobenzimidazol-1-yl] pyrimidine (EXAMPLE 79), 41 mg of 4-imidazolecarboxylic acid, 70 mg of 1-(3-dimethylaminopropyl)-3-ethylcarbodiimide hydrochloride and 15 mg of 4-N,N-dimethylaminopyridine in 4 mL of THF using the procedure described in EXAMPLE 138, except that the reaction was stirred at 65° C. for 6 h and the residue was purified by preparative thin layer chromatography (10% 2N NH3 in MeOH/CH₂Cl₂) to provide 41 mg of the title product. Mass spectrum (ESI): 425 (M+1). ¹H NMR (500 MHz, CDCl₃ & a few drops of CD₃OD); δ 8.42 (br s, 1H); 8.23 (d,J=5.5 Hz, 1H); ); 8.14 (br s, 1H); 7.66 (br s, 1H); 7.58 (s, 1H); 7.54 (br d, 1H); 7.43 (br s, 1H); 7.36–7.10 (m, 5H); 6.71 (d, J=5.5 Hz, 1H); 5.05 (br s, 1H); 1.51 (d, J=6.9 Hz, 3H).

EXAMPLE 168

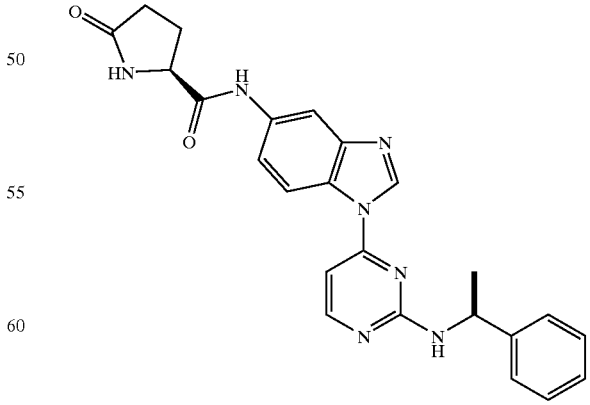

2-[(S)-1-Phenylethylamino]-4-[5-N-((S)-2-pyrrolidon-5-oyl)aminobenzimidazol-1-yl] pyrimidine

EXAMPLE 169

The title compound was prepared from 80 mg of 2-[(S)-1-phenylethylamino]-4-[5-aminobenzimidazol-1-yl]pyrimidine (EXAMPLE 79), 40 mg of L-2-pyrrolidone-5-carboxylic acid, 60 mg of 1-(3-dimethylaminopropyl)-3-ethylcarbodiimide hydrochloride and 29 mg of 4-N,N-dimethylaminopyridine in 4 mL of $CH_2Cl_2$ using the procedure described in EXAMPLE 138, except the residue was purified by preparative thin layer chromatography (11% of MeOH in $CH_2Cl_2$) to provide 30 mg of the title product. Mass spectrum (ESI): 442 (M+1). $^1$H NMR (500 MHz, $CDCl_3$): δ 9.30 (br s, 1H); 8.38 (br s, 1H); 8.23 (d,J=5.3 Hz, 1H); ); 8.00 (s, 1H); 7.80 (br s, 1H); 7.48 (br d, 1H); 7.43–7.15 (m, 5H); 6.52 (d, J=5.5 Hz, 1H); 6.22 (br s, 1H); 5.05 (br s, 1H); 4.38 (br t, 1H); 2.48 (m, 2H); 2.30 (m, 2H); 1.57 (d, J=6.1 Hz, 3H).

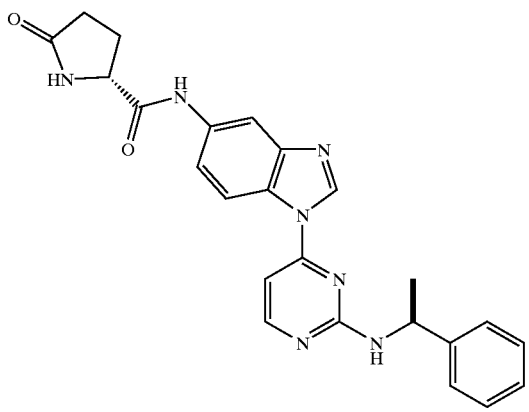

2-[(S)-1-Phenylethylamino]-4-[5-N-((R)-2-pyrrolidon-5-oyl)amino-benzimidazol-1-yl]pyrimidine The title compound was prepared from 80 mg of 2-[(S)-1-phenylethylamino]-4-[5-aminobenzimidazol-1-yl]pyrimidine (EXAMPLE 79), 40 mg of D-2-pyrrolidone-5-carboxylic acid, 60 mg of 1-(3-dimethylaminopropyl)-3-ethylcarbodiimide hydrochloride and 29 mg of 4-N,N-dimethylaminopyridine in 4 mL of CH2Cl2 using the procedure described in EXAMPLE 138, except the residue was purified by preparative thin layer chromatography (11% of MeOH in CH2Cl2) to provide 62 mg of the title product. Mass spectrum (ESI): 442 (M+1). $^1$H NMR (500 MHz, CDCl3): d 9.40 (br s, 1H); 8.34 (br s, 1H); 8.21 (d,J=5.2 Hz, 1H); ); 7.98 (s, 1H); 7.89 (s, 1H); 7.50–7.15 (m, 5H); 6.48 (d, J=5.1 Hz, 1H); 6.28 (br s, 1H); 5.05 (br s, 1H); 4.37 (br t, 1H); 2.46 (m, 2H); 2.30 (m, 2H); 1.56 (d, J=5.5 Hz, 3H).

EXAMPLE 170

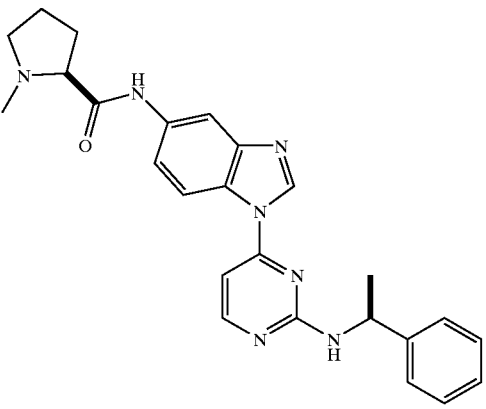

2-[(S)-1-Phenylethylamino]-4-[5-N-((S)-1-methylpyrrolidin-2-oyl)aminobenzimidazol-1-yl]pyrimidine The title compound was prepared from 200 mg of 2-[(S)-1-phenylethylamino]4-[5-aminobenzimidazol-1-yl]pyrimidine (EXAMPLE 79), 107 mg of N-methyl-L-proline monohydrate, 174 mg of 1-(3-dimethylaminopropyl)-3-ethylcarbodiimide hydrochloride and 74 mg of 4-N,N-dimethylaminopyridine in 4 mL of $CH_2Cl_2$ using the procedure described in EXAMPLE 138, except the residue was purified by preparative thin layer chromatography (50% of acetone in hexane) to provide 239 mg of the title product. Mass spectrum (ESI): 442 (M+1). $^1$H NMR (500 MHz, $CDCl_3$): δ 8.47 (br s, 1H); 8.38 (d,J=5.4 Hz, 1H); ); 8.03 (s, 1H); 7.80 (br s, 1H); 7.64 (br d, 1H); 7.50–7.25 (m, 5H); 6.76 (d, J=5.5 Hz, 1H); 5.76 (br s, 1H); 5.20 (br s, 1H); 3.26 (br s, 1H); 3.09 (br s, 1H); 2.52 (s, 3H); 2.48 (br s, 1H); 2.35 (m, 1H); 2.05 (m, 1H); 1.87 (m, 2H); 1.64 (d, J=6.9 Hz, 3H).

EXAMPLE 171

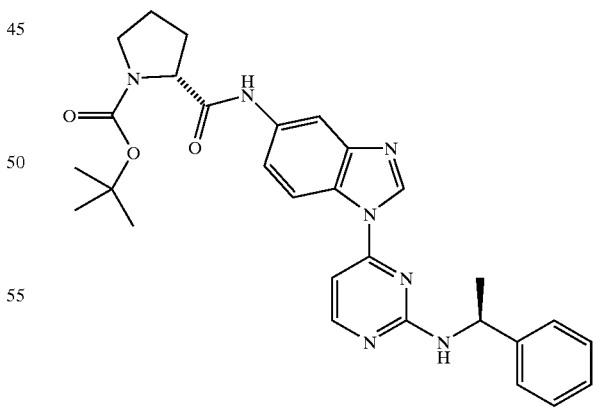

2-[(S)-1-Phenylethylamino]-4-[5-N-((R)-1-(tert-butyloxycarbonyl)-pyrrolidin-2-oyl)-aminobenzimidazol-1yl]-pyrimidine The title compound was prepared following the general procedure described in EXAMPLE 138 using (R)-1-(tert-butyloxycarbonyl)pyrrolidine-2-carboxylic acid. Mass spectrum (ESI): 528 (M+1). $^1$H NMR (500 MHz, CDCl$_3$): δ9.65 (br s, 1H); 8.43 (br s, 1H); ); 8.34 (br d, 1H); 8.00 (s, 1H); 7.70 (br d, 1H); 7.50–7.24 (m, 5H); 6.72 (d, J=5.0 Hz, 1H); 6.02 (br s, 1H); 5.20 (br s, 1H); 4.55 (br s, 1H); 3.50 (br t, 2H); 2.60 (br s, 1H); 2.17 (br s, 1H); 2.03 (br s, 1H); 1.96 (m, 1H); 1.64 (d, J=6.9 Hz, 3H); 1.53 (s, 9H).

EXAMPLE 172

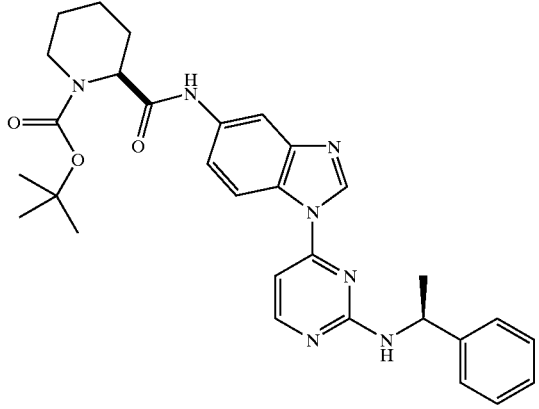

2-[(S)-1-Phenylethylamino]-4-[5-N-((S)-1-(tert-butyloxycarbonyl)piperidin-2-oyl)-aminobenzimidazol-1-yl]pyrimidine The title compound was prepared following the general procedure described in EXAMPLE 138 using (S)-1-(tert-butyloxycarbonyl)piperidine-2-carboxylic acid. Mass spectrum (ESI): 542 (M+1). $^1$H NMR (500 MHz, CDCl$_3$): δ8.46 (br s, 1H); ); 8.36 (d, J=5.3 Hz, 1H); 7.97 (s, 1H); 7.73 (br d, 1H); 7.50–7.25 (m, 5H); 6.75 (d, J=5.5 Hz, 1H); 6.05 (br s, 1H); 5.20 (br s, 1H); 4.93 (br s, 1H); 4.13 (br s, 1H); 2.91 (t, 1H); 2.40 (br d, 1H);1.74 (br s, 2H); 1.64 (d, J=6.8 Hz, 3H); 1.60 (m, 1H); 1.55 (s, 9H); 1.28 (m, 2H).

EXAMPLE 173

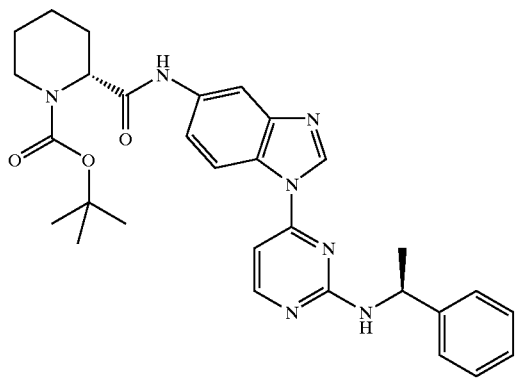

2-[(S)-1-Phenylethylamino]-4-[5-N-((R)-1-(tert-butyloxycarbonyl)piperidin-2-oyl)-aminobenzimidazol-1-yl]pyrimidine The title compound was prepared following the general procedure described in EXAMPLE 138 using (R)-1-(tert-butyloxycarbonyl)piperidine-2-carboxylic acid. Mass spectrum (ESI): 542 (M+1). $^1$H NMR (500 MHz, CDCl$_3$): δ8.46 (br s, 1H); ); 8.34 (br s, 1H); 7.99 (s, 1H); 7.74 (br s, 1H); 7.48 (br s, 1H); 7.47–7.25 (m, 5H); 6.78 (dd, J$_1$=1.9 Hz, J$_2$=5.7 Hz, 1H); 5.78 (br s, 1H); 5.20 (br s, 1H); 4.93 (br s, 1H); 4.13 (br s, 1H); 2.91 (t, 1H); 2.40 (br d, 1H); 1.8–1.44 (m, 5H); 1.64 (d, J=6.8 Hz, 3H).

EXAMPLE 174

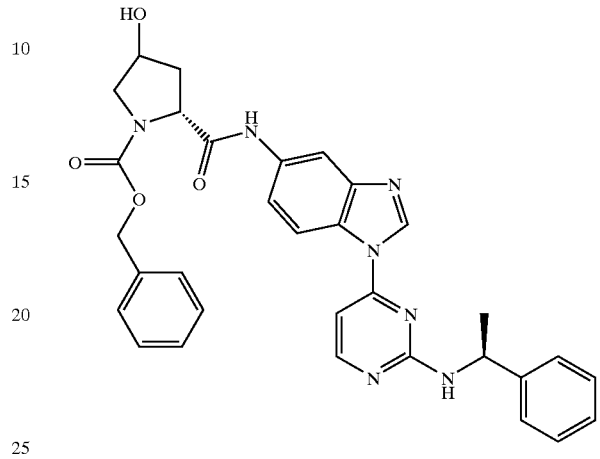

2-[(S)-1-Phenylethylamino]-4-[5-N-((R)-1-(benzyloxycarbonyl)-3-hydroxypyrrolidin-5-oyl) aminobenzimidazol-1-yl]pyrimidine The title compound was prepared following the general procedure described in EXAMPLE 138 using (R)-1-(benzyloxycarbonyl)-3-hydroxypyrrolidine-5-carboxylic acid. Additionally, pyridine was used as solvent instead of methylene chloride. Mass spectrum (ESI): 578 (M+1). $^1$H NMR (500 MHz, CDCl$_3$): δ 9.5 (s, 1H); 8.6–6.6 (m, 16H); 5.95 (br s, 1H); 5.20 (br s, 3H); 4.76 (br s, 1H); 4.6s (br d, 1H); 3.70 (br s, 2H); 2.60 (br s, 1H); 2.6–2.2 (m, 2H); 1.64 (d, J=6.8 Hz, 3H).

EXAMPLE 175

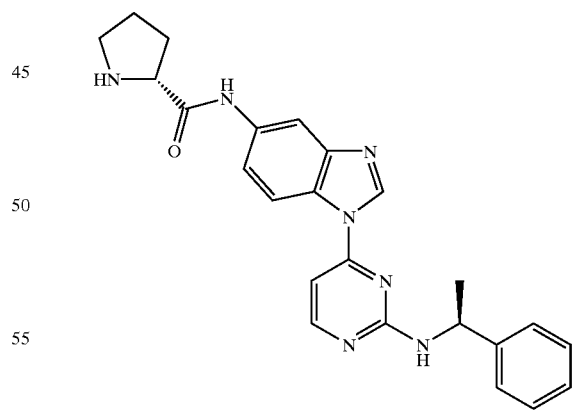

2-[(S)-1-Phenylethylamino]-4-[5-N-((R)-pyrrolidin-2-oyl)aminobenzimidazol-1-yl]pyrimidine A solution of 2-[(S)-1-phenylethylamino]-4-[5-N-((R)-1-(tert-butyloxycarbonyl)pyrrolidin-2-oyl)-aminobenzimidazol-1-yl]pyrimidine (100 mg) in 3:2 of 4M HCl/dioxane:water (2 mL) was stirred at room temperature for 5 h. The mixture was diluted with water, ethyl acetate, and separated. The aqueous layer was washed with EtOAc (twice) and then was basified with 5N NaOH to pH=11. The mixture was then extracted with methylene chloride (three times). The organic solution was washed with brine and dried over Na$_2$SO$_4$. Removal of the solvent provided the title compound (67 mg). Mass spectrum (ESI): 428 (M+1). $^1$H NMR (500 MHz, CDCl$_3$); δ 9.95 (br s, 1H); ); 8.46 (br s, 1H); 8.36 (d,J=5.1 Hz, 1H); 8.10 (br s, 1H); 7.72 (br s, 1H); 7.58 (br s, 1H); 7.50–7.22 (m, 5H); 6.71 (br d, 1H); 5.80 (br s, 1H); 5.20 (br s, 1H); 4.05 (br s, 1H); 3.20 (br s, 1H); 3.08 (m, 1H); 2.32 (br s, 1H); 2.12 (m, 1H); 1.85 (m, 2H); 1.63 (d, J=6.9 Hz, 3H).

EXAMPLE 176

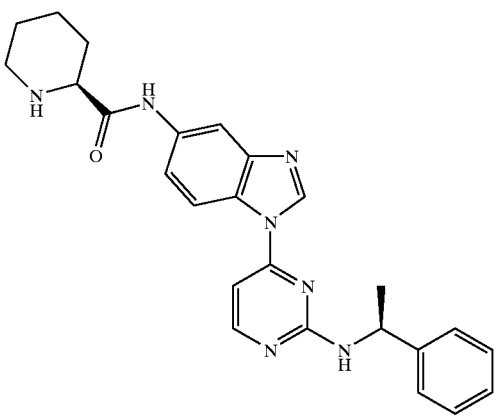

2-[(S)-1-Phenylethylamino]4-[5-N-((S)-piperidin-2-oyl)aminobenzimidazol-1-yl]pyrimidine A solution of 2-[(S)-1-phenylethylamino]-4-[5-N-((S)-1-(tert-butyloxycarbonyl)piperidin-2-oyl)-aminobenzimidazol-1-yl]pyrimidine (140 mg) in 1:1 of 4M HCl/dioxane:water (1.3 mL) was stirred at room temperature for 5 h. The mixture was diluted with water, ethyl acetate, and separated. The aqueous layer was washed with EtOAc (twice) and then was basified with 5N NaOH to pH=11. The mixture was then extracted with methylene chloride (three times). The organic solution was washed with brine and dried over Na$_2$SO$_4$. Removal of the solvent and subsequent purification by preparative thin layer chromatography (10% of 2N NH$_3$ in MeOH/CH$_2$Cl$_2$) provided the title compound (40 mg). Mass spectrum (ESI): 442 (M+1). $^1$H NMR (500 MHz, CDCl$_3$): δ 8.99 (br s, 1H); ); 8.46 (br s, 1H); 8.36 (br d, 1H); 8.04 (br s, 1H); 7.75 (br s, 1H); 7.56 (br s, 1H); 7.50–7.24 (m, 5H); 6.71 (br s, 1H); 5.83 (br s, 1H); 5.20 (br s, 1H); 3.42 (br s, 1H); 3.15 (br s, 1H); 2.80 (br s, 1H); 2.10 (br d, 1H); 1.92–1.75 (m, 2H); 1.64 (d, J=6.9 Hz, 3H); 1.5 (m, 3H).

EXAMPLE 177

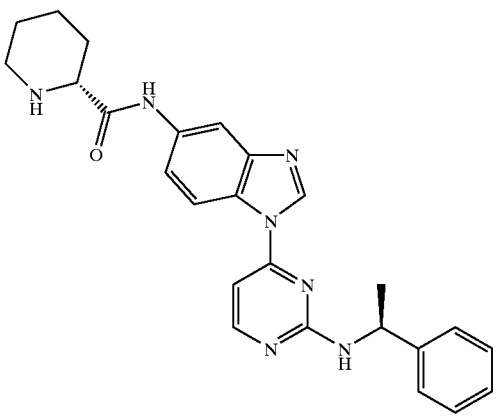

2-[(S)-1-Phenylethylamino]-4-[5-N-((R)-piperidin-2-oyl)aminobenzimidazol-1-yl]pyrimidine The title compound was prepared according to the procedure outlined in EXAMPLE 176 using 2-[(S)-1-phenylethylamino]-4-[5-N-((R)-1-(tert-butyloxycarbonyl)piperidin-2-oyl)-aminobenzimidazol-1-yl]pyrimidine as starting material. Mass spectrum (ESI): 442 (M+1). $^1$H NMR (500 MHz, CDCl$_3$): δ 9.20 (br s, 1H); ); 8.44 (br s, 1H); 8.33 (d, J=5.3 Hz, 1H); 8.02 (s, 1H); 7.74 (br s, 1H); 7.54 (br d, 1H); 7.47–7.24 (m, 5H); 6.71 (d, J=5.5 Hz, 1H); 6.06 (br s, 1H); 5.20 (br s, 1H); 3.41 (br d, 1H); 3.15 (br d, 1H); 2.80 (br t, 1H); 2.09 (br d, 1H); 1.92–1.75 (m, 2H); 1.62 (d, J=6.8 Hz, 3H); 1.5 (m, 3H).

EXAMPLE 178

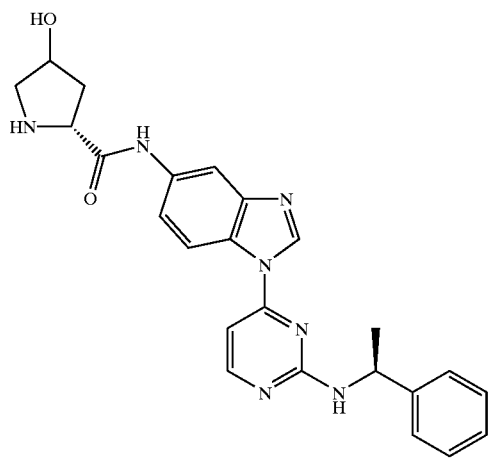

2-[(S)-1-Phenylethylamino]-4-[5-N-((R)-3-hydroxypyrrolidin-5-oyl)amino-benzimidazol-1-yl]pyrimidine To a solution of 2-[(S)-1-phenylethylamino]-4-[5-N-((R)-1-(benzyloxycarbonyl)-3-hydroxypyrrolidin-5-oyl)aminobenzimidazol-1-yl]pyrimidine (100 mg) in MeOH (2 ml) was added Pd(OH)$_2$ on carbon (100 mg). The flask was evacuated and charged with hydrogen three times, and then it was stirred under hydrogen at room temperature. for 2.5 h.

The catalyst was filtered. Removal of the solvent and subsequent purification by preparative thin layer chromatography (10% of 2N NH₃ in MeOH/CH₂Cl₂) provided the title compound (52 mg). Mass spectrum (ESI): 444 (M+1). ¹H NMR (500 MHz, CDCl₃): δ 9.87 (s, 1H); ); 8.46 (br s, 1H); 8.38 (d, J=5.2 Hz, 1H); 8.05 (s, 1H); 7.76 (br s, 1H); 7.60 (br d, 1H); 7.50–7.24 (m, 5H); 6.75 (d, J=5.2 Hz, 1H); 5.82 (br s, 1H); 5.20 (br s, 1H); 4.54 (s, 1H); 4.20 (t, J=8.3 Hz, 1H); 3.15 (d, J=11.4 Hz, 1H); 2.94 (dd, J₁=12.3 Hz, J₂=2.7 Hz, H); 2.40 (m, 1H); 2.14 (m, 1H); 2.02 (br s, 1H); 1.64 (d, J=6.9 Hz, 3H).

EXAMPLE 179

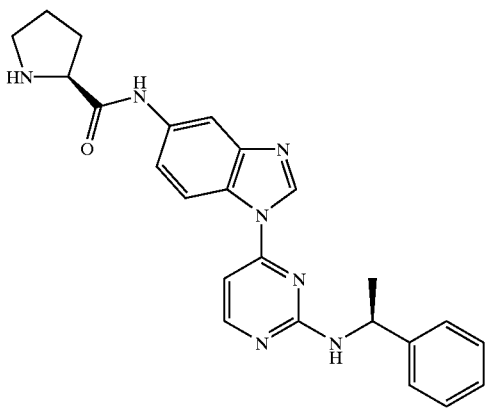

2-[(S)-1-Phenylethylamino]-4-[5-N-((S)-pyrrolidin-2-oyl)aminobenzimidazol-1-yl]pyrimidine Step A: 2-[(S)-1-Phenylethylamino]-4-[5-N-((S)-1-(benzyloxycarbonyl)-pyrrolidin-2-oyl)-aminobenzimidazol-1-yl]pyrimidine The title compound was prepared according to the procedure described in EXAMPLE 138 using (S)-1-(benzyloxycarbonyl)-pyrrolidine-2-carboxylic acid.

Step B: 2-[(S)-1-Phenylethylamino]4-[5-N-((S)-pyrrolidin-2-oyl)aminobenzimidazol-1-yl]pyrimidine The title compound was prepared from 2-[(S)-1-phenylethylamino]-4-[5-N-((S)-1-(benzyloxycarbonyl)pyrrolidin-2-oyl)-aminobenzimidazol-1-yl]pyrimidine according to the procedure described in EXAMPLE 178. Mass spectrum (ESI): 428 (M+1). 1H NMR (500 MHz, CDCl₃): δ 8.50 (br s, 1H); 8.41 (d, J=5.5 Hz, 1H); 7.86 (br s, 1H); 7.61 (br s, 1H); 7.47–7.26 (m, 5H); 7.09 (br s, 1H); 6.77 (d, J=5.3 Hz, 1H); 5.73 (br s, 1H); 5.20 (br s, 1H); 4.15 (dd, J₁=10.0 Hz, J₂=4.6 Hz, 1H); 3.08 (t, 1H); 2.76 (m, 1H); 2.28 (m, 1H); 2.17 (m, 1H); 2.0–1.85 (m, 2H); 1.64 (d, J=6.9 Hz, 3H).

EXAMPLE 180

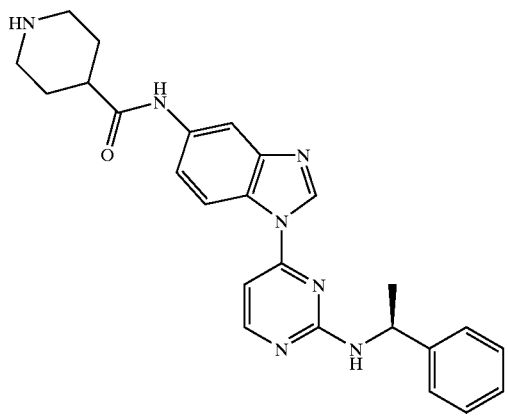

2-[(S)-1-Phenylethylamino]-4-[5-N-(piperidin-4-oyl)-aminobenzimidazol-1-yl]-pyrimidine Step A: 2-[(S)-1-Phenylethylamino]-4-[5-N-(N-(tert-butyloxycarbonyl)piperidin-4-oyl)aminobenzimidazol-1-yl]pyrimidine The title compound was prepared according to the procedure described in EXAMPLE 138 using N-(tert-butyloxycarbonyl)piperidine-4-carboxylic acid.

Step B: 2-[(S)-1-Phenylethylamino]-4-[5-N-(piperidin-4-oyl)amino-benzimidazol-1-yl]pyrimidine The title compound was prepared from 2-[(S)-1-phenylethylamino]-4-[5-N-(N-(tert-butyloxycarbonyl)piperidin-4-oyl)-aminobenzimidazol-1-yl]pyrimidine according to the procedure described in EXAMPLE 175. Mass spectrum (ESI): 442 (M+1). ¹H NMR (500 MHz, CDCl₃): δ 8.43 (br s, 1H); 8.32 (d, J=5.3 Hz, 1H); 7.92 (s, 1H); 7.88 (s, 1H); 7.70 (br s, 1H); 7.54 (br d, 1H); 7.45–7.22 (m, 5H); 6.68 (d, J=5.3 Hz, 1H); 6.10 (br s, 1H); 5.18 (br s, 1H); 3.17 (d, 2H); 2.64 (t, 2H); 2.42 (m, 1H); 1.92 (m, 2H); 1.75 (m, 2H); 1.62 (d, J=6.8 Hz, 3H).

EXAMPLE 181

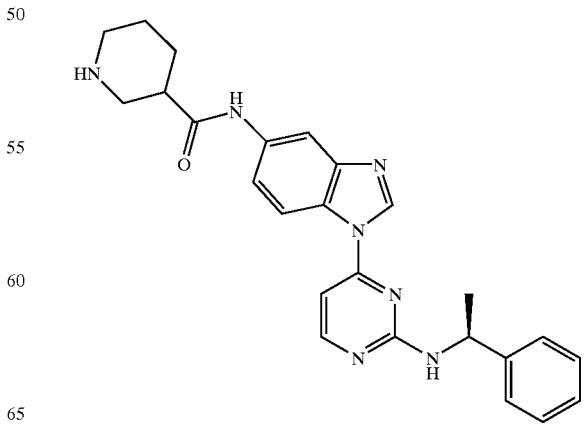

2-[(S)-1-Phenylethylamino]-4-[5-N-(piperidin-3-oyl)-aminobenzimidazol-1-yl]pyrimidine Step A: 2-[(S)-1-Phenylethylamino]-4-[5-N-(N-(tert-butyloxycarbonyl)-piperidin-3-oyl)aminobenzimidazol-1-yl]pyrimidine The title compound was prepared according to the procedure described in EXAMPLE 138 using N-(tert-butyloxycarbonyl)piperidine-3-carboxylic acid.

Step B: 2-[(S)-1-Phenylethylamino]-4-[5-N-(piperidine-3-oyl)amino-benzimidazol-1-yl]pyrimidine The title compound was prepared from 2-[(S)-1-phenylethylamino]-4-[5-(N-(tert-butyloxycarbonyl)piperidin-3-oyl)aminobenzimidazol-1-yl]pyrimidine according to the procedure described in EXAMPLE 175. Mass spectrum (ESI): 442 (M+1). $^1$H NMR (500 MHz, CDCl$_3$): δ 10.67 (br s, 1H); 8.47 (br s, 1H); 8.38 (d, J=5.3 Hz, 1H); 7.99 (s, 1H); 7.80 (s, 1H); 7.64 (br d, 1H); 7.50–7.22 (m, 5H); 6.76 (d, J=5.3 Hz, 1H); 5.75 (br s, 1H); 5.22 (br s, 1H); 3.34 (d, H); 3.13 (br d, 1H); 2.95 (dd, 1H); 2.79 (br t, 1H); 2.60 (br s, 1H); 2.13 (m, 1H); 1.83 (m, 2H); 1.65 (d, J=6.8 Hz, 3H); 1.62 (m, 1H). EXAMPLE 182
General Reductive Amination Procedure To a mixture of 2-[(S)-1-phenylethylamino]-4-[5-aminobenzimidazol-1-yl]pyrimidine (EXAMPLE 79) and an appropriate aldehyde (1–1.2 eq) in 1,2-dichloroethane is added sodium triacetoxyborohydride (1.5 eq) and acetic acid (1 eq). The reaction mixture is stirred under N$_2$ at room temperature for about 2–5 h and quenched with 1N NaOH. The mixture is extracted with ethyl acetate and the organic layer is washed with brine and dried over Na$_2$SO$_4$. Removal of the solvent and subsequent purification by preparative thin layer chromatography (acetone/hexane system) provides the desired amine product.

EXAMPLE 183

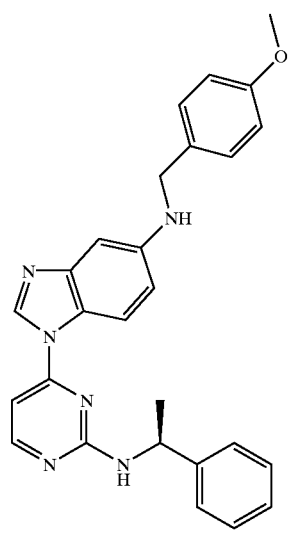

2-[(S)-1-Phenylethylamino]-4-[5-N-(4-methoxybenzyl)aminobenzimidazol-1-yl]-pyrimidine The title compound was prepared according to the general procedure described in EXAMPLE 182 using 4-methoxybenzaldehyde. Mass spectrum (ESI): 451 (M+1). $^1$H NMR (500 MHz, CDCl$_3$): δ 8.39 (br s, 1H); 8.34 (d, J=5.3 Hz, 1H); 7.60 (br s, 1H); 7.45 (s, 1H); 7.43 (s, 1H); 7.4–7.24 (m, 5H); 7.02 (s, 1H); 6.90 (d, J=8.4 Hz, 2H); 6.72 (d, J=5.5 Hz, 1H); 6.66 (br s, 1H); 5.63 (br s, 1H); 5.20 (br s, 1H); 4.32 (s, 2H); 4.04 (br s, 1H); 3.82 (s, 3H); 1.63 (d, J=6.9 Hz, 3H).

EXAMPLE 184

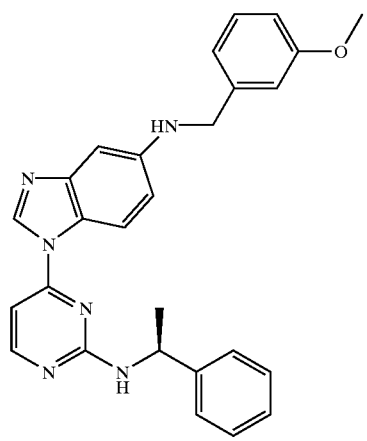

2-[(S)-1-Phenylethylamino]-4-[5-N-(3-methoxybenzyl)aminobenzimidazol-1-yl]-pyrimidine The title compound was prepared according to the general procedure described in EXAMPLE 182 using 3-methoxybenzaldehyde. Mass spectrum (ESI): 451 (M+1). $^1$H NMR (500 MHz, CDCl$_3$): δ 8.38 (br s, 1H); 8.34 (d, J=5.2 Hz, 1H); 7.63 (br s, 1H); 7.44 (s, 1H); 7.43 (s, 1H); 7.4–7.22 (m, 4H); 7.04 (s, 1H); 6.92 (m, 2H); 6.72 (d, J=5.5 Hz, 1H); 6.70 (br s, 1H); 5.64 (br s, 1H); 5.20 (br s, 1H); 4.41 (s, 2H); 4.23 (br s, 1H); 3.90 (s, 3H); 1.63 (d, J=7.0 Hz, 3H).

EXAMPLE 185

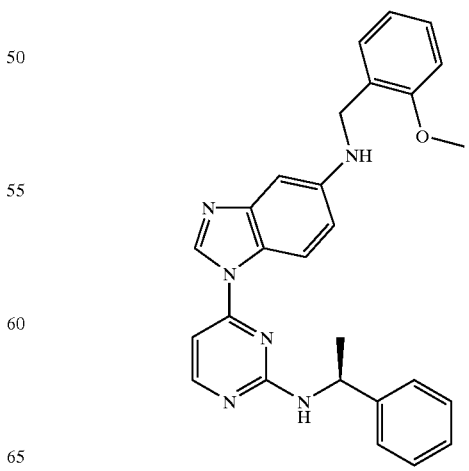

2-[(S)-1-Phenylethylamino]-4-[5-N-(2-methoxybenzyl)aminobenzimidazol-1-yl]-pyrimidine The title compound was prepared according to the general procedure described in EXAMPLE 182 using 2-methoxybenzaldehyde. Mass spectrum (ESI): 451 (M+1). $^1$H NMR (500 MHz, CDCl$_3$): δ 8.39 (br s, 1H); 8.34 (d, J=5.0 Hz, 1H); 7.63 (br s, 1H); 7.45 (s, 1H); 7.43 (s, 1H); 7.4–7.22 (m, 5H); 7.02 (s, 1H); 6.90 (d, J=8.2 Hz, 2H); 6.71 (d, J=5.3 Hz, 1H); 6.66 (br s, 1H); 5.71 (br s, 1H); 5.20 (br s, 1H); 4.32 (s, 2H); 4.05 (br s, 1H); 3.82 (s, 3H); 1.63 (d, J=6.8 Hz, 3H).

EXAMPLE 186

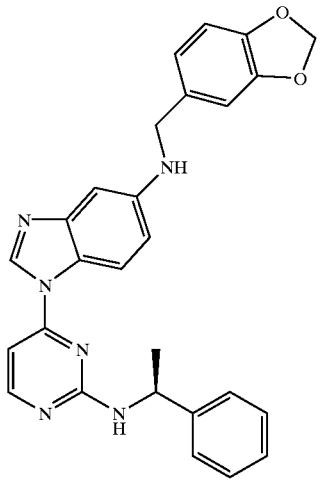

2-[(S)-1-Phenylethylamino]-4-[5-N-(3,4-methylenedioxybenzyl)aminobenzimidazol-1-yl] pyrimidine The title compound was prepared according to the general procedure described in EXAMPLE 182 using piperonal. Mass spectrum (ESI): 465 (M+1). $^1$H NMR (500 MHz, CDCl$_3$): δ 8.39 (br s, 1H); 8.31 (d, J=5.3 Hz, 1H); 7.60 (br s, 1H); 7.50–7.22 (m, 5H); 6.99 (d, J=1.8 Hz, 1H); 6.91 (d, J=1.6 Hz, 1H); 6.87 (dd, J$_1$=8.0 Hz, J$_2$=1.5 Hz, 1H); 6.78 (d, J=7.8 Hz, 1H); 6.69 (d, J=5.5 Hz, 1H); 6.64 (br s, 1H); 5.95 (s, 2H); 5.20 (br s, 1H); 4.27 (s, 2H); 4.10 (br s, 1H); 1.62 (d, J=7.1 Hz, 3H).

EXAMPLE 187

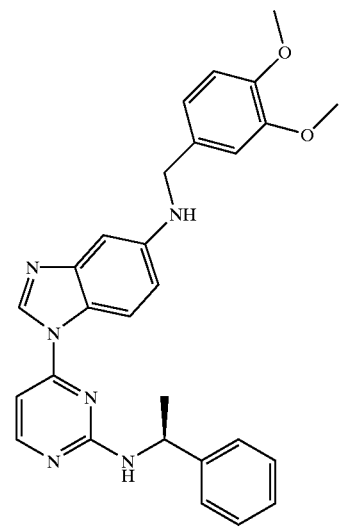

2-[(S)-1-Phenylethylamino]-4-[5-N-(3,4-dimethoxybenzyl)aminobenzimidazol-1-yl] pyrimidine The title compound was prepared according to the general procedure described in EXAMPLE 182 using 3,4-dimethoxy-benzaldehyde. Mass spectrum (ESI): 481 (M+1). $^1$H NMR (500 MHz, CDCl$_3$): δ 8.40 (br s, 1H); 8.33 (d, J=5.2 Hz, 1H); 7.60 (br s, 1H); 7.50–7.22 (m, 5H); 7.03 (s, 1H); 6.97 (s, 1H); 6.86 (d, J$_1$=8.4 Hz, 1H); 6.71 (d, J=5.5 Hz, 1H); 6.65 (br s, 1H); 5.75 (br s, 1H); 5.20 (br s, 1H); 4.32 (s, 2H); 4.07 (br s, 1H); 3.89 (s, 6H); 1.63 (d, J=6.9 Hz, 3H).

EXAMPLE 188

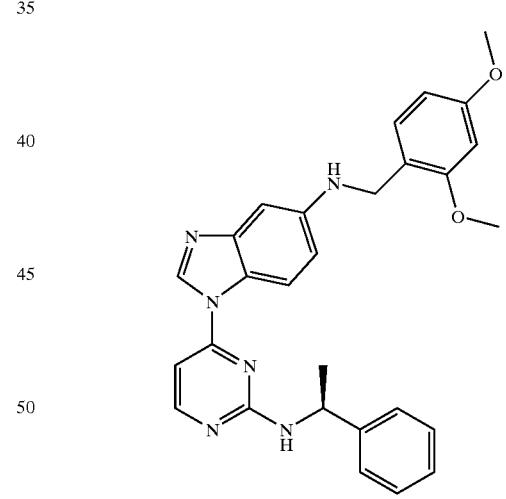

2-[(S)-1-Phenylethylamino]-4-[5-N-(2,4-dimethoxybenzyl)aminobenzimidazol-1-yl] pyrimidine The title compound was prepared according to the general procedure described in EXAMPLE 182 using 2,4-dimethoxy-benzaldehyde. Mass spectrum (ESI): 481 (M+1). $^1$H NMR (500 MHz, CDCl$_3$): δ 8.38 (br s, 1H); 8.32 (d, J=5.2 Hz, 1H); 7.60 (br s, 1H); 7.50–7.22 (m, 5H); 7.05 (d, J=1.9 Hz, 1H); 6.71 (d, J=5.5 Hz, 1H); 6.68 (br d, 1H); 6.50 (d, J=5.3 Hz, 1H); 6.44 (dd, J$_1$=8.3 Hz, J$_2$=2.5 Hz, 1H); 5.74 (br s, 1H); 5.20 (br s, 1H); 4.32 (s, 2H); 4.16 (br s, 1H); 3.87 (s, 3H); 3.80 (s, 3H); 1.63 (d, J=6.8 Hz, 3H).

EXAMPLE 189

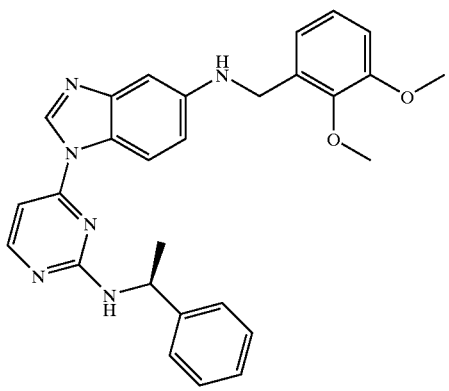

2-[(S)-1-Phenylethylamino]-4-[5-N-(2,3-dimethoxybenzyl)aminobenzimidazol-1-yl]pyrimidine The title compound was prepared according to the general procedure described in EXAMPLE 182 using 2,3-dimethoxy-benzaldehyde. Mass spectrum (ESI): 481 (M+1). $^1$H NMR (500 MHz, CDCl$_3$): δ 8.38 (br s, 1H); 8.33 (d, J=5.5 Hz, 1H); 7.60 (br s, 1H); 7.47–6.96 (m, 8H); 6.87 (dd, J$_1$=7.7 Hz, J$_2$=1.8 Hz, 1H); 6.71 (d, J=5.5 Hz, 1H); 6.68 (br s, 1H); 5.72 (br s, 1H); 5.20 (br s, 1H); 4.42 (s, 2H); 4.19 (br s, 1H); 3.92 (s, 3H); 3.89 (s, 3H); 1.63 (d, J=6.9 Hz, 3H).

EXAMPLE 190

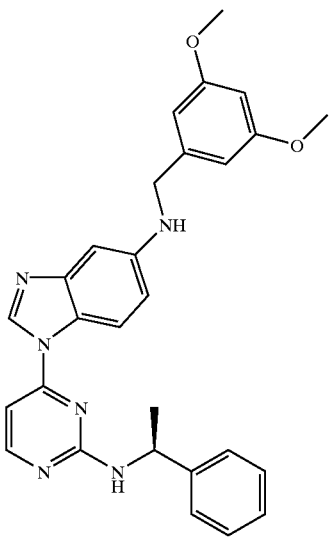

2-[(S)-1-Phenylethylamino]-4-[5-N-(3,5-dimethoxybenzyl)aminobenzimidazol-1-yl]pyrimidine The title compound was prepared according to the general procedure described in EXAMPLE 182 using 3,5-dimethoxy-benzaldehyde. Mass spectrum (ESI): 481 (M+1). $^1$H NMR (500 MHz, CDCl$_3$): δ 8.38 (br s, 1H); 8.33 (d, J=5.0 Hz, 1H); 7.60 (br s, 1H); 7.47–7.23 (m, 5H); 7.01 (s, 1H); 6.71 (d, J=5.2 Hz, 1H); 6.64 (br s, 1H); 6.59 (s, 2H); 6.39 (s, 1H); 5.80 (br s, 1H); 5.20 (br s, 1H); 4.33 (s, 2H); 4.14 (br s, 1H); 3.79 (s, 6H); 1.63 (d, J=6.9 Hz, 3H).

EXAMPLE 191

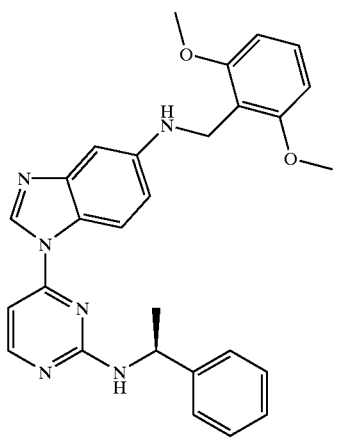

2-[(S)-1-Phenylethylamino]-4-[5-N-(2,6-dimethoxybenzyl)aminobenzimidazol-1-yl]pyrimidine The title compound was prepared according to the general procedure described in EXAMPLE 182 using 2,6-dimethoxybenzaldehyde. Mass spectrum (ESI): 481 (M+1). $^1$H NMR (500 MHz, CDCl$_3$): δ 8.39 (br s, 1H); 8.33 (d, J=5.5 Hz, 1H); 7.64 (br s, 1H); 7.46–7.17 (m, 7H); 6.75 (br s, 1H); 6.72 (d, J=5.5 Hz, 1H) 6.57 (d, J=8.2 Hz, 2H); 5.65 (br s, 1H); 5.20 (br s, 1H); 4.45 (s, 2H); 4.28 (br s, 1H); 3.89 (s, 6H); 1.63 (d, J=7.1 Hz, 3H).

EXAMPLE 192

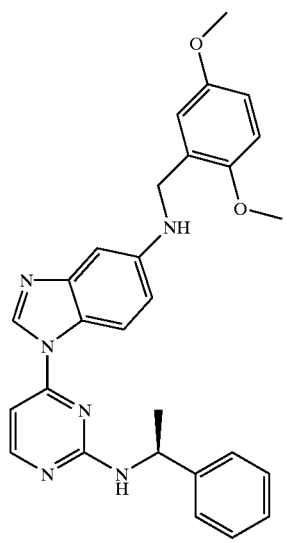

2-[(S)-1-Phenylethylamino]-4-[5-N-(2,5-dimethoxybenzyl)aminobenzimidazol-1-yl]pyrimidine The title compound was prepared according to the general procedure described in EXAMPLE 182 using 2,5-dimethoxy-benzaldehyde. Mass spectrum (ESI): 481 (M+1). $^1$H NMR (500 MHz, CDCl$_3$): δ 8.38 (br s, 1H); 8.34 (d, J=5.5 Hz, 1H); 7.63 (br s, 1H); 7.46–7.25 (m, 5H); 7.03 (s, 1H); 6.96 (d, J=3.0 Hz, 1H); 6.84 (d, J=8.9 Hz, 1H); 6.75

(dd, J$_1$=8.9 Hz, J$_2$=2.9 Hz, 1H); 6.72 (d, J=5.5 Hz, 1H); 5.64 (br s, 1H); 5.20 (br s, 1H); 4.38 (s, 2H); 4.22 (br s, 1H); 3.86 (s, 3H); 3.73 (s, 3H); 1.63 (d, J=7.1 Hz, 3H).

EXAMPLE 193

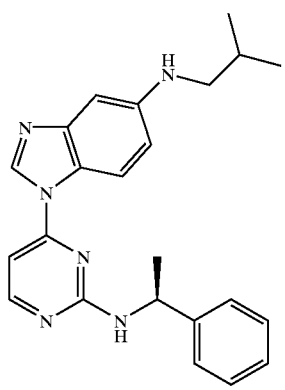

2-[(S)-1-Phenylethylamino]-4-[5-N-(2-methyl-1-propyl)aminobenzimidazol-1-yl]pyrimidine The title compound was prepared according to the general procedure described in EXAMPLE 182 using isobutyraldehyde. Mass spectrum (ESI): 387 (M+1). $^1$H NMR (500 MHz, CDCl$_3$): δ 8.40 (br s, 1H); 8.33 (d, J=5.5 Hz, 1H); 7.63 (br s, 1H); 7.47–7.25 (m, 5H); 6.98 (s, 1H); 6.72 (d, J=5.5 Hz, 1H); 6.64 (br d, 1H); 6.05 (br s, 1H); 5.20 (br s, 1H); 3.80 (br s, 1H); 3.00 (d, J=6.7 Hz, 2H); 1.96 (m, 1H); 1.63 (d, J=7.1 Hz, 3H); 1.02 (d, J=6.6 Hz, 6H).

EXAMPLE 194

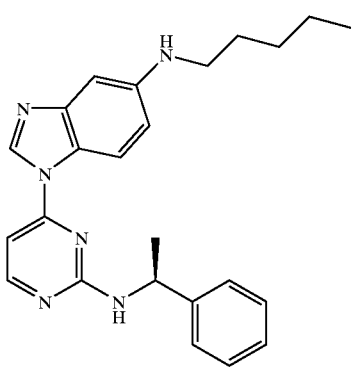

2-[(S)-1-Phenylethylamino]-4-[5-N-(1-pentyl)aminobenzimidazol-1-yl]pyrimidine

The title compound was prepared according to the general procedure described in EXAMPLE 182 using valeraldehyde. Mass spectrum (ESI): 401 (M+1). $^1$H NMR (500 MHz, CDCl$_3$): δ 8.40 (br s, 1H); 8.33 (d, J=5.5 Hz, 1H); 7.64 (br s, 1H); 7.47–7.25 (m, 5H); 6.99 (s, 1H); 6.72 (d, J=5.5 Hz, 1H); 6.64 (br d, 1H); 5.73 (br s, 1H); 5.20 (br s, 1H); 3.68 (s, 1H); 3.18 (t, J=7.3 Hz, 2H); 1.68 (m, 2H); 1.63 (d, J=6.8 Hz, 3H); 1.42 (m, 4H); 0.95 (t, J=6.7 Hz, 3H).

EXAMPLE 195

2-[(S)-1-Phenylethylamino]-4-[5-N-(3-methyl-1-butyl)aminobenzimidazol-1-yl]pyrimidine The title compound was prepared according to the general procedure described in EXAMPLE 182 using isovaleraldehyde. Mass spectrum (ESI): 401 (M+1). $^1$H NMR (500 MHz, CDCl$_3$): δ 8.40 (br s, 1H); 8.32 (d, J=5.3 Hz, 1H); 7.64 (br s, 1H); 7.47–7.25 (m, 5H); 6.99 (s, 1H); 6.71 (d, J=5.5 Hz, 1H); 6.63 (br d, 1H); 5.90 (br s, 1H); 5.20 (br s, 1H); 3.70 (br s, 1H); 3.19 (t, J=7.3 Hz, 2H); 1.76 (m, 2H); 1.63 (d, J=6.9 Hz, 3H); 1.57 (q, J=7.3 Hz, 2H); 0.97 (t, J=6.4 Hz, 6H).

EXAMPLE 196

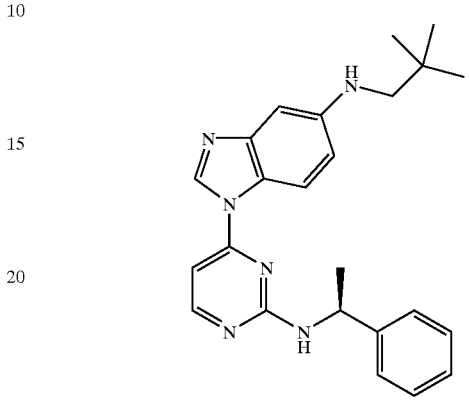

2-[(S)-1-Phenylethyl amino]-4-[5-N-(2,2-dimethyl-1-propyl)aminobenzimidazol-1-yl]pyrimidine The title compound was prepared according to the general procedure described in EXAMPLE 182 using trimethylacetaldehyde. Mass spectrum (ESI): 401 (M+1). $^1$H NMR (500 MHz, CDCl$_3$): δ 8.40 (br s, 1H); 8.32 (d, J=5.3 Hz, 1H); 7.64 (br s, 1H); 7.47–7.25 (m, 5H); 7.00 (s, 1H); 6.71 (d, J=5.5 Hz, 1H); 6.65 (br d, 1H); 5.83 (br s, 1H); 5.20 (br s, 1H); 3.76 (br s, 1H); 2.97 (s, 2H); 1.63 (d, J=7.1 Hz, 3H); 1.04 (s, 9H).

EXAMPLE 197

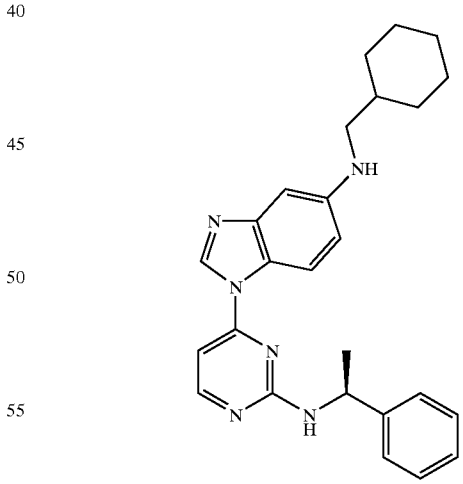

2-[(S)-1-Phenylethylamino]-4-[5-N-(cyclohexylmethyl)aminobenzimidazol-1-yl]pyrimidine The title compound was prepared according to the general procedure described in EXAMPLE 182 using cyclohexanecarboxaldehyde. Mass spectrum (ESI): 427 (M+1). $^1$H NMR (500 MHz, CDCl$_3$): δ 8.41 (br s, 1H); 8.32 (d, J=5.5 Hz, 1H); 7.63 (br s, 1H); 7.47–7.25 (m, 5H): 6.98 (s, 1H); 6.71 (d, J=5.5 Hz, 1H); 6.62 (br d, 1H); 5.90 (br s, 1H); 5.20 (br s, 1H); 3.95 (br s, 1H); 3.02 (d, J=6.6 Hz, 2H); 1.85 (m, 2H); 1.76 (m, 2H); 1.68 (m, 2H); 1.63 (d, J=6.9 Hz, 3H); 1.25 (m, 3H); 1.03 (m, 2H).

EXAMPLE 198

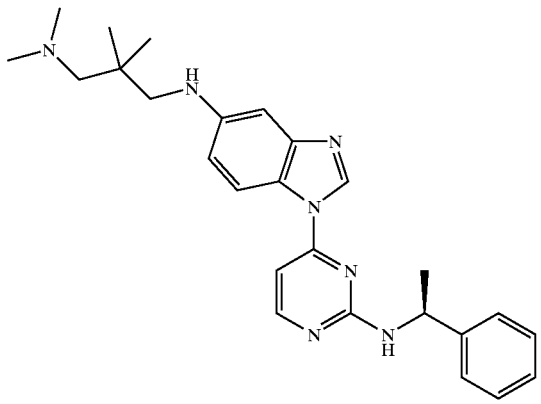

2-[(S)-1-Phenylethylamino]-4-[5-N-(2,2-dimethyl-3-N,N-dimethylaminopropyl)aminobenzimidazol-1-yl]pyrimidine The title compound was prepared according to the general procedure described in EXAMPLE 182 using 3-N,N-dimethyl-2-dimethylpropanal. Mass spectrum (ES+) 444 (M+1). $^1$H NMR (500 MHz, CDCl$_3$): δ 8.40 (br s, 1H); 8.33 (d, J=5.2 Hz, 1H); 7.68 (br s, 1H); 7.48–7.22 (m, 5H); 6.96 (s, 1H); 6.72 (d, J=5.5 Hz, 1H); 6.65 (br d, 1H); 5.74 (br s, 1H); 5.21 (br s, 1H); 3.05 (s, 2H); 2.34 (s, 6H); 2.31 (s, 2H); 1.63 (d, J=6.9 Hz, 3H); 1.05 (s, 6H).

EXAMPLE 199

2-[(S)-1-Phenylethylamino]-4-[5-N-((1-benzyloxycarbonylpyrrolidin-2-yl)methyl)-aminobenzimidazol-1-yl]pyrimidine Step A: 1-Benzyloxycarbonyl-2-pyrrolidinemethanol 2-Pyrrolidinemethanol (2 g, 20 mmol) was dissolved in CH$_2$Cl$_2$ (25 mL) followed by addition of saturated NaHCO$_3$ (25 mL). To this vigorously stirred mixture was added benzylchloroformate via syringe slowly at 0° C. The reaction mixture was then stirred at room temperature for 4 h. The organic layer was separated and the aqueous layer was extracted with CH$_2$Cl$_2$ (3×80 mL). The combined organic layer was washed with brine, and dried (Na$_2$SO$_4$). Removal of the solvent provided 4.7 g of the title compound, which was used, directly for next step. $^1$H NMR (CDCl$_3$): δ 7.50–7.30 (aromatic Hs, 5H); 5.17 (s, 2H); 4.04 (brs, 1H); 3.66 (m, 2H); 3.57 (m, 1H); 3.42 (m, 1H); 2.04 (m, 1H); 1.89 (m, 1H); 1.83 (m, 1H); 1.62 (m, 1H).

Step B: 1-Benzyloxycarbonylpyrrolidine-2-carboxaldehyde

To a mixture of 10 mL CH$_2$Cl$_2$ and 2.1 mL oxalyl chloride at −78° C. was added a solution of DMSO (1.04 mL) in CH$_2$Cl$_2$ (3 mL) dropwise over 10 min while stirring. After the mixture was stirred for 10 min, a solution of the (S)-(+)-1-benzyloxycarboxy-2-pyrrolidinemethanol (1.5 g) in CH$_2$Cl$_2$ (4 mL) was added slowly over 10 min. The reaction mixture was then stirred at −78° C. for 1.5 h followed by the addition of 4.46 mL triethylamine. After stirring at −78° C. for 30 min, the mixture was warmed up to 0° C. and then stirred for 20 min at 0° C. To the mixture was added 1 mL of MeOH followed by addition of 8 mL of water. The aquous layer was separated and extracted with CH$_2$Cl$_2$ (3×60 mL). The combined organic layer was washed with NaHCO$_3$, H$_2$O and brine, successively, and dried (Na$_2$SO$_4$). Removal of the solvent provided 1.5 g of the title compound which was used directly for next step.

Step C: 2-[(S)-1-Phenylethylamino]-4-[5-N-((1-benzyloxy-carbonylpyrrolidin-2-yl)methyl)aminobenzimidazol-1-yl]pyrimidine The title compound was prepared according to the general procedure described in EXAMPLE 182 using 1-benzyloxycarbonyl-pyrrolidine-2-carboxaldehyde. Mass spectrum (ES+) 548 (M+1). $^1$H NMR (500 MHz, CDCl$_3$): δ8.40 (br s, 1H); 8.32 (br d, 1H); 7.66 (br s, 1H); 7.50–7.25 (m, 10H); 6.96 (s, 1H); 6.72 (br d, 3H); 5.86 (br s, 1H); 5.26 (br s, 1H); 5.20 (s, 2H); 4.30 (br s, 1H); 3.48 (m, 2H); 3.34 (br t, 1H); 3.23 (m, 1H); 3.15 (br s, 1H); 2.60 (m, 1H); 1.80 (m, 1H); 1.92 (m, 2H); 1.64 (d, J=6.8 Hz, 3H).

EXAMPLE 200

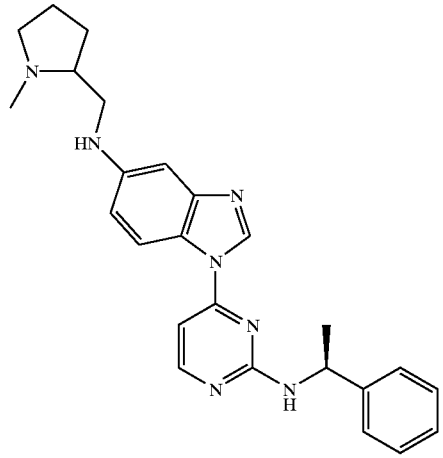

2-[(S)-1-Phenylethylamino]-4-[5-N-((1-methylpyrrolidin-2-yl)methyl)aminobenzimidazol-1-yl]pyrimidine Step A: N-Methylpyrrolidin-2-carboxaldehyde The title compound was prepared from 1-methy-2-pyrrolidinemethanol according to the procedure described in EXAMPLE 199, Step B.

Step B: 2-[(S)-1-Phenylethylamino]-4-[5-N-((1-methylpyrrolidin-2-yl)methyl)-aminobenzimidazol-1-yl]pyrimidine The title compound was prepared according to the general procedure described in EXAMPLE 182 using N-methylpyrrolidin-2-carboxaldehyde. Mass spectrum (ES+) 428 (M+1). $^1$H NMR (500 MHz, CDCl$_3$): δ 8.40 (br s, 1H); 8.35 (d, J=5.5 Hz, 1H); 7.63 (br s, 1H); 7.47–7.25 (m, 5H); 6.98 (s, 1H); 6.73 (d, J=5.4 Hz, 1H); 6.68 (br d, 1H); 5.63 (br s, 1H); 5.20 (br s, 1H); 4.23 (br s, 1H); 3.30 (br s, 1H); 3.18 (br d, 1H); 2.54 (br s, 1H); 2.39 (s, 2H); 2.30 (br s, 1H); 1.98 (br s, 1H); 1.84 (m, 1H); 1.77 (m, 1H); 1.64 (d, J=6.8 Hz, 3H).

EXAMPLE 201

2-[(S)-1-Phenylethylamino]-4-[5-N-((1-benzyloxycarbonylpiperidin-2-yl)methyl)-aminobenzimidazol-1-yl]pyrimidine

Step A: 1-Benzyloxycarbonyl-2-piperidinemethanol

The title compound was prepared from 2-piperidinemethanol according to the procedure described in EXAMPLE 199, Step A.

Step B: 1-Benzyloxycarbonylpiperidine-2-carboxaldehyde

The title compound was prepared from 1-Benzyloxycarboxy-2-piperidinemethanol according to the procedure described in EXAMPLE 199, Step B.

Step C: 2-[(S)-1-Phenylethylamino]-4-[5-N-((1-benzyloxy-arbonylpiperidin-2-yl)methyl)-aminobenzimidazol-1-yl]pyrimidine The title compound was prepared according to the general procedure described in EXAMPLE 182 using 1-Benzyloxycarboxypyrrolidine-2-carboxaldehyde. $^1$H NMR (500 MHz, CDCl$_3$): δ 8.40 (br s, 1H); 8.34 (d, J=5.2 Hz, 1H); 7.6 (br s, 1H); 7.50–7.22 (m, 10H); 6.94 (s, 1H); 6.72 (d, J=5.2 Hz, 1H); 6.52 (br s, 1H); 5.78 (br s, 1H); 5.20 (br s, 1H); 5.15 (s, 2H); 4.67 (br s, 1H); 4.12 (br s, 1H); 3.57 (br t, 1H); 3.18 (m, 1H); 2.92 (br t, 1H); 1.78 (br s, 1H); 1.70 (m, 2H); 1.64 (d, J=6.8 Hz, 3H); 1.50 (m, 1H); 1.30 (m, 1H);

EXAMPLE 202

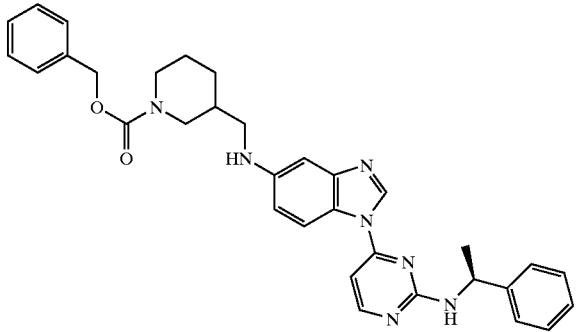

2-[(S)-1-Phenylethylamino]-4-[5-N-((1-benzyloxycarbonylpiperidin-3-yl)methyl)-aminobenzimidazol-1-yl]pyrimidine

Step A: 1-Benzyloxycarbonyl-3-piperidinemethanol

The title compound was prepared from 3-piperidinemethanol according to the procedure described in EXAMPLE 199, Step A.

Step B: 1-Benzyloxycarbonylpiperidine-3-carboxaldehyde

The title compound was prepared from 1-Benzyloxycarboxy-3-piperidinemethanol according to the procedure described in EXAMPLE 199, Step B.

Step C: 2-[(S)-1-Phenylethylamino]4-[5-N-((1-benzyloxy-carbonylpiperidin-3-yl)methyl)-aminobenzimidazol-1-yl]pyrimidine The title compound was prepared according to the general procedure described in EXAMPLE 182 using 1-Benzyloxycarbonylpiperidine-3-carboxaldehyde. Mass spectrum (API-ES) 562 (M+1). $^1$H NMR (500 MHz, CDCl$_3$): δ 8.40 (br s, 1H); 8.35 (d, J=5.5 Hz, 1H); 7.62 (br s, 1H); 7.47–7.25 (m, 10H); 6.95 (s, 1H); 6.72 (d, J=5.5 Hz, 1H); 6.60 (br d, 1H); 5.64 (br s, 1H); 5.20 (br s, 1H); 5.16 (s, 2H); 4.08 (br s, 1H); 3.95 (br s, 1H); 3.90 (td, 1H); 3.10 (d, J=6.9 Hz, 2H); 3.06 (br s, 1H); 2.90 (br s, 1H); 1.94 (m, 2H); 1.72 (br s, 1H); 1.64 (d, J=6.8 Hz, 3H); 1.52 (br s, 1H); 1.35 (m, 1H).

EXAMPLE 203

2-[(S)-1-Phenylethylamino]-4-[5-N-((4-benzyloxycarbonylmorpholin-2-yl)methyl)-aminobenzimidazol-1-yl]pyrimidine

Step A: Methyl 4-fluorenyloxycarbonyl-morpholine-2-carboxylate

To a solution of 3.00 g of 4-fluorenyloxycarbonyl-morpholine-2-carboxylic acid in 150 mL of acetone was added 1.77 g of potassium carbonate and 1.33 g of dimethyl sulfate. The mixture was heated to reflux and stirred at this temperature for 6 h, then cooled, filtered, and concentrated. The residue was dissolved in 125 mL of Et$_2$O and washed with 50 mL each of saturated NaHCO$_3$, water, and brine. The organic phase was dried over MgSO$_4$ and concentrated to yield 3.10 g of the title compound, which was used without further purification.

Step B: 4-Fluorenyloxycarbonyl-2-hydroxymethylmorpholine

To a solution of 3.56 g of methyl 4-fluorenyloxycarbonylmorpholine-2-carboxylate in 25 mL of THF was added 0.58 g of lithium chloride, 0.52 g of sodium borohydride, and 25 mL of ethanol. The mixture was stirred overnight at room temperature, concentrated, and redissolved in 200 mL of CH$_2$Cl$_2$. This CH$_2$Cl$_2$ solution was washed with 2×100 mL of water and 100 mL of brine, dried over MgSO$_4$, and concentrated. The residue was purified by flash chromatography, eluting with 1:1 hexanes-EtOAc, to yield 2.34 g of the title compound as a colorless oil.

Step C: 4-Benzyloxycarbonyl-2-hydroxymethylmorpholine

To a solution of 2.20 g of 4-fluorenyloxycarbonyl-2-hydroxymethyl morpholine in 25 mL of CH$_2$Cl$_2$ was added 1.29 g of piperidine. The mixture was stirred at room temperature for 2 days. Diisopropylethylamine (7.15 g) and 6.30 g of benzyl chloroformate were added and the mixture was stirred overnight at room temperature, then diluted with 100 mL of EtOAc and washed with 50 mL each of 1 N HCl, saturated NaHCO$_3$, and brine, dried over MgSO$_4$, and concentrated. The residue was purified by flash chromatography, eluting with a gradient system of 20:1 CH$_2$Cl$_2$-acetone to 9:1 CH$_2$Cl$_2$-acetone, to yield 638 mg of the title compound.

Step D: 4-Benzyloxycarbonyl-morpholine-2-carboxaldehyde

The title compound was prepared from 4-Benzyloxycarbonyl-2-hydroxymethylmorpholine according to the procedure described in EXAMPLE 199, Step B.

Step E: 2-[(S)-1-Phenylethylamino]-4-[5-N-((4-benzyloxy-carbonylmorpholin-2-yl)methyl)-aminobenzimidazol-1-yl]pyrimidine The title compound was prepared according to the general procedure described in EXAMPLE 182 using 4-Benzyloxycarbonyl-morpholine-2-carboxaldehyde. Mass spectrum (ES+) 564 (M+1). $^1$H NMR (500 MHz, CDCl$_3$): δ8.41 (br s, 1H); 8.34 (d, J=5.2 Hz, 1H); 7.64 (br s, 1H); 7.47–7.25 (m, 10H); 7.00 (s, 1H); 6.73 (d, J=5.2 Hz, 1H); 6.66 (br s, 1H); 5.82 (br s, 1H); 5.20 (m, 3H); 4.15 (br s, 1H); 3.98 (br s, 2H); 3.73 (br s, 1H); 3.60 (br s, 1H); 3.32 (br d, 1H); 3.20 (br s, 1H); 3.10 (br s, 1H); 2.90 (br s, 1H); 1.64 (d, J=6.8 Hz, 3H).

EXAMPLE 204

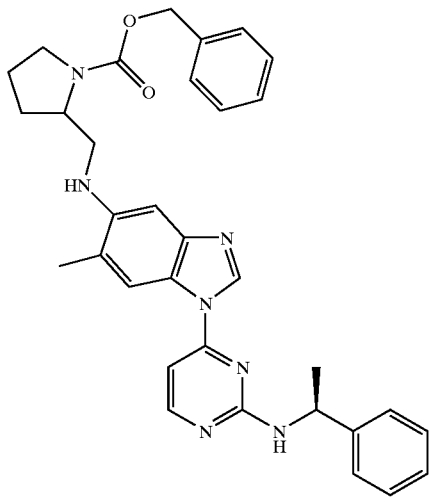

2-[(S)-1-Phenylethylamino]-4-[5-N-((1-benzyloxycarbonylpyrrolidin-2-yl)methyl)-amino-6-methylbenzimidazol-1-yl]pyrimidine The title compound was prepared according to the general procedure described in EXAMPLE 182 using 2-[(S)-1-phenylethylamino]-4-[5-amino-6-methylbenzimidazol-1-yl]pyrimidine and 1-benzyloxycarbonylpyrrolidine-2-carboxaldehyde. $^1$H NMR (500 MHz, CDCl$_3$): δ 8.40 (br s, 1H); 8.34 (d, J=5.3 Hz, 1H); 7.72 (br s, 1H); 7.48–7.25 (m, 10H); 6.89 (s, 1H); 6.76 (d, J=5.5 Hz, 1H); 5.81 (br s, 1H); 5.26 (t, 1H); 5.20 (s, 2H); 4.42 (br s, 1H); 3.56 (m, 1H); 3.50 (m, 1H); 3.25 (s, 2H); 2.27 (s, 3H); 2.12 (br s, 1H); 2.2 (m, 1H); 1.96 (br s, 1H); 1.87 (br s, 1H); 1.78 (br s, 1H); 1.65 (d, J=6.8 Hz, 3H).

EXAMPLE 205

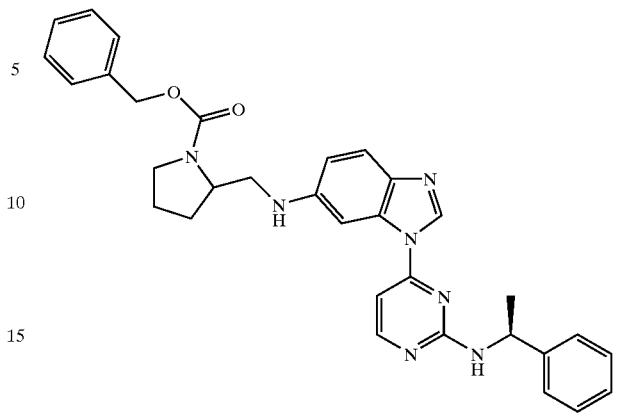

2-[(S)-1-Phenylethylamino]-4-[6-N-((1-benzyloxycarbonylpyrrolidin-2-yl)methyl)-aminobenzimidazol-1-yl]pyrimidine The title compound was prepared according to the general procedure described in EXAMPLE 182 using 2-[(S)-1-phenylethylamino]-4-[6-amino-benzimidazol-1-yl]pyrimidine and 1-benzyloxy-carbonylpyrrolidine-2-carboxaldehyde. Mass spectrum (API-ES) 548 (M+1). $^1$H NMR (500 MHz, CDCl$_3$): δ 8.34 (s, 2H); 7.58 (d, J=8.0 Hz, 1H); 7.50–7.22 (m, 10H); 6.91 (s, 1H); 6.69 (br d, J=8.5 Hz, 1H); 6.21 (br s, 1H); 5.26 (br s, 1H); 5.15 (s, 2H); 4.30 (br s, 1H); 3.58 (br s, 1H); 3.48 (s, 2H); 3.15 (m, 1H); 2.00 (m, 1H); 1.92 (m, 2H); 1.82 (br s, 1H); 1.65 (d, J=6.0 Hz, 3H).

EXAMPLE 206

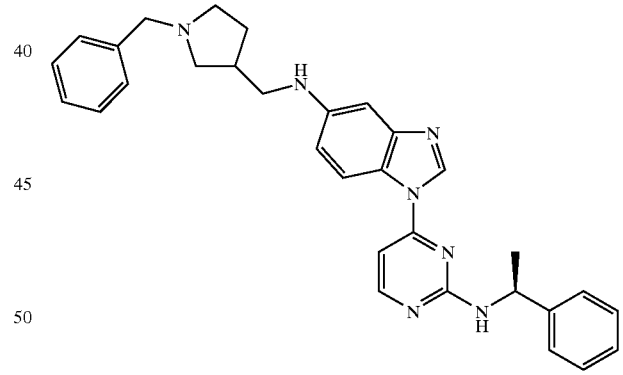

2-[(S)-1-Phenylethylamino]4-[5-N-((1-benzylpyrrolidin-3-yl)methyl)amino-benzimidazol-1-yl]pyrimidine

Step A: 1-Benzyl-3-hydroxymethylpyrrolidine

To a suspension of 0.50 g of lithium aluminum hydride in 35 mL of THF at 0° C. was added (dropwise via cannula) a solution of 2.00 g of methyl 1-benzyl-5-oxo-3-pyrrolidinecarboxylate in 10 mL of THF. The cooling bath was removed and the mixture was stirred for 2.5 h at room temperature. The mixture was recooled to 0° C. and quenched by careful, sequential addition of 0.5 mL of water, 0.5 mL of 15% aqueous NaOH, and 1.5 mL of water. The mixture was stirred at room temperature for 1 h, at which point all solids were white, then filtered. The solids were washed thoroughly with Et₂O, and the filtrate was dried over MgSO₄ and concentrated to give 1.61 g of the title compound as a colorless oil.

Step B: 1-Benzyl-pyrrolidine-3-carboxaldehyde

The title compound was prepared from 1-Benzyl-3-hydroxymethylpyrrolidine according to the procedure described in EXAMPLE 199, Step B.

Step C: 2-[(S)-1-Phenylethylamino]-4-[5-N-((1-benzylpyrrolidin-3-yl)methyl)-aminobenzimidazol-1-yl]pyrimidine The title compound was prepared according to the general procedure described in EXAMPLE 182 using 1-Benzyl-pyrrolidine-3-carboxaldehyde. Mass spectrum (ES+) 504 (M+1). 1H NMR (500 MHz, CDCl₃): δ 8.40 (br s, 1H); 8.34 (d, J=5.5 Hz, 1H); 7.62 (br s, 1H); 7.47–7.25 (m, 10H); 6.95 (s, 1H); 6.72 (d, J=5.5 Hz, 1H); 6.62 (br d, 1H); 5.70 (br s, 1H); 5.20 (s, 3H); 4.22 (br s, 1H); 3.66 (s, 2H); 3.17 (d, J=5.9 Hz, 2H); 2.77 (m, 1H); 2.70 (t, 1H); 2.57 (m, 1H); 1.52 (m, 2H); 2.10 (m, 1H); 1.89 (m, 1H); 1.64 (d, J=7.1 Hz, 3H).

EXAMPLE 207

2-[(S)-1-Phenylethylamino]-4-[5-N-((1-benzyloxycarbonyl-4-tert-butyloxycarbonyl-piperazin-2-yl)methyl)-aminobenzimidazol-1-yl]pyrimidine Step A: Methyl 1-(benzyloxycarbonyl)-4-(tert-butyloxycarbonyl)piperazine-2-carboxylate To a solution of 3.00 g of piperazine-2-carboxylic acid in 100 mL of 1:1 dioxane-water at pH 11 was added dropwise a solution of 4.0 g of 2-(tert-butyloxycarbonyloxyimino)-2-phenylacetonitrile in 25 mL of dioxane, maintaining the pH of the solution at 11 during the addition with the use of 5 N NaOH. The mixture was stirred for 6 h at room temperature, then cooled to 0° C. The pH was adjusted to 9.5 with the use of 1 N HCl. Benzyl chloroformate (2.8 g) was added dropwise, maintaining the pH of the solution at 9.5 during the addition with the use of 5 N NaOH. The mixture was allowed to warm to room temperature and stirred for 20 h, then extracted with 2×75 mL of Et₂O, acidified to pH≦2 with 1 N HCl, and extracted with 4×50 mL of EtOAc. The combined EtOAc extracts were washed with 50 mL of brine, dried over MgSO₄, and concentrated to a pale yellow oil. This oil was dissolved in 150 mL of acetone. Dimethyl sulfate (2.25 g) and potassium carbonate (2.89 g) were added. The mixture was heated to reflux and stirred at this temperature for 6 h, then cooled, filtered, and concentrated. The residue was dissolved in 125 mL of Et₂O and washed with 50 mL each of saturated NaHCO₃, water, and brine. The organic phase was dried over MgSO₄ and concentrated to yield 6.06 g of the title compound, which was used without further purification.

Step B: 1-(Benzyloxycarbonyl)-4-(tert-butyloxycarbonyl)-2-hydroxymethylpiperazine To a solution of 5.32 g of methyl 1-(benzyloxycarbonyl)-4-(tert-butyloxycarbonyl)piperazine-2-carboxylate in 30 mL of THF was added 834 mg of lithium chloride, 744 mg of sodium borohydride, and 30 mL of ethanol. The mixture was stirred overnight at room temperature, concentrated, and redissolved in 200 mL of CH₂Cl₂. This CH₂Cl₂ solution was washed with 100 mL of water and 100 mL of brine, dried over MgSO₄, and concentrated. The residue was purified by flash chromatography, eluting with a gradient system of 2:1 hexanes-EtOAc to 1:1 hexanes-EtOAc, to yield 2.65 g of the title compound as a colorless oil.

Step C: 1-(Benzyloxycarbonyl)-4-(tert-butyloxycarbonyl)piperazine-2-carboxaldehyde The title compound was prepared from 1-(benzyloxy-carbonyl)-4-(tert-butyloxycarbonyl)-2-hydroxymethylpiperazine according to the procedure described in EXAMPLE 199, Step B.

Step D: 2-[(S)-1-Phenylethylamino]-4-[5-N-((1-benzyloxycarbonyl-4-tert-butyloxycarbonyl-piperazin-2-yl)methyl)aminobenzimidazol-1-yl] pyrimidine The title compound was prepared according to the general procedure described in EXAMPLE 182 using 1-(benzyloxycarbonyl)-4-(tert-butyloxycarbonyl) piperazine-2-carboxaldehyde. ¹H NMR (500 MHz, CDCl₃): δ 8.41 (br s, 1H); 8.35 (d, J=5.3 Hz, 1H); 7.60 (br s, 1H); 7.47–7.25 (m, 10H); 7.00 (br s, 1H); 6.71 (d, J=5.5 Hz, 1H); 6.54 (br s, 1H); 5.78 (br s, 1H); 5.20 (s, 3H); 4.50 (br s, 1H); 4.20 (br s, 2H); 4.00 (br s, 2H); 3.42 (br s, 1H); 3.22 (m, 1H); 3.10 (br s, 1H); 2.92 (br s, 1H); 1.80 (br s, 1H); 1.64 (d, J=6.8 Hz, 3H); 1.52 (s, 9H).

EXAMPLE 208

General Hydrogenation Procedure for Hydrogenolysis of the Benzyloxycarbonyl Protecting Group To a solution of a benzyloxycarbonyl-protected amine in MeOH is added Pd(OH)₂ on carbon. The flask is evacuated and charged with hydrogen three times, and then stirred under hydrogen at room temperature for 5 h. The catalyst is filtered. Removal of the solvent and subsequent purification by preparative thin layer chromatography (10% of 2N NH₃ in MeOH/CH₂Cl₂) provides the desired amines.

EXAMPLE 209

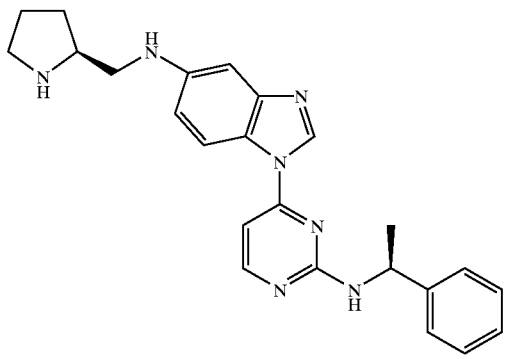

2-[(S)-1-Phenylethylamino]-4-[5-N-((pyrrolidin-2-yl)methyl)aminobenzimidazol-1-yl]pyrimidine The title compound was prepared from 2-[(S)-1-phenylethylamino]-4-[5-N-((1-benzyloxycarbonylpyrrolidin-2-yl)methyl)-aminobenzimidazol-1-yl]-pyrimidine according to the general procedure described in EXAMPLE 208. Mass spectrum (ESI): 414 (M+1). ¹H NMR (500 MHz, CDCl₃): δ 8.38

(s, 1H); 8.32 (d, J=5.3 Hz, 1H); 7.62 (br s, 1H); 7.47–7.24 (m, 5H); 6.99 (s, 1H); 6.69 (d, J=5.5 Hz, 1H); 6.66 (br s, 1H); 5.82 (br s, 1H); 5.20 (br s, 1H); 4.32 (br s, 1H); 3.49 (m, 1H); 3.26 (m, 1H); 3.04 (m, 1H); 2.98 (m, 2H); 2.48 (br s, 1H); 1.98 (m, 1H); 1.86 (m, 1H); 1.76 (m, 1H); 1.63 (d, J=6.8 Hz, 3H); 1.53 (m, 1H).

EXAMPLE 210

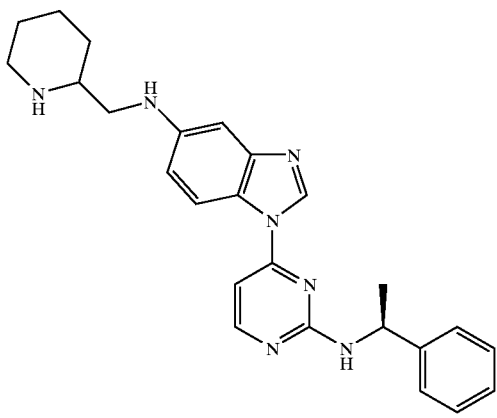

2-[(S)-1-Phenylethylamino]-4-[5-N-((piperidin-2-yl)methyl)aminobenzimidazol-1-yl]pyrimidine The title compound was prepared from 2-[(S)-1-phenylethylamino]-4-[5-N-((1-benzyloxycarbonylpiperidin-2-yl)methyl)-aminobenzimidazol-1-yl]-pyrimidine according to the general procedure described in EXAMPLE 208. Mass spectrum (ESI): 428 (M+1). $^1$H NMR (500 MHz, CDCl$_3$): δ 8.39 (br s, 1H); 8.34 (d, J=5.5 Hz, 1H); 7.60 (br s, 1H); 7.47–7.25 (m, 5H); 6.99 (d, J=1.6 Hz, 1H); 6.71 (d, J=5.5 Hz, 1H); 6.66 (br s, 1H); 5.65 (br s, 1H); 5.20 (s, 1H); 4.20 (br s, 1H); 3.25 (br d, 1H); 3.13 (m, 2H); 2.90 (m, 1H); 2.67 (dt, 1H); 1.88 (br d, 1H); 1.76 (br d, 1H); 1.68 (br t, 1H); 1.64 (d, J=6.8 Hz, 3H); 1.46 (m, 2H); 1.32 (m, 1H).

EXAMPLE 211

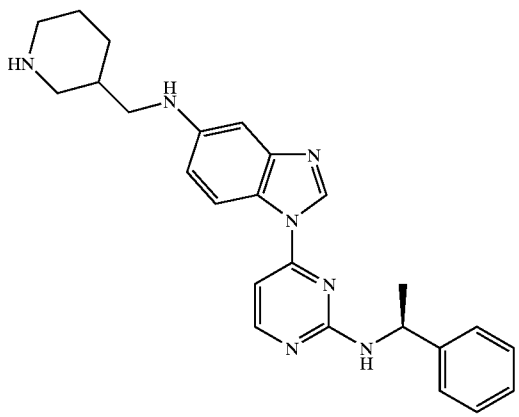

2-[(S)-1-Phenylethylamino]-4-[5-N-((piperidin-3-yl)methyl)aminobenzimidazol-1-yl]pyrimidine The title compound was prepared from 2-[(S)-1-phenylethylamino]-4-[5-N-((1-benzyloxycarbonylpiperidin-3-yl)methyl)-aminobenzimidazol-1-yl]-pyrimidine according to the general procedure described in EXAMPLE 208. Mass spectrum (API-ES) 428 (M+1). $^1$H NMR (500 MHz, CDCL$_3$): δ 8.38 (br s, 1H); 8.32 (d, J=5.3 Hz, 1H); 7.60 (br s, 1H); 7.47–7.25 (m, 5H); 6.95 (s, 1H); 6.68 (d, J=5.5 Hz, 1H); 6.63 (br d, J=7.3 Hz, 1H); 5.77 (s, 1H); 5.20 (br s, 1H); 4.08 (br s, 1H); 3.94 (s, 1H); 3.36 (d, J=12.1 Hz, 1H); 3.16 (d, J=11.9 Hz, 1H); 3.06 (d, J=5.7 Hz, 2H); 2.69 (dt, J$_1$=2.7 Hz, J$_2$=11.8 Hz, 1H); 2.52 (t, J=11.3 Hz, 1H); 2.02 (m, 1H); 1.95 (br d, J=13.5 Hz, 1H); 1.78 (td, 1H); 1.67 (m, 1H); 1.63 (d, J=6.9 Hz, 3H); 1.23 (m, 1H).

EXAMPLE 212

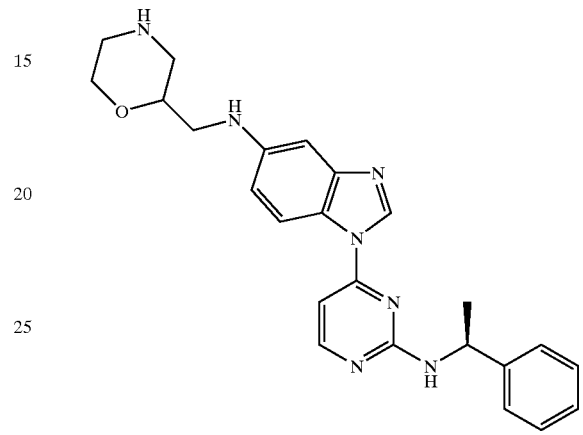

2-[(S)-1-Phenylethylamino]-4-[5-N-((morpholin-2-yl)methyl)aminobenzimidazol-1-yl]pyrimidine The title compound was prepared from 2-[(S)-1-phenylethylamino]-4-[5-N-((4-benzyloxycarbonylmorpholin-2-yl)methyl)-aminobenzimidazol-1-yl]-pyrimidine according to the general procedure described in EXAMPLE 208. Mass spectrum (ES+) 430 (M+1). $^1$H NMR (500 MHz, CDCl$_3$): δ 8.40 (br s, 1H); 8.35 (d, J=5.5 Hz, 1H); 7.62 (br s, 1H); 7.47–7.25 (m, 5H); 6.99 (s, 1H); 6.73 (d, J=5.5 Hz, 1H); 6.65 (br s, 1H); 5.64 (br s, 1H); 5.20 (br s, 1H); 4.11 (br s, 1H); 3.95 (d, J=11.5 Hz, 1H); 3.79 (m, 1H); 3.68 (dt, J$_1$=2.8 Hz, J$_2$=11.5 Hz, 1H); 3.26 (br d, 1H); 3.16 (m, 1H); 3.02 (d, J=11.3 Hz, 1H); 2.90 (m, 2H); 2.77 (t, J=11.2 Hz, 1H); 1.85 (br s, 1H); 1.64 (d, J=6.8 Hz, 3H).

EXAMPLE 213

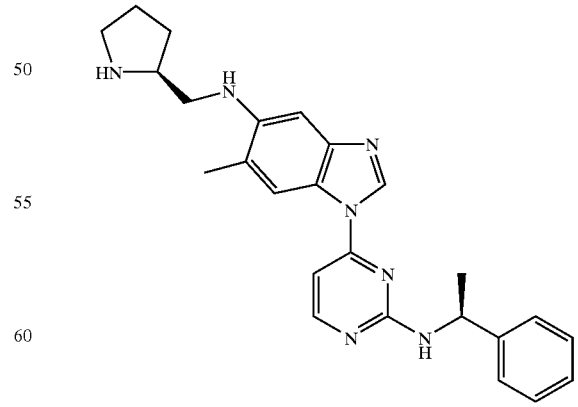

2-[(S)-1-Phenylethylamino]-4-[5-N-((pyrrolidin-2-yl)methyl)-amino-6-methyl-benzimidazol-1-yl]pyrimidine The title compound was prepared from 2-[(S)-1-phenylethylamino]-4-[5-N-((1-benzyloxycarbonylpyrrolidin-2-yl)methyl)-amino-6-methyl-benzimidazol-1-yl]pyrimidine according to the general procedure described in EXAMPLE 208. Mass spectrum (ESI): 428 (M+1). ¹H NMR (500 MHz, CDCl₃): δ 8.36 (s, 1H); 8.34 (d, J=5.0 Hz, 1H); 7.72 (br s, 1H); 7.47–7.24 (m, 5H); 6.98 (s, 1H); 6.73 (dd, J₁=2.5 Hz, J₂=5.5 Hz, 1H); 5.60 (br s, 1H); 5.25 (br t, 1H); 4.20 (br s, 1H); 3.61 (br s, 1H); 3.34 (br d, 1H); 3.14 (br t, 1H); 3.03 (t, J=6.6 Hz, 1H); 2.30 (s, 3H); 2.03 (m, 1H); 1.90 (m, 1H); 1.80 (m, 2H); 1.65 (d, J=6.9 Hz, 3H); 1.60 (m, 1H).

EXAMPLE 214

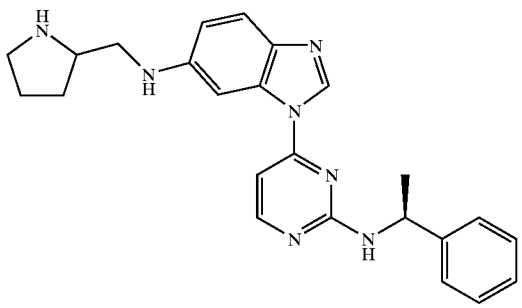

2-[(S)-1-Phenylethylamino]-4-[6-N-((pyrrolidin-2-yl)methyl)-aminobenzimidazol-1-yl]pyrimidine The title compound was prepared from 2-[(S)-1-phenylethylamino]-4-[6-N-((1-benzyloxycarbonylpyrrolidin-2-yl)methyl)-aminobenzimidazol-1-yl]-pyrimidine according to the general procedure described in EXAMPLE 208. Mass spectrum (API-ES) 414 (M+1). ¹H NMR (500 MHz, CDCl₃): δ 8.33 (d, J=5.7 Hz, 1H); 8.28 (s, 1H); 7.55 (d, J=8.5 Hz, 1H); 7.50–7.22 (m, 5H); 7.29 (d, J=8.7 Hz, 3H); 5.72 (br s, 1H); 5.27 (br t, 1H); 4.42 (br s, 1H); 3.52 (br s, 1H); 3.10 (br s, 1H); 3.00 (m, 2H); 1.96 (br s, 1H); 1.86 (br s, 1H); 1.78 (br s, 1H); 1.66 (d, J=6.9 Hz, 3H); 1.54 (br s, 1H).

EXAMPLE 215

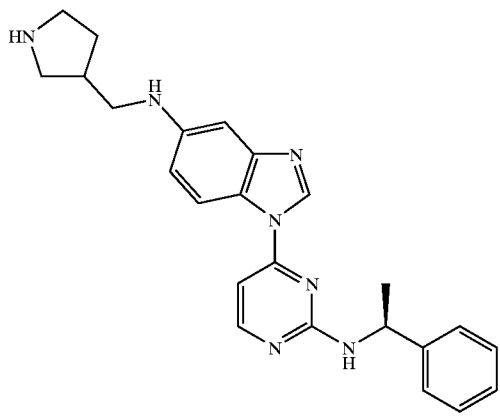

2-[(S)-1-Phenylethylamino]-4-[5-N-((pyrrolidin-3-yl)methyl)aminobenzimidazol-1-yl]pyrimidine To a solution of 2-[(S)-1-phenylethylamino]-4-[5-N-((N-benzyl-pyrrolidin-3-yl)methyl)-aminobenzimidazol-1-yl]pyrimidine (36 mg) in methanol (1 mL) was added 5 eq. ammonium formate (23 mg) followed by palladium hydroxide on carbon (40 mg). The reaction was heated to reflux for one hour and filtered through celite. Removal of the solvent and subsequent purification by preparative thin layer chromatography (10% of 2N NH₃ in MeOH/CH₂Cl₂) provided the title compound (9 mg). Mass spectrum (ES+) 414 (M+1). ¹H NMR (500 MHz, CDCl₃): δ8.40 (s, 1H); 8.33 (d, J=5.5 Hz, 1H); 7.63 (br d, 1H); 7.50–7.22 (m, 5H); 6.98 (s, 1H);6.72 (d, J=5.5 Hz, 1H); 6.64 (s, 1H); 5.72 (br s, 1H); 5.20 (br s, 1H); 3.90 (br s, 1H); 3.18 (m, 3H); 3.10 (m, 1H); 3.00 (m, 2H); 2.81 (m, 1H); 2.50 (m, 1H); 2.25 (m, 1H); 1.64 (d, J=6.8 Hz, 3H); 1.59 (m, 1H).

EXAMPLE 216

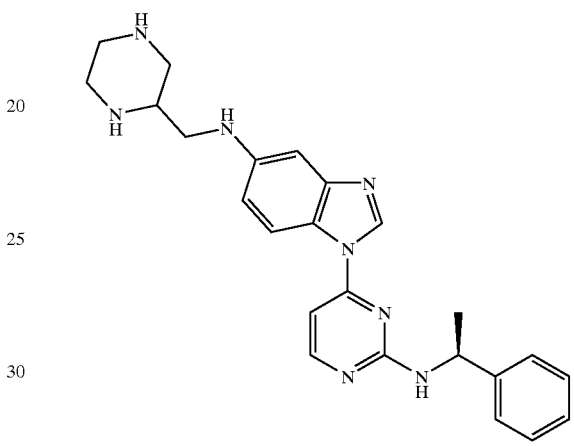

2-[(S)-1-Phenylethylamino]-4-[5-N-((piperazin-2-yl)methyl)aminobenzimidazol-1-yl]pyrimidine Step A: 2-[(S)-1-phenylethylamino]-4-[5-N-((1-benzyloxycarbonylpiperazin-2-yl)methyl)aminobenzimidazol-1-yl]pyrimidine To a solution of 2-[(S)-1-phenylethylamino]-4-[5-N-((1-benzyloxy-carbonyl-4-tert-butyloxycarbonyl-piperazin-2-yl)methyl)-aminobenzimidazol-1-yl]pyrimidine (130 mg) in methylene chloride (2 mL) at 0° C. was added trifluoroacetic acid (0.6 mL) dropwise. The reaction was stirred at room temperature for 45 min, and the solvent was removed. The residue was treated with 1N NaOH to pH about 11 and extracted with methylene chloride three times. The organic layer was washed with brine and dried over sodium sulfate. Removal of the solvent and subsequent purification by preparative thin layer chromatography (10% 2N NH₃ in MeOH/CH₂Cl₂) afforded the title compound (87 mg).

Step B: 2-[(S)-1-Phenylethylamino]-4-[5-N-((piperazin-2-yl)methyl)-aminobenzimidazol-1-yl] pyrimidine 2-[(S)-1-phenylethylamino]-4-[5-N-((1-benzyloxycarbonylpiperazin-2-yl)methyl)-aminobenzimidazol-1-yl]pyrimidine (30 mg) was deprotected via hydrogenolysis according to the procedure outlined in EXAMPLE 208 providing the title compound (24 mg). Mass spectrum (ES+) 429 (M+1). ¹H NMR (500 MHz, CDCl₃): δ 8.40 (s, 1H); 8.34 (d, J=5.5 Hz, 1H); 7.62 (br s, 1H); 7.47–7.25 (m, 5H); 6.95 (s, 1H); 6.72 (d, J=5.5 Hz, 1H); 6.66 (s, 1H); 5.62 (br s, 1H); 5.20 (br s, 1H); 4.07 (br s, 1H); 3.22 (m, 1H); 3.10 (m, 1H); 3.05 (m, 2H); 2.98

(m, 1H); 2.87 (dt, 1H); 2.80 (dt, 1H); 2.62 (t, 1H); 1.90 (br s, 2H); 1.64 (d, J=6.8 Hz, 3H).

EXAMPLE 217

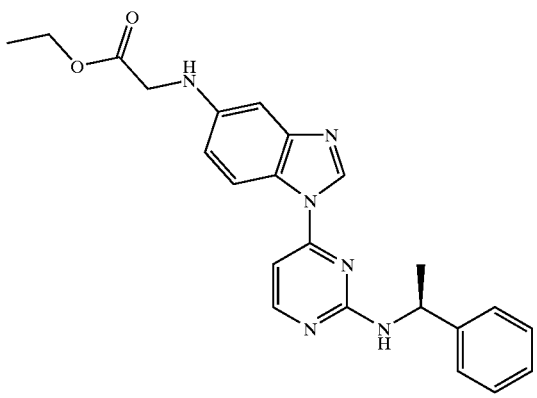

2-[(S)-1-Phenylethylamino]-4-[5-N-((ethoxycarbonyl)methyl)aminobenzimidazol-1-yl]pyrimidine To a mixture of 2-[(S)-1-phenylethylamino]4-[5-aminobenzimidazol-1-yl]pyrimidine (EXAMPLE 79) (80 mg) and 1.5 eq of ethyl bromoacetate (30 μL) in dry ethanol (2 mL) was added 2 eq. freshly dried sodium acetate (39 mg). The reaction was stirred at reflux for 6 h. Removal of the solvent and subsequent purification by preparative thin layer chromatography (acetone:hexane=2:1) provided the title product (40 mg). Mass spectrum (ESI): 417 (M+1). $^1$H NMR (500 MHz, CDCl$_3$): δ 8.40 (br s, 1H); 8.34 (d, J=5.5 Hz, 1H); 7.63 (br s, 1H); 7.47–7.25 (m, 5H); 6.95 (s, 1H); 6.73 (d, J=5.7 Hz, 1H); 6.70 (br s, 1H); 5.88 (br s, 1H); 5.20 (br s, 1H); 4.38 (br s, 1H); 4.28 (q, J=7.2 Hz, 2H); 3.98 (s, 2H); 1.64 (d, J=6.8 Hz, 3H); 1.33 (t, J=7.3 Hz, 3H).

EXAMPLE 218

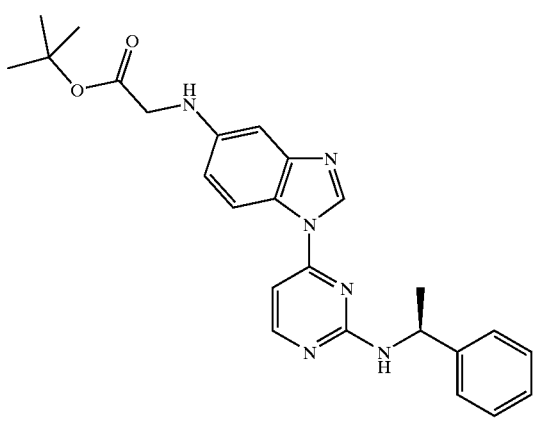

2-[(S)-1-Phenylethylamino]-4-[5-N-((tert-butyloxycarbonyl)methyl)amino-benzimidazol-1-yl]pyrimidine The title compound was prepared according to the procedure described in EXAMPLE 217 using t-butyl bromoacetate instead of ethyl bromoacetate. Mass spectrum (ESI): 445 (M+1). $^1$H NMR (500 MHz, CDCl$_3$): δ 8.40 (br s, 1H); 8.34 (d, J=5.5 Hz, 1H); 7.63 (br s, 1H); 7.47–7.25 (m, 5H); 6.93 (s, 1H); 6.72 (d, J=5.5 Hz, 1H); 6.68 (br s, 1H); 5.85 (br s, 1H); 5.20 (br s, 1H); 4.38 (br s, 1H); 3.88 (s, 2H); 1.63 (d, J=6.8 Hz, 3H); 1.52 (s, 9H).

EXAMPLE 219

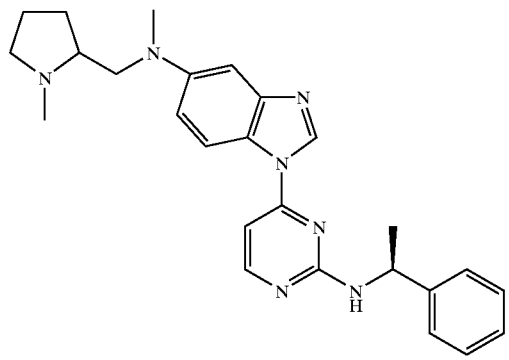

2-[(S)-1-Phenylethylamino]-4-[5- N-methyl-N-((1-methylpyrrolidin-2-yl)methyl))-aminobenzimidazol-1-yl]pyrimidine The title compound was prepared from 2-[(S)-1-phenylethylamino]-4-[5-N-((1-methylpyrrolidin-2-yl)methyl)-aminobenzimidazol-1-yl]pyrimidine and formaldehyde according to the general procedure described in EXAMPLE 182. Mass spectrum (API-ES) 442 (M+1). $^1$H NMR (500 MHz, CDCl$_3$): δ 8.42 (br s, 1H); 8.34 (d, J=5.5 Hz, 1H); 7.72 (br s, 1H); 7.47–7.25 (m, 5H); 7.10 (s, 1H); 6.84 (br s, 1H); 6.74 (d, J=5.5 Hz, 1H); 5.75 (br s, 1H); 5.20 (br s, 1H); 3.66 (dd, J$_1$=4.5 Hz, J$_2$=14.5 Hz, 1H); 3.25 (dd, J$_1$=7.6 Hz, J$_2$=14.6 Hz, 1H); 3.12 (br t, 1H); 3.05 (s, 3H); 2.56 (br s, 1H); 2.47 (s, 3H); 2.23 (q, J=8.3 Hz, 1H); 1.97 (m, 1H); 1.83 (m, 1H); 1.72 (m, 1H); 1.64 (d, J=6.9 Hz, 3H).

EXAMPLE 220

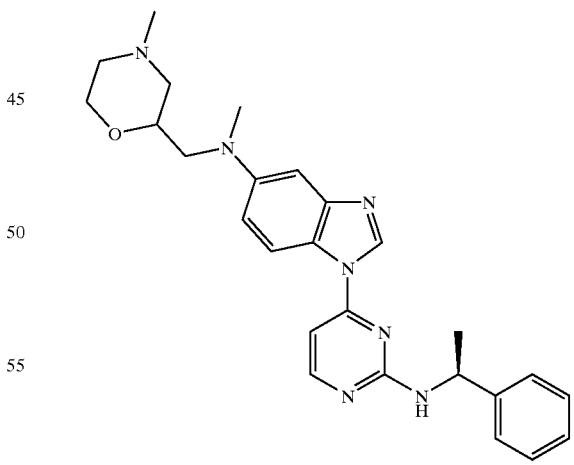

2-[(S)-1-Phenylethylamino]-4-[5-N-methyl-N-((4-methylmorpholin-2-yl)methyl)-aminobenzimidazol-1-yl]pyrimidine The title compound was prepared from 2-[(S)-1-phenylethylamino]4-[5-N-((4-methylmorpholin-2-yl)methyl)-aminobenzimidazol-1-yl]pyrimidine and formaldehyde according to the general procedure described in EXAMPLE 182. Mass spectrum (ES+) 458 (M+1). ¹H NMR (500 MHz, CDCl₃): δ 8.42 (br s, 1H); 8.33 (d, J=5.5 Hz, 1H); 7.72 (br s, 1H); 7.47–7.25 (m, 5H); 7.12 (s, 1H); 6.83 (br s, 1H); 6.74 (d, J=5.5 Hz, 1H); 5.95 (br s, 1H); 5.20 (br s, 1H); 3.93 (d, J=10.1 Hz, 1H); 3.89 (m, 1H); 3.69 (m, 1H); 3.42 (m, 2H); 3.04 (s, 3H); 2.82 (d, J=11.2 Hz, 1H); 2.69 (d, J=10.3 Hz, 1H); 2.31 (s, 3H); 2.18 (dt, 1H); 1.94 (t, J=10.8 Hz, 1H); 1.64 (d, J=7.1 Hz, 3H).

EXAMPLE 221

2-[(S)-1-Phenylethylamino]-4-[5-N-methyl-N-((1-benzyloxycarbonylpyrrolidin-2-yl)methyl)-aminobenzimidazol-1-yl]pyrimidine The title compound was prepared from 2-[(S)-1-phenylethylamino]-4-[5-N-((1-benzyloxycarbonylpyrrolidin-2-yl)methyl)-aminobenzimidazol-1-yl]pyrimidine and formaldehyde according to the general procedure described in EXAMPLE 182. Mass spectrum (ES+) 562 (M+1).

EXAMPLE 222

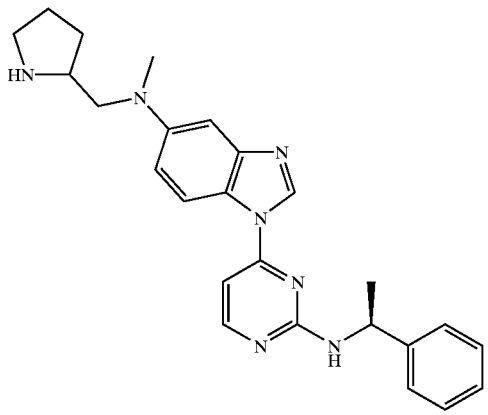

2-[(S)-1-Phenylethylamino]-4-[5-N-methyl-N-((pyrrolidin-2-yl)methyl)amino-benzimidazol-1-yl]pyrimidine The title compound was prepared from 2-[(S)-1-phenylethylamino]4-[5-N-methyl-N-((1-benzyloxycarbonylpyrrolidin-2-yl)methyl)-aminobenzimidazol-1-yl]pyrimidine according to the procedure described in EXAMPLE 208. Mass spectrum (ES+) 428 (M+1). ¹H NMR (500 MHz, CDCl₃): δ 8.42 (br s, 1H); 8.35 (d, J=5.5 Hz, 1H); 7.74 (br s, 1H); 7.47–7.25 (m, 5H); 7.13 (s, 1H); 6.87 (br s, 1H); 6.74 (d, J=5.5 Hz, 1H); 5.60 (br s, 1H); 5.20 (br s, 1H); 3.50 (m, 1H); 3.40 (m, 2H); 3.08 (m, 1H); 3.06 (s, 3H); 2.93 (m, 1H); 1.92 (m, 1H);1.86 (m, 1H); 1.78 (m, 1H); 1.64 (d, J=6.8 Hz, 3H); 1.46 (m, 1H).

EXAMPLE 223

2-[(S)-1-Phenylethylamino]-4-[5-N-((1-tert-butyloxycarbonyl-4-phenylpiperidin-4-yl)methyl)-aminobenzimidazol-1-yl]pyrimidine The title compound was prepared according to the general reductive amination procedure described in EXAMPLE 182 using 1-tert-butyloxycarbonyl-4-phenylpiperidin-4-carboxaldehyde. ¹H NMR (500 MHz, CDCl₃): δ 8.38 (br s, 1H); 8.33 (d, J=4.8 Hz, 1H); 7.58 (br s, 1H); 7.47–7.25 (m, 10H); 6.91 (s, 1H); 6.70 (d, J=5.5 Hz, 1H); 6.48 (br s, 1H); 5.70 (br s, 1H); 5.20 (br s, 1H); 3.74 (br s, 2H); 3.32 (s, 2H); 3.15 (br t, 2H); 2.28 (br d, 1H); 1.89 (br t, 2H); 1.63 (d, J=6.6 Hz, 3H); 1.46 (s, 9H).

EXAMPLE 224

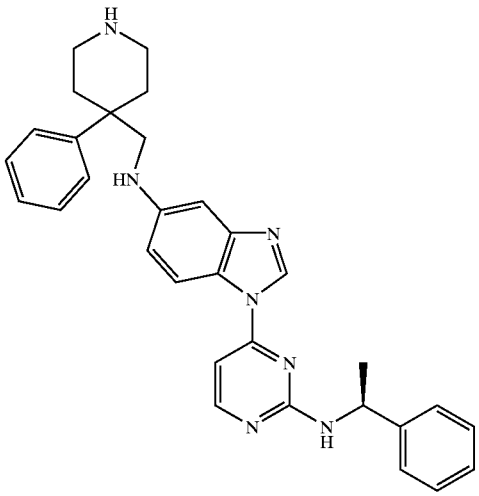

2-[(S)-1-Phenylethylamino]-4-[5-N-((4-phenylpiperidin-4-yl)methyl)amino-benzimidazol-1-yl]pyrimidine The title compound was prepared from 2-[(S)-1-phenylethylamino]-4-[5-N-((1-tert-butyloxycarbonyl-4-phenylpiperidin-4-yl)methyl)-aminobenzimidazol-1-yl]pyrimidine according to the procedure described in EXAMPLE 216 Step A. Mass spectrum (ES+) 504 (M+1) ¹H NMR (500 MHz, CDCl₃): δ 8.38 (br s, 1H); 8.33 (d, J=5.5 Hz, 1H); 7.58 (br s, 1H); 7.47–7.25 (m, 10H); 6.92 (s, 1H); 6.70 (d, J=5.5 Hz, 1H); 6.48 (br s, 1H); 5.65 (br s, 1H); 5.20 (br s, 1H); 3.33 (s, 2H); 3.30 (br s, 2H); 3.00 (m, 2H); 2.82 (m, 2H); 2.28 (br d, J=13.7 Hz, 2H); 1.94 (m, 2H); 1.88 (br s, 1H); 1.63 (d, J=6.8 Hz, 3H).

EXAMPLE 225

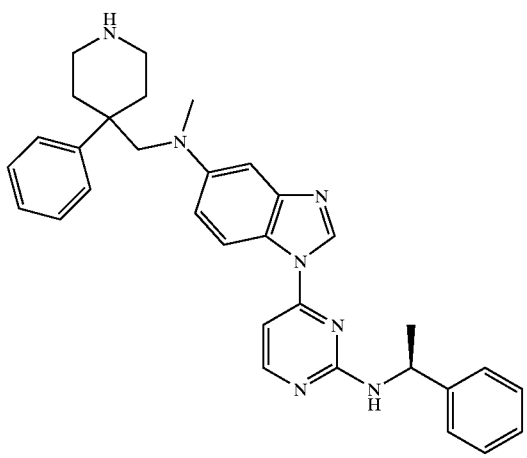

2-[(S)-1-Phenylethylamino]-4-[5-N-methyl-N-((4-phenylpiperidin-4-yl)methyl)-aminobenzimidazol-1-yl]pyrimidine The title compound was prepared from 2-[(S)-1-phenylethylamino]-4-[5-N-((1-tert-butyloxycarbonyl4- phenylpiperidin4-yl)methyl)-aminobenzimidazol-1-yl]pyrimidine and formaldehyde according to the general reductive amination procedure described in EXAMPLE 182 followed by deprotection according to the procedure described in EXAMPLE 216 Step A. Mass spectrum (ES+) 518 (M+1) $^1$H NMR (500 MHz, CDCl$_3$): δ 8.41 (br s, 1H); 8.34 (d, J=5.5 Hz, 1H); 7.64 (br s, 1H); 7.47–7.22 (m, 10H); 6.99 (s, 1H); 6.72 (d, J=5.5 Hz, 1H); 6.64 (br s, 1H); 5.60 (br s, 1H); 5.20 (br s, 1H); 3.51 (s, 2H); 2.99 (d, J=12.9 Hz, 2H); 2.74 (t, J=12.2Hz, 2H); 2.64 (s, 3H); 2.41 (d, J=12.8 Hz, 2H); 1.94 (t, J=11.7 Hz, 2H); 1.65 (d, J=6.8 Hz, 3H).

EXAMPLE 226

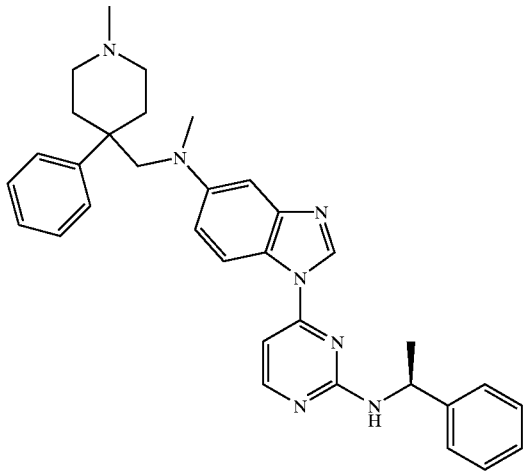

2-[(S)-1-Phenylethylamino]-4-[5-N-methyl-N-((1-methyl-4-phenylpiperidin-4-yl)-methyl)aminobenzimidazol-1-yl]pyrimidine The title compound was prepared from 2-[(S)-1-phenylethylamino]-4-[5-N-methyl-N-((4-phenylpiperidin-4-yl)methyl)-aminobenzimidazol-1-yl]pyrimidine and formaldehyde according to the general reductive amination procedure described in EXAMPLE 182. Mass spectrum (API-ES) 532 (M+1) $^1$H NMR (500 MHz, CDCl$_3$): δ 8.41 (br s, 1H); 8.33 (d, J=5.5 Hz, 1H); 7.64 (br s, 1H); 7.47–7.20 (m, 10H); 6.97 (d, J=2.1 Hz, 1H); 6.72 (d, J=5.5 Hz, 1H); 6.64 (ds, J=7.8 Hz, 1H); 5.66 (br s, 1H); 5.20 (br s, 1H); 3.44 (s, 2H); 2.70 (m, 2H); 2.65 (s, 3H); 2.40 (m, 2H); 2.19 (s, 3H); 2.07 (m, 4H); 1.65 (d, J=6.8 Hz, 3H).

EXAMPLE 227

General Procedure for Borane Reduction of Amides to Amines

To a solution of amide (0.11 mmol) in THF (2 mL) at 0° C. is added BH$_3$.Me$_2$S in THF solution. The reaction is stirred at 50° C. for 1–4 h and cooled to room temperature. Saturated citric acid is added and stirred for 20 to 60 min. The mixture is basified with 5N NaOH to pH 9–10 and extracted with methylene chloride three times. The organic solution is washed with water and brine, and dried over anhydrous sodium sulfate. Removal of the solvent and subsequent purification by preparative thin layer chromatography (50% of acetone in hexane) provides the desired products.

EXAMPLE 228

2-[(S)-1-Phenylethylamino]-4-[5-N-(2-(tert-butyloxycarbonyl)aminoethyl)amino-benzimidazol-1-yl]pyrimidine The title compound was prepared from 2-[(S)-1-phenylethylamino]4-[5-N-(2-(tert-butyloxycarbonyl)-aminoacetyl)-aminobenzimidazol -1-yl ]pyrimidine according to the general amide reduction procedure described in EXAMPLE 227. Mass spectrum (ESI): 474 (M+1).

EXAMPLE 229

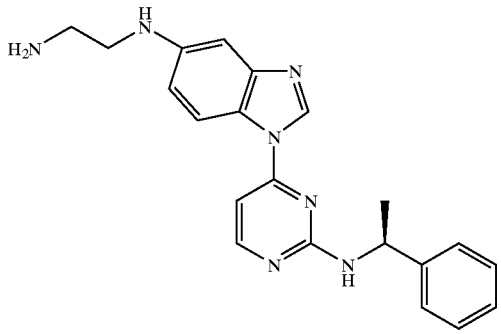

2-[(S)-1-Phenylethylamino]-4-[5-N-(2-aminoethyl)aminobenzimidazol-1-yl]-pyrimidine The title compound was prepared from 2-[(S)-1-phenylethylamino]-4-[5-N-(2-(tert-butyloxycarbonyl)aminoethyl)-aminobenzimidazol-1-yl]pyrimidine according to the general deprotection procedure described in EXAMPLE 216 Step A. Mass spectrum (ESI): 374 (M+1). $^1$H NMR (500 MHz, CDCl$_3$): δ 8.39 (br s, 1H); 8.32 (d, J=5.2 Hz, 1H);. 7.62 (br s, 1H); 7.47–7.24 (m, 5H); 7.00 (s, 1H); 6.70 (d, J=5.2 Hz, 1H); 6.68 (br s, 1H); 5.83 (br s, 1H); 5.20 (br s, 1H); 4.20 (br s, 1H); 3.46 (m, 1H); 3.26 (t, J=5.7 Hz, 2H); 3.03 (t, J=5.7 Hz, 2H); 1.63 (d, J=6.9 Hz, 3H).

EXAMPLE 230

2-[(S)-1-Phenylethylamino]-4-[5-N-(((R)-1-tert-butyloxycarbonylpyrrolidin-2-yl)-methyl)aminobenzimidazol-1-yl]pyrimidine The title compound was prepared from 2-[(S)-1-phenylethylamino]-4-[5-N-((R)-1-(tert-butyloxycarbonyl)pyrrolidine-2-oyl)-aminobenzimidazol-1-yl]pyrimidine according to the general amide reduction procedure described in EXAMPLE 227. Mass spectrum (ESI): 514 (M+1).

EXAMPLE 231

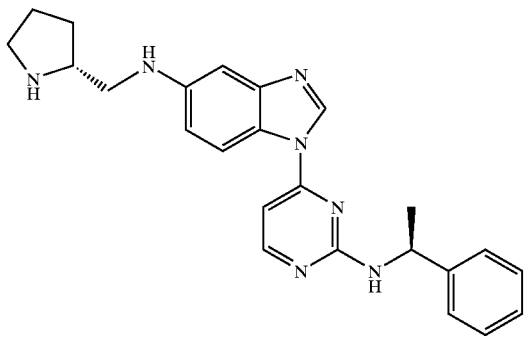

2-[(S)-1-Phenylethylamino]-4-[5-N-((pyrrolidin-2-yl)methyl)aminobenzimidazol-1-yl]pyrimidine The title compound was prepared from 2-[(S)-1-phenylethylamino]-4-[5-N-(((R)-1-tert-butyloxycarbonylpyrrolidin-2-yl)methyl)-aminobenzimidazol-1-yl]
pyrimidine according to the general deprotection procedure described in EXAMPLE 216 Step A. Mass spectrum (ES+) 414 (M+1). $^1$H NMR (500 MHz, CDCl$_3$): δ 8.38 (br s, 1H); 8.33 (d, J=5.5 Hz, 1H); 7.62 (br s, 1H); 7.47–7.25 (m, 5H); 6.99 (s, 1H); 6.71 (d, J=5.4 Hz, 1H); 6.68 (br s, 1H); 5.68 (br s, 1H); 5.20 (br s, 1H); 4.30 (br s, 1H); 3.50 (m, 1H); 3.27 (dd, J$_1$=4.2 Hz, J$_2$=12.0 Hz, 1H); 3.05 (m, 1H); 2.99 (t, J=6.8 Hz, 2H); 2.08 (br s, 1H); 1.99 (m, 1H); 1.87 (m, 1H); 1.78 (m, 1H); 1.63 (d, J=6.9 Hz, 3H); 1.55 (m, 1H).

EXAMPLE 232

2-[(S)-1-Phenylethylamino]-4-[5-N-(((R)-1-tert-butyloxycarbonylpiperidin-2-yl)methyl)aminobenzimidazol-1-yl]pyrimidine The title compound was prepared from 2-[(S)-1-phenylethylamino]-4-[5-N-((R)-1-(tert-butyloxycarbonyl)piperidine-2-oyl)-aminobenzimidazol-1-yl]pyrimidine according to the general amide reduction procedure described in EXAMPLE 227. Mass spectrum (ESI): 528 (M+1). $^1$H NMR (500 MHz, CDCl$_3$): δ8.39 (br s, 1H); ); 8.33 (d, J=5.4 Hz, 1H); 7.60 (br s, 1H); 7.47–7.25 (m, 5H); 6.94 (s, 1H); 6.72 (d, J=5.5 Hz, 1H); 6.59 (br s, 1H); 5.75 (br s, 1H); 5.20 (br s, 1H); 4.60 (br s, 1H); 4.05 (br s, 2H); 3.54 (t, J=11.2 Hz, 1H); 3.14 (dd, J$_1$=4.9 Hz, J$_2$=12.3 Hz, 1H); 2.83 (t, 1H); 1.77–1.66 (m, 5H); 1.63 (d, J=7.1 Hz, 3H); 1.57 (m, 1H).

EXAMPLE 233

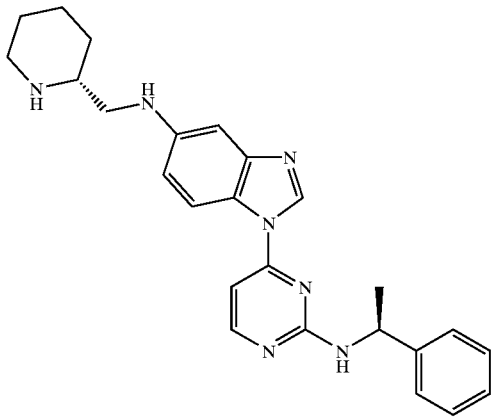

2-[(S)-1-Phenylethylamino]-4-[5-N-(((R)-piperidin-2-yl)methyl)aminobenzimidazol-1-yl]pyrimidine The title compound was prepared from 2-[(S)-1-phenylethylamino]-4-[5-N-(((R)-1-tert-butyloxycarbonylpiperidin-2-yl)methyl)-aminobenzimidazol-1-yl]pyrimidin according to the general deprotection procedure described in EXAMPLE 216 Step A. Mass spectrum (ES+) 428 (M+1). $^1$H NMR (500 MHz, CDCl$_3$): δ 8.39 (br s, 1H); ); 8.33 (d, J=5.5 Hz, 1H); 7.60 (br s, 1H); 7.47–7.25 (m, 5H); 6.98 (s, 1H); 6.71 (d, J=5.5 Hz, 1H); 6.65 (br s, 1H); 5.80 (br s, 1H); 5.20 (br s, 1H); 4.19 (br s, 1H); 3.22 (dd, 1H); 3.10 (m, 2H); 2.87 (m, 1H); 2.65 (t, 1H); 2.20 (br s, 1H); 1.87 (br d, 1H); 1.74 (d, 1H); 1.63 (d, J=6.9 Hz, 3H); 1.44 (m, 2H); 1.27 (m, 2H).

EXAMPLE 234

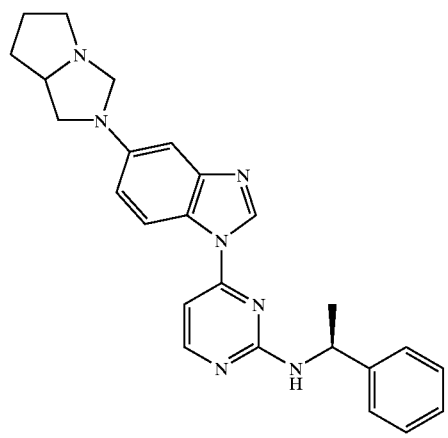

2-[(S)-1-Phenylethylamino]-4-[5-(1,3-diazobicyclo[3.3.0]octan-3-yl)benzimidazol-1-yl]pyrimidine To a solution of 2-[(S)-1-phenylethylamino]-4-[5-N-((pyrrolidin-2-yl)methyl)-aminobenzimidazol-1-yl]pyrimidine (41 mg) in methanol (1 mL) was added 10 eq formaldehyde (75 μL). The reaction was stirred at room temperature for three hours. The solvent was removed, and the residue was dissolved in methylene chloride. The organic solution was washed with brine and dried over anhydrous sodium sulfate. Removal of the solvent and subsequent purification by preparative thin layer chromatography (10% of 2N NH$_3$ in MeOH/CH$_2$Cl$_2$) provided the title product (40 mg). Mass spectrum (ES+) 426 (M+1). $^1$H NMR (500 MHz, CDCl$_3$): δ8.43 (s, 1H); 8.35 (d, J=5.5 Hz, 1H); 7.75 (br s, 1H); 7.47–7.24 (m, 5H); 6.94 (d, J=1.9 Hz, 1H); 6.74 (d, J=5.5 Hz, 1H); 6.63 (br d, J=6.8 Hz, 1H); 5.68 (br s, 1H); 5.22 (br s, 1H); 4.30 (ABq, J=7.5 Hz, 2H); 3.90 (m, 1H); 3.37 (t, J=8.2 Hz, 1H); 3.26 (m, 1H); 3.22 (m, 1H); 2.79 (q, J=7.3 Hz, 1H); 2.22 (m, 1H); 2.02 (m, 1H); 1.92 (m, 1H); 1.84 (m, 1H); 1.64 (d, J=6.9 Hz, 3H).

EXAMPLE 235

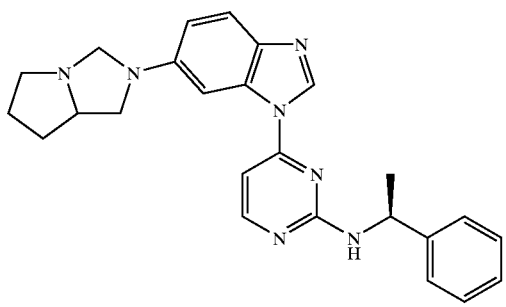

2-[(S)-1-Phenylethylamino]-4-[6-(1,3-diazobicyclo[3.3.0]octan-3-yl)benzimidazol-1-yl]pyrimidine To a solution of 2-[(S)-1-phenylethylamino]-4-[6-N-((pyrrolidin-2-yl)methyl)-aminobenzimidazol-1-yl]

pyrimidine (78 mg) in methanol (1.5 mL) was added 10 eq formaldehyde (0.14 mL). The reaction was stirred at room temperature for 1.5 h. The solvent was removed, and the residue was dissolved in methylene chloride. The organic solution was washed with brine and dried over anhydrous sodium sulfate. Removal of the solvent and subsequent purification by preparative thin layer chromatography (10% of 2N $NH_3$ in MeOH/$CH_2Cl_2$) provided the title product (57 mg). Mass spectrum (API-ES) 426 (M+1). $^1$H NMR (500 MHz, $CDCl_3$): δ 8.38 (d, J=5.4 Hz, 1H); 8.33 (s, 1H); 7.67 (d, J=8.9 Hz, 1H); 7.47–7.25 (m, 5H);7.20 (s, 1H); 6.78 (d, J=5.5 Hz, 1H); 6.66 (dd, $J_1$=2.1 Hz, $J_2$=8.8 Hz, 1H); 5.65 (br s, 1H); 5.33 (m, 1H); 4.28 (s, 2H); 3.86 (m, 1H); 3.36 (t, J=7.9 Hz, 1H); 3.22 (m, 1H); 3.18 (m, 1H); 2.73 (q, J=8.2 Hz, 1H); 2.21 (m, 1H); 2.00 (m, 1H); 1.92 (m, 1H); 1.81 (m, 1H); 1.67 (d, J=6.9 Hz, 3H).

EXAMPLE 236

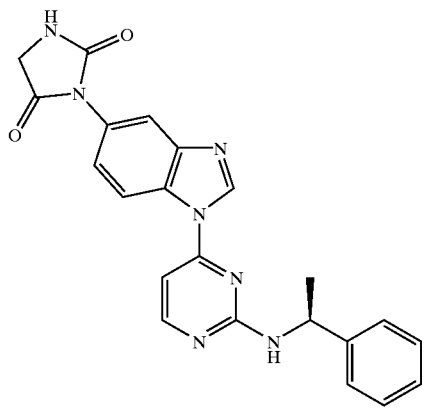

2-[(S)-1-Phenylethylamino]-4-[5-(2,4-imidazolidinedione-1-yl)benzimidazol-1-yl]-pyrimidine To a mixture of 2-[(S)-1-phenylethylamino]-4-[5-N-(aminoacetyl)-aminobenzimidazol-1-yl]pyrimidine (79 mg) in acetonitrile (3 ml) was added 1.3 eq. 1,1'-carbonyldiimidazole (43 mg). The reaction was stirred at 50° C. for 3.5 h. and cooled. Removal of the solvent and subsequent silica gel preparative thin layer chromatography purification (10% of 2N $NH_3$ in MeOH/$CH_2Cl_2$) provided the title compound (64 mg). Mass spectrum (ESI): 414 (M+1). $^1$H NMR (500 MHz, $CDCl_3$): δ 8.52 (br s, 1H); 8.41 (d, J=5.2 Hz, 1H); 8.38 (d, 1H); 7.87 (s, 1H); 7.47–7.25 (m, 5H); 6.77 (d, J=5.3 Hz, 1H); 5.85 (s, 2H); 5.19 (br s, 1H); 4.21 (s, 2H); 1.64 (d, J=6.9 Hz, 3H).

EXAMPLE 237

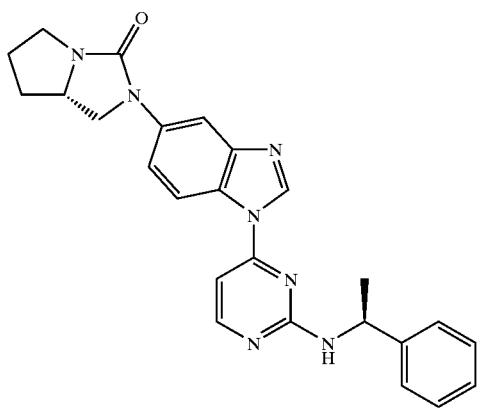

2-[(S)-1-Phenylethylamino]-4-[5-(1,3-diazobicyclo[3.3.0]octan-2-one-3-yl)benzimidazol-1-yl]pyrimidine To a mixture of 2-[(S)-1-phenylethylamino]-4-[5-N-((pyrrolidin-2-yl)methyl)-aminobenzimidazol-1-yl]pyrimidine (130 mg) in $CH_3CN$ was added 66 mg of 1,1'-carbonyldiimidazole. The reaction was stirred at 50° C. for 5 h. To this was added 88 μL of triethylamine and 26 mg of 1,1'-carbonyldiimidazole. The reaction was stirred at 50° C. for another hour and cooled to room temperature. Removal of the solvent and subsequent silica gel preparative thin layer chromatography purification (10% of 2 N $NH_3$ in MeOH/$CH_2Cl_2$) provided 147 mg of an intermediate. The intermediate was dissolved in DMF (2 mL) and stirred at 100° C. for 6 h, 120° C. for 5 h. Triethylamine (100 μL) was added, then the reaction was stirred again for 5 h at reflux. The mixture was cooled to room temperature, diluted with ethyl acetate, washed with water three times to remove most of the DMF. The organic layer was then washed with brine and dried over sodium sulfate. Removal of the solvent and subsequent silica gel preparative thin layer chromatography purification (acetone/hexane=2/1) provided 70 mg of the titled compound 106. Mass spectrum (ESI): 440 (M+1). $^1$H NMR (500 MHz, $CDCl_3$): δ 8.47 (br s, 1H); 8.37 (d, J=5.5 Hz, 1H); 8.03 (s, 1H); 8.02 (br s, 1H); 7.80 (br s, 1H); 7.64 (s, 1H); 7.47–7.25 (m, 5H); 6.77 (d, J=5.5 Hz, 1H); 5.90 (br s, 1H); 5.20 (br s, 1H); 4.09 (m, 1H); 3.83 (m, 3H); 3.21 (m, 1H); 2.12 (m, 1H); 2.06 (m, 1H); 1.92 (m, 1H); 1.64 (d, J=7.1 Hz, 3H); 1.52 (m, 1H).

EXAMPLE 238

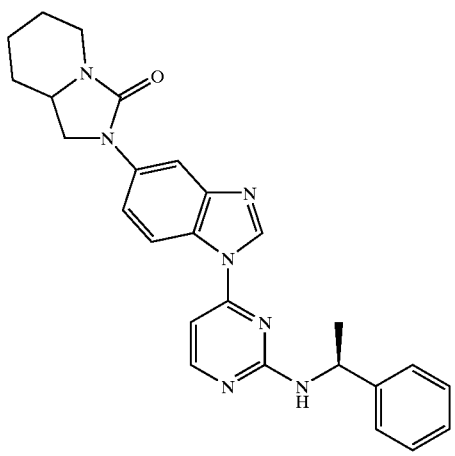

2-[(S)-1-Phenylethylamino]-4-[5-(1,3-diazobicyclo [4.3.0]nonan-2-one-3-yl)-benzimidazol-1-yl] pyrimidine To a mixture of 2-[(S)-1-phenylethylamino]-4-[5-N-((piperidin-2-yl)methyl)-aminobenzimidazol-1-yl] pyrimidine (65 mg) in DMF (2mL) was added 32 mg of 1,1'-carbonyldiimidazole. The reaction was stirred at 100° C. for 6 h. Then 7.4 mg of 1,1'-carbonyldiimidazole was added, the mixture was stirred at 120° C. for 5 h. 10 mg of 1,1'-carbonyldiimidazole and 100 μL of triethylamine were added, the mixture was stirred at 120° C. for another 5 h. The mixture was cooled to room temperature, diluted with ethyl acetate, washed with water three times to remove most of DMF. The organic layer was then washed with brine and dried over sodium sulfate. Removal of the solvent and subsequent silica gel preparative thin layer chromatography purification (acetone/hexane=2/1) provided 20 mg of the titled compound 107. Mass spectrum (ESI): 454 (M+1). $^1$H NMR (500 MHz, CDCl$_3$): δ8.47 (br s, 1H); 8.36 (d, J=5.5 Hz, 1H); 8.05 (br s, 1H); 8.04 (s, 1H); 7.84 (br s, 1H); 7.58 (s, 1H); 7.47–7.25 (m, 5H); 6.78 (d, J=5.7 Hz, 1H); 6.01 (br s, 1H); 5.20 (br s, 1H); 4.06 (m, 1H); 3.99 (m, 1H); 3.62 (m, 1H); 3.50 (m, 1H); 2.82 (m, 1H); 1.95 (m, 2H); 1.73 (m, 2H); 1.65 (d, J=6.9 Hz, 3H); 1.50 (m, 2H).

EXAMPLE 239

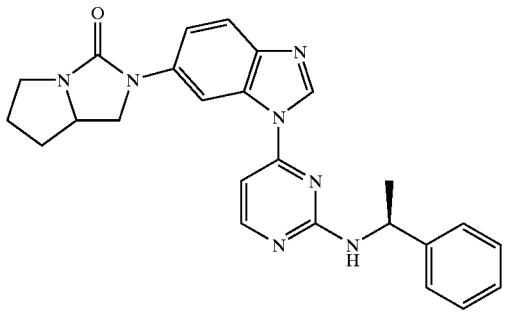

2-[(S)-1-Phenylethylamino]-4-[6-(1,3-diazobicyclo [3.3.0]octan-2-one-3-yl)-benzimidazol-1-yl] pyrimidine To a solution of 2-[(S)-1-phenylethylamino]-4-[6-N-((pyrrolidin-2-yl)methyl)-aminobenzimidazol-1-yl] pyrimidine (46 mg) in methylene chloride (1 mL) at −40° C. was added 1.3 eq. triethylamine (20 mL) followed by a solution of 0.37 eq. triphosgene (12 mg) in methylene chloride (1 mL). The reaction mixture was stirred for 30 min at −30° C. to −40° C. and poured into brine. The mixture was extracted with methylene chloride three times. The combined extracts were washed with brine and dried over anhydrous sodium sulfate. Removal of the solvent and subsequent silica gel preparative thin layer chromatography purification (acetone/hexane=2/1) provided the title compound (37 mg). Mass spectrum (API-ES) 440 (M+1). $^1$H NMR (500 MHz, CDCl$_3$): δ 8.71 (s, 1H); 8.48 (br s, 1H); 8.35 (d, J=4.8 Hz, 1H); 7.75 (d, J=8.7 Hz, 1H); 7.47–7.22 (m, 6H); 6.85 (d, J=5.3 Hz, 1H); 6.04 (br s, 1H); 5.30 (quintet, J=7.0 Hz, 1H); 4.03 (t,J=8.9 Hz, 1H); 3.79 (m, 3H); 3.19 (m, 1H); 2.09 (m, 1H); 2.03 (m, 1H); 1.90 (m, 1H); 1.63 (d, J=6.9 Hz, 3H); 1.47 (quintet, J=10.5 Hz, 1H).

EXAMPLE 240

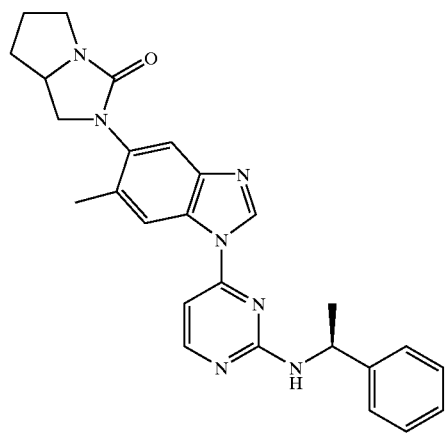

2-[(S)-1-Phenylethylamino]-4-[5-(1,3-diazobicyclo [3.3.0]octan-2-one-3-yl)-6-methyl-benzimidazol-1-yl]pyrimidine The title compound was prepared from 2-[(S)-1-phenylethylamino]-4-[5-N-((pyrrolidin-2-yl)methylamino)-6-methyl-benzimidazol-1-yl]pyrimidine according to the procedure described in EXAMPLE 239. Mass spectrum (ES+) 454 (M+1). $^1$H NMR (500 MHz, CDCl$_3$): δ 8.46 (br s, 1H); 8.40 (d, J=5.3 Hz, 1H); 7.90 (br s, 1H); 7.64 (s, 1H); 7.47–7.25 (m, 5H); 6.78 (d, J=5.5 Hz, 1H); 5.69 (br s, 1H); 5.24 (br s, 1H); 3.99 (t, J=8.6 Hz, 1H); 3.82 (m, 2H); 3.67 (dd, J$_1$=1.6 Hz, J$_2$=9.3 Hz, 1H); 3.18 (m, 1H); 2.40 (s, 3H); 2.10 (m, 2H); 1.92 (m, 1H); 1.65 (d, J=6.9 Hz, 3H); 1.62 (m, 1H).

EXAMPLE 241
General Procedure for Preparation of Urea Analogs

To a mixture of 2-[(S)-1-phenylethylamino]-4-[5-aminobenzimidazol-1-yl]pyrimidine (EXAMPLE 79) in methylene chloride or pyridine is added 1.05 eq. of the appropriate isocyanate. The reaction is then stirred at room temperature overnight. Removal of the solvent and subsequent purification by preparative thin layer chromatography (acetone-hexane system) yields the desired urea.

EXAMPLE 242

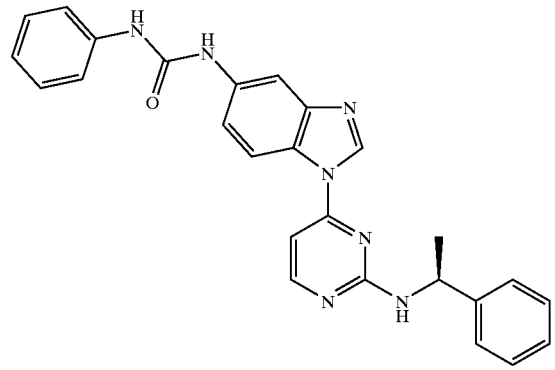

2-[(S)-1-Phenylethylamino]-4-[5-N-(N-phenylcarbamoyl)aminobenzimidazol-1-yl] pyrimidine The title compound was prepared according to the general procedure described in EXAMPLE 241 using phenyl isocyanate. Mass spectrum (ESI): 450 (M+1). $^1$H NMR (500 MHz, CDCl$_3$): δ 8.27 (s, 1H); 8.22 (d, J=5.5 Hz, 1H); 7.68 (br s, 1H); 7.63–7.16 (m, 11H); 7.00 (t, J=7.2 Hz, 1H); 6.43 (d, J=5.2 Hz, 1H); 5.8 (br d, 1H); 5.08 (br s, 1H); 1.58 (d, J=6.7 Hz, 3H).

EXAMPLE 243

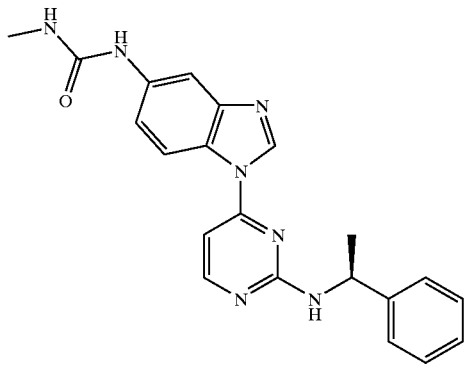

2-[(S)-1-Phenylethylamino]-4-[5-N-(N-methylcarbamoyl)aminobenzimidazol-1-yl]pyrimidine The title compound was prepared according to the general procedure described in EXAMPLE 241 using methyl isocyanate. Mass spectrum (ESI): 388 (M+1). $^1$H NMR (500 MHz, CDCl$_3$): δ 8.48 (br s, 1H); 8.22 (d, J=5.5 Hz, 1H); 7.93 (br s, 1H); 7.53 (s, 1H); 7.45–7.15 (m, 6H); 6.52 (d, J=5.3 Hz, 1H); 6.14 (br s, 1H); 5.68 (br s, 1H); 5.12 (br s, 1H); 2.77 (s, 3H); 1.56 (d, J=6.7 Hz, 3H).

EXAMPLE 244

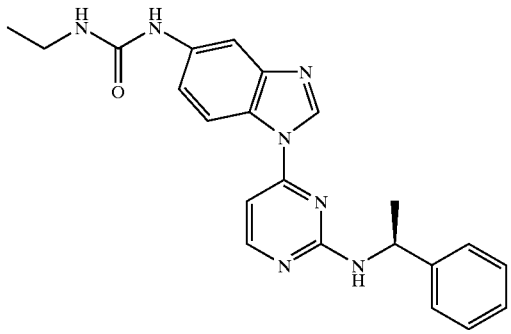

2-[(S)-1-Phenylethylamino]-4-[5-N-(N-ethylcarbamoyl)aminobenzimidazol-1-yl]pyrimidine The title compound was prepared according to the general procedure described in EXAMPLE 241 using ethyl isocyanate. Mass spectrum (ESI): 402 (M+1). $^1$H NMR (500 MHz, CDCl$_3$): δ 8.45 (br s, 1H); 8.33 (d, J=5.5 Hz, 1H); 7.64 (s, 1H); 7.50–7.20 (m, 6H); 7.20 (br s, 1H); 6.65 (d, J=5.5 Hz, 1H); 5.90 (br s, 1H); 5.17 (br s, 2H); 3.31 (quintet, J=6.2 Hz, 2H); 2.21 (br s, 1H); 1.62 (d, J=6.8 Hz, 3H); 1.15 (t, J=7.1 Hz, 3H).

EXAMPLE 245

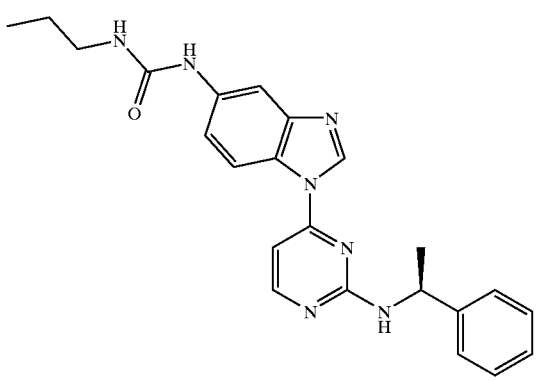

2-[(S)-1-Phenylethylamino]-4-[5-N-(N-propylcarbamoyl)aminobenzimidazol-1-yl]pyrimidine The title compound was prepared according to the general procedure described in EXAMPLE 241 using propyl isocyanate. Mass spectrum (ESI): 416 (M+1). $^1$H NMR (500 MHz, CDCl$_3$): δ 8.43 (br s, 1H); 8.33 (d, J=5.2 Hz, 1H); 7.64 (s, 1H); 7.46–7.23 (m, 6H); 7.12 (br s, 1H); 6.65 (d, J=5.3 Hz, 1H); 5.90 (br S, 1H); 5.20 (br s, 1H); 5.17 (br s, 1H); 3.23 (q, J=6.2 Hz, 2H); 2.34 (br s, 1H); 1.62 (d, J=6.9 Hz, 3H); 1.53 (m, J=7.3 Hz, 2H); 0.92 (t, J=7.3 Hz, 3H).

EXAMPLE 246

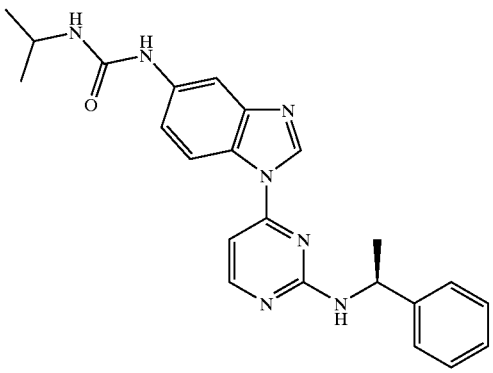

2-[(S)-1-Phenylethylamino]-4-[5-N-(N-((1-methyl)ethylcarbamoyl)aminobenzimidazol-1-yl]pyrimidine The title compound was prepared according to the general procedure described in EXAMPLE 241 using isopropyl isocyanate. Mass spectrum (ESI): 416 (M+1). $^1$H NMR (500 MHz, CDCl$_3$): δ 8.49 (br s, 1H); 8.35 (d, J=5.2 Hz, 1H); 7.64 (s, 1H); 7.48–7.22 (m, 6H); 6.82 (br s, 1H); 6.70 (d, J=5.3 Hz, 1H); 5.91 (br s, 1H); 5.18 (br s, 1H); 4.85 (br s, 1H); 4.05 (m, 1H); 2.70 (br s, 1H); 1.63 (d, J=6.9 Hz, 3H); 1.19 (d, J=6.4 Hz, 6H).

EXAMPLE 247

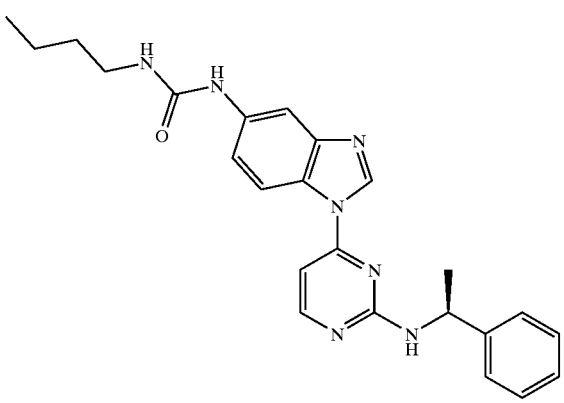

2-[(S)-1-Phenylethylamino]-4-[5-N-(N-butylcarbamoyl)-amino-benzimidazol-1-yl]pyrimidine The title compound was prepared according to the general procedure described in EXAMPLE 241 using butyl isocyanate. Mass spectrum (ESI): 430 (M+1). $^1$H NMR (500 MHz, CDCl$_3$): δ 8.43 (br s, 1H); 8.33 (d, J=5.3 Hz, 1H); 7.64 (s, 1H); 7.48–7.22 (m, 6H); 7.07 (br s, 1H); 6.66 (d, J=5.5 Hz, 1H); 5.89 (br s, 1H); 5.18 (br s, 2H); 3.27 (q, J=6.6 Hz, 2H); 2.13 (br s, 1H); 1.62 (d, J=6.9 Hz, 3H); 1.49 (quintet, J=7.3 Hz, 2H); 1.34 (m, J=7.6 Hz, 2H); 0.91 (t, J=7.4 Hz, 3H).

EXAMPLE 248

2-[(S)-1-Phenylethylamino]-4-[5-N-(N-(dimethylethyl)carbamoyl)aminobenzimidazol-1-yl]pyrimidine The title compound was prepared according to the general procedure described in EXAMPLE 241 using tert-butyl isocyanate. Mass spectrum (ESI): 430 (M+1). $^1$H NMR (500 MHz, CDCl$_3$): δ 8.48 (br s, 1H); 8.35 (d, J=5.2 Hz, 1H); 7.70 (br s, 1H); 7.62 (s, 1H); 7.48–7.22 (m, 5H); 6.78 (br s, 1H); 6.70 (d, J=5.3 Hz, 1H); 5.92 (br s, 1H); 5.18 (br s, 2H); 4.93 (s, 1H); 2.22 (br s, 1H); 1.63 (d, J=6.8 Hz, 3H); 1.39 (s, 9H).

EXAMPLE 249

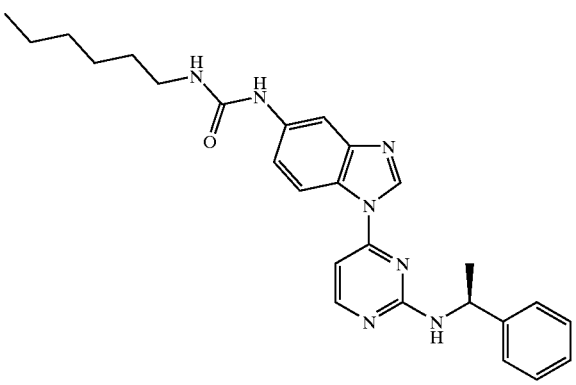

2-[(S)-1-Phenylethylamino]-4-[5-N-(N-hexylcarbamoyl)aminobenzimidazol-1-yl]pyrimidine The title compound was prepared according to the general procedure described in EXAMPLE 241 using n-hexyl isocyanate. Mass spectrum (ESI): 458 (M+1). $^1$H NMR (500 MHz, CDCl$_3$): δ 8.38 (br s, 1H); 8.29 (d, J=5.3 Hz, 1H); 7.61 (s, 2H); 7.48–7.20 (m, 6H); 6.59 (d, J=5.5 Hz, 1H); 5.97 (br s, 1H); 5.37 (s, 1H); 5.13 (br s, 1H); 3.24 (q, J=6.2 Hz, 2H); 2.30 (br s, 1H); 1.61 (d, J=6.9 Hz, 3H); 1.48 (m, 2H); 1.24 (m, 6H); 0.85 (t, J=6.9 Hz, 3H).

EXAMPLE 250

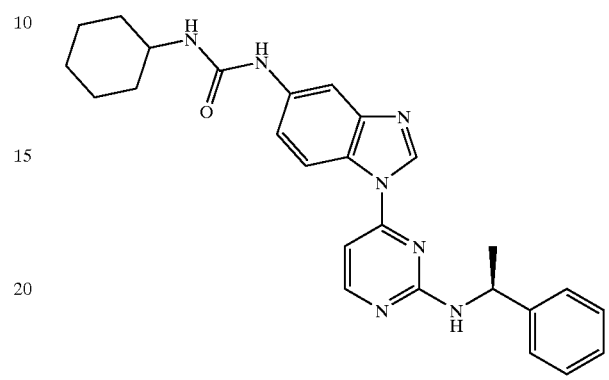

2-[(S)-1-Phenylethylamino]-4-[5-N-(N-cyclohexylcarbamoyl)aminobenzimidazol-1-yl]pyrimidine The title compound was prepared according to the general procedure described in EXAMPLE 241 using cyclohexyl isocyanate. Mass spectrum (ESI): 456 (M+1). $^1$H NMR (500 MHz, CDCl$_3$): δ 8.44 (br s, 1H); 8.33 (d, J=5.2 Hz, 1H); 7.64 (s, 1H); 7.46–7.24 (m, 6H); 6.94 (br s, 1H); 6.67 (d, J=5.5 Hz, 1H); 5.90 (br s, 1H) 5.17 (br s, 1H); 5.00 (br s, 1H); 3.72 (m, 1H); 2.38 (br s, 1H); 1.97 (m, 2H); 1.68 (m, 2H); 1.63 (d, J=6.9 Hz, 3H); 1.58 (m, 1H); 1.36 (m, 2H); 1.13 (m, 3H).

EXAMPLE 251

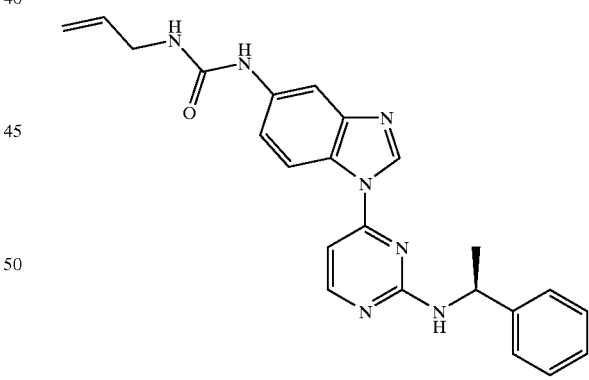

2-[(S)-1-Phenylethylamino]-4-[5-N-(N-allylcarbamoyl)aminobenzimidazol-1-yl]pyrimidine The title compound was prepared according to the general procedure described in EXAMPLE 241 using allyl isocyanate. Mass spectrum (ESI): 414 (M+1). $^1$H NMR (500 MHz, CDCl$_3$): δ 8.44 (br s, 1H); 8.33 (d, J=5.3 Hz, 1H); 7.65 (s, 1H); 7.45–7.24 (m, 6H);7.18 (br s, 1H); 6.65 (d, J=5.2 Hz, 1H); 5.88 (m, 2H); 5.27 (br s, 1H); 5.21 (d, J=17.2 Hz, 1H); 5.6 (br s, 1H); 5.11(d, J=10.3 Hz, 1H); 3.9 (t, J=5.1 Hz, 1H); 2.22 (br s, 1H); 1.62 (d, J=6.8 Hz, 3H).

EXAMPLE 252

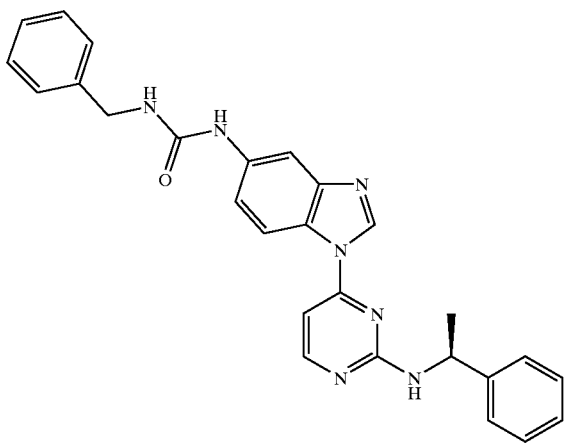

2-[(S)-1-Phenylethylamino]-4-[5-N-(N-benzylcarbamoyl)aminobenzimidazol-1-yl]pyrimidine The title compound was prepared according to the general procedure described in EXAMPLE 241 using benzyl isocyanate. Mass spectrum (ESI): 464 (M+1). $^1$H NMR (500 MHz, CDCl$_3$): δ 8.42 (br s, 1H); 8.32 (d, J=5.3 Hz, 1H); 7.63 (s, 1H); 7.45–7.30 (m, 11H); 7.08 (br s, 1H); 6.64 (d, J=5.5 Hz, 1H); 5.87 (br s, 1H); 5.48 (br s, 1H); 5.62 (br s, 1H); 4.43 (d, J=5.7 Hz, 2H); 2.22 (br s, 1H); 1.62 (d, J=6.9 Hz, 3H).

EXAMPLE 253 omitted

EXAMPLE 254

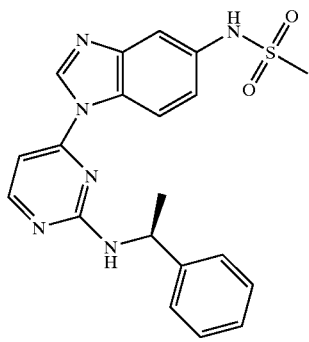

2-[(S)-1-Phenylethylamino]-4-[5-N-(methanesulfonyl)aminobenzimidazol-1-yl]pyrimidine The title compound was prepared according to the procedure described in EXAMPLE 124 using methanesulfonyl chloride instead of benzenesulfonyl chloride. Mass spectrum (ESI): 409 (M+1). $^1$H NMR (500 MHz, CDCl$_3$): δ 8.48 (br s, 1H); 8.35 (d, 1H); 7.95 (br s, 1H); 7.72 (s, 1H); 7.47–7.22 (m, 6H); 6.70 (d, J=5.2 Hz, 1H); 6.2 (br s, 1H); 5.18 (br s, 1H); 3.01 (s, 3H); 1.63 (d, J=7.1 Hz, 3H).

EXAMPLE 255

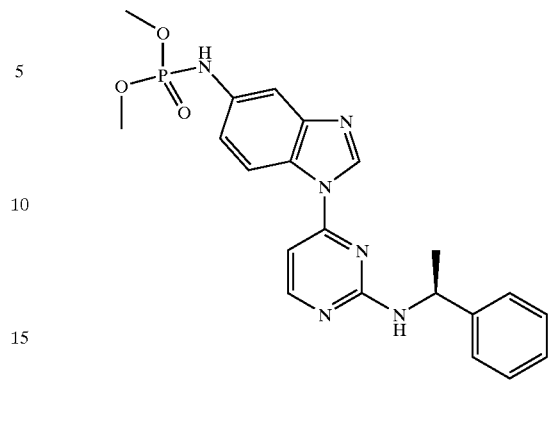

2-[(S)-1-Phenylethylamino]-4-[5-N-(dimethylphosphonyl)aminobenzimidazol-1-yl]pyrimidine To a mixture of 2-[(S)-1-phenylethylamino]-4-[5-aminobenzimidazol-1-yl]pyrimidine (EXAMPLE 79) (80 mg) in methylene chloride was added 1.1 eq. dimethyl chlorophosphate (29 μL) at 0° C. The reaction was then stirred at room temperature for 4 h. Removal of the solvent and subsequent purification by preparative thin layer chromatography (acetone:hexane=2:1) provided the title product (20 mg). Mass spectrum (ESI): 439 (M+1). $^1$H NMR (500 MHz, CDCl$_3$): δ8.46 (br s, 1H); 8.37 (d, J=5.2 Hz, 1H); 7.71 (br s, 1H); 7.72 (s, 1H); 7.50–7.25 (m, 6H); 6.98 (br s, 1H); 6.74 (d, J=5.5 Hz, 1H); 6.12 (d, J=8.2 Hz, 1H); 6.05 (br s, 1H); 5.20 (br s, 1H); 3.84 (s, 3H); 3.81 (s, 3H); 1.65 (d, J=6.8 Hz, 3H).

EXAMPLE 256

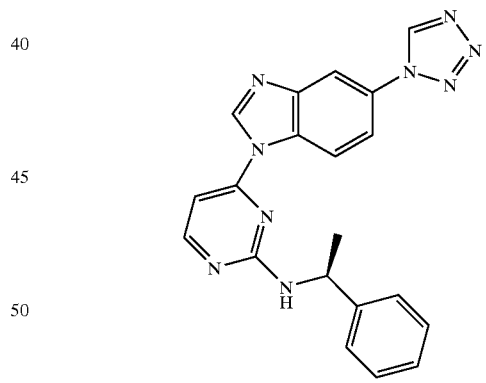

2-[(S)-1-Phenylethylamino]-4-[5-(tetrazol-1-yl)-benzimidazol-1-yl]pyrimidine

To a solution of 2-[(S)-1-phenylethylamino]-4-[5-aminobenzimidazol-1-yl]pyrimidine (EXAMPLE 79) (80 mg) in acetic acid (2 mL) was added triethyl orthoformate (123 μL). The reaction was stirred at room temperature for 1 h, at 75° C. for 2 h, and then at room temperature again overnight (≈14 h). NaN$_3$ (47 mg, 3 eq.) was added; the reaction was stirred at 75° C. for 5 h. The reaction was cooled, quenched with water, extracted with methylene chloride. The organic solution was washed with water and brine; it was dried over Na$_2$SO$_4$. Removal of the solvent and subsequent purification by preparative thin layer chromatography (acetone:hexane=1:1) provided the title compound (20 mg). Mass spectrum (ESI): 384 (M+1). $^1$H NMR (500 MHz, CDCl$_3$): δ 9.04 (s, 1H); 8.56 (br s, 1H); 8.46 (d, J=5.2 Hz, 1H); 8.08 (s, 1H); 7.82 (br s, 1H); 7.57 (br s, 1H); 7.50–7.25 (m, 5H); 6.79 (d, J=5.3 Hz, 1H); 5.88 (br s, 1H); 5.18 (br s, 1H); 1.67 (d, J=6.8 Hz, 3H).

EXAMPLE 257

2-[(S)-1-(3-Nitrophenyl)ethylamino]-4-[5-N-(t-butyloxycarbonyl)aminobenzimidazol-1-yl]pyrimidine Step A: 2-Methylthio-4-[5-N-(t-butyloxycarbonyl)aminobenzimidazol-1-yl]pyrimidine To 1 g of 2-methylthio-4-[5-aminobenzimidazol-1-yl]pyrimidine in 10 ml of tetrahydrofuran was added 1.7 g of di-t-butyldicarbonate and the mixture heated to 60° C. for 30 hours. The reaction mixture was then cooled and concentrated under reduced pressure to give a cloudy yellow residue. The residue was triturated with ether and the resulting pale yellow solid collected and dried under vacuum to give 675 mg of the title compound. $^1$H NMR (500 MHz, CDCl$_3$): δ 8.65 (s, 1H); 8.62 (d, J=4.5 Hz, 1H); 8.15 (d, J=9 Hz, 1H); 7.84 (d, J=1.8 Hz, 1H); 7.53 (br d, 1H); 7.18 (d, J=5.5 Hz, 1 H); 6.64 (br s, 1H); 2.68 (s, 3H); 1.56 (s, 9H).

Step B: 2-Methanesulphonyl-4-[5-N-(t-butyloxycarbonyl)aminobenzimidazol-1-yl]pyrimidine To 339 mg of 2-methylthio-4-[5-N-(t-butyloxycarbonyl)aminobenzimidazol-1-yl]pyrimidine in a mixture of 7.5 ml of methanol and 12.5 ml of dichloromethane at 0° C. was added a solution of 1.75 g of Oxone® in 7.5 ml of water resulting in a two phase mixture. The reaction was allowed to come to room temperature and was rapidly stirred for 3 hours. The reaction mixture was poured into water and extracted with dichloromethane. The dichloromethane extracts were washed with brine, dried (MgSO4) and concentrated under reduced pressure. The residue was purified by column chromatography on silica gel eluting with 3% (2M ammonia in methanol) in dichloromethane to give 184 mg of the title compound. 1H NMR (500 MHz, CDCl3): d 8.96 (d, J=5.7 Hz, 1H); 8.66 (s, 1H); 8.28 (d, J=9 Hz, 1 H); 7.98 (br s, 1H); 7.71 (d, J=5.7 Hz, 1H); 7.44 (br d, J=9 Hz, 1H); 6.67 (br s, 1H); 3.45 (s, 3H); 1.57 (s, 9H).

Step C: 2-[(S)-1-(3-Nitrophenyl)ethylamino]-4-[5-N-(t-butyloxycarbonyl)aminobenzimidazol-1-yl]pyrimidine 176 mg of 2-methanesulfonyl-4-[5-N-(t-butyloxycarbonyl)aminobenzimidazol-1-yl]pyrimidine and 150 mg of (S)-1-(3-nitrophenyl)ethylamine were mixed in 0.5 ml toluene and heated to 100° C. for 12 hours. The reaction mixture was then cooled, concentrated under reduced pressure and purified by column chromatography on silica gel eluting with 3% (2M ammonia in methanol) in dichloromethane to give 156 mg of the title compound. $^1$H NMR (500 MHz, CD$_3$OD): δ 8.70 (br s, 1H); 8.31 (br s, 2H); 8.06 (m, 1H); 7.85 (br d, J=6.5 Hz, 2H); 7.56 (t, J=7.8 Hz, 2H); 7.28 (br s, 1H); 6.94 (d, J=6 Hz, 1H); 5.23 (q, J=7.5 Hz); 1.60 (d, J=6.8 Hz); 1.52 (s, 9H).

EXAMPLE 258

2-[(S)-1-(3-Trifluoromethylphenyl)ethylamino]-4-[5-N-(t-butyloxycarbonyl)aminobenzimidazol-1-yl]pyrimidine The title compound was prepared according to the procedure described in EXAMPLE 257, Step C using (S)-1-(3-trifluoromethylphenyl)ethylamine. $^1$H NMR (500 MHz, CDCl$_3$): δ 8.46 (br s, 1H); 8.39 (d, J=5.7 Hz, 1H); 7.80 (s, 1H); 7.70 (s, 1H); 7.53 (d, J=7.8 Hz, 1H); 7.54 (d, J=7.1 Hz, 1H); 7.50 (t, J=7.1 Hz, 1H); 7.36 (br s, 1H); 6.78 (d, J=5.7 Hz, 1H); 6.52 (s, 1H); 5.80 (br s, 1H); 5.25 (br s, 1H); 1.65 (d, J=7.2 Hz, 3H); 1.56 (s, 9H).

EXAMPLE 259

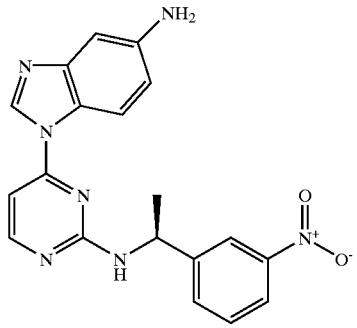

2-[(S)-1-(3-Nitrophenyl)ethylamino]-4-[5-aminobenzimidazol-1-yl]pyrimidine

To a solution of 156 mg of 2-[(S)-1-(3-nitrophenyl)-ethylamino]-4-[5-N-(t-butyloxycarbonyl)-aminobenzimidazol-1-yl]pyrimidine in 5 ml of dichloromethane at 0° C. was added 505 μl trifluoroacetic acid dropwise and the reaction mixture warmed slowly to room temperature. The reaction mixture was concentrated and azeotroped three times with toluene. The residue was dissolved in ethyl acetate and washed with saturated sodium bicarbonate solution and brine, dried (MgSO$_4$) and concentrated under reduced pressure. The crude material was purified by column chromatography on silica get eluting with 60% acetone: 40% hexane to give 115 mg of the title compound. Mass spectrum (ESI): 376 (M+1). $^1$H NMR (500 MHz, CD$_3$OD): δ 8.63 (br s, 1H); 8.33 (br s, 1H); 8.31 (br s, 1H); 8.07 (m, 1H); 7.85 (d, J=8.5 Hz, 1H); 7.56 (t, J=7.5 Hz, 1H); 7.01 (br s, 1H); 6.94 (d, J=5.5 Hz, 1H); 6.78 (br s, 1H); 5.25 (q, J=6.5 Hz, 1H); 1.61 (d, J=7.5 Hz).

EXAMPLE 260

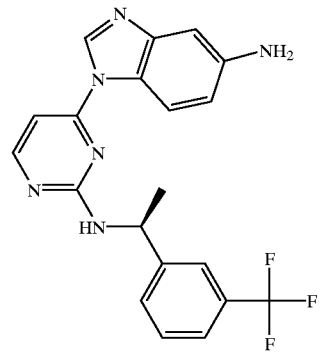

2-[(S)-1-(3-Trifluoromethylphenyl)ethylamino]-4-[5-aminobenzimidazol-1-yl]pyrimidine The title compound was prepared according to the procedure described in EXAMPLE 259 using 2-[(S)-1-(3-trifluoromethylphenyl)ethylamino]-4-[5-N-(t- butyloxycarbonyl)-aminobenzimidazol-1-yl]pyrimidine as the starting material. Mass spectrum (ESI): 399 (M+1). ¹H NMR (500 MHz, CDCl₃): δ 8.34 (br s, 1H); 8.39 (d, J=5.7 Hz, 1H); 7.70 (s, 1H); 7.63 (d, J=7.8 Hz, 1H); 7.54 (d, J=7.1 Hz, 1H); 7.48 (t, J=7.1 Hz, 1H); 7.09 (br s, 1H); 6.75 (d, J=5.7 Hz, 1H); 6.68 (s, 1H); 5.80 (br s, 1H); 5.25 (br s, 1H); 1.65 (d, J=7.2 Hz, 3H).

EXAMPLE 261

2-[(S)-1-(3-Nitrophenyl)ethylamino]-4-[5-N-((1-benzyloxycarbonylpyrrolidin-2-yl)methyl)aminobenzimidazol-1-yl]pyrimidine To a solution of 110 mg of 2-[(S)-1-(3-nitro-phenyl)ethylamino]-4-[5-aminobenzimidazol-1-yl]pyrimidine in 4 ml dichloromethane at room temperature was added 75 mg 1-benzyloxycarbonylpyrrolidine-2-carboxaldehyde and the reaction mixture stirred for 10 minutes before the addition of 93 mg of sodium triacetoxyborohydride. The reaction was stirred for 5 hours and then quenched by pouring into saturated sodium bicarbonate solution, extracting with dichloromethane. The combined dichloromethane extracts were dried (MgSO₄) and concentrated under reduced pressure. The residue was purified by column chromatography on silica gel eluting with 60% acetone:40% hexane to give 128 mg of the title compound. ). Partial ¹H NMR (500 MHz, CD₃OD): δ 8.61 (br s, 1H); 8.33 (br s, 1H); 8.08 (d, J=7.1 Hz, 1H); 7.85 (m, 1H); 7.57 (m, 1H); 7.38–7.18 (m, 4H); 6.98–8.86 (m, 3H); 6.77 (br s, 1H); 6.63 (br s, 1H); 5.27 (m, 1H); 5.20 (s, 1H); 5.12 (s, 1H); 4.13 (m, 2H); 1.61 (d, J=4.5 Hz, 3H).

EXAMPLE 262

2-[(S)-1-(3-Trifluoromethylphenyl)ethylamino]-4-[5-N-((1-benzyloxycarbonylpyrrolidin-2-yl)methyl)aminobenzimidazol-1-yl]pyrimidine The title compound was prepared according to the procedure described in EXAMPLE 261 using 2-[(S)-1-(3-trifluoromethylphenyl)ethylamino]-4-[5-aminobenzimidazol-1-yl]pyrimidine as the starting material. ¹H NMR (500 MHz, CDCl₃): δ 8.39 (m, 2H); 7.70 (s, 1H); 7.62 (d, J=7.8 Hz, 1H); 7.54 (d, J=7.1 Hz, 1H); 7.48 (t, J=7.1 Hz, 1H); 7.45–7.30 (m, 5H); 6.95 (s, 1H); 6.75 (m, 2H); 6.45 (br s, 1H); 5.63 (br s, 1H), 5.20 (m, 3H); 4.90 (br s, 1H) 4.30 (br s, 1H); 4.20 (br s, 1H); 3.95 (br s, 1H); 3.60–3.10 (m, 4H); 1.95 (m, 4H); 1.64 (d, J=4.5 Hz, 3H).

EXAMPLE 263

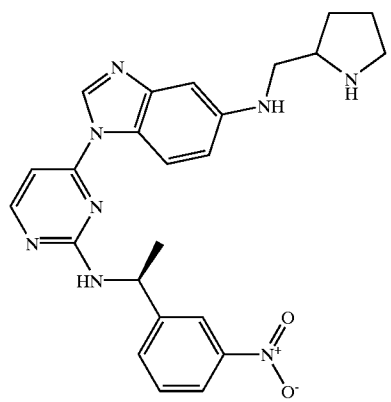

2-[(S)-1-(3-Nitrophenyl)ethylamino]-4-[5-N-((pyrrolidin-2-yl)methyl)aminobenzimidazol-1-yl]pyrimidine To a solution of 128 mg of 2-[(S)-1-(3-nitrophenyl)ethylamino]-4-[5-N-((1-benzyloxycarbonylpyrrolidin-2-yl)methyl)-aminobenzimidazol-1-yl]pyrimidine in dichloromethane at 0° C. was added 2 ml of 30% HBr/AcOH dropwise. The reaction was then stirred at room temperature for 30 minutes before being poured into water and washed with dichloromethane. The dichloromethane layer was discarded and the pH of the aqueous layer was adjusted to pH14 with 5N sodium hydroxide. The basic aqueous layer was then extracted with chloroform three times, checking the pH of the aqueous layer in between extractions and readjusting it with further 5N NaOH. The combined chloroform extracts were dried (MgSO₄) and concentrated under reduced pressure to give 75 mg of the title compound. Mass spectrum (ESI): 459 (M+1). ¹H NMR (500 MHz, CDCl₃): δ 8.33 (m, 3H); 8.13 (d, J=8.3 Hz, 1H); 7.78 (d, J=8.3 Hz, 1H); 7.55 (t, J=8.3 Hz, 1H); 7.38 (s, 1H); 6.99 (br s, 1H); 6.75 (d, J=5.8 Hz, 1H); 6.65 (br s, 1H); 5.69 (br s, 1H); 5.27 (br s, 1H); 3.55 (m, 1H); 3.29 (dd, J=12, 4 Hz, 1H); 3.10 (m, 1H); 3.03 (m, 2H); 2.06–1.70 (m, 1H); 1.67 (d, J=7.4 Hz, 3H); 1.58 (m, 1H).

EXAMPLE 264

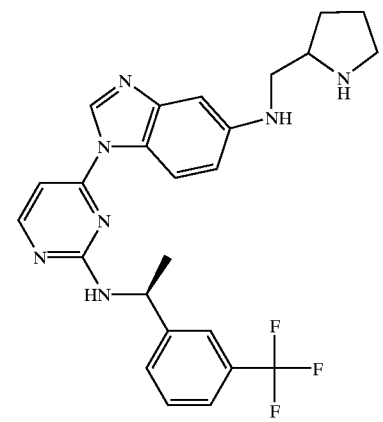

2-[(S)-1-(3-Trifluoromethylphenyl)ethylamino]-4-[5-N-((pyrrolidin-2-yl)methyl)-aminobenzimidazol-1-yl]pyrimidine The title compound was prepared according to the procedure described in EXAMPLE 263 using 2-[(S)-1-(3- trifluoromethylphenyl)ethylamino]-4-[5-N-((1-benzyloxycarbonyl-pyrrolidin-2-yl)methyl)-aminobenzimidazol-1-yl]pyrimidine as the starting material. Mass spectrum (ESI): 482 (M+1). ¹H NMR (500 MHz, CDCl₃): δ 8.38 (br s, 1H); 8.35 (d, J=5.5 Hz; 1H); 7.71 (s, 1H); 7.64 (d, J=7.5 Hz, 1H); 7.55 (d, J=7.8 Hz, 1H); 7.49 (t, J=7.8 Hz, 1H); 7.00 (d, J=2.1 Hz, 1H); 6.76 (d, J=5.5 Hz, 1H); 6.67 (s, 1H); 5.68 (br s, 1H); 5.23 (br s, 1H); 4.41 (br s, 1H); 3.47 (ddd, J=12.1, 7.5, 4.5 Hz, 1H); 3.25, (dd, J=11.9, 4.4 Hz, 1H); 3.01, (dd, J=11.9, 8.2 Hz, 1H); 2.98 (t, J=6.7 Hz, 1H); 1.98 (dddd, J=17.7, 12.6, 7.6, 5.3 Hz, 1H); 1.90–1.71 (m, 2H); 1.65 (d, J=7.1 Hz, 3H); 1.52 (ddt, J=19.2, 8.9, 6.8 Hz, 1H).

EXAMPLE 265

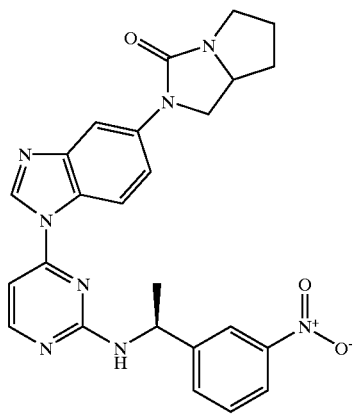

2-[(S)-1-(3-Nitrophenyl)ethylamino]-4-[5-(1,3-diazobicyclo[3.3.0]octan-2-one-3-yl)benzimidazol-1-yl]pyrimidine To a solution of 29 mg of 2-[(S)-1-(3-nitrophenyl)ethylamino]-4-[5-N-((pyrrolidin-2-yl)methyl)-aminobenzimidazol-1-yl]pyrimidine in 1 ml dichloromethane at −30° C. under a nitrogen atmosphere was added 14 μl of triethylamine followed by 7 mg of triphosgene as a solution in 0.5 ml of dichloromethane. After stirring for 45 minutes the reaction mixture was poured into brine and extracted with dichloromethane. The combined dichloromethane extracts were dried (MgSO₄) and concentrated under reduced pressure. The crude material was purified by preparative thin layer preparative chromatography eluting with 10% (2M ammonia in methanol) in dichloromethane to give 3.4 mg of the title compound. Mass spectrum (ESI): 485 (M+1). Partial ¹H NMR (500 MHz, CDCl₃): δ 8.44 (br s, 1H); 8.40 (d, J=5.7 Hz, 1H); 8.14 (m, 1H); 8.03 (br s, 1H); 7.97 (br s, 1H); 7.80 (d, J=8 Hz, 1H); 7.70 (s, 1H); 7.58 (m, 1H); 6.82 (d, J=6 Hz, 1H); 5.77 (br s, 1H); 5.30 (br s, 1H); 4.09 (m, 1H) 3.82 (m, 2H); 1.69 (d, J=7.7 Hz, 3H).

EXAMPLE 266

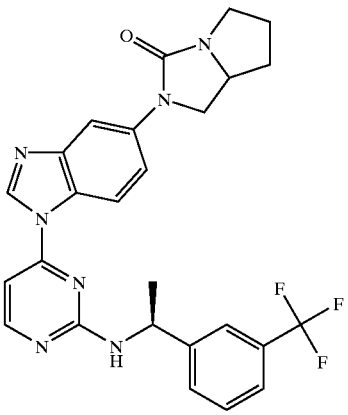

2-[(S)-1-(3-Trifluoromethylphenyl)ethylamino]-4-[5-(1,3-diazobicyclo[3.3.0]octan-2-one-3-yl)benzimidazol-1-yl]pyrimidine The title compound was prepared according to the procedure described in EXAMPLE 265 using 2-[(S)-1-(3-trifluoromethylphenyl)ethylamino]-4-[5-N-((pyrrolidin-2-yl)methyl)-aminobenzimidazol-1-yl]pyrimidine as the starting material. Mass spectrum (ESI): 508 (M+1). ¹H NMR (500 MHz, CDCl₃): δ 8.46 (br s, 1H); 8.40 (d, J=5.8 Hz, 1H); 7.96 (br s, 1H); 7.71, (s, 1H); 7.65 (d, J=7.7 Hz, 1H); 7.53 (m, 2H); 6.81 (d, J=5.7 Hz, 1H); 5.65 (br s, 1H); 5.25 (br s, 1H); 4.09 (t, J=8.8 Hz, 1H); 3.83 (m, 2H); 3.21 (ddd, J=11.3, 8.8, 3.8 Hz, 1H); 2.17–2.04 (m, 2H); 1.93 (m, 1H); 1.66 (d, J=6.5 Hz, 3H).

EXAMPLE 267

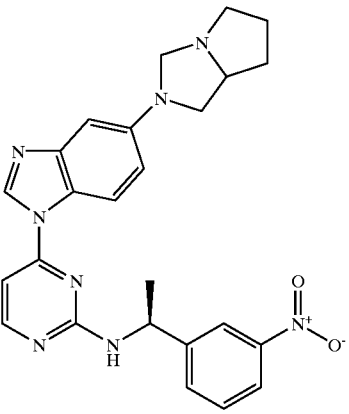

2-[(S)-1-(3-Nitrophenyl)ethylamino]-4-[5-(1,3-diazobicyclo[3.3.0]octan-3-yl)-benzimidazol-1-yl]pyrimidine To a solution of 20 mg of 2-[(S)-1-(3-nitrophenyl)ethylamino]-4-[5-N-((pyrrolidin-2-yl)methyl)-aminobenzimidazol-1-yl]pyrimidine in 250 μl of methanol was added 3.5 mg of aqueous formaldehyde solution. The reaction was then concentrated under reduced pressure, diluted with toluene and concentrated under reduced pressure. This concentration from toluene was then repeated. The residue was then purified by thin layer preparative chromatography eluting with 6% (2M ammonia in methanol) in dichloromethane to give 15 mg of the title compound. Mass spectrum (ESI): 471 (M+1). $^1$H NMR (500 MHz, CDCl$_3$): δ 8.39 (br s, 1H); 8.36 (d, J=5.5 Hz, 1H); 8.33 (br s, 1H); 8.14 (dm, J=9 Hz, 1H) 7.79 (d, J=8 Hz, 1H); 7.55 (t, J=9 Hz, 1H); 6.93 (s, 1H); 6.79 (d, J=5.9 Hz, 1H); 6.61 (br s, 1H); 5.70 (br s, 1H); 5.29 (m, 1H); 4.30 (ABq, J=8.6 Hz, 2H); 3.89 (m, 1H); 3.37 (t. J=8.6 Hz, 1H); 3.26 (m, 1H); 3.21 (dd, J=7.8, 5.2 Hz, 1H); 2.78 (q, J=7.8 Hz, 1H); 2.22 (m, 1H); 2.02 (m, 1H); 1.93 (m, 1H); 1.84 (m, 1H); 1.68 (d, J=6.5 Hz, 3H).

EXAMPLE 268

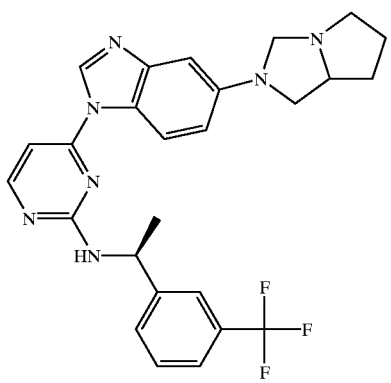

2-[(S)-1-(3-Trifluoromethylphenyl)ethylamino]-4-
[5-(1,3-diazobicyclo[3.3.0]octan-3-yl)benzimidazol-
1-yl]pyrimidine The title compound was prepared according to the procedure described in EXAMPLE 267 using 2-[(S)-1-(3-trifluoro-methylphenyl)ethylamino]-4-[5-((pyrrolidin-2-yl)methyl)-aminobenzimidazol-1-yl]pyrimidine as the starting material. Mass spectrum (ESI): 494 (M+1). $^1$H NMR (500 MHz, CDCl$_3$): δ 8.41 (br s, 1H); 8.35 (d, J=5.5 Hz, 1H); 7.72 (s, 1H); 7.65 (d, J=7.8 Hz, 1H); 7.55 (d, J=8.7 Hz, 1H); 7.49 (t, J=7.8 Hz, 1H); 6.93 (s, 1H); 6.76 (d, J=5.2 Hz, 1H); 6.60 (br s, 1H); 5.80 (br s, 1H); 5.25 (br s, 1H); 4.28 (ABq, J=7.4 Hz, 2H); 3.88 (ddd, J=13.4, 7.4, 3.7 Hz, 1H); 3.36 (t. J=7.5 Hz, 1H); 3.24 (ddd, J=9.6, 7.7, 3.8 Hz, 1H); 3.20 (dd, J=8.5, 6.5 Hz, 1H); 2.78 (q, J=7.7 Hz, 1H); 2.22 (m, 1H); 2.01 (m, 1H); 1.92 (m, 1H); 1.83 (m, 1H); 1.65 (d, J=6.5 Hz, 3H).

EXAMPLE 269

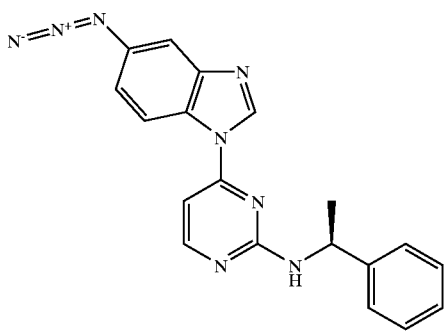

2-[(S)-1-Phenylethylamino]-4-[5-
azidobenzimidazol-1-yl]pyrimidine

A solution of 12 mg of NaNO$_2$ in 0.5 mL of H$_2$O was added to a 5° C. solution of 56 mg of 2-[(S)-1-phenylethylamino]-4-[5-aminobenzimidazol-1-yl]pyrimidine in 2 mL acetic acid. The solution was cooled to 0° C. and stirred for 0.5 hours. A solution of 16.5 mg NaN$_3$ in 0.5 mL H$_2$O was added and stirred for one hour. The solution was diluted with 100 mL of ethyl acetate and washed with water, saturated NaHCO$_3$ and brine. The organic phase was dried over MgSO$_4$, filtered and concentrated under reduced pressure. The residue was purified by flash chromatography eluting with methanol in methylene chloride to give 53 mg of the title compound. R$_F$: 0.6 (5% MeOH in CH$_2$Cl$_2$). $^1$H NMR (400 MHz, 1:1 CD$_3$OD/CDCl$_3$): δ 1.60 (d, J=7.0 Hz, 3H), 5.12 (q, J=7.0 Hz, 1H), 6.8 (m, 1H), 6.95 (d, J=6 Hz, 1H), 7.2–7.45 (m, 6H), 7.72 (m, 1H), 8.33 (br s, J=6.5 Hz, 1H), 8.74 (m, 1H). Mass Spectrum (CH$_3$CN-TFA-NH$_4$HCO$_2$-ESI): 357.1 (M+1).

EXAMPLE 270

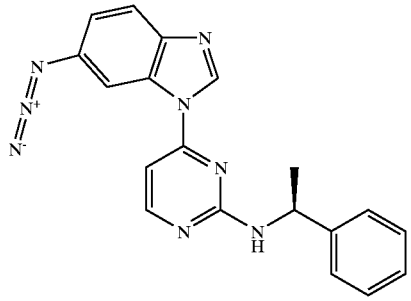

2-[(S)-1-Phenylethylamino]-4-[6-
azidobenzimidazol-1-yl]pyrimidine

A solution of 16.3 mg of NaNO$_2$ in 0.5 mL of H$_2$O was added to a 5° C. solution of 78 mg of 2-[(S)-1-phenylethylamino]-4-[6-aminobenzimidazol-1-yl]pyrimidine in 2 mL acetic acid. The solution was cooled to 0° C. and stirred for 0.5 hours. A solution of 23 mg of NaN$_3$ in 0.5 mL H$_2$O was added and stirred for one hour. The solution was diluted with 100 mL of ethyl acetate and washed with water, saturated NaHCO$_3$ and brine. The organic phase was dried over MgSO$_4$, filtered and concentrated under reduced pressure. The residue was purified by flash chromatography eluting with methanol in methylene chloride to give 62 mg of the title compound. R$_F$: 0.6 (5% MeOH in CH$_2$Cl$_2$). $^1$H NMR (300 MHz, CD$_3$OD): δ1.57 (d, J=7 Hz, 3H), 5.18 (q, J=8 Hz, 1H), 6.88 (d, J=6 Hz, 1H), 7.05 (dd, J=2.5, 9 Hz, 1H), 7.18 (m, 1H), 7.29 (t, J=6 Hz, 2H), 7.43 (d, J=9 Hz, 2H), 7.65 (d, J=9 Hz, 1H), 8.02 (m, 1H), 8.3 (d, J=6 Hz, 1H), 8.69 (b s, 1H). Mass Spectrum (CH$_3$CN-TFA-NH$_4$HCO$_2$-ESI): 357.2 (M+1).

EXAMPLE 271

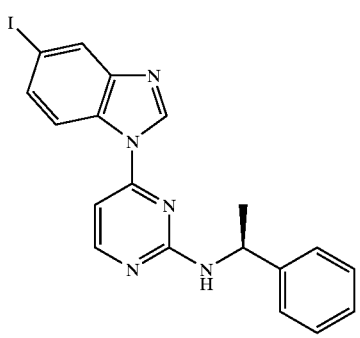

2-[(S)-1-Phenylethylamino]-4-[5-iodobenzimidazol-1-yl]pyrimidine

A solution of 26 mg of NaNO$_2$ in 0.5 mL of H$_2$O was added to a 10° C. solution of 124 mg of 2-[(S)-1-phenylethylamino]-4-[5-aminobenzimidazol-1-yl]pyrimidine in 1.5 mL acetic acid. The solution was cooled to 2° C. and stirred for 0.5 hours. A saturated solution of KI in 0.7 mL H$_2$O was added and stirred for 0.5 hours. Aqueous Na$_2$S$_2$O$_3$ (1 ml) and 5 mL ethyl acetate were added and stirred vigorously at room temperature for one hour. The mixture was added to 100 mL of ethyl acetate and washed with saturated NaHCO$_3$ and brine. The organic phase was dried over MgSO$_4$, filtered and concentrated under reduced pressure. The residue was purified by flash chromatography eluting with methanol in methylene chloride to give 57 mg of the title compound. Also recovered from the chromatography was 84 mg of a mixture containing 70% of the title compound. R$_F$: 0.55 (5% MeOH in CH$_2$Cl$_2$). $^1$H NMR (400 MHz, 3:1 CD$_3$OD/CDCl$_3$): δ 1.60 (d, J=7.0 Hz, 3H), 5.12 (q, J=6.9 Hz, 1H), 6.98 (d, J=5.8 Hz, 1H), 7.2–7.6 (m, 7H), 8.02 (br s, 1H), 8.33 (m, 1H), 8.65–8.78 (m, 1H). Mass Spectrum (CH$_3$CN-TFA-NH$_4$HCO$_2$-ESI): 442 (M+1).

EXAMPLE 272

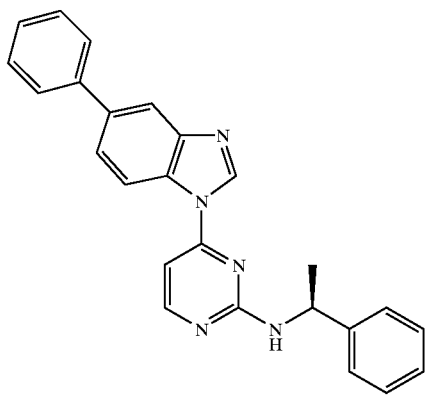

2-[(S)-1-Phenylethylamino]-4-[5-phenylbenzimidazol-1-yl]pyrimidine

A solution containing 27 mg of 2-[(S)-1-phenylethylamino]-4-[5-iodobenzimidazol-1-yl]pyrimidine, 22 mg phenyl boronic acid, 42 mg potasium carbonate, 0.7 mg Pd(PPh$_3$)$_4$, 1.5 mL of H$_2$O and 1.5 mL n-propanol was refluxed under nitrogen for 2 hours. The solution was cooled to room temperature, added to 100 mL of ethyl acetate and washed with saturated NaHCO$_3$ and brine. The organic phase was dried over MgSO$_4$, filtered and concentrated under reduced pressure. The residue was purified by MPLC eluting with methanol in methylene chloride to give 8.7 mg of the title compound. R$_F$: 0.55 (5% MeOH in CH$_2$Cl$_2$). $^1$H NMR (300 MHz, 3:1 CD$_3$OD/CDCl$_3$): δ 1.62 (d, J=6.9 Hz, 3H), 5.17 (q, J=7.0 Hz, 1H), 1H), 7.05 (d, J=5.8 Hz, 1H), 7.2–7.65 (m, 12H), 7.89 (br s, 1H), 8.36 (br s, J=5.6 Hz, 1H), 8.8–8.95 (m, 1H). Mass Spectrum (CH$_3$CN-TFA-NH$_4$HCO$_2$-ESI): 392.3 (M+1).

EXAMPLE 273

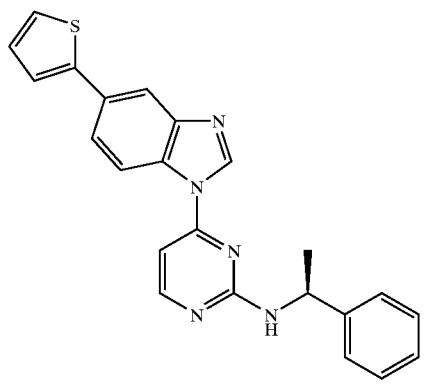

2-[(S)-1-Phenylethylamino]-4-[5-(thiazol-2-yl)benzimidazol-1-yl]pyrimidine

A solution containing 28 mg of 2-[(S)-1-phenylethylamino]-4-[5-iodobenzimidazol-1-yl]pyrimidine, 60 μL 2-(tributylstannyl)-thiophene, 0.7 mg Pd(PPh$_3$)$_4$ and 3 mL DMF was stirred under nitrogen at 100° C. for 2 hours. The solution was cooled to room temperature, added to 100 mL of ethyl ether, washed three times with water and then once with brine. The organic phase was dried over MgSO$_4$, filtered and concentrated under reduced pressure. The residue was purified by flash chromatography eluting with methanol in methylene chloride to give 11.1 mg of the title compound. R$_F$: 0.5 (5% MeOH in CH$_2$Cl$_2$). $^1$H NMR (500 MHz, CD$_3$OD): δ 1.59 (d, J=7.1 Hz, 3H), 5.13 (m, 1H), 6.90 (d, J=5.7 Hz, 1H), 7.06 (dd, J=5.0, 3.7 Hz, 1H), 7.22 (t, J=7.3 Hz, 1H), 7.29–7.54 (m, 7H), 7.76 (m, 1H), 7.86 (br s, 1H), 8.31 (br s, J=5.2 Hz, 1H), 8.68 (m, 1H). Mass Spectrum (CH$_3$CN-TFA-NH$_4$HCO$_2$-ESI): 398.1 (M+1).

EXAMPLE 274

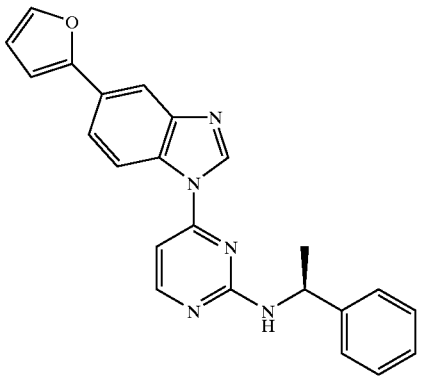

2-1[(S)-1-Phenylethylamino]-4-[5-(furan-2-yl)benzimidazol-1-yl]pyrimidine

The title compound was prepared from 28.5 mg of 2-[(S)-1-phenylethylamino]-4-[5-iodobenzimidazol-1-yl]pyrimidine, 61 μL 2-(tributylstannyl)-furan and 0.75 mg Pd(PPh$_3$)$_4$ using the procedure described in EXAMPLE 273 except that the residue was purified by flash chromatography eluting with acetone in hexane to give 10.6 mg of the title compound. R$_F$: 0.45 (50% acetone in hexane). $^1$H NMR (500 MHz, 3:1 CD$_3$OD/CDCl$_3$): δ 1.61 (d, J=7.1 Hz, 3H), 5.16 (t, J=6.8 Hz, 1H), 6.49 (dd, J=3.4, 1.8 Hz, 1H), 6.73 (d, J=2.7 Hz, 1H), 6.97 (d, J=5.7 Hz, 1H), 7.23 (br s, J=7.3 Hz, 1H), 7.35 (br s, J=7.4 Hz, 2H), 7.44 (br s, J=7.3 Hz, 2H), 7.48–7.9 (m, 3H), 7.95 (br s, 1H), 8.33 (br s, J=5.0 Hz, 1H), 8.7–8.84 (m, 1H). Mass Spectrum (CH$_3$CN-TFA-NH$_4$HCO$_2$-ESI): 382.1 (M+1)

EXAMPLE 275

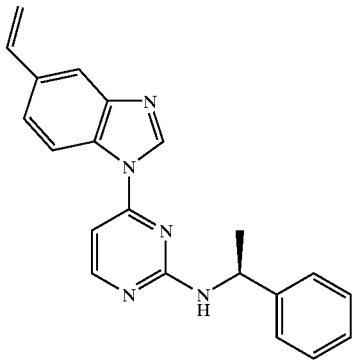

2-[(S)-1-Phenylethylamino]-4-[5-vinylbenzimidazol-1-yl]pyrimidine

The title compound was prepared from 44 mg of 2-[(S)-1-phenylethylamino]-4-[5-iodobenzimidazol-1-yl]pyrimidine, 87 μL tributylstannyl ethylene and 1.15 mg Pd(PPh$_3$)$_4$ using the procedure described in EXAMPLE 273 to give 8.5 mg of the title compound. R$_F$: 0.45 (5% MeOH in CH$_2$Cl$_2$). $^1$H NMR (500 MHz, 1:1 CD$_3$OD/CDCl$_3$): δ 1.59 (d, J=6.8 Hz, 3H), 5.13 (m, 1H), 5.24 (d, J=11.2 Hz, 1H), 5.76 (d, J=17.4 Hz, 1H), 6.79 (dd, J=17.6, 11 Hz, 1H), 6.87 (d, J=5.7 Hz, 1H), 7.21 (br s, J=7.3 Hz, 1H), 7.27–7.34 (m, 3H), 7.41 (br s, J=7.3 Hz, 2H), 7.6–7.8 (m, 1H), 7.67 (br s, 1H), 8.31 (br s, J=5.7 Hz, 1H), 8.55–8.7 (m, 1H). Mass Spectrum (CH$_3$CN-TFA-NH$_4$HCO$_2$-ESI): 342.3 (M+1).

EXAMPLE 276

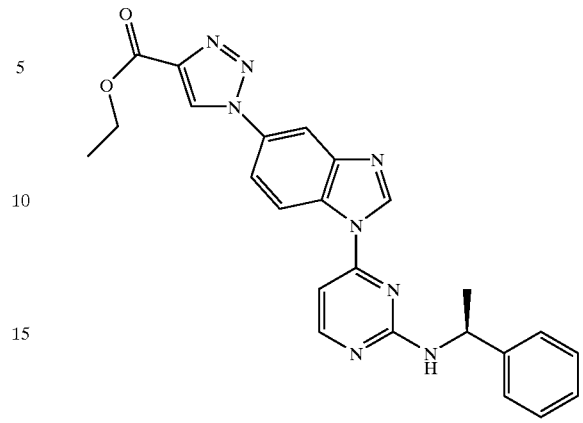

2-[(S)-1-Phenylethylamino]-4-[5-(4-ethoxycarbonyltriazol-1-yl)benzimidazol-1-yl]pyrimidine A solution containing 12.5 mg of 2-[(S)-1-phenylethylamino]-4-[5-azidobenzimidazol-1-yl]pyrimidine and about 100 μL ethyl-3,3-dimethylaminoacrylate in 2 mL 1,4-dioxane was stirred at 90° C. for 48 hours. The solution was concentrated under reduced pressure. The residue was purified by flash chromatography eluting with methanol in methylene chloride to give 6.0 mg of the title compound. R$_F$: 0.4 (5% MeOH in CH$_2$Cl$_2$). $^1$H NMR (500 MHz, 1:1 CD$_3$OD/CDCl$_3$): δ 1.42 (t, J=7.1 Hz, 3H), 1.59 (d, J=7.1 Hz, 3H), 4.44 (q, J=7.1 Hz, 2H), 5.16 (m, 1H), 6.92 (d, J=5.5 Hz, 1H), 7.24 (br s, J=7.3 Hz, 1H), 7.36 (br s, J=7.3 Hz, 2H), 7.45 (d, J=7.3 Hz, 2H), 7.68–7.8 (m, 1H), 7.95 (m, 1H), 8.14 (br s, 1H), 8.38 (br s, J=5.3 Hz, 1H), 8.77 (m, 1H), 8.92 (s, 1H). Mass Spectrum (CH$_3$CN-TFA-NH$_4$HCO$_2$-ESI): 455.2 (M+1).

EXAMPLE 277

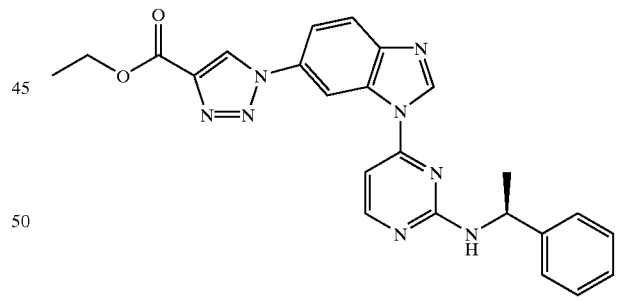

2-[(S)-1-Phenylethylamino]-4-[6-(4-ethoxycarbonyltriazol-1-yl)benzimidazol-1-yl]pyrimidine The title compound was prepared from 266 mg of 2-[(S)-1-phenylethylamino]-4-[6-azidobenzimidazol-1-yl]pyrimidine, about 100 μL ethyl-3,3-dimethylaminoacrylate and 5 mL 1,4-dioxane using the procedure described in EXAMPLE 276 to give 283 mg of the title compound. R$_F$: 0.4 (5% MeOH in CH$_2$Cl$_2$). $^1$H NMR (500 MHZ, DMSO): δ 1.33 (t, J=7.0 Hz, 3H), 1.50 (d, J=6.9 Hz, 3H), 4.38 (q, J=7.1 Hz, 2H), 5.24 (m, 1H), 7.05–7.45 (m, 5H), 7.87 (d, J=8.6 Hz, 1H), 7.94 (d, J=8.0 Hz, 1H), 8.2 (m, 1H), 8.44 (m, 1H), 8.91 (m, 1H), 9.14 (br s, 1H), 9.50 (s, 1H). Mass Spectrum (CH₃CN-TFA-NH₄HCO₂-ESI): 455.2 (M+1).

EXAMPLE 278

2-[(S)-1-phenylethylamino]-4-[6-(4-tributylstannyl-triazol-1-yl)benzimidazol-1-yl]pyrimidine A solution containing 95 mg of 2-[(S)-1-phenylethylamino]-4-[6-azidobenzimidazol-1-yl]pyrimidine and 386 μL tributyl-ethynylstannane in 2 mL 1,4-dioxane was stirred at 100° C. for 48 hours under 1 atm of nitrogen. The solution was concentrated under reduced pressure. The residue was purified by flash chromatography eluting with methanol in methylene chloride to give 139 mg of the title compound. R$_F$: 0.4 (5% MeOH in CH₂Cl₂). ¹H NMR (500 MHz, CD₃OD): δ0.91 (t, J=7.4 Hz, 3H), 1.25 (t, J=8.1 Hz, 2H), 1.39 (m, 2H), 1.57 (d, J=6.9 Hz, 3H), 1.65 (m, 2H), 5.22 (q, J=7.1 Hz, 1H), 7.03 (d, J=5.5 Hz, 1H), 7.0–7.4 (m, 5H), 7.76 (m, 1H), 7.85 (d, J=8.7 Hz, 1H), 8.35 (d, J=5.3 Hz, 1H), 8.50 (s, 1H), 8.91 (m, 2H). Mass Spectrum (CH₃CN-TFA-NH₄HCO₂-ESI): 673.2 (M+1).

EXAMPLE 279

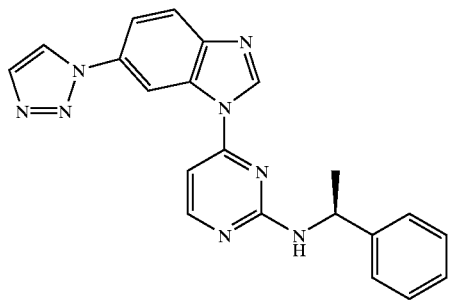

2-[(S)-1-Phenylethylamino]-4-[6-triazol-1-yl)benzimidazol-1-yl]pyrimidine

A room temperature solution containing 30.3 mg of 2-[(S)-1-phenylethylamino]-4-[6-(4-tributylstannyl-triazol-1-yl)benzimidazol-1-yl]pyrimidine in 3 mL of methanol was treated with 1 mL of 12 N HCl in water. After stirring for ½ hour, the reaction was diluted with 100 mL EtOAc and 25 mL water. NaHCO₃ was added until the pH was greater than 7. The organic phase was washed with saturated NaCl, dried over Na₂SO₄, filtered and concentrated under reduced pressure. The residue was purified by flash chromatography eluting with methanol in methylene chloride to give 12.7 mg of the title compound. R$_F$: 0.4 (5% MeOH in CH₂Cl₂). ¹H NMR (500 MHz, 1:1 CD₃OD/CDCl₃): δ 1.60 (d, J=6.9 Hz, 3H), 5.24 (m, 1H), 7.02 (br s, J=4.3 Hz, 1H), 7.1–7.4 (m, 5H), 7.74 (m, 1H), 7.86 (d, J=8.7 Hz, 1H), 7.90 (d, J=1.2 Hz, 1H), 8.34 (m, 2H), 8.85 (m, 2H). Mass Spectrum (CH₃CN-TFA-NH₄HCO₂-ESI): 383.2 (M+1).

EXAMPLE 280

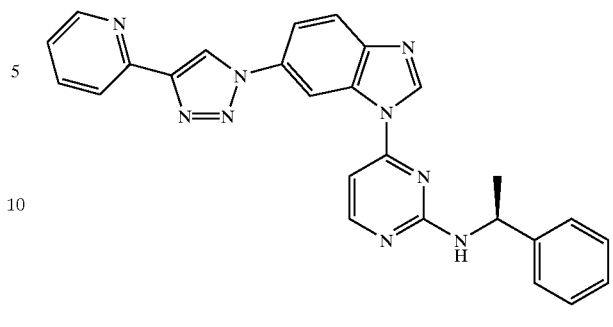

2-[(S)-1-Phenylethylamino]-4-[6-(4-(pyridine-2-yl)triazol-1-yl)benzimidazol-1-yl]pyrimidine The title compound was prepared from 30.5 mg of 2-[(S)-1-phenylethylamino]-4-[6-(4-tributylstannyl-triazol-1-yl)benzimidazol-1-yl]pyrimidine, 36.3 mg 2-bromopyridine and 0.5 mg Pd(PPh₃)₄ using the procedure described in EXAMPLE 273 except that the the reaction mixture was stirred for 16 hours. The residue was purified by flash chromatography eluting with acetone in hexanes to give 2.0 mg of the title compound. ¹H NMR (500 MHz, 1:1 CD₃OD/CDCl₃): δ 1.64 (d, J=6.8 Hz, 3H), 5.28 (m, 1H), 7.0–7.35 (m, 5H), 7.40 (br s, 6.4 Hz, 1H), 7.54 (t, J=7.1 Hz, 1H), 7.84 (m, 1H), 7.93 (d, J=8.4 Hz, 1H), 8.11 (t, J=7.5 Hz, 1H), 8.32 (d, J=8.3 Hz, 1H), 8.36 (m, 1H), 8.65 (d, J=4.6 Hz, 1H), 8.83–9.2 (m, 3H). Mass Spectrum (CH₃CN-TFA-NH₄HCO₂-ESI): 460.2 (M+1).

EXAMPLE 281

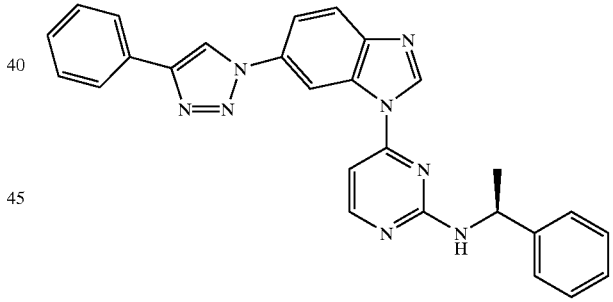

2-[(S)-1-Phenylethylamino]-4-[5-(4-phenyltriazol-1-yl)benzimidazol-1-yl]pyrimidine The title compound was prepared from 32.2 mg of 2-[(S)-1-phenylethylamino]-4-[6-(4-tributylstannyl-triazol-1-yl)benzimidazol-1-yl]pyrimidine, an excess of iodobenzene and Pd(PPh₃)₄ using the procedure described in EXAMPLE 273 except that the the reaction mixture was stirred for 16 hours. The residue was purified by flash chromatography eluting with acetone in hexanes to give 4.9 mg of the title compound. R$_F$: 0.4 (50% acetone in hexanes). ¹H NMR (500 MHz, 3:1 CD₃OD/CDCl₃): δ 1.61 (d, J=7.1 Hz, 3H), 5.25 (m, 1H), 7.05 (m, 1H), 7.06–7.25 (m, 3H), 7.37 (m, 4H), 7.45 (t, 7.3 Hz, 2H), 7.79 (m, 1H), 7.88 (t, 9 Hz, 3H) 8.35 (m, 1H), 8.70 (m, 1H), 8.85 (m, 1H). Mass Spectrum (CH₃CN-TFA-NH₄HCO₂-ESI): 459.2 (M+1).

EXAMPLE 282

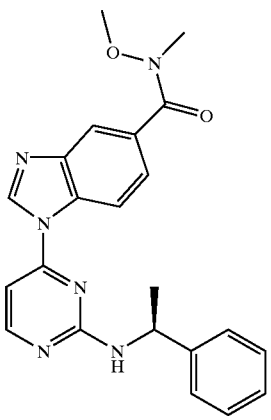

2-[(S)-1-phenylethylamino]-4-[5-(N-methyl-N-methoxyaminocarbonyl)benzimidazol-1-yl]pyrimidine

Step A: 5-(N-methyl-N-methoxyaminocarbonyl) benzimidazole

To a suspension of 5-benzimidazolecarboxylic acid (1.62 g, 10 mmol) in $CH_2Cl_2$ (30 mL) was added N,O-dimethylhydroxylamine (1.17 g, 12 mmol), N-methylmorpholine (1.65 mL, 15 mmol), and 1-(3-dimethylaminopropyl)-3-ethylcarbodiimide hydrochloride (2.3 g, 12 mmol), respectively at room temperature. After stirring for 24 h, the reaction mixture was filtered to remove solid and rinsed thoroughly with $CH_2Cl_2$. The combined filtrate was concentrated under reduced pressure. The crude product was purified by flash chromatography using 5% MeOH/$CH_2Cl_2$ as an eluent to obtain 890 mg of the title compound. Partial $^1H$ NMR (500 MHz, $CDCl_3$): δ 8.02 (s, 2H); 7.59 (d, J=7.6 Hz, 2H); 3.58 (s, 3H); 3.4 (s, 3H).

Step B: 2-Methylthio-4-[5-(N-methyl-N-methoxyaminocarbonyl)benzimidazol-1-yl]pyrimidine and 2-methylthio-4-[6-(N-methyl-N-methoxyaminocarbonyl)benzimidazol-1-yl]pyrimidine To a suspension of NaH (210 mg, 60% suspension in oil, 5.21 mmol) in DMF (10 mL) at 0° C. was added 5-(N-methyl-N-methoxyaminocarbonyl)benzimidazole (890 mg, 4.34 mmol) dissolved in DMF (10 mL) dropwise. The ice bath was removed, and the reaction mixture was stirred until the mixture became homogeneous (10 min) then added 2-methylthio-4-chloropyrimidine (610 μL, 5.21 mmol). The mixture was heated at 100° C. for 1.5 h then cooled down to 0° C. and quenched with $H_2O$ carefully. The reaction mixture was poured in to a separatory funnel and extracted with EtOAc. The combined extracts were washed with $H_2O$ followed by brine and dried over $Na_2SO_4$. The crude material was purified by flash chromatography (1:200 crude material:silica gel) using 1% MeOH/EtOAc system to obtain 516 mg of 2-methylthio-4-[5-(N-methyl-N-methoxyaminocarbonyl)-benzimidazol-1-yl]pyrimidine and 429 mg of 2-methylthio-4-[6-(N-methyl-N-methoxyaminocarbonyl)benzimidazol-1-yl]pyrimidine. 2-methylthio-4-[5-(N-methyl-N-methoxyaminocarbonyl)-benzimidazol-1-yl]pyrimidine: Partial $^1H$ NMR (500 MHz, $CDCl_3$): δ 8.71 (s, 1H); 8.65 (d, J=5.5 Hz, 1H); 8.25 (s, 1H); 8.24 (d, J=8.5 Hz, 1H); 7.82 (d, J=5.5 Hz, 1H); 7.22 (d, J=5.5 Hz, 1H); 3.58 (s, 3H); 3.42 (s, 3H); 2.68 (s, 3H). 2-methylthio-4-[6-(N-methyl-N-methoxyaminocarbonyl)-benzimidazol-1-yl]pyrimidine: Partial $^1H$ NMR (500 MHz, $CDCl_3$): δ 8.75 (s, 1H); 8.64 (d, J=5.5 Hz, 1H); 8.63 (s, 1H); 7.87 (d, J=8.5 Hz, 1H); 7.77 (d, J=8.5 Hz, 1H); 7.23 (d, J=5.5 Hz, 1H); 3.6 (s, 3H); 3.42 (s, 3H); 2.68 (s, 3H).

Step C: 2-[(S)-1-phenylethylamino]-4-[5-(N-methyl-N-methoxyaminocarbonyl)benzimidazol-1-yl] pyrimidine To a solution of 2-methylthio-4-[5-(N-methyl-N-methoxyaminocarbonyl)benzimidazol-1-yl]pyrimidine (115.5 mg, 0.35 mmol) in $CH_2Cl_2$/MeOH (1 mL/3 mL) at 0° C. was added a slurry of potassium peroxymonosulfate (Oxone®) (650 mg, 1.05 mmol) in $H_2O$ (2 mL). After stirring 10 min at 0° C., the mixture was stirred at room temperature for 2 h. It was diluted with $H_2O$ and extracted with $CH_2Cl_2$. The combined extracts were washed with brine and dried over $Na_2SO_4$. After removal of solvent, 126 mg of crude sulfone was obtained. The sulfone was dissolved in DMF (0.5 mL) and toluene (3 mL) and to this was added (S)-1-phenylethylamine (100 μL, 0.77 mmol). The mixture was heated at 100° C. for 6 h, cooled and diluted with EtOAc. It was washed with $H_2O$ followed by brine and dried over $Na_2SO_4$. The crude material was purified by flash chromatography using 1:2 acetone:hexane followed 1:1 acetone:hexane system to obtain 113 mg of the title compound. Partial $^1H$ NMR (500 MHz, $CDCl_3$): δ 8.49 (br s, 1H); 8.36 (d, J=5.5 Hz, 1H); 8.18 (s, 1H); 7.65 (br s, 1H); 7.43–7.25 (m, 5H); 6.74 (d, J=5.5 Hz, 1H); 5.16 (br s, 1H); 3.56 (s, 3H); 3.39 (s, 3H); 1.62 (d, J=6.9 Hz, 3H). Mass spectrum 403.2 (ESI, M+1).

EXAMPLE 283

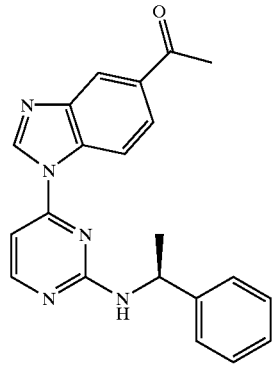

2-[(S)-1-phenylethylamino]-4-[5-(methylcarbonyl)-benzimidazol-1-yl]pyrimidine

To a solution of methylmagnesium bromide (980 μL, 1.4 M, 13.8 mmol) in $CH_2Cl_2$ (0.5 mL) at 0° C. was added 2-[(S)-1-phenylethylamino]-4-[5-(N-methyl-N-methoxyaminocarbonyl)-benzimidazol-1-yl]pyrimidine (55.4 mg, 0.138 mmol) in $CH_2Cl_2$ (1.0 mL) slowly. The reaction mixture was warmed to room temperature slowly and continued stirring for 5 h. The reaction mixture was quenched with saturated aqueous $NH_4Cl$ then extracted with $CH_2Cl_2$. The combined extracts were washed with brine and dried over $Na_2SO_4$. The crude material was purified by preparative thin layer chromatography eluting with 3% MeOH/$CH_2Cl_2$ to obtain 38 mg of the title compound.

Partial ¹H NMR (500 MHz, CDCl₃): δ 8.5 (br s, 1H); 8.4 (s, 1H); 8.38 (d, J=5.5 Hz, 1H); 7.93 (br s, 1H); 7.79 (br s, 1H); 7.44–7.28 (m, 5H); 6.74 (d, J=5.2 Hz, 1H); 5.17 (br s, 1H); 2.68 (s, 3H); 1.63 (d, J=6.8 Hz, 3H). Mass spectrum 358.2 (CI, M+1).

EXAMPLE 284

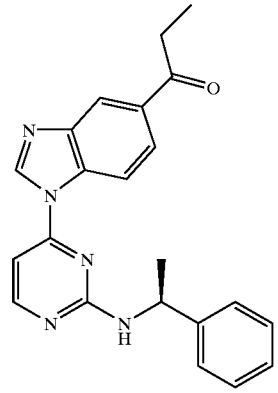

2-[(S)-1-phenylethylamino]-4-[5-(ethylcarbonyl)-benzimidazol-1-yl]pyrimidine

The title compound was prepared according to the procedure described in EXAMPLE 283 using ethylmagnesium bromide. Partial ¹H NMR (500 MHz, CDCl₃): δ 8.49 (br s, 1H); 8.4 (s, 1H); 8.37 (d, J=5.0 Hz, 1H); 7.94 (br s, 1H); 7.78 (br s, 1H); 7.44–7.28 (m, 5H); 6.74 (d, J=5.5 Hz, 1H); 5.16 (br s, 1H); 3.08 (q, J=7.3 Hz, 2H); 1.63 (d, J=7.1 Hz, 3H); 1.26 (t, J=7.3 Hz, 3H). Mass spectrum 372.1 (LC-MS, M+1).

EXAMPLE 285

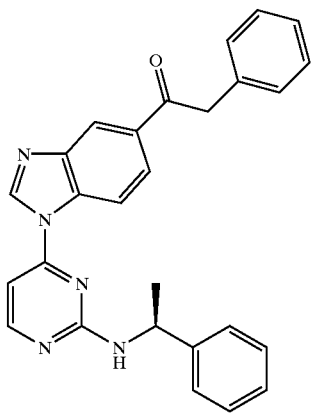

2-[(S)-1-phenylethylamino]-4-[5-(benzylcarbonyl)-benzimidazol-1-yl]pyrimidine

The title compound was prepared according to the procedure described in EXAMPLE 283 using benzylmagnesium chloride. Partial ¹H NMR (500 MHz, CDCl₃): δ 8.48 (br s, 2H); 8.4 (d, J=5.2 Hz, 1H); 7.94 (br s, 1H); 7.75 (br s, 1H); 7.43–7.24 (m, 10H); 6.74 (d, J=5.5 Hz, 1H); 5.15 (br s, 1H); 4.36 (s, 2H); 1.63 (d, J=7.1 Hz, 3H). Mass spectrum 434.1 (LC-MS, M+1).

EXAMPLE 286

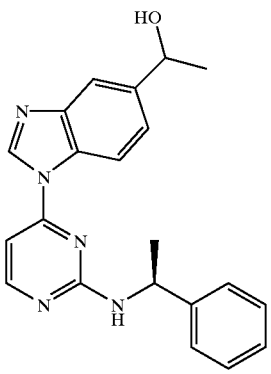

2-[(S)-1-phenylethylamino]-4-[5-(1-hydroxyethyl)-benzimidazol-1-yl]pyrimidine

To solution of 2-[(S)-1-phenylethylamino]-4-[5-(N-methyl-N-methoxyaminocarbonyl)-benzimidazol-1-yl]pyrimidine (44 mg, 0.11 mmol) in THF (1.1 mL) at −78° C. was added DIBAL-H (220 μL, 1.5M in toluene) dropwise. After stirring 30 minutes at −78° C., the bath was removed and added EtOAc to quench excess DIBAL-H followed by 1N HCl. The reaction mixture was poured in a separatory funnel and extracted with CH₂Cl₂. The combined organic layers were washed with brine and dried over Na₂SO₄. The solvent was removed under reduced pressure and dried to obtain 31.6 mg of crude aldehyde. The slurry of aldehyde in CH₂Cl₂ (1.0 mL) was added to the solution of CH₃MgBr (390 μL, 1.4M) in CH₂Cl₂ (0.2 mL) dropwise. The mixture was slowly warmed to 0° C. over 2 h, then quenched with saturated aqueous NH₄Cl. The reaction mixture was extracted with CH₂Cl₂, and the combined extracts were washed with brine and dried over Na₂SO₄. The product was purified by preparative thin layer chromatography eluting with 1:1 acetone:hexane to give 20.6 mg of the title compound. Partial ¹H NMR (500 MHz, CDCl₃): δ 8.41 (br s, 1H); 8.31 (d, J=5.0 Hz, 1H); 7.77 (br s, 1H); 7.42–7.25 (m, 6H); 6.68 (d, J=5.3 Hz, 1H); 5.17 (br s, 1H); 5.02 (m, 1H); 1.61 (d, J=6.9 Hz, 3H); 1.55 (d, J=6.5 Hz, 3H). Mass spectrum 360.2 (ESI, M+1).

EXAMPLE 287

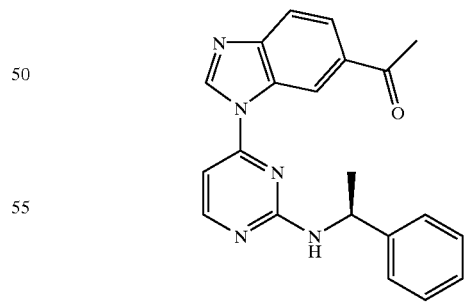

2-[(S)-1-phenylethylamino]-4-[6-(methylcarbonyl)-benzimidazol-1-yl]pyrimidine

Step A: 2-methylthio-4-[6-(methylcarbonyl)benzimidazol-1-yl]pyrimidine

To a solution of 2-methylthio-4-[6-(N-methyl-N-methoxyaminocarbonyl)benzimidazol-1-yl]pyrimidine (26 mg, 0.079 mmol) in CH$_2$Cl$_2$ (0.8 mL) at 0° C. was added CH$_3$MgBr (255 µL, 1.4M) dropwise and stirred for 3 h at 0° C. The reaction mixture was quenched with saturated aqueous NH$_4$Cl and extracted with CH$_2$Cl$_2$. The combined extracts were washed with brine and dried over Na$_2$SO$_4$. The crude material was purified by preparative thin layer chromatography eluting with 3% MeOH/CH$_2$Cl$_2$ to obtain 15.7 mg of the title compound. Partial $^1$H NMR (500 MHz, CDCl$_3$): δ 8.94 (s, 1H); 8.79 (s, 1H); 8.67 (d, J=5.0 Hz, 1H); 8.04 (d, J=7.5 Hz, 1H); 7.9 (d, J=7.5 Hz, 1H); 7.28 (d, J=5.0 Hz, 1H); 2.74 (s, 6H).

Step B: 2-[(S)-1-phenylethylamino]-4-[6-(methylketo)-benzimidazol-1-yl]-pyrimidine The title compound was prepared according to the procedure described in EXAMPLE 27, Step C starting with 2-methylthio-4-[6-(methylcarbonyl)-benzimidazol-1-yl]pyrimidine. Partial $^1$H NMR (500 MHz, CDCl$_3$): δ 8.79 (s, 1H); 8.6 (br s, 1H); 8.36 (br s, 1H); 7.96 (d, J=7.5 Hz, 1H); 7.84 (d, J=7.5 Hz, 1H); 7.45–7.23 (m, 5H); 6.79 (d, J=5.2 Hz, 1H); 5.18 (m, 1H); 2.65 (s, 3H); 1.63 (d, J=6.8 Hz, 3H). Mass spectrum 358.3 (ESI, M+1) and 399.3 (ESI, M+CH$_3$CN+1).

EXAMPLE 288

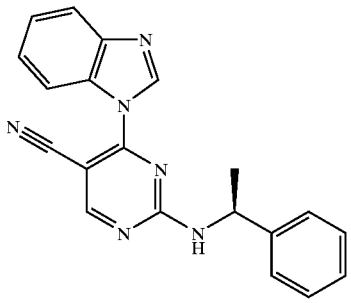

2-[(S)-1-phenylethylamino]-4-[benzimidazol-1-yl]-5-cyanopyrimidine

Step A: 2-Ethylthio-4-hydroxy-5-cyanopyrimidine

To a solution of potassium hydroxide (640 mg, 10 mmol) in methanol (6 mL) at 0° C. was added 2-ethyl-2-thiopseudourea (1.85 g, 10 mmol). The mixture was warmed to room temperature, stirred for 5 min, then filtered off potassium bromide under N$_2$. The filtrate was cooled down to 0° C. then ethyl (ethoxymethylene)cyanoacetate (420 mg, 2.5 mmol) was added. The mixture was gradually warmed to room temperature and stirred for 20 h. The solvent was removed under reduced pressure, and the crude material was purified by flash chromatography using 4% 2M NH$_3$ in MeOH/CH$_2$Cl$_2$ system to obtain 288 mg of the title compound. Mass spectrum 181 (EI, M$^+$).

Step B: 2-Ethylthio-4-chloro-5-cyanopyrimidine

To a solution of 2-ethylthio-4-hydroxy-5-cyanopyrimidine (196 mg, 1.08 mmol) in 1,4-dioxane (5 mL) was added (chloro-methylene)dimethylammonium chloride (550 mg, 4.32 mmol). The mixture was heated at 100° C. for 4 h, cooled, and the solvent was removed under reduced pressure. The crude material was purified by flash chromatography using 1:20 acetone:hexane system to yield 130 mg of the title compound. Mass spectrum 199.3 (EI, M$^+$).

Step C: 2-Ethylthio-4-(benzimidazol-1-yl)-5-cyanopyrimidine

To a suspension of sodium hydride (31 mg, 0.78 mmol) in DMF (2.5 mL) at 0° C. was added benzimidazole (86 mg, 0.72 mmol). After stirring for 5 min, the reaction mixture was warmed to room temperature. To this was added 2-ethylthio-4-chloro-5-cyanopyrimidine (130 mg, 0.65 mmol) dissolved in DMF (1.0 mL), then the mixture was heated at 100° C. for 1 h. The reaction mixture was cooled and carefully diluted with H$_2$O. The aqueous layer was extracted with EtOAc several times, and the combined extracts were washed with brine. After drying over Na$_2$SO$_4$, the crude material was purified by flash chromatography using 1:7 acetone:hexane system to give 126 mg of the title compound. Mass spectrum 282.2 (ESI, M+1).

Step D: 2-[(S)-1-phenylethylamino]-4-[benzimidazol-1-yl]-5-cyanopyrimidine

The title compound was prepared according to the procedure described in EXAMPLE 25, Step B using (S)-1-phenylethylamine. Partial $^1$H NMR (500 MHz, CDCl$_3$): δ 8.86 (s, 1H); 8.52 (s, 1H); 8.28 (d, J=8 Hz, 1H); 7.81 (d, J=8 Hz, 1H); 7.45–7.3 (m, 6H); 6.0 (d, J=6.6 Hz, 1H); 5.42 (m, 1H); 1.74 (d, J=7.0 Hz, 3H). Mass spectrum 340.2 (EI, M$^+$).

EXAMPLE 289

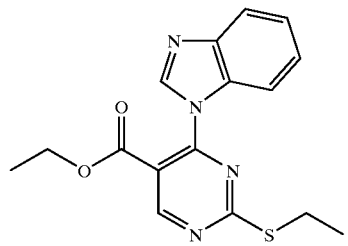

2-Ethylthio-4-(benzimidazol-1-yl)-5-(ethyloxycarbonyl)pyrimidine

Step A: 2-(Ethylthio)-4-hydroxy-5-(ethyloxycarbonyl)pyrimidine

The title compound was prepared according to the procedure described in EXAMPLE 288, Step A using diethyl ethoxymethylenemalonate. The product was purified by recrystallization. Mass spectrum 228.1 (EI, M$^+$).

Step B: 2-Ethylthio-4-chloro-5-(ethyloxycarbonyl)pyrimidine

The title compound was prepared from 2-(Ethylthio)-4-hydroxy-5-(ethyloxycarbonyl)pyrimidine according to the procedure described in EXAMPLE 288, Step B. Mass spectrum 246.2 (EI, M$^+$).

Step C: 2-Ethylthio-4-(benzimidazol-1-yl)-5-(ethyloxycarbonyl)pyrimidine

The title compound was prepared from 2-Ethylthio-4-chloro-5-(ethyloxycarbonyl)pyrimidine according to the procedure described in EXAMPLE 288, Step C. Mass spectrum 329.3 (CI, M+1).

EXAMPLE 290

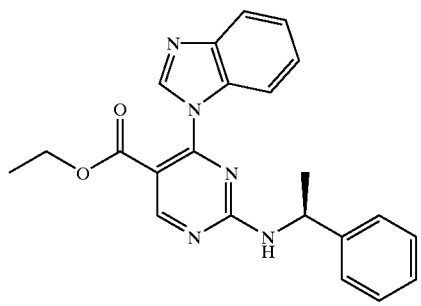

2-[(S)-1-phenylethylamino]-4-[benzimidazol-1-yl]-
5-(ethyloxycarbonyl)pyrimidine The title compound was prepared according to the procedure described in EXAMPLE 282, Step C starting from 2-Ethylthio-4-(benzimidazol-1-yl)-5-(ethyloxycarbonyl)pyrimidine. Mass spectrum 388.4 (EI, M+1).

EXAMPLE 291

2-Ethylsulfonyl-4-(benzimidazol-1-yl)-5-methylpyrimidine

Step A: 2-(Ethylthio)-4-hydroxy-5-methylpyrimidine

To a solution of ethyl propionate (1.2 mL, 10 mmol) in DMF (1 mL) was added sodium methoxide (740 mg, 13 mmol), and to this was added ethyl formate (560 µL, 6.7 mmol) very slowly over 1 h period. The reaction mixture was stirred for 30 min then 2-ethyl-2-thiopseudourea (1.3 g, 6.7 mmol) in methanol (2.5 mL) was added at once. The mixture was heated and maintained at reflux for 2 h, cooled to room temperature and acidified to pH 6 with concentrated HCl. The resulting slurry was kept in ice bath for 30 minutes. The solid was collected and was rinsed with methanol. The solid was dried under vacuum to give 154 mg of the title compound. Mass spectrum 171.1 (CI, M+1).

Step B: 2-(Ethylthio)-4-chloro-5-methylpyrimidine

The title compound was prepared from 2-(Ethylthio)-4-hydroxy-5-methylpyrimidine according to the procedure described in EXAMPLE 288, Step B. $^1$H NMR (500 MHz, CDCl$_3$): δ 8.28 (s, 1H); 3.15 (q, J=7.3 Hz, 2H); 2.28 (s, 3H); 1.4 (t, J=7.3 Hz, 3H).

Step C: 2-Ethylthio-4-(benzimidazol-1-yl)-5-methylpyrimidine

The title compound was prepared from 2-(ethylthio)-4-chloro-5-methylpyrimidine according to the procedure described in EXAMPLE 288, Step C. $^1$H NMR (500 MHz, CDCl$_3$): δ 8.59 (s, 1H); 8.26 (s, 1H); 7.89 (m, 1H); 7.65 (m, 1H); 7.39 (m, 2H); 3.2 (q, J=7.3 Hz, 2H); 2.33 (s, 3H); 1.42 (t, J=7.3 Hz, 3H).

Step D: 2-Ethylsulfonyl-4-(benzimidazol-1-yl)-5-methylpyrimidine

To a solution of 2-Ethylthio-4-(benzimidazol-1-yl)-5-methylpyrimidine (127.5 mg, 0.47 mmol) in methanol (1.2 mmol) at 0° C. was added slurry of potassium peroxymonosulfate (Oxone®) (870 mg, 1.41 mmol) in H$_2$O (1.2 mL). The mixture was stirred at room temperature for 4 h, and was then diluted with H$_2$O. The aqueous layer was extracted with CH$_2$Cl$_2$, and the combined organic layer was washed with H$_2$O followed by brine. The organic extract was dried over Na$_2$SO$_4$ then purified (20 mg of crude material) by preparative thin layer chromatography eluting with 1:1 acetone-:hexane system to give the title compound. Mass spectrum 303 (ESI, M+1).

EXAMPLE 292 omitted

EXAMPLE 293

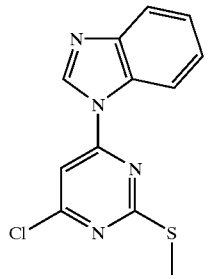

2-Methylthio-4-(benzimidazol-1-yl)-6-chloropyrimidine

The title compound was prepared according to the procedure described in EXAMPLE 288, Step C using 2-methylthio-4,6-dichloropyrimidine. Mass spectrum 277.1 (CI, M+1).

EXAMPLE 294

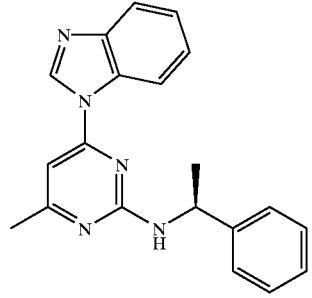

2-[(S)-1-Phenylethylamino]-4-[benzimidazol-1-yl]-6-methylpyrimidine

Step A: 2-[(S)-1-Phenylethylamino]-4-hydroxy-6-methylpyrimidine

To a solution of (S)-1-phenylethylguanidine (1 g, 6.13 mmol, 1 eq) [prepared by condensation of (S)-1-phenylethylamine with methylthiopseudourea sulfate in refluxing aqeous sodium bicarbonate] in methanol (5.8 mL) was added a solution of 25% NaOMe in MeOH (4.2 mL, 18.39 mmol, 3 eq). To this stirred solution was added methyl acetoacetate (0.66 mL, 6.13 mmol, 1 eq) dropwise via syringe. The mixture was allowed to stir overnight. The methanol was removed by warming under a flow of air. The residue was dissolved in 20 mL water, acidified with concentrated aqueous HCL and extracted with ether and the ether layer discarded. The aqueous layer was neutralized and extracted with ethyl acetate. The organic extracts were combined and dried over anhydrous Na₂SO₄, filtered and concentrated. The material was purified by flash column chromatography to give 181 mg of the title compound. Mass spectrum (NH₃/CI): 230.2 (M+1).

Step B: 2-[(S)-1-Phenylethylamino]-4-chloro-6-methylpyrimidine

To a solution of 2-[(S)-1-phenylethylamino]-4-hydroxy-6-methylpyrimidine (100 mg, 0.436 mmol, 1 eq) in chloroform (2 mL) was added (chloromethylene) dimethylammonium chloride (Vilsmeier reagent) (55.9 mg, 0.436 mmol, 1 eq). After 1 hour the solvent was removed under reduced pressure. The product was purified by silica gel chromatography (eluted with 3:1 hexanes/acetone) to give 19.8 mg of the title compound. Mass spectrum (NH3/CI): 248.1 (M+1).

Step C: 2-[(S)-1-Phenylethylamino]-4-[benzimidazol-1-yl]-6-methylpyrimidine

To a solution of 2-[(S)-1-phenylethylamino]-4-chloro-6-methylpyrimidine (11 mg, 0.044 mmol, 1 eq) in DMF (0.2 mL) was added a solution of benzimidazole sodium salt (0.088 mL of a 1M solution, 0.088 mmol, 2 eq). The mixture was warmed to 100° C. for 2 h. The mixture was cooled and the DMF was removed under reduced pressure. The residue was purified by preparative thin layer chromatography (eluted with 2:1 hexanes/acetone to give 9.9 mg of the title compound. ¹H NMR (500 MHz, CDCl₃): δ 1.23 (3H, d, J=7 Hz), 2.45 (3H, s), 5.2 (1H br s), 5.62 (1H, br s), 6.6 (1H, s), 7.2–7.5 (7H, m), 7.8 (2H, d, J=8 Hz), 8.46 (1H, br s). Mass spectrum (NH₃/CI): 330.1 (M+1).

EXAMPLE 295

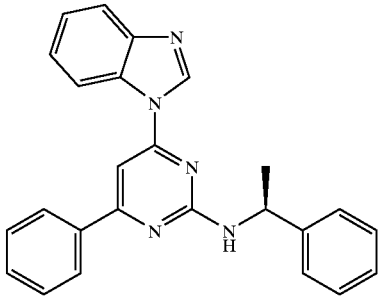

2-[(S)-1-Phenylethylamino]-4-[benzimidazol-1-yl]-6-phenylpyrimidine

The title compound was prepared according to the 3 step procedure described in EXAMPLE 294 using ethyl benzoylacetate. Mass spectrum (CH₃CN/TFA/NH₄O₂CH/ESI) 392.4 (M+1).

EXAMPLE 296

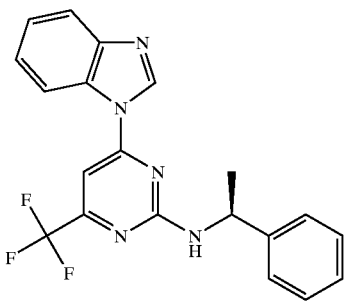

2-[(S)-1-Phenylethylamino]-4-[benzimidazol-1-yl]-6-tri-fluoromethylpyrimidine

The title compound was prepared according to the 3-step procedure described in EXAMPLE 294 using ethyl trifluoroacetoacetate. Mass spectrum (NH₃/CI) 384.3 (M+1).

EXAMPLE 297

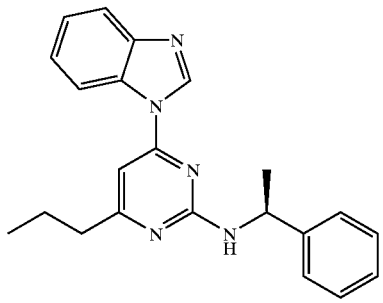

2-[(S)-1-Phenylethylamino]-4-[benzimidazol-1-yl]-6-propylpyrimidine

Step A: 2-Ethylthio-4-hydroxy-6-propylpyrimidine

To a cooled solution (0° C.) of potassium hydroxide (973 mg) in methanol (7 mL) was added 2-ethyl-2-thiopseudourea hydrobromide (2.8 g). The temperature was raised to room temperature and stirred under nitrogen for 10 min. The KBr was filtered off and the reaction mixture was cooled to 0° C. To this was added ethyl butyrylacetate (612 mg), and the reaction was stirred at room temperature for 16 h. Removal of solvent followed by purification on silica gel column (10% acetone/hexane) gave 410 mg of the title compound as a white solid. Partial ¹H NMR (500 MHz, CDCl₃): δ 6.07 (s, 1H); 3.21 (q, J=7.3 Hz, 2H); 2.48 (t, J=7.6 Hz, 2H); 1.70 (m, J=7.4 Hz, 2H); 1.39 (t, J=7.3 Hz, 3H); 0.97 (t, J=7.3 Hz, 3H).

Step B: 2-Ethylthio-4-chloro-6-propylpyrimidine

To the solution of 2-ethylthio-4-hydroxy-6-propylpyrimidine (406 mg) in CHCl₃ (6 mL) was added (chloromethylene)-dimethylammonium chloride (Villsmier reagent) (786 mg). The reaction was stirred at room temperature under nitrogen for 40 min. Filtration through silica gel followed by removal of solvent provided 380 mg of the title compound as yellowish oil. ¹H NMR (500 MHz, CDCl₃): δ 6.81 (s, 1H); 3.17 (q, J=7.3 Hz, 2H); 2.65 (t, J=7.5 Hz, 2H); 1.76 (m, J=7.6 Hz, 2H); 1.41 (t, J=7.3 Hz, 3H); 0.99 (t, J=7.3 Hz, 3H).

Step C: 2-Ethylthio-4-[benzimidazol-1-yl]-6-propylpyrimidine

To a suspension of NaH (76 mg) in DMF (2 mL) was added benzimidazole, and this was followed by addition of 2-ethylthio4-chloro-6-propylpyrimidine dissolved in DMF (3 mL). The reaction mixture was then placed in a 100° C. oil bath. After 1 h, the reaction was cooled to room temperature, quenched with 5 mL of water and extracted with ethyl acetate. The organic layer was washed with saturated NaCl and dried (anhydrous $Na_2SO_4$). Removal of solvent followed by purification on silica gel column (9% acetone/hexane) provided 390 mg of the title compound. Mass spectrum (CI) 298 (M+1). $^1$H NMR (500 MHz, $CDCl_3$): δ 8.69 (s, 1H); 8.17 (d, J=7.6 Hz, 1H); 7.88 (d, J=7.8 Hz, 1H); 7.42 (m, 2H); 7.05 (s, 1H); 3.27 (q, J=7.4 Hz, 2H); 2.78 (t, J=7.5 Hz, 2H); 1.85 (m, 2H); 1.49 (t, J=7.3 Hz, 3H); 1.05 (t, J=7.3 Hz, 3H).

Step D: 2-Ethanesulfonyl-4-[benzimidazol-1-yl]-6-propylpyrimidine

To a solution of 2-ethylthio-4-[benzimidazol-1-yl]-6-propylpyrimidine in MeOH (4 mL) was added a suspension of Oxone® (1.73 g) in water (4 mL). The resulting slurry was stirred at room temperature for 3.5 h. The reaction was diluted with water (10 mL) and extracted with methylene chloride (3×30 mL). The combined organic layer was washed with water, brine and dried (anhydrous $Na_2SO_4$). Removal of solvent gave 295 mg of the title compound which was used directly in the next step. $^1$H NMR (500 MHz, $CDCl_3$): δ 8.76 (s, 1H); 8.37 (d, J=8.0 Hz, 1H); 7.89 (d, J=8.1 Hz, 1H); 7.57 (s, 1H); 7.51 (dd, J=7.3, 8.3 Hz, 1H); 7.46 (dd, J=7.3, 7.6 Hz, 1H); 7.28 (s, 1H); 3.64 (q, J=7.4 Hz, 2H); 2.99 (t, J=7.5 Hz, 2H); 1.92 (m, J=7.5 Hz, 2H); 1.52 (t, J=7.5 Hz, 3H); 1.08 (t, J=7.3 Hz, 3H).

Step E: 2-[(S)-1-Phenylethylamino]-4-[benzimidazol-1-yl]-6-propylpyrimidine

To the suspension of 2-ethanesulfonyl-4-[benzimidazol-1-yl]-6-propylpyrimidine (150 mg) in toluene (3 mL) was added (S)-methylbenzylamine (74 mL). The mixture became homogeneous and was stirred for 3.5 h in a 100° C. oil bath. The reaction was cooled to room temperature. Removal of solvent followed by purification on silica gel column (11% acetone/hexane) gave 295 mg of the title compound. Pure product was obtained by further purification using preparative thin layer chromatography (33% ethyl acetate/hexane). Partial $^1$H NMR (500 MHz, $CDCl_3$): δ 8.48 (br s, 1H); 7.82 (d, 1H); 6.63 (s, 1H); 5.65 (br s, 1H); 5.20 (br s, 1H); 2.64 (t, J=7.5 Hz, 2H); 1.79 (m, J=7.5 Hz, 2H); 1.63 (t, J=7.5 Hz, 3H); 1.03 (t, J=7.3 Hz, 3H).

EXAMPLE 298

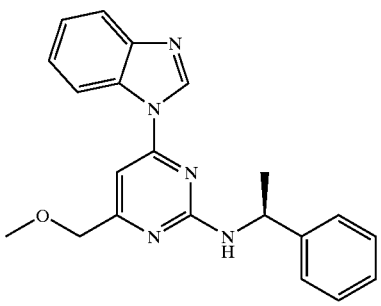

2-[(S)-1-Phenylethylamino]-4-[benzimidazol-1-yl]-6-(methoxy-methyl)pyrimidine

The title compound was prepared from methyl 4-methoxyacetoacetate according to the 5-step procedure described in EXAMPLE 297. Mass spectrum ($NH_3$/CI) 360.2 (M+1).

EXAMPLE 299

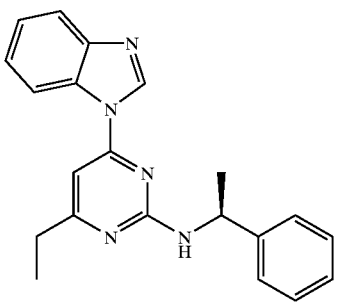

2-[(S)-1-Phenylethylamino]-4-[benzimidazol-1-yl]-6-ethylpyrimidine

The title compound was prepared from ethyl propionylacetate according to the 5 step procedure described in EXAMPLE 297. Mass spectrum ($NH_3$ CI) 344.2 (M+1).

EXAMPLE 300

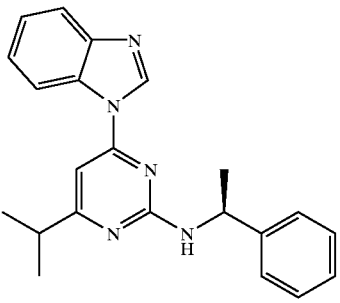

2-[(S)-1-Phenylethylamino]-4-[benzimidazol-1-yl]-6-(1-methyl-ethyl)pyrimidine

The title compound was prepared from methyl isobutyrylacetate according to the 5-step procedure described in EXAMPLE 297. Mass spectrum ($NH_3$ CI) 358.0 (M+1).

EXAMPLE 301

Omitted

EXAMPLE 302

Omitted

EXAMPLE 303

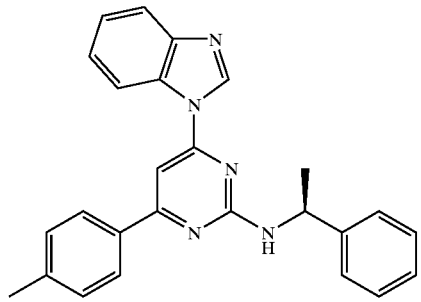

2-[(S)-1-Phenylethylamino]-4-[benzimidazol-1-yl]-
6-(4-methyl-phenyl)pyrimidine

Step A: Potassium Ethyl Malonate

To a solution of diethyl malonate (10 g, 62.4 mmol, 1 eq) in absolute ethanol (40 mL) was added a solution of potassium hydroxide (4.2 g, 65.52 mmol, 1.05 eq) in absolute ethanol (40 mL) at room temperature over 30 minutes. The mixture was allowed to stir for 3 days. The precipitate was collected, washed with ether and dried under reduced pressure.

Step B: Ethyl 4-methylbenzoylacetate

To a stirred suspension of potassium ethyl malonate (1.62 g, 9.51 mmol, 2.1 eq) in acetonitrile (14 mL) at 10° C. under nitrogen was added triethylamine (1.8 mL) followed by $MgCl_2$ (1.1 g, 11.3 mmol, 2.5 eq). The mixture was allowed to stir at room temperature for 2.5 hours. The mixture was cooled to 0° C. and 4-methylbenzoyl chloride (700 mg, 4.53 mmol, 1 eq) was added dropwise over 15 minutes followed by addition of triethylamine (0.3 mL). The mixture was allowed to warm to room temperature and was stirred overnight. The solvent was removed under reduced pressure. The residue was dissolved in ethyl acetate and cooled to 10° C. The solution was washed (cautiously) with 4N aqueous HCl. The aqueous layer was back extracted with ethyl acetate. The organic extracts were combined, washed with water and brine, dried over anhydrous $Na_2SO_4$, filtered and concentrated. The residue was dissolved in aqueous 2N NaOH and extracted 3× with diethyl ether. The ether extracts were combined, washed with water, then brine, dried over anhydrous $Na_2SO_4$, filtered and concentrated. The title compound was used in the next step without further purification.

Step C: 2-[(S)-1-Phenylethylamino]-4-[benzimidazol-1-yl]-6-(4-methylphenyl)pyrimidine The title compound was prepared from ethyl 4-methylbenzoylacetate according to the 5-step procedure described in EXAMPLE 297. Mass spectrum (CI) 406.3 (M+1).

EXAMPLE 304

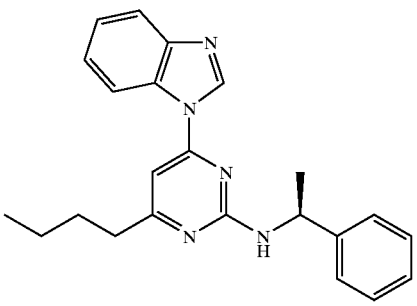

2-[(S)-1-Phenylethylamino]-4-[benzimidazol-1-yl]-
6-butylpyrimidine

The title compound was prepared from methyl pentanoylacetate according to the 5-step procedure described in EXAMPLE 297. Mass spectrum (CI) 372.2 (M+1).

EXAMPLE 305 omitted

EXAMPLE 306

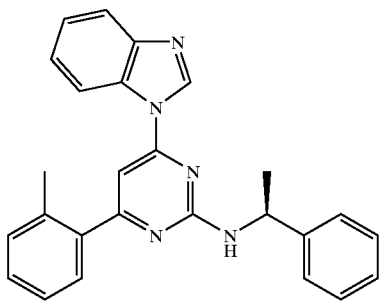

2-[(S)-1-Phenylethylamino]-4-[benzimidazol-1-yl]-
6-(2-methyl-phenyl)pyrimidine

Step A: 2-[(S)-1-Phenylethylamino]-4,6-dichloropyrimidine

To a solution of (S)-1-phenylethylamine (2.6 mL) in THF (20 mL) at room temperature was added 2,4,6-trichloropyrimidine (1.83 g) dissolved in THF (10 mL) dropwise. The reaction mixture was stirred for 2 h, and then the solid was filtered and washed thoroughly with EtOAc. Combined filtrate was concentrated under reduced pressure, and the crude product was purified by flash chromatography (silica, 1:2), followed by 1:6 EtOAc:hexanes) to give 2-[(S)-1-phenylethylamino]-4,6-dichloropyrimidine (1.2 g) and 4-[(S)-1-phenylethylamino]-2,6-dichloropyrimidine (1.5 g). 2-[(S)-1-phenylethylamino]-4,6-dichloropyrimidine $^1$H NMR (500 MHz, $CDCl_3$): δ 7.4–7.25 (m, 5H); 6.6 (s, 1H); 5.65 (br s, 1H); 5.2 (m, 1H); 1.58 (d, J=7.1 Hz, 3H). Mass spectrum (CI) 268.2 (M+1). 4-[(S)-1-phenylethylamino]-2,6-dichloropyrimidine $^1$H NMR (500 MHz, $CDCl_3$): δ 7.41–7.3 (m, 5H); 6.1 (br s, 1H); 5.8 (br s, 1H); 4.6 (br s, 1H); 1.6 (d, J=7.1 Hz, 3H). Mass spectrum (CI) 268.2 (M+1).

Step B: 2-[(S)-1-Phenylethylamino]-4-[benzimidazol-1-yl]-6-chloropyrimidine

To a suspension of NaH (74 mg) in DMF (5 mL) at 0° C. was added benzimidazole (204 mg). The reaction mixture was stirred at 0° C. until gas evolution ceased, then stirred at room temperature until the mixture became homogeneous (ca. 10 min.). A solution of 2-[(S)-1-phenylethylamino]-4,6-dichloropyrimidine (412 mg) in DMF (2 mL) was added to the mixture, which was then placed in 100° C. oil bath for 1 h. The reaction mixture was cooled and carefully quenched with water. The layers were separated, and the aqueous layer was extracted $CH_2Cl_2$ (2×15 mL). Combined organic layers was washed with water and brine and dried over anhydrous $Na_2SO_4$. The solvent was concentrated under reduced pressure, and the crude product was purified by flash chromatography (1:5 EtOAc:hexanes) to give 330 mg of the title compound. $^1$H NMR (500 MHz, $CDCl_3$): δ 8.21 (br s, 1H); 7.82 (d, J=7.5 Hz, 1H); 7.75 (br s, 1H); 7.45–7.28 (m, 7H); 6.8 (s, 1H); 5.92 (br s, 1H); 5.2 (br s, 1H); 1.62 (d, J=7.1 Hz, 3H). Mass spectrum (CI) 350.2 (M+1).

Step C: 2-[(S)-1-Phenylethylamino]-4-[benzimidazol-1-yl]-6-(2-methylphenyl)pyrimidine To a solution of 2-[(S)-1-phenylethylamino]-4-[benzimidazol-1-yl]-6-chloropyrimidine (30 mg) and 2-methylphenyboronic acid (18 mg) in 10:1 toluene:EtOH was added 1M $Na_2CO_3$ (0.215 mL) and $Pd(PPh_3)_4$ (5 mg). The resulting mixture was heated and maintained at reflux for 9 h, then cooled and filtered through $MgSO_4$. The filtrate was concentrated under reduced pressure and purified by preparative thin layer chromatography (1:50 EtOAc:$CH_2Cl_2$) to give 17 mg of the title compound. $^1$H NMR (500 MHz, $CDCl_3$): δ 8.58 (br s, 1H); 7.85–7.3 (m, 13H); 6.9 (s, 1H); 5.9 (br s, 1H); 5.25 (br s, 1H); 2.45 (br s, 3H); 1.7 (d, J=7.1 Hz, 3H). Mass spectrum (CI) 406.3 (M+1).

EXAMPLE 307

Omitted

EXAMPLE 308

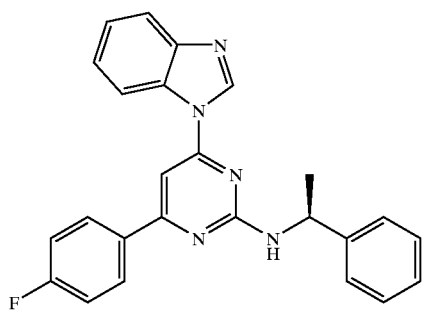

2-[(S)-1-Phenylethylamino]-4-[benzimidazol-1-yl]-6-(4-fluoro-phenyl)pyrimidine

The title compound was prepared according to the procedure described in EXAMPLE 306, Step C using 4-fluorophenylboronic acid. Mass spectrum ($NH_3$/CI) 410.2 (M+1).

EXAMPLE 309

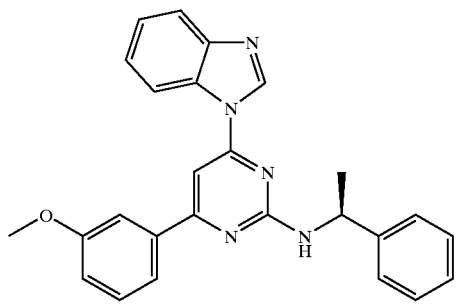

2-[(S)-1-Phenylethylamino]-4-[benzimidazol-1-yl]-6-(3-methoxy-phenyl)pyrimidine

The title compound was prepared according to the procedure described in EXAMPLE 306, Step C using 3-methoxyphenylboronic acid. Mass spectrum ($NH_3$/CI) 422.2 (M+1).

EXAMPLE 310

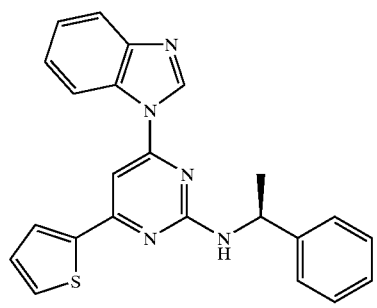

2-[(S)-1-Phenylethylamino]-4-[benzimidazol-1-yl]-6-(thiophen-2-yl)pyrimidine

The title compound was prepared according to the procedure described in EXAMPLE 306, Step C using thiophene-2-boronic acid. Mass spectrum ($CH_3CN$/TFA/$NH_4O_2CH$/ESI) 398.4 (M+1).

EXAMPLE 311

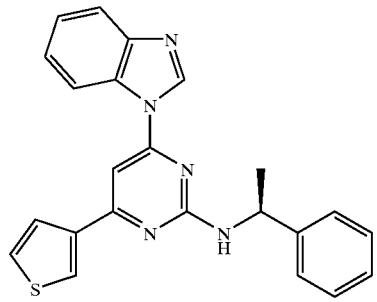

2-[(S)-1-Phenylethylamino]-4-[benzimidazol-1-yl]-6-(thiophen-3-yl)pyrimidine

The title compound was prepared according to the procedure described in EXAMPLE 306, Step C using thiophene-3-boronic acid. Mass spectrum ($CH_3CN$/TFA/$NH_4O_2CH$/ESI) 398.2 (M+1).

EXAMPLE 312

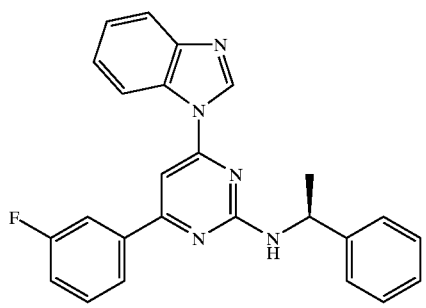

2-[(S)-1-Phenylethylamino]-4-[benzimidazol-1-yl]-
6-(3-fluoro-phenyl)pyrimidine

The title compound was prepared according to the procedure described in EXAMPLE 306, Step C using 3-fluorophenylboronic acid. Mass spectrum (CH$_3$CN/TFA/NH$_4$O$_2$CH/ESI) 410.5 (M+1).

EXAMPLE 313

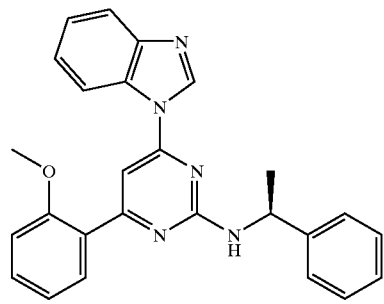

2-[(S)-1-Phenylethylamino]-4-[benzimidazol-1-yl]-
6-(2-methoxy-phenyl)pyrimidine The title compound was prepared according to the procedure described in EXAMPLE 306, Step C using 2-methoxyphenylboronic acid. Mass spectrum (NH$_3$/CI) 422.3 (M+1).

EXAMPLE 314

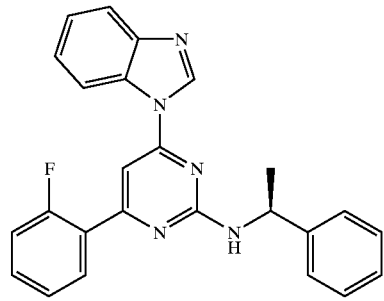

2-[(S)-1-Phenylethylamino]-4-[benzimidazol-1-yl]-
6-(2-fluoro-phenyl)pyrimidine

The title compound was prepared according to the procedure described in EXAMPLE 306, Step C using 2-fluorophenylboronic acid. Mass spectrum (NH$_3$/CI) 410.2 (M+1).

EXAMPLE 315

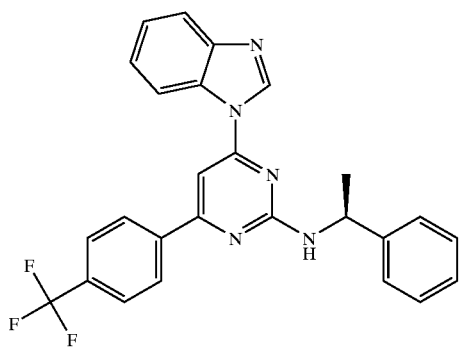

2-[(S)-1-Phenylethylamino]-4-[benzimidazol-1-yl]-
6-(4-trifluoromethylphenyl)pyrimidine The title compound was prepared according to the procedure described in EXAMPLE 306, Step C using 4-trifluoromethylphenylboronic acid. Mass spectrum (NH$_3$/CI) 460.2 (M+1).

EXAMPLE 316

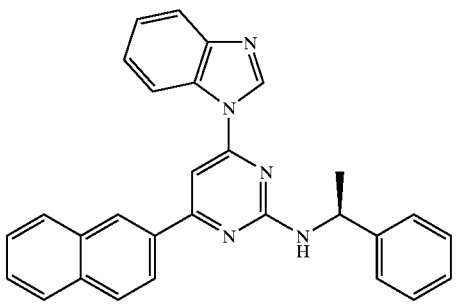

2-[(S)-1-Phenylethylamino]-4-[benzimidazol-1-yl]-
6-(naphth-2-yl)pyrimidine

The title compound was prepared according to the procedure described in EXAMPLE 306, Step C using 2-naphthylboronic acid. Mass spectrum (NH$_3$/CI) 442.3 (M+1).

EXAMPLE 317

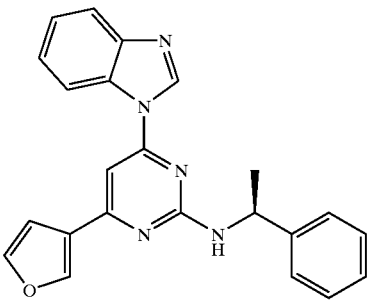

2-[(S)-1-Phenylethylamino]-4-[benzimidazol-1-yl]-
6-(furan-3-yl)pyrimidine

The title compound was prepared according to the procedure described in EXAMPLE 306, Step C using furan-3- boronic acid and [1,1'-bis(diphenylphosphino)ferrocene] dichloropalladium(II) as catalyst. Mass spectrum (CH₃CN/TFA/NH₄O₂CH/ESI) 382.4 (M+1).

EXAMPLE 318
omitted

EXAMPLE 319

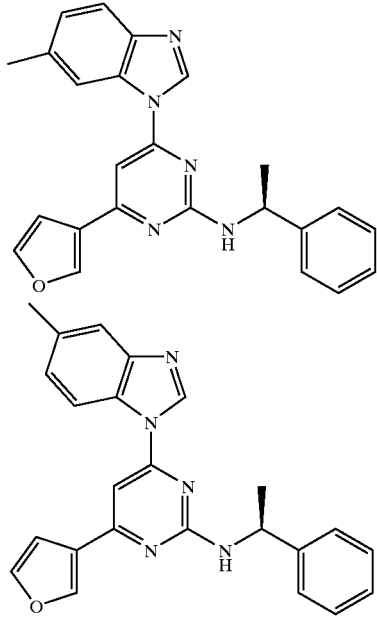

2-[(S)-1-Phenylethylamino]-4-[6-methylbenzimidazol-1-yl]-6-(furan-3-yl)pyrimidine and 2-[(S)-1-Phenylethylamino]-4-[5-methylbenzimidazol-1-yl]-6-(furan-3-yl)pyrimidine Step A: 2-[(S)-1-Phenylethylamino]-4-[5-methylbenzimidazol-1-yl]-6-chloropyrimidine and 2-[(S)-1-Phenylethylamino]-4-[6-methylbenzimidazol-1-yl]-6-chloropyrimidine The title compounds were prepared according to the procedure described in EXAMPLE 306, Step B using 5-methylbenzimidazole instead of benzimidazole. The mixture of regioisomers was used in the next step without separation.

Step B: 2-[(S)-1-Phenylethylamino]-4-[6-methylbenzimidazol-1-yl]-6-(furan-3-yl)pyrimidine and 2-[(S)-1-Phenylethylamino]-4-[5-methylbenzimidazol-1-yl]-6-(furan-3-yl)pyrimidine The title compounds were prepared from 2-[(S)-1-phenylethylamino]-4-[5-methylbenzimidazol-1-yl]-6-chloropyrimidine and 2-[(S)-1-phenylethylamino]-4-[6-methylbenzimidazol-1-yl]-6-chloropyrimidine and furan-3-boronic acid according to the precedure described in EXAMPLE 306, Step C and using [1,1'-bis(diphenylphosphino)ferrocene]dichloropalladium(II) as catalyst. The regioisomers were separated by HPLC on a Chiralpak AD 2 cm×25 cm column eluted with 90:10 hexanes:ethanol at 10 mL/min. 2-[(S)-1-phenylethylamino]-4-[6-methylbenzimidazol-1-yl]-6-(furan-3-yl)pyrimidine ¹H NMR (500 MHz, CDCl₃): δ 8.47 (br s, 1H), 8.13 (s, 1H), 7.83 (br s, 1H), 7.72 (d, J=8.2 Hz, 1H), 7.54 (s, 1H), 7.5–7.2 (m, 5H), 7.19 (d, J=8.5 Hz, 1H), 6.9 (s, 1H), 6.58 (s, 1H), 5.70 (br s, 1H), 5.29 (br t, 1H), 2.52 (s, 3H), 1.66 (d, J=6.9 Hz, 3H). 2-[(S)-1-phenylethylamino]-4-[5-methylbenzimidazol-1-yl]-6-(furan-3-yl)pyrimidine ¹H NMR (500 MHz, CDCl₃): δ 8.48 (br s, 1H), 8.13 (s, 1H), 7.65 (br s, 1H), 7.62 (s, 1H), 7.54 (s, 1H), 7.50–7.25 (m, 5H), 7.13 (br s, 1H), 6.89(s, 1H), 6.87 (s, 1H0, 5.68 (br s, 1H), 5.23 (br s, 1H0, 2.51 (s, 3H), 1.65 (d, J=6.9 Hz, 3H).

EXAMPLE 320

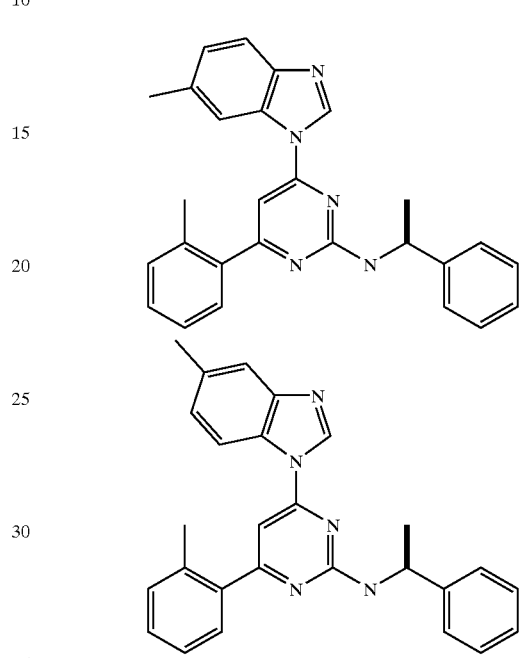

2-[(S)-1-Phenylethylamino]-4-[6-methylbenzimidazol-1-yl]-6-(2-methylphenyl) pyrimidine and 2-[(S)-1-Phenylethylamino]-4-[5-methylbenzimidazol-1-yl]-6-(2-methylphenyl) pyrimidine The title compounds were prepared from 2-[(S)-1-phenylethylamino]-4-[5-methylbenzimidazol-1-yl]-6-chloropyrimidine and 2-[(S)-1-phenylethylamino]-4-[6-methylbenzimidazol-1-yl]-6-chloropyrimidine and 2-methylphenylboronic acid according to the precedure described in EXAMPLE 306, Step C and using [1,1'-bis(diphenylphosphino)ferrocene]dichloropalladium(II) as catalyst. The regioisomers were separated by HPLC on a Chiralpak AD 2 cm×25 cm column eluted with 93:7 hexanes:ethanol at 10 mL/min.

2-[(S)-1-phenylethylamino]-4-[6-methylbenzimidazol-1-yl]-6-(2-methylphenyl) pyrimidine ¹H NMR (500 MHz, CDCl₃): δ 8.50 (br s, 1H), 7.83 (br s, 1H), 7.72 (d, J=8 Hz, 1H), 7.50–7.25 (m, 9H), 7.19 (d, J=8 Hz, 1H), 6.89 (s, 1H), 5.78 (br s, 1H), 5.30 (br s(1H), 2.51 (s, 3H), 2.46 (br s, 3H), 1.66 (d, J=7.1 Hz, 3H).

2-[(S)-1-phenylethylamino]-4-[5-methylbenzimidazol-1-yl]-6-(2-methylphenyl) pyrimidine ¹H NMR (500 MHz, CDCl₃): δ 8.51 (br s, 1H), 7.71 (br s, 1H), 7.62 (s, 1H), 7.50–7.25 (m, 9H), 7.13 (br s, 1H), 6.87 (s, 1H0, 2.51 (s, 3H), 2.46 (br s, 3H), 1.64 (d, J=7.1 Hz, 3H).

EXAMPLE 321

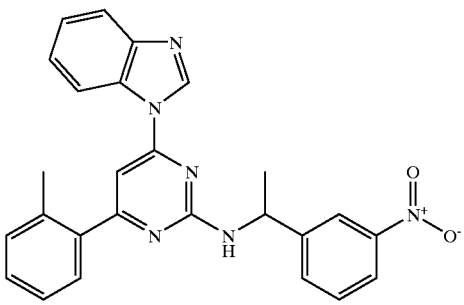

2-[1-(3-Nitrophenyl)ethylamino]-4-[benzimidazol-1-yl]-6-(2-methylphenyl)pyrimidine Step A: 2-[1-(3-Nitrophenyl)ethylamino]-4,6-dichloropyrimidine The title compound was prepared from 1-(3-nitrophenyl) ethylamine and 2,4,6-trichloropyrimidine according to the procedure described in EXAMPLE 306, Step A.

Step B: 2-[1-(3-Nitrophenyl)ethylamino]-4-[benzimidazol-1-yl]-6-chloropyrimidine The title compound was prepared from 2-[1-(3-nitrophenyl)ethylamino]-4,6-dichloropyrimidine and benzimidazole according to the procedure described in EXAMPLE 306, Step B.

Step C: 2-[1-(3-Nitrophenyl)ethylamino]-4-[benzimidazol-1-yl]-6-(2-methylphenyl)pyrimidine The title compound was prepared from 2-[1-(3-nitrophenyl)ethylamino]-4-[benzimidazol-1-yl]-6-chloropyrimidine and 2-methylphenylboronic acid according to the precedure described in EXAMPLE 306, Step C and using [1,1'-bis(diphenylphosphino)-ferrocene] dichloropalladium(II) as catalyst. Mass spectrum (CH$_3$CN/TFA/NH$_4$O$_2$CH/ESI) 451.3 (M+1).

EXAMPLE 322

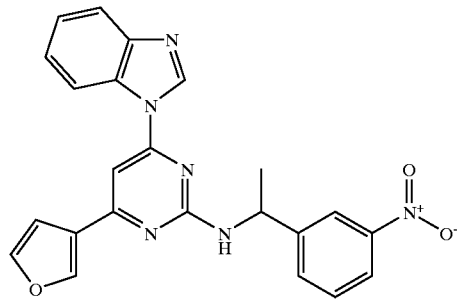

2-[1-(3-Nitrophenyl)ethylamino]-4-[benzimidazol-1-yl]-6-(furan-3-yl)pyrimidine

The title compound was prepared from 2-[1-(3-nitrophenyl)ethylamino]-4-[benzimidazol-1-yl]-6-chloropyrimidine and furan-3-boronic acid according to the precedure described in EXAMPLE 306, Step C and using [1,1'-bis(diphenylphosphino)ferrocene]-dichloropalladium (II) as catalyst. Mass spectrum (CH$_3$CN/TFA/NH$_4$O$_2$CH/ESI) 427.0 (M+1).

EXAMPLE 323

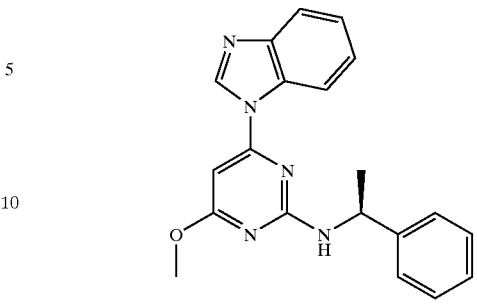

2-[(S)-1-phenylethylamino]-4-[benzimidazol-1-yl]-6-methoxypyrimidine

To a suspension of 2-[(S)-1-phenylethylamino]-4-[benzimidazol-1-yl]-6-chloropyrimidine (EXAMPLE 306 Step B) (34.5 mg, 0.098 mmol) in methanol (1 mL) was added sodium methoxide (56 µL, 25 wt. % in MeOH) dropwise. The mixture was heated at 60° C. for 2 h (the mixture became homogeneous), then was cooled and the solvent was removed under reduced pressure. The crude mixture was purified by flash chromatography using 1:4 EtOAc:hexane system to give 26 mg of the title compound. Mass spectrum 346.0 (CI, M+1).

EXAMPLE 324

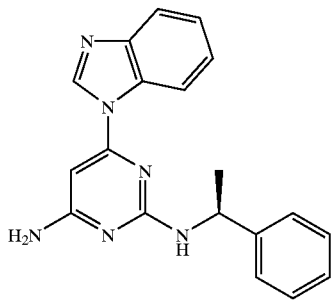

2-[(S)-1-phenylethylamino]-4-[benzimidazol-1-yl]-6-aminopyrimidine

Step A: 2-[(S)-1-phenylethylamino]-4-[benzimidazol-1-yl]-6-azidopyrimidine

To a solution of of 2-[(S)-1-phenylethylamino]-4-[benzimidazol-1-yl]-6-chloropyrimidine (EXAMPLE 306 Step B) (55.8 mg, 0.16 mmol) in DMF (1 mL) was added sodium azide (16 mg, 0.24 mmol) and the mixture was heated at 80° C. for 7 h. It was cooled and diluted with EtOAc, then the organic layer was washed with H$_2$O followed by brine. The organic extract was dried over Na$_2$SO$_4$, and the crude material was purified by flash chromatography using 1:3 EtOAc:hexane to yield 48.8 mg of the title compound. Mass spectrum 357.1 (CI, M+1).

Step B: 2-[(S)-1-phenylethylamino]-4-[benzimidazol-1-yl]-6-aminopyrimidine

To a suspension of of 2-[(S)-1-phenylethylamino]-4-[benzimidazol-1-yl]-6-azidopyrimidine (11 mg, 0.03 mmol) in ethanol (1 mL) was added 10% palladium on carbon (11 mg), then the mixture was charged with H$_2$ via balloon. The reaction mixture was stirred for 2 h, then filtered over packed Celite and rinsed thoroughly with EtOAc. The solvent was concentrated under reduced pressure, and the crude material was purified by preparative thin layer chromatography eluting with 3% MeOH/CH$_2$Cl$_2$ to afford 6.2 mg of the title compound. Mass spectrum 331.2 (CI, M+1).

EXAMPLE 325

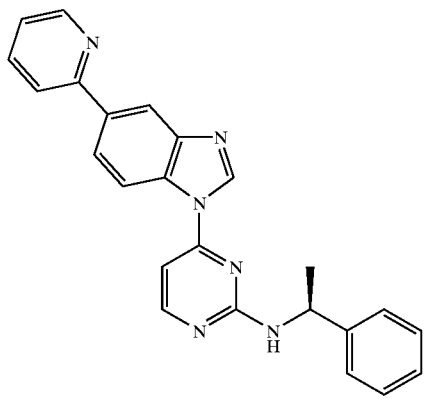

2-[(S)-1-Phenylethylamino]-4-[5-(pyridin-2-yl)-benzimidazol-1-yl]pyrimidine

To a stirred solution of 37 mg of 2-[(S)-1-phenylethylamino]-4-[5-aminobenzimidazol-1-yl]pyrimidine (EXAMPLE 79) in acetic acid (1.0 mL) was added NaNO$_2$ (7.7 mg) in H$_2$O (0.5 mL). The mixture was stirred 1 h at 0° C. Pyridine (1 mL) was added followed by CuCN (9.8 mg). Gas evolution was observed. The reaction mixture was poured into ethyl acetate and washed with water and brine. The organic layer was dried over MgSO$_4$, filtered and concentrated. The product mixture was purified by silica gel chromatography eluting with a gradient solvent system of 100% CH$_2$Cl$_2$ going to 10% MeOH CH$_2$Cl$_2$ giving 18.3 mg of the title compound. Mass spectrum (ESI): 293.3 (M+1).

EXAMPLE 326

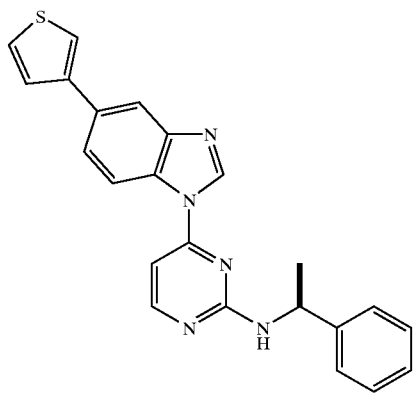

2-[(S)-1-Phenylethylamino]-4-[5-(thiophen-3-yl)-benzimidazol-1-yl]pyrimidine

A stirred solution of 2-[(S)-1-phenylethylamino]-4-[5-iodobenzimidazol-1-yl]pyrimidine (EXAMPLE 271) (37 mg), 3-thiophene boronic acid (16 mg), K$_2$CO$_3$ (35 mg) and Pd(PPh$_3$)$_4$ (0.97 mg) in 1:1 n-propanol:water (4 mL) was stirred under N$_2$ at 100° C. for 16 h. The reaction mixture was cooled and poured into 100 mL EtOAc and washed with water, then brine. The organic layer was dried over anhydrous MgSO$_4$, filtered and concentrated under reduced pressure. The product was purified by silica gel chromatography eluting successively with 10% acetone/hexanes, 20% acetone/hexanes and 30% acetone/hexanes giving 25.3 mg of the title compound. Mass spectrum (ESI): 398.1 (M+1).

EXAMPLE 327

2-[(S)-1-Phenylethylamino]-4-[5-(tributylstannyl)-benzimidazol-1-yl]pyrimidine

A solution of 2-[(S)-1-phenylethylamino]-4-[5-iodobenzimidazol-1-yl]pyrimidine (EXAMPLE 271) (553 mg), hexamethylditin (1.9 mL) and Pd(PPh$_3$)$_4$ (14.5 mg) in xylene (12.5 mL) was stirred under N$_2$ at 100° C. for 2 h. HPLC analysis indicated no reaction had taken place. Pd(PPh$_3$)$_2$Cl$_2$ (25 mg) was added and the mixture was stirred overnight at 100° C. The mixture was cooled to room temperature, filtered through celite, concentrated and purified by column chromatography on silica gel (gradient elution 10% acetone in hexanes going to 50% acetone in hexanes) yielding 227 mg of the title compound. Mass spectrum (ESI): 606.2 (M+1).

EXAMPLE 328

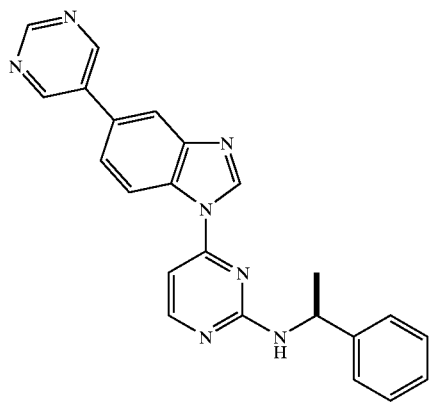

2-[(S)-1-Phenylethylamino]-4-[5-(pyrimidin-5-yl)-benzimidazol-1-yl]pyrimidine

To a stirred solution of 2-[(S)-1-phenylethylamino]-4-[5-(tributylstannyl)-benzimidazol-1-yl]pyrimidine (27.7 mg) in THF (3 mL) was added 5-bromopyrimidine (22 mg), Pd$_2$DBA$_3$ (0.26 mg) and tri-o-tolylphosphine (0.47 mg). The mixture was heated and maintained at reflux for 2 h. Thin layer chromatographic analysis indicated there was mostly starting material present. DMF (3 mL) was added and the THF was removed under a stream of nitrogen. Tetrakis(triphenylphosphine)palladium(0) (1 mg) was added and the mixture was heated under nitrogen and maintained at 100° C. overnight. The mixture was then cooled and poured into 100 mL of 3:1 ether/ethyl acetate and washed 2× with water and then brine. The organic layer was dried over anhydrous Na$_2$SO$_4$, filtered and concentrated. The product was purified by silica gel chromatography eluting with methanol in dichloromethane to give 11.3 mg of the title compound. Mass spectrum (ESI): 394.2 (M+1).

EXAMPLE 329

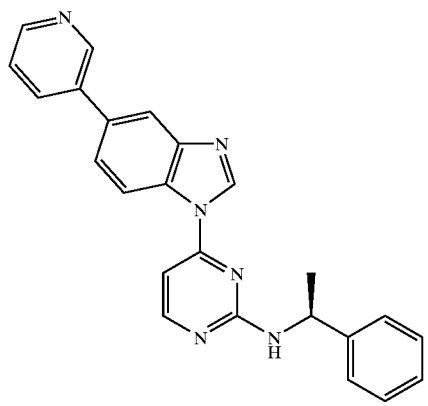

2-[(S)-1-Phenylethylamino]-4-[5-(pyridin-3-yl)-benzimidazol-1-yl]pyrimidine

A stirred solution of 2-[(S)-1-phenylethylamino]-4-[5-(tributylstannyl)-benzimidazol-1-yl]pyrimidine (27 mg), 3-bromopyridine (44 μL) and tetrakis(triphenylphosphine)palladium(0) (0.5 mg) in DMF (4 mL) was heated and maintained at 100° C. overnight. The reaction mixture was cooled and transferred to a separatory funnel containing 100 mL ether plus 25 mL ethyl acetate. The organic layer was washed 3x with water and 1x with brine. The organic layer was dried over anhydrous MgSO$_4$, filtered and concentrated. The product was purified by silica gel chromatography eluting with methanol in dichloromethane to give 9.1 mg of the title compound. Mass spectrum (ESI): 393.2 (M+1).

EXAMPLE 330

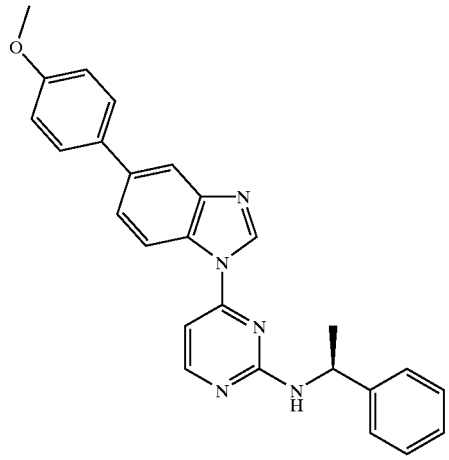

2-[(S)-1-Phenylethylamino]-4-[5-(4-methoxyphenyl)-benzimidazol-1-yl]pyrimidine

The title compound was prepared according to the procedure described in EXAMPLE 326 using 4-methoxyphenyl boronic acid. Mass spectrum (ESI): 422.2 (M+1).

EXAMPLE 331

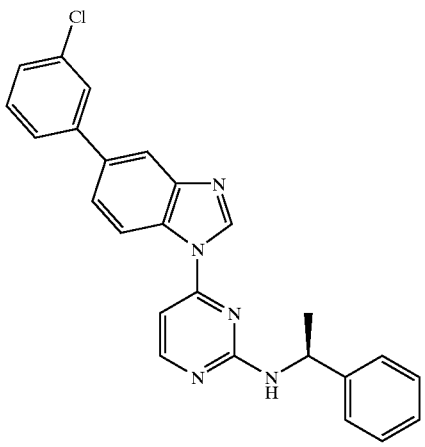

2-[(S)-1-Phenylethylamino]-4-[5-(3-chlorophenyl)-benzimidazol-1-yl]pyrimidine

The title compound was prepared according to the procedure described in EXAMPLE 326 using 3-chlorophenyl boronic acid. Mass spectrum (ESI): 426.1 (M+1).

EXAMPLE 332

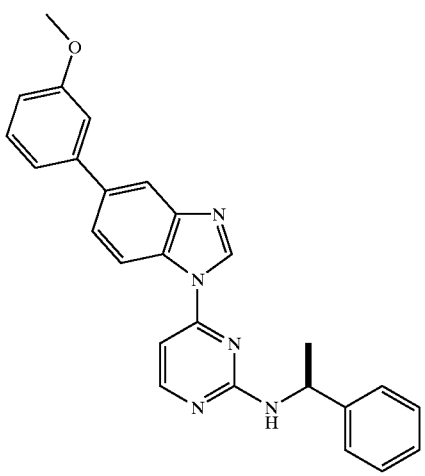

2-[(S)-1-Phenylethylamino]-4-[5-(3-methoxyphenyl)-benzimidazol-1-yl]pyrimidine

The title compound was prepared according to the procedure described in EXAMPLE 329 using 3-iodoanisole. Mass spectrum (ESI): 422.2 (M+1).

EXAMPLE 333

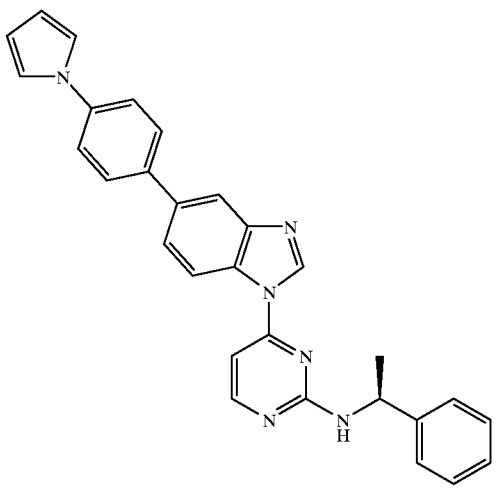

2-[(S)-1-Phenylethylamino]-4-[5-(4-(pyrrol-1-yl)-phenyl)-benzimidazol-1-yl]pyrimidine The title compound was prepared according to the procedure described in EXAMPLE 329 using 1-(4-iodophenyl) pyrrole. Mass spectrum (ESI): 457.2 (M+1).

EXAMPLE 334

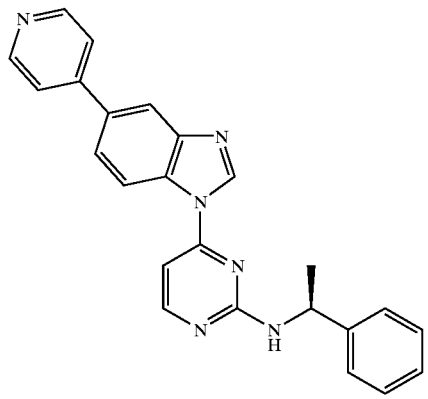

2-[(S)-1-Phenylethylamino]-4-[5-(pyridin-4-yl)-benzimidazol-1-yl]pyrimidine

The title compound was prepared according to the procedure described in EXAMPLE 329 using 4-bromopyridine hydrochloride plus 100 μL diisopropylethylamine and stirring at 80° C. overnight. Mass spectrum (ESI): 393.0 (M+1).

EXAMPLE 335

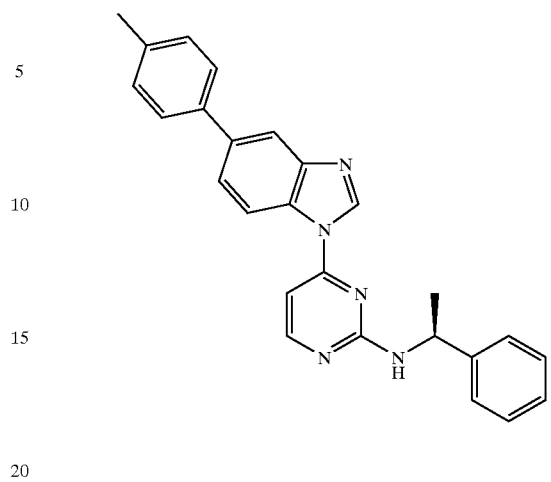

2-[(S)-1-Phenylethylamino]-4-[5-(4-methylphenyl)-benzimidazol-1-yl]pyrimidine

The title compound was prepared according to the procedure described in EXAMPLE 326 using 4-methylphenyl boronic acid. Mass spectrum (ESI): 406.2 (M+1).

EXAMPLE 336

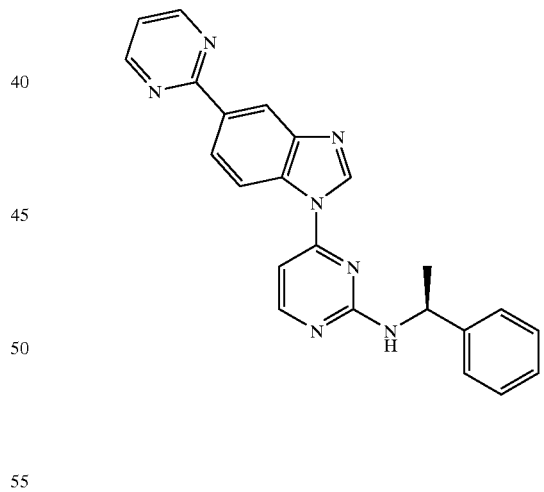

2-[(S)-1-Phenylethylamino]-4-[5-(pyrimidin-2-yl)-benzimidazol-1-yl]pyrimidine

The title compound was prepared according to the procedure described in EXAMPLE 329 using 2-bromopyrimidine plus 100 μL diisopropylethylamine and stirring at 80° C. overnight. Mass spectrum (ESI): 394.0 (M+1).

EXAMPLE 337

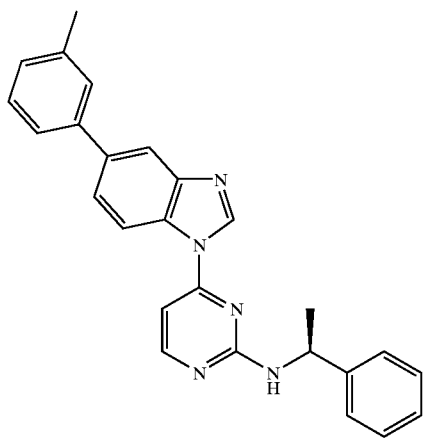

2-[(S)-1-Phenylethylamino]-4-[5-(3-methylphenyl)-benzimidazol-1-yl]pyrimidine

The title compound was prepared according to the procedure described in EXAMPLE 326 using 3-methylphenyl boronic acid. Mass spectrum (ESI): 406.0 (M+1).

EXAMPLE 338

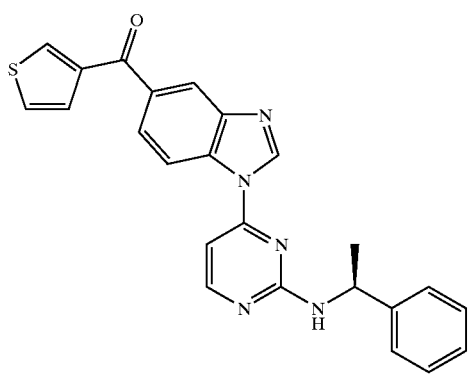

2-[(S)-1-Phenylethylamino]-4-[5-(thiophen-3-yl-carbonyl)-benzimidazol-1-yl]pyrimidine A mixture of 2-[(S)-1-phenylethylamino]-4-[5-iodobenzimidazol-1-yl]pyrimidine (EXAMPLE 271) (66 mg), $K_2CO_3$ (103 mg), 3-thiopheneboronic acid (58 mg) and $Pd(PPh_3)_2Cl_2$ (1 mg) in anisole (6 mL) was stirred overnight at 100° C. under 1 Atm CO. The reaction mixture was poured into a separatory funnel containing 100 mL ethyl acetate and was washed with water and brine. The organic extracts were combined, dried over anhydrous $MgSO_4$, filtered and concentrated. The product was purified by silica gel chromatography (eluted with a gradient of 100% $CH_2Cl_2$ going to 5% MeOH in $CH_2Cl_2$) followed by reverse phase chromatography (eluted with a gradient going from 50% water in methanol (with 0.1% TFA) to 100% methanol (with 0.1% TFA)). The resulting salt was then subjected to preparative thin layer chromatography (eluted with 5% (2N $NH_3$ in MeOH) in $CH_2Cl_2$) to give 6.9 mg of the title compound. Mass spectrum (ESI): 426.0 (M+1).

EXAMPLE 339

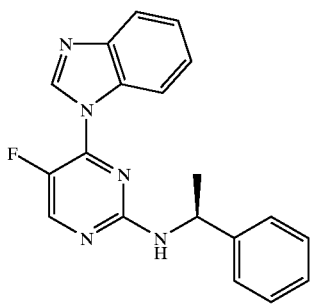

2-[(S)-1-Phenylethylamino]-4-[benzimidazol-1-yl]-5-fluoropyrimidine

To a suspension of 2-[(S)-1-phenylethylamino]-4-[benzimidazol-1-yl]pyrimidine (EXAMPLE 1) (10 mg, 0.0317 mmol) in acetonitrile was added Selectfluor™ (17 mg, 0.048 mmol). The reaction mixture was stirred at room temperature for 6 h (it became homogeneous after 2 h), then the solvent was removed in vacuo. The crude material was purified by preparative thin layer chromatography eluting with 1:2 acetone:hexane system to obtain 2.5 mg of the title compound as the only product along with recovered starting material. Mass spectrum 334.2 (M+1).

EXAMPLE 340

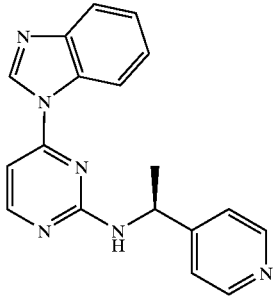

2-[1-(Pyridin-4-yl)ethylamino]-4-[benzimidazol-1-yl]pyrimidine

The title compound was prepared from 1-(pyridin-4-yl)ethylamine according to the procedure outlined in EXAMPLE 1, Step C. 1-(Pyridin-4-yl)ethylamine was prepared from 4-acetylpyridine according to the procedure outlined in EXAMPLE 55, Steps A and B. Mass spectrum 317.2 (M+1).

EXAMPLE 341

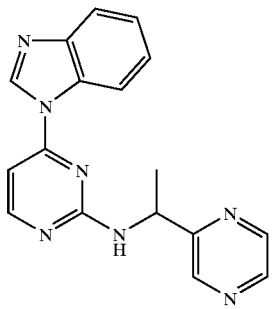

2-[1-(Pyrazin-2-yl)ethylamino]-4-[benzimidazol-1-yl]pyrimidine

Step A: 1-(Pyrazin-2-yl)ethylamine

To a solution of 2-acetylpyrazine (206.7 mg, 1.7 mmol) and ammonium acetate (1.3 g, 17 mmol) in methanol (5.0 mL) was added sodium cyanoborohydride (75 mg, 1.19 mmol) followed by 3 Å molecular sieves (0.85 g). The reaction mixture was stirred for 1 day at room temperature. It was acidified to pH 2 with concentrated HCl then filtered, and the solid was washed with methanol and H$_2$O. The filtrate was concentrated in vacuo. The residue was dissolved in water and was made basic (pH 10–12) with 5N NaOH. The aqueous layer was extracted with CH$_2$Cl$_2$ several times while maintaining ~pH 10. The combined extracts were dried over Na$_2$SO$_4$, filtered, and concentrated the solvent in vacuo. The crude product was purified by preparative thin layer chromatography eluting with 5% 2M NH$_3$ in MeOH/CH$_2$Cl$_2$ to give 74 mg of the title compound. $^1$H NMR (500 MHz, CDCl$_3$): 8.61 (s, 1H); 8.5 (d, J=1.6 Hz, 1H); 8.44 (d, J=1.6 Hz, 1H); 4.21 (q, J=6.8 Hz, 1H); 1.46 (d, J=6.8 Hz).

Step B: 2-[1-(Pyrazin-2-yl)ethylamino]-4-[benzimidazol-1-yl]pyrimidine

The title compound was prepared from 1-(pyrazin-2-yl)ethylamine according to the procedure outlined in the EXAMPLE 1, Step C. Mass spectrum 318.2 (M+1).

EXAMPLE 342

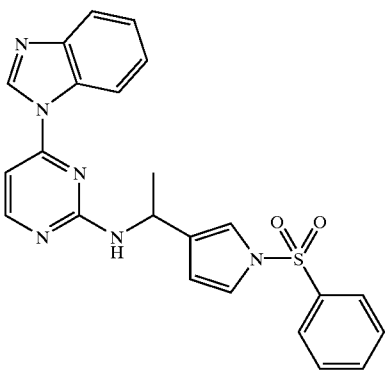

2-[1-(1-(Phenylsulfonyl)pyrrol-3-yl)ethylamino]-4-[benzimidazol-1-yl]pyrimidine

The title compound was prepared from 3-acetyl-1-(phenylsulfonyl)pyrrole according to the procedure outlined in the EXAMPLE 341, Steps A and B. Mass spectrum (ESI) 445.3 (M+1).

EXAMPLE 343

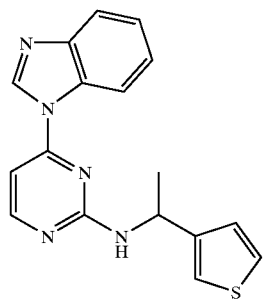

2-[1-(Thien-3-yl)ethylamino]-4-[benzimidazol-1-yl]pyrimidine

The title compound was prepared from 3-acetylthiophene according to the procedure outlined in the EXAMPLE 341, Steps A and B. Mass spectrum (ESI) 322.1 (M+1).

EXAMPLE 344

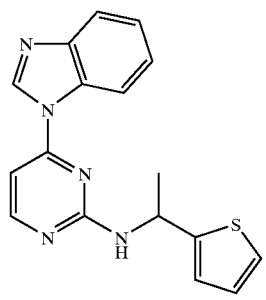

2-[1-(Thien-2-yl)ethylamino]-4-[benzimidazol-1-yl]pyrimidine

The title compound was prepared from 2-acetylthiophene according to the procedure outlined in the EXAMPLE 341, Steps A and B. Mass spectrum (ESI) 322.1 (M+1).

EXAMPLE 345

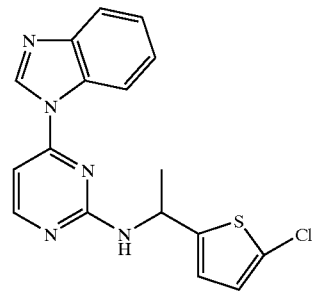

2-[1-(5-Chlorothien-2-yl)ethylamino]-4-[benzimidazol-1-yl]pyrimidine

The title compound was prepared from 2-acetyl-5-chlorothiophene according to the procedure outlined in the EXAMPLE 341, Steps A and B. Mass spectrum (ESI) 356.2 (M+1).

EXAMPLE 346

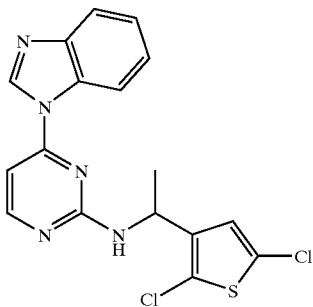

2-[1-(2,5-Dichlorothien-3-yl)ethylamino]-4-[benzimidazol-1-yl]pyrimidine

The title compound was prepared from 3-acetyl-2,5-dichlorothiophene according to the procedure outlined in the EXAMPLE 341, Steps A and B. Mass spectrum (ESI) 390.1 (M+1).

EXAMPLE 347

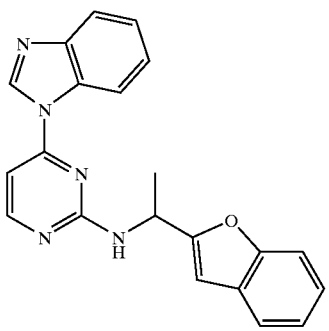

2-[1-(Benzofuran-2-yl)ethylamino]-4-[benzimidazol-1-yl]pyrimidine

The title compound was prepared from benzofuran-2-yl methyl ketone according to the procedure outlined in the EXAMPLE 341, Steps A and B. Mass spectrum (ESI) 356.3 (M+1).

EXAMPLE 348

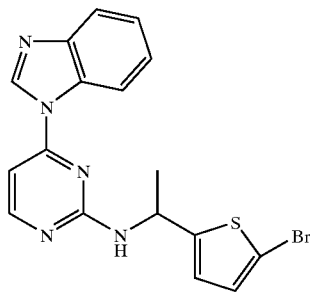

2-[1-(5-Bromothien-2-yl)ethylamino]-4-[benzimidazol-1-yl]pyrimidine

The title compound was prepared from 2-acetyl-5-bromothiophene according to the procedure outlined in the EXAMPLE 341, Steps A and B. Mass spectrum (ESI) 402.1 (M+1).

EXAMPLE 349

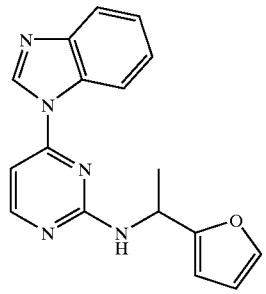

2-[1-(Furan-2-yl)ethylamino]-4-[benzimidazol-1-yl]pyrimidine

The title compound was prepared from 1-(furan-2-yl)ethyl ammonium maleate according to the procedure outlined in the EXAMPLE 341, Step B except that two equivalents of triethylamine were used. Mass spectrum (ESI) 306.2 (M+1).

EXAMPLE 350

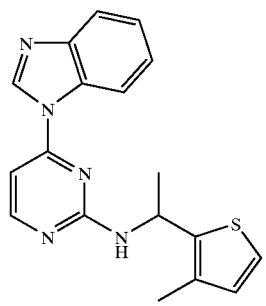

2-[1-(3-Methylthienyl)ethylamino]-4-[benzimidazol-1-yl]pyrimidine

The title compound was prepared from 2-acetyl-3-methylthiophene according to the procedure outlined in the EXAMPLE 341, Steps A and B. Mass spectrum (ESI) 336.1 (M+1).

EXAMPLE 351

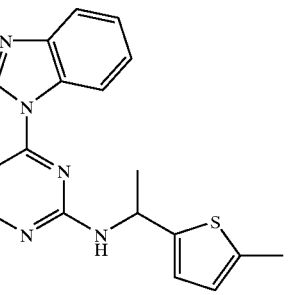

2-[1-(5-Methylthien-2-yl)ethylamino]-4-[benzimidazol-1-yl]pyrimidine

The title compound was prepared from 2-acetyl-5-methylthiophene according to the procedure outlined in the EXAMPLE 341, Steps A and B. Mass spectrum (ESI) 336.2 (M+1).

EXAMPLE 352

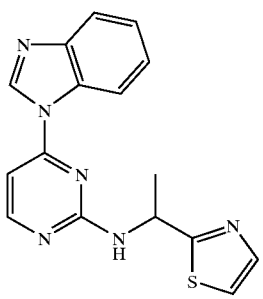

2-[1-(Thiazol-2-yl)ethylamino]-4-[benzimidazol-1-yl]pyrimidine

The title compound was prepared from 2-acetylthiazole according to the procedure outlined in the EXAMPLE 341, Steps A and B. Mass spectrum (ESI) 323.2 (M+1).

EXAMPLE 353

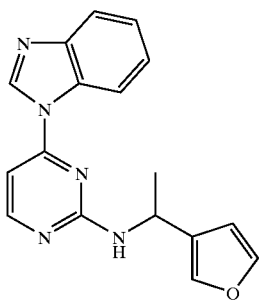

2-[1-(Furan-3-yl)ethylamino]-4-[benzimidazol-1-yl]pyrimidine

The title compound was prepared from 1-(furan-3-yl)ethyl ammonium oxalate according to the procedure outlined in the EXAMPLE 341, Step B except that two equivalents of triethylamine were used. Mass spectrum (ESI) 306.3 (M+1).

EXAMPLE 354

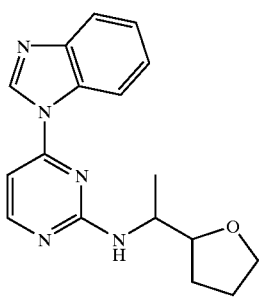

2-[1-(Tetrahydrofuran-2-yl)ethylamino]-4-[benzimidazol-1-yl]pyrimidine

The title compound was prepared from 1-(tetrahydrofuran-2-yl)ethyl ammonium fumarate according to the procedure outlined in the EXAMPLE 341, Step B except that two equivalents of triethylamine were used. Mass spectrum (ESI) 310.3 (M+1).

EXAMPLE 355

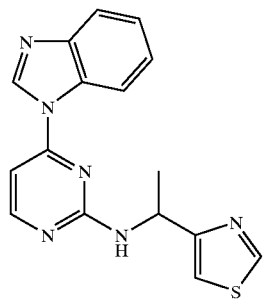

2-[1-(Thiazol-4-yl)ethylamino]-4-[benzimidazol-1-yl]pyrimidine

The title compound was prepared from 1-(4-thiazol-2-yl)ethyl ammonium oxalate according to the procedure outlined in the EXAMPLE 341, Step B except that two equivalents of triethylamine were used. Mass spectrum (ESI) 323.1 (M+1).

EXAMPLE 356

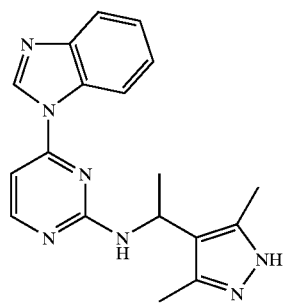

2-[1-(3,5-Dimethyl-pyrrazol-4-yl)ethylamino]-4-[benzimidazol-1-yl]pyrimidine

The title compound was prepared from 1-(3,5-dimethyl-pyrazol-4-yl)ethyl ammonium oxalate according to the procedure outlined in the EXAMPLE 341, Step B except that two equivalents of triethylamine were used. Mass spectrum (ESI) 334.3 (M+1).

EXAMPLE 357

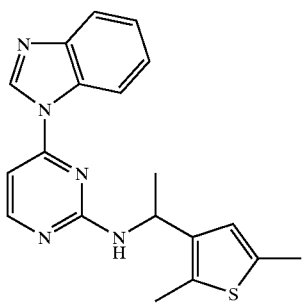

2-[1-(2,5-Dimethylthien-3-yl)ethylamino]-4-[benzimidazol-1-yl]pyrimidine

The title compound was prepared from 3-acetyl-2,5-dimethylthiophene according to the procedure outlined in the EXAMPLE 341, Steps A and B. Mass spectrum (ESI) 350.9 (M+1).

EXAMPLE 358

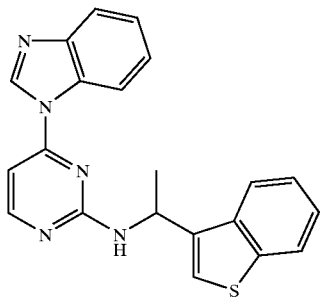

2-[1-(Benzothiophen-3-yl)ethylamino]-4-[benzimidazol-1-yl]pyrimidine

The title compound was prepared from 3-acetylbenzothiophene according to the procedure outlined in the EXAMPLE 341, Steps A and B. Mass spectrum (ESI) 372.9 (M+1).

EXAMPLE 359

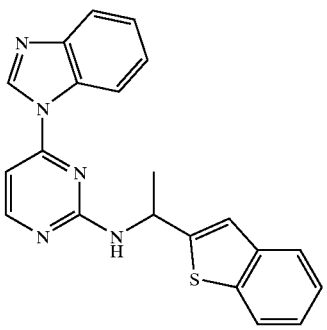

2-[1-(Benzothiophen-2-yl)ethylamino]-4-[benzimidazol-1-yl]pyrimidine

The title compound was prepared from 2-acetylbenzothiophene according to the procedure outlined in the EXAMPLE 341, Steps A and B. Mass spectrum (ESI) 372.3 (M+1).

EXAMPLE 360

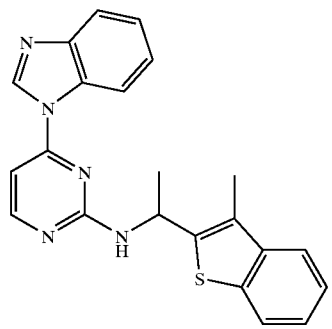

2-[1-(2-(3-Methyl-benzothiophen-2-yl)ethylamino]-4-[benzimidazol-1-yl]pyrimidine The title compound was prepared from 2-acetyl-3-methyl-benzothiophene according to the procedure outlined in the EXAMPLE 341, Steps A and B. Mass spectrum (ESI) 386.3 (M+1).

EXAMPLE 361

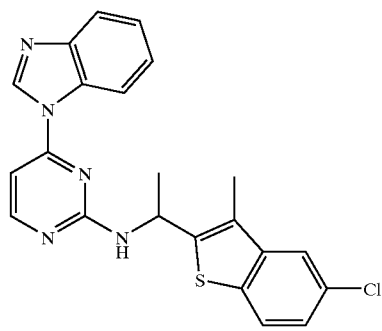

2-[1-(2-(3-Methyl-5-chloro-benzothiophen-2-yl)ethylamino]-4-[benzimidazol-1-yl]pyrimidine The title compound was prepared from 2-acetyl-3-methyl-5-chloro-benzothiophene according to the procedure outlined in the EXAMPLE 341, Steps A and B. Mass spectrum. (ESI) 420.3 (M+1).

EXAMPLE 362

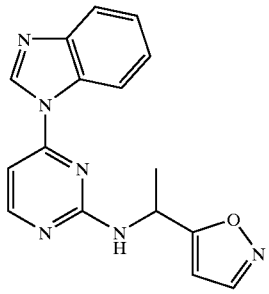

2-[1-(Oxazol-5-yl)ethylamino]-4-[benzimidazol-1-yl]pyrimidine

The title compound was prepared from 1-(oxazol-5-yl)ethylammonium chloride according to the procedure out-

EXAMPLE 363

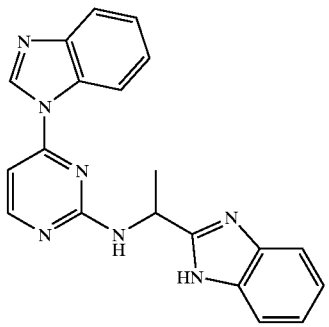

2-[1-(Benzimidazol-2-yl)ethylamino]-4-
[benzimidazol-1-yl]pyrimidine

The title compound was prepared from 1-(benzimidazol-2-yl)ethylamine according to the procedure outlined in the EXAMPLE 341, step B. Mass spectrum (ESI) 356.3 (M+1).

EXAMPLE 364

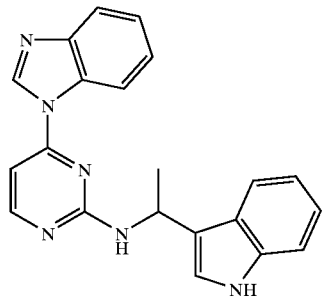

2-[1-(Indol-3-yl)ethylamino]-4-[benzimidazol-1-yl]
pyrimidine

Step A: 2-[1-(1-N-tert-butoxycarbonyl-indol-3-yl)
ethylamino]-4-[benzimidazol-1-yl]pyrimidine The title compound was prepared from 1-(N-tert-butoxycarbonylindol-3-yl)ethylamine according to the procedure outlined in the EXAMPLE 341, step B. Mass spectrum (ESI) 455.2 (M+1).

Step B: 2-[1-(Indol -3-yl )ethylamino]-4-
[benzimidazol-1-yl]pyrimidine

To a solution of 2-[1-(1-N-tert-butoxycarbonyl-indol-3-yl)ethylamino]-4-[benzimidazol-1-yl]pyrimidine (25 mg, 0.055 mmol) in methylene chloride (0.25 ml) was added TFA (0.25 ml). The reaction mixture was stirred at 0° C. for an hour and room temperature for 30 min. The solvents were concentrated in vacuo. The crude product was purified by preparative thin layer chromatography eluting with 5% 2M NH3 in MeOH/CH2Cl2 to give 6 mg of the title compound. Mass spectrum (ESI) 355.3 (M+1).

lined in the EXAMPLE 341, Step B except that two equivalents of triethylamine were used. Mass spectrum (ESI) 307.3 (M+1).

EXAMPLE 365

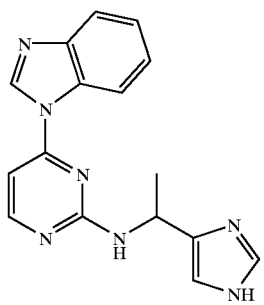

2-[1-(Imidazol-4-yl)ethylamino]-4-[benzimidazol-1-
yl]pyrimidine

Step A: 2-[1-(N-tert-butoxycarbonyl-imidazol-4-yl)
ethylamino]-4-[benzimidazol-1-yl]pyrimidine The title compound was prepared from 1-(N-tert-butoxycarbonyl)-4-(1-aminoethyl)imidazolium oxalate according to the procedure outlined in the EXAMPLE 341, Step B except that two equivalents of triethylamine were used.

Step B: 2-[1-(Imidazol-4-yl)ethylamino]-4-
[benzimidazol-1-yl]pyrimidine

The title compound was prepared from 2-[1-(N-tert-butoxycarbonyl-imidazol-4-yl)ethylamino]-4-[benzimidazol-1-yl]pyrimidine according to the procedure outlined in the EXAMPLE 364, step B. Mass spectrum (ESI) 306.3 (M+1).

EXAMPLE 366

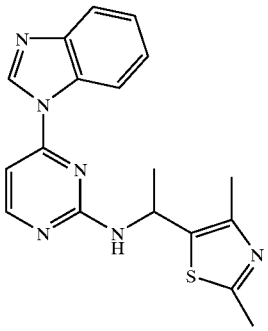

2-[1-(2,4-Dimethylthiazol-5-yl)ethylamino]-4-
[benzimidazol-1-yl]pyrimidine

The title compound was prepared from 5-acetyl-2,4-Dimethylthiazole according to the procedure outlined in the EXAMPLE 341, Steps A and B. The enantiomers were separated on HPLC (YMC Chiralpak AD column, 50:50 hexane:EtOH system). Mass spectrum (ESI) 351.3 (M+1).

EXAMPLE 367

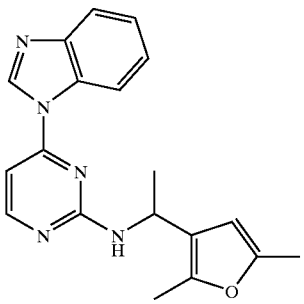

2-[1-(2,5-Dimethylfuran-3-yl)ethylamino]-4-[benzimidazol-1-yl]pyrimidine

Step A: 2,5-Dimethyl-3-acetylfuranhydroxime

The title compound was prepared from 2,5-Dimethyl-3-acetylfuran according to the procedure outlined in the EXAMPLE 55, step A, except that pyridine was used instead of triethylamine. $^1$H NMR (500 MHz, CDCl$_3$): δ 6.05 (s, 1H); 3.93 (s, 3H); 2.43 (s, 3H); 2.25 (s, 3H); 2.10 (s, 3H).

Step B: 1-(2,5-Dimethylfuran-3-yl)ethylamine

A solution of 2,5-dimethyl-3-acetylfuranhydroxime (4.78 mmol) in anhydrous THF (6 ml) was added to borane.THF complex in THF solution (1.0 M, 10.5 ml) dropwise at 0° C. The reaction mixture was then stirred at room temperature for three days. The reaction was quenched with 2N HCl solution to make pH~2 and then poured into water (20 ml). The mixture was washed with ether (2×25 ml); the aqueous layer was treated with 5N NaOH to pH~9 and extracted with ether and methylene chloride. The organic extracts were combined, washed with brine, dried over sodium sulfate, and concentrated to provide 430 mg of the desired product as yellow oil. $^1$H NMR (500 MHz, CDCl$_3$): δ 5.93 (s, 1H); 3.98 (q, J=6.7 Hz, 1H); 2.23 (s, 3H); 2.22 (s, 3H); 1.56 (br s, 2H); 2.25 (s, 3H); 1.30 (d, J=6.6 Hz, 3H).

Step C: 2-[1-(2,5-Dimethylfuran-3-yl)ethylamino]-4-[benzimidazol-1-yl]pyrimidine The title compound was prepared from 1-(2,5-Dimethylfuran-3-yl)ethylamine according to the procedure outlined in the EXAMPLE 341, step B. Mass spectrum (ESI) 334.2 (M+1).

EXAMPLE 368

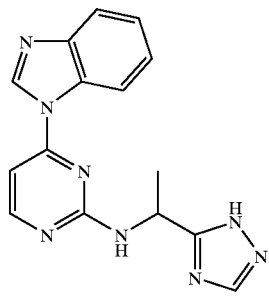

2-[1-(1,2,4-Triazol-4-yl)ethylamino]-4-[benzimidazol-1-yl]pyrimidine

The title compound was prepared from 1-(1,2,4-triazol-4-yl)ethylamine according to the procedure outlined in the EXAMPLE 341, step B. Mass spectrum (ESI) 307.3 (M+1).

EXAMPLE 369

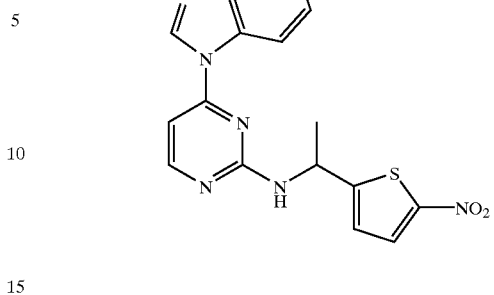

2-[1-(5-Nitrothien-2-yl)ethylamino]-4-[benzimidazol-1-yl]pyrimidine

The title compound was prepared from 2-acetyl-5-nitrothiophene according to the procedure outlined in the EXAMPLE 341, step A and B. Mass spectrum (ESI) 367.3 (M+1).

EXAMPLE 370

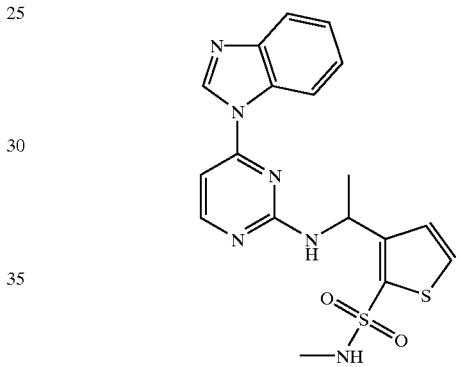

2-[1-(2-Methylaminosulfonyl)thien-3-yl)ethylamino]-4-[benzimidazol-1-yl]pyrimidine The title compound was prepared from 3-acetyl-2-(methylaminosulfonyl)thiophene according to the procedure outlined in the EXAMPLE 341, step A and B. Mass spectrum (ESI) 415.1 (M+1).

EXAMPLE 371

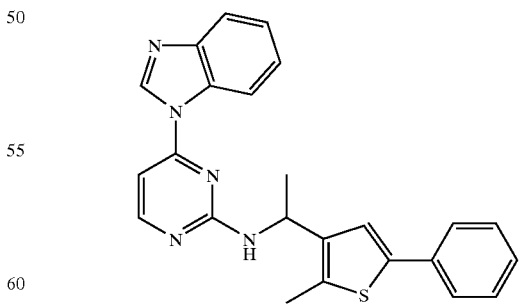

2-[1-(2-Methyl-5-phenylthien-3-yl)ethylamino]-4-[benzimidazol-1-yl]pyrimidine

The title compound was prepared from 3-acetyl-2-methyl-5-phenylthiophene according to the procedure outlined in the EXAMPLE 341, step A and B. Mass spectrum (ESI) 412.2 (M+1).

EXAMPLE 372

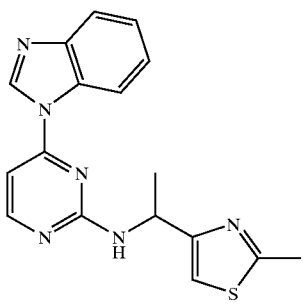

2-[1-(2-Methylthiazol-4-yl)ethylamino]-4-[benzimidazol-1-yl]pyrimidine

The title compound was prepared from 1-(2-methylthiazol-4-yl)ethylamino according to the procedure outlined in the EXAMPLE 341, step B. Mass spectrum (ESI) 337.6 (M+1).

EXAMPLE 373

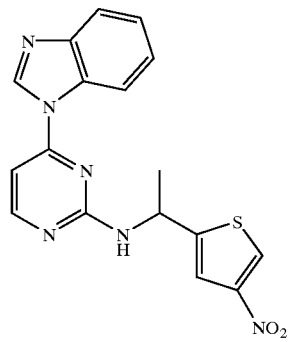

2-[1-(4-nitrothien-2-yl)ethylamino]-4-[benzimidazol-1-yl]pyrimidine

The title compound was prepared from 2-acetyl-4-nitrothiophene according to the procedure outlined in the EXAMPLE 367, steps A, B and C. Mass spectrum (ESI) 367.3 (M+1).

EXAMPLE 374

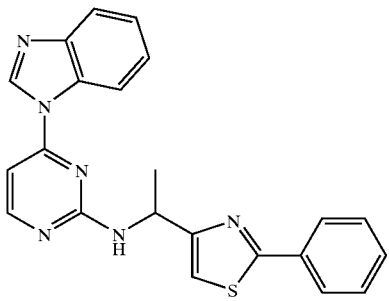

2-[1-(2-Phenylthiazol-4-yl)ethylamino]-4-[benzimidazol-1-yl]pyrimidine

The title compound was prepared from 4-acetyl-2-phenylthiazole according to the procedure outlined in the EXAMPLE 367, steps A, B and C. Mass spectrum (ESI) 399.3 (M+1).

EXAMPLE 375

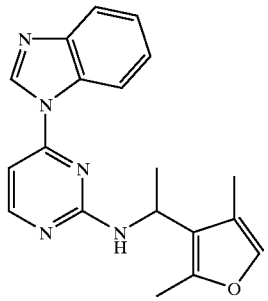

2-[1-(2,4-Dimethylfuran-3-yl)ethylamino]-4-[benzimidazol-1-yl]pyrimidine

The title compound was prepared from 3-acetyl-2,4-dimethylfuran according to the procedure outlined in the EXAMPLE 367, steps A, B and C. Mass spectrum (ESI) 334.2 (M+1).

EXAMPLE 376

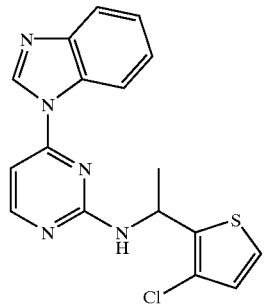

2-[1-(3-Chlorothien-2-yl)ethylamino]-4-[benzimidazol-1-yl]pyrimidine

The title compound was prepared from 2-acetyl-3-chlorothiophene according to the procedure outlined in the EXAMPLE 341, steps A and B. Mass spectrum (ESI) 356.2 (M+1).

EXAMPLE 377

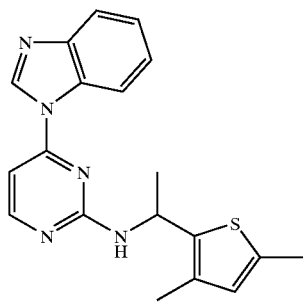

2-[1-(3,5-Dimethylthien-2-yl)ethylamino]-4-[benzimidazol-1-yl]pyrimidine

The title compound was prepared from 2-acetyl-3,5-dimethylthiophene according to the procedure outlined in the EXAMPLE 341, steps A and B. Mass spectrum (ESI) 350.2 (M+1).

EXAMPLE 378

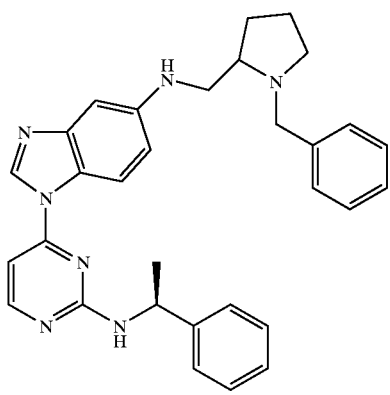

2-[(S)-1-Phenylethylamino]-4-[5-N-((1-benzylpyrrolidin-2-yl)methyl)aminobenzimidazol-1-yl]pyrimidine The title compound was prepared from 2-[(S)-1-phenylethylamino]-4-[5-N-((pyrrolidin-2-yl)methyl) aminobenzimidazol-1-yl]pyrimidine (Example 209) and benzaldehyde according to the procedure outlined in the EXAMPLE 182. Mass spectrum (ESI) 504.3 (M+1).

EXAMPLE 379

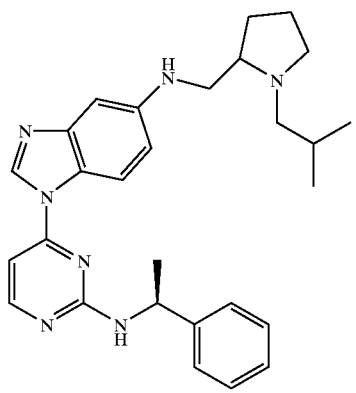

2-[(S)-1-Phenylethylamino]-4-[5-N-((1-isobutylpyrrolidin-2-yl)methyl)aminobenzimidazol-1-yl]pyrimidine The title compound was prepared from 2-[(S)-1-phenylethylamino]-4-[5-N-((pyrrolidin-2-yl)methyl) aminobenzimidazol-1-yl]pyrimidine (Example 209) and isobutyraldehyde according to the procedure outlined in the EXAMPLE 182. Mass spectrum (ESI) 470.3 (M+1).

EXAMPLE 380

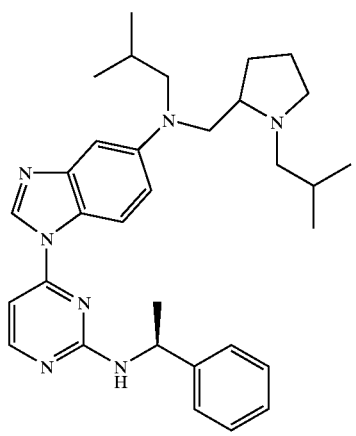

2-[(S)-1-Phenylethylamino]-4-[5-N-isobutyl-N-(1-isobutylpyrrolidin-2-yl)-methylaminobenzimidazol-1-yl]pyrimidine The title compound was prepared as a byproduct according to the procedure outlined in the EXAMPLE 379. Mass spectrum (ESI) 526.3 (M+1).

EXAMPLE 381

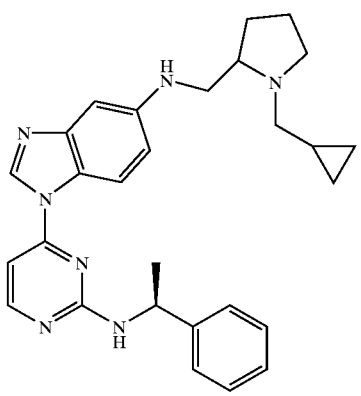

2-[(S)-1-Phenylethylamino]-4-[5-N-((1-cyclopropylmethylpyrrolidin-2-yl)methyl)aminobenzimidazol-1-yl]pyrimidine The title compound was prepared from 2-[(S)-1-phenylethylamino]-4-[5-N-((pyrrolidin-2-yl)methyl)aminobenzimidazol-1-yl]pyrimidine (Example 209) and cyclopropanecarboxaldehyde according to the procedure outlined in the EXAMPLE 182. Mass spectrum (ESI) 468.3 (M+1).

EXAMPLE 382

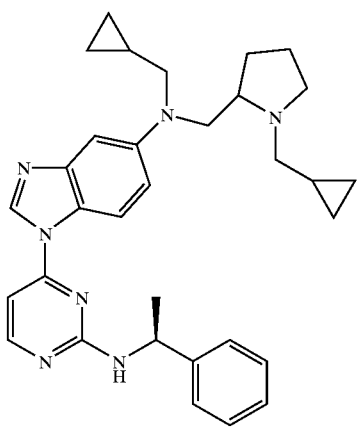

2-[(S)-1-Phenylethylamino]-4-[5-N-cyclopropylmethyl-N-((1-cyclopropylmethylpyrrolidin-2-yl)methyl)aminobenzimidazol-1-yl]pyrimidine The title compound was prepared as a byproduct according to the procedure outlined in the EXAMPLE 381. Mass spectrum (ESI) 522.3 (M+1).

EXAMPLE 383

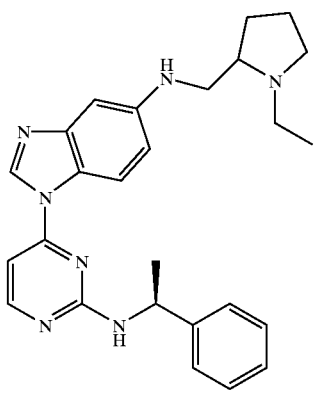

2-[(S)-1-Phenylethylamino]-4-[5-N-((1-ethylpyrrolidin-2-yl)methyl)aminobenzimidazol-1-yl]pyrimidine The title compound was prepared from 2-[(S)-1-phenylethylamino]-4-[5-N-((pyrrolidin-2-yl)methyl)aminobenzimidazol-1-yl]pyrimidine (Example 209) and acetaldehyde according to the procedure outlined in the EXAMPLE 182. Mass spectrum (ESI) 442.2 (M+1).

EXAMPLE 384

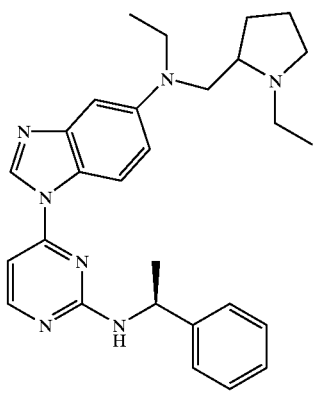

2-[(S)-1-Phenylethylamino]-4-[5-N-ethyl-N-((1-ethylpyrrolidin-2-yl)methyl)aminobenzimidazol-1-yl]pyrimidine The title compound was prepared as a byproduct according to the procedure outlined in the EXAMPLE 383. Mass spectrum (ESI) 470.3 (M+1).

EXAMPLE 385

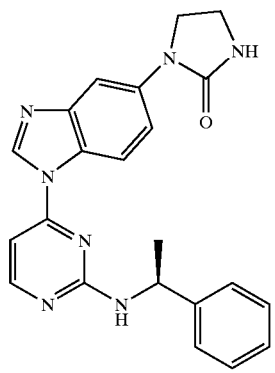

2-[(S)-1-Phenylethylamino]-4-[5-(imidazolidin-2-on-1-yl)benzimidazol-1-yl]pyrimidine The title compound was prepared from 2-[(S)-1-phenylethylamino]-4-[5-N-(2-aminoethyl)aminobenzimidazol-1-yl]pyrimidine (Example 229) according to the procedure outlined in the EXAMPLE 239. Mass spectrum (ESI) 400.3 (M+1).

EXAMPLE 386

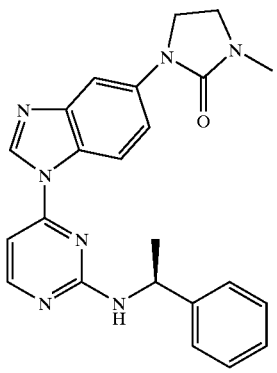

2-[(S)-1-Phenylethylamino]-4-[5-(3-methylimidazolidin-2-on-1-yl)benzimidazol-1-yl]pyrimidine To a solution of 2-[(S)-1-Phenylethylamino]-4-[5-(imidazolidin-2-on-1-yl)benzimidazol-1-yl]pyrimidine (Example 385) (0.025 mmol) in anhydrous DMF (0.2 ml) under nitrogen was added NaH (60%) in one portion. After stirring for ten minutes, iodomethane (0.028 mmol) was added dropwise. The reaction was stirred at room temperature for 2.5 h. and quenched with water. The mixture was extracted with methylene chloride. The organic extracts were combined, washed with brine and dried over $MgSO_4$. Removal of the solvent and subsequent purification by preparative thin layer chromatography (acetone/hexane system) provided 4.5 mg of the title compound. Mass spectrum (ESI) 414.3 (M+1).

EXAMPLE 387

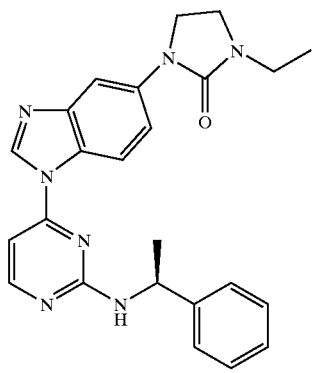

2-[(S)-1-Phenylethylamino]-4-[5-(3-ethylimidazolidin-2-on-1-yl)benzimidazol-1-yl]pyrimidine The title compound was prepared according to the procedure outlined in the EXAMPLE 386 using iodoethane. Mass spectrum (ESI) 428.2 (M+1).

EXAMPLE 388

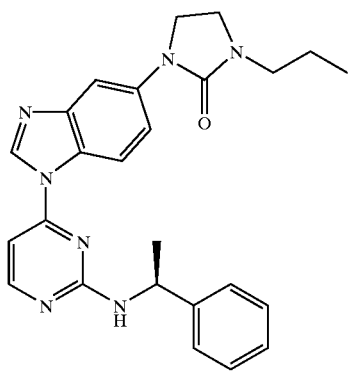

2-[(S)-1-Phenylethylamino]-4-[5-(3-propylimidazolidin-2-on-1-yl)benzimidazol-1-yl]pyrimidine The title compound was prepared according to the procedure outlined in the EXAMPLE 386 using iodopropane. Mass spectrum (ESI) 442.3 (M+1).

EXAMPLE 389

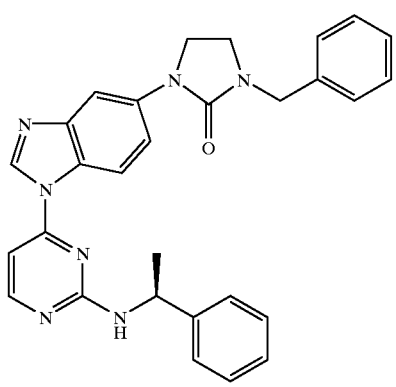

2-[(S)-1-Phenylethylamino]-4-[5-(3-benzylimidazolidin-2-on-1-yl)benzimidazol-1-yl]pyrimidine The title compound was prepared according to the procedure outlined in the EXAMPLE 386 using benzylbromide. Mass spectrum (ESI) 490.2 (M+1).

EXAMPLE 390

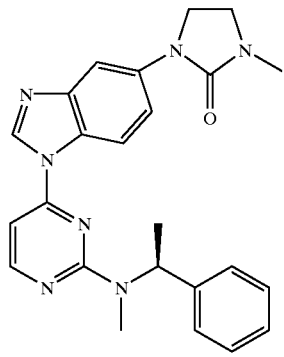

2-[(S)-N-Methyl-N-1-phenylethylamino]-4-[5-(3-methylimidazolidin-2-on-1-yl)benzimidazol-1-yl]pyrimidine The title compound was prepared according to the procedure outlined in the EXAMPLE 386 except that two equivalents NaH and three equivalents MeI were used. Mass spectrum (ESI) 428.3 (M+1).

EXAMPLE 391

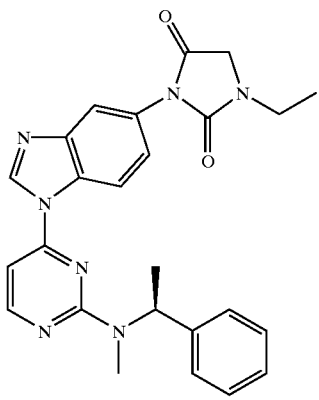

2-[(S)-1-Phenylethylamino]-4-[5-(1-ethyl-imidazolidin-2,4-dion-3-yl)benzimidazol-1-yl]pyrimidine The title compound was prepared from 2-[(S)-1-phenylethylamino]-4-[5-(2,5-imidazolidin-2-on-1-yl)benzimidazol-1-yl]pyrimidine (Example 236) according to the procedure outlined in the EXAMPLE 386. Mass spectrum (ESI) 442.3 (M+1).

EXAMPLE 392

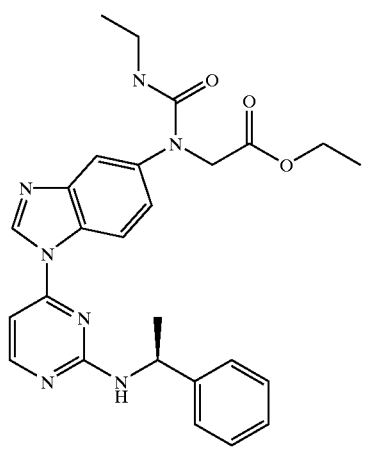

2-[(S)-1-Phenylethylamino]-4-[5-N-(ethylcarbamoyl)-N-(ethoxycarbonylmethyl)aminobenzimidazol-1-yl]pyrimidine The title compound was prepared from 2-[(S)-1-phenylethylamino]-4-[5-N-(ethoxycarbonylmethyl)aminobenzimidazol-1-yl]pyrimidine (Example 217) according to the procedure outlined in EXAMPLE 241. Mass spectrum (ESI) 488.5 (M+1).

EXAMPLE 393

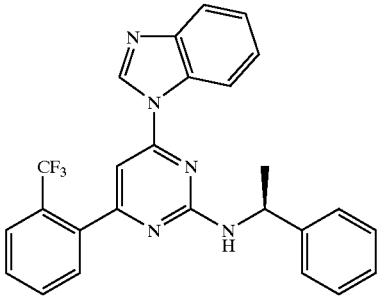

2-[(S)-1-Phenylethylamino]-4-(benzimidazol-1-yl)-6-(2-trifluoromethylphenyl)pyrimidine The title compound was prepared from 2-trifluoromethylphenylboronic acid according to the procedure outlined in the EXAMPLE 306, Step C except that [1,1'-bis(diphenylphosphino)ferrocene]dichloropalladium (II) complex with dichloromethane was used instead of tetrakis(triphenylphosphine)palladium(0). Mass spectrum (ESI) 460.4 (M+1).

EXAMPLE 394

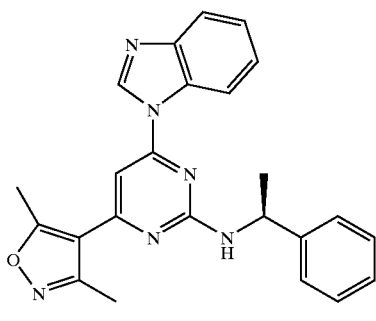

2-[(S)-1-Phenylethylamino]-4-(benzimidazol-1-yl)-6-(3,5-dimethyloxazol-4-yl)pyrimidine The title compound was prepared from 3,5-dimethyloxazol-4-ylboronic acid according to the procedure outlined in the EXAMPLE 393. Mass spectrum (ESI) 411.3 (M+1).

EXAMPLE 395

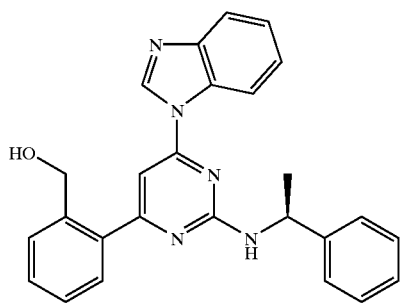

2-[(S)-1-Phenylethylamino]-4-(benzimidazol-1-yl)-6-(2-hydroxymethylphenyl)pyrimidine The title compound was prepared from 2-hydroxymethylphenyl boronic acid according to the procedure outlined in the EXAMPLE 393. Mass spectrum (ESI) 422.3 (M+1).

EXAMPLE 396

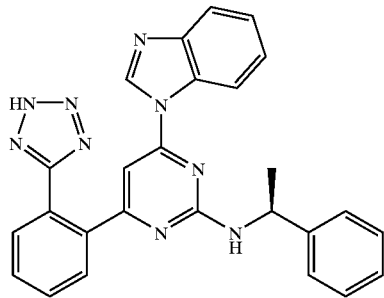

2-[(S)-1-Phenylethylamino]-4-(benzimidazol-1-yl)-6-[2-(tetrazol-5-yl)phenyl]pyrimidine The title compound was prepared from 2-(tetrazol-5-yl) phenylboronic acid according to the procedure outlined in the EXAMPLE 393. Mass spectrum (ESI) 460.5 (M+1).

EXAMPLE 397

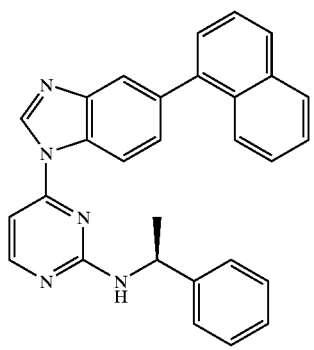

2-[(S)-1-Phenylethylamino]-4-[5-(1-naphthyl)-benzimidazol-1-yl]pyrimidine

2-[(S)-1-Phenylethylamino]-4-[5-iodobenzimidazol-1-yl] pyrimidine (EXAMPLE 271) (50 mg), 1-naphthyl boronic acid (22 mg), potassium carbonate (31 mg), and tetrakis (triphenylphosphine)palladium(0) (5 mg) were dissolved in degassed n-propanol (2.6 mL) and water (0.4 mL) and stirred at 80° C. under argon atmosphere. for 15 hours. Upon cooling, the reaction mixture was filtered through Celite® (the ppt was washed with 10 mL of EtOAc) and evaporated. The residue was purified by preparative thin layer chromatography eluted with 5% MeOH/CH$_2$Cl$_2$ giving 43 mg of the title compound. $^1$H NMR (500 MHz, CDCl$_3$), δ 8.58 (br s, 1H), 8.40 (s, 1H), 7.96–7.90 (m, 4H), 7.59–7.27 (m, 10H), 6.85 (d, 1H, J=5.5 Hz), 6.45 (br s, 1H), 5.25 (s, 1H), 1.67 (d, 3H, J=7.0 Hz); Mass spectrum (ESI) 442.2 (M+1).

EXAMPLE 398

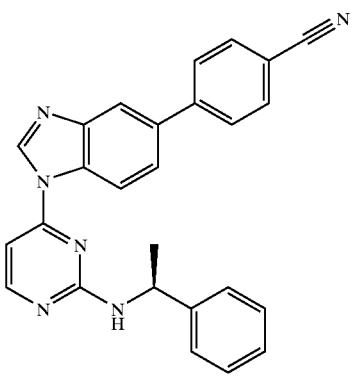

2-[(S)-1-Phenylethylamino]-4-[5-(4-cyanophenyl)benzimidazol-1-yl]pyrimidine

The title compound was prepared according to the procedure described in EXAMPLE 397, starting from 2-[(S)-1-Phenylethylamino]-4-[5-iodobenzimidazol-1-yl] pyrimidine and 4-cyanophenyl boronic acid. Mass spectrum (ESI) 417.2 (M+1).

EXAMPLE 399

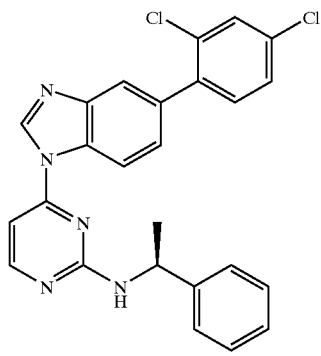

2-[(S)-1-Phenylethylamino]-4-[5-(2,4-dichlororophenyl)benzimidazol-1-yl]pyrimidine The title compound was prepared according to the procedure described in EXAMPLE 397, starting from 2-[(S)-1-Phenylethylamino]-4-[5-iodobenzimidazol-1-yl]pyrimidine and 2,4-dichlorophenyl boronic acid. Mass spectrum (ESI) 461.2 (M+1).

EXAMPLE 400

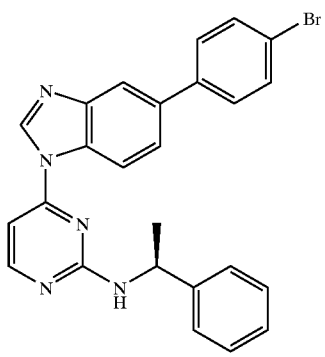

2-[(S)-1-Phenylethylamino]-4-[5-(4-bromophenyl)benzimidazol-1-yl]pyrimidine

The title compound was prepared according to the procedure described in EXAMPLE 397, starting from 2-[(S)-1-Phenylethylamino]-4-[5-iodobenzimidazol-1-yl]pyrimidine and 4-bromophenyl boronic acid. Mass spectrum (ESI) 472.2 (M+1)

EXAMPLE 401

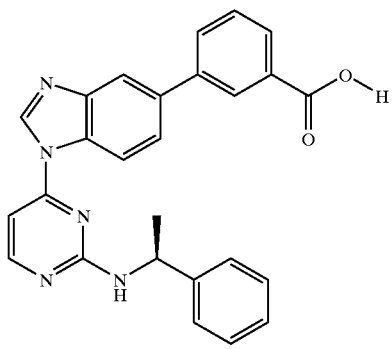

2-[(S)-1-Phenylethylamino]-4-[5-(3-carboxyphenyl)benzimidazol-1-yl]pyrimidine

The title compound was prepared according to the procedure described in EXAMPLE 397, starting from 2-[(S)-1-Phenylethylamino]-4-[5-iodobenzimidazol-1-yl]pyrimidine and 3-carboxyphenyl boronic acid. Mass spectrum (ESI) 436.1 (M+1).

EXAMPLE 402

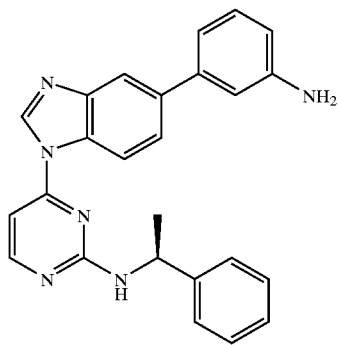

2-[(S)-1-Phenylethylamino]-4-[5-(3-aminophenyl)benzimidazol-1-yl]pyrimidine

The title compound was prepared according to the procedure described in EXAMPLE 397, starting from 2-[(S)-1-Phenylethylamino]-4-[5-iodobenzimidazol-1-yl]pyrimidine and 3-aminophenyl boronic acid. Mass spectrum (ESI) 407.2 (M+1)

EXAMPLE 403

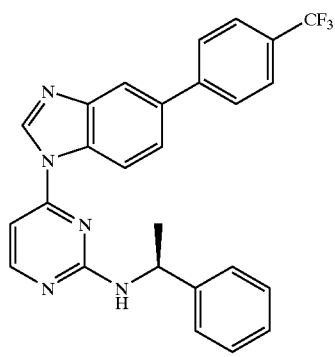

2-[(S)-1-Phenylethylamino]-4-[5-(4-trifluoromethylphenyl)benzimidazol-1-yl]pyrimidine The title compound was prepared according to the procedure described in EXAMPLE 397, starting from 2-[(S)-1-Phenylethylamino]-4-[5-iodobenzimidazol-1-yl]pyrimidine and 4-trifluoromethylphenyl boronic acid. Mass spectrum (ESI) 460.4 (M+1).

EXAMPLE 404

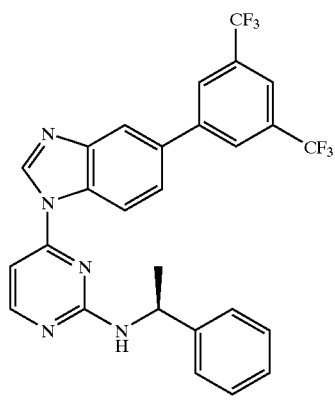

2-[(S)-1-Phenylethylamino]-4-[5-(3,5-bis(trifluoromethyl)phenyl)benzimidazol-1-yl]pyrimidine The title compound was prepared according to the procedure described in EXAMPLE 397, starting from 2-[(S)-1-Phenylethylamino]-4-[5-iodobenzimidazol-1-yl]pyrimidine and 3,5-bis(trifluoromethyl)phenyl boronic acid. Mass spectrum (ESI) 528.3 (M+1).

EXAMPLE 405

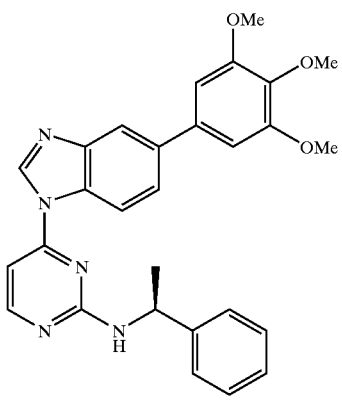

2-[(S)-1-Phenylethylamino]-4-[5-(3,4,5-trimethoxyphenyl)benzimidazol-1-yl]pyrimidine The title compound was prepared according to the procedure described in EXAMPLE 397, starting from 2-[(S)-1-Phenylethylamino]-4-[5-iodobenzimidazol-1-yl]pyrimidine and 3,4,5-trimethoxyphenyl boronic acid. Mass spectrum (ESI) 415.4 (M+).

EXAMPLE 406

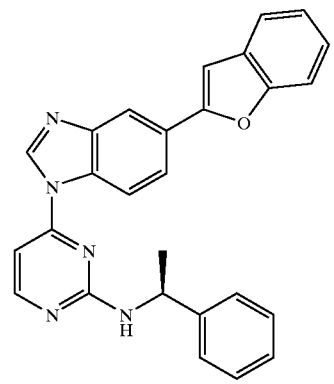

2-[(S)-1-Phenylethylamino]-4-[5-(1-benzofuran)benzimidazol-1-yl]pyrimidine

The title compound was prepared according to the procedure described in EXAMPLE 397, starting from 2-[(S)-1-Phenylethylamino]-4-[5-iodobenzimidazol-1-yl]pyrimidine and benzofuran-3-boronic acid. Mass spectrum (ESI) 432.3 (M+1).

EXAMPLE 407

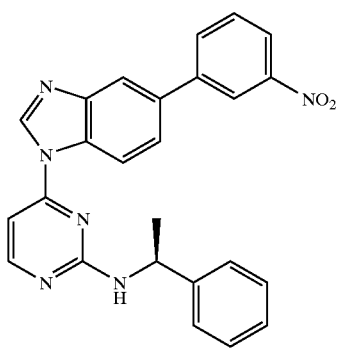

2-[(S)-1-Phenylethylamino]-4-[5-(3-nitrophenyl)benzimidazol-1-yl]pyrimidine

The title compound was prepared according to the procedure described in EXAMPLE 397, starting from 2-[(S)-1-Phenylethylamino]-4-[5-iodobenzimidazol-1-yl]pyrimidine and 3-nitrophenyl boronic acid. Mass spectrum (ESI) 437.3 (M+1).

EXAMPLE 408

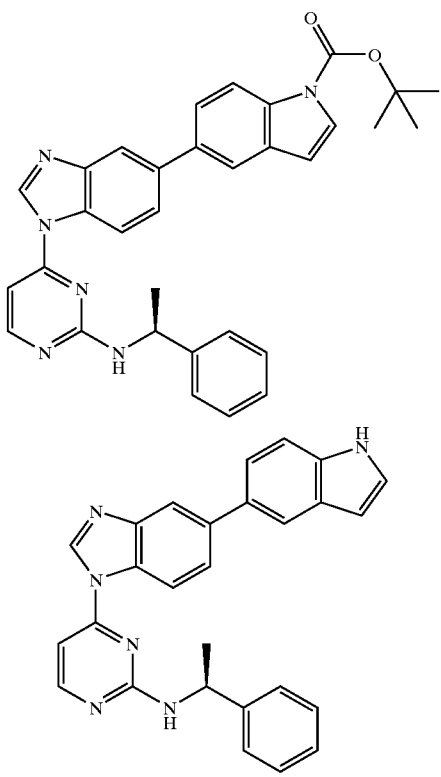

2-[(S)-1-Phenylethylamino]-4-[5-(N-(tert-butyloxycarbonyl)-indol-5-yl)benzimidazol-1-yl]pyrimidine and 2-[(S)-1-Phenylethylamino]-4-[5-(indol-5-yl)benzimidazol-1-yl]pyrimidine The title compounds, isolated in a ratio of 1.2:1 were prepared according to the procedure described in EXAMPLE 397, starting from 2-[(S)-1-Phenylethylamino]-4-[5-iodobenzimidazol-1-yl]pyrimidine and N-tert-butoxycarbonylindole-5-boronic acid. Mass spectrum (ESI) 531.2 (M+1) and 431.1 (M+1) respectively.

EXAMPLE 409

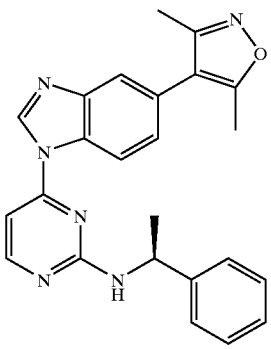

2-[(S)-1-Phenylethylamino]-4-[5-(4-[3,5-dimethylisoxazole)benzimidazol-1-yl]pyrimidine The title compound was prepared according to the procedure described in EXAMPLE 397, starting from 2-[(S)-1-Phenylethylamino]-4-[5-iodobenzimidazol-1-yl]pyrimidine and 3,5-dimethylisoxazole-4-boronic acid. Mass spectrum (ESI) 411.1 (M+1).

EXAMPLE 410

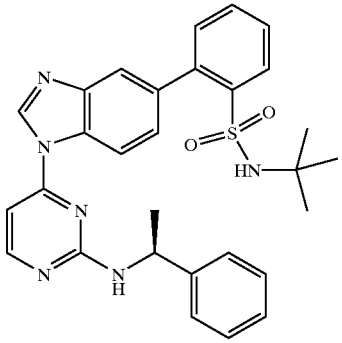

2S)-1-Phenylethylamino]-4-[5-(2-N-tert-butylsulfamidophenyl)benzimidazol-1-yl]pyrimidine The title compound was prepared according to the procedure described in EXAMPLE 397, starting from 2-[(S)-1-Phenylethylamino]-4-[5-iodobenzimidazol-1-yl]pyrimidine and 2-N-tert-butylsulfamidophenyl boronic acid. Mass spectrum (ESI) 531.2 (M+1).

EXAMPLE 411

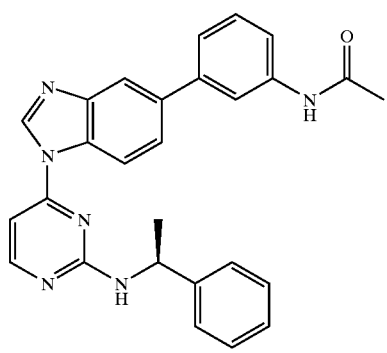

2-[(S)-1-Phenylethylamino]-4-[5-(3-N-acetylaminophenyl)benzimidazol-1-yl]pyrimidine The title compound was prepared according to the procedure described in EXAMPLE 397, starting from 2-[(S)-1-Phenylethylamino]-4-[5-iodobenzimidazol-1-yl]pyrimidine and 3-N-acetylaminophenyl boronic acid. Mass spectrum (ESI) 449.3 (M+1).

EXAMPLE 412

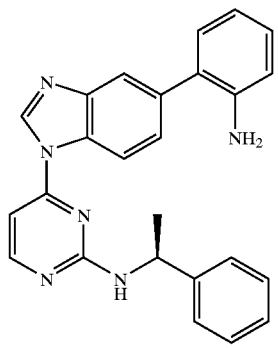

2-[(S)-1-Phenylethylamino]-4-[5-(2-aminophenyl)benzimidazol-1-yl]pyrimidine

The title compound was prepared according to the procedure described in EXAMPLE 397, starting from 2-[(S)-1-Phenylethylamino]-4-[5-iodobenzimidazol-1-yl]pyrimidine and 2-aminophenylboronic acid. Mass spectrum (ESI) 437.3 (M+1).

EXAMPLE 413

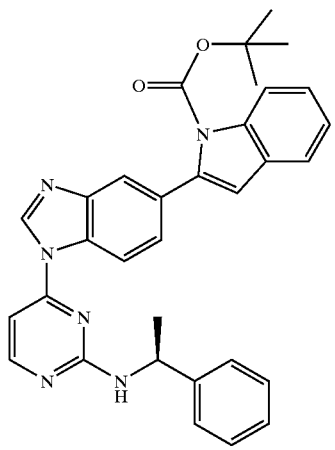

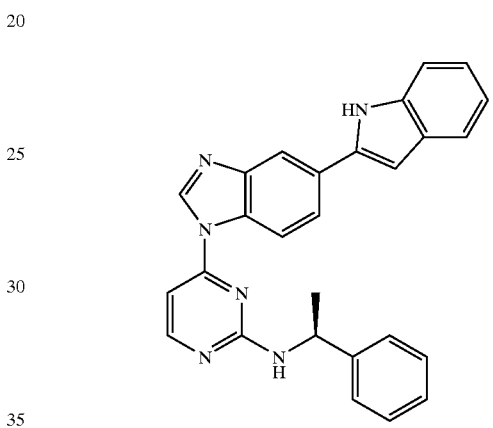

2-[(S)-1-Phenylethylamino]-4-[5-(N-tert-butoxycarbonyl-indol-2-yl)benzimidazol-1-yl]pyrimidine and 2-[(S)-1-Phenylethylamino]-4-[5-(indol-2-yl)benzimidazol-1-yl]pyrimidine The title compounds isolated in a ratio of 1:1.3, were prepared according to the procedure described in EXAMPLE 397, starting from 2-[(S)-1-Phenylethylamino]-4-[5-iodobenzimidazol-1-yl]pyrimidine and 3-(N-tert-butoxycarbonyl-indole-2-boronic acid. Mass spectrum (ESI) 531.2 (M+1) and 431.1 (M+1) respectively.

EXAMPLE 414

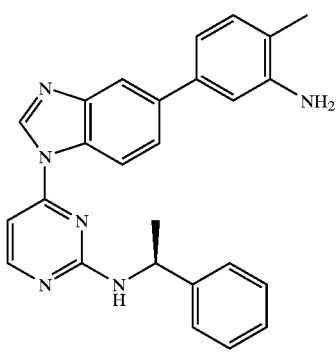

2-[(S)-1-Phenylethylamino]-4-[5-(3-amino-4-methyl-phenyl)benzimidazol-1-yl]pyrimidine The title compound was prepared according to the procedure described in EXAMPLE 397, starting from 2-[(S)-1-Phenylethylamino]-4-[5-iodobenzimidazol-1-yl]pyrimidine and 3-amino-4-methyl-phenylboronic acid. Mass spectrum (ESI) 421.3 (M+1).

EXAMPLE 415

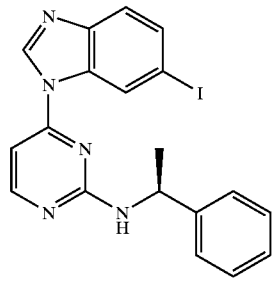

2-[(S)-Phenylethylamino]-4-[6-iodobenzimidazol-1-yl]pyrimidine

The title compound was prepared from 2-[(S)-phenylethylamino]-4-[6-aminobenzimidazol-1-yl]pyrimidine (EXAMPLE 79) according to the procedure outlined in EXAMPLE 271. Mass spectrum 422.0(M+1).

EXAMPLE 416

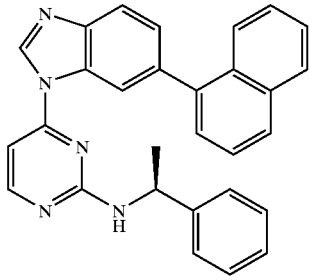

2-[(S)-1-Phenylethylamino]-4-[6-(1-naphthyl)benzimidazol-1-yl]pyrimidine

2-[(S)-1-Phenylethylamino]-4-[6-iodobenzimidazol-1-yl]pyrimidine (EXAMPLE 415) (50 mg), 1-naphthyl boronic acid (22 mg), potassium carbonate (31 mg), and tetrakis(triphenylphosphine)palladium(0) (5 mg) were dissolved in degassed n-propanol (2.6 mL) and water (0.4 mL) and stirred at 80° C. under argon atmosphere for 15 hours. Upon cooling, the reaction mixture was filtered through Celite® (the ppt was washed with 10 mL of EtOAc) and evaporated. The residue was purified by preparative thin layer chromatoraphy eluted with 5% MeOH/CH$_2$Cl$_2$) giving 44 mg of the title compound. $^1$H NMR (500 MHz, CDCl3), δ 8.82 (br s, 1H), 8.38 (s, 1H), 7.97–7.75 (m, 4H), 7.54–7.29 (m, 9H), 7.19 (t, 1 H, J=7.5 Hz), 7.01 (d, 1H, J=Hz), 5.7 (s, 1H), 1.67 (d, 3H, J=7.0 Hz); Mass spectrum (ESI) 442.3 (M+1).

EXAMPLE 417

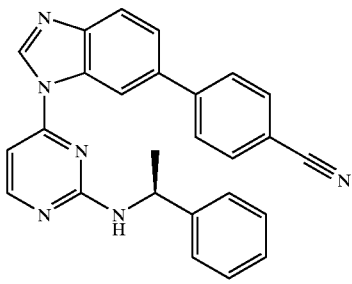

2-[(S)-1-Phenylethylamino]-4-[6-(4-cyanophenyl)benzimidazol-1-yl]pyrimidine

The title compound was prepared according to the procedure described in EXAMPLE 416, starting from 2-[(S)-1-Phenylethylamino]-4-[6-iodobenzimidazol-1-yl]pyrimidine and 4-cyanophenylboronic acid. Mass spectrum (ESI) 417.3 (M+1).

EXAMPLE 418

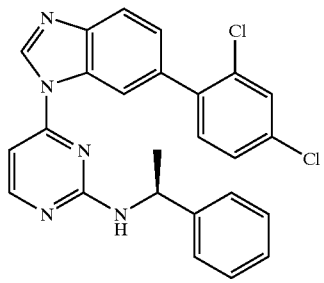

2-[(S)-1-Phenylethylamino]-4-[6-(2,4-dichlororophenyl)benzimidazol-1-yl]pyrimidine The title compound was prepared according to the procedure described in EXAMPLE 416, starting from 2-[(S)-1-Phenylethylamino]-4-[6-iodobenzimidazol-1-yl]pyrimidine and 2,4-dichlorophenyl boronic acid. Mass spectrum (ESI) 460.3 (M+)

EXAMPLE 419

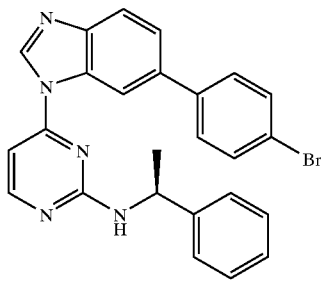

2-[(S)-1-Phenylethylamino]-4-[6-(4-bromophenyl)benzimidazol-1-yl]pyrimidine

The title compound was prepared according to the procedure described in EXAMPLE 416, starting from 2-[(S)-1-Phenylethylamino]-4-[6-iodobenzimidazol-1-yl]

pyrimidine and 4-bromophenylboronic acid. Mass spectrum (ESI) 472.1 (M+1)

EXAMPLE 420

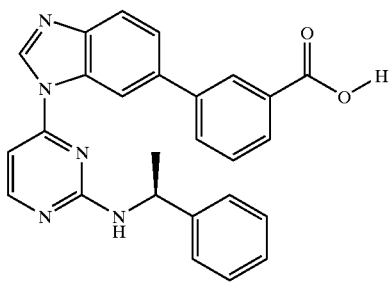

2-[(S)-1-Phenylethylamino]-4-[6-(3-carboxyphenyl) benzimidazol-1-yl]pyrimidine

The title compound was prepared according to the procedure described in EXAMPLE 416, starting from 2-[(S)-1-Phenylethylamino]-4-[6-iodobenzimidazol-1-yl]pyrimidine and 3-carboxyphenylboronic acid. Mass spectrum (ESI) 436.3 (M+1).

EXAMPLE 421

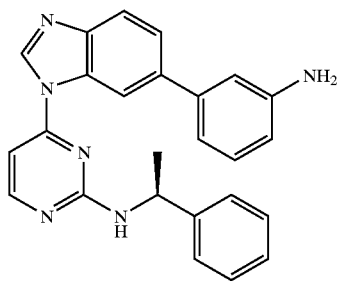

2-[(S)-1-Phenylethylamino]-4-[6-(3-aminophenyl) benzimidazol-1-yl]pyrimidine

The title compound was prepared according to the procedure described in EXAMPLE 416, starting from 2-[(S)-1-Phenylethylamino]-4-[6-iodobenzimidazol-1-yl]pyrimidine and 3-aminophenylboronic acid. Mass spectrum (ESI) 407.3 (M+1).

EXAMPLE 422

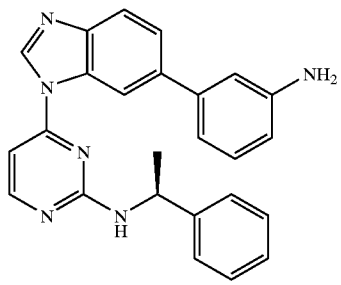

2-[(S)-1-Phenylethylamino]-4-[6-(3-aminophenyl) benzimidazol-1-yl]pyrimidine

The title compound was prepared according to the procedure described in EXAMPLE 416, starting from 2-[(S)-1-Phenylethylamino]-4-[6-iodobenzimidazol-1-yl]pyrimidine and 3-aminophenylboronic acid. Mass spectrum (ESI) 407.3 (M+1).

EXAMPLE 423

2-[(S)-1-Phenylethylamino]-4-[5-trimethylstannylbenzimidazol-1-yl]pyrimidine

The title compound was prepared from 2-[(S)-1-Phenylethylamino]-4-[5-iodobenzimidazol-1-yl]pyrimidine using hexamethylditin according to the procedure outlined in EXAMPLE 327.

EXAMPLE 424

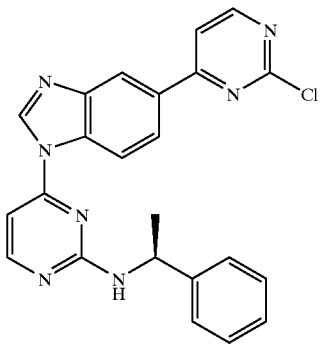

2-[(S)-1-Phenylethylamino]-4-[5-(2-chloropyrimidin-4-yl)benzimidazol-1-yl]pyrimidine 2-[(S)-1-Phenylethylamino]-4-[5-trimethylstannylbenzinidazol-1-yl]pyrimidine (120 mg), 2,4-dichloropyrimidine (113 mg), and Pd(Ph$_3$P)$_2$Cl$_2$ (10 mg) were dissolved in degassed N,N-dimethylformamide (2.0 mL) and the resulting solution was stirred at 100° C. under argon atmosphere for 3 hours. Upon cooling, the reaction mixture was filtered through Celite® (the precipitate was washed with 30 mL of EtOAc) and evaporated. The residue was purified by preparative thin layer chromatography eluted with 5% MeOH/CH$_2$Cl$_2$ giving 92 mg of the title compound. $^1$H NMR (500 MHz, 2:1, CD$_3$OD/CDCl$_3$), δ 8.61 (br s, 1H), 8.35 (d, 1H, J=5.5 Hz), 8.34 (s, 1H), 8.27 (d, 1H, J=5.5 Hz), 7.91 (br s, 1H), 7.42 (d, 1H, J=7.5 Hz), 7.34 (t, 1H, J=7.5 Hz), 7.23 (d, 1H, J=7.0 Hz), 7.11 (d, 1H, J=5.0 Hz), 6.87 (d, 1H, J=5.5 Hz), 5.14 (m, 1H), 1.59 (d, 3H, J=7.0 Hz); Mass spectrum (ESI) 428.1 (M+1).

EXAMPLE 425

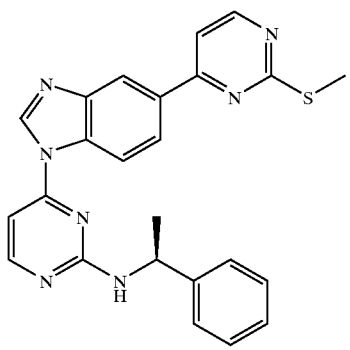

2-[(S)-1-Phenylethylamino]-4-[5-(2-methylthiopyrimidin-4-yl)benzimidazol-1-yl]pyrimidine The title compound was prepared according to the procedure described in EXAMPLE 424, starting from 2-[(S)-1-Phenylethylamino]-4-[5-trimethylstannylbenzimidazol-1-yl]pyrimidine and 4-chloro-2-methylthio-pyrimidine. Mass spectrum (ESI) 440.4 (M+1).

EXAMPLE 426

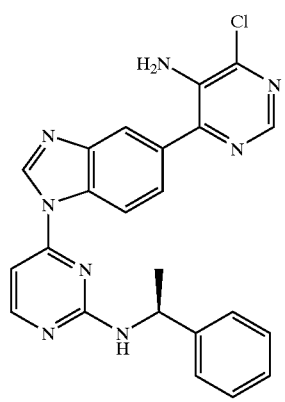

2[(S)-1-Phenylethylamino]-4-[5-(5-amino-6-chloropyrimidin-4-yl)benzimidazol-1-yl]pyrimidine The title compound was prepared according to the procedure described in EXAMPLE 424, starting from 2-[(S)-1-Phenylethylamino]-4-[5-trimethylstannylbenzimidazol-1-yl]pyrimidine and 5-amino-4,6-dichloropyrimidine. Mass spectrum (ESI) 443.4 (M+).

EXAMPLE 427

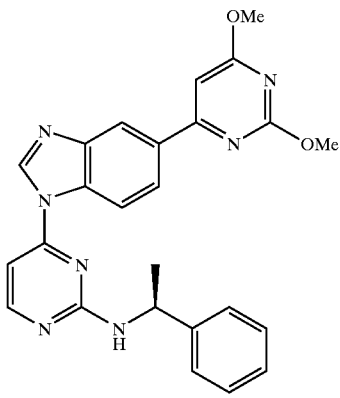

2-[(S)-1-Phenylethylamino]-4-[5-(2,6-dimethoxypyrimidin-4-yl)benzimidazol-1-yl]pyrimidine The title compound was prepared according to the procedure described in EXAMPLE 424, starting from 2-[(S)-1-Phenylethylamino]-4-[5-trimethylstannylbenzimidazol-1-yl]pyrimidine and 4-chloro-2,6-dimethoxypyrimidine. Mass spectrum (ESI) 443.4 (M+).

EXAMPLE 428

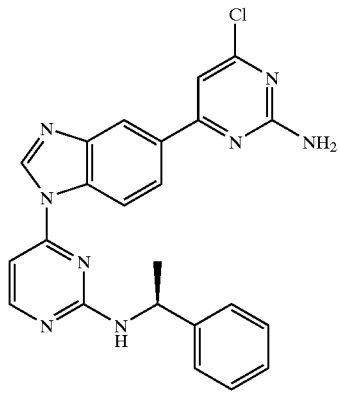

2-[(S)-1-Phenylethylamino]-4-[5-(2-amino-6-chloro-pyrimidin-4-yl)benzimidazol-1-yl]pyrimidine The title compound was prepared according to the procedure described in EXAMPLE 424, starting from 2-[(S)-1-Phenylethylamino]-4-[5-trimethylstannylbenzimidazol-1-yl]pyrimidine and 2-amino4,6-dichloropyrimidine. Mass spectrum (ESI) 443.4 (M+).

EXAMPLE 429

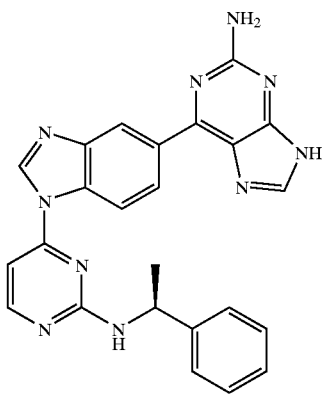

2-[(S)-1-Phenylethylamino]-4-[5-(purin-4-yl)benzimidazol-1-yl]pyrimidine

The title compound was prepared according to the procedure described in EXAMPLE 424, starting from 2-[(S)-1-Phenylethylamino]-4-[5-trimethylstannylbenzimidazol-1-yl]pyrimidine and 4-chloropurine. Mass spectrum (ESI) 443.4 (M+).

EXAMPLE 430

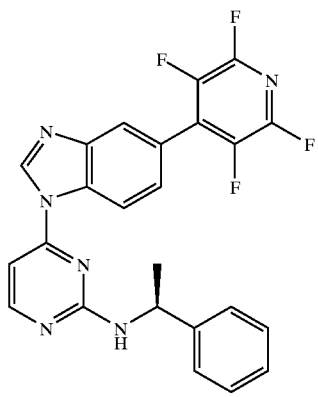

2-[(S)-1-Phenylethylamino]-4-[5-(tetrafluoropyridin-4-yl)benzimidazol-1-yl]pyrimidine The title compound was prepared according to the procedure described in EXAMPLE 424, starting from 2-[(S)-1-Phenylethylamino]-4-[5-trimethylstannylbenzimidazol-1-yl]pyrimidine and 4-bromo-2,3,5,6-tetrafluoropyridine. Mass spectrum (ESI) 465.5 (M+1).

EXAMPLE 431

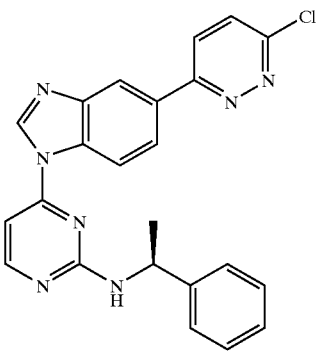

2-[(S)-1-Phenylethylamino]-4-[5-(3-chloropyridazin-6-yl)benzimidazol-1-yl]pyrimidine The title compound was prepared according to the procedure described in EXAMPLE 424, starting from 2-[(S)-1-Phenylethylamino]-4-[5-trimethylstannylbenzimidazol-1-yl]pyrimidine and 3,6-dichloropyridazine. Mass spectrum (ESI) 427.9 (M+).

EXAMPLE 432

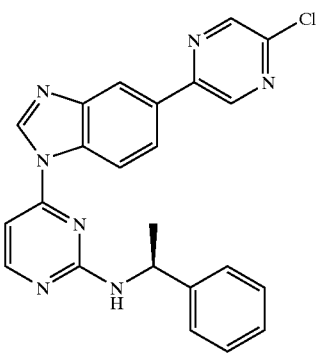

2-[(S)-1-Phenylethylamino]-4-[5-(2-chloropyrazin-5-yl)benzimidazol-1-yl]pyrimidine The title compound was prepared according to the procedure described in EXAMPLE 424, starting from 2-[(S)-1-Phenylethylamino]-4-[5-trimethylstannylbenzimidazol-1-yl]pyrimidine and 2,5-dichloropyrazine. Mass spectrum (ESI) 427.9 (M+).

EXAMPLE 433

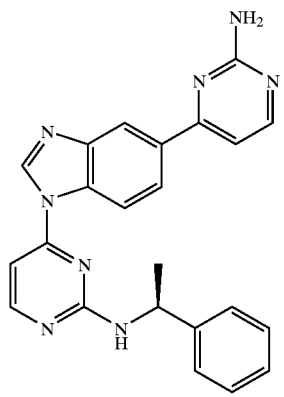

2-[(S)-1-Phenylethylamino]-4-[5-(2-aminopyrimidin-4-yl)benzimidazol-1-yl]pyrimidine Step A: 2-[(S)-1-Phenylethylamino]-4-[5-(2-(3,4,5-trimethoxybenzylamino)pyrimidin-4-yl)benzimidazol-1-yl]pyrimidine 2-[(S)-1-Phenylethylamino]-4-[5-(2-chloropyrimidin-4-yl)benzimidazol-1-yl]pyrimidine (EXAMPLE 424) (80 mg), 3,4,5-trimethoxybenzylamine hydrochloride (219 mg), and N,N-diisopropylethylamine (0.16 mL) were dissolved DMSO (4 mL) and the resulting solution was heated to 100° C. for 15 hours. Upon cooling the reaction mixture was diluted with water (20 mL) and extracted with EtOAc (2×25). The combined organic extracts were dried (MgSO$_4$) and evaporated.

Step B: 2-[(S)-1-Phenylethylamino]-4-[5-(2-aminopyrimidin-4-yl)benzimidazol-1-yl]pyrimidine The resulting residue was taken up in CH$_2$Cl$_2$ (8 mL) and 30% HBr in acetic acid was added dropwise. After stirring for 15 minutes at rt, the reaction mixture was diluted with water (10 mL) and washed with hexanes (2×10 mL). The aqueous extract was made basic with conc. aq. NH$_4$OH (pH 10) and extracted with EtOAc (2×25 mL). The combined organic extracts were dried (MgSO$_4$) and evaporated. The residue was purified by preparative thin layer chromatography eluted with 1:5:94 triethylamine/MeOH/CH$_2$Cl$_2$ giving 66 mg of the title compound. $^1$H NMR (500 MHz, 2:1 CD$_3$OD:CDCl$_3$), δ 8.6 (br s, 1H); 8.35(d, J=5.5 Hz,1H); 8.35 (s, 1H); 8.27 (d, J=5.5 Hz, 1H); 7.93 (br s, 2H); 7.43 (d, J=7.2 Hz, 2H); 7.35 (t, J=7.6 Hz, 3H); 7.23 (t, J=7.2H, 1H); 7.12 (d, J=5.4 Hz, 1H); 6.90 (d, J=5.5 Hz, 1H); 5.14 (br q, J=7 Hz, 1H); 1.59 (d, J=7 Hz, 3H). Mass spectrum (ESI) 409.1 (M+1).

EXAMPLE 434

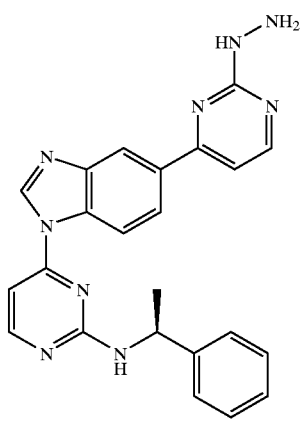

2-[(S)-1-Phenylethylamino]-4-[5-(2-hydrazinylpyrimidin-4-yl)benzimidazol-1-yl]pyrimidine The title compound was prepared according to the procedure described in EXAMPLE 433, Step A, starting from 2-[(S)-1-Phenylethylamino]-4-[5-(2-chloropyrimidin-4-yl)benzimidazol-1-yl]pyrimidine and hydrazine. Mass spectrum (ESI) 424.3 (M+).

EXAMPLE 435

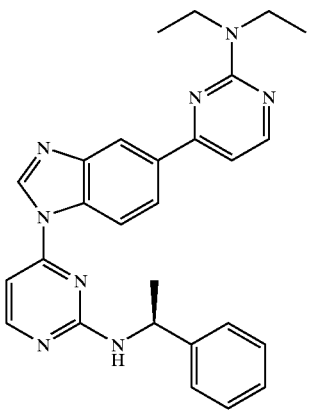

2-[(S)-1-Phenylethylamino]-4-[5-(4-[2-N,N-diethylaminopyrimidin-4-yl)benzimidazol-1-yl]pyrimidine The title compound was prepared according to the procedure described in EXAMPLE 433, Step A starting from 2-[(S)-1-Phenylethylamino]-4-[5-(2-chloropyrimidin-4-yl)benzimidazol-1-yl]pyrimidine and diethylamine. Mass spectrum (ESI) 465.5 (M+1).

EXAMPLE 436

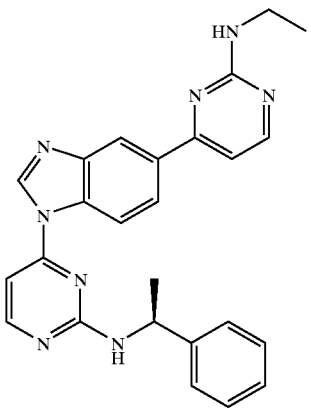

2-[(S)-1-Phenylethylamino]-4-[5-(2-N-ethylaminopyrimidin-4-yl)benzimidazol-1-yl]pyrimidine The title compound was prepared according to the procedure described in EXAMPLE 433, Step A starting from 2-[(S)-1-Phenylethylamino]-4-[5-(2-chloropyrimidin-4-yl)benzimidazol-1-yl]pyrimidine and ethylamine. Mass spectrum (ESI) 465.5 (M+1).

EXAMPLE 437

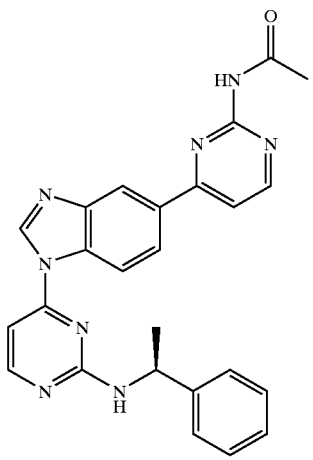

2-[(S)-1-Phenylethylamino]-4-[5-(2-N-acetylaminopyrimidin-4-yl)benzimidazol-1-yl]pyrimidine 2-[(S)-1-Phenylethylamino]-4-[5-(2-aminopyrimidin-4-yl)benzimidazol-1-yl]pyrimidine (10 mg) was heated to 80° C. in acetic anhydride for 2 hours. Upon cooling the reaction mixture was diluted with saturated aqueous sodium bicarbonate (5 mL) and extracted with EtOAc (2×10 mL). The combined organic extracts were dried (MgSO$_4$) and evaporated. The product was purified by preparative thin layer chromatography eluted with 5% MeOH/CH$_2$Cl$_2$ to give 6 mg of the title compound. Mass spectrum (ESI) 451.2 (M+1).

EXAMPLE 438

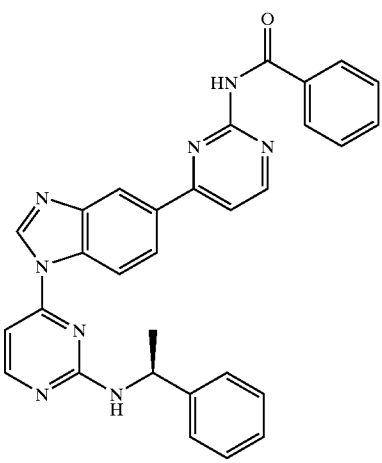

2-[(S)-1-Phenylethylamino]-4-[5-(4-[2-N-benzoylamino-pyrimidine)benzimidazol-1-yl]pyrimidine 2-[(S)-1-Phenylethylamino]-4-[5-(2-aminopyrimidin-4-yl)benzimidazol-1-yl]pyrimidine (10 mg) was dissolved in anhydrous pyridine and benzoyl chloride was added. The resulting solution was stirred at rt for 2 hours. Upon cooling the reaction mixture was diluted with saturated aqueous ammonium chloride (5 mL) and extracted with EtOAc (2×10 mL). The combined organic extracts were dried (MgSO$_4$) and evaporated. The product was purified by preparative thin layer chromatography eluted with 5% MeOH/CH$_2$Cl$_2$ to give 10 mg of the title compound. Mass spectrum (ESI) 413.2 (M+1).

EXAMPLE 439

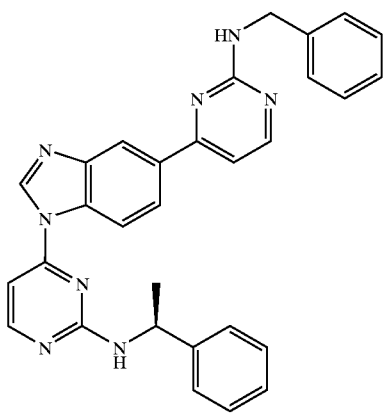

2-[(S)-1-Phenylethylamino]-4-[5-(4-[2-N-benzylamino-pyrimidine)benzimidazol-1-yl]pyrimidine The title compound was prepared according to the procedure described in EXAMPLE 433, Step A starting from 2-[(S)-1-Phenylethylamino]-4-[5-(2-chloropyrimidin-4-yl)benzimidazol-1-yl]pyrimidine and benzylamine. Mass spectrum (ESI) 499.5 (M+1).

EXAMPLE 440

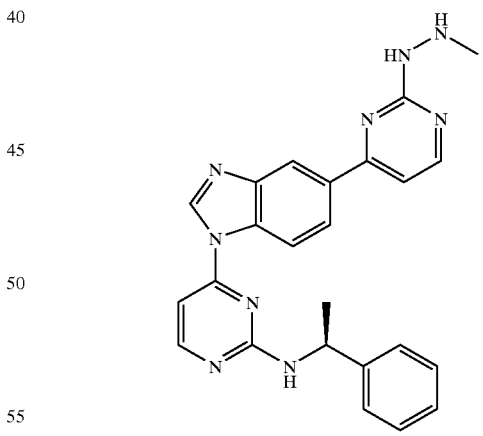

2-[(S)-1-Phenylethylamino]-4-[5-(2-N-methylhydrazinylpyrimidin-4-yl)benzimidazol-1-yl]pyrimidine The title compound was prepared according to the procedure described in EXAMPLE 433, Step A starting from 2-[(S)-1-Phenylethylamino]-4-[5-(2-chloropyrimidin-4-yl)benzimidazol-1-yl]pyrimidine and methyl hydrazine. Mass spectrum (ESI) 438.6 (M+).

EXAMPLE 441

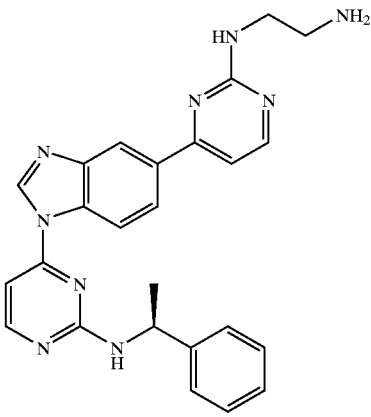

2-[(S)-1-Phenylethylamino]-4-[5-(2-N-(aminoethyl)aminopyrimidin-4-yl)benzimidazol-1-yl]pyrimidine The title compound was prepared according to the procedure described in EXAMPLE 433, Step A starting from 2-[(S)-1-Phenylethylamino]-4-[5-(2-chloropyrimidin-4-yl)benzimidazol-1-yl]pyrimidine and ethylenediamine. Mass spectrum (ESI) 452.3 (M+).

EXAMPLE 442

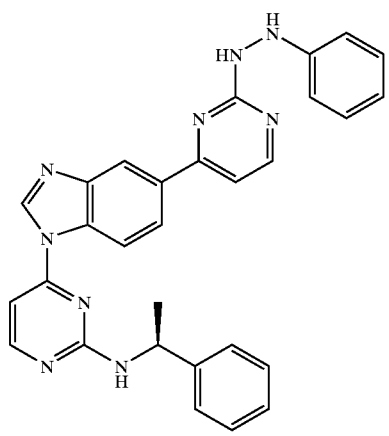

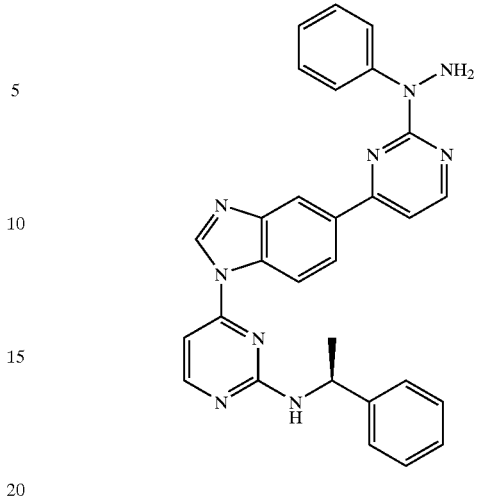

2-[(S)-1-Phenylethylamino]-4-[5-(2-(1-N-phenylhydrazinyl)pyrimidin-4-yl)benzimidazol-1-yl]pyrimidine and 2-[(S)-1-Phenylethylamino]-4-[5-(2-(2-N-phenylhydrazinyl)pyrimidin-4-yl)benzimidazol-1-yl]pyrimidine The title compounds were prepared according to the procedure described in EXAMPLE 433, Step A starting from 2-[(S)-1-Phenylethylamino]-4-[5-(2-chloropyrimidin-4-yl)benzimidazol-1-yl]pyrimidine and phenylhydrazine. Mass spectra (ESI) 500.5 (M+1) and 500.5 (M+1) respectively.

EXAMPLE 443

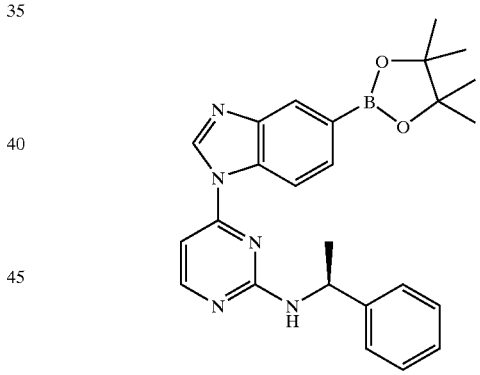

2-[(S)-1-Phenylethylamino]-4-[5-(pinacolatoboronyl)benzimidazol-1-yl]pyrimidine

2-[(S)-1-Phenylethylamino]-4-[5-iodobenzimidazol-1-yl]pyrimidine (1.65 g), bis-pinacolatoboronyl (1.04 g), potassium acetate (1.12 g), and [1,1'-bis(diphenylphosphino)ferrocene]dichloropalladium(II) complex with dichloromethane (1:1) (50 mg) were dissolved in degassed DMSO (30 mL) and the resulting solution was stirred at 80° C. under argon atmosphere for 15 hours. Upon cooling to room temperature the reaction mixture was diluted with water (100 mL), washed with $Et_2O$ (2×100 mL), and the combined organic layer was washed with brine, dried over $MgSO_4$ and evaporated. The residue was purified by silica gel chromatography (5% $MeOH/CH_2Cl_2$) to yield 1.35 g of the title compound. $^1H$ NMR (500 MHz, $CDCl_3$), δ 8.57 (br s, 1H), 8.36 (br s, 1H), 8.31 (s, 1H), 7.94 (br s, 1H), 7.78 (d, 1H, J=8.5 Hz), 7.45–7.26 (m, 4H), 6.78 (d, 1H, J=4.5 Hz), 6.19 (br s, 1H), 5.23 (m, 1H), 1.64 (d, 3H, J=7.0 Hz), 1.40 (s, 12H); Mass spectrum (ESI) 442.3 (M+1).

EXAMPLE 444

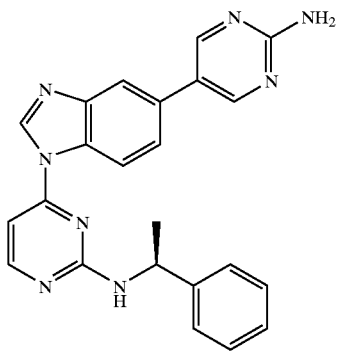

2-[(S)-1-Phenylethylamino]-4-[5-(5-[2-aminopyrimidin-4-yl)benzimidazol-1-yl]pyrimidine 2-[(S)-1-Phenylethylamino]-4-[5-(pinacolatoboronyl)benzimidazol-1-yl]pyrimidine (60 mg) was dissolved in degassed (argon) DMF (2.6 mL) and degassed (argon) water (0.4 mL). Potassium carbonate (40 mg), 2-amino-5-bromopyrimidine (47 mg), tris(dibenzylideneacetone)dipalladium(0) (4.0 mg), and tri-o-tolylphosphine (2.5 mg) were added and the resulting reaction mixture heated to 90° C. and stirred for 15 hours. Upon cooling to room temperature the reaction mixture was diluted with water (10 mL), washed with EtOAc (2×10 mL), and the combined organic layers were washed with brine, dried over MgSO$_4$ and evaporated. The residue was purified by preparative thin-layer silica gel chromatography (5% MeOH/CH$_2$Cl$_2$) to yield 43 mg of the title compound. $^1$H NMR (500 MHz, 1:2 CD$_3$OD/CDCl$_3$), Λ8.63 (br s, 1H), 8.55 (s, 2H), 8.34 (s, 1H), 7.82 (s, 2H), 7.45–7.32 (m, 5H), 7.23 (t, 1H, J=7.0Hz), 6.88 (d, 1H, J=5.5Hz), 5.14 (m, 1H), 1.60 (d, 3H, J=6.5 Hz); Mass spectrum (ESI) 409.1 (M+1).

EXAMPLE 445

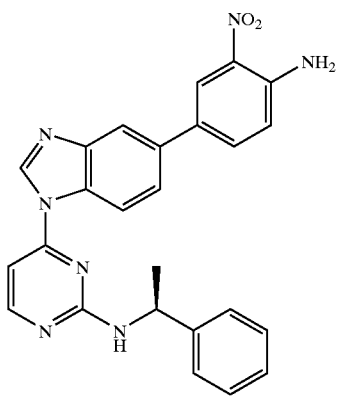

2-[(S)-1-Phenylethylamino]-4-[5-(4-amino-3-nitrophenyl)benzimidazol-1-yl]pyrimidine The title compound was prepared according to the procedure described in EXAMPLE 444, starting from 2-[(S)-1-Phenylethylamino]-4-[5-(pinacolatoboronyl)benzimidazol-1-yl]pyrimidine and 1-amino-4-bromo-2-nitrobenzene. Mass spectrum (ESI) 452.2 (M+1).

EXAMPLE 446

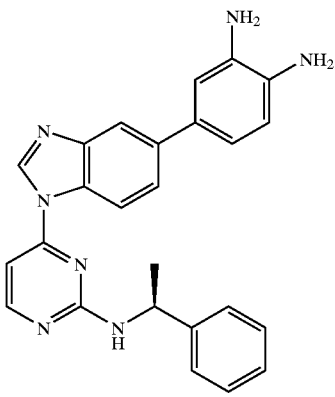

2-[(S)-1-Phenylethylamino]-4-[5-(3,4-diaminophenyl)benzimidazol-1-yl]pyrimidine

The title compound was prepared according to the procedure described in EXAMPLE 444, starting from 2-[(S)-1-Phenylethylamino]-4-[5-(pinacolatoboronyl)benzimidazol-1-yl]pyrimidine and 1,2-diamino-4-bromobenzene. Mass spectrum (ESI) 422.3 (M+1).

EXAMPLE 447

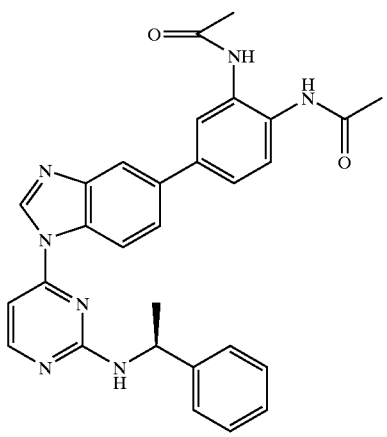

2-[(S)-1-Phenylethylamino]-4-[5-(3,4-di-(N-acetylamino)phenyl)benzimidazol-1-yl]pyrimidine 2-[(S)-1-Phenylethylamino]-4-[5-(3,4-diaminophenyl)benzimidazol-1-yl]pyrimidine (10 mg) was heated in acetic anhydride (1.0 mL) for two hours. Upon cooling, the reaction mixture evaporated. The residue was loaded onto one 20×20 cm 1000 micron silica gel plates (5% MeOH/CH$_2$Cl$_2$) and 6 mg of the title compound was isolated. Mass spectrum (ESI) 506.7 (M+1).

EXAMPLE 448

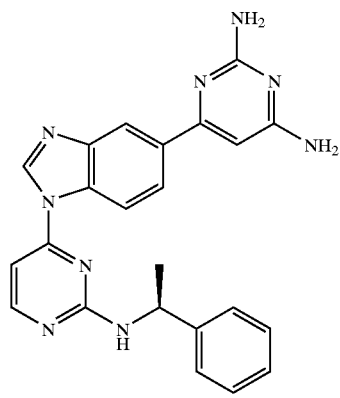

2-[(S)-1-Phenylethylamino]-4-[5-(2,6-diaminopyrimidin-4-yl)benzimidazol-1-yl]pyrimidine The title compound was prepared according to the procedure described in EXAMPLE 444, starting from 2-[(S)-1-Phenylethylamino]-4-[5-(pinacolatoboronyl)benzimidazol-1-yl]pyrimidine and 2,6-diamino-4-bromopyrimidine. Mass spectrum (ESI) 424.3 (M+1).

EXAMPLE 449

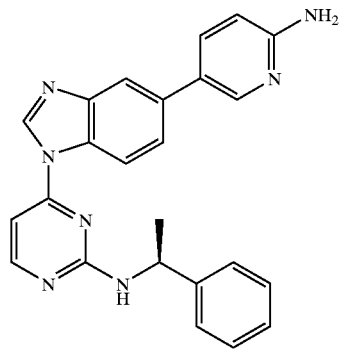

2-[(S)-1-Phenylethylamino]-4-[5-(2-aminopyridin-5-yl)benzimidazol-1-yl]pyrimidine The title compound was prepared according to the procedure described in EXAMPLE 444, starting from 2-[(S)-1-Phenylethylamino]-4-[5-(pinacolatoboronyl)benzimidazol-1-yl]pyrimidine and 2-amino-5-bromopyridine. Mass spectrum (ESI) 406.5 (M+).

EXAMPLE 450

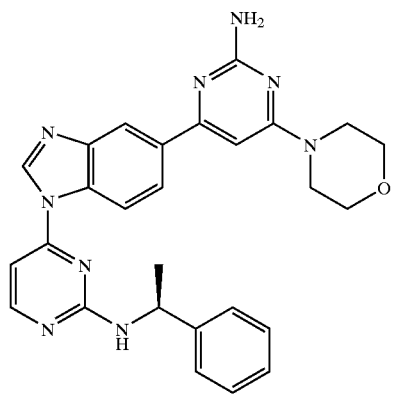

2-[(S)-1-Phenylethylamino]-4-[5-(2-amino-6-(morpholin-1-yl)pyrimidin-4-yl)benzimidazol-1-yl]pyrimidine The title compound was prepared according to the procedure described in EXAMPLE 444, starting from 2-[(S)-1-Phenylethylamino]-4-[5-(pinacolatoboronyl)benzimidazol-1-yl]pyrimidine and 2-amino-4-bromo-6-(morpholin-1-yl)pyrimidine. Mass spectrum (ESI) 493.2 (M+).

EXAMPLE 451

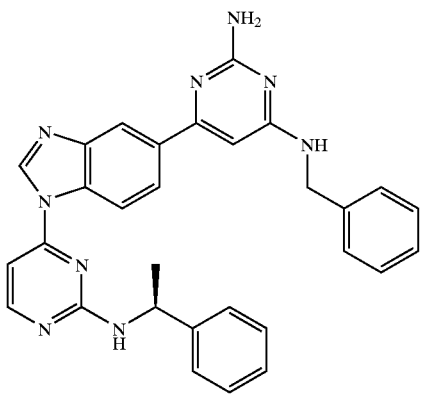

2-[(S)-1-Phenylethylamino]-4-[5-(2-amino-6-N-benzylaminepyrimidin-4-yl)benzimidazol-1-yl]pyrimidine The title compound was prepared according to the procedure described in EXAMPLE 444, starting from 2-[(S)-1-Phenylethylamino]-4-[5-(pinacolatoboronyl)benzimidazol-1-yl]pyrimidine and 2-amino-4-bromo-6-N-benzylamino-pyrimidine. Mass spectrum (ESI) 513.1 (M+).

EXAMPLE 452

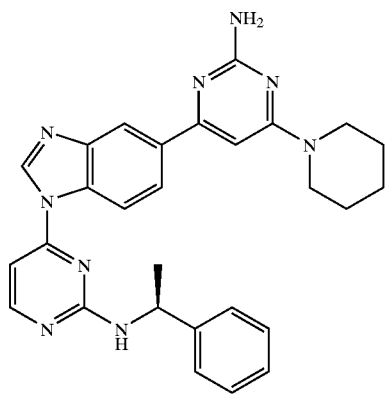

2-[(S)-1-Phenylethylamino]-4-[5-(2-amino-6-(piperidin-1-yl)pyrimidin-4-yl)benzimidazol-1-yl]pyrimidine The title compound was prepared according to the procedure described in EXAMPLE 444, starting from 2-[(S)-1-Phenylethylamino]-4-[5-(pinacolatoboronyl)benzimidazol-1-yl]pyrimidine and 2-amino-6-bromo-4-(piperidin-1-yl)pyrimidine. Mass spectrum (ESI) 492.4 (M+1).

EXAMPLE 453

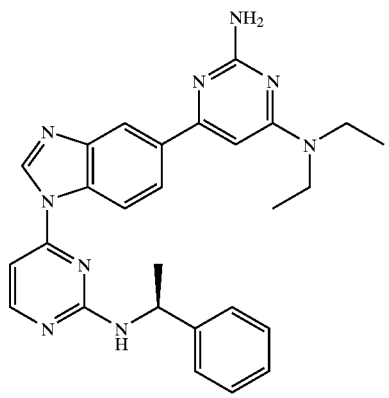

2-[(S)-1-Phenylethylamino]-4-[5-(2-amino-6-N,N-diethylaminopyrimidin-4-yl)benzimidazol-1-yl]pyrimidine The title compound was prepared according to the procedure described in EXAMPLE 444, starting from 2-[(S)-1-Phenylethylamino]-4-[5-(pinacolatoboronyl)benzimidazol-1-yl]pyrimidine and 2-amino-4-bromo-6-N,N-diethylaminopyrimidine. Mass spectrum (ESI) 480.6 (M+1).

EXAMPLE 454

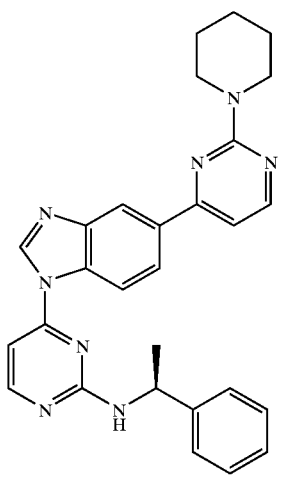

2-[(S)-1-Phenylethylamino]-4-[5-(2-(piperidin-1-yl)pyrimidin-4-yl)benzimidazol-1-yl]pyrimidine The title compound was prepared according to the procedure described in EXAMPLE 444, starting from 2-[(S)-1-Phenylethylamino]-4-[5-(pinacolatoboronyl)benzimidazol-1-yl]pyrimidine and 4-bromo-2-(piperidin-1-yl)pyrimidine. Mass spectrum (ESI) 477.4 (M+1).

EXAMPLE 455

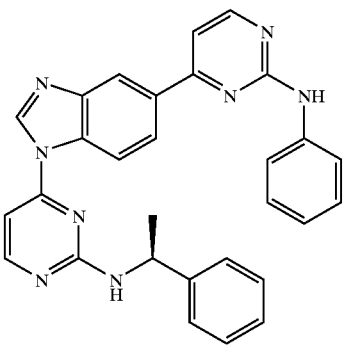

2-[(S)-1-Phenylethylamino]-4-[5-(2-N-phenylaminopyrimidin-4-yl)benzimidazol-1-yl]pyrimidine The title compound was prepared according to the procedure described in EXAMPLE 444, starting from 2-[(S)-1-Phenylethylamino]-4-[5-(pinacolatoboronyl)benzimidazol-1-yl]pyrimidine and 2-(N-phenylamino)-4-bromopyrimidine. Mass spectrum (ESI) 485.6 (M+1).

EXAMPLE 456

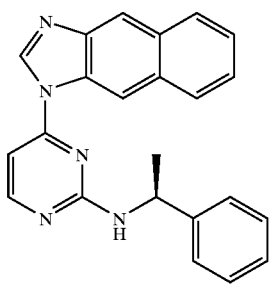

2-[(S)-1-Phenylethylamino]-4-[naphtho[2,3,d]imidazol-1-yl]pyrimidine

Step A: Naphtho[2,3,d]imidazole 1,2-diaminonapthylene (1.0 g) was dissolved in 97% formic acid (25 mL) and heated to 110° C. for 15 hours. The reaction mixture was then evaporated and the resulting residue was diluted with EtOAc (100 mL) and washed with sat. aq. Sodium bicarbonate (2×50 mL). The combined organic extracts were dried (MgSO$_4$) and concentrated under reduced pressure to yield the title compound as a brown oil. No further purification was performed. Mass spectrum (ESI) 169 (M+1).

Step B: 2-[(S)-1-Phenylethylamino]-4-[N-naptho[2,3,d]imidazol-1-yl]pyrimidine Naptho[2,3,d]imidazole (100 mg) was dissolved in DMF (5 mL) and NaH [60%] (29 mg) and 2-[(S)-1-phenylethylamino]-4-chloropyrimidine were added and the reaction was heated to 100° C. for 3 hours. After cooling to room temperature, the solution was then diluted with 10 mL of water and extracted with 2×10 mL of of EtOAc. The combined organic extracts were then dried (MgSO$_4$) and concentrated under reduced pressure. The residue was purified with preparative thin-layer chromatography (SiO$_2$, 5% MeOH in CH$_2$Cl$_2$) to yield 121 mg of the title compound. $^1$H NMR (500 MHz, CDCl$_3$), δ 8.78 (br S, 1H), 8.25 (d, 1H, J=5.0 Hz), 8.04 (s, 1H), 7.86 (d, 1H, J=8.0 Hz), 7.46 (d, 2H, J=7.5 Hz), 7.41–7.29 (m, 6H), 7.21–7.20 (m, 1H), 6.86 (d, 1H, J=5.5 Hz), 5.18 (q, 1H, J=7.0 Hz), 1.59 (d, 3H, J=7.5 Hz); Mass spectrum (ESI) 366.1 (M+1).

EXAMPLE 457

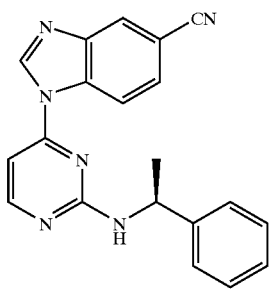

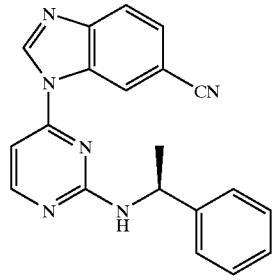

2-[(S)-1-Phenylethylamino]-4-[5-cyanobenzimidazol-1-yl]pyrimidine and 2-[(S)-1-Phenylethylamino]-4-[6-cyanobenzimidazol-1-yl]pyrimidine

Step A: 5-Cyanobenzimidazole

The title compound was prepared according to the procedure described in EXAMPLE 456 Step A, starting from 1,2-diamino-4-cyanobenzene. Mass spectrum (ESI) 144.2 (M+1).

Step B: 2-[(S)-1-Phenylethylamino]-4-[5-cyanobenzimidazol-1-yl]pyrimidine and 2-[(S)-1-Phenylethylamino]-4-[6-cyanobenzimidazol-1-yl]pyrimidine The title compounds were prepared as a 1:1 separable mixture according to the procedure described in EXAMPLE 456 Step B, starting with 2-[(S)-1-phenylethylamino]-4-chloropyrimidine and 5-cyanobenzimidazole. Mass spectrum (ESI) 341.3 (M+1) and 341.3 (M+1) respectively.

EXAMPLE 458

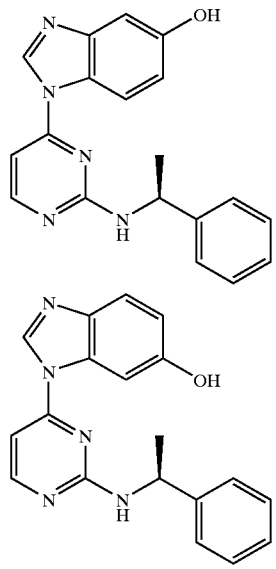

2-[(S)-1-Phenylethylamino]-4-[5-hydroxybenzimidazol-1-yl]pyrimidine and 2-[(S)-1-Phenylethylamino]-4-[6-hydroxybenzimidazol-1-yl]pyrimidine

Step A: 5-Hydroxybenzimidazole

The title compound was prepared according to the procedure described in EXAMPLE 456 Step A, starting from 1,2-diamino-4-hydroxybenzene. Mass spectrum (ESI) 144.2 (M+1).

Step B: 2-[(S)-1-Phenylethylamino]-4-[5-hydroxybenzimidazol-1-yl]pyrimidine and 2-[(S)-1-Phenylethylamino]-4-[6-hydroxybenzimidazol-1-yl]pyrimidine The title compounds were prepared as a 1:1 separable mixture according to the procedure described in EXAMPLE 456 Step B, starting with 2-[(S)-1-phenylethylamino]-4-chloropyrimidine and 5-hydroxybenzimidazole. Mass spectrum (ESI) 332.0 (M+1) and 332.0 (M+1) respectively.

EXAMPLE 459

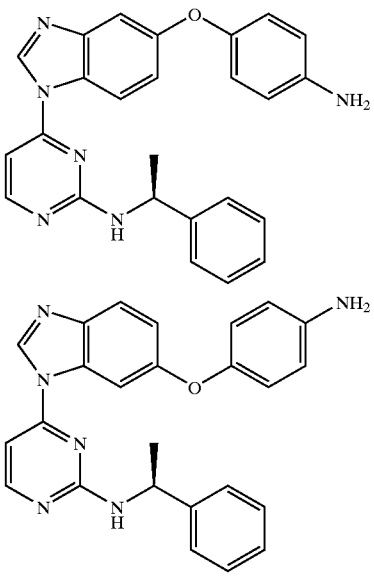

2-[(S)-1-Phenylethylamino]-4-[5-(4-aminophenoxy)benzimidazol-1-yl]pyrimidine and 2-[(S)-1-Phenylethylamino]-4-[6-(4-aminophenoxy)benzimidazol-1-yl]pyrimidine

Step A: 5-(4-amino-phenoxy)benzimidazole

The title compound was prepared according to the procedure described in EXAMPLE 456 Step A, starting from 1,2-diamino-4-(4-aminophenoxy)benzene. Mass spectrum (ESI) 225.3 (M+).

Step B: 2-[(S)-1-Phenylethylamino]-4-[5-(4-aminophenoxy)benzimidazol-1-yl]pyrimidine and 2-[(S)-1-Phenylethylamino]-4-[6-(4-aminophenoxy)benzimidazol-1-yl]pyrimidine The title compounds were prepared as a 1:1 separable mixture according to the procedure described in EXAMPLE 456 Step B, starting with 2-[(S)-1-phenylethylamino]-4-chloropyrimidine and 5-(4-aminophenoxy)benzimidazole. Mass spectrum (ESI) 423.1 (M+1) and 423.1 (M+1) respectively.

EXAMPLE 460

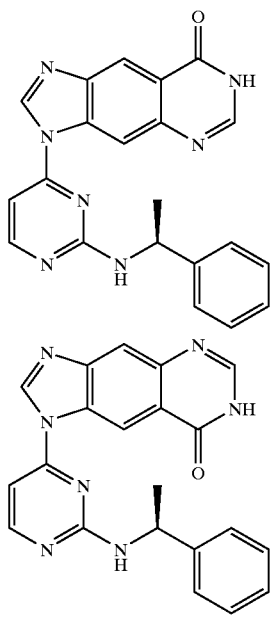

2-[(S)-1-Phenylethylamino]-4-[imidazo[4,5,g]quinazolin-4-one-8-yl]pyrimidine and 2-[(S)-1-Phenylethylamino]-4-[imidazo[4,5,g]quinazolin-4-one-6-yl]pyrimidine

Step A: lin-benzohypoxanthine

The title compound was prepared according to the procedure described in Leonard, N. J.; Kazmierczak, F.; Rykowski, A.; *J. Org. Chem.*, 1987, 52, 2933–2935.

Step B: 2-[(S)-1-Phenylethylamino]-4-[imidazo[4,5,g]quinazolin-4-one-8-yl]pyrimidine and 2-[(S)-1-Phenylethylamino]-4-[imidazo[4,5,g]-quinazolin-4-one-6-yl]pyrimidine The title compounds were prepared as a 1:1 separable mixture according to the procedure described in EXAMPLE 456 Step B, starting with 2-[(S)-1-phenylethylamino]-4-chloropyrimidine and lin-benzohypoxanthine. Mass spectrum (ESI) 384.1 (M+1) and 384.1 (M+1) respectively.

EXAMPLE 461

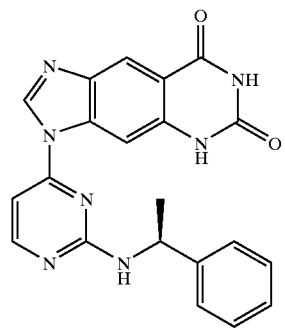

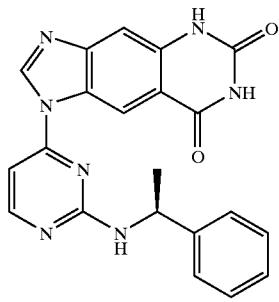

2-[(S)-1-Phenylethylamino]-4-[imidazo[4,5,g]
quinazolin-2,4-dione-8-yl]pyrimidine and 2-[(S)-1-
Phenylethylamino]-4-[imidazo[4,5,g]quinazolin-2,4-
dione-6-yl]-pyrimidine Step A: lin-Benzoxanthine The title compound was prepared according to the procedure described in Leonard, N. J.; Kazmierczak, F.; Rykowski, A.; *J. Org. Chem.*, 1987, 52, 2933–2935.

Step B: 2-[(S)-1-Phenylethylamino]-4-[imidazo[4,5,
g]quinazolin-2,4-dione-8-yl]pyrimidine and 2-[(S)-
1-Phenylethylamino]-4-[imidazo[4,5,g]quinazolin-2,
4-dione-6-yl]pyrimidine The title compounds were prepared as a 1:1 separable mixture according to the procedure described in EXAMPLE 456 Step B, starting with 2-[(S)-1-phenylethylamino]-4-chloropyrimidine and lin-benzoxanthine. Mass spectrum (ESI) 400.1 (M+1) and 400.1 (M+1) respectively.

EXAMPLE 462

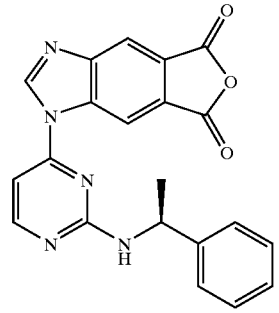

2-[(S)-1-Phenylethylamino]-4-[5,6-dicarboxylic
Anhydride-benzimidazol-1-yl]pyrimidine Step A: Benzimidazole-5,6-dicarboxylic Anhydride The title compound was prepared according to the procedure described in Leonard, N. J.; Kazmierczak, F.; Rykowski, A.; *J. Org. Chem.*, 1987, 52, 2933–2935.

Step B: 2-[(S)-1-Phenylethylamino]-4-[5,6-
dicarboxylic Anhydride-benzimidazol-1-yl]
pyrimidine The title compound was made according to the procedure described in EXAMPLE 456 Step B, starting with 2-[(S)-1-phenylethylamino]-4-chloropyrimidine and benzimidazole-5,6-dicarboxylic anhydride. Mass spectrum (ESI) 385.2 (M+).

EXAMPLE 463

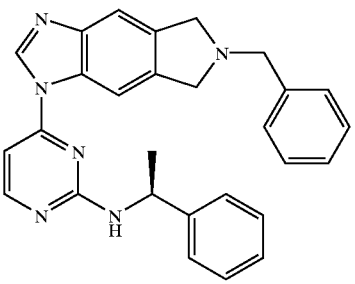

2-[(S)-1-Phenylethylamino]-4-[6-benzyl-pyrrolidino
[3,4,f]benzimidazol-1-yl]pyrimidine Step A: 6-Benzyl-pyrrolidino[3,4,f]benzimidazole Benzimidazole-5,6-N-benzylsuccinimide (130 mg) was dissolved in THF (5 mL) at 0° C. and LiAlH$_4$ (40 mg) was added and the reaction mixture was maintined at reflux for 1 hour. The solution was then diluted slowly with 10 mL of water and extracted with 2×10 mL of of EtOAc. The combined organic extracts were then dried (MgSO$_4$) and concentrated under reduced pressure. The residue was purified with preparative thin-layer chromatography (SiO$_2$, 5% MeOH in CH$_2$Cl$_2$) to yield 53 mg of the title compound. Mass spectrum (ESI) 249.2 (M+).

Step B: 2-[(S)-1-Phenylethylamino]-4-[6-
benzylpyrrolidino[3,4,f]-benzimidazol-1-yl]
pyrimidine The title compound was according to the procedure described in EXAMPLE 456 Step B, starting with 2-[(S)-1-phenylethylamino]-4-chloropyrimidine and 6-benzyl-pyrrolidino[3,4,f]benzimidazole. Mass spectrum (ESI) 446.2 (M+).

EXAMPLE 464

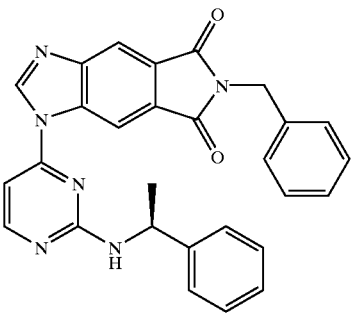

2-[(S)-1-Phenylethylamino]-4-[6-benzyl-5,7-dioxo-
pyrrolidino[3,4,f]benzimidazol-1-yl]pyrimidine Step A: Benzimidazol-5,6-N-benzylsuccinimide Benzimidazole-5,6-dicarboxylic acid (see Leonard, N. J.; Kazmierczak, F.; Rykowski, A.; *J. Org. Chem.*, 1987, 52, 2933–2935) (200 mg) was dissolved in DMF (15 mL) at 0° C. Benzylamine (321 mg), 1-hydroxybenzotriazole (455 mg) and 1-(3-dimethylaminopropyl)-3-ethylcarbodiimide hydrochloride (576 mg) was added and the reaction mixture was allowed to warm to rt and stir for 15 h. The solution was then diluted with 10 mL of water and extracted with 2×10 mL of of EtOAc. The combined organic extracts were then dried (MgSO₄) and concentrated under reduced pressure. The residue was purified with preparatory thin-layer chromatography (SiO₂, 5% MeOH in CH₂Cl₂) to yield 230 mg of the title compound. Mass spectrum (ESI) 278.1 (M+1).

Step B: 2-[(S)-1-Phenylethylamino]-4-[6-benzyl-5, 7-dioxopyrrolidino[3,4,f]-benzimidazol-1-yl] pyrimidine The title compound was made according to the procedure described in EXAMPLE 456 Step B, starting with 2-[(S)-1-phenylethylamino]-4-chloropyrimidine and 6-benzyl-5,7-dioxo-pyrrolidino[3,4,f]benzimidazole. Mass spectrum (ESI) 474.1 (M+).

EXAMPLE 465

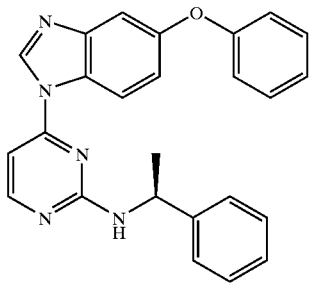

2-[(S)-1-Phenylethylamino]-4-[5-phenoxybenzimidazol-1-yl]pyrimidine 1.5 equiv. Of tert-butylnitrite was dissolved in anhydrous, degassed DMF (2.0 mL). The solution was heated to 65° C. and 2-[(S)-1-Phenylethylamino]-4-[5-(4-amino-phenoxy) benzimidazol-1-yl]pyrimidine (15 mg) was added and the resulting reaction mixture was stirred for 30 minutes. The solution was then diluted slowly with 5 mL of water and extracted with 2×5 mL of EtOAc. The combined organic extracts were then dried (MgSO₄) and concentrated under reduced pressure. The residue was purified with preparative thin-layer chromatography (SiO₂, 5% MeOH in CH₂Cl₂) to yield 2.5 mg of the title compound. Mass spectrum (ESI) 408.4 (M+1).

EXAMPLE 466

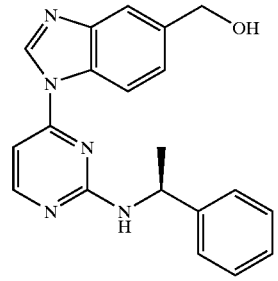

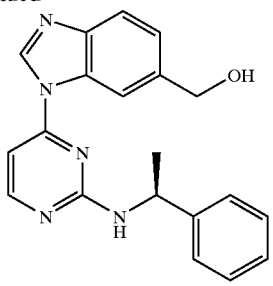

2-[(S)-1-Phenylethylamino]-4-[5-hydroxymethylbenzimidazol-1-yl]pyrimidine and 2-[(S)-1-Phenylethylamino]-4-[6-hydroxymethylbenzimidazol-1-yl]pyrimidine Step A: 5-hydroxymethylbenzimidazole The title compound was prepared according to the procedure described in EXAMPLE 456 Step A, starting from 1,2-diamino-4-hydroxymethylbenzene. Mass spectrum (ESI) 149.1 (M+1).

Step B: 2-[(S)-1-Phenylethylamino]-4-[5-hydroxymethylbenzimidazol-1-yl]pyrimidine and 2-[(S)-1-Phenylethylamino]-4-[6-hydroxymethylbenzimidazol-1-yl]pyrimidine The title compounds were prepared as a 1:1 separable mixture according to the procedure described in EXAMPLE 456 Step B, starting with 2-[(S)-1-phenylethylamino]-4-chloropyrimidine and 5-hydroxymethylbenzimidazole. Mass spectrum (ESI) 346.1 (M+1) and 346.1 (M+1) respectively.

EXAMPLE 467

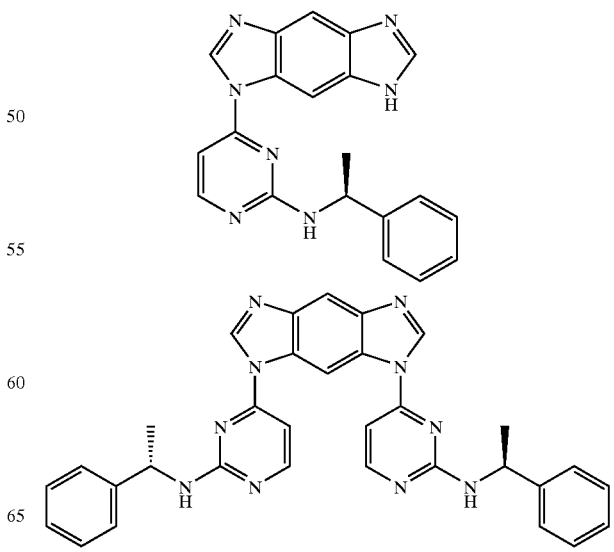

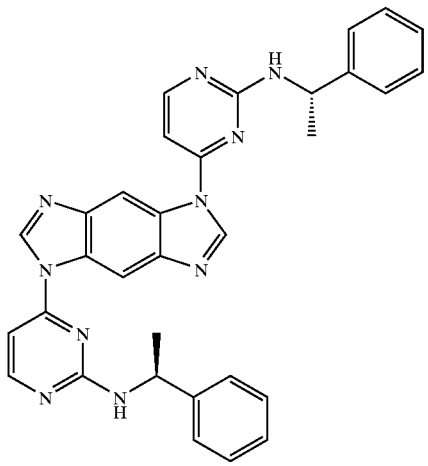

2-[(S)-1-Phenylethylamino]-4-[imidazo[4,5,f]
benzimidazol-1-yl]pyrimidine and 1,7-bis-[2-((S)-1-
phenylethylamino)pyrimidin-4-yl]imidazo[4,5,f]
benzimidazole and 1,5-bis-[2-((S)-1-
phenylethylamino)pyrimidin-4-yl]imidazo[4,5,f]
benzimidazole The title compounds I, II, and III were made as a separable mixture of isomers in a 4:1:2 ratio according to the procedure described in EXAMPLE 456 Step B, starting 2-[(S)-1-phenylethylamino]-4-chloropyrimidine and imidazo[4,5,f]-benzimidazole (for preparation, see Mataka, S.; Shimojyo, Y.; Hashimoto, I.; Tashiro, M.; *Liebigs Ann*, 1995, 10, 1823–1825). 2-[(S)-1-Phenylethylamino]-4-[imidazo[4,5,f]benzimidazol-1-yl]pyrimidine Mass spectrum (ESI) 356.1 (M+1). 1,7-bis-[2-((S)-1-phenylethylamino)pyrimidin-4-yl]imidazo-[4,5,f]benzimidazole Mass spectrum (ESI) 524.4 (M+1). 1,5-bis-[2-((S)-1-phenyl-ethylamino)pyrimidin-4-yl]imidazo[4,5,f]benzimidazole Mass spectrum (ESI) 524.4 (M+1).

EXAMPLE 468

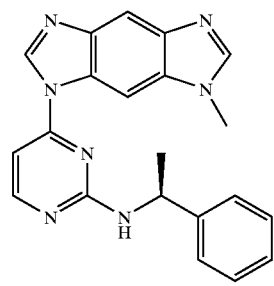

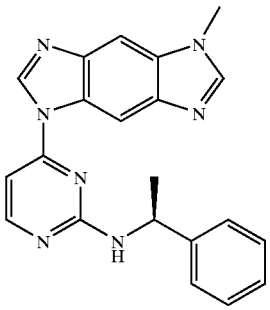

2-[(S)-1-Phenylethylamino]-4-[7-methyl-imidazo[4,5-f]benzimidazol-1-yl]pyrimidine and 2-[(S)-1-Phenylethylamino]-4-[5-methyl-imidazo[4,5-f]benzimidazol-1-yl]pyrimidine 2-[(S)-1-Phenylethylamino]-4-[imidazo[4,5,f]benzimidazol-1-yl]pyrimidine (40 mg) was dissolved in 3N aqueous KOH solution (1.0 mL). Methyl iodide (0.008 mL) and 18-crown-6 (3 mg) were added and the reaction was stirred at rt for 15 hours. The solution was then diluted with 5 mL of water and extracted with 2×10 mL of of EtOAc. The combined organic extracts were then dried ($MgSO_4$) and concentrated under reduced pressure. The residue was purified with preparatory thin-layer chromatography ($SiO_2$, 5% MeOH in $CH_2Cl_2$) to yield 12 mg and 16 mg of the title compounds respectively. Mass spectrum (ESI) 370.2(M+1) and 370.2 (M+1) respectively.

EXAMPLE 469

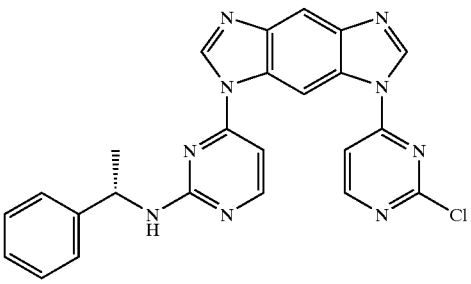

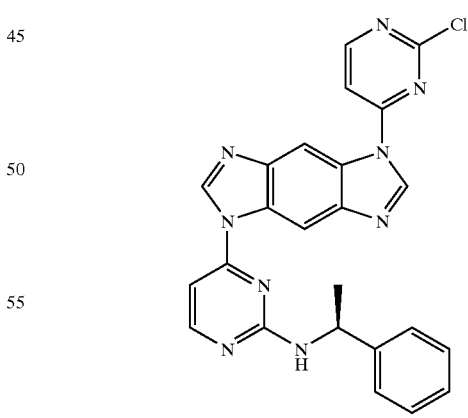

2-[(S)-1-Phenylethylamino]-4-[7-(2-chloropyrimidin-4-yl)imidazo[4,5-f]benzimidazol-1-yl]pyrimidine and 2-[(S)-1-Phenylethylamino]-4-[5-(2-chloropyrimidin-4-yl)imidazo[4,5-f]benzimidazol-1-yl]pyrimidine The title compounds were prepared as a separable mixture of isomers in a 1:1 ratio in an analogous manner to the procedure described in EXAMPLE 456 Step B, starting with 2-[(S)-1-Phenylethylamino]-4-[imidazo[4,5,f]benzimidazol-1-yl]pyrimidine and 2,4-dichloropyrimidine. Mass spectrum (ESI) 468.3 (M+) and 468.3 (M+) respectively.

EXAMPLE 470

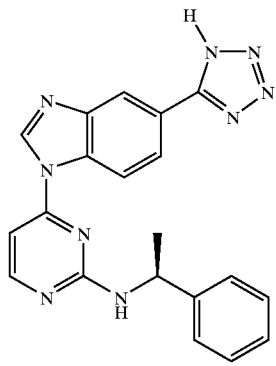

2-[(S)-1-Phenylethylamino]-4-[5-(tetrazol-5-yl)benzimidazol-1-yl]pyrimidine

2-[(S)-1-Phenylethylamino]-4-[5-cyanobenzimidazol-1-yl]pyrimidine (20 mg) and trimethylstannylazide (18 mg) were heated (110° C.) in xylene for 15 hours. Upon cooling, the solution was evaporated to dryness and the residue was purified with preparatory thin-layer chromatography (SiO$_2$, 5% MeOH/1% triethylamine in CH$_2$Cl$_2$) to yield 6 mg of the title compound Mass spectrum (ESI) 384.1 (M+1).

EXAMPLE 471

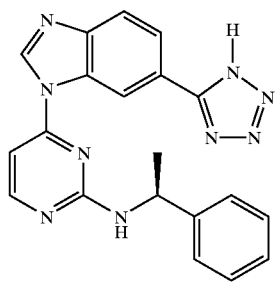

2-[(S)-1-Phenylethylamino]-4-[6-(tetrazol-5-yl)benzimidazol-1-yl]pyrimidine

2-[(S)-1-Phenyl ethylamino]-4-[6-(tetrazol-5-yl)benzimidazol-1-yl]pyrimidine was prepared from 2-[(S)-1-Phenylethylamino]-4-[6-cyanobenzimidazol-1-yl]pyrimidine according to the procedure outlined in EXAMPLE 470. Mass spectrum (ESI) 384.1 (M+1).

EXAMPLE 472

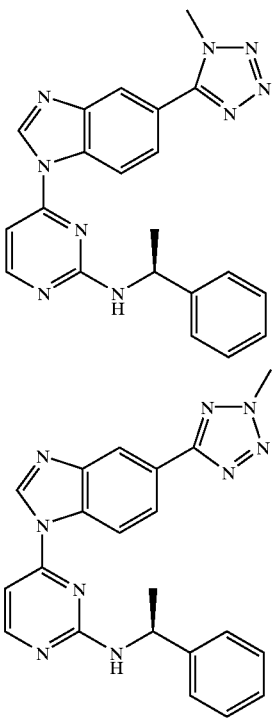

2-[(S)-1-Phenylethylamino]-4-[5-(1-methyltetrazol-5-yl)benzimidazol-1-yl]pyrimidine and 2-[(S)-1-Phenylethylamino]-4-[5-(2-methyl-tetrazol-5-yl)benzimidazol-1-yl]pyrimidine 2-[(S)-1-Phenylethylamino]-4-[5-(tetrazol-5-yl)benzimidazol-1-yl]pyrimidine (10 mg), triethylamine (0.016 mL), and methyl iodide (0.01 mL) were dissolved in dry acetone (0.5 mL) and stirred at room temperature for 15 hours. The reaction mixture was evaporated to dryness and the residue was purified with preparatory thin-layer chromatography (SiO$_2$, 5% MeOH/1% triethylamine in CH$_2$Cl$_2$) to yield 1.8 mg and 1.5 mg respectively of the title compounds. Mass spectrum (ESI) 398.2 (M+1) and (ESI) 398.2 (M+).

EXAMPLE 473

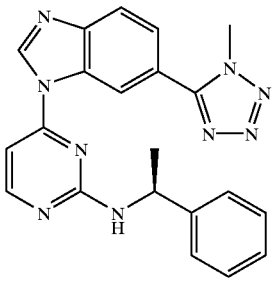

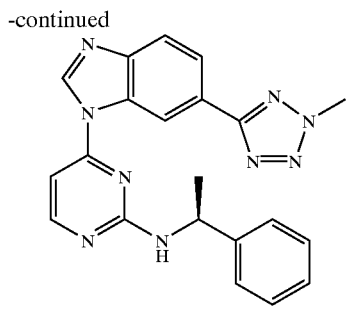

2-[(S)-1-Phenylethylamino]-4-[6-(1-methyltetrazol-5-yl)benzimidazol-1-yl]pyrimidine and 2-[(S)-1-Phenylethylamino]-4-[6-(2-methyltetrazol-5-yl)benzimidazol-1-yl]-pyrimidine The title compounds were made as a separable mixture of isomers in a 1:1 ratio according to the procedure described in EXAMPLE 472, starting from 2-[(S)-1-Phenylethylamino]-4-[6-(tetrazol-5-yl)benzimidazol-1-yl]pyrimidine. Mass spectrum 398.2 (ESI) (M+1) and 398.2 (M+1) respectively.

EXAMPLE 474

2-Hexanethio-4-[benzimidazol-1-yl]pyrimidine

Step A: 2-Hexanethio-4-hydroxypyrimidine

To a stirred suspension of 10 g of thiouracil in THF (100 mL) was added triethylamine (22 mL) and iodohexane (11.5 mL). The mixture was heated to and maintained at reflux for 3 h. The heating bath was removed and the mixture was stirred overnight. Iodohexane (2 mL) was added and the mixture was brought to and maintained at reflux for 8 h. The heating bath was removed and the mixture was stirred overnight. Iodohexane (2 mL) was added and the mixture was brought to and maintained at reflux for 3 h. The mixture was allowed to cool to room temperature and the THF was removed under reduced pressure. The residue was diluted with water and extracted 3× with ethyl acetate. The organic extracts were combined, dried over anhydrous $Na_2SO_4$, filtered and concentrated. The product was recrystallized from hexanes giving 8.45 g of the title compound. $^1$H NMR (500 MHz, $CDCl_3$): δ 7.78 (1H,d, J=7 Hz); 6.23 (1H, d, J=7 Hz); 3.20 (2H, t, J=7.5 Hz); 1.73 (2H, m); 1.44 (2H, m); 1.32 (4H, m); 0.90 (3H, t, J=7 Hz).

Step B: 4-Chloro-2-hexanethiopyrimidine

To a stirred solution of 2-hexanethio-4-hydroxypyrimidine (8.45 g) in $CHCl_3$ (passed over basic alumina) at 0° C. under $N_2$ was added chloromethylene dimethylammonium chloride (7.64 g) in two portions. The mixture was stirred 10 min at 0° C. and the cooling bath was removed. The mixture was stirred 2.5 h under $N_2$, then poured into a separatory funnel containing water plus saturated aqueous $NaHCO_3$. The layers were mixed carefully (much $CO_2$ liberation). The layers were separated and the aqueous layer was extracted 2× with $CH_2Cl_2$. The organic extracts were combined, dried over anhydrous $Na_2SO_4$, filtered and concentrated. The residue was loaded onto a large silica gel plug and eluted with 5:1 hexanes/acetone. The product containing fractions were concentrated giving 7.8 g of the title compound. $^1$H NMR (500 MHz, $CDCl_3$): δ 8.37 (1H, d, J=5.5 Hz); 6.99 (1H, d, J=5.5 Hz); 3.16 (2H, t, J=7.5 Hz); 1.74 (2H, m); 1.47 (2H, m); 1.34 (4H, m); 0.91 (3H, t, J=7 Hz).

Step C: 2-Hexanethio-4-[benzimidazol-1-yl]pyrimidine

To a stirred solution of benzimidazole (1 g) in DMF (20 mL) at 0° C. under $N_2$ was added NaH (in two portions totalling 340 mg of a 60% dispersion in oil). After 15 min the cooling bath was removed and the mixture stirred. After an additional 15 min the benzimidazole sodium salt solution was added to a solution of 4-chloro-2-hexanethiopyrimidine (1.63 g) in DMF (20 mL) via syringe. The resulting mixture was stirred overnight under $N_2$. The DMF was removed under reduced pressure. The residue was diluted with $CH_2Cl_2$ and washed with water. The aqueous layer was back extracted with $CH_2Cl_2$. The organic extracts were combined, dried over anhydrous $Na_2SO_4$, filtered and concentrated. The residue was triturated with diethyl ether to afford 1.3 g of the title compound. $^1$H NMR (500 MHz, $CDCl_3$); δ8.68 (1H, s); 8.63 (1H, d, J=5.5 Hz), 8.21 (1H, m); 7.89 (1H, m); 7.44 (2H m); 7.22 (1H, d, J=5.5 Hz); 3.26 (2H, t, J=7.5 Hz); 1.83 (2H, m); 1.53 (2H, m); 1.36 (4H, m); 0.92 (3H, t, J=7 Hz).

EXAMPLE 475

2-Hexanethio-4-[5-aminobenzimidazol-1-yl]pyrimidine and 2-hexanethio-4-[6-aminobenzimidazol-1-yl]pyrimidine To a stirred solution of 5-aminobenzimidazole (2.15 g) in DMF (40 mL) at 0° C. under $N_2$ was added NaH (in three portions totalling 645 mg of a 60% dispersion in oil). After 15 min the cooling bath was removed and the mixture stirred. After an additional 15 min the benzimidazole sodium salt solution was added to a solution of 4-chloro-2-hexanethiopyrimidine (EXAMPLE 474 Step B, 3.1 g) in DMF (40 mL) via syringe. The resulting mixture was stirred overnight under $N_2$. The DMF was removed under reduced pressure. The residue was diluted with $CH_2Cl_2$ and washed with water. The aqueous layer was back extracted with $CH_2Cl_2$. The organic extracts were combined, dried over anhydrous $Na_2SO_4$, filtered and concentrated. The residue was purified by column chromatography on silica gel (eluted with 1.75%MeOH in $CH_2Cl_2$) affording the title compounds.

2-Hexanethio-4-[6-aminobenzimidazol-1-yl]pyrimidine (faster regioisomer): $_1$H NMR (500 MHz, $CD_3OD$): Λ8.66 (1H, s); 8.58 (1H, d, J=5.5 Hz); 7.63 (1H, d, J=2 Hz); 7.45 (2H, m); 6.82 (1H, dd, J=8.5 Hz, J=2 Hz); 3.25 (2H, t, J=7.5 Hz); 1.78 (2H, m); 1.50 (2H, m); 1.33 (4H, m); 0.89 (3H, t, J=7 Hz).

2-Hexanethio-4-[5-aminobenzimidazol-1-yl]pyrimidine (slower regioisomer): $^1$H NMR (500 MHz, $CD_3OD$): δ 8.80(1H, s); 8.55 (1H, d, J=5.5 Hz); 8.09 (1H, d, J=8.5 Hz); 7.46 (1H, d, J=5.5 Hz); 7.05 (1H, d, J=2 Hz); 6.86 (1H, dd, J=8.5 Hz, J=2 Hz); 3.22 (2H, t, J=7.5 Hz); 1.78 (2H, m); 1.50 (2H, m); 1.34 (4H, m); 0.90 (3H, t, J=7 Hz).

EXAMPLE 476

2-Hexanethio-4-[5-iodobenzimidazol-1-yl]pyrimidine

A solution of 2-hexanethio-4-[5-aminobenzimidazol-1-yl]pyrimidine (EXAMPLE 475, 680 mg) and isoamylnitrite (0.335 mL) in diiodomethane (5 mL) was heated to 100° C. for 30 minutes. The mixture was cooled to room temperature. To the mixture was added CH$_2$Cl$_2$ (5 mL) and methanol (0.1 mL) to effect dissolution of the precipitate. The product was purified by preparative HPLC (25 mm×300 mm silica column eluted with CH$_2$Cl$_2$ going to 5% methanol in CH$_2$Cl$_2$) affording 220 mg of the title compound. Mass spectrum (ESI) 439 (M+1).

EXAMPLE 477

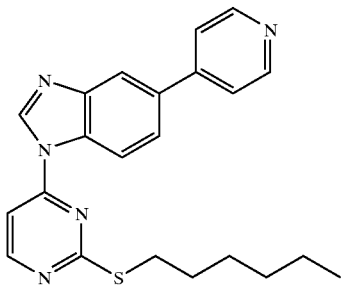

2-Hexanethio-4-[5-(pyridin-4-yl)benzimidazol-1-yl]pyrimidine

Step A: 2-Hexanethio-4-[5-trimethylstannyl-benzimidazol-1-yl]pyrimidine.

2-Hexanethio-4-[5-iodobenzimidazol-1-yl]pyrimidine (EXAMPLE 476, 1.5 gm), hexamethylditin (1.50 mL), and Pd(Ph$_3$P)$_4$ (150 mg) were dissolved in toluene (25 mL) and heated to 100° C. for 1 hour. Upon cooling to rt, the reaction mixture was directly purified by column chromatography (SiO$_2$, 5% MeOH in CH$_2$Cl$_2$) to yield 898 mg of 2-hexylsulfide-4-[5-trimethylstannyl-benzimidazol-1-yl]pyrimidine. Mass spectrum 356.3 (ESI) (M+1).

Step B: 2-Hexanethio-4-[5-(pyridin-4-yl)benzimidazol-1-yl]pyrimidine

2-Hexanethio-4-[5-trimethylstannyl-benzimidazol-1-yl]pyrimidine (780 mg), 4-bromo-pyridine (1.0 mL), tri-o-tolylphosphine (10 mg) and tris(dibenzylidineacetone)dipalladium(0) (15 mg) were dissolved in DMF (15 mL) and heated to 100° C. for 1 hour. Upon cooling to rt and evaporation of solvent, the reaction residue was directly purified by column chromatography (SiO$_2$, 5% MeOH in CH$_2$Cl$_2$) to yield 440 mg of the title compound. Mass spectrum 389.1 (ESI) (M+).

EXAMPLE 478

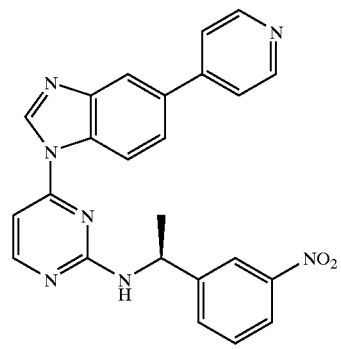

2-[(S)-3-Nitro-1-phenylethylamino]-4-[5-(4-pyridinyl)benzimidazol-1-yl]pyrimidine Step A: 2-Hexanesulfonyl-4-[5-(pyridin-4-yl)benzimidazol-1-yl]pyrimidine and 2-hexanesulfoxide-4-[5-(pyridin-4-yl)benzimidazol-1-yl]pyrimidine 1:1 mixture 2-Hexanethio-4-[5-(pyridin-4-yl)benzimidazol-1-yl]pyrimidine (EXAMPLE 477, 320 mg) was dissolved in methylene chloride (6 mL) and MeOH (18 mL) and cooled to 0° C. Oxone® (1.26 gm) was added and the reaction mixture was allowed to warm to rt over 2 hours. The solution was then diluted with 50 mL of water and extracted with 2×25 mL of of EtOAc. The combined organic extracts were then dried (MgSO$_4$) and concentrated under reduced pressure. The residue was purified with preparative thin-layer chromatography (SiO$_2$, 5% MeOH in CH$_2$Cl$_2$) to yield 210 mg of a 1:1 mixture of the title compounds. Mass spectrum (ESI) 422.2 (M+1) and 406.1 (M+1) respectively.

Step B: 2-[(S)-3-Nitro-1-phenylethylamino-4-[5-(4-pyridinyl)benzimidazol-1-yl]pyrimidine 2-Hexanesulfonyl-4-[5-(pyridin-4-yl)benzimidazol-1-yl]pyrimidine and 2-hexylsulfoxide-4-[5-(pyridin-4-yl)benzimidazol-1-yl]pyrimidine (1:1 mixture) (50 mg) and (S)-1-(3-nitrophenyl)ethylamine (40 mg) were dissolved in dimethylsulfoxide (1.0 mL) and heated to 100° C. for 15 hours. After cooling to room temperature, the solution was then diluted with 10 mL of water and extracted with 2×10 mL of of EtOAc. The combined organic extracts were then dried (MgSO$_4$) and concentrated under reduced pressure. The residue was purified with preparatory thin-layer chromatography (SiO$_2$, 5% MeOH in CH$_2$Cl$_2$) to yield 8 mg of the title compound. Mass spectrum (ESI) 438.4 (M+1).

EXAMPLE 479

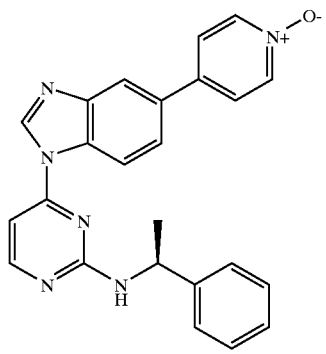

2-[(S)-1-phenylethylamino]-4-[5-(4-pyridinyl-N-oxide)benzimidazol-1-yl]pyrimidine 2-[(S)-1-Phenylethylamino]-4-[5-(pyridin-4-yl)benzimidazol-1-yl]pyrimidine EXAMPLE 334 (15 mg) and 3-chloroperoxybenzoic acid (30 mg) were dissolved in dichloromethane (1.0 mL) and the resulting suspension was stirred at room temperature for 15 hours. The solution was then diluted with 10 mL of saturated aqueous NaHCO$_3$ and extracted with 2×10 mL of EtOAc. The combined organic extracts were then dried (MgSO$_4$) and concentrated under reduced pressure. The residue was purified with preparative thin-layer chromatography (SiO$_2$, 10% MeOH in CH$_2$Cl$_2$) to yield 2.0 mg of the title compound. Mass spectrum (ESI) 409.1 (M+1).

EXAMPLE 480

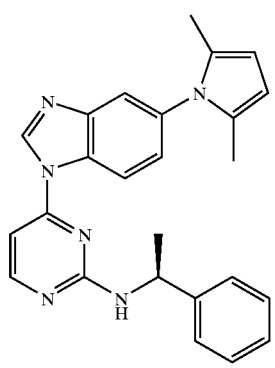

2-[(S)-1-phenylethylamino]-4-[5-(2,5-dimethylpyrrol-1-yl)benzimidazol-1-yl]pyrimidine 2-[(S)-1-Phenylethylamino]-4-[5-aminobenzimidazol-1-yl]pyrimidine (EXAMPLE 79) (100 mg) and acetonyl acetone(0.04 mL)and acetic acid (20 drops) were dissolved in benzene (10 mL) and refluxed with Dean-Stark apparatus for 2 hours. After cooling to room temperature, the solution was then diluted with 10 mL of aqueous saturated NaHCO$_3$ and extracted with 2×10 mL of of EtOAc. The combined organic extracts were then dried (MgSO$_4$) and concentrated under reduced pressure. The residue was purified with preparatory thin-layer chromatography (SiO$_2$, 5% MeOH in CH$_2$Cl$_2$) to yield 17 mg of the title compound. Mass spectrum (ESI) 408.1 (M+).

EXAMPLE 481

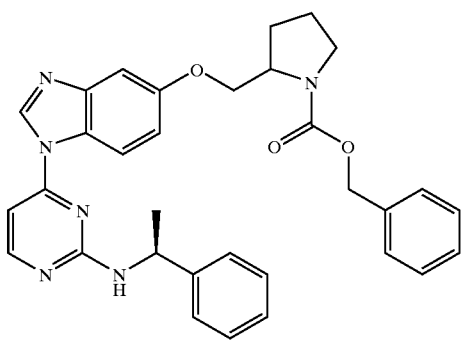

2-[(S)-1-Phenylethylamino]-4-[5-((N-benzyloxycarbonyl-pyrrolidin-2-yl)methoxy)-benzimidazol-1-yl]pyrimidine 2-[(S)-1-Phenylethylamino]-4-[5-hydroxybenzimidazol-1-yl]-pyrimidine (25 mg) was dissolved in DMF (2.0 mL) and NaH (60%, 6.0 mg) was added followed by N-benzyloxycarbonyl-2-(methanesulfonyloxy) methylpyrrolidine (20 mg) and the resulting suspension was heated to 80° C. for 1 hour. After cooling to room temperature, the solution was then diluted with 10 mL of aqueous saturated NaHCO$_3$ and extracted with 2×10 mL of of EtOAc. The combined organic extracts were then dried (MgSO$_4$) and concentrated under reduced pressure. The residue was purified with preparative thin-layer chromatography (SiO$_2$, 5% MeOH in CH$_2$Cl$_2$) to yield 17 mg of 2-[(S)-1-Phenylethylamino]-4-[5-((N-benzyloxycarbonyl-pyrrolidin-2-yl)methoxy)benzimidazol-1-yl]pyrimidine. Mass spectrum (ESI) 549.3 (M+1).

EXAMPLE 482

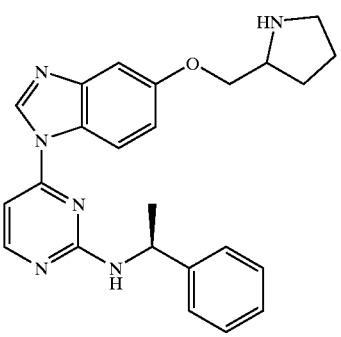

2-[(S)-1-Phenylethylamino]-4-[5-((pyrrolidin-2-yl)methoxy)benzimidazol-1-yl]-pyrimidine 2-[(S)-1-Phenylethylamino]-4-[5-((N-benzyloxycarbonyl-pyrrolidin-2-yl)methoxy)benzimidazol-1-yl]pyrimidine (11 mg) was dissolved in methanol (1.0 mL) and catalytic Pd(OH)$_2$ and trifluoroacetic acid were added and the resulting suspension was stirred under hydrogen atmosphere for 15 hours. Filtration and evaporation of solvent gave N-[(1S)-1-phenylethyl]-4-[5-(2-pyrrolidinylmethoxy)-1H-benzimidazol-1-yl]-2-pyrimidinamine (7.0 mg). Mass spectrum (ESI) 415.5 (M+1).

EXAMPLE 483
omitted

EXAMPLE 484
omitted

EXAMPLE 485

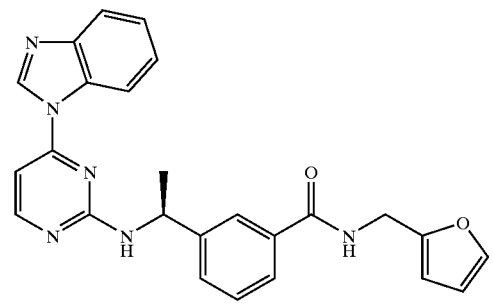

2-[(S)-1-(3-((furan-2-yl-methyl)aminocarbonyl)phenyl)ethylamino]-4-[benzimidazol-1-yl]pyrimidine 2-[(S)1-(3-carboxyphenyl)ethylamino]-4-[benzimidazol-1-yl]pyrimidine (EXAMPLE 58, 14.2 mg) and furfurylamine (11 μL, 0.12 mmol) were mixed in CH$_2$Cl$_2$ (2 mL) under nitrogen. Triethylamine (28 μL), 1-(3-dimethylaminopropyl)-3-ethylcarbodiimide hydrochloride (26.3 mg) and dimethylaminopyridine (approx. 1 mg) were added and the mixture stirred at room temperature. After 16 h the mixture was concentrated in vacuo then eluted directly on silica gel (60:40 hexanes:acetone to 50:50

EXAMPLE 486

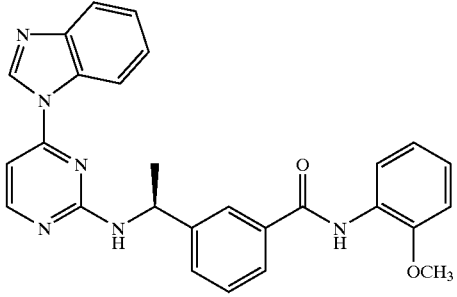

2-[(S)-1-(3-((2-methoxyphenyl)aminocarbonyl)phenyl)ethylamino]-4-(benzimidazol-1-yl]pyrimidine 2-[(S)-1-(3-carboxyphenyl)ethylamino]-4-[benzimidazol-1-yl]pyrimidine (EXAMPLE 58, 23.0 mg) and o-anisidine (22 μL, 0.20 mmol) were mixed in CH$_2$Cl$_2$ (2 mL) under nitrogen. Triethylamine (45 μL), 1-(3-dimethylaminopropyl)-3-ethylcarbodiimide hydrochloride (38.5 mg) and dimethylaminopyridine (approx. 1 mg) were added and the mixture stirred at room temperature. After 19 h the mixture was concentrated in vacuo then eluted directly on silica gel (2:1 hexanes:acetone to 1:1 hexanes:acetone) to yield 9.1 mg of the title compound. Mass spectrum (ESI) 465.2 (M+1).

EXAMPLE 487

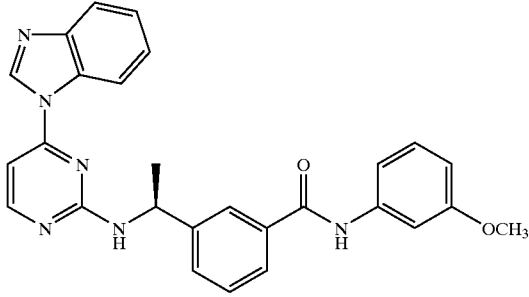

2-[(S)-1-(3-((3-methoxyphenyl)aminocarbonyl)phenyl)ethylamino)]-4-[benzimidazol-1-yl]pyrimidine 2-[(S)-1-(3-carboxyphenyl)ethylamino]-4-[benzimidazol-1-yl]pyrimidine (EXAMPLE 58, 26.1 mg) and 3-methoxyaniline (25 μL, 0.22 mmol) were mixed in CH$_2$Cl$_2$ (2 mL) under nitrogen. Triethylamine (51 μL), 1-(3-dimethylaminopropyl)-3-ethylcarbodiimide hydrochloride (37.9 mg) and dimethylaminopyridine (approx. 1 mg) were added and the mixture stirred at room temperature. After 20 h the mixture was concentrated in vacuo then eluted directly on silica gel (1:1 hexanes:acetone) to yield 9.1 mg of the title compound. Mass spectrum (ESI) 465.2 (M+1).

EXAMPLE 488

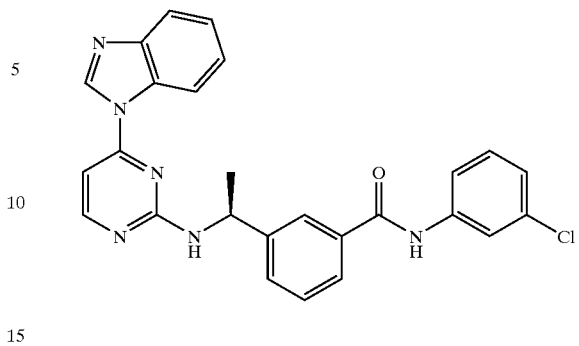

2-[(S)-1-(3-((3-chlorophenylaminocarbonyl)phenyl)ethylamino]-4-[benzimidazol-1-yl]pyrimidine 2-[(S)-1-(3-carboxyphenyl)ethylamino]-4-[benzimidazol-1-yl]pyrimidine (EXAMPLE 58, approx. 20 mg) and 3-chloroaniline (18 mL, 0.17 mmol) were mixed in CH$_2$Cl$_2$ (2 μL) under nitrogen. Triethylamine (39 μL), 1-(3-dimethylaminopropyl)-3-ethylcarbodiimide hydrochloride (25.7 mg) and dimethylaminopyridine (approx. 1 mg) were added and the mixture stirred at room temperature. After 20 h the mixture was concentrated in vacuo then eluted directly on silica gel (1–4%(2M NH$_3$ in MeOH)/CH$_2$Cl$_2$) to yield 9.6 mg of impure product which was purified further by HPLC (Zorbax Rx-SIL, 70:30 hexanes:ethanol) to yield 9.1 mg of the title compound. Mass spectrum (ESI) 469.2 (M+1).

EXAMPLE 489

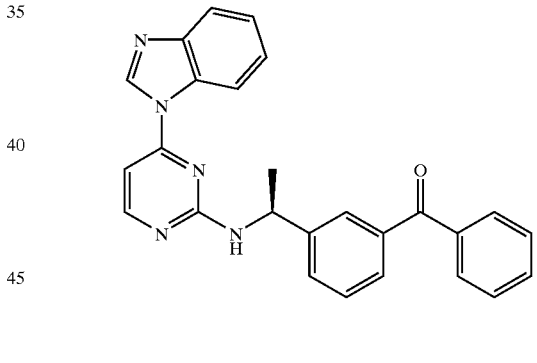

2-[(S)-1-(3-benzoylphenyl)ethylamino]-4-[benzimidazol-1-yl]pyrimidine

Step A: 2-[(S)-1-(3-(N-methoxy-N-methylamido)phenyl)ethylamino]-4-[benzimidazol-1-yl]pyrimidine 2-[(S)-1-(3-carboxyphenyl)ethylamino]-4-[benzimidazol-1-yl]pyrimidine (EXAMPLE 58, approx. 20 mg) and N,O-dimethylhydroxylamine hydrochloride (52.8 mg, 0.541 mmol) were mixed in CH$_2$Cl$_2$ (5 mL) under nitrogen. Triethylamine (100 μL), 1-(3-dimethylaminopropyl)-3-ethylcarbodiimide hydrochloride (85.8 mg) and dimethylaminopyridine (approx. 1 mg) were added and the mixture stirred at room temperature. After 2 h the mixture was concentrated in vacuo then eluted directly on silica gel (1–4%(2M NH$_3$ in MeOH)/CH$_2$Cl$_2$) to yield 41.8 mg of the title compound. $^1$H NMR (500 MHz, CDCl$_3$, partial): δ 8.39 (d, J=5.3 Hz, 1H); 7.83 (br d, J=7.1 Hz, 1H); 7.77 (s, 1H); 7.60 (d, J=7.8 Hz, 1H); 7.54 (d, J=7.8 Hz, 1H);

--- hexanes:acetone) to yield 10.7 mg of the title compound. Mass spectrum (ESI) 439.2 (M+1).

7.43 (t, J=7.7 Hz, 1H); 6.81 (d, J=5.5 Hz, 1H); 3.45 (br s, 3H); 3.33 (s, 3H); 1.66 (d, J=6.9 Hz, 3H). Mass spectrum (ESI) 403.2 (M+1).

Step B: 2-[(S)-1-(3-benzoylphenyl)ethylamino]-4-[benzimidazol-1-yl]pyrimidine

2-[(S)-1-(3-(N-methoxy-N-methylamido)phenyl)ethylamino]-4-[benzimidazol-1-yl]pyrimidine (25.4 mg) was dissolved in dry THF (2 mL), and the resultant solution cooled to 0° C. A 1.0 M solution of phenylmagnesium bromide in THF (315 µL) was added and the cold bath removed. 30 min later another aliquot (315 µL) of phenylmagnesium bromide solution was added, and the resultant mixture stirred 30 min longer. Saturated aqueous ammonium chloride solution (10 mL) was added and the mixture left stirring overnight at room temperature. More aqueous ammonium chloride was added and the mixture was extracted 3×with ethyl acetate. The combined organic was washed with brine, dried over magnesium sulfate and concentrated in vacuo. The residue was purified on silica gel (70:30 to 50:50 hexanes:acetone) to yield 10.1 mg of the title compound. $^1$H NMR (500 MHz, CDCl$_3$, partial): δ 8.41 (d, J=5.5Hz, 1H); 7.93 (s, 1H) 7.83 (d, J=8.0 Hz, 1H); 7.76 (d, J =7.6 Hz, 2H); 7.69 (m, 2H); 7.57 (m, 1H); 7.50 (t, J =7.7 Hz, 1H); 7.44 (t, J=7.7 Hz, 2H); 6.82 (d, J=5.5 Hz, 1H); 5.77 (br s, 1H); 5.29 (br s, 1H); 1.68 (d, J=6.9 Hz, 3H). Mass spectrum (ESI) 420.2 (M+1).

EXAMPLE 490

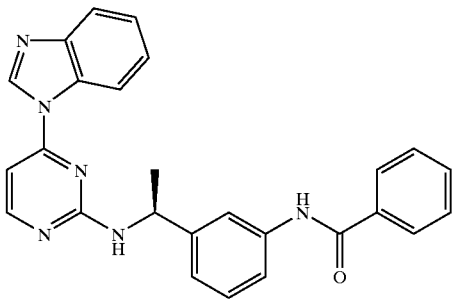

2-[(S)-1-(3-(benzoylamino)phenyl)ethylamino]-4-[benzimidazol-1-yl]pyrimidine

Step A: (R)-1-(3-nitrophenyl)ethanol

To a solution of (S)-tetrahydro-1-methyl-3,3-diphenyl-1H,3H-pyrrolo[1,2-c]-[1,3,2]-oxazaborole-borane (6.06 mmol) in CH$_2$Cl$_2$ (6 mL) at −20° C. was added a solution of 3-nitroacetophenone (6.06 mmol) in CH$_2$Cl$_2$ (6 mL) in a dropwise fashion over 30 min. The resulting mixture was stirred 45 min. longer then poured into cold methanol (−20° C.), and this mixture allowed to stir overnight while warming to room temperature. The mixture was then concentrated in vacuo then more methanol (100 mL) added and concentrated, and then added another 100 mL methanol and concentrated. The resulting crude was purified on silica gel in 60:40 hexanes:ethyl acetate to yield 0.98 g of the title compound. $^1$H NMR (500 MHz, CDCl$_3$): δ 8.22 (m, 1H); 8.08 (m, 1H); 7.69 (d, J=7.8 Hz, 1H); 7.50 (t, J=7.8 Hz, 1H); 5.00 (m, 1H); 2.62 (s, 1H); 1.53 (d, J=7.1 Hz, 3H).

Step B: (S)-1-(3-nitrophenyl)-1-azidoethane

To a solution of (R)-1-(3-nitrophenyl)ethanol (2.93 mmol) in toluene (15 mL) was added Zn(N$_3$)$_2$.py$_2$ (5.88 mmol), imidazole (4.04 mmol) and triphenylphosphine (7.97 mmol). 1-(3-dimethylaminopropyl)-3-ethylcarbodiimide hydrochloride (7.91 mmol) was added dropwise, and the mixture stirred at room temperature for 18 h. The mixture was diluted with ethyl acetate, filtered through Celite®, then concentrated in vacuo. This crude was purified on silica gel (70:30 hexanes:ethyl acetate) to yield 298 mg of the title compound (53%). $^1$H NMR (500 MHz, CDCl$_3$): δ 8.19–8.23 (m, 2H); 7.70 (d, J=7.4 Hz, 1H); 7.58 (t, J=7.4 Hz, 1H); 4.78 (q, J=8.1 Hz, 1H); 1.62 (d, 3H).

Step C: (S)-1-(3-nitrophenyl)-1-aminoethane

To a solution of (S)-1-(3-nitrophenyl)-1-azidoethane (1.55 mmol) in benzene (8 mL) was added water (1.0 mL) and triphenylphosphine (3.18 mmol). The resulting mixture was heated to 80° C. for 19 h. This mixture was cooled, diluted with diethyl ether (50 mL) and washed with 50 mL of 2N aqueous HCl. The aqueous phase was made basic by adding 50 mL of 5N aqueous NaOH then extracted with diethyl ether (3×50 mL). These ether extracts were combined, washed with brine, dried (MgSO$_4$) and concentrated in vacuo. The residue was purified on silica gel in 3%(2M NH$_3$ in MeOH)/CH$_2$Cl$_2$ to yield 78.4 mg of pure title compound and 159 mg of the title compound that is approximately 80% pure by NMR. $^1$H NMR (500 MHz, CDCl$_3$): δ 8.23 (m, 1H); 8.06 (m, 1H); 7.70 (d, J=8.1 Hz, 1H); 7.48 (t, J=8.1 Hz, 1H); 4.25 (q, J=6.9 Hz, 1H); 1.40 (d, J=6.9 Hz, 3H).

Step D: (S)-1-(3-aminophenyl)-1-aminoethane (S)-1-(3-nitrophenyl)-1-aminoethane (approx. 80% pure, 75.2 mg) was dissolved in THF (2 mL) and 10% Pd/C (13.8 mg) was added. The system was fitted with a balloon of hydrogen and purged 3×, the mixture left stirring 16 h at room temperature. Filtered the solution through Celite®, washing thoroughly with methanol, and the solvent removed in vacuo. The residue was eluted on silica gel (3–6%(2M NH$_3$ in MeOH)/CH$_2$Cl$_2$) to yield 23.7 mg of the title compound. $^1$H NMR (500 MHz, CDCl$_3$): δ 7.13 (t, J=7.7 Hz, 1H); 6.74 (m, 1H); 6.71 (m, 1H); 6.58 (m, 1H); 4.03 (q, J=6.7 Hz, 1H); 3.68 (br s, 2H); 1.37 (d, J=6.7 Hz, 3H).

Step E: 2-[(S)-1-(3-aminophenyl)ethylamino]-4-[benzimidazol-1-yl]pyrimidine (S)-1-(3-aminophenyl)-1-aminoethane (23.7 mg) was dissolved in DMF (1 mL), diisopropylethylamine (90 µL) was added followed by 2-methylsulfonyl-4-[benzimidazol-1-yl]pyrimidine (43.2 mg). The resulting mixture was left heating at 100° C. for 65 h then cooled, concentrated in vacuo then the residue purified on silica gel twice (3% then 2% (2M NH$_3$ in MeOH)/CH$_2$Cl$_2$) to yield 27.9 mg of the title compound (98%). $^1$H NMR (500 MHz, CDCl$_3$, partial): δ 8.52 (br s, 1H); 8.39 (d, J=5.3 Hz, 1H); 7.83 (m, 1H); 7.36 (m, 2H); 7.18 (t, J=7.8 Hz, 1H); 6.84 (d, J=7.8 Hz, 1H); 6.77 (m, 2H); 6.61 (m, 1H); 1.61 (d, J=7.1 Hz, 3H).

Step F: 2-[(S)-1-(3-(benzoylamino)phenyl)ethylamino]-4-[benzimidazol-1-yl]pyrimidine To a solution of 2-[(S)-1-(3-aminophenyl)ethylamino]-4-[benzimidazol-1-yl]pyrimidine (10.0 mg) in CH$_2$Cl$_2$ (2 mL) was added triethylamine (13 µL) and benzoyl chloride (3.5 µL). The resulting solution was stirred at room temperature for 30 min. then the volatiles removed in vacuo. The residue was purified on silica gel (2%(2M NH$_3$ in MeOH)/CH$_2$Cl$_2$) then HPLC (Zorbax Rx-SIL, 70:30 hexanes:ethanol) to yield 1.8 mg of the title compound. ¹H NMR (500 MHz, CDCl₃, partial): δ 8.41 (d, J=5.5 Hz, 1H); 7.87 (m, 2H); 7.82 (m, 2H); 7.76 (s, 1H); 7.58 (m, 2H); 7.51 (m, 2H); 7.41 (t, J=7.9 Hz, 1H); 6.80 (d, J=5.5 Hz, 1H); 1.67 (d, J=6.9 Hz, 3H).

EXAMPLE 491

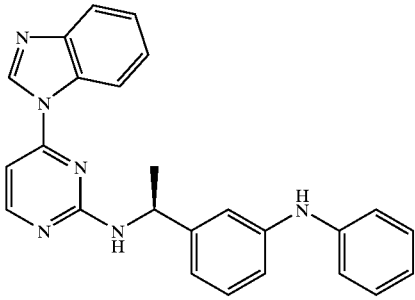

2-[(S)-1-(3-phenylamninophenyl)ethylamino]-4-[benzimidazol-1-yl]pyrimidine

Triphenylbismuth (52.8 mg) was dissolved in THF (1 mL), and 32 wt % peracetic acid added (45 μL). This solution was stirred and monitored by TLC for oxidation of the bismuthine; reaction not complete after 10 min. so added another 45 μL peracetic acid, and the reaction was complete shortly thereafter. To this solution was added a solution of 2-[(S)-1-(3-aminophenyl)ethylamino]-4-[benzimidazol-1-yl]pyrimidine (see example 7, step E, 17.9 mg) in THF (1 mL) and then solid copper (II) acetate (approx. 5 mg). The resulting mixture was heated to 60° C. for 1.5 h then left stirring overnight at room temperature. This mixture was concentrated in vacuo then purified on silica gel (2%(2M NH₃ in MeOH)/CH₂Cl₂) to yield 10.7 mg of impure product which was purified further by HPLC (3 injections, Zorbax Rx-SIL, 80:20 hexanes:ethanol) to yield 4.9 mg of the title compound. ¹H NMR (500 MHz, CDCl₃, partial): δ 8.52 (br s, 1H); 8.40 (d, J=5.5 Hz, 1H); 7.83 (d, J=7.6 Hz, 1H); 7.13 (m, 1H); 7.06 (d, J=7.7 Hz, 2H); 7.01 (dd, J=7.9, 2.0 Hz, 2H); 6.93 (m, 1H); 6.80 (d, J=5.3 Hz, 1H); 1.64 (d, J=6.9 Hz, 3H). Mass spectrum (ESI) 407.3 (M+1).

EXAMPLES 492–493

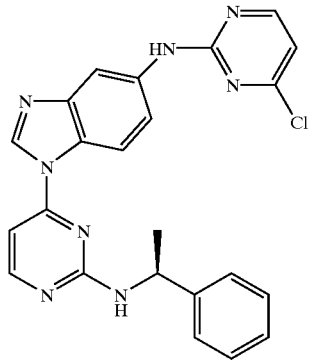

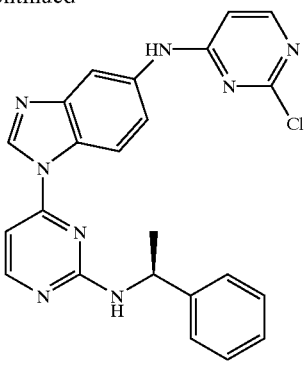

2-[(S)-1-phenylethylamino]-4-[5-(2-chloropyrimidin-4-yl)aminobenzimidazol-1-yl]pyrimidine and 2-[(S)-1-phenylethylamino]-4-[5-(4-chloropyrimidin-2-yl)amino-benzimidazol-1-yl]pyrimidine To a solution of 2-[(S)-1-phenylethylamino]-4-[5-aminobenzimidazol-1-yl]pyrimidine (45.9 mg) in DMF (2 mL) was added diisopropylethylamine (73 μL) followed by 2,4-dichloropyrimidine (24.9 mg). The resulting solution was heated to 100° C. for 16 h then the mixture concentrated in vacuo. This crude was purified on silica gel (2–5%(2M NH₃ in MeOH)/CH₂Cl₂) to yield 18.3 mg of 2-((S)-1-phenylethylamino)-4-(5-(2-chloropyrimidin-4-yl)aminobenzimidazol-1-yl)pyrimidine (L-860,182). ¹H NMR (500 MHz, CDCl₃, partial): δ 8.51 (br s, 1H); 8.42 (d, J=5.5 Hz, 1H); 8.13 (d, J=5.9 Hz, 1H); 7.75 (s, 1H); 7.45 (d, J=7.3 Hz, 2H); 7.40 t, J=7.7 Hz, 2H); 6.77 (d, J=5.3 Hz, 1H); 6.56 (d, J=6.0 Hz, IH); 1.66 (d, J=6.9 Hz, 3H). Mass spectrum (ESI) 443.3 (M+1).

From this chromatography was isolated 4.0 mg of another component which was purified further by HPLC (Zorbax Rx-SIL, 80:20 hexanes:ethanol) to yield 2.5 mg of 2-((S)-1-phenylethylamino)-4-(5-(4-chloropyrimidin-2-yl)aminobenzimidazol-1-yl)pyrimidine (L-860,185). ¹H NMR (500 MHz, CDCl₃, partial): δ 8.49 (br s, 1H); 8.39 (d, J=5.5 Hz, 1H); 8.31 (d, J=5.2 Hz, 1H); 8.20 (s, 1H); 7.46 (d, J=5.3 Hz, 2H); 7.40 (t, J=7.7 Hz, 2H); 7.36 (s, 1H); 6.78 (d, J=5.1 Hz, 1H); 6.76 (d, J=5.5 Hz,1H); 1.65 (d, J=6.8 Hz, 3H). Mass spectrum (ESI) 443.3 (M+1).

EXAMPLE 494

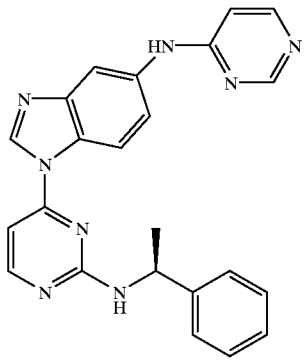

2-[(S)-1-phenylethylamino]-4-[5-(pyrimidin-4-yl)aminobenzimidazol-1-yl]pyrimidine 2-[(S)-1-phenylethylamino]-4-[5-aminobenzimidazol-1-yl]pyrimidine (14.0 mg) was dissolved in 2 mL MeOH, 10%Pd/C (20.3 mg) added, the system fitted with a balloon of hydrogen, purging the system twice and leaving the reaction stirring at room temperature for 23 h. The mixture was then filtered through Celite®, washing thoroughly with methanol, and the solvent removed in vacuo. The residue was purified on silica gel (2–5%(2M NH₃ in MeOH)/CH₂Cl₂) to yield 5.5 mg of the title compound. Mass spectrum (ESI) 409.4 (M+1).

EXAMPLE 495

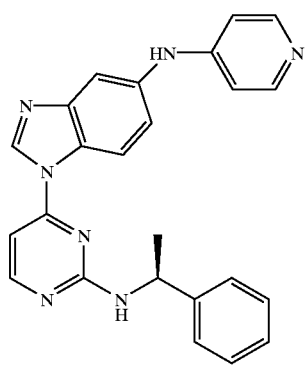

2-[(S)-1-phenylethylamino]-4-[5-(pyridin-4-yl) aminobenzimidazol-1-yl]pyrimidine 2-[(S)-1-phenylethylamino]-4-[5-aminobenzimidazol-1-yl]pyrimidine (49.8 mg) was dissolved in DMF (2 mL). Diisopropylethylamine (79 μL) and 4-bromopyridine hydrochloride (43.2 mg) were added, and the mixture left heating overnight at 100° C. After 17 h added more diisopropylethylamine (79 μL) and 4-bromopyridine hydrochloride (40.2 mg) and continued heating at 100° C. for another 24 h. The volatiles were removed in vacuo and the residue purified on silica gel (2–5%(2M NH₃ in MeOH)/CH₂Cl₂) to yield 5.0 mg of impure product that was purified by HPLC (Zorbax Rx-SIL, 60:40 hexanes:ethanol) to yield 3.0 mg of the title compound. Mass spectrum (ESI) 408.4 (M+1).

EXAMPLE 496

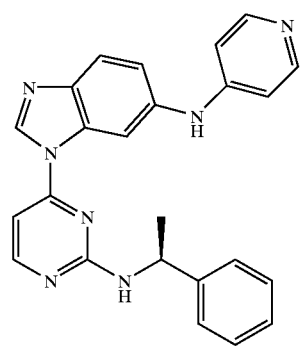

2-[(S)-1-phenylethylamino]-4-[6-(4-pyridylamino) benzimidazol-1-yl]pyrimidine

To a solution of 2-[(S)-1-phenylethylamino]-4-[6-aminobenzimidazol-1-yl]pyrimidine (97.0 mg) in isopropyl alcohol (5 mL) was added 4-bromopyridine hydrochloride (59.3 mg). The resulting mixture was heated to 80° C. for 17 h. Triethylamine (approx. 1 mL) was added and the mixture concentrated in vacuo. Purified twice on silica gel (2–5% (2M NH₃ in MeOH)/CH₂Cl₂ then 3–10%(2M NH₃ in MeOH)/CH₂Cl₂) to yield 54.8 mg of impure product. Approximately 25 mg of this impure product was purified on HPLC (Zorbax Rx-SIL, 70:30 hexanes:ethanol) to yield 23.9 mg of the title compound. Mass spectrum (ESI) 408.3 (M+1).

EXAMPLE 497

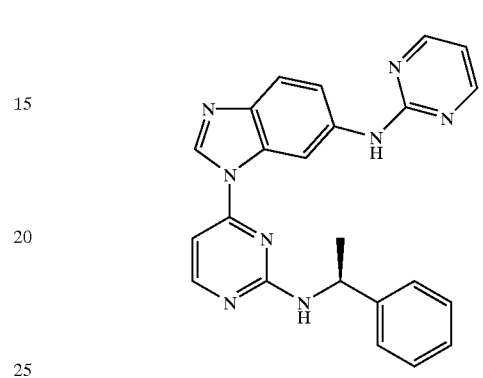

2-[(S)-1-phenylethylamino]-4-[6-(pyrimidin-2-ylamino)benzimidazol-1-yl]pyrimidine To a solution of 2-[(S)-1-phenylethylamino]-4-[6-aminobenzimidazol-1-yl]pyrimidine (94.5 mg) in isopropyl alcohol (5 mL) was added 2-chloropyrimidine (47.3 mg). This mixture was heated to 80° C. for 18 h then more 2-chloropyrimidine (63.5 mg) added and heating continued for 6 h longer and the solvent removed in vacuo. The crude was purified twice on silica gel (6%(2M NH₃ in MeOH)/ CH₂Cl₂ then in 2%(2M NH₃ in MeOH)/CH₂Cl₂) to yield 53.9 mg of an impure product. A portion of this material was purified further on HPLC (Zorbax Rx-SIL, 80:20 hexanes:ethanol) to yield 10.0 mg of the title compound. Mass spectrum (ESI) 409.3 (M+1).

EXAMPLE 498

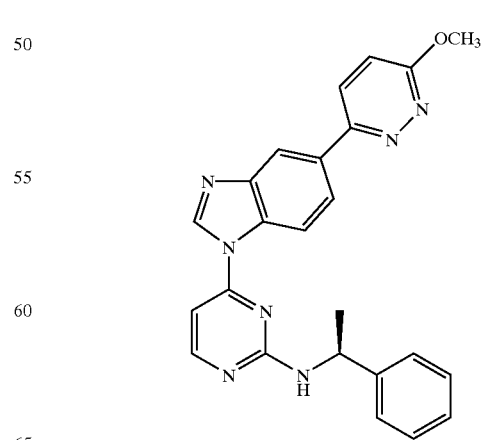

2-[(S)-1-phenylethylamino]-4-[5-(6-methoxypyridazin-3-yl)benzimidazol-1-yl]pyrimidine 2-[(S)-1-Phenylethylamino]-4-[5-(pinacolatoboronyl)benzimidazol-1-yl]pyrimidine (EXAMPLE 443, 41.9 mg), 3-chloro-6-methoxypyridazine (17.6 mg), tris(dibenzylideneacetone)dipalladium (6.1 mg) and tri-o-tolylphosphine (10.5 mg) were dissolved in 2 mL DMF in a vial then 1.0 M aqueous potassium carbonate solution (190 µL) added and the mixture degassed by bubbling argon through for approx. 2 min. The vial was tightly stoppered and the mixture heated to 90° C. for 1 h then left at room temperature overnight. Worked up by pouring into water (20 mL) then extracting with ethyl acetate (3×10 mL). The combined organic was washed with water (20 mL) and brine (20 mL) then dried over sodium sulfate and concentrated. Purified this mixture on silica gel (2–6%MeOH/CH$_2$Cl$_2$) and further purified using a 250-micron prep plate (5%MeOH/ CH$_2$Cl$_2$) to yield 11.5 mg of the title compound. $^1$H NMR (500 MHz, CDCl$_3$, partial): δ 8.53 (br s, 1H); 8.43 (d, J=5.3 Hz, 1H); 8.33 (s, 1H); 8.15 (br s, 1H); 7.89 (d, J=9.4 Hz, 1 h); 7.10 (D, J=9.4 Hz, 1H); 6.81 (d, J=5.5 Hz, 1H); 4.23 (s, 3H); 1.66 (d, J=6.8 Hz, 3H). Mass spectrum (ESI) 424.3 (M+1).

EXAMPLE 499

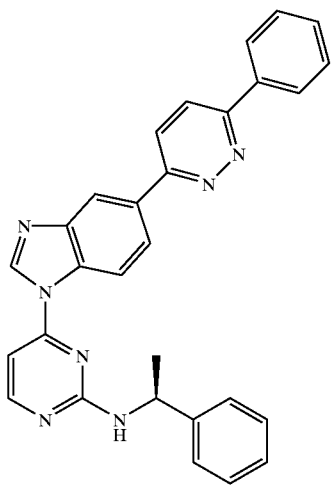

2-[(S)-1-phenylethylamino]-4-[5-(6-phenylpyridazin-3-yl)benzimidazol-1-yl]-pyrimidine The title compound was prepared according to the procedure given in EXAMPLE 444 using 3-chloro-6-phenylpyridazine. 1H NMR (500 MHz, CDCl$_3$, partial): δ 8.54 (br s, 1H); 8.47 (s, 1H); 8.43 (d, J=5.3 Hz, 1H); 8.32 (br s, 1H); (m, 2H); 8.03 (d, J=9.2 Hz, 1H); 7.97 (d, J=8.9 Hz, 1H); 6.82 (d, J =5.3 Hz, 1H); 1.67 (d, J=7.1 Hz, 3H). Mass spectrum (ESI) 470.4 (M+1).

EXAMPLE 500

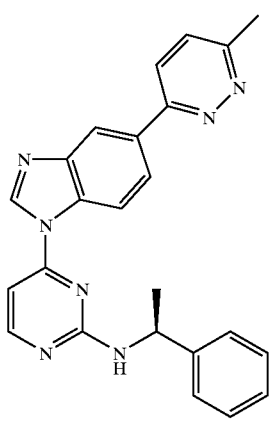

2-[(S)-1-phenylethylamino]-4-[5-(6-methylpyridazin-3-yl)benzimidazol-1-yl]-pyrimidine The title compound was prepared according to the procedure given in EXAMPLE 444 using 3-chloro-6-methylpyridazine. $^1$H NMR (500 MHz, CDCl$_3$, partial): δ 8.53 (br s, 1H); 8.43 (d, J=5.5 Hz, 1H); 8.22 (br s, 1H); 7.86 (d, J=9.7 Hz, 1H); 6.81 (d, J=5.3 Hz, 1H); 2.80 (s, 3H); 1.66 (d, J=6.9 Hz, 3H). Mass spectrum (ESI) 408.4 (M+1).

EXAMPLE 501

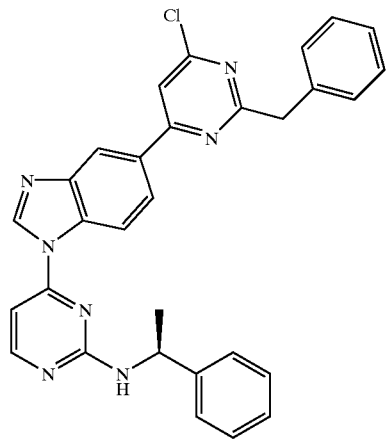

2-[(S)-1-phenylethylamino]-4-[5-(2-benzyl-6-chloropyrimidin-4-yl)benzimidazol-1-yl]pyrimidine The title compound was prepared according to the procedure given in EXAMPLE 444 using 2-benzyl-4,6-dichloropyrimidine. $^1$H NMR (500 MHz, CDCl$_3$, partial): δ 8.54 (s, 2H); 8.44 (d, J=5.4 Hz, 1H); 8.02 (br s, 1H); 7.63 (s, 1H); 7.51 (d, J=7.3 Hz, 2H); 4.35 (s, 2H); 1.67 (d, J=6.8 Hz, 3H). Mass spectrum (ESI) 518.4 (M+1).

EXAMPLE 502

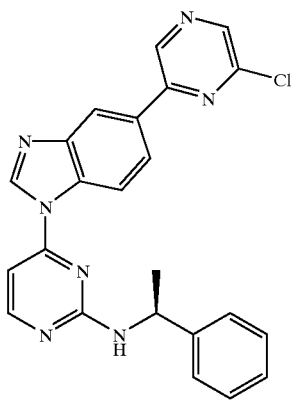

2-[(S)-1-phenylethylamino]-4-[5-(6-chloropyrazin-2-yl)benzimidazol-1-yl]pyrimidine The title compound was prepared according to the procedure given in EXAMPLE 444 using 2,6-dichloropyrazine. $^1$H NMR (500 MHz, CDCl$_3$, partial): δ9.02 (s, 1H); 8.54 (s, 1H); 8.47 (s, 1H); 8.44 (d, J=5.3 Hz, 1H); 8.03 (br s, 1H); 7.47 (d, J=7.5 Hz, 2H); 7.41 (t, J=7.3 Hz, 2H); 6.81 (d, J=5.5Hz, 1H); 1.67 (d, J=6.9 Hz, 3H). Mass spectrum (ESI) 428.1 (M+1).

EXAMPLE 503

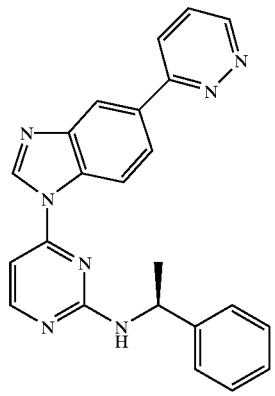

2-[(S)-1-phenylethylamino]-4-[5-(pyridazin-3-yl)benzimidazol-1-yl]pyrimidine

2-[(S)-1-phenylethylamino]-4-[5-(6-chloropyridazin-3-yl)-benzimidazol-1-yl]pyrimidine (24.0 mg) was dissolved in 2 mL ethanol and 2 mL THF. Added 10%Pd/C (23.0 mg), fitted the system with a balloon of hydrogen and purged 3 times, and the system was left stirring for 20 h at room temperature. No apparent progress at this point so 1-drop of glacial acetic acid was added and refitted with the balloon and purged. Stirred approximately 20 h longer then filtered off the catalyst, the solvent was removed and the residue purified by preparative thin layer chromatography (1:1 hexanes:acetone then another in 90:10 CH$_2$Cl$_2$:MeOH to yield 2.0 mg of the title compound. $^1$H NMR (500 MHz, CDCl$_3$, partial): δ 9.20 (dd, J=1.5, 4.9 Hz, 1H); 8.54 (br s, IH); 8.44 (d, J=5.3 Hz, 1H); 8.42 (s, 1H); 8.23 (br s, 1H); 7.97 (dd, J=1.5, 8.5 Hz, 1H); 7.59 (dd, J=4.9, 8.6 Hz, 1H); 7.47 (d, J=7.3 Hz, 2H); 7.42 (t, J=7.5 Hz, 2H); 6.82 (d, J=5.3 Hz, 1H); 1.66 (d, J=6.9 Hz, 3H). Mass spectrum (ESI) 394.4 (M+1).

EXAMPLE 504

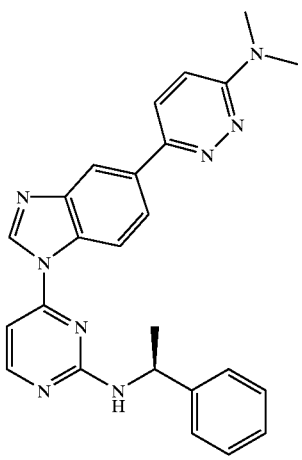

2-[(S)-1-phenylethylamino]-4-[5-(6-(N,N-dimethylamino)pyridazin-3-yl)-benzimidazol-1-yl]pyrimidine 2-[(S)-1-phenylethylamino]-4-[5-(6-chloropyridazin-3-yl)benzimidazol-1-yl]pyrimidine (13.2 mg) was mixed with 33% dimethylamine in ethanol (1 mL) in a sealed tube, the system heated to 60° C. for 15 h. The mixture was cooled, concentrated and the residue purified on silica gel (2.5%MeOH in CH$_2$Cl$_2$) to yield 11.2 mg of the title compound. $^1$H NMR (500 MHz, CDCl$_3$): δ 8.51 (br s, 1H); 8.41 (d, J=5.5 Hz, 1H); 8.27 (s, 1H); 8.19 (br s, 1H); 7.89 (br s, 1H); 7.73 (d, J=9.6 Hz, 1H); 7.46 (m, 2H); 7.41 (t, J=7.5 Hz, 2H); 7.30 (m, 1H); 6.93 (d, J=1H); 6.81 (d, J=5.5 Hz, 1H); 5.80 (br s, 1H); 5.22 (br s, 1H); 3.26 (s, 6H); 1.65 (d, J=6.9 Hz, 3H). Mass spectrum (ESI) 437.4 (M+1).

EXAMPLE 505

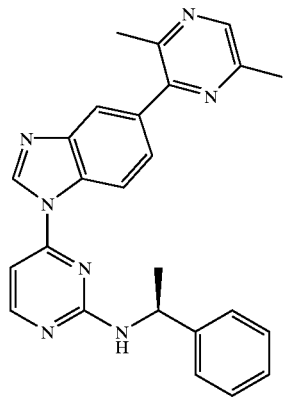

2-[(S)-1-phenylethylamino]-4-[5-(2,5-dimethylpyrazin-3-yl)benzimidazol-1-yl]-pyrimidine 50 mg of 2-[(S)-1-phenylethylamino]-4-[5-(pinacolatoboronyl)-benzimidazol-1-yl]pyrimidine (EXAMPLE 443), 31 mg of potassium carbonate, 5.2 mg of tris(dibenzylideneactone)dipalladium, 6.9 mg of tri-o-tolyphosphine and 16.4 μl of 3-chloro-2,5-dimethylpyrazine were dissolved in an argon degassed mixture of 2.1 mL of dimethylformamide and 0.3 mL of water and were heated to 90° C. in a sealed tube for 4 hours. The reaction mixture was then cooled, poured into water and extracted with ethyl acetate, dried and concentrated in vacuo to give the crude product which was purified by preparative plate chromatography on silica gel eluting with 50% hexane:50% acetone to give 25 mg of the title compound. Mass spectrum ESI: 422 (M+H).

EXAMPLE 506

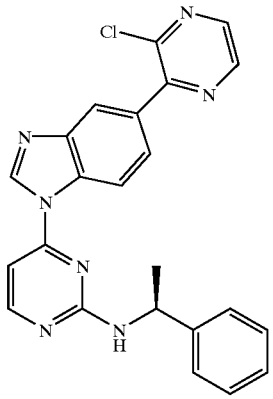

2-[(S)-1-phenylethylamino]-4-[5-(3-chloropyrazin-2-yl)benzimidazol-1-yl]pyrimidine Prepared as described in EXAMPLE 505 using 2,3-dichloropyrazine as the reagent to give the title compound. Mass spectrum ESI: 428 (M+H).

EXAMPLE 507

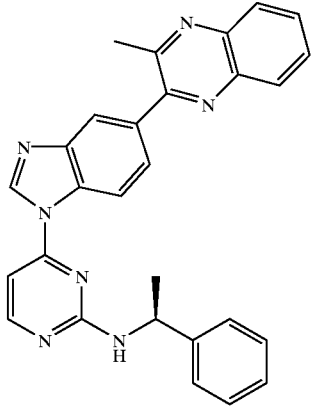

2-[(S)-1-phenylethylamino]-4-[5-(3-methylquinoxalin-2-yl)benzimidazol-1-yl]pyrimidine Prepared as described in EXAMPLE 505 using 2-chloro-3-methylquinoxaline as the reagent to give the title compound. Mass spectrum ESI: 458 (M+H).

EXAMPLE 508

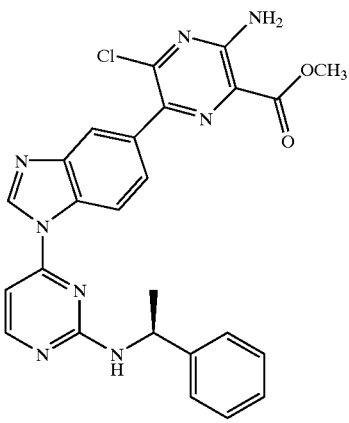

2-[(S)-1-phenylethylamino]-4-[5-(3-amino-5-chloro-2-carboxymethylpyrazin-6-yl)benzimidazol-1-yl]pyrimidine Prepared as described in EXAMPLE 505 using methyl 3-amino-5,6-dichloro-2-pyrazine carboxylate as the reagent to give the title compound. Mass spectrum ESI: 501 (M+H).

EXAMPLE 509

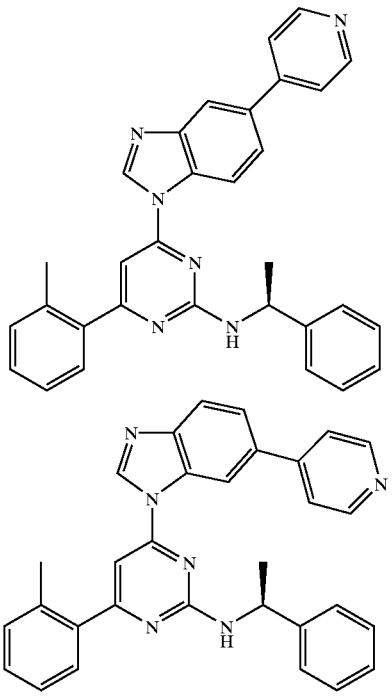

2-[(S)-1-Phenethylamino]-4-[5-(pyridin-4-yl)benzimidazo-1-yl]-6-(2-methyl-phenyl)pyrimidine and 2-[(S)-1-phenethylamino]-4-[6-(pyridin-4-yl)benzimidazo-1-yl]-6-(2-methylphenyl)pyrimidine Step A: 5-Nitro-1-trimethylsilylethoxymethyl-benzimidazole and 6-nitro-1-trimethylsilylethoxymethyl-benzimidazole To a suspension of 5-nitrobenzimidazole (5.00 g) in 100 mL of THF at 0° C. was added NaH (0.81 g) in portions. The mixture was stirred for 10 min; then trimethylsilylethoxymethylchloride (6 mL) was added via syringe and stirring was continued for 2 h at 0° C. Water (ca. 3 mL) was added to quench the reaction, and the mixture was concentrated to a yellow oil, which was redissolved in 150 mL of EtOAc. This solution was washed with 2×75 mL of water and 75 mL of brine, then dried over $Na_2SO_4$ and concentrated. The residue was filtered through a plug of silica gel to yield 8.8 g of a mixture of the title compounds. Mass spectrum (ESI) 294.1 (M+1).

Step B: 5-Amino-1-trimethylsilylethoxymethyl-benzimidazole and 6-amino-1-trimethylsilylethoxymethyl-benzimidazole A 100 mL flask charged with a solution of 5- and 6-nitro-1-trimethylsilylethoxymethyl-benzimidazole (1.16 g) in 30 mL of MeOH was evacuated and flushed with dry $N_2$; then 10% Pd on carbon (0.61 g) was added in portions. The flask was evacuated and flushed with $N_2$ three times, then evacuated and filled with $H_2$ and stirred under an $H_2$ atmosphere for 20 h, at which point thin layer chromatographic analysis showed that no starting material remained. The mixture was filtered through a pad of Celite®, washing liberally with MeOH, then concentrated to yield 1.03 g of a mixture of the title compounds as a light brown oil that was used without further purification. Mass spectrum (ESI) 264.2 (M+1).

Step C: 5-Iodo-1-trimethylsilylethoxymethyl-benzimidazole and 6-iodo-1-trimethylsilylethoxymethyl-benzimidazole To a solution of 5- and 6-amino-1-trimethylsilylethoxymethyl-benzimidazole (1.03 g) in 8 mL of diiodomethane was added isoamyl nitrite (0.68 mL). The mixture was heated to 80° C. and stirred at this temperature for 2 h, then allowed to cool to 70° C. Solvent was removed by short-path vacuum distillation and the residue was added directly to a silica gel column, eluting with 2:1 hexanes-EtOAc, to yield 658 mg of a mixture of the title compounds as a yellow oil. Mass spectrum (ESI) 375.2 (M+1).

Step D: 5-(Pinacolatoboron)-1-trimethylsilylethoxymethyl-benzimidazole and 6-(pinacolatoboron)-1-trimethylsilylethoxymethyl-benzimidazole To a solution of 5 and 6-iodo-1-trimethylsilylethoxymethyl-benzimidazole (658 mg) and bis(pinacolato)diboron (670 mg) in 15 mL of DMSO was added [1,1'-bis(diphenylphosphino)ferrocene]-dichloropalladium(II) complex with dichloromethane (1:1) (43 mg) and KOAc (518 mg). The flask was fitted with a reflux condenser and the apparatus was evacuated and flushed with Ar three times. The mixture was stirred under an Ar atmosphere at 60° C. for 5 h, then cooled and diluted with 60 mL of EtOAc and 25 mL of water. The phases were separated and the organic phase was washed with 2×20 mL of water and 20 mL of brine, dried over $Na_2SO_4$ and concentrated. The residue was purified by flash chromatography, eluting with a gradient system of 1:1 to 2:1 hexanes-EtOAc, to yield 585 mg of a mixture of the title compounds as a brown oil. Mass spectrum (ESI) 375.2 (M+1).

Step E: 5-(Pyridin-4-yl)-1-trimethylsilylethoxymethyl-benzimidazole and 6-(pyridin-4-yl)-1-trimethylsilylethoxymethyl-benzimidazole To a solution of 5- and 6-(pinacolatoboron)-1-trimethylsilyl-ethoxymethyl-benzimidazole (426 mg) in 15 mL of DMF was added 2.5 mL of water, tri-o-tolylphosphine (1.39 g) tris(dibenzylidineacetone)dipalladium(0) (73 mg), $K_2CO_3$ (393 mg), and 4-bromopyridine (360 mg). The flask was fitted with a reflux condenser and the apparatus was evacuated and flushed with Ar three times. The mixture was stirred under an Ar atmosphere at 90° C. for 1.25 h, then cooled and concentrated. The residue was redissolved in $CH_2Cl_2$ and purified by flash chromatography, eluting with a gradient system of 1:1 to 2:1 acetone-hexanes to 100% acetone, to yield 285 mg of a mixture of the title compounds as a brown solid. Mass spectrum (ESI) 326.2 (M+1).

Step F: 5-(Pyridin-4-yl)benzimidazole

To a solution of 5- and 6-(pyridin-4-yl)-1-trimethylsilylethoxymethyl-benzimidazole (100 mg) in 2 mL of THF was added 0.6 mL of tetrabutylammonium fluoride. The mixture was heated to reflux and stirred at this temperature overnight, then cooled and concentrated. The residue was dissolved in minimal MeOH and added to a MegaBondElut SCX column (2 g; Varian Sample Prep Products), washing with MeOH to remove the tetrabutylammonium fluoride, then with 2M $NH_3$ in MeOH to elute product, to yield 58 mg of the title compound as a white solid. Mass spectrum (ESI) 196.1 (M+1).

Step G: 2-[(S)-1-Phenethylamino]-4-[5-(pyridin-4-yl)benzimidazo-1-yl]-6-chloropyrimidine and 2-[(S)-1-phenethylamino]-4-[6-(pyridin-4-yl)benzimidazo-1-yl]-6-chloropyrimidine The title compounds were prepared from 5-(pyridin-4-yl)benzimidazole (58 mg), NaH (11 mg), and 2-[(S)-1-phenethylamino]-4,6-dichloropyrimidine (19 mg; EXAMPLE 306, step A) according to the procedure described in EXAMPLE 306, Step B. Purification by preparative thin layer chromatography, eluting with 9:1 $CH_2Cl_2$-MeOH, provided 73 mg of a mixture of the two isomers. Mass spectrum (ESI) 427.2 (M+1).

Step H: 2-[(S)-1-Phenethylamino]-4-[5-(pyridin-4-yl)benzimidazo-1-yl]-6-(2-methylphenyl)pyrimidine and 2-[(S)-1-phenethylamino]-4-[6-(pyridin-4-yl)benzimidazo-1-yl]-6-(2-methylphenyl)pyrimidine The title compounds were prepared from 2-[(S)-1-phenethylamino]-4-[5-(pyridin-4-yl)benzimidazo-1-yl]-6-chloropyrimidine and 2-[(S)-1-phenethylamino]-4-[6-(pyridin-4-yl)benzimidazo-1-yl]-6-chloropyrimidine (38 mg), 2-methylphenylboronic acid (18 mg),[1,1 '-bis(diphenylphosphino)ferrocene]-dichloropalladium(II) complex with dichloromethane (1: 1) (4 mg), and 1 M $Na_2CO_3$ (225 μL) according to the procedure described in EXAMPLE 304, Step C. Purification by preparative thin layer chromatography, eluting with 2:1 hexanes-acetone, provided 15 mg of 2-[(S)-1-phenethylamino]-4-[5-(pyridin- 4-yl)benzimidazo-1-yl]-6-(2-methylphenyl)pyrimidine [polar isomer; mass spectrum (ESI) 483.3 (M+1)]- and 20 mg of 2-[(S)-1-phenethylamino]-4-[6-(pyridin-4-yl) benzimidazo-1-yl]-6-(2-methylphenyl)pyrimidine[nonpolar isomer; mass spectrum (ESI) 483.3 (M+1)]-.

EXAMPLE 510

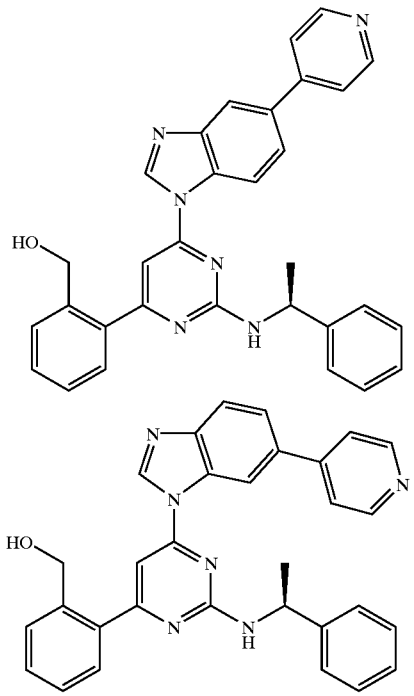

2-[(S)-1-Phenethylamino]-4-[5-(pyridin-4-yl) benzimidazo-1-yl]-6-(2-hydroxymethyl-phenyl) pyrimidine and 2-[(S)-1-phenethylamino]-4-[6-(pyridin-4-yl)benzimidazo-1-yl]-6-(2-hydroxymethylphenol)pyrimidine The title compounds were prepared from 2-[(S)-1-phenethylamino]-4-[5-(pyridin-4-yl)benzimidazo-1-yl]-6-chloropyrimidine and 2-[(S)-1-phenethylamino]-4-[6-(pyridin-4-yl)benzimidazo-1-yl]-6-chloropyrimidine (34 mg; EXAMPLE 509, Step G), 2-hydroxymethylphenylboronic acid (16 mg), [1,1'-bis (diphenylphosphino)-ferrocene]dichloropalladium(II) complex with dichloromethane (1:1) (4 mg), and 1 M $Na_2CO_3$ (200 μL) according to the procedure described in EXAMPLE 306, Step C. Purification by preparative thin layer chromatography, eluting with 1:1 hexanes-acetone, provided 19 mg of 2-[(S)-1-phenethylamino]-4-[5-(pyridin-4-yl)-benzimidazo-1-yl]-6-(2-hydroxymethylphenyl) pyrimidine[polar isomer; mass spectrum (ESI) 499.2 (M+1)] and 17 mg of 2-[(S)-1-phenethylamino]-4-[6-(pyridin-4-yl) benzimidazo-1-yl]-6-(2-hydroxymethylphenyl)pyrimidine [nonpolar isomer; mass spectrum (ESI) 499.3 (M+1)].

EXAMPLE 511

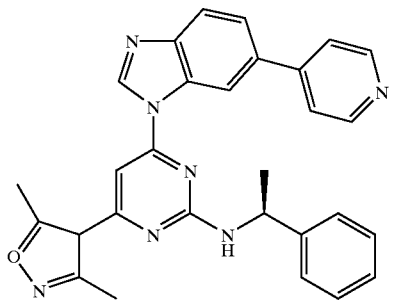

2-[(S)-1-phenethylamino]-4-[6-(pyridin-4-yl) benzimidazo-1-yl]-6-(3,5-dimethyl-isoxaol-4-yl) pyrimidine The title compound was prepared from 2-[(S)-1-phenethylamino]-4-[5-(pyridin-4-yl)benzimidazo-1-yl]-6-chloropyrimidine and 2-[(S)-1-phenethylamino]-4-[6-(pyridin-4-yl)benzimidazo-1-yl)]-6-chloropyrimidine (33 mg; EXAMPLE 509, Step G), 3,5-dimethyl-isoxazol-4-ylboronic acid (16 mg),[1,1'-bis(diphenylphosphino)-ferrocene]-dichloropalladium(ll) complex with dichloromethane (1:1) (4 mg), and 1M $Na_2CO_3$ (200 μL) according to the procedure described in EXAMPLE 306, Step C. Mass spectrum (ESI) 488.4 (M+1).

EXAMPLE 512

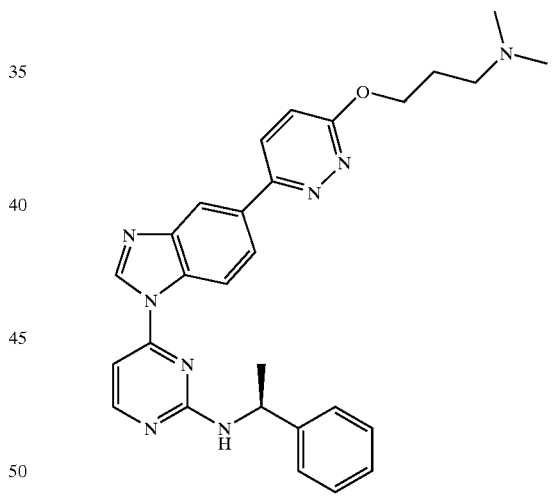

2-[(S)-1-Phenethylamino]-4-[5-(3-(3-dimethylaminopropan-1-oxy)pyridazin-6-yl) benzimidazo-1-yl]pyrimidine Step A: 3-chloro-6-(3-dimethylaminopropan-1-oxy) pyridazin To a solution of 3-dimethylamino-propanol (95 μL) in 5 mL of THF at 0° C. was added NaH (20 mg). The mixture was stirred for 5 min; then 3,6-dichloropyridazine (100 mg) was added and the mixture was allowed to warm to room temperature and stirred overnight at this temperature. The mixture was diluted with 5 mL of water and 5 mL of EtOAc, the phases were separated, and the aqueous phase was extracted with 2×5 mL of EtOAc. The combined organics were washed with 5 mL of brine, dried over Na$_2$SO$_4$ and concentrated to a colorless oil (128 mg) that was used without further purification. Mass spectrum (ESI) 215.9 (M+).

Step B: 2-[(S)-1-Phenethylamino]-4-[5-(3-(3-dimethylaminopropan-1-oxy)pyridazin-6-yl) benzimidazo-1-yl]pyrimidine The title compound was prepared from 3-chloro-6-(3-dimethylamino-propan-1-oxy)pyridazine (100 mg), 2-[(S)-1-phenethylamino]-4-[5-(pinacolatoboron)-benzimidazo-1-yl]pyrimidine (136 mg; EXAMPLE 443), tri-o-tolylphosphine (377 mg) tris(benzylidineacetone) dipalladium(0) (14 mg), and K$_2$CO$_3$ (107 mg) according to the procedure described inEXAMPLE 510, Step E. Mass spectrum (ESI) 495.2 (M+1).

EXAMPLE 513
omitted

What is claimed is:
1. The compound of Formula I

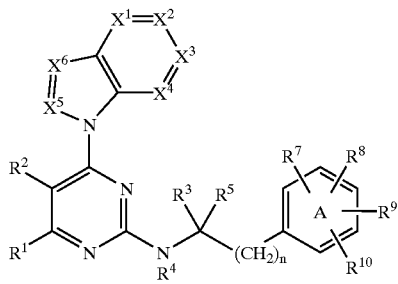

or pharmaceutically acceptable salts, hydrates, solvates, crystal forms or diastereomers thereof, wherein
$R^1$ and $R^2$ are independently:
 a) H,
 b) halo (Br, Cl, I or F)
 c) OH,
 d) SH,
 e) CN,
 f) NO$_2$,
 g) $R^{11}$,
 h) OR$^{11}$,
 i) OC(=O)R$^{11}$,
 j) OC(=O)OR $^{11}$,
 k) OC(=O)NHR$^{11}$,
 l) OC(=O)NR $^{11}$R$^{12}$,
 m) SR$^{11}$,
 n) SOR$^{11}$,
 o) SO$_2$R$^{11}$,
 p) C(=O)R$^{11}$,
 q) C(=O)OR $^{11}$,
 r) C(=O)NHR$^{11}$,
 s) C(=O)NR $^{11}$R$^{12}$,
 t) NH$_2$,
 u) NHR$^{11}$,
 v) NR$^{11}$R$^{12}$,
 w) NHC(=O)R$^{11}$,
 x) NR$^{11}$C(=O)R$^{12}$,
 y) NR$^{11}$C(=O)NHR$^{12}$,
 z) NR$^{11}$C(=O)NR$^{12}$R$^{13}$,
 aa) SO$_2$NHR$^{11}$,
 ab) SO$_2$NR$^{11}$R$^{12}$,
 ac) NHSO$_2$R$^{11}$,
 ad) NR$^{11}$SO$_2$R$^{12}$, $R^3$ and $R^5$ independently are:
 a) H,
 b) C$_1$–C$_6$-alkyl, unsubstituted or substituted with one, two, or three substituents selected from oxo, X', Y' and Z',
 c) aryl, wherein aryl is defined as phenyl or naphthyl unsubstituted or substituted with one, two or three substituents selected from: X', Y' and Z', or
 d) $R^3$ and $R^5$ taken together can represent =O;
 e) $R^3$ or $R^5$ can represent a 2 or 3 carbon methylene bridge forming a ring of 5 to 8 atoms fused to the A ring;
$R^4$ is:
 a) H, or
 b) C$_1$–C$_6$-alkyl, or
 c) C$_1$–C$_6$-alkoxyl;
$X^5$ and $X^6$ are independently CR$^a$ or N;
$R^a$ is: H, or C$_1$–C$_6$-alkyl;
n is 0, 1 or 2;
—X$^1$—X$^2$—X$^3$—X$^4$— is:
 a) —CR$^6$=CR$^6$—CR$^{6a}$=CR$^6$—,
 b) —CR$^{6a}$=CR$^6$—CR$^6$=CR$^6$—,
 c) —CR$^6$=CR$^{6a}$—CR$^6$=CR$^6$—,
 d) —CR$^6$=CR$^6$—CR$^6$=CR$^{6a}$—,
 e) —N=CR$^6$—CR$^6$=CR$^6$—,
 f) —CR$^6$=N—CR$^6$=CR$^6$—,
 g) —CR$^6$=CR$^6$—N=CR$^6$—,
 h) —CR$^6$=CR$^6$—CR$^6$=N—,
 i) —N=CR$^6$—N=CR$^6$—,
 j) —CR$^6$=N—CR$^6$=N—,
 k) —CR$^6$=N—N=CR$^6$—, or
 l) —N=CR$^6$—CR$^6$=N—;
$R^6$ and $R^{6a}$ are independently:
 a) H,
 b) halo(Br, Cl, I, or F)
 c) OH,
 d) SH,
 e) CN,
 f) NO$_2$,
 g) N$_3$,
 h) N$_2$+BF$_4$—,
 i) R$^{11}$,
 j) OR$^{11}$,
 k) OC(=O)R$^{11}$,
 l) OC(=O)OR$^{11}$,
 m) OC(=O)NHR$^{11}$,
 n) OC(=O)NR$^{11}$R$^{12}$,
 o) SR$^{11}$,
 p) SOR$^{11}$,
 q) SO$_2$R$^{11}$,
 r) C$_1$–C$_6$-alkyl, unsubstituted or substituted with one, two, or three substituents selected from R$^{11}$,R$^{12}$, and R$^{13}$,
 s) C(=O)R$^{11}$,
 t) C(=O)OR$^{11}$,
 u) C(=O)NHR$^{11}$,
 v) C(=O)NR$^{11}$R$^{12}$,
 w) C(=O)N(OR$^{11}$)R$^{12}$,
 x) NH$_2$,
 y) NHR$^{11}$,
 z) NHC$_1$–C6-alkyl, unsubstituted or substituted with one, two, or three substituents selected from R$^{11}$,R$^{12}$, and R$^{13}$,
 aa) NR$^{11}$R$^{12}$,
 ab) NHC(=O)R$^{11}$,
 ac) NR$^{11}$C(=O)R$^{12}$, ad) $NHC(=O)NHR^{11}$,
ae) $NR^{11}C(=O)NHR^{12}$,
af) $NR^{11}C(=O)NR^{12}R^{13}$,
ag) $SO_2NH_2$,
ah) $SO_2NHR_{11}$,
ai) $SO_2NR_{11}R_{12}$,
aj) $NHSO_2R_{11}$,
ak) $NR^{11}SO_2R^{12}$,
al) $NHP(=O)(OC_1-C_6\text{-alkyl})_2$, or
am) $R^6$ and $R^{6a}$ when on adjacent carbons can be joined to form a 5- or 6-membered ring having the following bridging atoms:
  i) —CH=CH—CH=CH—,
  ii) —OCH$_2$O—,
  iii) —C(O)N(R$^{11}$)C(O)—,
  iv) —CH$_2$N(R$^{11}$)CH$_2$—,
  v) —N=CHNHC(O)—,
  vi) —C(O)NHCH=N—,
  vii) —C(O)OC(O)—,
  viii) —NHC(O)NHC(O)—,
  ix) —C(O)NHC(O)NH—,
  x) —N=CHNH—,
  xi) —NHCH=N—,
  xii) —N=CHNR$^{11}$,
  xiii) —NR$^{11}$CH=N—,
  xiv)

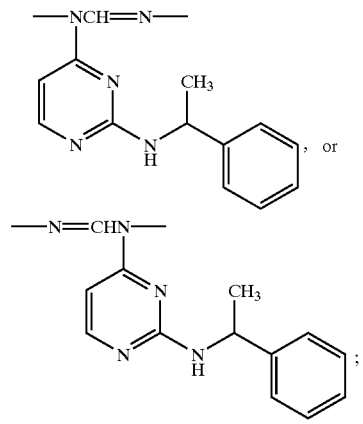

xv)

represents:
a) phenyl,
b) naphthyl,
c) pyridyl,
d) pyrazinyl,
e) pyrimidinyl,
f) pyrrolyl,
g) thienyl,
h) oxazolyl,
i) isoxazolyl,
j) thiazolyl,
k) pyrazolyl,
l) triazolyl,
m) tetrazolyl,
n) furanyl,
o) benzothienyl,
p) benzofuranyl,
q) indolyl,
r) imidazolyl,
s) benzimidazolyl, or
t) thiadiazolyl, $R^7$, $R^8$, $R^9$, and $R^{10}$ independently are selected from:
a) H,
b) halo(Br, Cl, I, or F)
c) OH,
d) SH,
e) CN,
f) $NO_2$,
g) $N_3$
h) $N_2+BF_4$—
i) $R^{11}$,
j) $OR^{11}$,
k) $SR^{11}$,
l) $SOR^{11}$,
m) $SO_2R^{11}$,
n) $C_1-C_6$-alkyl, unsubstituted or substituted with one, two, or three substituents selected from $R^{11}R^{12}$, and $R^{13}$,
o) $C_1-C_6$-perfluoroalkyl,
p) $C(=O)R^{11}$,
q) $C(=O)OR^{11}$,
r) $C(=O)NHR^{11}$,
s) $C(=O)NR^{11}R^{12}$,
t) $NH_2$,
u) $NHR^{11}$,
v) $NHC_1-C_6$-alkyl, unsubstituted or substituted with one, two, or three substituents selected from $R^{11}$, $R^{12}$, and $R^{13}$,
w) $NR^{11}R^{12}$,
x) $NHC(=O)R^{11}$,
y) $NR^{11}C(=O)R^{12}$,
z) $NR^{11}C(=O)NHR^{12}$,
aa) $NR^{11}C(=O)NR^{12}R^{13}$,
ab) $SO_2NHR^{11}$,
ac) $SO_2NR^{11}R^{12}$,
ad) $NHSO_2R^{11}$,
ae) $NR^{11}SO_2R^{12}$, or
af) two of $R^7$, $R^8$, $R^9$, and $R^{10}$ when on adjacent carbons join together to form a methylenedioxy bridge;

$R^{11}$, $R^{12}$, and $R^{13}$ independently are selected from:
a) $C_1-C_6$-perfluoroalkyl,
b) $C_1-C_6$-alkyl, unsubstituted or substituted with one, two, or three substituents selected from oxo, X', Y' and Z',
c) $C_2$–C6-alkenyl, unsubstituted or substituted with one, two, or three substituents selected from oxo, X', Y' and Z',
d) $C_2$–C6-alkynyl, unsubstituted or substituted with one, two, or three substituents selected from oxo, X', Y' and Z',
e) aryl, wherein aryl is defined as phenyl or naphthyl, unsubstituted or substituted with one, two, or three substituents selected from X', Y' and Z',
f) heterocyclyl, wherein the heterocyclyl is unsubstituted or substituted with one, two, three or four substituents selected from oxo, X', Y', and Z', or
g) $C_3$–C6-cycloalkyl, unsubstituted or substituted with one, two, or three substituents selected from oxo, X', Y' and Z';

X', Y' and Z' independently are selected from:
a) H,
b) halo,
c) CN,
d) $NO_2$,
e) hydroxy,
f) $C_1$–$C_6$-perfluoroalkyl,
g) $C_1$–$C_6$-alkoxyl, alkoxyl unsubstituted or substituted with aryl, wherein aryl is defined as phenyl or naphthyl,
h) (C=O)($C_1$–$C_6$-alkyl), alkyl unsubstituted or substituted with aryl, wherein aryl is defined as phenyl or naphthyl,
i) (C=O)O($C_1$–$C_6$-alkyl), alkyl unsubstituted or substituted with aryl, wherein aryl is defined as phenyl or naphthyl,
j) (C=O)NH($C_1$–$C_6$-alkyl),
k) (C=O)N($C_1$–$C_6$-alkyl)$_2$,
l) $NH_2$,
m) NH$C_1$–$C_6$-alkyl, wherein alkyl is unsubstituted or substituted with aryl or $NH_2$,
n) N($C_1$–$C_6$-alkyl)$_2$,
o) NHaryl, wherein aryl is defined as phenyl or naphthyl, unsubstituted or substituted with one, two, or three substituents selected from halo, phenyl, CN, $NO_2$, hydroxy, $C_1$–$C_6$-alkyl, $C_1$–$C_6$-alkoxyl, $NH_2$, NH$C_1$-$C_6$-alkyl, N($C_1$–$C_6$-alkyl)$_2$, (C=O)($C_1$–$C_6$-alkyl), (C=O)O($C_1$–$C_6$-alkyl), (C=O)NH($C_1$–$C_6$-alkyl), (C=O)N($C_1$–$C_6$-alkyl)$_2$, NH(C=O)($C_1$–$C_6$-alkyl),
p) NHheterocyclyl, wherein heterocyclyl is unsubstituted or substituted with one, two or three substituents selected from halo, phenyl, oxo, CN, $NO_2$, hydroxy, $C_1$–$C_6$-alkyl, $C_1$–$C_6$-alkyl substituted with $C_3$–$C_7$-cycloalkyl, $C_1$–$C_6$-alkoxyl, $NH_2$, NH$C_1$–$C_6$-alkyl, N($C_1$–$C_6$-alkyl)$_2$, (C=O)($C_1$–$C_6$-alkyl), (C=O)O($C_1$–$C_6$-alkyl), (C=O)O$CH_2$phenyl, (C=O)NH($C_1$–$C_6$-alkyl), (C=O)N($C_1$–$C_6$-alkyl)$_2$, NH(C=O)($C_1$–$C_6$-alkyl),
q) NHCHO,
r) NH(C=O)($C_1$–$C_6$-alkyl),
s) NH(C=O)(O$C_1$–$C_6$-alkyl),
t) aryl, wherein aryl is as defined above in o,
u) $C_1$–$C_6$-alkyl, wherein alkyl is unsubstituted or substituted with hydroxy, $C_3$–$C_7$-cycloalkyl, aryl or heterocyclyl, wherein aryl is defined as above in o and heterocyclyl is as defined above in p,
v) heterocyclyl, wherein heterocyclyl is as defined above in p,
w) when two of X', Y' and Z' are on adjacent carbons they can join to form a methylenedioxy bridge,
x) NH(C=O)aryl,
y) —$NR^{14}NHR^{15}$,
z) —S(O)x $C_1$–$C_6$-alkyl,
aa) $SO_2$NH $C_1$–$C_6$-alkyl, or
ab) $CO_2H$;
$R^{14}$ and $R^{15}$ are independently: H, $C_1$–$C_6$-alkyl, aryl or $C_1$–$C_6$-alkylaryl; or
x is 0, 1 or 2.

2. A compound of Formula I

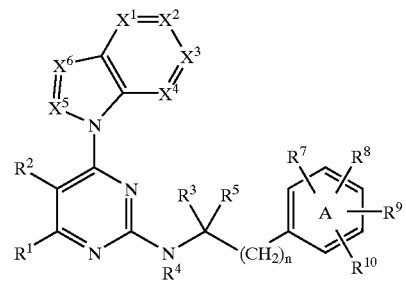

or pharmaceutically acceptable salts, hydrates, solvates, crystal forms or diastereomers thereof, wherein
$R^1$ and $R^2$ are independently:
a) H,
b) halo (Br, Cl, I, or F)
c) OH,
d) SH,
e) CN,
f) $NO_2$,
g) $R^{11}$,
h) $OR^{11}$,
i) OC(=O)$R^{11}$,
j) OC(=O)$OR^{11}$,
k) OC(=O)$NHR^{11}$,
l) OC(=O)$NR^{11}R^{12}$,
m) $SR^{11}$,
n) $SOR^{11}$,
o) $SO_2R^{11}$,
p) C(=O)$R^{11}$,
q) C(=O)$OR^{11}$,
r) C(=O)$NHR^{11}$,
s) C(=O)$NR^{11}R^{12}$,
t) $NH_2$,
u) $NHR^{11}$,
v) $NR^{11}R^{12}$,
w) NHC(=O)$R^{11}$,
x) $NR^{11}$C(=O)$R^{12}$,
y) $NR^{11}$C(=O)$NHR^{12}$,
z) $NR^{11}$C(=O)$NR^{12}R^{13}$,
aa) $SO_2NHR^{11}$,
ab) $SO_2NR^{11}R^{12}$,
ac) $NHSO_2R^{11}$,
ad) $NR^{11}SO_2R^{12}$,
$R^3$ and $R^5$ independently are:
a) H,
b) $C_1$–$C_6$-alkyl, unsubstituted or substituted with one, two, or three substituents selected from oxo, X', Y' and Z',
c) aryl, wherein aryl is defined as phenyl or naphthyl unsubstituted or substituted with one, two or three substituents selected from: X', Y' and Z', or
d) $R^3$ and $R^5$ taken together can represent =O;
e) $R^3$ or $R^5$ can represent a 2 or 3 carbon methylene bridge forming a ring of 5 to 8 atoms fused to the A ring;
$R^4$ is:
a) H, or
b) $C_1$–$C_6$-alkyl, or
c) $C_1$–$C_6$-alkoxyl;
$X^5$ and $X^6$ are independently $CR^a$ or N;
$R^a$ is: H, or $C_1$–$C_6$-alkyl;
n is 0, 1 or 2;

—X¹—X²—X³—X⁴— is:
a) —CR⁶=CR⁶—CR⁶ᵃ=CR⁶—,
b) —CR⁶ᵃ=CR⁶—CR⁶=CR⁶—,
c) —N=CR⁶—CR⁶=CR⁶—,
d) —CR⁶=N—CR⁶=CR⁶—,
e) —CR⁶=CR⁶—N=CR⁶—,
f) —CR⁶=CR⁶—CR⁶=N—,
g) —N=CR⁶—N=CR⁶—,
h) —CR⁶=N—CR⁶=N—,
i) —CR⁶=N—N=CR⁶—, or
j) —N=CR⁶—CR⁶=N—;

R⁶ and R⁶ᵃ are independently:
a) H,
b) halo(Br, Cl, I, or F)
c) OH,
d) SH,
e) CN,
f) NO₂,
g) N₃,
h) N₂+BF₄—,
i) R¹¹,
j) OR¹¹,
k) OC(=O)R₁₁,
l) OC(=O)OR¹¹,
m) OC(=O)NHR¹¹,
n) OC(=O)NR¹¹¹²,
o) SR¹¹,
p) SOR¹¹,
q) SO₂R¹¹,
r) C₁–C₆-alkyl, unsubstituted or substituted with one, two, or three substituents selected from R¹¹, R¹², and R¹³,
s) C(=O)R¹¹,
t) C(=O)OR¹¹,
u) C(=O)NHR¹¹,
v) C(=O)NR¹¹R¹²,
w) C(=O)N(OR¹¹)R¹²,
x) NH₂,
y) NHR¹¹,
z) NHC₁–C₆-alkyl, unsubstituted or substituted with one, two, or three substituents selected from R¹¹, R¹², and R¹³,
aa) NR¹¹R¹²,
ab) NHC(=O)R¹¹,
ac) NR¹¹C(=O)R¹²,
ad) NHC(=O)NHR¹¹,
ae) NR¹¹C(=O)NHR¹²,
af) NR¹¹C(=O)NR¹²R¹³,
ag) SO₂NH₂,
ah) SO₂NHR¹¹,
ai) SO₂NR¹¹R¹²,
aj) NHSO₂R¹¹,
ak) NR¹¹SO₂R¹²,
al) NHP(=O)(OC₁–C₆-alkyl)₂, or
am) R⁶ and R⁶ᵃ when on adjacent carbons can be joined to form a 5- or 6-membered ring having the following bridging atoms:
i) —CH=CH—CH=CH—,
ii) —OCH₂O—,
iii) —C(O)N(R¹¹)C(O)—,
iv) —CH₂N(R¹¹)CH₂—,
v) —N=CHNHC(O)—,
vi) —C(O)NHCH=N—,
vii) —C(O)OC(O)—,
viii) —NHC(O)NHC(O)—,
ix) —C(O)NHC(O)NH—,
x) —N=CHNH—, or xi) —N=CHNR¹¹—, or
xii)

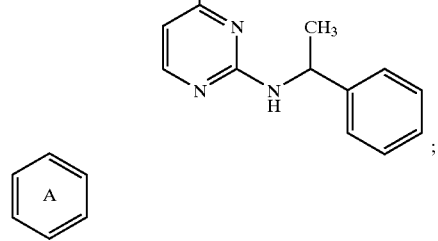

represens:
a) phenyl,
b) naphthyl,
c) pyridyl,
d) pyrazinyl,
e) pyrimidinyl,
f) pyrrolyll
g) thienyl,
h) oxazolyl,
i) isoxazolyl,
j) thiazolyl,
k) pyrazolyl,
l) triazolyl,
m) tetrazolyl,
n) furanyl,
o) benzothienyl,
p) benzofuranyl,
q) indolyl,
r) imidazolyl,
s) benzimidazolyl, or
t) thiadiazolyl, R⁷, R⁸, R⁹, and R¹⁰ independently are selected from:
a) H,
b) halo(Br, Cl, I, or F)
c) OH,
d) SH,
e) CN,
f) NO₂,
g) N₃
h) N₂+BF₄—
i) R₁₁,
j) OR¹¹,
k) SR¹¹,
l) SOR¹¹,
m) SO₂R¹¹,
n) C₁–C₆-alkyl, unsubstituted or substituted with one, two, or three substituents selected from R¹¹, R¹², and R¹³,
o) C₁–C₆-perfluoroalkyl,
p) C(=O)R₁₁,
q) C(=O)OR¹¹,
r) C(=O)NHR¹¹,
s) C(=O)NR¹¹R¹²,
t) NH₂,
u) NHR¹¹,
v) NHC₁–C₆-alkyl, unsubstituted or substituted with one, two, or three substituents selected from R¹¹, R¹², and R¹³,
w) NR¹¹R¹²,
x) NHC(=O)R¹¹,
y) NR¹¹C(=O)R¹², z) NR¹¹C(=O)NHR¹²,
aa) NR¹¹C(=O)NR¹²R¹³,
ab) SO₂NHR¹¹,
ac) SO₂NR¹¹R¹²,
ad) NHSO₂R¹¹,
ae) NR¹¹SO₂R¹², or
af) two of R⁷, R⁸, R⁹, and R¹⁰ when on adjacent carbons join together to form a methylenedioxy bridge;

R¹¹, R¹², and R¹³ independently are selected from:
a) $C_1-C_6$-perfluoroalkyl,
b) $C_1-C_6$-alkyl, unsubstituted or substituted with one, two, or three substituents selected from oxo, X', Y' and Z',
c) $C_2-C_6$-alkenyl, unsubstituted or substituted with one, two, or three substituents selected from oxo, X', Y' and Z',
d) $C_2-C_6$-alkynyl, unsubstituted or substituted with one, two, or three substituents selected from oxo, X', Y' and Z',
e) aryl, wherein aryl is defined as phenyl or naphthyl, unsubstituted or substituted with one, two, or three substituents selected from X', Y' and Z',
f) heterocyclyl, wherein the heterocyclyl is unsubstituted or substituted with one, two or three substituents selected from oxo, X', Y', and Z';
g) $C_3-C_6$-cycloalkyl, unsubstituted or substituted with one, two, or three substituents selected from oxo, X', Y' and Z', X', Y' and Z' independently are selected from:
a) H,
b) halo,
c) CN,
d) NO₂,
e) hydroxy,
f) $C_1-C_6$-perfluoroalkyl,
g) $C_1-C_6$-alkoxyl, alkoxyl unsubstituted or substituted with aryl, wherein aryl is defined as phenyl or naphthyl,
h) (C=O)($C_1-C_6$-alkyl), alkyl unsubstituted or substituted with aryl, wherein aryl is defined as phenyl or naphthyl,
i) (C=O)O($C_1-C_6$-alkyl), alkyl unsubstituted or substituted with aryl, wherein aryl is defined as phenyl or naphthyl,
j) (C=O)NH($C_1-C_6$-alkyl),
k) (C=O)N($C_1-C_6$-alkyl)₂,
l) NH₂,
m) NH$C_1-C_6$-alkyl,
n) N($C_1-C_6$-alkyl)₂,
o) NHaryl, wherein aryl is defined as phenyl or naphthyl, unsubstituted or substituted with one, two, or three substituents selected from halo, phenyl, CN, NO₂hydroxy, $C_1-C_6$-alkyl, $C_1-C_6$-alkoxyl, NH₂, NH$C_1-C_6$-alkyl, N($C_1-C_6$-alkyl)₂, (C=O)($C_1-C_6$-alkyl), (C=O)O($C_1-C_6$-alkyl), (C=O)NH($C_1-C_6$-alkyl), (C=O)N($C_1-C_6$-alkyl)₂, NH(C=O)($C_1-C_6$-alkyl),
p) NHheterocyclyl, wherein heterocyclyl is unsubstituted or substituted with one, two or three substituents selected from halo, phenyl, oxo, CN, NO₂, hydroxy, $C_1-C_6$-alkyl, $C_1-C_6$-alkoxyl, NH₂, NH$C_1-C_6$-alkyl, N($C_1-C_6$-alkyl)₂,(C=O)($C_1-C_6$-alkyl), (C=O)O($C_1-C_6$-alkyl), (C=O)OCH₂phenyl, (C=O)NH($C_1-C_6$-alkyl), (C=O)N($C_1-C_6$-alkyl)₂, NH(C=O)($C_1-C_6$-alkyl),
q) NHCHO,
r) NH(C=O)($C_1-C_6$-alkyl),
s) NH(C=O)(O$C_1-C_6$-alkyl),
t) aryl, wherein aryl is as defined above in o,
u) $C_1-C_6$-alkyl, wherein alkyl is unsubstituted or substituted with aryl or heterocyclyl, wherein aryl is defined as above in o and heterocyclyl is as defined above in p,
v) heterocyclyl, wherein heterocyclyl is as defined above in p, or
w) when two of X', Y' and Z' are on adjacent carbons they can join to form a methylenedioxy bridge.

3. The compound of Formula Ia:

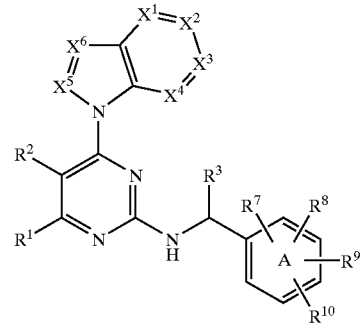

or pharmaceutically acceptable salts, hydrates, solvates, crystal forms, and individual diastereomers thereof, wherein R¹, R², and R³ are as defined below and all other substituents are as recited in claim 2, R¹ and R² are independently:
a) H,
b) R¹¹,
c) NH₂,
d) NHR¹¹, or
e) NR¹¹R¹²; and R³ is:
a) H, or
b) $C_1-C_6$-alkyl, unsubstituted or substituted with one, two, or three substituents selected from oxo, X', Y' and Z'.

4. The compound of Formula Ib:

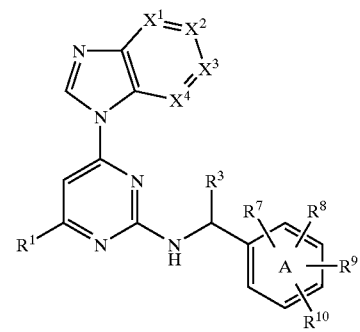

or a pharmaceutically acceptable salts, hydrates, solvates, crystal forms, and individual diastereomers thereof, wherein R¹ and —X¹—X²—X³—X⁴— are as defined below and all other substituents are as recited in claim 3, R¹ is:
a) H,
b) R¹¹,
c) NH₂, d) NHR¹¹, or
e) NR¹¹R¹²; and —X¹—X²—X³—X⁴— is:
a) —CR⁶=CR⁶—CR⁶ᵃ=CR⁶—, or
b) —R⁶ᵃ=CR⁶—CR⁶=CR⁶.

5. The compound of Formula Ic:

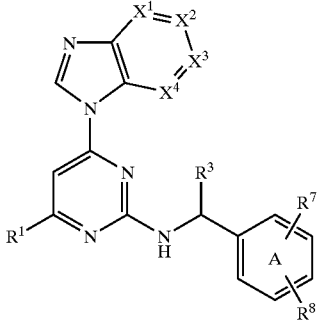

or pharmaceutically acceptable salts, hydrates, solvates, crystal forms, and individual diastereomers thereof, wherein R⁶ and R⁶ᵃ are as defined below and all other substituents are as recited in claim 4, R⁶ and R⁶ᵃ are independently:
a) H,
b) halo (Br, Cl, I, or F),
c) R¹¹,
d) OR¹¹,
e) C₁–C₆-alkyl, unsubstituted or substituted with one, two, or three substituents selected from R⁹, R¹⁰, and R¹¹,
f) NH₂,
g) NHR¹¹,
h) NHC₁–C₆-alkyl, unsubstituted or substituted with one, two, or three substituents selected from R⁹, R¹⁰, and R¹¹,
i) NR¹¹R¹²,
j) NHC(=O)R¹¹,
k) NR¹¹C(=O)R¹²,
l) NR¹¹C(=O)NHR¹²,
m) NR¹¹C(=O)NR¹²R¹³,
n) NHSO₂R¹¹, or
o) NR¹¹SO₂R¹².
j) imidazolyl, unsubstituted or substituted with one, two or three substituents selected from X', Y', and Z',
k) imidazolidinyl, unsubstituted or substituted with one, two or three substituents selected from oxo, X', Y', and Z',
l) 1,3-diazobicyclo[3.3.0]octan-2-onyl,
m) 1,3-diazobicyclo[4.3.0]nonan-2-onyl,
n) NH₂,
o) NHR¹¹,
p) NHC₁–C₆-alkyl, unsubstituted or substituted with one, two, or three substituents selected from R¹¹, R¹², and R¹³,
q) NR¹¹R¹²,
r) NHC(=O)R¹¹,
s) NR¹¹C(=O)R12,
t) NR¹¹C(=O)NHR¹²,
u) NR¹¹C(=O)NR¹²R¹³,
v) NHSO₂R¹¹ or
w) NR¹¹SO₂R¹².

6. The compound of Formula Ic:

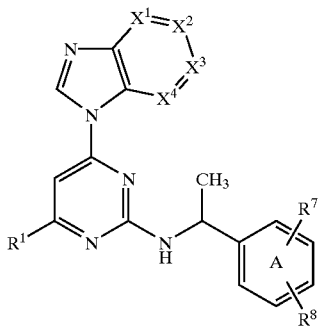

or pharmaceutically acceptable salts, hydrates, solvates, crystal forms, and individual diastereomers thereof, wherein R¹ is H, aryl, or heterocyclyl, and all other substituents are as recited in claim 5.

7. The compound of Formula Ic:

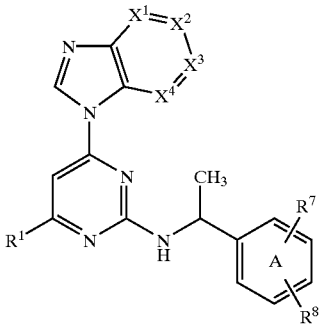

or pharmaceutically acceptable salts, hydrates, solvates, crystal forms, and individual diastereomers thereof, wherein A is defined as phenyl, naphthyl, pyridyl, pyrimidinyl, pyrazinyl, thienyl, oxazolyl, thiazolyl, pyrazolyl, tetrazolyl, imidazolyl, thiadiazolyl, and all other substituents are as recited in claim 6.

8. The compound of Formula Id:

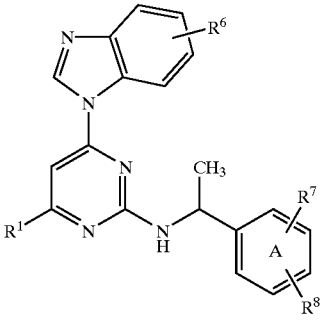

or pharmaceutically acceptable salts, hydrates, solvates, crystal forms, and individual diastereomers thereof, wherein the substituents are as recited in claim 7, except that R⁶ is attached to the 5- or 6-position of the benzimidazole.

9. The compound of Formula Ie:

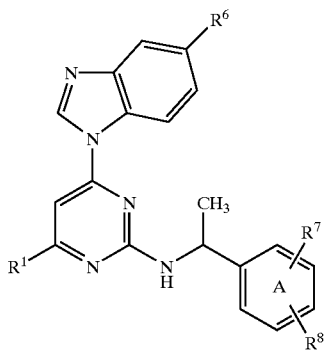

or pharmaceutically acceptable salts, hydrates, solvates, crystal forms, and individual diastereomers thereof, wherein $R^6$ is as defined below and all other substituents are as recited in claim 2, $R^6$ is:
a) H,
b) phenyl, unsubstituted or substituted with one, two, or three substituents selected from X', Y' and Z',
c) pyridyl, unsubstituted or substituted with one, two or three substituents selected from X', Y', and Z',
d) pyridazinyl, unsubstituted or substituted with one, two or three substituents selected from X', Y', and Z',
e) pyrimidinyl, unsubstituted or substituted with one, two or three substituents selected from X', Y', and Z',
f) thiazolyl, unsubstituted or substituted with one, two, or three substituents selected from X', Y', and Z',
g) thiadiazolyl, unsubstituted or substituted with one, two or three substituents selected from X', Y', and Z',
h) thienyl, unsubstituted or substituted with one, two or three substituents selected from X', Y', and Z',
i) pyrazinyl, unsubstituted or substituted with one, two or three substituents selected from X', Y', and Z',
j) imidazolyl, unsubstituted or substituted with one, two or three substituents selected from X', Y', and Z',
k) imidazolidinyl, unsubstituted or substituted with one, two or three substituents selected from oxo, X', Y', and Z',
l) 1,3-diazobicyclo[3.3.0]octan-2-onyl,
m) 1,3-diazobicyclo[4.3.0]nonan-2-onyl,
n) $NH_2$,
o) $NHR^8$,
p) $NHC_1$–C6-alkyl, unsubstituted or substituted with one, two, or three substituents selected from $R^8$, $R^9$, and $R^{10}$,
q) $NR^8R^9$,
r) $NHC(=O)R^8$,
s) $NR^8C(=O)R^9$,
t) $NR^8C(=O)NHR^9$,
u) $NR^8C(=O)NR^9R^{10}$,
v) $NHSO_2R^8$, or
w) $NR^8SO_2R^9$.

10. The compound of Formula If:

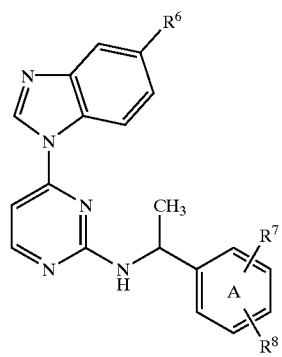

or pharmaceutically acceptable salts, hydrates, solvates, crystal forms, and individual diastereomers thereof, wherein $R^6$ is as defined below and all other substituents are as recited in claim 9, $R^6$ is:
a) H,
b) phenyl, unsubstituted or substituted with one, two, or three substituents selected from X', Y' and Z',
c) pyridyl, unsubstituted or substituted with one, two or three substituents selected from X', Y', and Z',
d) pyridazinyl, unsubstituted or substituted with one, two or three substituents selected from X', Y', and Z',
e) pyrimidinyl, unsubstituted or substituted with one, two or three substituents selected from X', Y', and Z',
f) imidazolidinyl, unsubstituted or substituted with one, two or three substituents selected from oxo, X', Y', and Z',
g) 1,3-diazobicyclo[3.3.0]-octan-2-onyl,
h) 1,3-diazobicyclo[4.3.0]-nonan-2-onyl,
i) $NH_2$,
j) $NHR^{11}$,
k) $NHC_1$–$C_6$-alkyl, unsubstituted or substituted with one, two, or three substituents selected from $R^{11}$, $R^{12}$, and $R^{13}$,
l) $NR^{11}R^{12}$,
m) $NHC(=O)R^{11}$,
n) $NR^{11}C(=O)R^{12}$,
o) $NR^{11}C(=O)NHR^{12}$,
p) $NR^{11}C(=O)NR^{12}R^{13}$,
q) $NHSO_2R^{11}$, or
r) $NR^{11}SO_2R^{12}$.

11. The compound of Formula If:

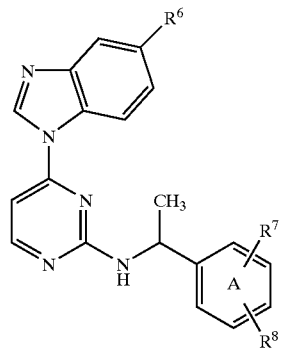

or pharmaceutically acceptable salts, hydrates, solvates, crystal forms, and individual diastereomers thereof, wherein A is phenyl, naphthyl, pyridyl, pyrimidinyl, thienyl, or thiazolyl, and all other substituents are as recited in claim 10.

12. The compound of Formula I as recited in claim 2, or pharmaceutically acceptable salts, hydrates, solvates, crystal forms, and individual diastereomers thereof, which is selected from the group consisting of:

2-[(S)-1-Phenylethylamino]-4-[5-methylbenzimidazol-1-yl]pyrimidine;
2-[(S)-1-Phenylethylamino]-4-[6-methylbenzimidazol-1-yl]pyrimidine;
2-[(S)-1-Phenylethylamino]-4-[5-aminobenzimidazol-1-yl]pyrimidine;
2-[(S)-1-Phenylethylamino]-4-[6-aminobenzimidazol-1-yl]pyrimidine;
2-[(S)-1-Phenylethylamino]-4-[5-N,N-(dimethyl)-amninobenzimidazol-1-yl]pyrimidine;
2-((S)-1-(3-nitro-phenyl)ethylamino)-4-[5-methyl-benzimidazol-1-yl]pyrimidine;
2-((S)-1-(3-nitro-phenyl)ethylamino)-4-[6-methyl-benzimidazol-1-yl]pyrimidine;
2-((R)-1-(3-nitro-phenyl)ethylamino)-4-[5-methyl-benzimidazol-1-yl]pyrimidine;
2-((R)-1-(3-nitro-phenyl)ethylamino)4-[6-methyl-benzimidazol-1-yl]pyrimidine;
2-[(S)-1-Phenylethylamino]-4-[5-N-((morpholin-2-yl)methyl)-aminobenzimidazol-1-yl]pyrimidine;
2-[(S)-1-Phenylethylamino]-4-[5-N-((piperazin-2-yl)methyl)-aminobenzimidazol-1-yl]pyrimidine;
2-[(S)-1-Phenylethylamino]-4-[5-N-(2-aminoethyl)-aminobenzimidazol-1-yl]pyrimidine;
2-[(S)-1-Phenylethylamino]-4-[5-N-((pyrrolidin-2-yl)methyl)-aminobenzimidazol-1-yl]pyrimidine;
2-[(S)-1-Phenylethylamino]-4-[5-N-(((R)-piperidin-2-yl)methyl)-aminobenzimidazol-1-yl]pyrimidine;
2-[(S)-1-Phenylethylamino]-4-[5-(1,3-diazobicyclo[3.3.0]-octan-3-yl)benzimidazol-1-yl]pyrimidine;
2-[(S)-1-Phenylethylamino]-4-[5-(1,3-diazobicyclo[3.3.0]-octan-2-one-3-yl)benzimidazol-1-yl]pyrimidine;
2-[(S)-1-Phenylethylamino]-4-[5-(1,3-diazobicyclo[4.3.0]-nonan-2-one-3-yl)benzimidazol-yl]pyrimidine;
2-[(S)-1-Phenylethylamino]-4-[5-N-(N-methylcarbamoyl)-aminobenzimidazol-1-yl]pyrimidine;
2-[(S)-1-Phenylethylamino]-4-[5-N-(N-ethylcarbamoyl)-aminobenzimidazol-1-yl]pyrimidine;
2-[(S)-1-Phenylethylamino]-4-[5-N-(N-propylcarbamoyl)-aminobenzimidazol-1-yl]pyrimidine;
2-[(S)-1-Phenylethylamino]-4-[5-N-(N-((1-methyl)ethylcarbamoyl)amino-benzimidazol-1-yl]pyrimidine;
2-[(S)-1-Phenylethylamino]-4-[5-(tetrazol-1-yl)-benzimidazol-1-yl]pyrimidine;
2-[(S)-1-(3-Nitrophenyl)ethylamino]-4-[5-N-(pyrrolidin-2-yl)methyl)-aminobenzimidazol-1-yl]pyrimidine;
2-[(S)-1-(3-Trifluoromethylphenyl)ethylamino]-4-[5-N-((pyrrolidin-2-yl)methyl)-aminobenzimidazol-1-yl]pyrimidine;
2-[(S)-1-(3Nitrophenyl)ethylamino]-4-[5-(1,3-diazobicyclo[3.3.0]-octan-2-one-3-yl)benzimidazol-1-yl]pyrimidine;
2-[(S)-1-(3-Trifluoromethylphenyl)ethylamino]-4-[5-(1,3-diazobicyclo[3.3.0]octan-2-one-3-yl)benzimidazol-1-yl]pyrimidine;
2-[(S)-1-(3Nitrophenyl)ethylamino]-4-[5-(1,3-diazobicyclo[3.3.0]-octan-3-yl)benzimidazol-1-yl]pyrimidine;
2-[(S)-1-(3-Trifluoromethylphenyl)ethylamino]-4-[5-(1,3-diazobicyclo[3.3.0]octan-3-yl)benzimidazol-1-yl]pyrimidine;
2-[(S)-1-Phenylethylamino]-4-[5-phenylbenzimidazol-1-yl]pyrimidine;
2-[(S)-1-Phenylethylamino]-4-[5-(thiazol-2-yl)benzimidazol-1-yl]pyrimidine;
2-[(S)-1-Phenylethylamino]-4-[5-(furan-2-yl)benzimidazol-1-yl]pyrimidine;
2-[(S)-1-Phenylethylamino]-4-[benzimidazol-1-yl]-6-(2-methyl-phenyl)pyrimidine;
2-[(S)-1-Phenylethylamino]-4-[5-(pyridin-2-yl)benzimidazol-1-yl]pyrimidine;
2-[(S)-1-Phenylethylamino]-4-[5-(thiophen-3-yl)benzimidazol-1-yl]pyrimidine;
2-[(S)-1-Phenylethylamino]-4-[5-(pyrimidin-5-yl)benzimidazol-1-yl]pyrimidine;
2-[(S)-1-Phenylethylamino]-4-[5-(pyridin-3-yl)-benzimidazol-1-yl]pyrimidine;
2-[(S)-1-Phenylethylamino]-4-[5-(4-methoxyphenyl)benzimidazol-1-yl]pyrimidine;
2-[(S)-1-Phenylethylamino]-4-[5-(3-chlorophenyl)benzimidazol-1-yl]pyrimidine;
2-[(S)-1-Phenylethylamino]-4-[5-(3-methoxyphenyl)benzimidazol-1-yl]pyrimidine;
2-[(S)-1-Phenylethylamino]-4-[5-(4-(pyrrol-1-yl)phenyl)benzimidazol-1-yl]-pyrimidine;
2-[(S)-1-Phenylethylamino]-4-[5-(pyridin-4-yl)benzimidazol-1-yl]pyrimidine;
2-[(S)-1-Phenylethylamino]-4-[5-(4-methylphenyl)benzimidazol-1-yl]pyrimidine;
2-[(S)-1-Phenylethylamino]-4-[5-(pyrimidin-2-yl)benzimidazol-1-yl]pyrimidine;
2-[(S)-1-Phenylethylamino]-4-[5-(3-methylphenyl)benzimidazol-1-yl]pyrimidine;
2-[(S)-1-Phenylethylamino]-4-[5-(thiophen-3-yl-carbonyl)benzimidazol-1-yl]-pyrimidine;
2-[(S)-1-Phenylethylamino]-4-[5-(2-aminopyridine-5-yl)benzimidazol-1-yl]-pyrimidine;
2-[(S)-1-Phenylethylamino]-4-[5-(2-aminopyrimidin-4-yl)benzimidazol-1-yl]-pyrimidine;
2-[(S)-1-Phenylethylamino]-4-[5-(2-aminopyridin-5-yl)benzimidazol-1-yl]pyrimidine;
2-[(S)-1-Phenylethylamino]-4-[5-(4-pyridyl)benzimidazol-1-yl]pyrimidine;
2-[(S)-1-Phenylethylamino]-4-[5-(3-methoxypyridazin-6-yl)benzimidazol-1-yl]-pyrimidine;
2-[(S)-1-Phenylethylamino]-4-[5-(3-chloropyridazin-6-yl)benzimidazol-1-yl]-pyrimidine;
2-[(S)-1-Phenylethylamino]-4-[5-(6-methylpyridazin-3-yl)benzimidazol-1-yl]pyrimidine;
2-[(S)-1-Phenylethylamino]-4-[5-(pyridazin-3-yl)benzimidazol-1-yl]pyrimidine;
2-[(S)-1-Phenylethylamino]-4-[5-(3-N,N-dimethylaminopyridazin-6-yl)-benzimidazol-1-yl]pyrimidine;
2-[(S)-1-Phenylethylamino]-4-[benzimidazol-1-yl]-6-[2-hydroxymethylphenyl]-pyrimidine;
2-[(S)-1-Phenylethylamino]-4-[5-(2-aminopyridin-4-yl)benzimidazol-1-yl]pyrimidine;
2-[(S)-1-(3-Nitrophenyl)ethylamino]-4-[5-(2-aminopyrimidin-4-yl)benzimidazol-1-yl]pyrimidine;
2-[(S)-1-(3-Trifluoromethylphenyl)ethylamino]-4-[5-(2-aminopyrimidin-4-yl)benzimidazol -1-yl]pyrimidine;
2-[(S)-1-(3-Nitrophenyl)ethylamino]-4-[5-(pyridin-4-yl)benzimidazol-1-yl]pyrimidine;
2-[(S)-1-(3-Trifluoromethylphenyl)ethylamino]-4-[5-(pyridin-4-yl)benzimidazol-1-yl]pyrimidine;
2-[(S)-1-(3-Nitrophenyl)ethylamino]-4-[5-(pyridazin-3-yl)benzimidazol-1-yl]pyrimidine;
2-[(S)-1-(3-Trifluoromethylphenyl)ethylamino]-4-[5-(pyridazin-3-yl)benzimidazol-1-yl]pyrimidine;
2-[(S)-1-(3-Nitrophenyl)ethylamino]-4-[5-(3-N,N-dimethylpyridazin-6-yl)benzimidazol-1-yl]pyrimidine;

2-[(S)-1-(3-Trifluoromethylphenyl)ethylamino]-4-[5-(3-N,N-dimethylpyridazin-6-yl)benzimidazol-1-]pyrimidine;
2-[(S)-1-Phenylethylamino]-4-[5-(2-amninopyrimidin-4-yl)benzimidazol-1-yl]-6-[2-methylphenyl]pyrimidine;
2-[(S)-1-Phenylethylamino]-4-[5-(pyridin-4-yl)benzimidazol-1-yl]-6-[2-methylphenyl]pyrimidine;
2-[(S)-1-Phenylethylamino]-4-[5-(pyridazin-3-yl)benzimidazol-1-yl]-6-[2-methylphenyl]pyrimidine;
2-[(S)-1-Phenylethylamino]-4-[5-(3-N,N-dimethylpyridazin-6-yl)benzimidazol-1-yl]-6-[2-methylphenyl]pyrimidine;
2-[(S)-1-Phenylethylamino]-4-[5-(2-aminopyrimidin-4-yl)benzimidazol-1-yl]-6-[2-hydroxymethylphenyl]pyrimidine;
2-[(S)-1-Phenylethylamino]-4-[5-(pyridin-4-yl)benzimidazol-1-yl]-6-[2-hydroxymethylphenyl]pyrimidine;
2-[(S)-1-Phenylethylamino]-4-[5-(pyridazin-3-yl)benzimidazol-1-yl]-6-[2-hydroxymethylphenyl]pyrimidine;
2-[(S)-1-Phenylethylamino]-4-[5-(3-N,N-dimethylpyridazin-6-yl)benzimidazol-1-yl]-6-[2-hydroxymethylphenyl]pyrimidine;
2-[(S)-1-(3-Nitrophenyl)ethylamino]-4-[5-(2-aminopyrimidin-4-yl)benzimidazol-1-yl]-6-[2-hydroxymethylphenyl]pyrimidine;
2-[(S)-1-(3-Nitromethylphenyl)ethylamino]-4-[5-(pyridin-4-yl)benzimidazol-1-yl]-6-[2-hydroxymethylphenyl]pyrimidine;
2-[(S)-1-(3-Trifluorophenyl)ethylamino]-4-[5-(2-aminopyrimidin-4-yl)benzimidazol-1-yl]-6-[2-hydroxymethylphenyl]pyrimidine;
2-[(S)-1-(3-Trifluoromethylphenyl)ethylamino]-4-[5-(pyridin-4-yl)benzimidazol-1-yl]-6-[2-hydroxymethylphenyl]pyrimidine;
2-[(S)-1-(3-Nitrophenyl)ethylamino]-4-[5-(2-aminopyrimidin-4-yl)benzimidazol-1-yl]-6-[2-methylphenyl]pyrimidine;
2-[(S)-1-(3-Nitromethylphenyl)ethylamino]-4-[5-(pyridin-4-yl)benzimidazol-1-yl]-6-[2-methylphenyl]pyrimidine;
2-[(S)-1-(3-Trifluorophenyl)ethylamino]-4-[5-(2-aminopyrimidin-4-yl)benzimidazol-1-yl]-6-[2-methylphenyl]pyrimidine; and
2-[(S)-1-(3-Trifluoromethylphenyl)ethylamino]-4-[5-(pyridin-4-yl)benzimidazol-1-yl]-6-[2-methylphenyl]pyrimidine.

13. A method of treating a protein tyrosine kinase-associated disorder, comprising the administration of a therapeutically effective amount of at least one protein tyrosine kinase inihibitor compound of the Formula I, or its pharmaceutically acceptable salts, hydrates, solvates, crystal forms and individual diastereomers thereof, as recited in claim 2, to a subject in need of such treatment.

14. The method of claim 13, wherein the protein tyrosine kinase-associated disorder is transplant rejection.

15. The method of claim 13, wherein the protein tyrosine kinase-associated disorder is rheumatoid arthritis.

16. The method of claim 13, wherein the protein tyrosine kinase-associated disorder is psoriasis.

17. The method of claim 13, wherein the protein tyrosine kinase-associated disorder is inflammatory bowel disease.

18. The method of claim 13, wherein the protein tyrosine kinase is Lck.

19. The method of claim 13, wherein the protein tyrosine kinase is Fyn(T) or Fyn(B).

20. The method of claim 13, wherein the protein tyrosine kinase is Lyn.

21. The method of claim 13, wherein the protein tyrosine kinase is Hck.

22. The method of claim 13, wherein the protein tyrosine kinase is Fgr.

23. The method of claim 13, wherein the protein tyrosine kinase is Src.

24. The method of claim 13, wherein the protein tyrosine kinase is Blk.

25. The method of claim 13, wherein the protein tyrosine kinase is Yes.

26. A method of treating a protein tyrosine kinase-associated disorder, comprising the simultaneous or sequential administration of a therapeutically effective amount of at least one protein tyrosine kinase inihibitor compound of the Formula I, or its pharmaceutically acceptable salts, hydrates, solvates, crystal forms and individual diastereomers thereof, as recited in claim 2, with an antiinflammatory, antiproliferative chemotherapeutic agent, immunosuppressant or a protein tyrosine kinase inhibitor, other than a compound of the formula I, to a subject in need of such treatment.

27. The method of claim 26, wherein the protein tyrosine kinase inihibitor compound of Formula I or its pharmaceutically acceptable salts, hydrates, solvates, crystal forms and individual diastereomers thereof is administered with one or more of another PTK inhibitor, cyclosporin A; CTLA4-Ig; antibodies selected from anti-ICAM-3, anti-IL-2 receptor (Anti-Tac), anti-CD45RB, anti-CD2, anti-CD3 (OKT-3), anti-CD4, anti-CD80, and anti-CD86; agents blocking the interaction between CD40 and gp39; fusion proteins constructed from CD40 and gy39; inhibitors of NF-kappa B function; nuclear translocation inhibitors; cholesterol biosynthesis inhibitors; HMG CoA reductase inhibitors; non-steroidal antiinflammatory drugs (NSAIDs); cyclooxygenase inhibitors; steroids; gold compounds; antiproliferative agents; FK506 (tacrolimus, Prograf); mycophenolate mofetil; cytotoxic drugs; TNF-□ inhibitors; anti-TNF antibodies or soluble TNF receptor; and rapamycin (sirolimus or Rapamune) or derivatives thereof.

28. A method for treating a T-cell mediated disorder, comprising the administration of a therapeutically effective amount of at least one compound of the Formula I, or its pharmaceutically acceptable salts, hydrates, solvates, crystal forms salts and individual diastereomers thereof, as recited in claim 2, to a subject in need of such treatment.

29. A pharmaceutical composition for the treatment of a protein tyrosine kinase-associated disorder, comprising a pharmaceutically acceptable carrier and at least one compound of Formula I or its pharmaceutically acceptable salts, hydrates, solvates, crystal forms or an individual diastereomer thereof, as recited in claim 2.

30. A process for making a pharmaceutical composition comprising a combination of a compound of the Formula I, or its pharmaceutically acceptable salts, hydrates, solvates, crystal forms salts and individual diastereomers thereof, as recited in claim 2 and a pharmaceutically acceptable carrier.

31. A method of treating a protein tyrosine kinase-associated disorder, comprising the administration of a therapeutically effective amount of at least one compound of the Formula I, or its pharmaceutically acceptable salts, hydrates, solvates, crystal forms and individual diastereomers thereof, as recited in claim 1, to a subject in need of such treatment.

32. The method of claim 31, wherein the protein tyrosine kinase-associated disorder is transplant rejection.

33. The method of claim 31, wherein the protein tyrosine kinase-associated disorder is rheumatoid arthritis.

34. The method of claim 31, wherein the protein tyrosine kinase-associated disorder is psoriasis.

35. The method of claim 31, wherein the protein tyrosine kinase-associated disorder is inflammatory bowel disease.

36. A method of treating a protein tyrosine kinase-associated disorder, comprising the simultaneous or sequential administration of a therapeutically effective amount of at least one compound of the Formula I, or its pharmaceutically acceptable salts, hydrates, solvates, crystal forms and individual diastereomers thereof, as recited in claim 1, with an antiinflammatory, antiproliferative chemotherapeutic agent, immunosuppressant or a protein tyrosine kinase inhibitor, other than a compound of the Formula I, to a subject in need of such treatment.

37. A method for treating a T-cell mediated disorder, comprising the administration of a therapeutically effective amount of at least one compound of the Formula I, or its pharmaceutically acceptable salts, hydrates, solvates, crystal forms salts and individual diastereomers thereof, as recited in claim 1, to a subject in need of such treatment.

38. A pharmaceutical composition for the treatment of a protein tyrosine kinase-associated disorder, comprising a pharmaceutically acceptable carrier and at least one compound of Formula I or its pharmaceutically acceptable salts, hydrates, solvates, crystal forms or an individual diastereomer thereof, as recited in claim 1.

39. A process for making a pharmaceutical composition comprising a combination of a compound of the Formula I, or its pharmaceutically acceptable salts, hydrates, solvates, crystal forms salts and individual diastereomers thereof, as recited in claim 1 and a pharmaceutically acceptable carrier.

* * * * *